US012612607B2

(12) United States Patent
Doudna et al.

(10) Patent No.: US 12,612,607 B2
(45) Date of Patent: Apr. 28, 2026

(54) CRISPR-Cas EFFECTOR POLYPEPTIDES AND METHODS OF USE THEREOF

(71) Applicant: The Regents of the University of California, Oakland, CA (US)

(72) Inventors: Jennifer A. Doudna, Berkeley, CA (US); Jillian F. Banfield, Berkeley, CA (US); Basem Al-Shayeb, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 960 days.

(21) Appl. No.: 17/781,674

(22) PCT Filed: Dec. 22, 2020

(86) PCT No.: PCT/US2020/066672
§ 371 (c)(1),
(2) Date: Jun. 1, 2022

(87) PCT Pub. No.: WO2021/133829
PCT Pub. Date: Jul. 1, 2021

(65) Prior Publication Data
US 2023/0028178 A1      Jan. 26, 2023

Related U.S. Application Data

(60) Provisional application No. 62/952,909, filed on Dec. 23, 2019.

(51) Int. Cl.
| | |
|---|---|
| *C12N 9/22* | (2006.01) |
| *C07K 14/47* | (2006.01) |
| *C12N 15/11* | (2006.01) |
| *C12N 15/62* | (2006.01) |
| *C12N 15/70* | (2006.01) |
| *C12N 15/90* | (2006.01) |
| *C12Q 1/6818* | (2018.01) |

(52) U.S. Cl.
CPC ................ *C12N 9/22* (2013.01); *C07K 14/47* (2013.01); *C12N 15/11* (2013.01); *C12N 15/62* (2013.01); *C12N 15/70* (2013.01); *C12N*

*15/907* (2013.01); *C12Q 1/6818* (2013.01); *C07K 2319/09* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 10,808,245 | B2 | 10/2020 | Chong et al. |
| 11,168,324 | B2 | 11/2021 | Chong et al. |
| 11,912,992 | B2 | 2/2024 | Chong et al. |
| 2019/0241954 | A1 | 8/2019 | Doudna et al. |
| 2019/0276842 | A1 | 9/2019 | Doudna et al. |

FOREIGN PATENT DOCUMENTS

| | | |
|---|---|---|
| WO | WO 2014/093622 | 6/2014 |
| WO | WO 2021/050534 | 3/2021 |

OTHER PUBLICATIONS

Al-Shayeb, et al.; "Diverse virus-encoded CRISPR-Cas systems include streamlined genome editors"; vol. 185, No. 24, pp. 4574-4586 (Nov. 23, 2022).
Goltsman, et al.; "Novel Type V-A CRISPR Effectors Are Active Nucleases with Expanded Targeting Capabilities"; The CRISPR Journal; vol. 3, No. 6, pp. 454-461 (Dec. 17, 2020).
Rusk; "Spotlight on Cas12"; Nature Methods; vol. 16, pp. 215 (Mar. 2019).
Yan, et al.; "Functionally diverse type V CRISPR-Cas systems"; Science; vol. 363; pp. 88-91 (Jan. 4, 2019).

*Primary Examiner* — Arthur S Leonard
(74) *Attorney, Agent, or Firm* — Kyle A. Gurley; Bozicevic, Field & Francis LLP

(57) ABSTRACT

The present disclosure provides RNA-guided CRISPR-Cas effector proteins, nucleic acids encoding same, and compositions comprising same. The present disclosure provides ribonucleoprotein complexes comprising: an RNA-guided CRISPR-Cas effector protein of the present disclosure; and a guide RNA. The present disclosure provides methods of modifying a target nucleic acid, using an RNA-guided CRISPR-Cas effector protein of the present disclosure and a guide RNA.

20 Claims, 64 Drawing Sheets
Specification includes a Sequence Listing.

FIG. 2A

>Cas12L_1_257905508 (SEQ ID NO:102)

MASHKKTESNQIIKTFSFKIKNANGLSLDVLNDAITEYQNYYNICSDWIKDHLTMKISELYKYIPNEKKN

SGYALTLISDEWKDKPMYMMFKKGYPANNRDNAIYETLNTCNTEHYTGNILNFSDTYYRRFGYVASAISN

YVTKISKMSTGSRSKNISNDSDVDTIMEQVIYEMEHNGWTSVKDWENQMEYLESKTDSNPNFVYRMTTLY

EFYKSHIDEVNSKMETMSIDSLIKFGGCRRKDSKKSMYIMGGSNTPFDITQIGGNSLNIKFSKNLNVDVF

GRYDVIKDNTLLVDIINGHGASFVLKIINDEIYIDINVSVPFDKKIATTNKVVGIDVNIKHMLLATNILD

DGNVKGYVNIYKEVINDSDFKKVCNSTVMQYFTDFSKFVTFCPLEFDFLFSRVCNQKGIYNDNSAMEKSF

SDVLNKLKWNFIETGDNTKRIYIENVMKLRSQMKAYAIVKNAYYKQQSEYDFGKSEEFIQEHPFSNTDKG

IEILNKLDNISKKILGCRNNIIQYSYNLFEINGYDMVSLEKLTSSQFKKKPFPTVNSLLKYHKILGCTQE

EMEKKDIYSVIKKGYYDIIFDNDVVTDAKLSAKGELSKFKDDFFNLMIKSIHFADIKDYFITLSNNGTAG

VSLVPSYFTSQMDSIDHKIYFVQDNKSGKLKLANKHKVRSSQEKHINGLNADYNAARNIAYIMENTDCRN

MFMKQSRTDKSLYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2B

>Cas12L_2_196848753 (SEQ ID NO:103)
MAHKKNVGAEIVKTYSFKVKNTNGITMEKLMNAIDEFQSYYNLCSDWICKNLTTMTIGDLDQYIP
EKAKGNTYATVLLDEAWKNQPLYKIFGKKYSSNNRNNALYCALSSVIDMTKENVLGFSKTHYIR
NDYILNVISNYASKLSKLNTGVKSRAIKETSDEATIIEQVIYEMEHNKWESIEDWKNQIEYLNSKT
DYNPTYMERMKTLSAYYSTHKSEVDAKMQEMAVENLVKFGGCRRNNSKKSMFIMGSNTTNYT
ISYIGGNSFNINFANILNFDVYGRRDVVKNGEVLVDIMANHGDSIVLKIVNGELYADVPCSVTLNK
VESNFDKVVGIDVNMKHMLLSTSITDNGSSDFLNIYKEMSNNAEFMALCPEEDRKYYKDISKYV
TFAPLELDLLFSRISKQGKVKMEKVYSEILEALKWKFFANGDNKNRIYVESIQKIRQQIKALCVIK
NAYYEQQSAYDIDKTQEYIETHPFSLTEKGMSIKSKMDKICQTIIGCRNNIIDYAYSFFERNGYSII
GLEKLTSSQFEKTKSMPTCKSLLNFHKVLGHTLSELETLPINDVVKKGYYTFTTDNEGKITDASL
SEKGKVRKMKDDFFNQAIKAIHFADVKDYFATLSNNGQTGIFFVPSQFTSQMDSNTHNLYFENA
KNGGLKLAPKYKVRQTQEYHLNGLPADYNAARNIAYIGLDETMRNTFLKKANSNKSLYNQPIYD
TGIKKTAGVFSRMKKLKRYEII*

Repeat: ATTGTTGTAGACCTCTTTTTATAAGGATTGAACAAC (SEQ ID NO:3)
Spacer length: 30

FIG. 2C

>Cas12L_3_66741167 (SEQ ID NO:104)
MRISPHLFYIFFKKIWKCHFFVLSLYQLNQYIMASHEKTESNQIIKTFSFKIKNANGLSLDVLNDAI
TEYQNYYNICSDWIKDHLTMKIGELYKYIPDEKKNSGYALTLISDEWKDKPMYMMFKKGYPANN
RDNAIYETLNTCNTEHYTGNILNFSDTYYRRFGYVASAISNYVTKISKMSTGSRSKNISNDSDVD
TIMEQVIYEMEHNGWTSVKDWENQMEYLESKTDSNPNFVYRMTTLYEFYKSHIDEVNSKMET
MSIDSLIKFGGCRRKDSKKSMYIMGGSNTPFDITQIGGNSLNIKFSKNLNVDVFGRYDVIKDNTL
LVDIINGHGASFVLKIINGEIYIDINVSVPFDKKIATTNKVVGIDVNIKHMLLATNILDDGNVNGYVNI
YKEVINDSDFKKVCNSTVMKYFTDFSKFVTFCPLEFDFLFSRVCNQKGIYNDNSAMEKSFSDVL
NKLKWNFIETGDNTKRIYIENVMKLRSQMKAYAIVKNAYYKQQSEYDFGKSEEFIQEHPFSNTD
KGIEILNKLDNISKKILGCRNNIIQYSYNLFEINGYDMISLEKLTSSQFKKKPFPTVNSLLKYHKILG
CTQEEMEKKDIYSVIKKGYYDIIFDNDVVTDAKLSTKGELSKFKDDFFNLMIKSIHFADIKDYFITL
SNNGTAGVSLVPSYFTSQMDSIDHKIYFVQDNKSGKLKLANKHKVRSSQEKHINGLNADYNAA
RNIAYIMENTECRNMFMKQSRTDKSLYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2D

>Cas12L_4_67031163 (SEQ ID NO:105)
MRISPHLFYIFFKKIWKSHFFVLSLYQLNQYIMASHKKTESNQIIKTFSFKIKNANGLSLDVLNDAI
TEYQNYYNICSDWIKDHLTMKIGELYKYIPDEKKNSGYALTLISDEWKDKPMYMMFKKGYPANN
RDNAIYETLNTCNTEHYTGNILNFPDTYYRRFGYVASTISNYVTKISKMSTGSRSKNISNDSDVD
TIMEQVIYEMEHNGWTSVKDWENQMEYLESKTDSNPNFVYRMTTLYEFYKSHIDEVNSKMET
MSIDSLIKFGGCRRKDSKKSMYIMGGSNTPFDITQIGGNSLNIKFSKNLNVDVFGRYDVIKDNTL
LVDIINGHGASFVLKIINGEIYIDINVSVPFDKKIATTNKVVGIDVNIKHMLLATNILDDGNVNGYVNI
YKEVINDSDFKKVCNSTVMKYFTDFSKFVTFCPLEFDFLFSRVCNQKGIYNDNSAMEKSFSDVL
NKLKWNFIETGDNTKRIYIENVMKLRSQMKAYAIVKNAYYKQQSEYDFGKSEEFIQEHPFSNTD
KGIEILNKLDNISKKILGCRNNIIQYSYNLFEINGYDMISLEKLTSSQFKKNPFPTVNSLLKYHKILG
CTQEEMEKKDIYSVIKKGYYDIIFDNDVVTDAKLSTKGELSKFKDDFFNLMIKSIHFADIKDYFITL
SNNGTAGVSLVPSYFTSQMDSIDHKIYFVQDNKSGKLKLANKHKVRSSQEKHINGLNADYNAA
RNIAYIMENTECRNMFMKQSRTDKSLYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2E

>Cas12L_5_67793351 (SEQ ID NO:106)
MRISPHLFYIFFKKIWKCHIFVLSLYQLNQYIMASHKKTESNQIIKTFSFKIKNANGLSLDVLNDAIT
EYQNYYNICSDWIKDHLTMKIGELYKYIPDEKKNSGYALTLISDEWKDKPMYMMFKKGYPANNR
DNAIYETLNTCNTEHYTGNILNFSDTYYRRFGYVASTISNYVTKISKMSTGSRSKNISNDSDVDTI
MEQVIYEMEHNGWTSVKDWENQMEYLESKTDSNPNFVYRMTTLYEFYKSHIDEVNSKMETMS
IDSLIKFGGCRRKDSKKSMYIMGGSNTPFDITQIGGNSLNIKFSKNLNVDVFGRYDVIKDNTLLVD
IINGHGASFVLKIINGEIYIDINVSVPFDKKIATTNKVVGVDVNIKHMLLATNILDDGNVNGYVNIYK
EVINDSDFKKVCNSTVMKYFTDFSKFVTFCPLEFDFLFSRVCNQKGIYNDNSAMEKSFSDVLNK
LKWNFIETGDNTKRIYIENVMKLRSQMKAYAIVKNAYYKQQSEYDFGKSEEFIQEHPFSNTDKGI
EILNKLDNISKKILGCRNNIIQYSYNLFEINGYDMISLEKLTSSQFKKKPFPTVNSLLKYHKILGCTQ
EEMEKKDIYSVIKKGYYDIIFDNDVVTDAKLSTKGELSKFKDDFFNLMIKSIHFADIKDYFITLSNN
GTAGVSLVPSYFTSQMDSIDHKIYFVQDNKSGKLKLANKHKVRSSQEKHINGLNADYNAARNIA
YIMENTDCRNMFMKQSRTDKSLYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2F

>Cas12L_6_67912869_partial (SEQ ID NO:107)

QYVTFAPLELDLLFSRISKQGKVKMEKAYSEILEALKWKFFANGDNKNRIYVESIQKIRQQIKALC
VIKNAYYEQQSAYDIDKTQEYIETHPFSLTEKGMSIKSKMDKICQTIIGCRNNIIDYAYSFFERNGY
TIIGLEKLTSSQFEKTKSMPTCKSLLNFHKVLGHTLSELETLPINDVVKKGYYAFTTDNEGRITDA
SLSEKGKVRKMKDDFFNQAIKAIHFADVKDYFATLSNNGQTGIFFVPSQFTSQMDSNTHNLYFE
NAKNGGLKLASKSKVRKSQEYHLNGLPADYNAARNIAYIGLDEIMRNTFLKKANSNKSLYNQPI
YDTGIKKTAGVFSRMKKLKKYKVI*

Repeat: ATTGTTGTAGATACCTTTTTGTAAGGATTGAACAAC (SEQ ID NO:5)
Spacer length: 30

FIG. 2G

>Cas12L_7_68090316_partial (SEQ ID NO:108)

VLNDAITEYQNYYNICSDWIKDHLTMKIGELYKYIPDEKKNSGYALTLISDEWKDKPMYMMFKK
GYPANSRDNAIYEALNTCNTEHYTGNILNFSDTYYRRFGYVASAISNYVTKISKMSTGSRSKNIS
NDSDVDTIMEQVIYEMEHNGWTSVKDWENQMEYLESKTDSNPNFVYRMTTLYEFYKSHIDEV
NSKMETMSIDSLIKFGGCRRKDSKKSMYIMGGSNTPFDITQIGGNSLNIKFSKNLNVDVFGRYD
VIKDNTLLVDIINGHGASFVLKIINDEIYIDINVSVPFDKKIATTNKVVGIDVNIKHMLLATNILDDGN
VNGYVNIYKEVINDSDFKKVCNSTVMKYFTDFSKFVTFCPLEFDFLFSRVCNQKGIYNDNSAME
KSFSNVLNKLKWNFIETGDNTKRIYIENVMKLRSQMKAYAIVKNAYYKQQSEYDFGKSEEFIQE
HPFSNTDKGIEILHKLDNISKKILGCRNNIIQYSYNLFEINGYDMISLEKLTSSQFKKKPFPTVNSLL
KYHKILGCTQEEMEKKDIYSVIKKGYYDIIFDNDVVTDAKLSTKGELSKFKDDFFNLMIKSIHFADI
KDYFITLSNNGTAGVSLVPSYFTSQMDSIDHKIYFVQDNKSGKLKLANKHKVRSSQEKHINGLN
ADYNAARNIAYIMENTDCRNMFMKQSRTDKSLYNKPSYETFIKTQGSAVAKLKKEGFMKILDEA
SV*

Repeat: ATTGTTGTAACTCTTATTTTGTATGGAGTAAACAAC (SEQ ID NO:1)
Spacer length: 30

FIG. 2H

>Cas12L_8_68328292_partial (SEQ ID NO:109)

IFFKKIWKCHIFVLSLYQLNQYIMASHKKTESNQIIKTFSFKIKNANGLSLDVLNDAITEYQNYYNIC
SDWIKDHLTMKIGELYKYIPDEKKNSGYALTLISDEWKDKPMYMMFKKGYPANSRDNAIYEALN
TCNTEHYTGNILNFSDTYYRRFGYVASAISNYVTKISKMSTGSRSKNISNDSDVDTIMEQVIYEM
EHNGWTSVKDWENQMEYLESKTDSNPNFVYRMTTLYEFYKSHIDEVNSKMETMSIDSLIKFGG
CRRKDSKKSMYIMGGSNTPFDITQIDGNSLNIKFSKNLNVDVFGRYDVIKDNTLLVDIINGHGAS
FVLKIINDEIYIDINVSVPFDKKIATTNKVVGVDVNIKHMLLATNILDDGNVNGYVNIYKEVINDSDF
KKVCNSTVMKYFTDFSKFVTFCPLEFDFLFSRVCNQKGIYNDNSAMEKSFSDVLNKLKWNFIET
GDNTKRIYIENVMKLRSQMKAYAIVKNAYYKQQSEYDFGKSEEFIQEHPFSNTDKGIEILHKLDNI
SKKILGCRNNIIQYSYNLFEINGYDMISLEKLTSSQFKKKPFPTVNSLLKYHKILGCTQEEMEKKDI
YSVIKKGYYDIIFDNDVVTDAKLSTKGELSKFKDDFFNLMIKSIHFADIKDYFITLSNNGTAGVSLV
PSYFTSQMDSIDHKIYFVQDNKSGKLKLANKHKVRSSQEKHINGLNADYNAARNIAYIMENTEQ
GSAVAKLKKEGFVKILDEASV*

Repeat: ATTGTTGTAACTCTTATTTTGTATGGAGTAAACAAC (SEQ ID NO:1)
Spacer length: 30

FIG. 2I

>Cas12L_9_68454124 (SEQ ID NO:110)

MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANNRDNAIYETLNTCNTEHYTGNILNFSDTYYRR
FGYVASAISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNSLNIKFSKNLNVDVFGRYDVIKDNTLLVDIINGHGASFVLKIINGEIYIDINVSVPFDKKI
ATTNKVVGVDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKPFPTVNSLLKYHKILGCTQEEMEKKDIYSVIKKGYYDIIFDNDVVTDA
KLSAKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTECRNMFMKQSRTDKSLYNKPS
YETFIKTQGSAVSKLKKDGFVKILDEASV*

Repeat: ATTGTTGTAACTCTTATTTTGTATGGAGTAAACAAC (SEQ ID NO:1)
Spacer length: 30

FIG. 2J

>Cas12L_10_68605313 (SEQ ID NO:111)

MMKKMRTNPHLFYICFKKIWKCHFFALSLYQLNQYIMASHKKTESNQIIKTFSFKIKNANGLSLD
VLNDAITEYQNYYNICSDWIKDHLTMKIGELYKYIPDEKKNSGYALTLISDEWKDKPMYMMFKK
GYPANSRDNAIYEALNTCNTEHYTGNILNFSDTYYRRFGYVASTISNYVTKISKMSTGSRSKNIS
NDSDVDTIMEQVIYEMEHNGWTSVKDWENQMEYLESKTDSNPNFVYRMTTLYEFYKSHIDEV
NSKMETMSIDSLIKFGGCRRKDSKKSMYIMGGSNTPFDITQIGGNSLNIKFSKNLNVDVFGRYD
VIKDNTLLVDIINEHGASFVLKIINDEIYIDINVSVPFDKKIATTNKVVGVDVNIKHMLLATNILDDGN
VNGYVNIYKEVINDSDFKKVCNSTVMKYFTDFSKFVTFCPLEFDFLFSRVCNQKGIYNDNSAME
KSFSDVLNKLKWNFIETGDNTKRIYIENVMKLRSQMKAYAIVKNAYYKQQSEYDFGKSEEFIQE
HPFSNTDKGIEILNKLDNISKKILGCRNNIIQYSYNLFEINGYDMISLEKLTSSQFKKKPFPTVNSLL
KYHKILGCTQEEMEKKDIYSVIKKGYYDIIFDNDVVTDAKLSTKGELSKFKDDFFNLMIKSIHFADI
KDYFITLSNNGTAGVSLVPSYFTSQMDSIDHKIYFVQDNKSGKLKLANKHKVRSSQEKHINGLN
ADYNAARNIAYIMENTECRNMFMKQSRTDKSLYNKPSYETFIKTQGSAVAKLKKEGFVKILDEA
SA*

Repeat: ATTGTTGTAACTCTTATTTTGTATGGAGTAAACAAC (SEQ ID NO:1)
Spacer length: 30

FIG. 2K

>Cas12L_11_69266821_partial (SEQ ID NO:112)

NKSGKLKLANKHKVRSSQEKHINGLNADYNAARNIAYIMENTECRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2L

>Cas12L_12_69417229_partial (SEQ ID NO:112)

NKSGKLKLANKHKVRSSQEKHINGLNADYNAARNIAYIMENTECRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2M

>Cas12L_13_69733214 (SEQ ID NO:113)

MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANSRDNAIYEALNTCNTEHYTGNILNFSDTYYRR
FGYVASTISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNSLNIKFSKNLNVDVFGRYDVIKDNTLLVDIINGHGASFVLKIINGEIYIDINVSVPFDKKI
ATTNKVVGVDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFEKKPFPTVNSLLKYHKILGCTQEEMEKKDIYSVIKKGYYDIIFDNDVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTDCRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2N

>Cas12L_14_70235246_partial (SEQ ID NO:114)

VPFDKKIATTNKVVGVDVNIKHMLLATNILDDGNVNGYVNIYKEVINDSDFKKVCNSTVMKYFTD
FSKFVTFCPLEFDFLFSRVCNQKGIYNDNSAMEKSFSDVLNKLKWNFIETGDNTKRIYIENVMKL
RSQMKAYAIVKNAYYKQQSEYDFGKSEEFIQEHPFSNTDKGIEILNKLDNISKKILGCRNNIIQYS
YNLFEINGYDMISLEKLTSSQFKKKSFPTVDSLLKYHKILGCTQEEMEKKDIYSVIKKGYYDIIFDN
DVVTDAKLSTKGELSKFKDDFFNLMIKSIHFADIKDYFITLSNNGTAGVSLVPSYFTSQMDSIDHK
IYFVQDNKSGKLKLANKHKVRSSQEKHINGLNADYNAARNIAYIMENTDCRNMFMKQSRTDKS
LYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2O

>Cas12L_15_70724743 (SEQ ID NO:115)

MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANNRDNAIYETLNTCNTEHYTGNILNFSDTYYRR
FGYVASAISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNSLNIKFSKNLNVDVFGRYDVIKDNTLLVDIINGHGASFVLKIINGEIYIDINVSVPFDKKI
ATTNKVVGVDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKPFPTVNSLLKYHKILGCTQEEMEKKDIYSVIKKGYYDIIFDNDVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTECRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2P

>Cas12L_16_70731038 (SEQ ID NO:116)

MAHKKNIGAEIVKTYSFKVKNTNGITMEKLMNAIDEYQSYYNLCSDWICKNLTTMTIGDLDRYIP
EKAKDNIYATVLLDEVWKNQPLYKIFGKKYSSNNRINALYCTLSSVIDINKKNILGLSQTYYARNG
YILNVISNYASKLSKLNTGVKRHTIKETSDEATIVEQVIYEMEHNKWESIEDWKNQIEYLNSKTDY
NPTYMERMKTLSAYYSEHKSEVDAKMQEMAVENLVKFGGCRRNNSKKSMFIMGSSKTTYTIS
YIGDNCFNINFANILNFDVYGRRDVVKNGEVLVDIMANHGDSIVLKIVNGELYADVPCSTTLNKV
ESTFDKVAGIDVNMKHMLLSTSVTDNGNSDFVNIYKEMSNNAEFMALCPEEDRKYYKDISQYV
TFAPLELDLLFSRISKQGKVKMEKAYSEILEALKWKFFANGDNKNRIYVENIQKIRQQIKALCVIK
NAYYEQQSAYDIDKTQEYIEAHPFSLTEKGMSIKSKMDNICRTIIGCRNNIIDYAYSFFERNDYSII
GLEKLTSSQFEKTKSLPTCKSLLNFHKVLGHTLSELETLPINDVVKKGYYTFTTDNEGRITDASL
SEKGKVRKMKDDFFNQAIKAIHFADVKDYFATLSNNGQTGIFFVPSQFTSQMDSNTHTLYFENA
KNGGLKLASKYKVRKSQEYHLNGLPADYNAARNIAYIGLDEIMRNTFLKKANSNKSLYNQPIYDT
GIKKTAGVFSRMKKLKKYKVI*

Repeat: TATTGTTGTAGATACCTTTTTGTAAGGATTAAACAAC (SEQ ID NO:7)
Spacer length: 30

FIG. 2Q

>Cas12L_17_70959391 (SEQ ID NO:117)
MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANSRDNAIYEALNTCNTEHYTGNILNFSDTYYRR
FGYVASTISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNSLNIKFSKNLNVDVFGRYDVIKDNTLLVDIINGHGASFVLKIINGEIYIDINVSVPFDKKI
ATTNKVVGVDVNIKHMLLATNILDDGNVNGYVNIYKEVINDSDFKKVCNSTVMQYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKPFPTVNSLLKYHKILGCTQEEMEKKDIYSVIKKGYYDIIFDNDVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTECRNMFMKQSRTDKSLYNKPS
YETFIKTQGSAVAKLKKEGFVKIIDEASV*

FIG. 2R

>Cas12L_18_71078086 (SEQ ID NO:118)
MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANNRDNAIYEALNTCNTEHYTGNILNFSDTYYRR
FGYVASTISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNSLNIKFSKNLNVDVFGRYDVIKDNTLLVDIINGHGASFVLKIINGEIYIDINVSVPFDKKI
ATTNKVVGVDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKPFPTVNSLLKYHKILGCTQEEMEKKDIYSVIKKGYYDIIFDNGVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTECRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2S

>Cas12L_19_71193509_partial (SEQ ID NO:119)
EKKNSGYALTLISDEWKDKPMYMMFKKGYPANNRDNAIYETLNTCNTEHYTGNILNFSDTYYR
RFGYVASAISNYVTKISKMSTGSRSKNISNDSDVDTIMEQVIYEMEHNGWTSVKDWENQMEYL
ESKTDSNPNFVYRMTTLYEFYKSHIDEVNSKMETMSIDSLIKFGGCRRKDSKKSMYIMGGSNTP
FDITQIGGNSLNIKFSKNLNVDVFGRYDVIKDNTLLVDIINEHGASFVLKIINDEIYIDINVSVPFDKK
IATTNKVVGVDVNIKHMLLATNILDDGNVNGYVNIYKEVINDSDFKKVCNSTVMKYFTDFSKFVT
FCPLEFDFLFSRVCNQKGIYNDNSAMEKSFSDVLNKLKWNFIETGDNTKRIYIENVMKLRSQMK
AYAIVKNAYYKQQSEYDFGKSEEFIQEHPFSNTDKGIEILNKLDNISKKILGCRNNIIQYSYNLFEI
NGYDMISLEKLTSSQFKKKPFPTVNSLLKYHKILGCTQEEMEKKDIYSVIKKGYYDIIFDNDVVTD
AKLSTKGELSKFKDDFFNLMIKSIHFADIKDYFITLSNNGTVGVSLVPSYFTSQMDSIDHKIYFVQ
DNKSGKLKLANKHKVRSSQEKHINGLNADYNAARNIAYIMENNECRNMFMKQSRTDKSLYNKP
SYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2T

>Cas12L_20_71210958_partial (SEQ ID NO:120)
DAKMQEMAVENLVKFGGCRRNNSKKSMFIMGSSKTTYTISYIGDNCFNINFANILNFDVYGRRD
VVKNGEVLVDIMANHGDSIVLKIVNGELYADVPCSTTLNKVESTFDKVAGIDVNMKHMLLSTSVT
DNGNSDFVNIYKEISNNAEFMALCPEEDRKYYKDISQYVTFAPLELDLLFSRISKQGKVKMEKAY
SEILETLKWKFFANGDNKNRIYVESIQKIRQQIKALCVIKNAYYEQQSAYDIDKTQEYIEAHPFSLT
EKGMSIKSKMDNICRTIIGCRNNIIDYAYSFFERNDYSIIGLEKLTSSQFEKTKSLPTCKSLLNFHK
VLGHTLSELETLPINDVVKKGYYTFTTDNEGRITDASLSEKGKVRKMKDDFFNQAIKAIHFADVK
DYFATLSNNGQTGIFFVPSQFTSQMDSNTHTLYFENAKNGGLKLASKYQVRQTQEYHLNGLPA
DYNAARNIAYIGLDETMRNTFLKKANSNKSLYNQPIYDTGIKKTAGVFSRMKKLKRYEII*

Repeat: AATGTTGTAGATGCCTTTTTATAAGGATTAAACAACTTG (SEQ ID NO:9)
Spacer length: 27

FIG. 2U

>Cas12L_21_71317321_partial (SEQ ID NO:121)

DVDTIMEQVIYEMEHNGWTSVKDWENQMEYLESKTDSNPNFVYRMTTLYEFYKSHIDEVNSK
METMSIDSLIKFGGCRRKDSKKSMYIMGGSNTPFDITQIGGNSLNIKFSKNLNVDVFGRYDVIKD
NTLLVDIINGHGASFVLKIINGEIYIDINVSVPFDKKIATTNKVVGVDVNIKHMLLATNILDDGNVNG
YVNIYKEVINDSDFKKVCNSTVMKYFTDFSKFVTFCPLEFDFLFSRVCNQKGIYNDNSAMEKSF
SDVLNKLKWNFIETGDNTKRIYIENVMKLRSQMKAYAIVKNAYYKQQSEYDFGKSEEFIQEHPF
SNTDKGIEILNKLDNISKKILGCRNNIIQYSYNLFEINGYDMISLEKLTSSQFKKKPFPTVNSLLKYH
KILGCTQEEMEKKDIYSVIKKGYYDIIFDNDVVTDAKLSTKGELSKFKDDFFNLMIKSIHFADIKDY
FITLSNNGTAGVSLVPSYFTSQMDSIDHKIYFVQDNKSGKLKLANKHKVRSSQEKHINGLNADY
NAARNIAYIMENTECRNMFMKQSRTDKSLYNKPSYETFIKTQGSAVAKLKKEGFVKIIDEASV*

Repeat: ATTGTTGTAACTCTTATTTTGTATGGAGTAAACAAC (SEQ ID NO:1)
Spacer length: 30

FIG. 2V

>Cas12L_22_71456687 (SEQ ID NO:122)

MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANSRDNAIYEALNTCNTEHYTGNILNFSDTYYRR
FGYVASAISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNSLNIKFSKNLNVDVFGRYDVIKDNTLLVDIINEHGASFVLKIINDEIYIDINVSVPFDKKI
ATTNKVVGVDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFEKKPFPTVNSLLKYHKILGCTQEEMEKKDIYSVIKKGYYDIIFDNDVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTECRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2W

>Cas12L_23_71708971 (SEQ ID NO:123)

DVDTIMEQVIYEMEHNGWTSVKDWENQMEYLESKTDSNPNFVYRMTTLYEFYKSHIDEVNSK
METMSIDSLIKFGGCRRKDSKKSMYIMGGSNTPFDITQIGGNSLNIKFSKNLNVDVFGRYDVIKD
NTLLVDIINEHGASFVLKIINDEIYIDINVSVPFDKKIATTNKVVGVDVNIKHMLLATNILDDGNVNG
YVNIYKEVINDSDFKKVCNSTVMKYFTDFSKFVTFCPLEFDFLFSRVCNQKGIYNDNSAMEKSF
SDVLNKLKWNFIETGDNTKRIYIENVMKLRSQMKAYAIVKNAYYKQQSEYDFGKSEEFIQEHPF
SNTDKGIEILNKLDNISKKILGCRNNIIQYSYNLFEINGYDMISLEKLTSSQFKKKPFPTVDSLLKYH
KILGCTQEEMEKKDIYSVIKKGYYDIIFDNDVVTDAKLSTKGELSKFKDDFFNLMIKSIHFADIKDY
FITLSNNGTAGVSLVPSYFTSQMDSIDHKIYFVQDNKSGKLKLANKHKVRSSQEKHINGLNADY
NAARNIAYIMENTDCRNMFMKQSRTDKSLYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2X

>Cas12L_24_46035167_partial (SEQ ID NO:124)

FVLSLYQLNQYIMASHKKTESNQIIKTFSFKIKNANGLSLDVLNDAITEYQNYYNICSDWIKDHLT
MKIGELYKYIPDEKKNSGYALTLISDEWKDKPMYMMFKKGYPANNRDNAIYETLNTCNTEHYTG
NILNFSDTYYRRFGYVASTISNYVTKISKMSTGSRSKNISNDSDVDTIMEQVIYEMEHNGWTSVK
DWENQMEYLESKTDSNPNFVYRMTTLYEFYKSHIDEVNSKMETMSIDSLIKFGGCRRKDSKKS
MYIMGGSNTPFDITQIGGNSLNIKFSKNLNVDVFGRYDVIKDNTLLVDIINGHGASFVLKIINGEIYI
DINVSVPFDKKIATTNKVVGVDVNIKHMLLATNILDDGNVNGYVNIYKEVINDSDFKKVCNSTVM
KYFTDFSKFVTFCPLEFDFLFSRVCNQKGIYNDNSAMEKSFSDVLNKLKWNFIETGDNTKRIYIE
NVMKLRSQMKAYAIVKNAYYKQQSEYDFGKSEEFIQEHPFSNTDKGIEILNKLDNISKKILGCRN
NIIQYSYNLFEINGYDMISLEKLTSSQFKKKSFPTVDSLLKYHKILGCTQEEMEKKDIYSVIKKGYY
DIIFDNDVVTDAKLSTKGELSKFKDDFFNLMIKSIHFADIKDYFITLSNNGTAGVSLVPSYFTSQM
DSIDHKIYFVQDNKSGKLKLANKHKVRSSQEKHINGLNADYNAARNIAYIMENNECRNMFMKQS
RTDKSLYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2Y

>Cas12L_25_46784254_partial (SEQ ID NO:125)

GSRSKNISNDSDVDTIMEQVIYEMEHNGWTSVKDWENQMEYLESKTDSNPNFVYRMTTLYEF
YKSHIDEVNSKMETMSIDSLIKFGGCRRKDSKKSMYIMGGSNTPFDITQIGGNSLNIKFSKNLNV
DVFGRYDVIKDNTLLVDIINGHGASFVLKIINGEIYIDINVSVPFDKKIATTNKVVGVDVNIKHMLLA
TNILDDGNVNGYVNIYKEVINDSDFKKVCNSTVMKYFTDFSKFVTFCPLEFDFLFSRVCNQKGIY
NDNSAMEKSFSDVLNKLKWNFIETGDNTKRIYIENVMKLRSQMKAYAIVKNAYYKQQSEYDFG
KSEEFIQEHPFSNTDKGIEILNKLDNISKKILGCRNNIIQYSYNLFEINGYDMISLEKLTSSQFKKKS
FPTVDSLLKYHKILGCTQEEMEKKDIYSVIKKGYYDIIFDNDVVTDAKLSTKGELSKFKDDFFNLM
IKSIHFADIKDYFITLSNNGTAGVSLVPSYFTSQMDSIDHKIYFVQDNKSGKLKLANKHKVRSSQE
KHINGLNADYNAARNIAYIMENNECRNMFMKQSRTDKSLYNKPSYETFIKTQGSAVAKLKKEGF
VKILDEASV*

Repeat: ATTGTTGTAACTCTTATTTTGTATGGAGTAAACAAC (SEQ ID NO:1)
Spacer length: 30

FIG. 2Z

>Cas12L_26_46464451 (SEQ ID NO:126)

MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANNRDNAIYETLNTCNTEHYTGNILNFSDTYYRR
FGYVASTISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIDGNSLNIKFSKNLNVDVFGRYDVIKDNTLLVDIINGHGASFVLKIINGEIYIDINVSVPFDKKI
ATTNKVVGVDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKPFPTVNSLLKYHKILGCTQEEMEKKDIYSVIKKGYYDIIFDNGVVIDA
KLSAKGELSKFKDDFFNLMIKSIHFADIKDYFITLSNNGTAGVSLVDLFCPR*

Repeat: ATTGTTGTAACTCTTATTTTGTATGGAGTAAACAAC (SEQ ID NO:1)
Spacer length: 30

FIG. 2AA

>Cas12L_27_254489164 (SEQ ID NO:102)

MASHKKTESNQIIKTFSFKIKNANGLSLDVLNDAITEYQNYYNICSDWIKDHLTMKISELYKYIPNE
KKNSGYALTLISDEWKDKPMYMMFKKGYPANNRDNAIYETLNTCNTEHYTGNILNFSDTYYRR
FGYVASAISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNSLNIKFSKNLNVDVFGRYDVIKDNTLLVDIINGHGASFVLKIINDEIYIDINVSVPFDKKI
ATTNKVVGIDVNIKHMLLATNILDDGNVKGYVNIYKEVINDSDFKKVCNSTVMQYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMVSLEKLTSSQFKKKPFPTVNSLLKYHKILGCTQEEMEKKDIYSVIKKGYYDIIFDNDVVTD
AKLSAKGELSKFKDDFFNLMIKSIHFADIKDYFITLSNNGTAGVSLVPSYFTSQMDSIDHKIYFVQ
DNKSGKLKLANKHKVRSSQEKHINGLNADYNAARNIAYIMENTDCRNMFMKQSRTDKSLYNKP
SYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2BB

>Cas12L_28_255238293 (SEQ ID NO:127)

MAHKKNLEGENLQVKTICLKANLSKEEVKEKWLPVINEYNVYYNRMSDYICSLLGTNITIGEFAE
QLSIEKRKNGYFTICQDDKFKNESLYKIFHKSFPINHGTNIINNIISEKNIDQYDGNTLGFRPTMYR
LRGYVDSVIGNYRTTIRTIKPSVKRHKISVDSSFDEKMEQCIYEIQKGNLKTVSEWNNKIDYLLSK
SDMNPLTIDRFNLLRDFYVDNETEVNEKSNNSSIEQLVKFGGCHRKGDNMTLSLTEANFSIEEID
DSYGYLLTLHTDSGDYKIPLMGSKMLKKGDKCLIDFVNCKKGKSLTAKIDNDYNLYFHFVVYSN
FEKIEDDNINNVVGVDVNSKHMLLMTNVIDDNIDGYVNIYKALVNDDEFKSLVTKSEYDDYVTMS
KYVTFCPIELKYLYARYCVQKDYPISNKDVAIEQCISRVIDKLCKETLDSRANNYLCMVRRIRHYY
KSYYVLKMTYYDKMSEYDTNMEYNDISTTSKETMDQRRFENSFRETDCAKEILSKLDKIGNDIL
GCRNNILTYAYKLFEELGYDTIALENLESSQFDKMKSLPSCQSMLKYHKLEGKTMEEVMSNTSV
KSLIENEYYDFSLNDNKTVENITYTKNGLMKKGFDEFFNLFMKIIHFADIKDKFLQLYNNGSVKVI
LVPSYFTSQMDSSNHSIYMEKSKNDKLVFASKHKVRKTQETHLNGLNADYNAACNIAYIAKDIK
WREKFCKKTSNNGYSTPFYDCATKNQIEMVKRIKQLNAIKMLA*

Repeat: ATTGTTGAAATAGTACTTTATAGTCTATATACAAC (SEQ ID NO:11)
Spacer length: 30

FIG. 2CC

>Cas12L_29_72167294 (SEQ ID NO:128)

MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANSRDNAIYEALNTCNTEHYTGNILNFSDTYYRR
FGYVASTISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNSLNIKFSKNLNVDVFGRYDVIKDNTLLVDIINGHGASFVLKIINDEIYIDINVSVPFDKKI
ATTNKVVGVDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKSFPTVDSLLKYHKILGCTQEEMEKKDIYSVIKKGYYDIIFDNDVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTECRNMFMKQSRTDKSLYNKPS
YETFIKTQGSAVAKLKKEGFVKILDEASV*

Repeat: TATTGTTGTAACTCTTATTTTGTATGGAGTAAACAAC (SEQ ID NO:13)
Spacer length: 29

FIG. 2DD

>Cas12L_30_72369269 (SEQ ID NO:129)

MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANSRDNAIYEALNTCNTEHYTGNILNFSDTYYRR
FGYVASAISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIDGNSLNIKFSKNLNVDVFGRYDVIKDNTLLVDIINGHGASFVLKIINDEIYIDINVSVPFDKKI
ATTNKVVGIDVNIKHMLLATNILDDGNVNGYVNIYKEVINDSDFKKVCNSTVMKYFTDFSKFVTF
CPLEFDFLFSRVCNQKGIYNDNSAMEKSFSNVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKPFPTVNSLLKYHKILGCTQEEMEKKDIYSVIKKGYYDIIFDNDVVTDA
KLSAKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTDCRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2EE

>Cas12L_31_72503976 (SEQ ID NO:130)

MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANNRDNAIYETLNTCNTEHYTGNILNFSDTYYRR
FGYVASTISNYVTKISKMSTRSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNSLNIKFSKNLNVDVFGRYDVIKDNTLLVDIINGHGASFVLKIINGEIYIDINVSVPFDKKI
ATTNKVVGIDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKPFPTVNSLLKYHKILGCTQEEMEKKDIYSVIKKGYYDIIFDNDVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTDCRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2FF

>Cas12L_32_72547654_partial (SEQ ID NO:131)
NMFMKQSRTDKSLYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2GG

>Cas12L_33_72907394 (SEQ ID NO:132)

MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANNRDNAIYETLNTCNTEHYTGNILNFSDTYYRR
FGYVASTISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNFLNIKFSKNLNVDVFGRYDVIKDNTLLVDIINEHGASFVLKIINDEIYIDINVSVPFDKKI
ATTNKVVGVDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILHKLDNISKKILGCRNNIIQYSYNLFEIN
GYDMISLEKLTSSQFKKKPFPTVNSLLKYHKILGCTQEEMEKKDIYSVIKKGYYDIIFDNDVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTECRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2HH

>Cas12L_34_73124743_partial (SEQ ID NO:133)

KKILGCRNNIIQYSYNLFEINGYDMISLEKLTSSQFKKKPFPTVNSLLKYHKILGCTQEEMEKKDIY
SVIKKGYYDIIFDNDVVTDAKLSTKGELSKFKDDFFNLMIKSIHFADIKDYFITLSNNGTAGVSLVP
SYFTSQMDSIDHKIYFVQDNKSGKLKLANKHKVRSSQEKHINGLNADYNAARNIAYIMENTECR
NMFMKQSRTDKSLYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2II

>Cas12L_35_73503649_partial (SEQ ID NO:134)

NAYYKQQSEYDFGKSEEFIQEHPFSNTDKGIEILHKLDNISKKILGCRNNIIQYSYNLFEINGYDMI
SLEKLTSSQFEKKPFPTVNSLLKYHKILGCTQEEMEKKDIYSVIKKGYYDIIFDNDVVTDAKLSTK
GELSKFKDDFFNLMIKSIHFADIKDYFITLSNNGTVGVSLVPSTV*

Repeat: ATTGTTGTAACTCTTATTTTGTATGGAGTAAACAAC (SEQ ID NO:1)
Spacer length: 30

FIG. 2JJ

>Cas12L_36_73503649_partial (SEQ ID NO:135)

MANKHKVRSSQEKHINGLNADYNAARNIAYIIENTECRNMFMKQSRTDKSLYNKPSYETFIKTQ
GSTVAKLKKEGFVKILDEASV*

FIG. 2KK

>Cas12L_37_73472625 (SEQ ID NO:136)

MAHKKQKEENEIIKTISLKVKDYAGYPIVEAMREYTKYYNKISQWINSNLLTIKIGELSAFMPDEC
KTHNYYTYMMSPDWVNEPLYKMFMKGFHAQHCDNILFNVVKTLNIDEYAGNSLGLSASCFRR
SGYFQNVVSNYKSKFANPHISIRRKNLSDLPTEDELVEQCIYEIQNGLSSKTKWEEQIEYLKERD
DSKQIYLTRLNTLFMYYKANKDFVDEQIQIKSVESLANFGGCVRKDDKLSMNLVFSSNSPYKVV
LNEKRNGYILSYSNNFSIELYGNRMGLLNGVEVFNVGDKHSNNITFKMDNDELFVNIPVSVNFV
KKANETNKVVGVDVNLKHSIFATNIIDDGKLDGFVNIYRELLNDVDFVKSCPNELLNFILDVEKYA
FFMPLELGLLSSRVMNQCGYSTIGKYEKLFTTEEHFFRVLRQLEKRFQESGENQKRIYIENVIKM
RAQVKAYFTLKYAYNKANKDYDLKMGFVDESTANKETMDQRRFENQFVNTYTAKEILGKMRRI
ANVITSCRNNIICYMYKIFENNGYGVVALEKLQSSQMKKEKRIPSLLSLLKKQKVEGYTINELKDK
SVFKFIERGYYTFDFDDDNKITGVQFSDAGEVVNMETELHNLALKTIHFADAKDYFVTLSNNGS
VSVALVPSQFTSQMDSTKHVLYAKKNNKGKLGIVSEHEVRPKQECHINGLNGDYNAACNIAYIF
ENDEWRNAFMKMNPNEYGKALFETNMESTSTIINTLKKINPDNIISFDEYEKTKKVAA*

Repeat: ATTGTTGTAACATCTATTTTGTAAGGTGTAAACAAC (SEQ ID NO:15)
Spacer length: 30

FIG. 2LL

>Cas12L_38_73764039_partial (SEQ ID NO:137)

YPANSRDNAIYEALNTCNTEHYTGNILNFSDTYYRRFGYVASAISNYVTKISKMSTGSRSKNISN
DSDVDTIMEQVIYEMEHNGWTSVKDWENQMEYLESKTDSNPNFVYRMTTLYEFYKSHIDEVN
SKMETMSIDSLIKFGGCRRKDSKKSMYIMGGSNTPFDITQIGGNSLNIKFSKNLNVDVFGRYDVI
KDNTLLVDIINGHGASFVLKIINGEIYIDINVSVPFDKKIATTNKVVGVDVNIKHMLLATNILDDGNV
KGYVNIYKEVINDSDFKKVCNSTVMKYFTDFSKFVTFCPLEFDFLFSRVCNQKGIYNDNSAMEK
SFSDVLNKLKWNFIETGDNTKRIYIENVMKLRSQMKAYAIVKNAYYKQQSEYDFGKSEEFIQEH
PFSNTDKGIEILNKLDNISKKILGCRNNIIQYSYNLFEINGYDMISLEKLTSSQFKKKSFPTVNSLLK
YHKILGCTQEEMEKKDIYSVIKKGYYDIIFDNDVVTDAKLSTKGELSKFKDDFFNLMIKSIHFADIK
DYFITLSNNGTAGVSLVPSYFTSQMDSIDHKIYFVQDNKSGKLKLANKHKVRSSQEKHINGLNA
DYNAARNIAYIMENTECRNMFMKQSRTDKSLYNKPSYETFIKTQGSAVAKLKKEGFVKILDEAS
V*

Repeat: ATTGTTGTAACTCTTATTTTGTATGGAGTAAACAAC (SEQ ID NO:1)
Spacer length: 30

FIG. 2MM

>Cas12L_40_74037305 (SEQ ID NO:138)

MMKKMRISPHLFYIFFKKIWKCHFFVLSLYQLNQYIMASHKKTESNQIIKTFSFKIKNANGLSLDV
LNDAITEYQNYYNICSDWIKDHLTMKIGELYKYIPDEKKNSGYALTLISDEWKDKPMYMMFKKG
YPANNRDNAIYETLNTCNTEHYTGNILNFSDTYYRRFGYVASAISNYVTKISKMSTGSRSKNISN
DSDVDTIMEQVIYEMEHNGWTSVKDWENQMEYLESKTDSNPNFVYRMTTLYEFYKSHIDEVN
SKMETMSIDSLIKFGGCRRKDSKKSMYIMGGSNTPFDITQIGGNSLNIKFSKNLNVDVFGRYDVI
KDNTLLVDIINEHGASFVLKIINDEIYIDINVSVPFDKKIATTNKVVGVDVNIKHMLLATNILDDGNV
NGYVNIYKEVINDSDFKKVCNSTVMKYFTDFSKFVTFCPLEFDFLFSRVCNQKGIYNDNSAMEK
SFSNVLNKLKWNFIETGDNTKRIYIENVMKLRSQMKAYAIVKNAYYKQQSEYDFGKSEEFIQEH
PFSNTDKGIEILNKLDNISKKILGCRNNIIQYSYNLFEINGYDMISLEKLTSSQFKKKPFPTVNSLLK
YHKILGCTQEEMEKKDIYSVIKKGYYDIIFDNDVVTDAKLSTKGELSKFKDDFFNLMIKSIHFADIK
DYFITLSNNGTAGVSLVPSYFTSQMDSIDHKIYFVQDNKSGKLKLANKHKVRSSQEKHINGLNA
DYNAARNIAYIMENTDCRNMFMKQSRTDKSLYNKPSYETFIKTQGSAVAKLKKEGFVKILDEAS
V*

Repeat: ATTGTTGTAACTCTTATTTTGTATGGAGTAAACAAC (SEQ ID NO:1)
Spacer length: 30

FIG. 2NN

>Cas12L_41_74408273_partial (SEQ ID NO:139)

WTDEDYCKFFAKYGMSEECQKWMCRDVYDYRIKDFVDYEKFDDSKIEEEQEEYSEIPVESED
SSPSTSETLPKSIYDLDLRRLDPNPEIPEDEKYNEEDLKNAYPDKYERFEKDGEDYSIFFKKIW
KCHFFVLSLYQLNQYIMASHKKTESNQIIKTFSFKIKNANGLSLDVLNDAITEYQNYYNICSDWIK
DHLTMKIGELYKYIPDEKKNSGYALTLISDEWKDKPMYMMFKKGYPANNRDNAIYEALNTCNTE
HYTGNILNFSDTYYRRFGYVASTISNYVTKISKMSTGSRSKNISNDSDVDTIMEQVIYEMEHNG
WTSVKDWENQMEYLESKTDSNPNFVYRMTTLYEFYKSHIDEVNSKMETMSIDSLIKFGGCRRK
DSKKSMYIMGGSNTPFDITQIDGNSLNIKFSKNLNVDVFGRYDVIKDNTLLVDIINGHGASFVLKII
NDEIYIDINVSVPFDKKIATTNKVVGVDVNIKHMLLATNILDDGNVNGYVNIYKEVINDSDFKKVC
NSTVMKYFTDFSKFVTFCPLEFDFLFSRVCNQKGIYNDNSAMEKSFSDVLNKLKWNFIETGDNT
KRIYIENVMKLRSQMKAYAIVKNAYYKQQSEYDFGKSEEFIQEHPFSNTDKGIEILNKLDNISKKIL
GCRNNIIQYSYNLFEINGYDMISLEKLTSSQFEKKPFPTVNSLLKYHKILGCTQEEMEKKDIYSVI
KKGYYDIIFDNGVVTDAKLSTKGELSKFKDDFFNLMIKSIHFADIKDYFITLSNNGTAGVSLVPSY
FTSQMDSIDHKIYFVQDNKSGKLKLANKHKVRSSQEKHINGLNADYNAARNIAYIMENTECRNM
FMKQSRTDKSLYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2OO

>Cas12L_42_75186079_partial (SEQ ID NO:140)

YDMISLEKLTSSQFKKKPFPTVNSLLKYHKILGCTEEEMEKKDIYSVIKKGYYDIIFDNDVVTDAKL
STKGELSKFKDDFFNLMIKSIHFADIKDYFITLSNNGTAGVSLVPSYFTSQMDSIDHKIYFVQDNK
SGKLKLANKHKVRSSQEKHINGLNADYNAARNIAYIMENTECRNMFMKQSRTDKSLYNKPSYE
TFIKTQGSAVAKLKKEGFVKILDEASA*

Repeat: AATTGTTGTAACTCTTATTTTGTATGGAGTAAACAAC (SEQ ID NO:17)
Spacer length: 29

FIG. 2PP

>Cas12L_43_75257103_partial (SEQ ID NO:141)

MKIGELYKYIPDEKKNSGYALTLISDEWKDKPMYMMFKKGYPANNRDNAIYETLNTCNTEHYTG
NILNFSDTYYRRFGYVASAISNYVTKISKMSTGSRSKNISNDSDVDTIMEQVIYEMEHNGWTSVK
DWENQMEYLESKTDSNPNFVYRMTTLYEFYKSHIDEVNSKMETMSIDSLIKFGGCRRKDSKKS
MYIMGGSNTPFDITQIDGNSLNIKFSKNLNVDVFGRYDVIKDNTLLVDIINGHGASFVLKIINGEIYI
DINVSVPFDKKIATTNKVVGVDVNIKHMLLATNILDDGNVNGYVNIYKEVINDSDFKKVCNSTVM
KYFTDFSKFVTFCPLEFDFLFSRVCNQKGIYNDNSAMEKSFSDVLNKLKWNFIETGDNTKRIYIE
NVMKLRSQMKAYAIVKNAYYKQQSEYDFGKSEEFIQEYDFFGETYQFSI*

Repeat: ATTGTTGTAACTCTTATTTTGTATGGAGTAAACAAC (SEQ ID NO:1)
Spacer length: 30

FIG. 2QQ

>Cas12L_44_75257103_partial (SEQ ID NO:142)

MISLEKLTSSQFKKKPFPTVNSLLKYHKILGCTQEEMEKKKGYYDIIFDNDVVTDAKLSTKGELS
KFKDDFFNLMIKSIHFADIKDYFITLSNNGTAGVSLVPSYFTSQMDRANKHKVRSSQEKHINGLN
ADYNAARNIAYIMENTECRNMFMKQSRTDKSLYNKPSYETFIKTQGSAVAKLKKEGFVKILDEA
SV*

Repeat: ATTGTTGTAACTCTTATTTTGTATGGAGTAAACAAC (SEQ ID NO:1)
Spacer length: 30

FIG. 2RR

>Cas12L_45_75616607_partial (SEQ ID NO:143)

YIMASHKKTESNQIIKTFSFKIKNANGLSLDVLNDAITEYQNYYNICSDWIKDHLTMKIGELYKYIP
DEKKNSGYALTLISDEWKDKPMYMMFKKGYPANSRDNAIYETLNTCNTEHYTGNILNFSDTYY
RRFGYVASTISNYVTKISKMSTGSRSKNISNDSDVDTIMEQVIYEMEHNGWTSVKDWENQMEY
LESKTDSNPNFVYRMTTLYEFYKSHIDEVNSKMETMSIDSLIKFGGCRRKDSKKSMYIMGGSNT
PFDITQIGGNSLNIKFSKNLNVDVFGRYDVIKDNTLLVDIINGHGASFVLKIINGEIYIDINVSVPFDK
KIATTNKVVGVDVNIKHMLLATNILDDGNVNGYVNIYKEVINDSDFKKVCNSTVMKYFTDFSKFV
TFCPLEFDFLFSRVCNQKGIYNDNSAMEKSFSNVLNKLKWNFIETGDNTKRIYIENVMKLRSQM
KAYAIVKNAYYKQQSEYDFGKSEEFIQEHPFSNTDKGIEILNKLDNISKKILGCRNNIIQYSYNLFE
INGYDMISLEKLTSSQFEKKPFPTVNSLLKYHKILGCTQEEMEKKDIYSVIKKGYYDIIFDNGVVT
DAKLSTKGELSKFKDDFFNLMIKSIHFADIKDYFITLSNNGTAGVSLVPSYFTSQMDSIDHKIYFV
QDNKSGKLKLANKHKVRSSQEKHINGLNADYNAARNIAYIMENTECRNMFMKQSRTDKSLYNK
PSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2SS

>Cas12L_46_75784289_partial (SEQ ID NO:144)

SLNIKFSKNLNVDVFGRYDVIKDNTLLVDIINGHGASFVLKIINGEIYIDINVSVPFDKKIATTNKVV
GVDVNIKHMLLATNILDDGNVNGYVNIYKEVINDSDFKKVCNSTVMKYFTDFSKFVTFCPLEFDF
LFSRVCNQKGIYNDNSAMEKSFSDVLNKLKWNFIETGDNTKRIYIENVMKLRSQMKAYAIVKNA
YYKQQSEYDFGKSEEFIQEHPFSNTDKGIEILNKLDNISKKILGCRNNIIQYSYNLFEINGYDMISL
EKLTSSQFKKKPFPTVNSLLKYHKILGCTQEEMEKKDIYSVIKKGYYDIIFDNGVVIDAKLSAKGE
LSKFKDDFFNLMIKSIHFADIKDYFITLSNNGTAGVSLVPSYFTSQMDSIDHKIYFVQDNKSGKLK
LANKHKVRSSQEKHINGLNADYNAARNIAYIMENTECRNMFMKQSRTDKSLYNKPSYETFIKTQ
GSAVAKLKKEGFVKILDEASV*

Repeat: ATTGTTGTAACTCTTATTTTGTATGGAGTAAACAAC (SEQ ID NO:1)
Spacer length: 30

FIG. 2TT

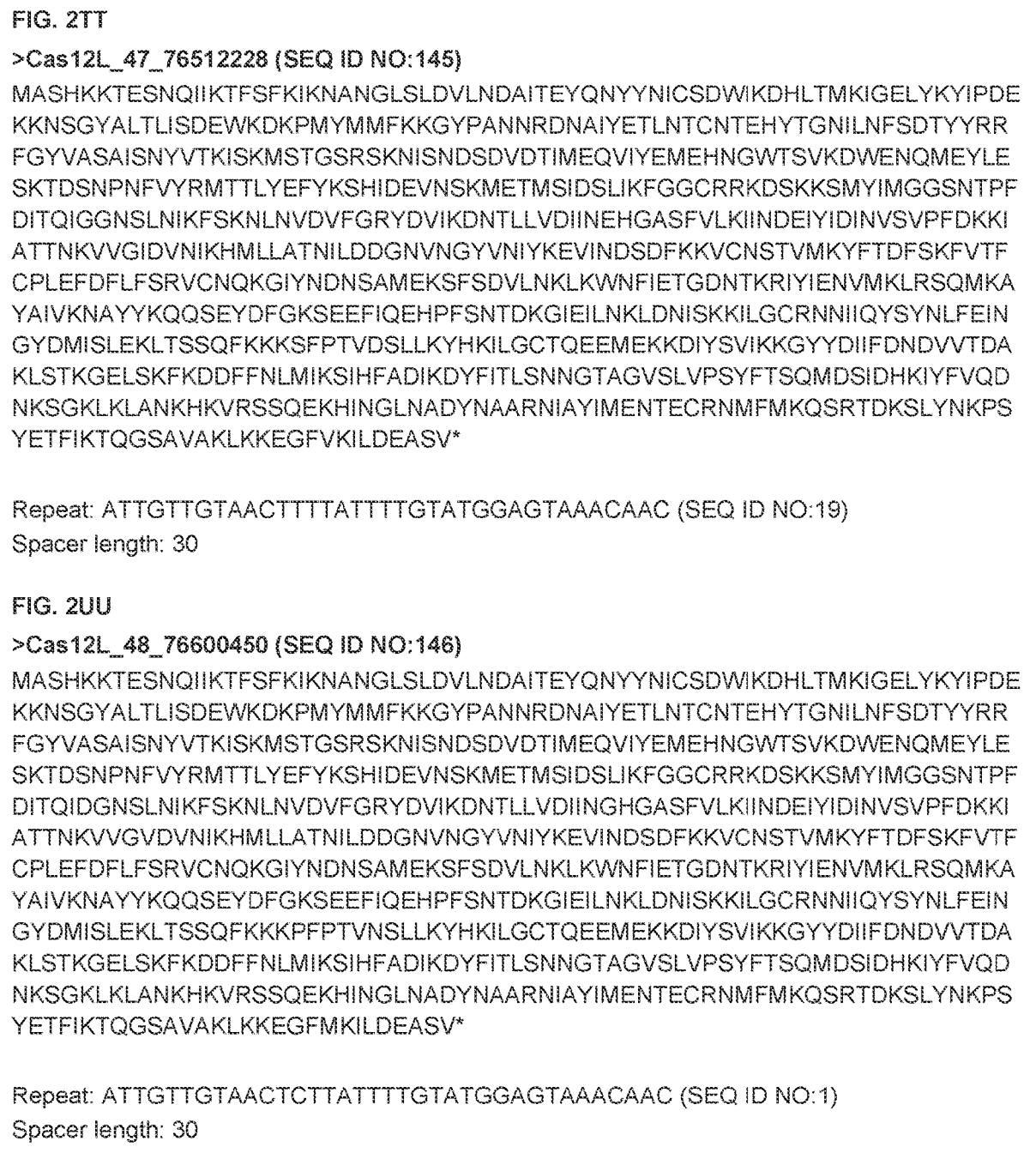

>Cas12L_47_76512228 (SEQ ID NO:145)
MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANNRDNAIYETLNTCNTEHYTGNILNFSDTYYRR
FGYVASAISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNSLNIKFSKNLNVDVFGRYDVIKDNTLLVDIINEHGASFVLKIINDEIYIDINVSVPFDKKI
ATTNKVVGIDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKSFPTVDSLLKYHKILGCTQEEMEKKDIYSVIKKGYYDIIFDNDVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTECRNMFMKQSRTDKSLYNKPS
YETFIKTQGSAVAKLKKEGFVKILDEASV*

Repeat: ATTGTTGTAACTTTTATTTTGTATGGAGTAAACAAC (SEQ ID NO:19)
Spacer length: 30

FIG. 2UU

>Cas12L_48_76600450 (SEQ ID NO:146)
MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANNRDNAIYETLNTCNTEHYTGNILNFSDTYYRR
FGYVASAISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIDGNSLNIKFSKNLNVDVFGRYDVIKDNTLLVDIINGHGASFVLKIINDEIYIDINVSVPFDKKI
ATTNKVVGVDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKPFPTVNSLLKYHKILGCTQEEMEKKDIYSVIKKGYYDIIFDNDVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTECRNMFMKQSRTDKSLYNKPS
YETFIKTQGSAVAKLKKEGFMKILDEASV*

Repeat: ATTGTTGTAACTCTTATTTTGTATGGAGTAAACAAC (SEQ ID NO:1)
Spacer length: 30

FIG. 2VV

>Cas12L_49_44880081 (SEQ ID NO:147)

MASHKKTESNQIIKTFSFKLKNANGLSLDVLNDAITEYQNYYNICSDWIKDHLTMKIGELYKYIPD
EKKNSGYALTLISDEWKDKPMYMMFKKGYPANNRDNAIYEALNTCNTEHYTGNILNFSDTYYR
RFGYVASTISNYVTKISKMSTGSRSKNISNDSDVDTIMEQVIYEMEHNGWTSVKDWENQMEYL
ESKTDSNPNFVYRMTTLYEFYKSHIDEVNSKMETMSIDSLIKFGGCRRKDSKKSMYIMGGSNTP
FDITQIGSNSLNIKFSKNLNVDVFGRYDVIKDNTLLVDIIKGHGASFALKIINDEIYIDINVSVPFDKK
IATTNKVVGIDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILHKLDNISKKILGCRNNIIQYSYNLFEIN
GYDMISLEKLTSSQFKKKPFPTVNSLLKYHKILGCTQEEMEKKDIYSVIKKGYYDIIFDNDVVTDA
KLSTKGELSKFKDDFFNLMIKSIHFADIKDYFITLSNNGTAGVSLVPSFFTSQMDSIDHKIYFVQD
NKSGKLKLANKHKVRSSQEKHINGLNADYNAARNIAYIMENTECRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2WW

>Cas12L_50_83012613 (SEQ ID NO:148)

MAHKKNIGAEIVKTYSFKVKNTNGITMEKLMNAIDEYQSYYNLCSDWICKNLTTMTIGDLDQYIP
EKAKDNTYATVLLDEAWKNQPLYKIFGKKYSSNNRDAVLYHALSSIVNASEKNILGISKTYYARK
GYVLNVASNYASKLSKLNTGVKSRAIKETSDEETIIEQVIYEMEHNKWESIEDWKNQIEYLNSKT
DYNPTYMERMKTLSAYYSEHKSEVDAKMQEMAVENLVKFGGCRRNNSKKSMFIMGTTNTNYT
ISYIGGNSFNINFANILNFDVYGRRDVVKNGEVLVDIMANHGDSIVLKIVNGELYADVPCSVTLNK
VESNFDKVVGIDVNMKHMLLSTSVTDNGSLDFLNIYKEMSNNAEFMALCSEDDRKYYKDISQY
VTFAPLELDLLFSRISKQGKVKMEKAYSEILEALKWKFFANGDNKNRIYVESIQKIRQQIKALCIIK
NAYYEQQSAYDIDKTQEYIEAHPFSLTEKGMSIKSKMDNICRTIIGCRNNIIDYAYSFFERNDYSII
GLEKLTSAQFEKTKSLPTCKSLLNFHKVLGHTLSELGTLPINDVVKKGYYTFTTDNEGRITDASL
SEKGKVRKMKDDFFNQTIKAIHFADVKDYFATLSNNGQTGIFFVPSQFTSQMDSSTHNLYFENA
KNGGLKLAPKYKVRQMQEYHLNGLPADYNAARNIAYIGLDETMRNTFLKKANSNKSLYNQPIYD
TGIKKTAGVFYRMKKLKRYEII*

Repeat: AATGTTGTAGATACCTTTTTGTAAGGATTGAACAAC (SEQ ID NO:21)
Spacer length: 30

FIG. 2XX

>Cas12L_51_82983331 (SEQ ID NO:149)

MKRNQKHIKNIEESETIKTISFKVKDYAGIPIVEAMHEYRNYYNRLSRFINSKLLTMTIGELASLLP
ERCKSKGYYLYMTSDEWVNEYVYKMFMESFNSQSCDNIWFNYIKMNNPEEYNGNILGISDSYY
RRNGYFINVISNYKTKFKSPQINVKSKKLSESPTEEELKEQCVYEYVKHNLHSKKDWEEQIKYLD
ERGESKINILERIRTLYQYYKENIPTIKEYIELKSIESIEKFGGCVRKEDKLSMSLQYVSTHNYEIKL
NDTRNGYIISGISKDLSFEVYGNRMGLLGGEEILNIPEKHSTSITFVMRNNSLYVDIPVAVPFSKVI
NDCDGKTVGIDVNLKHALFATSEVDNGQFYDYVNVYAELLKDENFVKVCHKELLDYIKDVSKYV
FFAPIELNLLLSRVMQKGYENIDNYKKLYKVEEAYLCVLDKLQKRFIDEGNNTKRIYIENLKKMR
AQMKAYYILKDTYSKYQKDYDIEMGFVDESTESKETMDARRSENPFRSTDIAQDILKKMNNVGK
TVEACRNNIIAYIYKVFENSDFATIVLEKLQSSQMKKHKRIPTVNSLLKYHHVEGHTIEETKEMKIY
DVVEKGYYNFIVNEKNEIIDATLTDKGKVIMIEAEFYNFALKSIHFADAKDYFITLSNNGSVNIALV
PSQFTSQMDSIRHAIFVTKGKKGKKVIVDKKYVRPKQEKHINGLNGDYNASRNIAYIFENEELRE
ELLKKEEEYNKYGKVLYDTLIKFPSGVINKLKKFGDKYMTTIENLDEIQVEDVAYV*

Repeat: ATTGTTGTAATACTATTTTTGTAAAGTATAAACAAC (SEQ ID NO:23)
Spacer length: 30

FIG. 2YY

>Cas12L_52_76767885 (SEQ ID NO:150)

MSKLNTGVKRHTIKETSDEATIVEQVIYEMEHNKWESIEDWKNQIEYLNSKTDYNPTYMERMKT
LSAYYSEHKSEVDAKMQEMAVENLVKFGGCRRNNSKKSMFIMGSSKTTYTISYIGDNCFNINFA
NILNFDVYGRRDVVKNGEVLVDIMANHGDSIVLKIVNGELYADVPCSTTLNKVESTFDKVAGIDV
NMKHMLLSTSVTDNGNSDFVNIYKEMSNNAEFMALCPEEDRKYYKDISQYVTFAPLELDLLFSR
ISKQGKVKMEKAYSEILETLKWKFFANGDNKNRIYVESIQKIRQQIKALCVIKNAYYEQQSAYDID
KTQEYIEAHPFSLTEKGMSIKSKMDNICRTIIGCRNNIIDYAYSFFERNDYSIIGLEKLTSSQFEKT
KSLPTCKSLLNFHKVLGHTLSELETLPINDVVKKGYYTFTTDNEGRITDASLSEKGKVRKMKDDF
FNQAIKAIHFADVKDYFATLSNNGQTGIFFVPSQFTSQMDSNTHTLYFENAKNGGLKLASKYKV
RQTQEYHLNGLPADYNAARNIAYIGLDETMRNTFLKKANSNKSLYNQPIYDTGIKKTAGVFSRM
KKLKRYEII*

Repeat: AATGTTGTAGATGCCTTTTTATAAGGATTAAACAAC (SEQ ID NO:25)
Spacer length: 30

FIG. 2ZZ

>Cas12L_53_77216451 (SEQ ID NO:151)

MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANNRDNAIYEALNTCNTEHYTGNILNFSDTYYRR
FGYVASAISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIGGNSLNIKFSKNLNVDVFGRYDVIKDNTLLVDIINGHGASFVLKIINDEIYIDINVSVPFDKKI
ATTNKVVGIDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKPFPTVNSLLKYHKILGCTQEEMEKKDIYSVIKKGYYDIIFDNDVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTDCRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2AAA

>Cas12L_54_77468912_partial (SEQ ID NO:152)
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2BBB

>Cas12L_55_77738117 (SEQ ID NO:153)

MASHSSLSNNQIFKTFSFKVKSSNLSKDFFDVIKEYQEYYNKCSDVILENLTCIKIGDIFDMIPEKS
KKSDYAQYAISDEWKNVPLYNIFSKAFAPMHRDNLLYIWLTKLVPYTGNLLKISDTFYKRNGFIK
SVISNYTTSFTNIKPKVKFQKLTGDDSHEMLLTQTICDMVKFNLYDIKSWEEMVSYFEMKSETSE
DTLNRIHTLFDFYKNNTPEVEDKYNELVTESLSKFGGCRRDMSKLTMSIQLSKKVIKVTHGYNTL
NYKYGKLIDLELWGRKDIINNDELLINLENVCEMIVFKIKNGEIYVDIPFKVDFIKKDQTIDKIAGVD
ANIKHMLLSTSVKDENLIGYTNIYKEVINDSDFQKVCDNKTMKILQEISNYVTFAPIEFDMLFSRIS
KQREMKDKYINMEIAFTNVLNKLKQKFIVNSDNKNRIYIESILKIRSQLKSYAILEEVKYKKASEYD
SAIVEEFGVEYLETHPFKDTETYKEINKKILNISENIIGCRNNIIQYAYKIFESNGFDMISLENLTNS
NFKKEKNMPTIKSLLSYHHVLGKTNEEIEKLDVYSVIKKGYYTFEYKDGKVVNAKLSEIGEMIKIK
TTMFNMMIKSIHFAEIKDYFITLANNGEVGVSLVPSYYTSQMDSTDHKVFGLLSKKGKWTLVDK
RKVRKNQETHINGLNADYNAAKNIAFILSDEVWRNKFTKKTKTPKYNTPSYYTSINSQGKMLRA
LKSLKAFKEFKI*

Repeat: ATTGTTGTAATACACTTTTTATAAGGTATGAACAAC (SEQ ID NO:27)
Spacer length: 30

FIG. 2CCC

>Cas12L_56_65286425 (SEQ ID NO:154)

MKIGELYKYIPDEKKNSGYALTLISDEWKDKPMYMMFKKGYPANNRDNAIYEALNTCNTEHYTG
NILNFSDTYYRRFGYVASAISNYVTKISKMSTGSRSKNISNDSDVDTIMEQVIYEMEHNGWTSVK
DWENQMEYLESKTDSNPNFVYRMTTLYEFYKSHIDEVNSKMETMSIDSLIKFGGCRRKDSKKS
MYIMGGSNTPFDITQIGGNSLNIKFSKNLNVDVFGRYDVIKDNTLLVDIINEHGASFVLKIINDEIYI
DINVSVPFDKKIATTNKVVGIDVNIKHMLLATNILDDGNVNGYVNIYKEVINDSDFKKVCNSTVMQ
YFTDFSKFVTFCPLEFDFLFSRVCNQKGIYNDNSAMEKSFSDVLNKLKWNFIETGDNTKRIYIEN
VMKLRSQMKAYAIVKNAYYKQQSEYDFGKSEEFIQEHPFSNTDKGIEILNKLDNISKKILGCRNNI
IQYSYNLFEINGYDMISLEKLTSSQFKKKPFPTVNSLLKYHKILGCTQEEMEKKDIYSVIKKGYYDI
IFDNDVVTDAKLSTKGELSKFKDDFFNLMIKSIHFADIKDYFITLSNNGTAGVSLVPSYFTSQMDS
IDHKIYFVQDNKSGKLKLANKHKVRSSQEKHINGLNADYNAARNIAYIMENTECRNMFMKQSRT
DKSLYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2DDD

>Cas12L_57_65567118_partial (SEQ ID NO:155)

KIINDEIYIDINVSVPFDKKIATTNKVVGIDVNIKHMLLATNILDDGNVNGYVNIYKEVINDSDFKKV
CNSTVMKYFTDFSKFVTFCPLEFDFLFSRVCNQKGIYNDNSAMEKSFSDVLNRLKWNFIETGD
NTKRIYIENVMKLRSQMKAYAIVKNAYYKQQSEYDFGKSEEFIQEHPFSNTDKGIEILNKLDNISK
KILGCRNNIIQYSYNLFEINGYDMISLEKLTSSQFKKKPFPTVNSLLKYHKIRGGTQEEMEKKDIY
SVIKKGYYDIIFDNDVVTDAKLSTKGELSKFKDDFFNLMIKSIHFADIKDYFITLSNNGTAGVSLVP
SYFTSQMDSIDHKIYFVQDNKSGKLKLANKHKVRSSQEKHINGLNADYNAARNIAYIMENNECR
NMFMKQSRTDKSLYNKPSYETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 2EEE

>Cas12L_58_66287853_partial (SEQ ID NO:156)

DDGNVNGYVNIYKEVINDSDFKKVCNSTVMKYFTDFSKFVTFCPLEFDFLFSRVCNQKGIYNDN
SAMEKSFSDVLNKLKWNFIETGDNTKRIYIENVMKLRSQMKAYAIVKNAYYKQQSEYDFGKSEE
FIQEHPFSNTDKGIEILNKLDNISKKILGCRNNIIQYSYNLFEINGYDMISLEKLTSSQFKKKPFPTV
NSLLKYHKILGCTQEEMEKKDIYSVIKKGYYDIIFDNDVVTDAKLSTKGELSKFKDDFFNLMIKSIH
FADIKDYFITLSNNGTAGVSLVPSYFTSQMDSIDHKIYFVQDNKSGKLKLANKHKVRSSQEKHIN
GLNADYNAARNIAYIMENTECRNMFMKQSRTDKSLYNKPSYETFIKTQGSAVAKLKKDGFVKIL
DEASA*

Repeat: ATTGTTGTAACTCTTATTTTGTATGGAGTAAACAAC (SEQ ID NO:1)
Spacer length: 30

FIG. 2FFF

>Cas12L_39_73877227 (SEQ ID NO:157)

MASHKKTESNQIIKTFSFKIKNANGLSLDVLNDAITEYQNYYNICSDWIKDHLTMKIGELYKYIPDE
KKNSGYALTLISDEWKDKPMYMMFKKGYPANSRDNAIYEALNTCNTEHYTGNILNFSDTYYRR
FGYVASAISNYVTKISKMSTGSRSKNISNDSDVDTIMEQVIYEMEHNGWTSVKDWENQMEYLE
SKTDSNPNFVYRMTTLYEFYKSHIDEVNSKMETMSIDSLIKFGGCRRKDSKKSMYIMGGSNTPF
DITQIDGNSLNIKFSKNLNVDVFGRYDVIKDNTLLVDIINGHGASFVLKIINGEIYIDINVSVPFDKKI
ATTNKVVGIDVNIKHMLLATNILDDGNVNGYVNIYKEVINDSDFKKVCNSTVMKYFTDFSKFVTF
CPLEFDFLFSRVCNQKGIYNDNSAMEKSFSDVLNKLKWNFIETGDNTKRIYIENVMKLRSQMKA
YAIVKNAYYKQQSEYDFGKSEEFIQEHPFSNTDKGIEILNKLDNISKKILGCRNNIIQYSYNLFEIN
GYDMISLEKLTSSQFKKKPFPTVNSLLKYHKILGCTQEEMEKKDIYSVIKKGYYDIIFDNDVVTDA
KLSTKGELSKFKDDFFNLMIKSIHFADIKDYFITLSNNGTAGVSLVPSYFTSQMDSIDHKIYFVQD
NKSGKLKLANKHKVRSSQEKHINGLNADYNAARNIAYIMENTECRNMFMKQSRTDKSLYNKPS
YETFIKTQGSAVAKLKKEGFVKILDEASV*

Repeat: ATTGTTGTAACTCTTATTTTGTATGGAGTAAACAAC (SEQ ID NO:1)
Spacer length: 30

FIG. 3A

| | RuvC-I | RuvC-II | RuvC-III |
|---|---|---|---|
| Cas12L_1_257905508 | 336 | 530 | 682 |
| Cas12L_2_196848753 | 335 | 523 | 676 |
| Cas12L_3_66741167 | 368 | 562 | 714 |
| Cas12L_4_67031163 | 368 | 562 | 714 |
| Cas12L_5_67793351 | 368 | 562 | 714 |
| Cas12L_6_67912869_partial | | 139 | 292 |
| Cas12L_7_68090316_partial | 302 | 501 | 653 |
| Cas12L_8_68328292_partial | 359 | 553 | 705 |
| Cas12L_9_68454124 | 336 | 530 | 682 |
| Cas12L_10_68605313 | 372 | 566 | 718 |
| Cas12L_11_69266821_partial | | | 28 |
| Cas12L_12_69417229_partial | | | 28 |
| Cas12L_13_69733214 | 336 | 530 | 682 |
| Cas12L_14_70235246_partial | 17 | 211 | 363 |
| Cas12L_15_70724743 | 336 | 530 | 682 |
| Cas12L_16_70731038 | 335 | 523 | 676 |
| Cas12L_17_70959391 | 336 | 530 | 682 |
| Cas12L_18_71078086 | 336 | 530 | 682 |
| Cas12L_19_71193509_partial | 270 | 464 | 616 |
| Cas12L_20_71210958_partial | 116 | 304 | 457 |
| Cas12L_21_71317321_partial | 175 | 369 | 521 |
| Cas12L_22_71456687 | 336 | 530 | 682 |
| Cas12L_23_71708971 | 175 | 369 | 521 |
| Cas12L_24_46035167_partial | 348 | 542 | 594 |
| Cas12L_25_46784254_partial | 186 | 380 | 532 |
| Cas12L_26_46464451 | 336 | 530 | |
| Cas12L_27_254489164 | 336 | 530 | 682 |
| Cas12L_28_255238293 | 343 | 542 | 701 |
| Cas12L_29_72167294 | 336 | 530 | 682 |
| Cas12L_30_72369269 | 336 | 530 | 682 |
| Cas12L_31_72503976 | 336 | 530 | 682 |
| Cas12L_33_72907394 | 336 | 530 | 682 |
| Cas12L_34_73124743_partial | | 29 | 181 |
| Cas12L_35_73503649_partial | | 70 | |
| Cas12L_36_73503649_partial | | | 21 |
| Cas12L_37_73472625 | 334 | 545 | 698 |
| Cas12L_38_73764039_partial | 242 | 436 | 588 |
| Cas12L_39_73877227 | 336 | 530 | 682 |
| Cas12L_40_74037305 | 372 | 566 | 718 |

FIG. 3B

| | | | |
|---|---|---|---|
| Cas12L_41_74408273_partial | 479 | 673 | 825 |
| Cas12L_42_75186079_partial | | 7 | 159 |
| Cas12L_43_75257103_partial | 282 | | |
| Cas12L_44_75257103_partial | | 5 | 132 |
| Cas12L_45_75616607_partial | 338 | 532 | 684 |
| Cas12L_46_75784289_partial | 71 | 265 | 417 |
| Cas12L_47_76512228 | 336 | 530 | 682 |
| Cas12L_48_76600450 | 336 | 530 | 682 |
| Cas12L_49_44880081 | 336 | 530 | 682 |
| Cas12L_50_83012613 | 335 | 523 | 676 |
| Cas12L_51_82983331 | 341 | 552 | 705 |
| Cas12L_52_76767885 | 192 | 380 | 533 |
| Cas12L_53_77216451 | 336 | 530 | 682 |
| Cas12L_55_77738117 | 330 | 527 | 679 |
| Cas12L_56_65286425 | 282 | 476 | 628 |
| Cas12L_57_65567118_partial | 31 | 225 | 377 |
| Cas12L_58_66287853_partial | | 181 | 333 |

```
Cas12L_1_257905508        ..................................................................
Cas12L_2_196848753        ..................................................................
Cas12L_3_66741167         ..................................................................
Cas12L_4_67031163         ..................................................................
Cas12L_5_67793351         ..................................................................
Cas12L_6_67912869_partial ..................................................................
Cas12L_7_68090316_partial ..................................................................
Cas12L_8_68328292_partial ..................................................................
Cas12L_9_68454124         ..................................................................
Cas12L_10_68605313        ..................................................................
Cas12L_11_69266821_partial ..................................................................
Cas12L_12_69417229_partial ..................................................................
Cas12L_13_69733214        ..................................................................
Cas12L_14_70235246_partial ..................................................................
Cas12L_15_70724743        ..................................................................
Cas12L_16_70731038        ..................................................................
Cas12L_17_70959391        ..................................................................
Cas12L_18_71078086        ..................................................................
Cas12L_19_71193509_partial ..................................................................
Cas12L_20_71210958_partial ..................................................................
Cas12L_21_71317321_partial ..................................................................
Cas12L_22_71456687        ..................................................................
Cas12L_23_71708971        ..................................................................
Cas12L_24_46035167_partial ..................................................................
Cas12L_25_46784254_partial ..................................................................
Cas12L_26_46464451        ..................................................................
Cas12L_27_254489164       ..................................................................
Cas12L_28_255238293       ..................................................................
Cas12L_29_72167294        ..................................................................
Cas12L_30_72369269        ..................................................................
Cas12L_31_72503976        ..................................................................
Cas12L_32_72547654_partial ..................................................................
Cas12L_33_72907394        ..................................................................
Cas12L_34_73124743_partial ..................................................................
Cas12L_35_73503649_partial ..................................................................
Cas12L_36_73503649_partial ..................................................................
Cas12L_37_73472625        ..................................................................
Cas12L_38_73764039_partial ..................................................................
Cas12L_39_73877227        ..................................................................
Cas12L_40_74037305        ..................................................................
Cas12L_41_74408273_partial WTDEDYCKFFAKYGMSEECQKWMCRDVYDYRIKDFVDYEKFDDSKIEEEQEEYSEIPVES
Cas12L_42_75186079_partial ..................................................................
Cas12L_43_75257103_partial ..................................................................
Cas12L_44_75257103_partial ..................................................................
Cas12L_45_75616607_partial ..................................................................
Cas12L_46_75784289_partial ..................................................................
Cas12L_47_76512228        ..................................................................
Cas12L_48_76600450        ..................................................................
Cas12L_49_44880081        ..................................................................
Cas12L_50_83012613        ..................................................................
Cas12L_51_82983331        .........................MKRN.....................................
Cas12L_52_76767885        ..................................................................
Cas12L_53_77216451        ..................................................................
Cas12L_54_77468912_partial ..................................................................
Cas12L_55_77738117        ..................................................................
Cas12L_56_65286425        ..................................................................
Cas12L_57_65567118_partial ..................................................................
Cas12L_58_66287853_partial ..................................................................
```

FIG. 5A

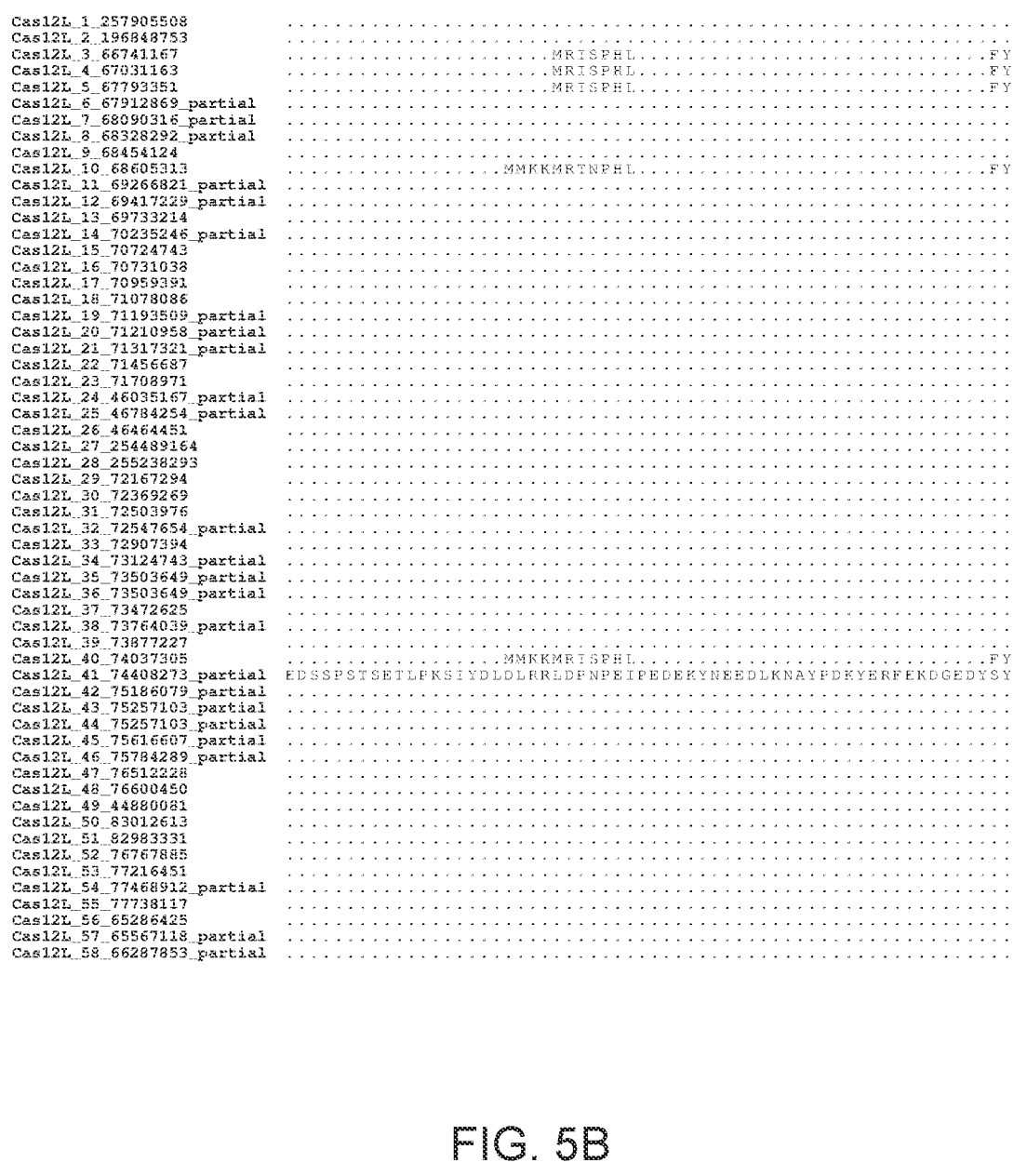

```
Cas12L_1_257905508          ...........................................................................
Cas12L_2_196848753          ...........................................................................
Cas12L_3_66741167           .........................MRISPHL.................................FY
Cas12L_4_67031163           .........................MRISPHL.................................FY
Cas12L_5_67793351           .........................MRISPHL.................................FY
Cas12L_6_67912869_partial   ...........................................................................
Cas12L_7_68090316_partial   ...........................................................................
Cas12L_8_68328292_partial   ...........................................................................
Cas12L_9_68454124           ...........................................................................
Cas12L_10_68605313          ......................MMKKMRTNPHL.................................FY
Cas12L_11_69266821_partial  ...........................................................................
Cas12L_12_69417229_partial  ...........................................................................
Cas12L_13_69733214          ...........................................................................
Cas12L_14_70235246_partial  ...........................................................................
Cas12L_15_70724743          ...........................................................................
Cas12L_16_70731038          ...........................................................................
Cas12L_17_70959391          ...........................................................................
Cas12L_18_71078086          ...........................................................................
Cas12L_19_71193509_partial  ...........................................................................
Cas12L_20_71210958_partial  ...........................................................................
Cas12L_21_71317321_partial  ...........................................................................
Cas12L_22_71456687          ...........................................................................
Cas12L_23_71708971          ...........................................................................
Cas12L_24_46035167_partial  ...........................................................................
Cas12L_25_46784254_partial  ...........................................................................
Cas12L_26_46464451          ...........................................................................
Cas12L_27_254489164         ...........................................................................
Cas12L_28_255238293         ...........................................................................
Cas12L_29_72167294          ...........................................................................
Cas12L_30_72369269          ...........................................................................
Cas12L_31_72503976          ...........................................................................
Cas12L_32_72547654_partial  ...........................................................................
Cas12L_33_72907394          ...........................................................................
Cas12L_34_73124743_partial  ...........................................................................
Cas12L_35_73503649_partial  ...........................................................................
Cas12L_36_73503649_partial  ...........................................................................
Cas12L_37_73472625          ...........................................................................
Cas12L_38_73764039_partial  ...........................................................................
Cas12L_39_73877227          ...........................................................................
Cas12L_40_74037305          ......................MMKKMRISPHL.................................FY
Cas12L_41_74408273_partial  EDSSPSTSETLFKSIYDLDLRRLDFNPEIPEDEKYNEEDLKNAYFDKYERFEKDGEDYSY
Cas12L_42_75186079_partial  ...........................................................................
Cas12L_43_75257103_partial  ...........................................................................
Cas12L_44_75257103_partial  ...........................................................................
Cas12L_45_75616607_partial  ...........................................................................
Cas12L_46_75784289_partial  ...........................................................................
Cas12L_47_76512228          ...........................................................................
Cas12L_48_76600450          ...........................................................................
Cas12L_49_44880081          ...........................................................................
Cas12L_50_83012613          ...........................................................................
Cas12L_51_82983331          ...........................................................................
Cas12L_52_76767885          ...........................................................................
Cas12L_53_77216451          ...........................................................................
Cas12L_54_77468912_partial  ...........................................................................
Cas12L_55_77738117          ...........................................................................
Cas12L_56_65286425          ...........................................................................
Cas12L_57_65567118_partial  ...........................................................................
Cas12L_58_66287853_partial  ...........................................................................
```

FIG. 5B

```
                                                      1        10         20         30
Cas12L_1_257905508          .........................MASHKKTE.SNQIIKTFSFKIKNANGLSLDVLNDAIT
Cas12L_2_196848753          ........................MAHKKNV..GAEIVKTYSFKVKNTNGITMEKLMNAID
Cas12L_3_66741167           IFFKKIWKCHFFVLSLYQLNQYIMASHKKTE.SNQIIKTFSFKIKNANGLSLDVLNDAIT
Cas12L_4_67031163           IFFKKIWKSHFFVLSLYQLNQYIMASHKKTE.SNQIIKTFSFKIKNANGLSLDVLNDAIT
Cas12L_5_67793351           IFFKKIWKCHIFVLSLYQLNQYIMASHKKTE.SNQIIKTFSFKIKNANGLSLDVLNDAIT
Cas12L_6_67912869_partial   ............................................................
Cas12L_7_68090316_partial   .....................................................VLNDAIT
Cas12L_8_68328292_partial   IFFKKIWKCHIFVLSLYQLNQYIMASHKKTE.SNQIIKTFSFKIKNANGLSLDVLNDAIT
Cas12L_9_68454124           .........................MASHKKTE.SNQIIKTFSFKIKNANGLSLDVLNDAIT
Cas12L_10_68605313          ICFKKIWKCHFFALSLYQLNQYIMASHKKTE.SNQIIKTFSFKIKNANGLSLDVLNDAIT
Cas12L_11_69266821_partial  ............................................................
Cas12L_12_69417229_partial  ............................................................
Cas12L_13_69733214          .........................MASHKKTE.SNQIIKTFSFKIKNANGLSLDVLNDAIT
Cas12L_14_70235246_partial  ............................................................
Cas12L_15_70724743          .........................MASHKKTE.SNQIIKTFSFKIKNANGLSLDVLNDAIT
Cas12L_16_70731038          ........................MAHKKNI..GAEIVKTYSFKVKNTNGITMEKLMNAID
Cas12L_17_70959391          .........................MASHKKTE.SNQIIKTFSFKIKNANGLSLDVLNDAIT
Cas12L_18_71078086          .........................MASHKKTE.SNQIIKTFSFKIKNANGLSLDVLNDAIT
Cas12L_19_71193509_partial  ............................................................
Cas12L_20_71210958_partial  ............................................................
Cas12L_21_71317321_partial  ............................................................
Cas12L_22_71456687          .........................MASHKKTE.SNQIIKTFSFKIKNANGLSLDVLNDAIT
Cas12L_23_71708971          ............................................................
Cas12L_24_46035167_partial  .........FVLSLYQLNQYIMASHKKTE.SNQIIKTFSFKIKNANGLSLDVLNDAIT
Cas12L_25_46784254_partial  ............................................................
Cas12L_26_46464451          .........................MASHKKTE.SNQIIKTFSFKIKNANGLSLDVLNDAIT
Cas12L_27_254489164         .........................MASHKKTE.SNQIIKTFSFKIKNANGLSLDVLNDAIT
Cas12L_28_255238293         .........................MAHKKNLEGENLQVKTICLKANLSKEEVKEKWLFVIN
Cas12L_29_72167294          .........................MASHKKTE.SNQIIKTFSFKIKNANGLSLDVLNDAIT
Cas12L_30_72369269          .........................MASHKKTE.SNQIIKTFSFKIKNANGLSLDVLNDAIT
Cas12L_31_72503976          .........................MASHKKTE.SNQIIKTFSFKIKNANGLSLDVLNDAIT
Cas12L_32_72547654_partial  ............................................................
Cas12L_33_72907394          .........................MASHKKTE.SNQIIKTFSFKIKNANGLSLDVLNDAIT
Cas12L_34_73124743_partial  ............................................................
Cas12L_35_73503649_partial  ............................................................
Cas12L_36_73503649_partial  ............................................................
Cas12L_37_73472625          .........................MAHKKQKE.ENEIIKTISLRVKDYAGY...PIVEAMR
Cas12L_38_73764039_partial  ............................................................
Cas12L_39_73877227          .........................MASHKKTE.SNQIIKTFSFKIKNANGLSLDVLNDAIT
Cas12L_40_74037305          IFFKKIWKCHFFVLSLYQLNQYIMASHKKTE.SNQIIKTFSFKIKNANGLSLDVLNDAIT
Cas12L_41_74408273_partial  IFFKKIWKCHFFVLSLYQLNQYIMASHKKTE.SNQIIKTFSFKIKNANGLSLDVLNDAIT
Cas12L_42_75186079_partial  ............................................................
Cas12L_43_75257103_partial  ............................................................
Cas12L_44_75257103_partial  ............................................................
Cas12L_45_75616607_partial  .....................YIMASHKKTE.SNQIIKTFSFKIKNANGLSLDVLNDAIT
Cas12L_46_75784289_partial  ............................................................
Cas12L_47_76512228          .........................MASHKKTE.SNQIIKTFSFKIKNANGLSLDVLNDAIT
Cas12L_48_76600450          .........................MASHKKTE.SNQIIKTFSFKIKNANGLSLDVLNDAIT
Cas12L_49_44880081          .........................MASHKKTE.SNQIIKTFSFKLKNANGLSLDVLNDAIT
Cas12L_50_83012613          ........................MAHKKNI..GAEIVKTYSFKVKNTNGITMEKLMNAID
Cas12L_51_82983331          .........................QKHIKNIE.ESEIIKTISFKVKDYAGI...PIVEAMH
Cas12L_52_76767885          ............................................................
Cas12L_53_77216451          .........................MASHKKTE.SNQIIKTFSFKIKNANGLSLDVLNDAIT
Cas12L_54_77468912_partial  ............................................................
Cas12L_55_77738117          .........................MASHSSLS.NNQIFKTFSFKVKSSN..LSKDFFDVIK
Cas12L_56_65286425          ............................................................
Cas12L_57_65567118_partial  ............................................................
Cas12L_58_66287853_partial  ............................................................
```

FIG. 5C

```
                          40        50        60        70        80        90
                          .    .         .         .         .         .         .
Cas12L_1_257905508        EYQNYYNICSDWIKDHL..TMKISELYKYIPNEKKNSGYALTLISDEWKDKPMYMMFKKG
Cas12L_2_196848753        EFQSYYNLCSDWICKNL.TIMTIGDLDQYIPEKAKGNTYATVLLDEAWKNQPLYKIFGKK
Cas12L_3_66741167         EYQNYYNICSDWIKDHL..TMKIGELYKYIPDEKKNSGYALTLISDEWKDKPMYMMFKKG
Cas12L_4_67031163         EYQNYYNICSDWIKDHL..TMKIGELYKYIPDEKKNSGYALTLISDEWKDKPMYMMFKKG
Cas12L_5_67793351         EYQNYYNICSDWIKDHL..TMKIGELYKYIPDEKKNSGYALTLISDEWKDKPMYMMFKKG
Cas12L_6_67912869_partial .............................................................
Cas12L_7_68090316_partial EYQNYYNICSDWIKDHL..TMKIGELYKYIPDEKKNSGYALTLISDEWKDKPMYMMFKKG
Cas12L_8_68328292_partial EYQNYYNICSDWIKDHL..TMKIGELYKYIPDEKKNSGYALTLISDEWKDKPMYMMFKKG
Cas12L_9_68454124         EYQNYYNICSDWIKDHL..TMKIGELYKYIPDEKKNSGYALTLISDEWKDKPMYMMFKKG
Cas12L_10_68605313        EYQNYYNICSDWIKDHL..TMKIGELYKYIPDEKKNSGYALTLISDEWKDKPMYMMFKKG
Cas12L_11_69266821_partial ............................................................
Cas12L_12_69417229_partial ............................................................
Cas12L_13_69733214        EYQNYYNICSDWIKDHL..TMKIGELYKYIPDEKKNSGYALTLISDEWKDKPMYMMFKKG
Cas12L_14_70235246_partial ............................................................
Cas12L_15_70724743        EYQNYYNICSDWIKDHL..TMKIGELYKYIPDEKKNSGYALTLISDEWKDKPMYMMFKKG
Cas12L_16_70731038        EYQSYYNLCSDWICKNL.TIMTIGDLDRYIPEKAKDNIYATVLLDEVWKNQPLYKIFGKK
Cas12L_17_70959391        EYQNYYNICSDWIKDHL..TMKIGELYKYIPDEKKNSGYALTLISDEWKDKPMYMMFKKG
Cas12L_18_71078086        EYQNYYNICSDWIKDHL..TMKIGELYKYIPDEKKNSGYALTLISDEWKDKPMYMMFKKG
Cas12L_19_71193509_partial ........................EKKNSGYALTLISDEWKDKPMYMMFKKG
Cas12L_20_71210958_partial ............................................................
Cas12L_21_71317321_partial ............................................................
Cas12L_22_71456687        EYQNYYNICSDWIKDHL..TMKIGELYKYIPDEKKNSGYALTLISDEWKDKPMYMMFKKG
Cas12L_23_71708971        .............................................................
Cas12L_24_46035167_partial EYQNYYNICSDWIKDHL..TMKIGELYKYIPDEKKNSGYALTLISDEWKDKPMYMMFKKG
Cas12L_25_46784254_partial ............................................................
Cas12L_26_46464451        EYQNYYNICSDWIKDHL..TMKIGELYKYIPDEKKNSGYALTLISDEWKDKPMYMMFKKG
Cas12L_27_254489164       EYQNYYNICSDWIKDHL..TMKISELYKYIPNEKKNSGYALTLISDEWKDKPMYMMFKKG
Cas12L_28_255238293       EYNVVYNRMSDYICSLLGTNITIGEFAEQLSIEKRKNGYFTICQDDKFKNESLYKIFHKS
Cas12L_29_72167294        EYQNYYNICSDWIKDHL..TMKIGELYKYIPDEKKNSGYALTLISDEWKDKPMYMMFKKG
Cas12L_30_72369269        EYQNYYNICSDWIKDHL..TMKIGELYKYIPDEKKNSGYALTLISDEWKDKPMYMMFKKG
Cas12L_31_72503976        EYQNYYNICSDWIKDHL..TMKIGELYKYIPDEKKNSGYALTLISDEWKDKPMYMMFKKG
Cas12L_32_72547654_partial ............................................................
Cas12L_33_72907394        EYQNYYNICSDWIKDHL..TMKIGELYKYIPDEKKNSGYALTLISDEWKDKPMYMMFKKG
Cas12L_34_73124743_partial ............................................................
Cas12L_35_73503649_partial ............................................................
Cas12L_36_73503649_partial ............................................................
Cas12L_37_73472625        EYIKYYNKISQWINSNL.LTIKIGELSAFMPDECKIHNYYTYMMSPDWVNEPLYKMFMKG
Cas12L_38_73764039_partial ............................................................
Cas12L_39_73877227        EYQNYYNICSDWIKDHL..TMKIGELYKYIPDEKKNSGYALTLISDEWKDKPMYMMFKKG
Cas12L_40_74037305        EYQNYYNICSDWIKDHL..TMKIGELYKYIPDEKKNSGYALTLISDEWKDKPMYMMFKKG
Cas12L_41_74408273_partial EYQNYYNICSDWIKDHL..TMKIGELYKYIPDEKKNSGYALTLISDEWKDKPMYMMFKKG
Cas12L_42_75186079_partial ............................................................
Cas12L_43_75257103_partial ....................MKIGELYKYIPDEKKNSGYALTLISDEWKDKPMYMMFKKG
Cas12L_44_75257103_partial ............................................................
Cas12L_45_75616607_partial EYQNYYNICSDWIKDHL..TMKIGELYKYIPDEKKNSGYALTLISDEWKDKPMYMMFKKG
Cas12L_46_75784289_partial ............................................................
Cas12L_47_76512228        EYQNYYNICSDWIKDHL..TMKIGELYKYIPDEKKNSGYALTLISDEWKDKPMYMMFKKG
Cas12L_48_76600450        EYQNYYNICSDWIKDHL..TMKIGELYKYIPDEKKNSGYALTLISDEWKDKPMYMMFKKG
Cas12L_49_44880081        EYQNYYNICSDWIKDHL..TMKIGELYKYIPDEKKNSGYALTLISDEWKDKPMYMMFKKG
Cas12L_50_83012613        EYQSYYNLCSDWICKNL.TIMTIGDLDQYIPEKAKDNTYATVLLDEAWKNQPLYKIFGKK
Cas12L_51_82983331        EYRNYYNRLSRFINSKL.LIMTIGELASLLPERCKSKGYYLYMTSDEWVNEYVYKMFMES
Cas12L_52_76767885        ............................................................
Cas12L_53_77216451        EYQNYYNICSDWIKDHL..TMKIGELYKYIPDEKKNSGYALTLISDEWKDKPMYMMFKKG
Cas12L_54_77468912_partial ............................................................
Cas12L_55_77738117        EYQRYYNKCSDVILENL.TCIKIGDIFDMIPEKSKKSDYAQYAISDEWKNVPLYNIFSKA
Cas12L_56_65286425        ....................MKIGELYKYIPDEKKNSGYALTLISDEWKDKPMYMMFKKG
Cas12L_57_65567118_partial ............................................................
Cas12L_58_66287853_partial ............................................................
```

FIG. 5D

Figure 5G:
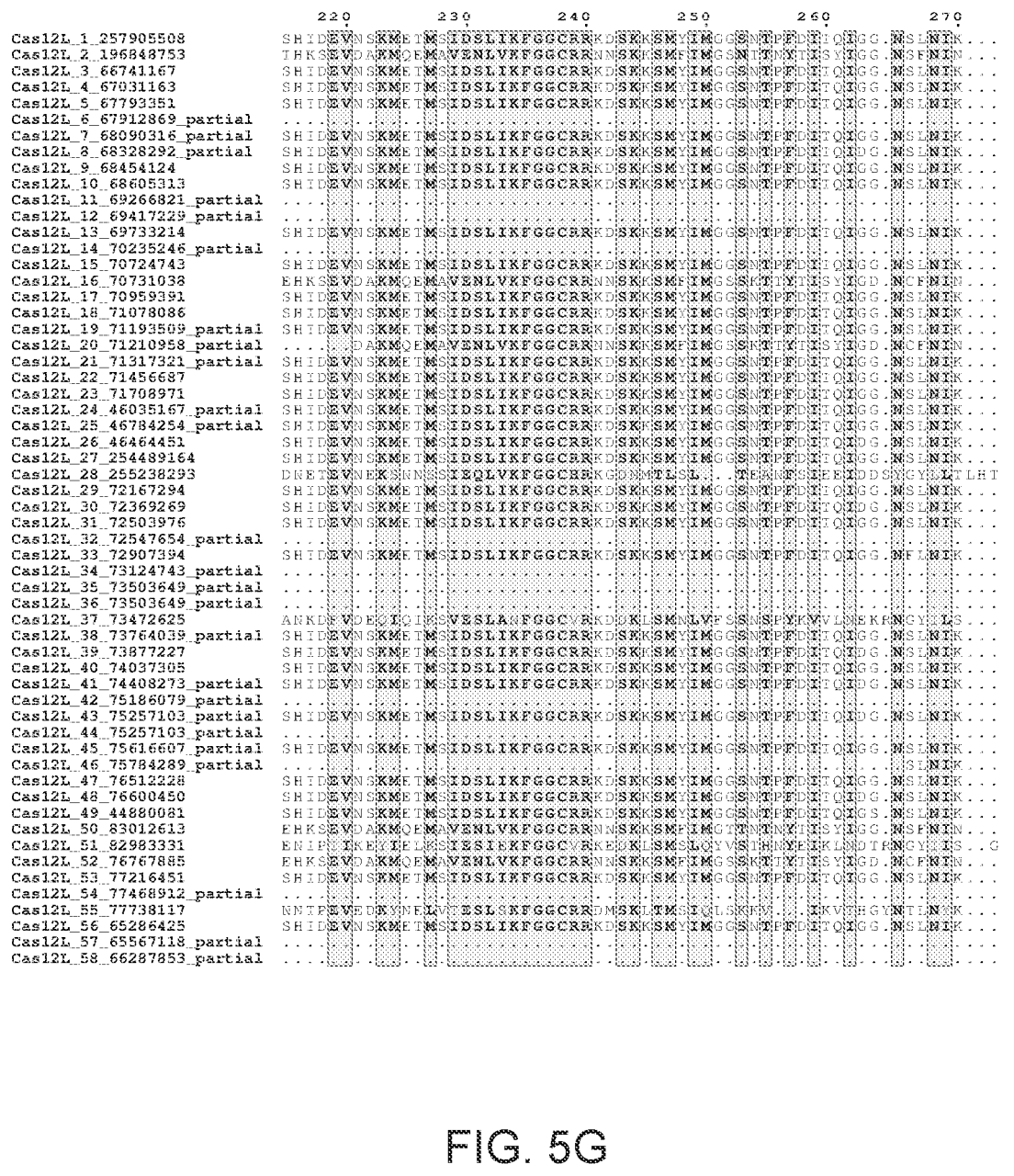

Cas12L_1_257905508
Cas12L_2_196848753
Cas12L_3_66741167
Cas12L_4_67031163
Cas12L_5_67793351
Cas12L_6_67912869_partial
Cas12L_7_68090316_partial
Cas12L_8_68328292_partial
Cas12L_9_68454124
Cas12L_10_68605313
Cas12L_11_69266821_partial
Cas12L_12_69417229_partial
Cas12L_13_69733214
Cas12L_14_70235246_partial
Cas12L_15_70724743
Cas12L_16_70731038
Cas12L_17_70959391
Cas12L_18_71078086
Cas12L_19_71193509_partial
Cas12L_20_71210958_partial
Cas12L_21_71317321_partial
Cas12L_22_71456687
Cas12L_23_71708971
Cas12L_24_46035167_partial
Cas12L_25_46784254_partial
Cas12L_26_46464451
Cas12L_27_254489164
Cas12L_28_255238293
Cas12L_29_72167294
Cas12L_30_72369269
Cas12L_31_72503976
Cas12L_32_72547654_partial
Cas12L_33_72907394
Cas12L_34_73124743_partial
Cas12L_35_73503649_partial
Cas12L_36_73503649_partial
Cas12L_37_73472625
Cas12L_38_73764039_partial
Cas12L_39_73877227
Cas12L_40_74037305
Cas12L_41_74408273_partial
Cas12L_42_75186079_partial
Cas12L_43_75257103_partial
Cas12L_44_75257103_partial
Cas12L_45_75616607_partial
Cas12L_46_75784289_partial
Cas12L_47_76512228
Cas12L_48_76600450
Cas12L_49_44880081
Cas12L_50_83012613
Cas12L_51_82983331
Cas12L_52_76767885
Cas12L_53_77216451
Cas12L_54_77468912_partial
Cas12L_55_77738117
Cas12L_56_65286425
Cas12L_57_65567118_partial
Cas12L_58_66287853_partial

Figure 5M:
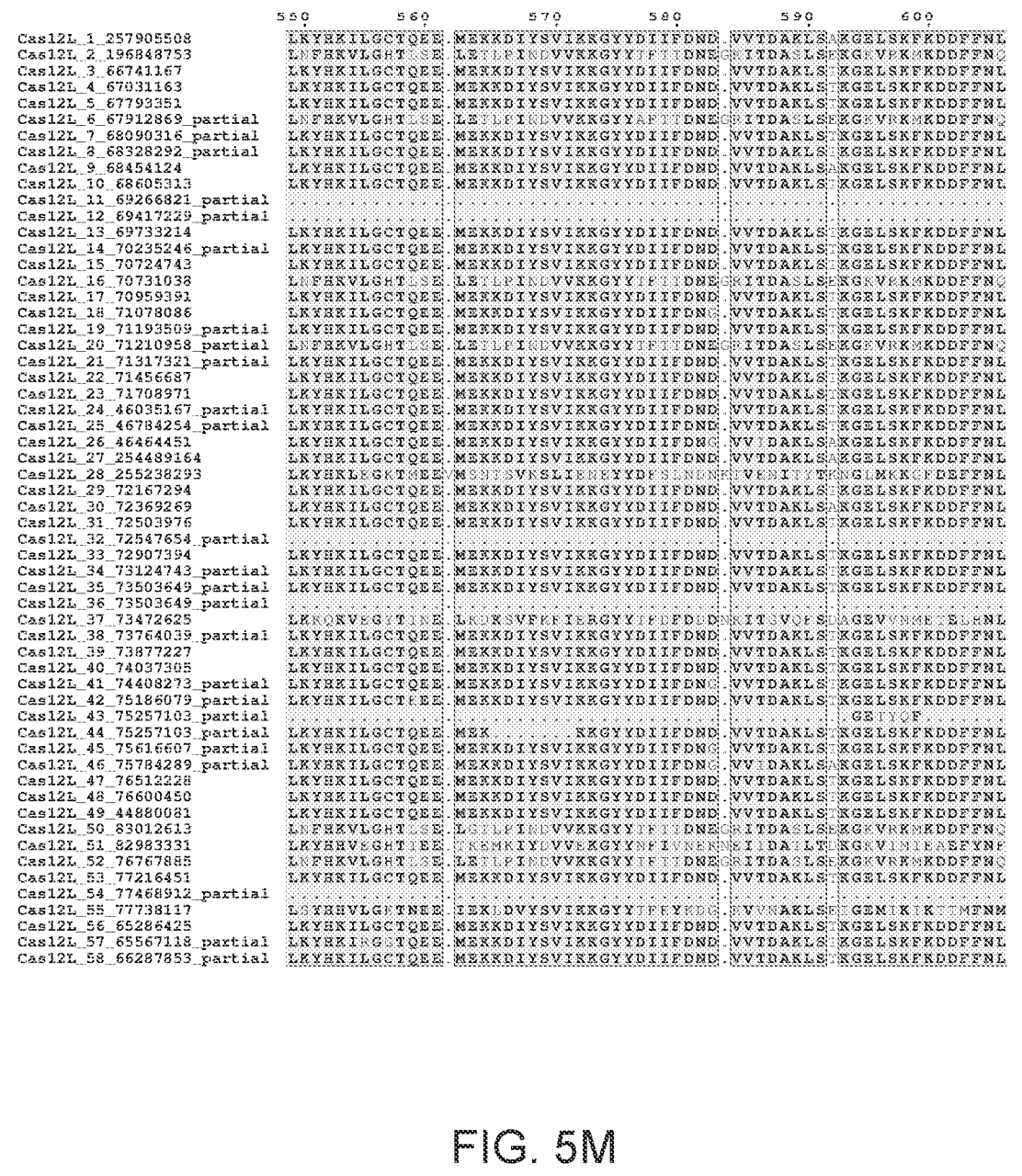

```
                                        550        560        570        580        590        600
Cas12L_1_257905508          LKYSKILGCTQEE MSKKDIYSVIKKGYYDIIFDND VVTDAKLS KGELSKFKDDFFNL
Cas12L_2_196848753          LNFSKVLGHT SE LETLPINDVVKKGYYIF IDNEG ITDA LS KGKVPKMKDDFFNQ
Cas12L_3_66741167           LKYSKILGCTQEE MSKKDIYSVIKKGYYDIIFDND VVTDAKLS KGELSKFKDDFFNL
Cas12L_4_67031163           LKYSKILGCTQEE MSKKDIYSVIKKGYYDIIFDND VVTDAKLS KGELSKFKDDFFNL
Cas12L_5_67793351           LKYSKILGCTQEE MSKKDIYSVIKKGYYDIIFDND VVTDAKLS KGELSKFKDDFFNL
Cas12L_6_67912869_partial   LNFSKVLGHT SE LETLPINDVVKKGYYAF IDNEG ITDA LS KGKVPKMKDDFFNQ
Cas12L_7_68090316_partial   LKYSKILGCTQEE MSKKDIYSVIKKGYYDIIFDND VVTDAKLS KGELSKFKDDFFNL
Cas12L_8_68328292_partial   LKYSKILGCTQEE MSKKDIYSVIKKGYYDIIFDND VVTDAKLS KGELSKFKDDFFNL
Cas12L_9_68454124           LKYSKILGCTQEE MSKKDIYSVIKKGYYDIIFDND VVTDAKLS KGELSKFKDDFFNL
Cas12L_10_68605313          LKYSKILGCTQEE MSKKDIYSVIKKGYYDIIFDND VVTDAKLS KGELSKFKDDFFNL
Cas12L_11_69266821_partial
Cas12L_12_69417229_partial
Cas12L_13_69733214          LKYSKILGCTQEE MSKKDIYSVIKKGYYDIIFDND VVTDAKLS KGELSKFKDDFFNL
Cas12L_14_70235246_partial  LKYSKILGCTQEE MSKKDIYSVIKKGYYDIIFDND VVTDAKLS KGELSKFKDDFFNL
Cas12L_15_70724743          LKYSKILGCTQEE MSKKDIYSVIKKGYYDIIFDND VVTDAKLS KGELSKFKDDFFNL
Cas12L_16_70731038          LNFSKVLGHT SE LETLPINDVVKKGYYIF IDNEG ITDA LS KGKVPKMKDDFFNQ
Cas12L_17_70959391          LKYSKILGCTQEE MSKKDIYSVIKKGYYDIIFDND VVTDAKLS KGELSKFKDDFFNL
Cas12L_18_71078086          LKYSKILGCTQEE MSKKDIYSVIKKGYYDIIFDN VVTDAKLS KGELSKFKDDFFNL
Cas12L_19_71193509_partial  LKYSKILGCTQEE MSKKDIYSVIKKGYYDIIFDND VVTDAKLS KGELSKFKDDFFNL
Cas12L_20_71210958_partial  LNFSKVLGHT SE LETLPINDVVKKGYYIF IDNEG ITDA LS KGKVPKMKDDFFNQ
Cas12L_21_71317321_partial  LKYSKILGCTQEE MSKKDIYSVIKKGYYDIIFDND VVTDAKLS KGELSKFKDDFFNL
Cas12L_22_71456687          LKYSKILGCTQEE MSKKDIYSVIKKGYYDIIFDND VVTDAKLS KGELSKFKDDFFNL
Cas12L_23_71708971          LKYSKILGCTQEE MSKKDIYSVIKKGYYDIIFDND VVTDAKLS KGELSKFKDDFFNL
Cas12L_24_46035167_partial  LKYSKILGCTQEE MSKKDIYSVIKKGYYDIIFDND VVTDAKLS KGELSKFKDDFFNL
Cas12L_25_46784254_partial  LKYSKILGCTQEE MSKKDIYSVIKKGYYDIIFDND VVTDAKLS KGELSKFKDDFFNL
Cas12L_26_46464451          LKYSKILGCTQEE MSKKDIYSVIKKGYYDIIFDNG VV DAKLSA KGELSKFKDDFFNL
Cas12L_27_254489164         LKYSKILGCTQEE MSKKDIYSVIKKGYYDIIFDND VVTDAKLS KGELSKFKDDFFNL
Cas12L_28_255238293         LKYSKLKGKTMEE VMSII SVKSLIEKEYDFS NDNK VEN IT YTK GLMKK FDEFFNL
Cas12L_29_72167294          LKYSKILGCTQEE MSKKDIYSVIKKGYYDIIFDND VVTDAKLS KGELSKFKDDFFNL
Cas12L_30_72369269          LKYSKILGCTQEE MSKKDIYSVIKKGYYDIIFDND VVTDAKLSA KGELSKFKDDFFNL
Cas12L_31_72503976          LKYSKILGCTQEE MSKKDIYSVIKKGYYDIIFDND VVTDAKLS KGELSKFKDDFFNL
Cas12L_32_72547654_partial
Cas12L_33_72907394          LKYSKILGCTQEE MSKKDIYSVIKKGYYDIIFDND VVTDAKLS KGELSKFKDDFFNL
Cas12L_34_73124743_partial  LKYSKILGCTQEE MSKKDIYSVIKKGYYDIIFDND VVTDAKLS KGELSKFKDDFFNL
Cas12L_35_73503649_partial  LKYSKILGCTQEE MSKKDIYSVIKKGYYDIIFDND VVTDAKLS KGELSKFKDDFFNL
Cas12L_36_73503649_partial
Cas12L_37_73472625          LKKQRVEGYTINE LKDKSVFKFIKRGYYIFDFDLDN KITGVQFSD AGEVVNME ELRNL
Cas12L_38_73764039_partial  LKYSKILGCTQEE MSKKDIYSVIKKGYYDIIFDND VVTDAKLS KGELSKFKDDFFNL
Cas12L_39_73877227          LKYSKILGCTQEE MSKKDIYSVIKKGYYDIIFDND VVTDAKLS KGELSKFKDDFFNL
Cas12L_40_74037305          LKYSKILGCTQEE MSKKDIYSVIKKGYYDIIFDND VVTDAKLS KGELSKFKDDFFNL
Cas12L_41_74408273_partial  LKYSKILGCTQEE MSKKDIYSVIKKGYYDIIFDNG VVTDAKLS KGELSKFKDDFFNL
Cas12L_42_75186079_partial  LKYSKILGCTREE MSKKDIYSVIKKGYYDIIFDND VVTDAKLS KGELSKFKDDFFNL
Cas12L_43_75257103_partial                                                   GS IQF
Cas12L_44_75257103_partial  LKYSKILGCTQEE MSK        KKGYYDIIFDND VVTDAKLS KGELSKFKDDFFNL
Cas12L_45_75616607_partial  LKYSKILGCTQEE MSKKDIYSVIKKGYYDIIFDNG VVTDAKLS KGELSKFKDDFFNL
Cas12L_46_75784289_partial  LKYSKILGCTQEE MSKKDIYSVIKKGYYDIIFDNG VV DAKLSA KGELSKFKDDFFNL
Cas12L_47_76512228          LKYSKILGCTQEE MSKKDIYSVIKKGYYDIIFDND VVTDAKLS KGELSKFKDDFFNL
Cas12L_48_76600450          LKYSKILGCTQEE MSKKDIYSVIKKGYYDIIFDND VVTDAKLS KGELSKFKDDFFNL
Cas12L_49_44880081          LKYSKILGCTQEE MSKKDIYSVIKKGYYDIIFDND VVTDAKLS KGELSKFKDDFFNL
Cas12L_50_83012613          LNFSKVLGHT SE LG LPIND VVKKGYYIF IDNE ITDA LS KGKVRKMKDDFFNQ
Cas12L_51_82983331          LKYSRVEGHTIEE KREMKIYDVVKKGYYNFIVKKN I IDA LT KGVINIEAEFYNF
Cas12L_52_76767885          LNFSKVLGHT SE LETLPINDVVKKGYYIF IDNEG ITDA LS KGKVPKMKDDFFNQ
Cas12L_53_77216451          LKYSKILGCTQEE MSKKDIYSVIKKGYYDIIFDND VVTDAKLS KGELSKFKDDFFNL
Cas12L_54_77468912_partial
Cas12L_55_77738117          LSYSKVLGKTNEE IEKLDVYSVIKKGYYIFFYKDG EVVNAKLSK GENIKIK MFNM
Cas12L_56_65286425          LKYSKILGCTQEE MSKKDIYSVIKKGYYDIIFDND VVTDAKLS KGELSKFKDDFFNL
Cas12L_57_65567118_partial  LKYSKINGCTQEE MSKKDIYSVIKKGYYDIIFDND VVTDAKLS KGELSKFKDDFFNL
Cas12L_58_66287853_partial  LKYSKILGCTQEE MSKKDIYSVIKKGYYDIIFDND VVTDAKLS KGELSKFKDDFFNL
```

Figure 5P:
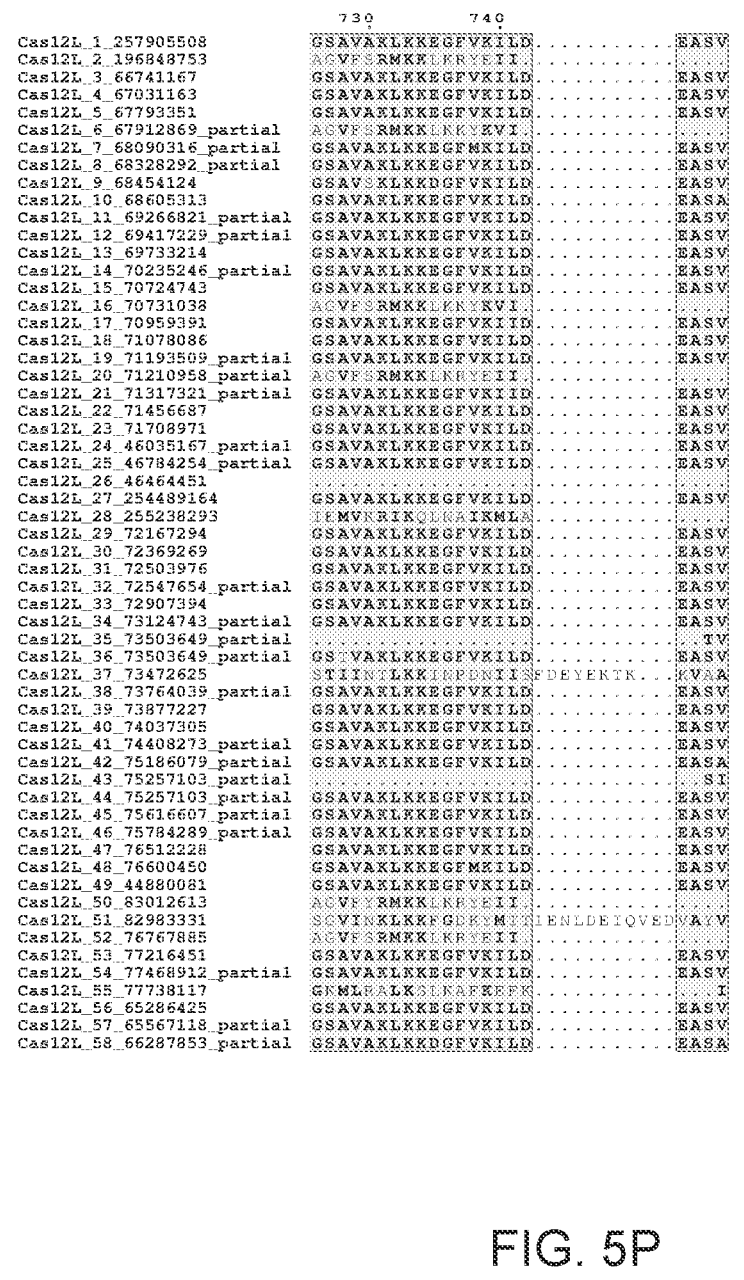

```
                                        730          740
Cas12L_1_257905508            GSAVAKLKKEGFVKILD.......... EASV
Cas12L_2_196848753            ACVFSRMKKLKRYEII...........
Cas12L_3_66741167             GSAVAKLKKEGFVKILD.......... EASV
Cas12L_4_67031163             GSAVAKLKKEGFVKILD.......... EASV
Cas12L_5_67793351             GSAVAKLKKEGFVKILD.......... EASV
Cas12L_6_67912869_partial     ACVFSRMKKLKKYRVI...........
Cas12L_7_68090316_partial     GSAVAKLKKEGFMKILD.......... EASV
Cas12L_8_68328292_partial     GSAVAKLKKEGFVKILD.......... EASV
Cas12L_9_68454124             GSAVSKLKKDGFVKILD.......... EASV
Cas12L_10_68605313            GSAVAKLKKEGFVKILD.......... EASA
Cas12L_11_69266821_partial    GSAVAKLKKEGFVKILD.......... EASV
Cas12L_12_69417229_partial    GSAVAKLKKEGFVKILD.......... EASV
Cas12L_13_69733214            GSAVAKLKKEGFVKILD.......... EASV
Cas12L_14_70235246_partial    GSAVAKLKKEGFVKILD.......... EASV
Cas12L_15_70724743            GSAVAKLKKEGFVKILD.......... EASV
Cas12L_16_70731038            ACVFSRMKKLKKYRVI...........
Cas12L_17_70959391            GSAVAKLKKEGFVKIID.......... EASV
Cas12L_18_71078086            GSAVAKLKKEGFVKILD.......... EASV
Cas12L_19_71193509_partial    GSAVAKLKKEGFVKILD.......... EASV
Cas12L_20_71210958_partial    ACVFSRMKKLKRYEII...........
Cas12L_21_71317321_partial    GSAVAKLKKEGFVKIID.......... EASV
Cas12L_22_71456687            GSAVAKLKKEGFVKILD.......... EASV
Cas12L_23_71708971            GSAVAKLKKEGFVKILD.......... EASV
Cas12L_24_46035167_partial    GSAVAKLKKEGFVKILD.......... EASV
Cas12L_25_46784254_partial    GSAVAKLKKEGFVKILD.......... EASV
Cas12L_26_46464451            .......... .
Cas12L_27_254489164           GSAVAKLKKEGFVKILD.......... EASV
Cas12L_28_255238293           IEMVKRIKQLKAIKMLA...........
Cas12L_29_72167294            GSAVAKLKKEGFVKILD.......... EASV
Cas12L_30_72369269            GSAVAKLKKEGFVKILD.......... EASV
Cas12L_31_72503976            GSAVAKLKKEGFVKILD.......... EASV
Cas12L_32_72547654_partial    GSAVAKLKKEGFVKILD.......... EASV
Cas12L_33_72907394            GSAVAKLKKEGFVKILD.......... EASV
Cas12L_34_73124743_partial    GSAVAKLKKEGFVKILD.......... EASV
Cas12L_35_73503649_partial    .......... .TV
Cas12L_36_73503649_partial    GSTVARLKKEGFVKILD.......... EASV
Cas12L_37_73472625            STIINTLKKIMPDNIISFDEYEKTK...KVAA
Cas12L_38_73764039_partial    GSAVAKLKKEGFVKILD.......... EASV
Cas12L_39_73877227            GSAVAKLKKEGFVKILD.......... EASV
Cas12L_40_74037305            GSAVAKLKKEGFVKILD.......... EASV
Cas12L_41_74408273_partial    GSAVAKLKKEGFVKILD.......... EASV
Cas12L_42_75186079_partial    GSAVAKLKKEGFVKILD.......... EASA
Cas12L_43_75257103_partial    .......... SI
Cas12L_44_75257103_partial    GSAVAKLKKEGFVKILD.......... EASV
Cas12L_45_75616607_partial    GSAVAKLKKEGFVKILD.......... EASV
Cas12L_46_75784289_partial    GSAVAKLKKEGFVKILD.......... EASV
Cas12L_47_76512228            GSAVAKLKKEGFVKILD.......... EASV
Cas12L_48_76600450            GSAVAKLKKEGFMKILD.......... EASV
Cas12L_49_44880081            GSAVAKLKKEGFVKILD.......... EASV
Cas12L_50_83012613            ACVFSRMKKLKRYEII...........
Cas12L_51_82983331            SCVINKLKKFGDKYMTIENLDEIQVEDVAYV
Cas12L_52_76767885            ACVFSRMKKLKRYEII...........
Cas12L_53_77216451            GSAVAKLKKEGFVKILD.......... EASV
Cas12L_54_77468912_partial    GSAVAKLKKEGFVKILD.......... EASV
Cas12L_55_77738117            GKMLEALKSLKAFKEFK.......... I
Cas12L_56_65286425            GSAVAKLKKEGFVKILD.......... EASV
Cas12L_57_65567118_partial    GSAVAKLKKEGFVKILD.......... EASV
Cas12L_58_66287853_partial    GSAVAKLKKDGFVKILD.......... EASA
```

Figure 6A:
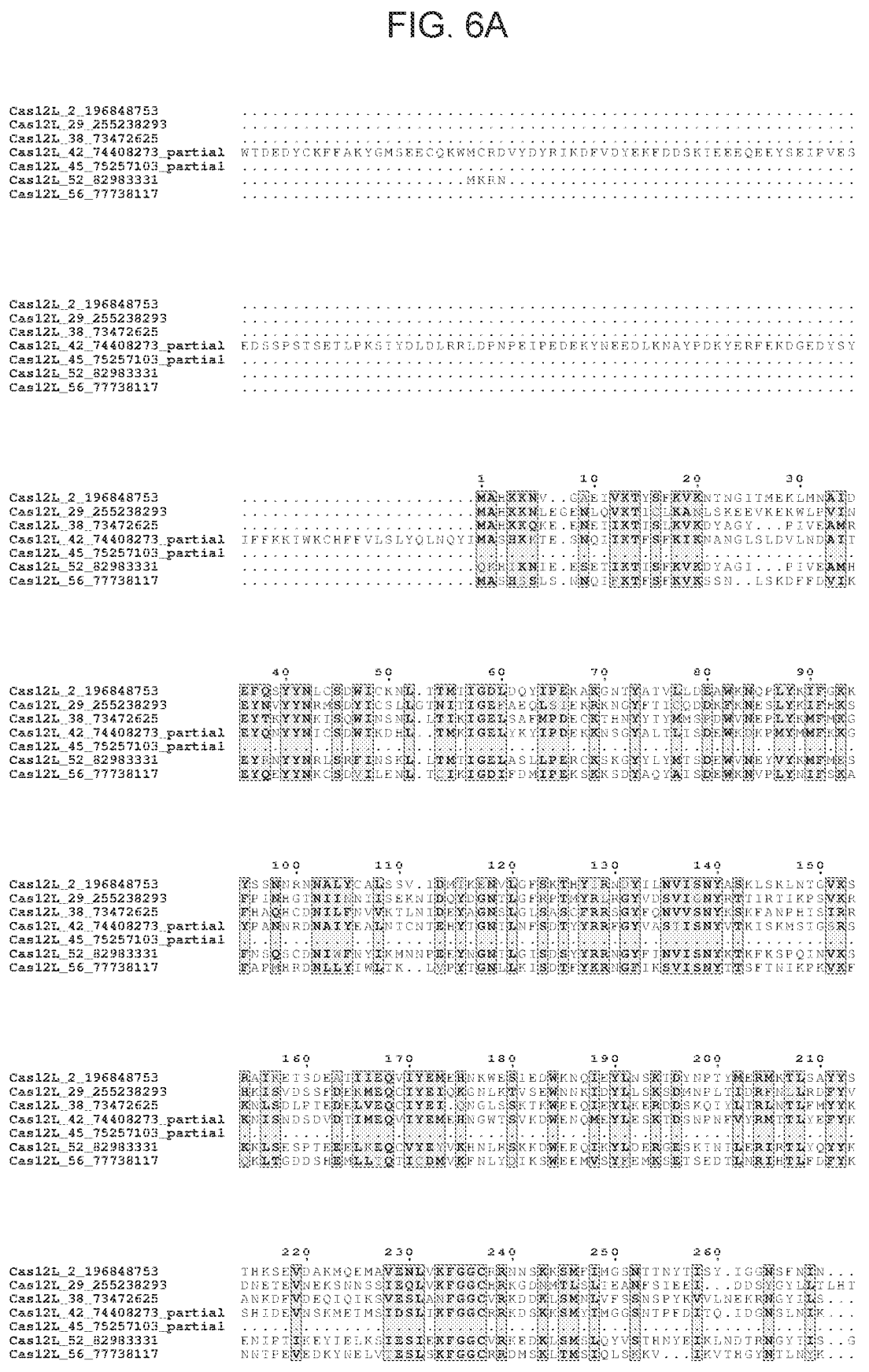

```
Cas12L_2_196848753
Cas12L_29_255238293
Cas12L_38_73472625
Cas12L_42_74408273_partial    WTDEDYCKFFAKYGMSEECQKWMCRDVYDYRIKDFVDYEKFDDSKIEEEQEEYSEIPVES
Cas12L_45_75257103_partial
Cas12L_52_82983331                                              MKRN
Cas12L_56_77738117

Cas12L_2_196848753
Cas12L_29_255238293
Cas12L_38_73472625
Cas12L_42_74408273_partial    EDSSPSTSETLPKSIYDLDLRRLDPNPEIPEDEKYNEEDLKNAYPDKYERFEKDGEDYSY
Cas12L_45_75257103_partial
Cas12L_52_82983331
Cas12L_56_77738117

1        10        20        30
Cas12L_2_196848753                          MAHKKNV..GREIVKTYSFKVKNTNGITMEKLMNAID
Cas12L_29_255238293                         MAFKKNLEGEKLQVRTICLKANLSKEEVKEKWLPVIN
Cas12L_38_73472625                          MAHKTQKE.ENEIIKTISLKADYAGY...PIVEAMR
Cas12L_42_74408273_partial    IFFKKIWKCHFFVLSLYQLNQYIMASBKITE.SKQIIKTFSFKISNANGLSLDVLNDAIT
Cas12L_45_75257103_partial
Cas12L_52_82983331                          QFHIKNIE.ESETIKTISFKVKDYAGI...PIVEAMH
Cas12L_56_77738117                          MASHSSLS.UNQIIKTFSFKVKSSN..LSKDFFDVIK 40        50        60        70        80        90
Cas12L_2_196848753            EFQSYYNLCSDWICKNL.ITKIIGDLDQYIPEKANGNTVATVLLDEAMKNQPLYKIFGRK
Cas12L_29_255238293          EYNVYYNRMSDYICSLIGTNITIGEHAEQLSIEKRKNGYFTICQDDKFANESLYKIFHKS
Cas12L_38_73472625          EYTKYYNKISQWINSNIL.ITIKIGELSAFMPDECRTHNKYTYMMSFDWVNEPLYKMFMRG
Cas12L_42_74408273_partial    EYQNYYRICSDWIKDHHI.TMKIGELYKYIPDEKRNSGYALTLISDENKQKPMYMMFKKG
Cas12L_45_75257103_partial
Cas12L_52_82983331          EYPNYYNRLSRFINSKHI.ITKIIGELASLLPERCKSKGKYLYKTSDEWVNEYVYKMFMES
Cas12L_56_77738117          EYQEYYNKCSDVILENL.TCIKIGDIFDMIPEKSSKSDYAQYAISDEWKNVPLYNIFSKA 100       110       120       130       140       150
Cas12L_2_196848753            YSSNRNNALYCALS SV.ID4IKERVLGFSKTHYIRNDYILNVISNYASKLSKLNTCVKS
Cas12L_29_255238293          FPINHGINIINIISEKNIDQYDGNTLGFRNPIYRLRGYVDSVICNYRTIRTIKPSVKR
Cas12L_38_73472625          FHAQHCDNILFNVVKTLNIDFYAGNSLGLSASFRRSGYFQNVVSNYKSKFANPHISIER
Cas12L_42_74408273_partial    YPANNRDNAIYEALNTCNTEHYTGKILNFSDTYRRFGYVASIISNYVTKISKMSIGSRS
Cas12L_45_75257103_partial
Cas12L_52_82983331          FNSQGCDNIKFNYIKMNNPEFYNGKILGISDSYRRNGYFINVISNXTKFKSPQINVKS
Cas12L_56_77738117          FAPKRRDNLLYIWLTK..LKPKTGNLLKISDTFYKRNGTIKSVISMYRTSFTNIKPKVKF 160       170       180       190       200       210
Cas12L_2_196848753            RAYNEISDEAIIIEQVIYEMERNKWESIEDRKNQPEYLNSKIDYNPTYMERMKTLSAYYS
Cas12L_29_255238293          HKISVDSSFDEKMSQCIYEIQKGNLKTVSEWNNKIDYLLSKSDMNPLTIDRFNLLRDFYV
Cas12L_38_73472625          KNLSDLPTEDELVEQCIYEIQNGLSSKTKMEEQEEYLKERDDSKQIYLRLNTLFMYYK
Cas12L_42_74408273_partial    KNISNDSDVDTIMEQVIYEMERNGWTSVKDMENQMEYLESKTDSNPNFMVRNTTLYEFYK
Cas12L_45_75257103_partial
Cas12L_52_82983331          KNLSESPTEEELKEQCVYEYVKHNLRSKKDMEEQIRYLDERGESKTNILERIRTLYQYYK
Cas12L_56_77738117          QKLTGDDSHEMLLIQTICDMVKFNLYDIKSMEEMVSYIFEMKSETSEDTLNRIHTLFDYYK 220       230       240       250       260
Cas12L_2_196848753            THKSEVDAKMQEMAVENLVKFGGCRNNSKKSKFIMGSNTTNYTKSY.IGGKSFNIN...
Cas12L_29_255238293          DNETEVNEKSNNSSISQLVKFGGCHKGDMTLSLIEANFSIEEI...DDSKCYLTLHT
Cas12L_38_73472625          ANKDFVDEQIQIKSVESLANFGGCKDDKLSNNLVFSSNSPYKVVLNEKRMGYILS...
Cas12L_42_74408273_partial    SHIDEVDNSKMETMSIDSLIKFGGCRRKDSKFSMYIMGGSNTPFDITQ.IDGNSLNIK...
Cas12L_45_75257103_partial
Cas12L_52_82983331          ENIPTIKEYIELKSIESIFKFGGCVRKEDKLSMSLQYVSTHNYEIKLNDTRNGYIKS..G
Cas12L_56_77738117          NNTPEVEDKYNELVKESLSKFGGCRBDMSKLTKSIQLSKKV...IKVTHGYNTLNKK...
```

FIG. 6B

```
                    270       280       290       300       310       320
Cas12L_2_196848753        FANILNFDVYGRRDVVKNGEVLVDIMA.NHGDSIVLKIVNG.ELYADVPCSVIENR.VES
Cas12L_29_255238293       DSGDYKIPLMGSKMLKGDKCLIDFVNCKKGKSLTAKIDMDYNLYFHVVYSMFEKIEDD
Cas12L_38_73472625        YSNNFSIELYGNRMGLLNGVEVFNVGD.KHSNNIFFMDMD.ELFVNIPVSVNFVK.KAN
Cas12L_42_74408273_partial FSKNLNVDVFGRYDVIKDNTILVDIIN.GHGASFVLKIIMD.EIYIDINVSVPFDK.KIA
Cas12L_45_75257103_partial ......................................................
Cas12L_52_82983331        ISKDLSFEVYGNRMGLLGGEEILNIPE.KHSTSIFVMRMN.SLYVDIPVAVPFSK.VIN
Cas12L_56_77738117        YGKLIDLELWGRKDIINNDELLINLE..NVCEMIVFKIKMG.EIYVDIPFKVDFIK.KDQ 330       340       350       360       370       380
Cas12L_2_196848753        NFD.KVVGIDVNMKHMLLSTSITDNG.SSDFLNIYKEMSNRAEFMALCPEEDRKYYKDIS
Cas12L_29_255238293       NIN.KVVGVDVNKKHMLLMTNVIDDN.IDGYVNIYKALVNDDEFKSLVIKSEYDDYVMS
Cas12L_38_73472625        EIN.KVVGVDVNLKKSIFATNIIDDGKLDGFVNIYRELLNDVDFVKSCPHELLNFILDVE
Cas12L_42_74408273_partial TTN.KVVGVDVNKIKHMLLATNIIDDGNVNGYVNIYKEVINDSDFKKVCNSTVMKYFTDFS
Cas12L_45_75257103_partial ......................................................
Cas12L_52_82983331        DCDGKIVGIDVNLKRALFATSEVDNGQFYDYVNVYAELLKDEKFVKVCHKELLDYIKDVS
Cas12L_56_77738117        TID.KIAGVDANIKHMLLSTSVKDEN.LIGYINIYKEVINDSDEQKVCDNKTMKILQEIS 390       400       410       420       430
Cas12L_2_196848753        KYVIFAPLELDLLFSRISKQGKV..........KMEKVYSEILEALKWKFFANGDMKNRI
Cas12L_29_255238293       KYVIFCPIELKYLYARXCVQKDYPI...SNKDVAIEQCISRVIDKLCKEIL...DSRANN
Cas12L_38_73472625        KYAFFMPLELGLLSSRVMNQCGYSTIGKYKLDGFVNIYRELLNDVDFVKSCPHELLNFIL
Cas12L_42_74408273_partial KFVIFCPLEFDFLFSRVCNQKGI.....YNDNSAMEKSFSDVLNKLKWNFIETGDMTHRI
Cas12L_45_75257103_partial ......................................................
Cas12L_52_82983331        KYVFFAPIELNLLLSRVMKQKGYENIDNYKKLYFVEEAYLCVLDKLQKRFIDEGNMTKRI
Cas12L_56_77738117        KYVIFAPIEFDMLFSRISKQREM.....KDKYINMEIAFTNVLNKLKQKFIVNSDNKNRI 440       450       460       470       480
Cas12L_2_196848753        YVESIQKIRQQIRALCVIKNAYYEQQSKYDI.....DK.TQEYIET.......HPFSLTE
Cas12L_29_255238293       YLCMVHRIRHIYKSYYFLKMTKYDKMSEYDTNMEYNDI.SITSKETMDQRRFENSFKETD
Cas12L_38_73472625        YIENVIKMRAQVKAYFTLKYAYNKANKDYDLKMGFVDE.STANKETMDQRRFENQFVNTY
Cas12L_42_74408273_partial YIENVMKLFSQMKAYAIVKNAYYKQQSKYDF.....GK.SEEFIQE.......HPFSNTD
Cas12L_45_75257103_partial ......................................................
Cas12L_52_82983331        YIENLKKMRAQMKAYYILKDIYSKYQKDYDIEMGFVDE.STESKETMDARRSENPFKRSTD
Cas12L_56_77738117        YIESILKIRSQLKSYAILEEVKYKKASEYDS..AIVKEFCVEYLET.......HPFKDTE 490       500       510       520       530       540
Cas12L_2_196848753        KGMSIKSKMDKICQIIIGCRNNIILYAYSFFERNGYSIIG.KTTSQFEINSMTIN
Cas12L_29_255238293       CAKEILSKLDKIGNDILGCRNNILIYAYKLFEELGYDIIA.NESQFDVSLSCQ
Cas12L_38_73472625        TAKEILGFMPRIANVITSCRNNIICYMYKIFENGYGVVA.KQSQHFFRISLI
Cas12L_42_74408273_partial KGIEILNKLDMISKKILGCRNNIIQYSYNLFENGYDMIS.KTSQFFPFFTVN
Cas12L_45_75257103_partial ................MISKKILGCRNNIIQYSYNLFENGYDMIS.KTSQFFPFFTVN
Cas12L_52_82983331        IAQDILFKMNNVGKTVEACRNNIIAYIYKVFESDFATIV.KQSQMKSRISTVN
Cas12L_56_77738117        TYKEINKKILNISENIIGCRNNIIQIAYKIFENGFDMIS.TNMFKRENMLTIK 550       560       570       580       590       600
Cas12L_2_196848753        LSNFHKVLKHLSN.LETLPIND VVKKG.TFITDNEGKITDASLSEK.FVKMKDDFF
Cas12L_29_255238293       MIKYHKLEKKMEVMSNTSVKSLIEKG.DFSLNDNKTVENITYTKN.LMKKCPDEFF
Cas12L_38_73472625        LIKKQRVELYINK.LKDKSVFKFIERG.IFDFDDDNKITCVQFSDA.FMVKMETELH
Cas12L_42_74408273_partial LIKYKKILCKQEL.MEKKDIYSVIKKG.DIIFDN.GVKIDAKLSTIKFELSKFKDDFF
Cas12L_45_75257103_partial LIKYKKILCKQEL.MEK.......KKG.DIIFDN.DVKIDAKLSTIKFELSKFKDDFF
Cas12L_52_82983331        LIKYHKVEHHIEL.TKEMKIYDVVFKG.NFIVNEKNEIIDATLTDK.KVIKIEAEFY
Cas12L_56_77738117        LIKIRKVLKKNEL.IEKLDVYSVIKKG.TFEYKD.GKVVRAKLSEIKEKIKIKTIMF 610       620       630       640       650
Cas12L_2_196848753        QAIQ...DVKYKATS...QGIFF....QFSNTHKLYF.ENAKNGCLKLAFK
Cas12L_29_255238293       LFM...DIYKLQFY...SVKVIL.YIF.SSNHSIYM.EKSKNDKLVFASK
Cas12L_38_73472625        LALT...DAKYVTS...SVSVAL.QFSTKHVLYA.KKNNFGKLGIVSE
Cas12L_42_74408273_partial LMIS...DIYYITS...TAGVSL.YFSIDHKIYFVQDNFSGKLKLANK
Cas12L_45_75257103_partial LMIS...DIYYITS...TAGVSL.YFSIDHKIYFVQDNFSGKLKLANK
Cas12L_52_82983331        FALS...DAYIITS...SVNIAL.QFSIRHAIFV.TKGFKGKKVIVDK
Cas12L_56_77738117        MKIS...EIYKITS...EVGVSL.YKSTDHKVFG.LLSKKGKWTLYDK
```

FIG. 6C

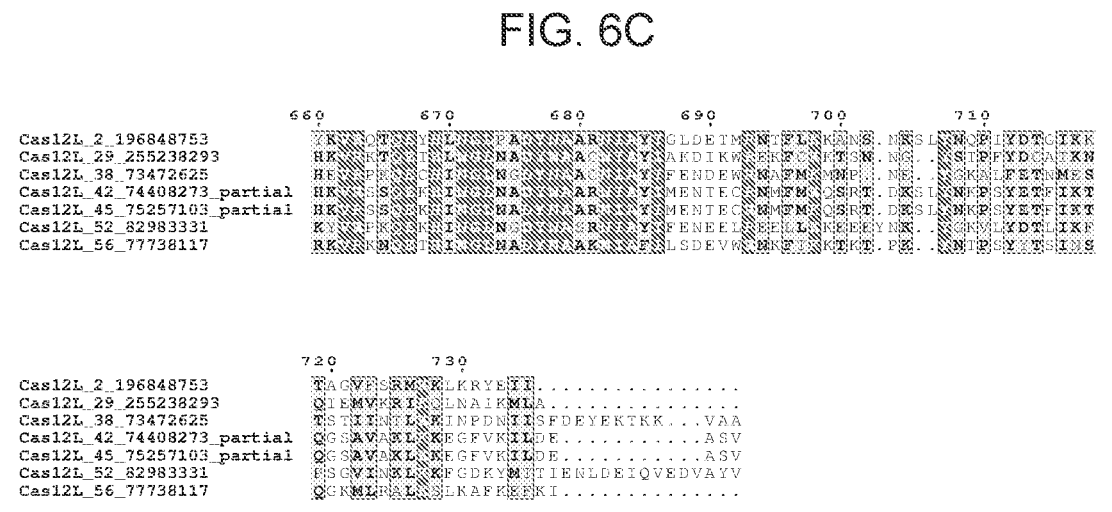

```
                      660          670          680          690          700          710
Cas12L_2_196848753         
Cas12L_29_255238293        
Cas12L_38_73472625         
Cas12L_42_74408273_partial 
Cas12L_45_75257103_partial 
Cas12L_52_82983331         
Cas12L_56_77738117

720          730
Cas12L_2_196848753         
Cas12L_29_255238293        
Cas12L_38_73472625         
Cas12L_42_74408273_partial 
Cas12L_45_75257103_partial 
Cas12L_52_82983331         
Cas12L_56_77738117         
```

Casλ1 (SEQ ID NO:59)

Casλ2 (SEQ ID NO:60)

Casλ6 (SEQ ID NO:164)

Casλ16 (SEQ ID NO:61)

Casλ20_52 (SEQ ID NO:68)

Casλ28 (SEQ ID NO:63)

Casλ29 (SEQ ID NO:64)

Casλ37 (SEQ ID NO:70)

Casλ42 (SEQ ID NO:163)

Casλ47 (SEQ ID NO:65)

Casλ50 (SEQ ID NO:66)

Casλ51 (SEQ ID NO:67)

Casλ55 (SEQ ID NO:69)

FIG. 9

CRISPR-Cas EFFECTOR POLYPEPTIDES AND METHODS OF USE THEREOF

CROSS-REFERENCE

This application is a national stage application under 35 U.S.C. § 371 of PCT/US2020/066672, filed Dec. 22, 2022, which claims the benefit of U.S. Provisional Patent Application No. 62/952,909, filed Dec. 23, 2019, which applications are incorporated herein by reference in their entirety.

INTRODUCTION

CRISPR-Cas systems include Cas proteins, which are involved in acquisition, targeting and cleavage of foreign DNA or RNA, and a guide RNA(s), which includes a segment that binds Cas proteins and a segment that binds to a target nucleic acid. For example, Class 2 CRISPR-Cas systems comprise a single Cas protein bound to a guide RNA, where the Cas protein binds to and cleaves a targeted nucleic acid. The programmable nature of these systems has facilitated their use as a versatile technology for use in modification of target nucleic acid.

SUMMARY

The present disclosure provides RNA-guided CRISPR-Cas effector proteins, nucleic acids encoding same, and compositions comprising same. The present disclosure provides ribonucleoprotein complexes comprising: an RNA-guided CRISPR-Cas effector protein of the present disclosure; and a guide RNA. The present disclosure provides methods of modifying a target nucleic acid, using an RNA-guided CRISPR-Cas effector protein of the present disclosure and a guide RNA.

BRIEF DESCRIPTION OF THE DRAWINGS

FIGS. 2A-2Z, 2AA-2ZZ, and 2AAA-2FFF provide amino acid sequences of Cas12L polypeptides.

FIG. 3A-3B provide the locations of active site residues of the RuvC-I, RuvC-II, and RuvC-III domains of Cas12L polypeptides.

FIG. 6A-6C provide an alignment of amino acid sequences of selected Cas12L polypeptides depicted in FIGS. 2A-2Z, 2AA-2ZZ, and 2AAA-2FFF (from top to bottom SEQ ID NOs: 158-161, 142-144).

FIG. 9 depicts the results of a PAM analysis.

DEFINITIONS

Figure 1:
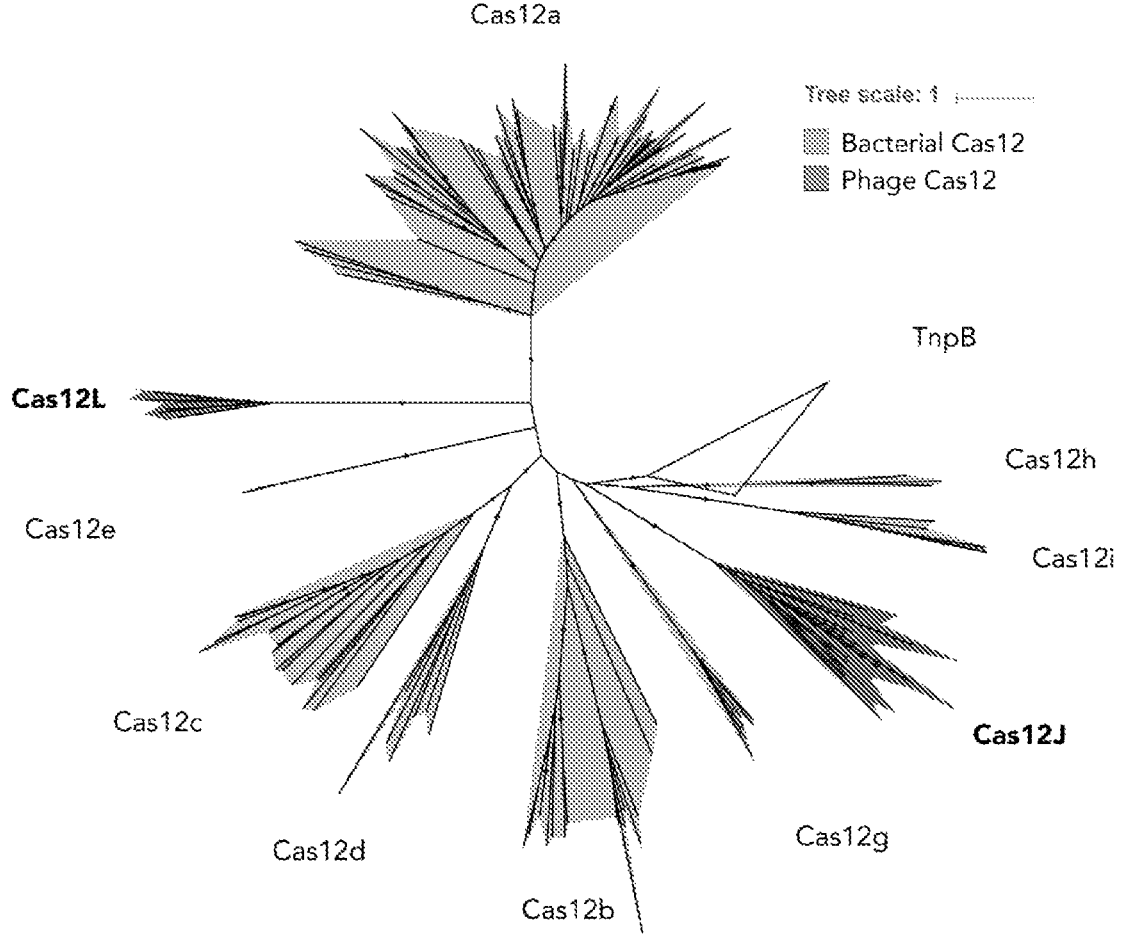
FIG. 1 presents a maximum Likelihood phylogenetic tree of the Cas12 superfamily, produced from a multiple sequence alignment with 1000 iterations. Cas12L forms a distinct clade separate from other Cas12 proteins.
Figure 4:
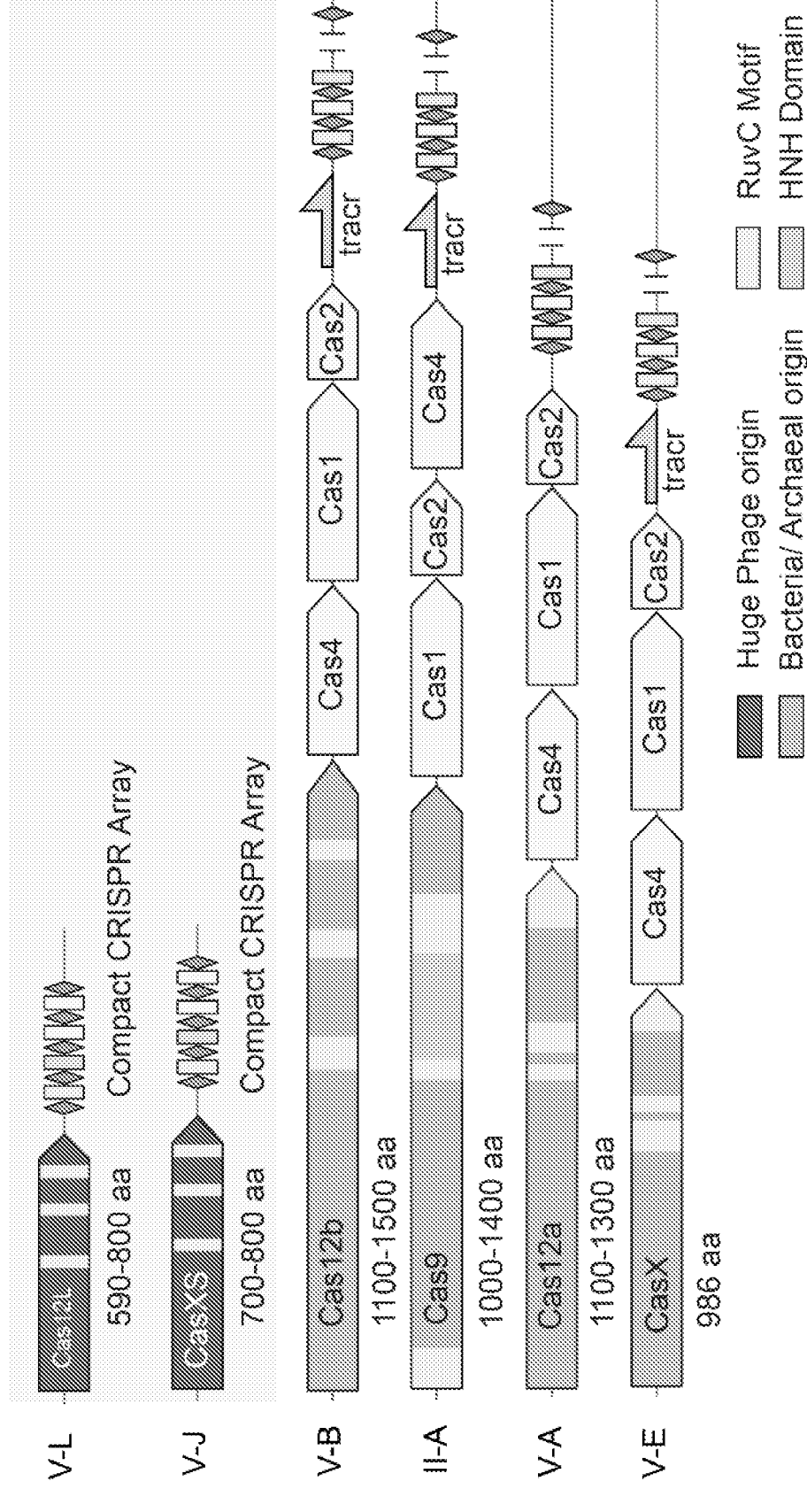
FIG. 4 depicts CRISPR locus architecture with active sites annotated.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a DNA target nucleic acid base pairs with a guide RNA, etc.): guanine (G) can also base pair with uracil (U). For example, G/U base-pairing is at least partially responsible for the degeneracy (i.e., redundancy) of the genetic code in the context of tRNA anti-codon base-pairing with codons in mRNA. Thus, in the context of this disclosure, a guanine (G) (e.g., of dsRNA duplex of a guide RNA molecule; of a guide RNA base pairing with a target nucleic acid, etc.) is considered complementary to both a uracil (U) and to an adenine (A). For example, when a G/U base-pair can be made at a given nucleotide position of a dsRNA duplex of a guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybrid-
izations between nucleic acids with short stretches of
complementarity (e.g. complementarity over 35 or less, 30
or less, 25 or less, 22 or less, 20 or less, or 18 or less
nucleotides) the position of mismatches can become important (see Sambrook et al., supra, 11.7-11.8). Typically, the
length for a hybridizable nucleic acid is 8 nucleotides or
more (e.g., 10 nucleotides or more, 12 nucleotides or more,
15 nucleotides or more, 20 nucleotides or more, 22 nucleo-
tides or more, 25 nucleotides or more, or 30 nucleotides or
more). Temperature, wash solution salt concentration, and
other conditions may be adjusted as necessary according to
factors such as length of the region of complementation and
the degree of complementation.

It is understood that the sequence of a polynucleotide
need not be 100% complementary to that of its target nucleic
acid to be specifically hybridizable or hybridizable. More-
over, a polynucleotide may hybridize over one or more
segments such that intervening or adjacent segments are not
involved in the hybridization event (e.g., a bulge, a loop
structure or hairpin structure, etc.). A polynucleotide can
comprise 60% or more, 65% or more, 70% or more, 75% or
more, 80% or more, 85% or more, 90% or more, 95% or
more, 98% or more, 99% or more, or 99.5% or more, or 100%
sequence complementarity to a target region within the
target nucleic acid sequence to which it will hybridize. For
example, an antisense nucleic acid in which 18 of 20
nucleotides of the antisense compound are complementary
to a target region, and would therefore specifically hybrid-
ize, would represent 90 percent complementarity. In this
example, the remaining noncomplementary nucleotides may
be clustered or interspersed with complementary nucleotides
and need not be contiguous to each other or to complemen-
tary nucleotides. Percent complementarity between particu-
lar stretches of nucleic acid sequences within nucleic acids
can be determined using any convenient method. Example
methods include BLAST programs (basic local alignment
search tools) and PowerBLAST programs (Altschul et al., J.
Mol. Biol., 1990, 215, 403-410; Zhang and Madden,
Genome Res., 1997, 7, 649-656), the Gap program (Wisconsin Sequence Analysis Package, Version 8 for Unix,
Genetics Computer Group, University Research Park, Madi-
son Wis.), e.g., using default settings, which uses the algo-
rithm of Smith and Waterman (Adv. Appl. Math., 1981, 2,
482-489), and the like.

The terms "peptide," "polypeptide," and "protein" are
used interchangeably herein, and refer to a polymeric form
of amino acids of any length, which can include coded and
non-coded amino acids, chemically or biochemically modi-
fied or derivatized amino acids, and polypeptides having
modified peptide backbones.

"Binding" as used herein (e.g. with reference to an
RNA-binding domain of a polypeptide, binding to a target
nucleic acid, and the like) refers to a non-covalent interac-
tion between macromolecules (e.g., between a protein and a
nucleic acid; between a Cas12L polypeptide/guide RNA
complex and a target nucleic acid; and the like). While in a
state of non-covalent interaction, the macromolecules are
said to be "associated" or "interacting" or "binding" (e.g.,
when a molecule X is said to interact with a molecule Y, it
is meant the molecule X binds to molecule Y in a non-
covalent manner). Not all components of a binding interac-
tion need be sequence-specific (e.g., contacts with phosphate
residues in a DNA backbone), but some portions of a
binding interaction may be sequence-specific. Binding interactions are generally characterized by a dissociation con-
stant ($K_D$) of less than $10^{-6}$ M, less than $10^{-7}$ M, less than $10^{-8}$ M, less than $10^{-9}$ M, less than $10^{-10}$ M, less than $10^{-11}$
M, less than $10^{-12}$ M, less than $10^{-13}$ M, less than $10^{-14}$ M,
or less than $10^{-15}$ M. "Affinity" refers to the strength of
binding, increased binding affinity being correlated with a
lower $K_D$.

By "binding domain" it is meant a protein domain that is
able to bind non-covalently to another molecule. A binding
domain can bind to, for example, a DNA molecule (a
DNA-binding domain), an RNA molecule (an RNA-binding
domain) and/or a protein molecule (a protein-binding
domain). In the case of a protein having a protein-binding
domain, it can in some cases bind to itself (to form homodi-
mers, homotrimers, etc.) and/or it can bind to one or more
regions of a different protein or proteins.

The term "conservative amino acid substitution" refers to
the interchangeability in proteins of amino acid residues
having similar side chains. For example, a group of amino
acids having aliphatic side chains consists of glycine, ala-
nine, valine, leucine, and isoleucine; a group of amino acids
having aliphatic-hydroxyl side chains consists of serine and
threonine; a group of amino acids having amide containing
side chains consisting of asparagine and glutamine; a group
of amino acids having aromatic side chains consists of
phenylalanine, tyrosine, and tryptophan; a group of amino
acids having basic side chains consists of lysine, arginine,
and histidine; a group of amino acids having acidic side
chains consists of glutamate and aspartate; and a group of
amino acids having sulfur containing side chains consists of
cysteine and methionine. Exemplary conservative amino
acid substitution groups are: valine-leucine-isoleucine, phe-
nylalanine-tyrosine, lysine-arginine, alanine-valine-glycine,
and asparagine-glutamine.

A polynucleotide or polypeptide has a certain percent
"sequence identity" to another polynucleotide or polypep-
tide, meaning that, when aligned, that percentage of bases or
amino acids are the same, and in the same relative position,
when comparing the two sequences. Sequence identity can
be determined in a number of different ways. To determine
sequence identity, sequences can be aligned using various
convenient methods and computer programs (e.g., BLAST,
T-COFFEE, MUSCLE, MAFFT, etc.), available over the
world wide web at sites including ncbi.nlm.nili.gov/BLAST,
ebi.ac.uk/Tools/msa/tcoffee/, ebi.ac.uk/Tools/msa/muscle/,
mafft.cbrc.jp/alignment/software/. See, e.g., Altschul et al.
(1990), J. Mol. Bioi. 215:403-10.

A DNA sequence that "encodes" a particular RNA is a
DNA nucleotide sequence that is transcribed into RNA. A
DNA polynucleotide may encode an RNA (mRNA) that is
translated into protein (and therefore the DNA and the
mRNA both encode the protein), or a DNA polynucleotide
may encode an RNA that is not translated into protein (e.g.
tRNA, rRNA, microRNA (miRNA), a "non-coding" RNA
(ncRNA), a guide RNA, etc.).

A "protein coding sequence" or a sequence that encodes
a particular protein or polypeptide, is a nucleotide sequence
that is transcribed into mRNA (in the case of DNA) and is
translated (in the case of mRNA) into a polypeptide in vitro
or in vivo when placed under the control of appropriate
regulatory sequences.

The terms "DNA regulatory sequences," "control ele-
ments," and "regulatory elements," used interchangeably
herein, refer to transcriptional and translational control
sequences, such as promoters, enhancers, polyadenylation
signals, terminators, protein degradation signals, and the
like, that provide for and/or regulate transcription of a
non-coding sequence (e.g., guide RNA) or a coding
sequence (e.g., RNA-guided endonuclease, GeoCas9 polypeptide, GeoCas9 fusion polypeptide, and the like) and/or regulate translation of an encoded polypeptide.

As used herein, a "promoter" or a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive expression by the various vectors of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism that can be isolated from a source in nature is naturally occurring.

The term "fusion" as used herein as applied to a nucleic acid or polypeptide refers to two components that are defined by structures derived from different sources. For example, where "fusion" is used in the context of a fusion polypeptide (e.g., a fusion Cas12L protein), the fusion polypeptide includes amino acid sequences that are derived from different polypeptides. A fusion polypeptide may comprise either modified or naturally-occurring polypeptide sequences (e.g., a first amino acid sequence from a modified or unmodified Cas12L protein; and a second amino acid sequence from a modified or unmodified protein other than a Cas12L protein, etc.). Similarly, "fusion" in the context of a polynucleotide encoding a fusion polypeptide includes nucleotide sequences derived from different coding regions (e.g., a first nucleotide sequence encoding a modified or unmodified Cas12L protein; and a second nucleotide sequence encoding a polypeptide other than a Cas12L protein).

The term "fusion polypeptide" refers to a polypeptide which is made by the combination (i.e., "fusion") of two otherwise separated segments of amino acid sequence, usually through human intervention.

"Heterologous," as used herein, means a nucleotide or polypeptide sequence that is not found in the native nucleic acid or protein, respectively. For example, in some cases, in a variant Cas12L protein of the present disclosure, a portion of naturally-occurring Cas12L polypeptide (or a variant thereof) may be fused to a heterologous polypeptide (i.e. an amino acid sequence from a protein other than a Cas12L polypeptide; or an amino acid sequence from another organism). As another example, a fusion Cas12L polypeptide can comprise all or a portion of a naturally-occurring Cas12L polypeptide (or variant thereof) fused to a heterologous polypeptide, i.e., a polypeptide from a protein other than a Cas12L polypeptide, or a polypeptide from another organism. The heterologous polypeptide may exhibit an activity (e.g., enzymatic activity) that will also be exhibited by the variant Cas12L protein or the fusion Cas12L protein (e.g., biotin ligase activity; nuclear localization; etc.). A heterologous nucleic acid sequence may be linked to a naturally-occurring nucleic acid sequence (or a variant thereof) (e.g., by genetic engineering) to generate a nucleotide sequence encoding a fusion polypeptide (a fusion protein).

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences"). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. An example of such a case is a DNA (a recombinant) encoding a wild-type protein where the DNA sequence is codon optimized for expression of the protein in a cell (e.g., a eukaryotic cell) in which the protein is not naturally found (e.g., expression of a CRISPR/Cas RNA-guided polypeptide such as Cas12L (e.g., wild-type Cas12L; variant Cas12L; fusion Cas12L; etc.) in a eukaryotic cell). A codon-optimized DNA can therefore be recombinant and non-naturally occurring while the protein encoded by the DNA may have a wild type amino acid sequence.

Thus, the term "recombinant" polypeptide does not necessarily refer to a polypeptide whose amino acid sequence does not naturally occur. Instead, a "recombinant" polypeptide is encoded by a recombinant non-naturally occurring DNA sequence, but the amino acid sequence of the polypeptide can be naturally occurring ("wild type") or non-naturally occurring (e.g., a variant, a mutant, etc.). Thus, a "recombinant" polypeptide is the result of human intervention, but may have a naturally occurring amino acid sequence.

A "vector" or "expression vector" is a replicon, such as plasmid, phage, virus, artificial chromosome, or cosmid, to which another DNA segment, i.e. an "insert", may be attached so as to bring about the replication of the attached segment in a cell.

An "expression cassette" comprises a DNA coding sequence operably linked to a promoter. "Operably linked"

refers to a juxtaposition wherein the components so described are in a relationship permitting them to function in their intended manner. For instance, a promoter is operably linked to a coding sequence (or the coding sequence can also be said to be operably linked to the promoter) if the promoter affects its transcription or expression.

The terms "recombinant expression vector," or "DNA construct" are used interchangeably herein to refer to a DNA molecule comprising a vector and an insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA or exogenous RNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al. Adv Drug Deliv Rev. 2012 Sep. 13. pii: 50169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "target nucleic acid" as used herein is a polynucleotide (e.g., DNA such as genomic DNA) that includes a site ("target site" or "target sequence") targeted by an RNA-guided endonuclease polypeptide (e.g., wild-type Cas12L; variant Cas12L; fusion Cas12L; etc.). The target sequence is the sequence to which the guide sequence of a subject Cas12L guide RNA (e.g., a dual Cas12L guide RNA or a single-molecule Cas12L guide RNA) will hybridize. For example, the target site (or target sequence) 5'-GAG-CAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the guide RNA is referred to as the "complementary strand" or "target strand"; while the strand of the target nucleic acid that is complementary to the "target strand" (and is therefore not complementary to the guide RNA) is referred to as the "non-target strand" or "non-complementary strand."

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events.

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.).

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov 6;282(5391):1145-7) whereas induced pluripotent stem cells (iPSCs) are derived from somatic cells (Takahashi et al., Cell. 2007 Nov. 30;131(5):

861-72; Takahashi et al., Nat Protoc. 2007; 2(12):3081-9; Yu et al., Science. 2007 Dec. 21;318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200, 806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos.

US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

In some instances, a component (e.g., a nucleic acid component (e.g., a Cas12L guide RNA); a protein component (e.g., wild-type Cas12L polypeptide; variant Cas12L polypeptide; fusion Cas12L polypeptide; etc.); and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels; e.g., a fluorescent label) and indirectly detectable labels (indirect labels; e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^{3}$H, $^{125}$I, $^{35}$S, $^{14}$C, or $^{32}$P); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplitt & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, humans, non-human primates, ungulates, felines, canines, bovines, ovines, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a Cas12L CRISPR-Cas effector polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides RNA-guided CRISPR-Cas effector proteins (referred to herein as "Cas12L" polypeptides or "CasLambda" polypeptides or "Cas," polypeptides), nucleic acids encoding same, and compositions comprising same. The present disclosure provides ribonucleoprotein complexes comprising: a Cas12L polypeptide of the present disclosure; and a guide RNA. The present disclosure provides methods of modifying a target nucleic acid, using a Cas12L polypeptide of the present disclosure and a guide RNA.

The present disclosure provides guide RNAs (referred to herein as "Cas12L guide RNAs" or "CasLambda guide RNAs" or "Cas, guide RNAs") that bind to and provide sequence specificity to the Cas12L proteins; nucleic acids encoding the Cas12L guide RNAs; and modified host cells comprising the Cas12L guide RNAs and/or nucleic acids encoding same. Cas12L guide RNAs are useful in a variety of applications, which are provided.

Compositions

Crispr/Cas12L Proteins and Guide RNAs

A Cas12L CRISPR/Cas effector polypeptide (e.g., a Cas12L protein) interacts with (binds to) a corresponding guide RNA (e.g., a Cas12L guide RNA) to form a ribonucleoprotein (RNP) complex that is targeted to a particular site in a target nucleic acid (e.g. a target DNA) via base pairing between the guide RNA and a target sequence within the target nucleic acid molecule. A guide RNA includes a nucleotide sequence (a guide sequence) that is complementary to a sequence (the target site) of a target nucleic acid. Thus, a Cas12L protein forms a complex with a Cas12L guide RNA and the guide RNA provides sequence specificity to the RNP complex via the guide sequence. The Cas12L protein of the complex provides the site-specific activity. In other words, the Cas12L protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the guide RNA.

The present disclosure provides compositions comprising a Cas12L polypeptide (and/or a nucleic acid comprising a nucleotide sequence encoding the Cas12L polypeptide) (e.g., where the Cas12L polypeptide can be a naturally existing protein, a nickase Cas12L protein, a catalytically inactive ("dead" Cas12L; also referred to herein as a "dCas12L protein"), a fusion Cas12L protein, etc.). The present disclosure provides compositions comprising a Cas12L guide RNA (and/or a nucleic acid comprising a nucleotide sequence encoding the Cas12L guide RNA). The present disclosure provides compositions comprising (a) a Cas12L polypeptide (and/or a nucleic acid encoding the Cas12L polypeptide) (e.g., where the Cas12L polypeptide can be a naturally existing protein, a nickase Cas12L protein, a dCas12L protein, a fusion Cas12L protein, etc.) and (b) a Cas12L guide RNA (and/or a nucleic acid encoding the Cas12L guide RNA). The present disclosure provides a nucleic acid/protein complex (RNP complex) comprising: (a) a Cas12L polypeptide of the present disclosure (e.g., where the Cas12L polypeptide can be a naturally existing protein, a nickase Cas12L protein, a dead Cas12L protein, a fusion Cas12L protein, etc.); and (b) a Cas12L guide RNA.

Cas12L Protein

A Cas12L polypeptide (this term is used interchangeably with the term "Cas12L protein") can bind and/or modify (e.g., cleave, nick, methylate, demethylate, etc.) a target nucleic acid and/or a polypeptide associated with target nucleic acid (e.g., methylation or acetylation of a histone tail) (e.g., in some cases, the Cas12L protein includes a fusion partner with an activity, and in some cases, the Cas12L protein provides nuclease activity). In some cases, the Cas12L protein is a naturally-occurring protein (e.g., naturally occurs in bacteriophage). In other cases, the Cas12L protein is not a naturally-occurring polypeptide (e.g., the Cas12L protein is a variant Cas12L protein, a fusion Cas12L protein, and the like).

Assays to determine whether given protein interacts with a Cas12L guide RNA can be any convenient binding assay that tests for binding between a protein and a nucleic acid. Suitable binding assays (e.g., gel shift assays) will be known to one of ordinary skill in the art (e.g., assays that include adding a Cas12L guide RNA and a protein to a target nucleic acid). Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art.

A naturally occurring Cas12L protein functions as an endonuclease that catalyzes a double strand break at a specific sequence in a targeted double stranded DNA (dsDNA). The sequence specificity is provided by the associated guide RNA, which hybridizes to a target sequence within the target DNA. The naturally occurring Cas12L guide RNA is a crRNA, where the crRNA includes (i) a guide sequence that hybridizes to a target sequence in the target DNA and (ii) a protein binding segment which includes a stem-loop (hairpin—dsRNA duplex) that binds to the Cas12L protein.

In some embodiments, the Cas12L protein of the subject methods and/or compositions is (or is derived from) a naturally occurring (wild type) protein. Examples of naturally occurring Cas12L proteins are depicted in FIGS. 2A-2Z, FIGS. 2AA-2ZZ, and FIGS. 2AAA-2FFF. In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the Cas12L amino acid sequences depicted in FIG. 2 (e.g., any one of FIGS. 2A-2Z, FIGS. 2AA-2ZZ, and FIGS. 2AAA-2FFF). In some cases, a FIGS. 2A-2Z, FIGS. 2AA-2ZZ, and FIGS. 2AAA-2FFF protein (of the subject compositions and/or methods) includes an amino acid sequence depicted in FIG. 2 (e.g., any one of FIGS. 2A-2Z, FIGS. 2AA-2ZZ, and FIGS. 2AAA-2FFF).

In some cases, a Cas12L protein (of the subject compositions and/or methods) has more sequence identity to an amino acid sequence depicted in FIG. 2 (e.g., any one of FIGS. 2A-2Z, FIGS. 2AA-2ZZ, and FIGS. 2AAA-2FFF) than to any of the following: Cas12a proteins, Cas12b proteins, Cas12c proteins, Cas12d proteins, Cas12e proteins, Cas12 g proteins, Cas12h proteins, and Cas12i proteins. In some cases, a Cas12L protein (of the subject compositions and/or methods) includes an amino acid sequence having a RuvC domain (which includes the RuvC-I, RuvC-II, and RuvC-III domains) that has more sequence identity to the RuvC domain of an amino acid sequence depicted in FIG. 2 (e.g., the RuvC domain of any of the Cas12L amino acid sequences depicted in FIG. 2) than to the RuvC domain of any of the following: Cas12a proteins, Cas12b proteins, Cas12c proteins, Cas12d proteins, Cas12e proteins, Cas12 g proteins, Cas12h proteins, and Cas12i proteins.

FIG. 3A-3B provides the locations of active site residues present in RuvC domains of various Cas12L polypeptides depicted in FIGS. 2A-2Z, FIGS. 2AA-2ZZ, and FIGS. 2AAA-2FFF. For example, active site residues of Cas12L_1_257905508 (FIG. 2A) are amino acid residues 336, 530, and 682.

Figure 5E:
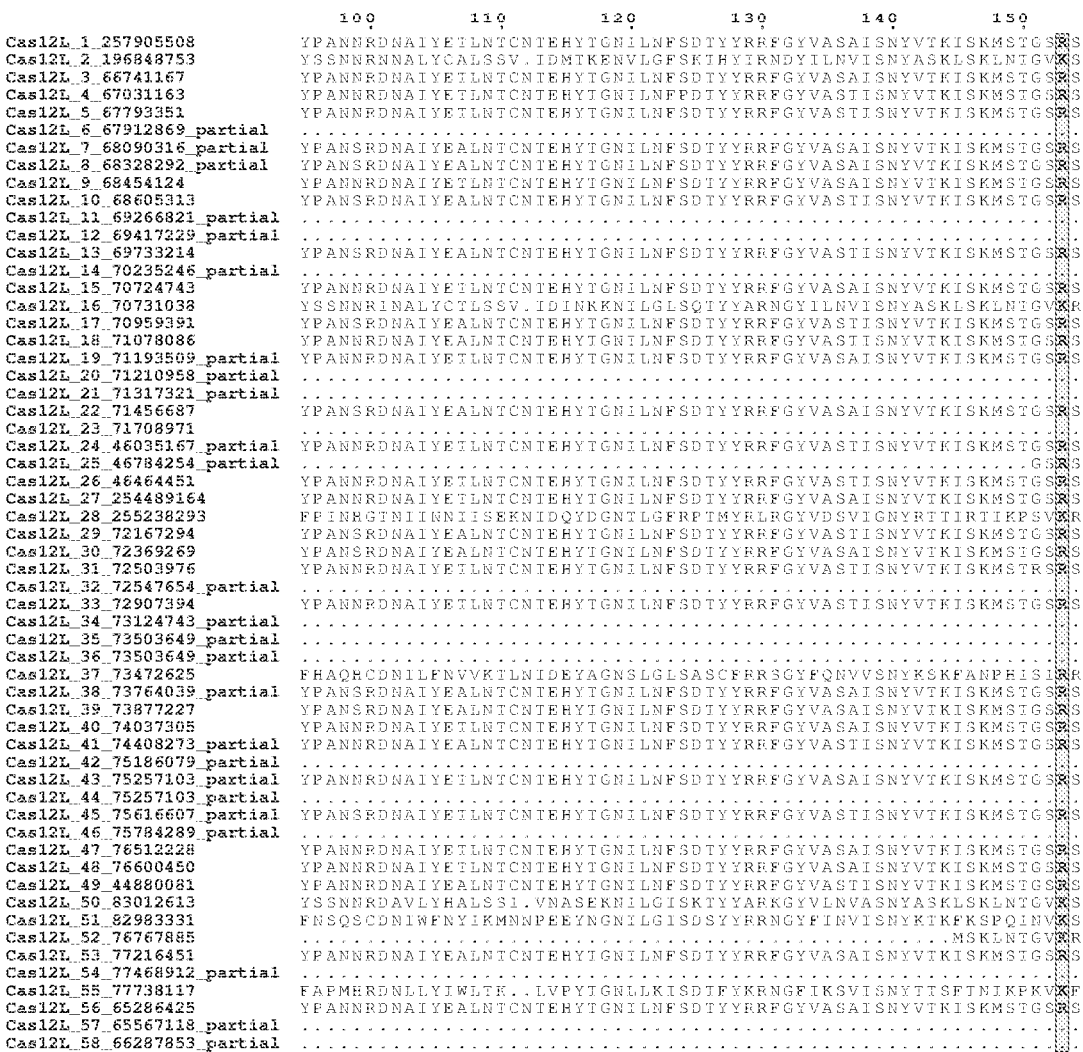
FIG. 5A-5P provide an alignment of amino acid sequences of Cas12L polypeptides depicted in FIGS. 2A-2Z, 2AA-2ZZ, and 2AAA-2FFF (from top to bottom SEQ ID NOs: 102-112, 112, 113-126, 102, 127-137, 157, 138-156).
Figure 5F:
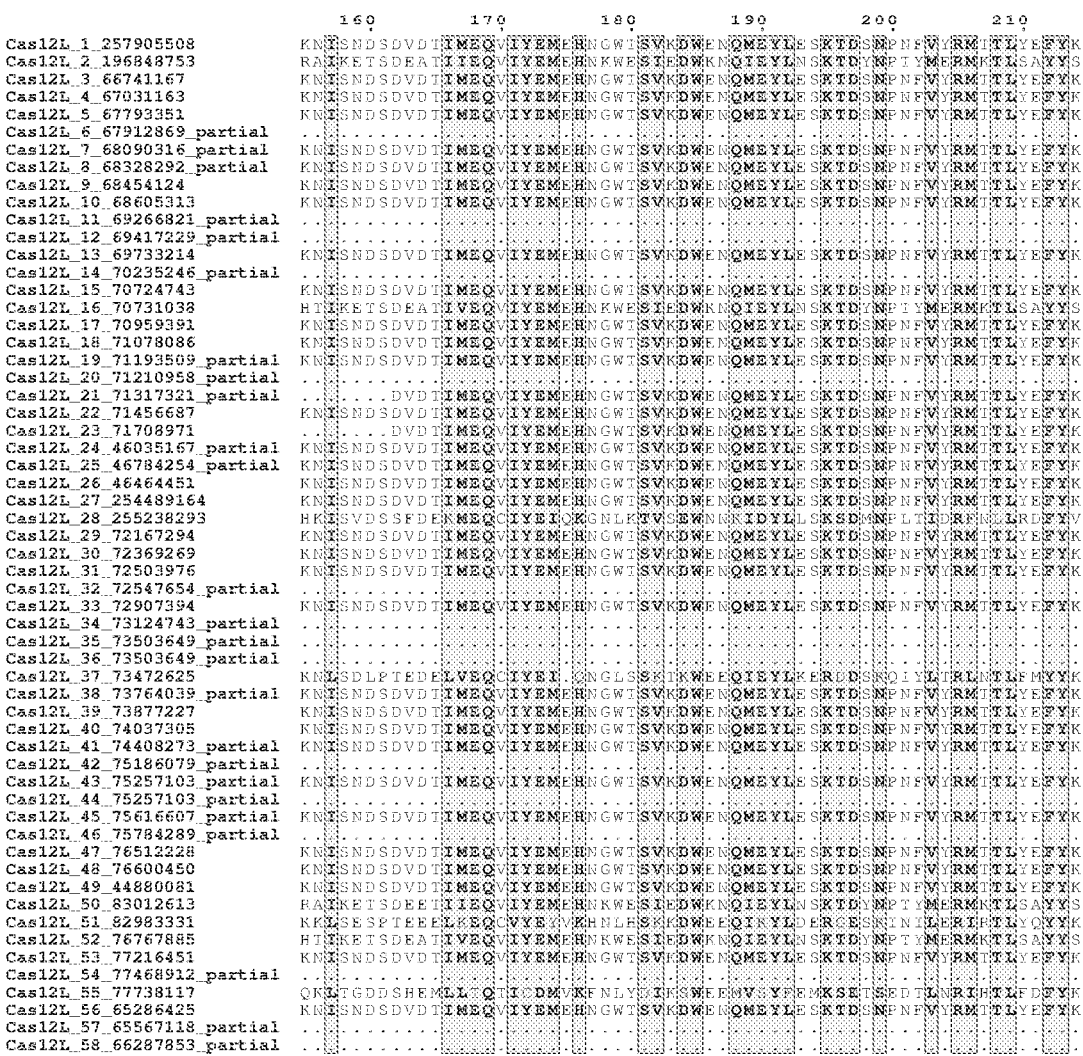
Figure 5H:
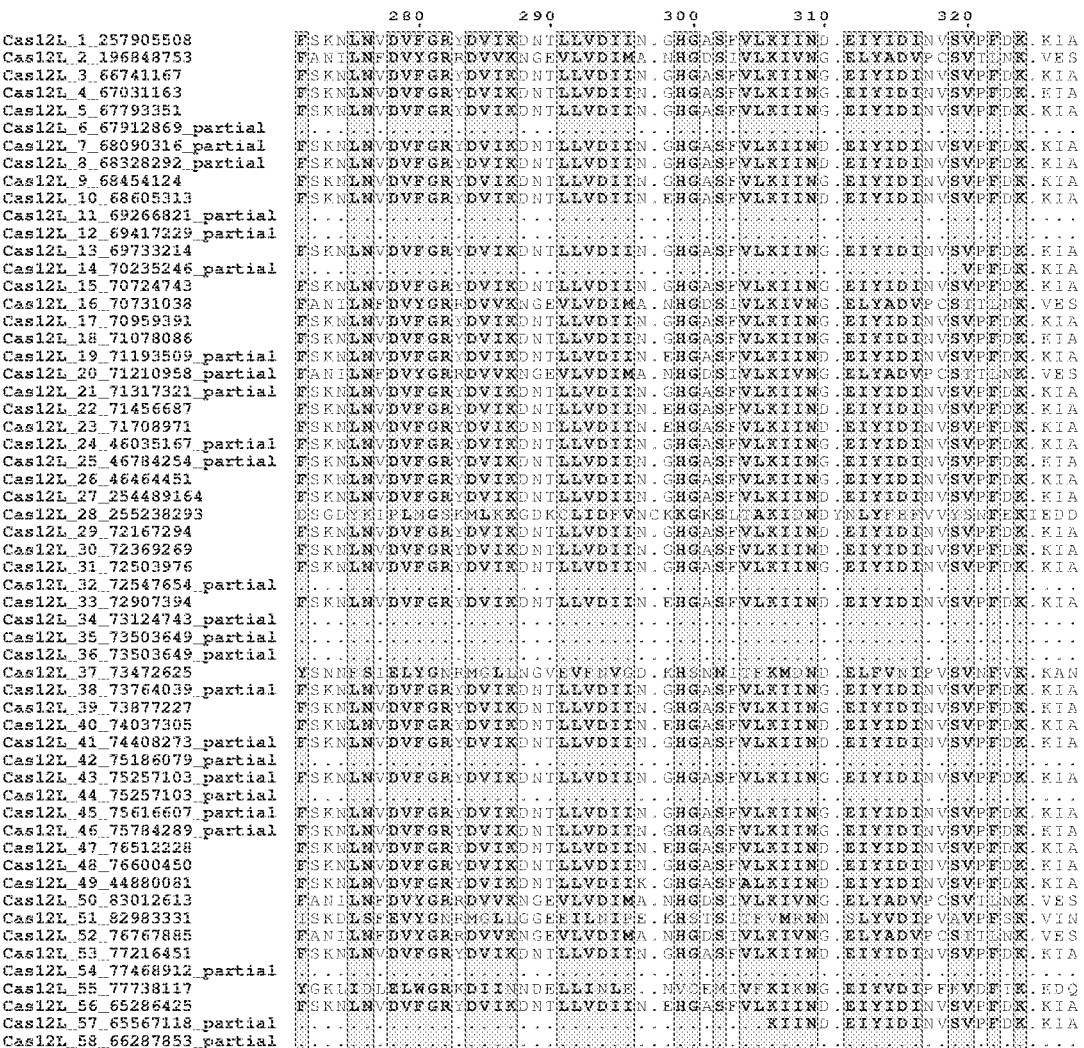
Figure 5I:
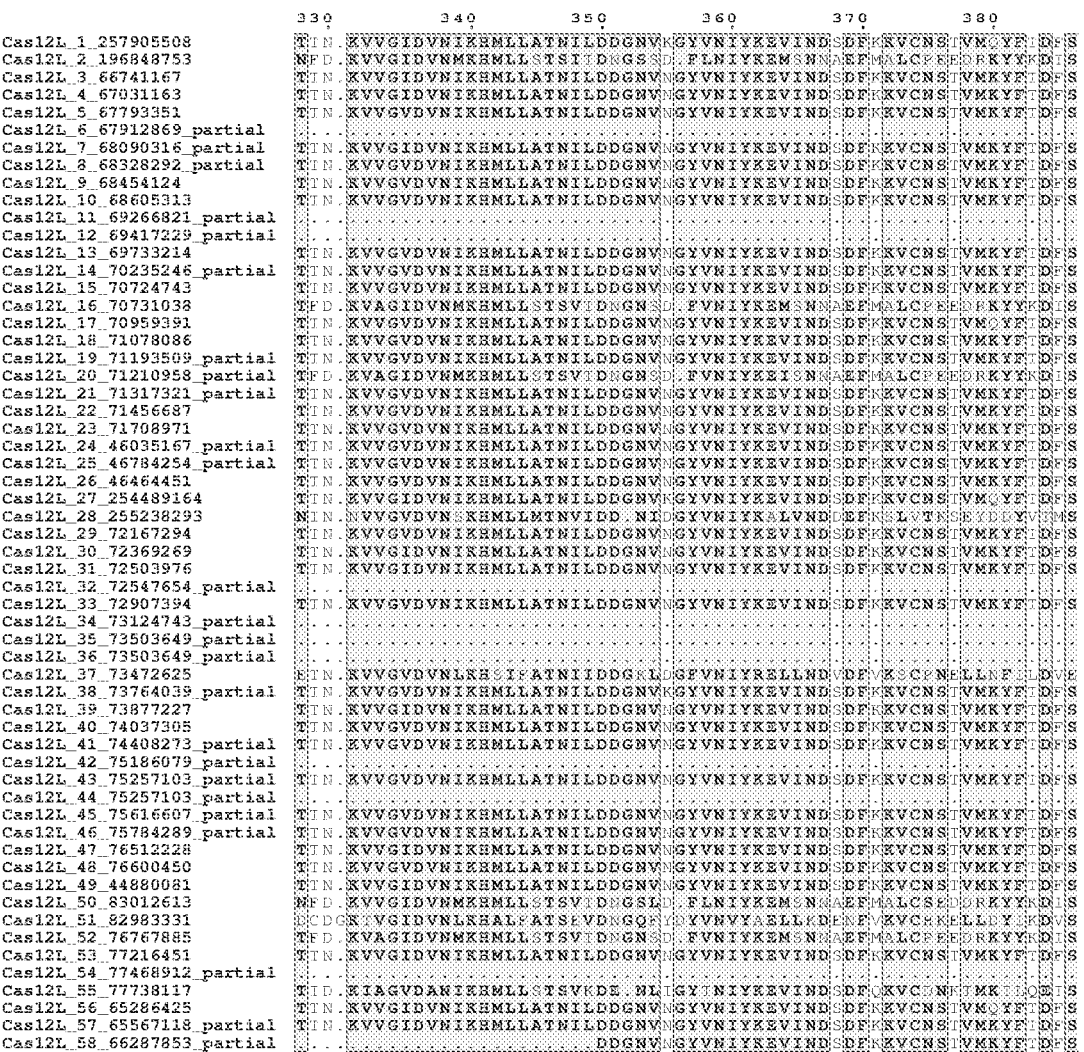
Figure 5J:
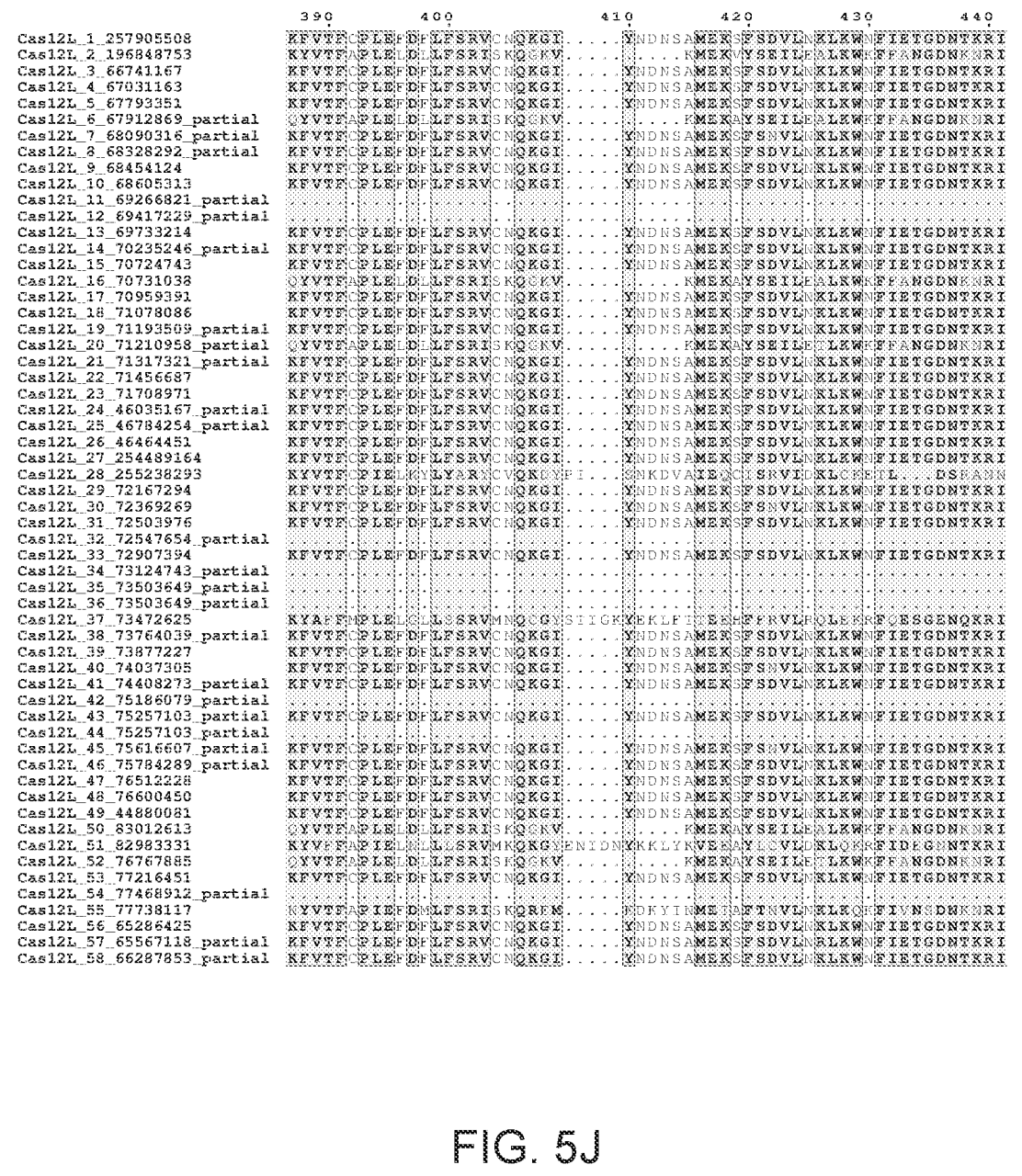
Figure 5K:
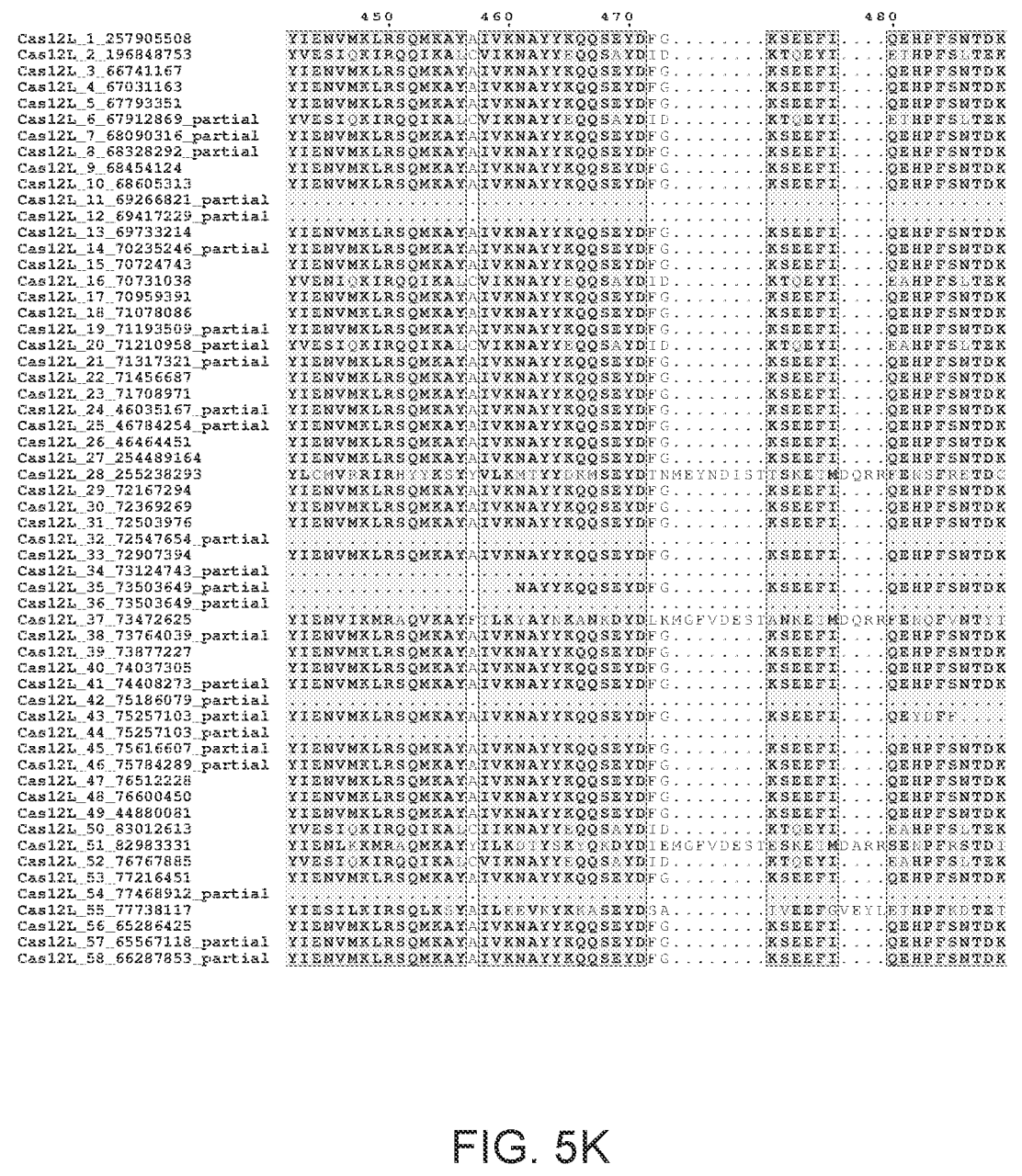
Figure 5L:
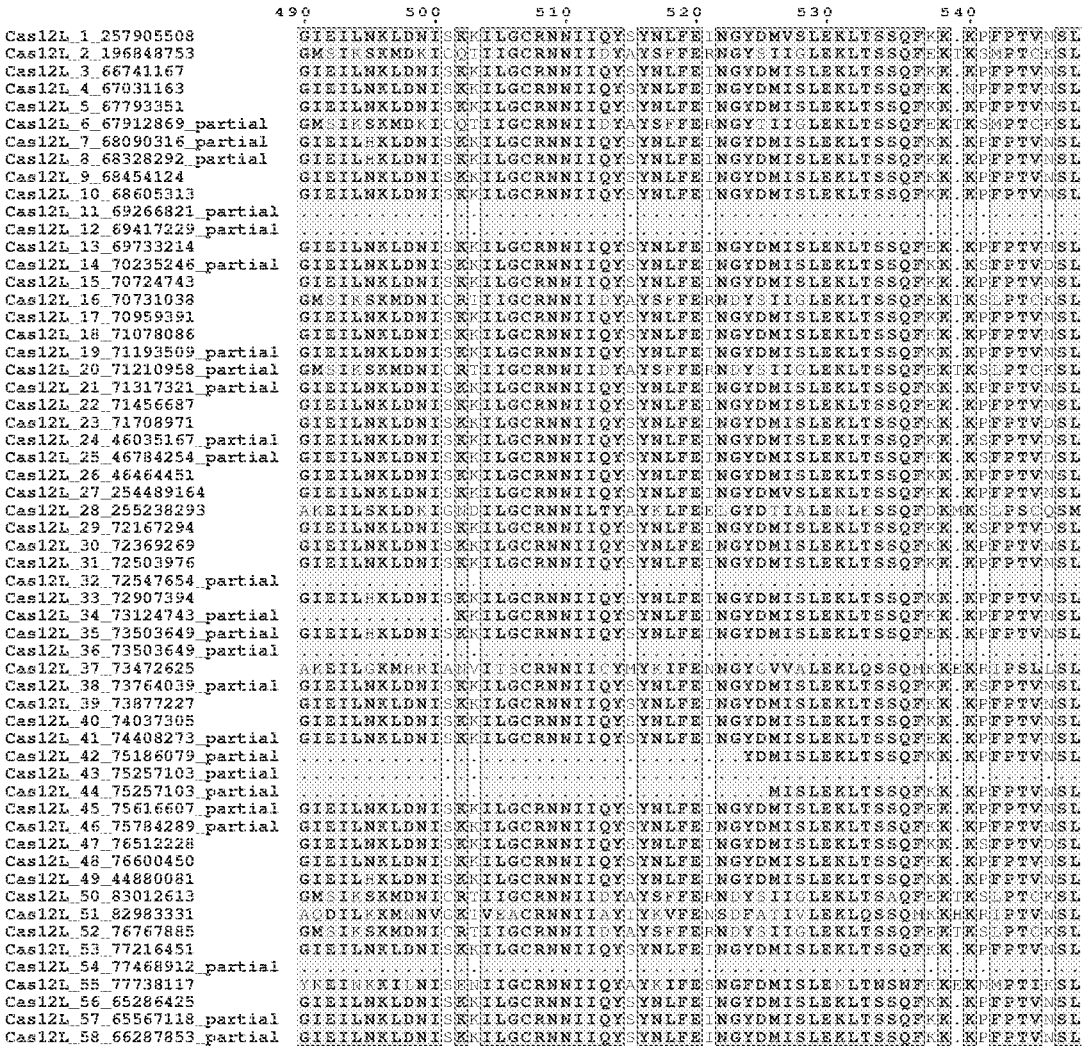
Figure 5N:
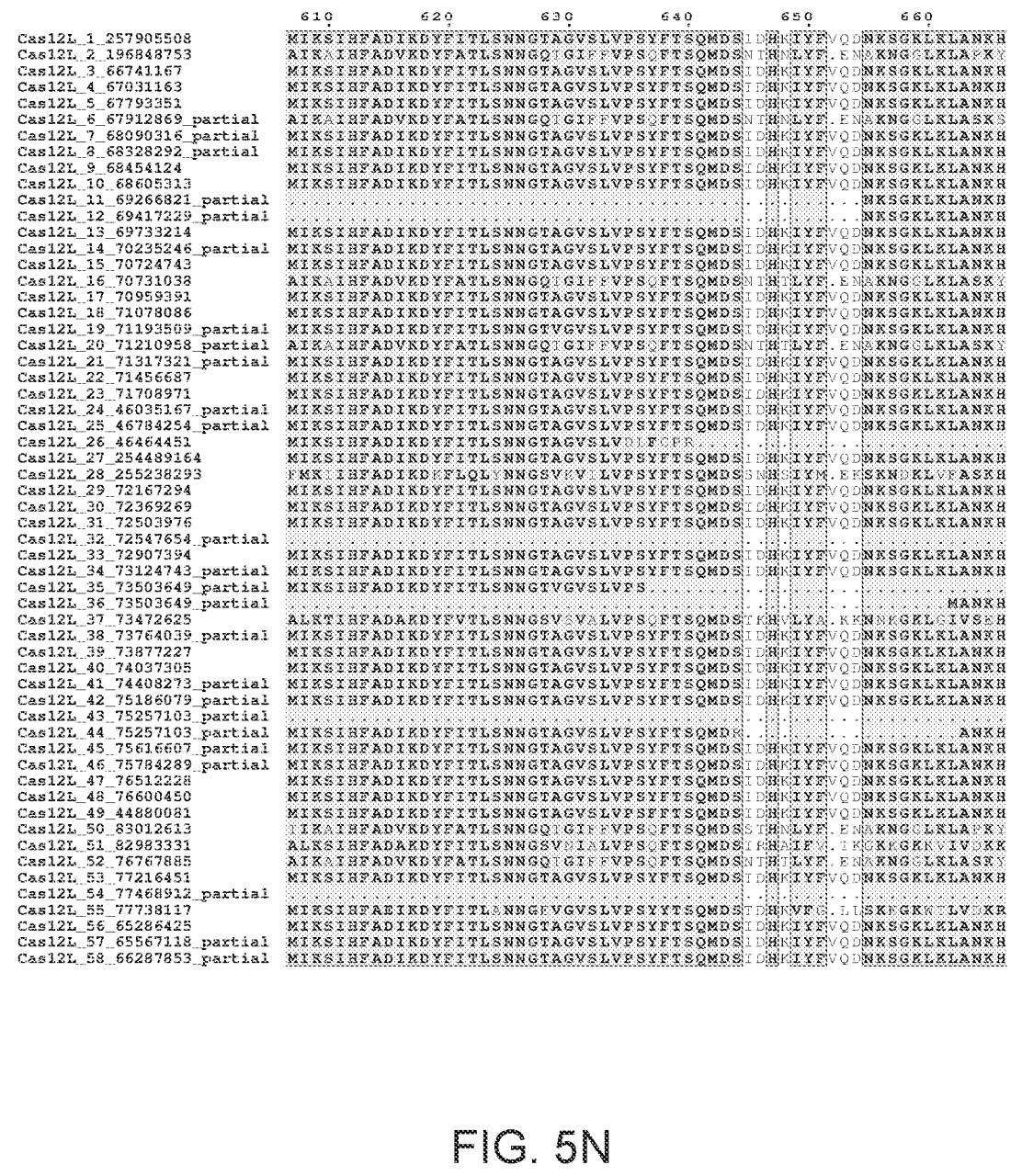
Figure 50:
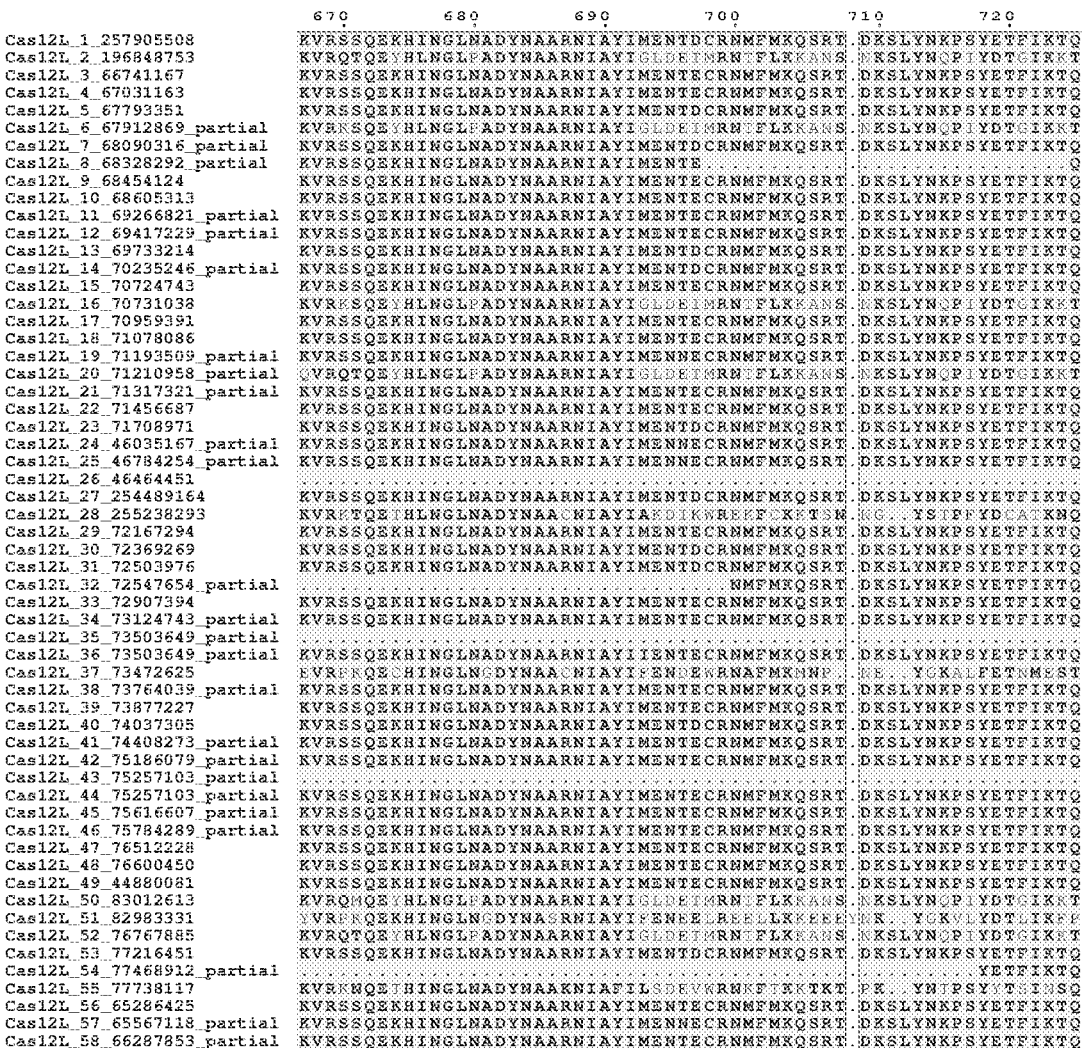

FIG. 5A-5P provide an amino acid sequence alignment of the 58 Cas12L polypeptides depicted in FIGS. 2A-2Z, FIGS. 2AA-2ZZ, and FIGS. 2AAA-2FFF. As shown in FIG. 5A-5P, a number of amino acids are conserved among the 58 Cas12L polypeptides. For example, K14, T15, E37, Y41, Y42, N43, S46, I49, I57, Y73, Y88, F91, N119, L121, N140, Y141, Q169, I171, E173, W185, Y191, Y205, L209, F212, Y213, F235, G236, G237, C238, R240, G281, N309, K324, 1335, T346, Y357, N359, 1360, Y361, V364, F370, F391, P393, L394, E395, L399, S401, R402, Q406, E417, V423, L424, Y442, K448, L449, R450, K454, A455, V459, K460, Y470, D471, E476, E477, and G594, based on the amino acid numbering of Cas12L_1_257905508 (FIG. 2A) are conserved. Thus, e.g., a Cas12L polypeptide can comprise one or more of K14, T15, E37, Y41, Y42, N43, S46, 149, 157, Y73, Y88, F91, N119, L121, N140, Y141, Q169, 1171, E173, W185, Y191, Y205, L209, F212, Y213, F235, G236, G237, C238, R240, G281, N309, K324, 1335, T346, Y357, N359, 1360, Y361, V364, F370, F391, P393, L394, E395, L399, S401, R402, Q406, E417, V423, L424, Y442, K448, L449, R450, K454, A455, V459, K460, Y470, D471, E476, E477, and G594, based on the amino acid numbering of Cas12L_1_257905508 (FIG. 2A), or the same amino acid at a corresponding position in another Cas12L polypeptide (e.g., a Cas12L polypeptide depicted in FIGS. 2A-2Z, FIGS. 2AA-2ZZ, and FIGS. 2AAA-2FFF), where those skilled in the art would understand, based on the alignment provided in FIG. 5A-5P, what a "corresponding position" would be. A Cas12L polypeptide can comprise a conservative amino acid substitution at one or more of K14, T15, E37, Y41, Y42, N43, S46, 149, 157, Y73, Y88, F91, N119, L121, N140, Y141, Q169, 1171, E173, W185, Y191, Y205, L209, F212, Y213, F235, G236, G237, C238, R240, G281, N309, K324, 1335, T346, Y357, N359, 1360, Y361, V364, F370, F391, P393, L394, E395, L399, S401, R402, Q406, E417, V423, L424, Y442, K448, L449, R450, K454, A455, V459, K460, Y470, D471, E476, E477, and G594, based on the amino acid numbering of Cas12L_1_257905508 (FIG. 2A), or at a corresponding position in another Cas12L polypeptide (e.g., a Cas12L polypeptide depicted in FIGS. 2A-2Z, FIGS. 2AA-2ZZ, and FIGS. 2AAA-2FFF).

FIG. 6A-6C provide an alignment of the amino acid sequences of Cas12L_2_196848753 (FIG. 2B), Cas12L_29_255238293 (FIG. 2BB; referred to as Cas12L_28_255238293 in FIG. 2BB), Cas12L_38_73472625 (FIG. 2KK; referred to as Cas12L_37_73472625 in FIG. 2KK), Cas12L_42_74408273_partial (FIG. 2NN; referred to as Cas12L_41_74408273_partial in FIG. 2NN), Cas12L_54_75257103_partial (FIG. 2PP; referred to as Cas12L_43_75257103_partial in FIG. 2PP), Cas12L_52_82983331 (FIG. 2XX; referred to as Cas12L_51_82983331 in FIG. 2XX), and Cas12L_56_77738117 (FIG. 2BBB; referred to as Cas12L_55_77738117 in FIG. 2BBB. Amino acids in boxes are conserved among the Cas12L polypeptides in FIG. 6A-6C. A Cas12L polypeptide can comprise the amino acids set out in the boxes in FIG. 6A-6C, or a conservative amino acid substitution of such amino acids, at the positions depicted in FIG. 6A-6C.

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the RuvC domain (which includes the RuvC-I, RuvC-II, and RuvC-III domains) of any one of the Cas12L amino acid sequences depicted in FIG. 2 (e.g., any one of FIGS. 2A-2Z, FIGS. 2AA-2ZZ, and FIGS. 2AAA-2FFF). In some cases, a Cas12L protein (of the subject compositions and/or methods) includes an amino acid sequence having 70% or more sequence identity (e.g., 75% or more, 80% or more, 85% or more, 90% or more, 95% or more, 97% or more, 98% or more, 99% or more, or 100% sequence identity) with the RuvC domain (which includes the RuvC-I, RuvC-II, and RuvC-III domains) of any one of the Cas12L amino acid sequences depicted in FIG. 2 (e.g., any one of FIGS. 2A-2Z, FIGS. 2AA-2ZZ, and FIGS. 2AAA-2FFF). In some cases, a Cas12L protein (of the subject compositions and/or methods) includes the RuvC domain (which includes the RuvC-I, RuvC-II, and RuvC-III domains) of any one of the Cas12L amino acid sequences depicted in FIG. 2 (e.g., any one of FIGS. 2A-2Z, FIGS. 2AA-2ZZ, and FIGS. 2AAA-2FFF).

In some cases, a guide RNA that binds a Cas12L polypeptide includes a nucleotide sequence depicted in FIG. 2 (e.g., any one of FIGS. 2A-2Z, FIGS. 2AA-2ZZ, and FIGS. 2AAA-2FFF; where "T" is replaced with "U") (or in some cases the reverse complement of same). In some cases, the guide RNA comprises the nucleotide sequence (N)nX or the reverse complement of same, where N is any nucleotide, n is an integer from 15 to 30 (e.g., from 15 to 20, from 17 to 25, from 17 to 22, from 18 to 22, from 18 to 20, from 20 to 25, or from 25 to 30), and X is any one of the nucleotide sequences depicted in FIG. 2 (e.g., any one of FIGS. 2A-2Z, FIGS. 2AA-2ZZ, and FIG. 2AAA-2FFF) (or in some cases the reverse complement of same).

Figure 7:
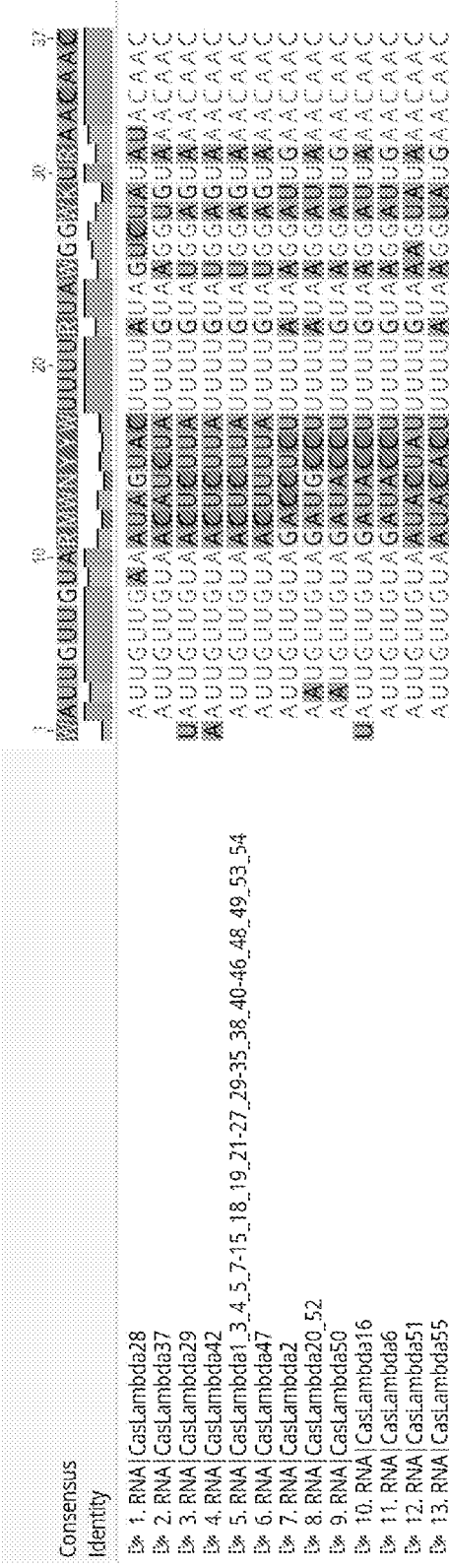
FIG. 7 provides an alignment of nucleotide sequences of the repeat region of Cas-Lambda (Cas12L) guide RNAs (from top to bottom SEQ ID NOs:63, 70, 64, 163, 59, 65, 60, 68, 66, 61, 164, 67, 69). A consensus sequence is provided (SEQ ID NO:162).
Figure 8A:
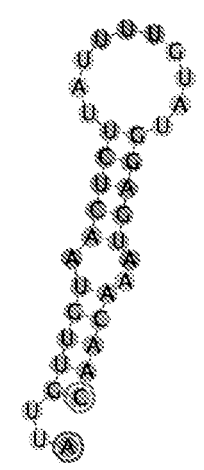
FIG. 8A-8M depict the secondary structure of various Cas-Lambda guide RNA repeat sequences.
Figure 8B:
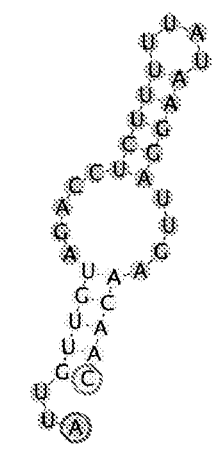
Figure 8C:
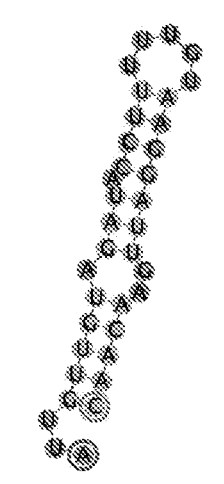
Figure 8D:
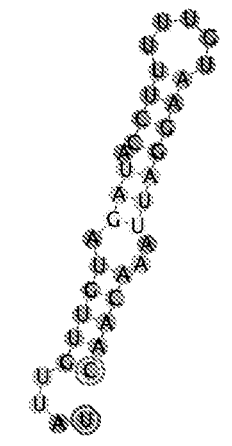
Figure 8E:
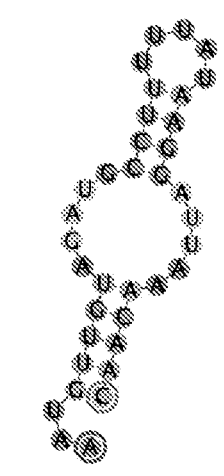
Figure 8F:
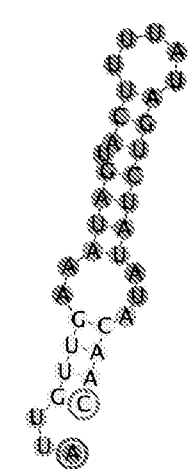
Figure 8G:
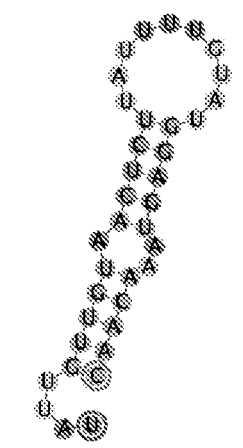
Figure 8H:
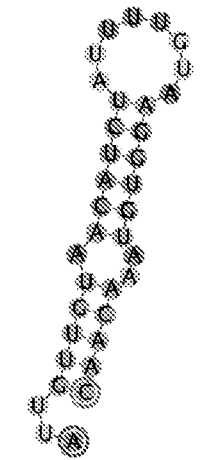
Figure 8I:
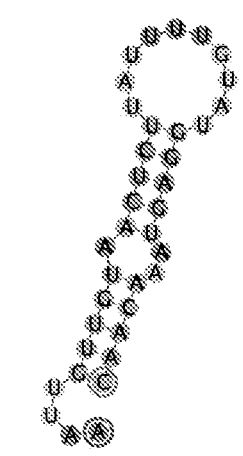
Figure 8J:
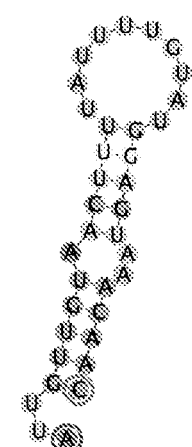
Figure 8K:
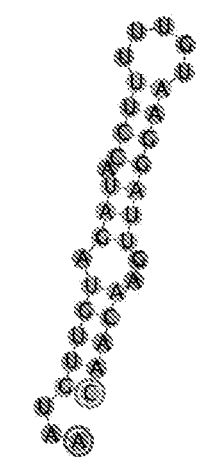
Figure 8L:
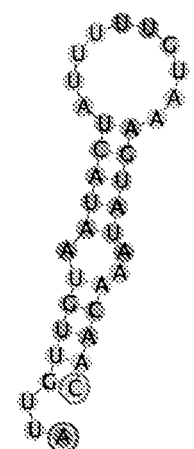
Figure 8M:
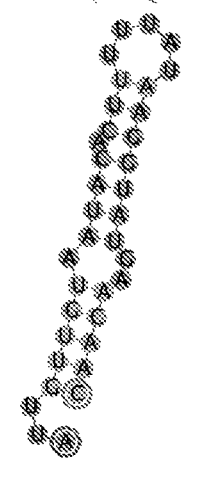

An alignment of nucleotide sequences of the repeat region of various CasLambda (Casλ; Cas12L) guide RNAs is provided in FIG. 7. As shown in FIG. 7, CRISPR repeat sequences contain conserved sequence motifs across homologs. In some cases, a guide RNA that binds a Cas12L polypeptide includes a nucleotide sequence (a repeat sequence; or protein-binding sequence) of the following consensus sequence: WAUUGUU-GUARMWNYYWUUUURUAWGGWKURAACAAC (SEQ ID NO:162), where W is A or U; R is G or A; M is A or C; N is A, G, C, or U; Y is U or C; and K is G or U. For example, a guide RNA that binds a CasLambda28 polypeptide (Cas12L 28; FIG. 2BB) can comprise a protein-binding segment comprising the nucleotide sequence: AUU-GUUGAAAUAGUACUUUUAUAGUCUAUAUACAAC (SEQ ID NO:63). As another example a guide RNA that binds a CasLambda37 polypeptide (Cas12L 37; FIG. 2KK) can comprise a protein-binding segment comprising the nucleotide sequence: AUUGUUGUAACAUCUAUUUU-GUAAGGUGUAAACAAC (SEQ ID NO:70). As another example a guide RNA that binds a CasLambda29 polypeptide (Cas12L 29; FIG. 2CC) can comprise a protein-binding segment comprising the nucleotide sequence: UAUUGUU-GUAACUCUUAUUUUGUAUGGAGUAAACAAC (SEQ ID NO:64). As another example a guide RNA that binds a CasLambda42 polypeptide (Cas12L 42; FIG. 00) can comprise a protein-binding segment comprising the nucleotide sequence: AAUUGUUGUAACUCUUAUUUUGUAUGG-AGUAAACAAC (SEQ ID NO:163). As another example a guide RNA that binds any one of CasLambda polypeptides 1, 3, 4, 5, 7-15, 18, 19, 21-27, 29-35, 38, 40-46, 48, 49, 53, and 54 (any one of Cas12L 1, 3, 4, 5, 7-15, 18, 19, 21-27, 29-35, 38, 40-46, 48, 49, 53, and 54; FIGS. 2A, 2C, 2D, 2E, 2G-2O, 2R, 2S, 2U-2AA, 2CC-2II, 2LL, 2MM-2SS, 2UU, 2VV, 2ZZ, and 2AAA, respectively) can comprise a protein-binding segment comprising the nucleotide sequence: AUU-GUUGUAACUCUUAUUUUGUAUGGAGUAAACAAC (SEQ ID NO:59). As another example a guide RNA that binds a CasLambda47 polypeptide (Cas12L 47; FIG. 2TT) can comprise a protein-binding segment comprising the nucleotide sequence: AUUGUUGUAACUUUUAUUUU-GUAUGGAGUAAACAAC (SEQ ID NO:65). As another example a guide RNA that binds a CasLambda2 polypeptide (Cas12L 2; FIG. 2B) can comprise a protein-binding segment comprising the nucleotide sequence: AUUGUUGUA-GACCUCUUUUUAUAAGGAUUGAACAAC (SEQ ID NO:60). A Cas12L polypeptide of the present disclosure can form a complex (a ribonucleoprotein (RNP) complex) with a guide RNA comprising a protein-binding segment depicted in FIG. 7. In some cases, a Cas12L polypeptide of the present disclosure can form an RNP complex with different guide RNAs comprising a protein-binding segment of different sequences depicted in FIG. 7.

As another example a guide RNA that binds a CasLambda20 polypeptide or a CasLambda52 polypeptide (Cas12L 20 or Cas12L 52; FIGS. 2T and 2YY, respectively) can comprise a protein-binding segment comprising the nucleotide sequence: AAUGUUGUAGAUGCC-UUUUUAUAAGGAUUAAACAAC (SEQ ID NO:68). As another example a guide RNA that binds a CasLambda50 polypeptide (Cas12L 50; FIG. 2WW) can comprise a protein-binding segment comprising the nucleotide sequence: AAUGUUGUAGAUACCUUUUU-GUAAGGAUUGAACAAC (SEQ ID NO:66). As another example a guide RNA that binds a CasLambda16 polypeptide (Cas12L 16; FIG. 2P) can comprise a protein-binding segment comprising the nucleotide sequence: UAUUGUU-GUAGAUACCUUUUUGUAAGGAUUAAACAAC (SEQ ID NO:61). As another example a guide RNA that binds a CasLambda6 polypeptide (Cas12L 6; FIG. 2F) can comprise a protein-binding segment comprising the nucleotide sequence: AUUGUUGUAGAUACCUUUUU-GUAAGGAUUGAACAAC (SEQ ID NO:164). As another example a guide RNA that binds a CasLambda51 polypeptide (Cas12L 51; FIG. 2XX) can comprise a protein-binding segment comprising the nucleotide sequence: AUUGUU-GUAAUACUAUUUUUGUAAAGUAUAAACAAC (SEQ ID NO:67). As another example a guide RNA that binds a CasLambda55 polypeptide (Cas12L 55; FIG. 2BBB) can comprise a protein-binding segment comprising the nucleotide sequence:

(SEQ ID NO: 69)
AUUGUUGUAAUACACUUUUUAUAAGGUAUGAACAAC.

In addition to containing conserved sequence motifs in the repeat (protein-binding) regions, the repeat region of a CasLambda guide RNA share conserved secondary structures across homologs. FIG. 8A-8M depict the secondary structures of the repeat regions of various CasLambda guide RNAs. For example, the repeat region can include palindromic regions that can form stem and stem-loop structures.

In some cases, a guide RNA that binds a Cas12L polypeptide includes a nucleotide sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the sequences depicted in FIG. 2 (e.g., any one of FIGS. 2A-2Z, FIGS. 2AA-2ZZ, and FIGS. 2AAA-2FFF) (or in some cases the reverse complement of same). In some cases, the guide RNA comprises the nucleotide sequence (N)nX or the reverse complement of same, where N is any nucleotide, n is an integer from 15 to 30 (e.g., from 15 to 20, from 17 to 25, from 17 to 22, from 18 to 22, from 18 to 20, from 20 to 25, or from 25 to 30), and X is a nucleotide sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the sequences depicted in FIG. 2 (e.g., any one of FIG. 2A-2Z, FIGS. 2AA-2ZZ, and FIGS. 2AAA-2FFF).

In some cases, a guide RNA that binds a Cas12L polypeptide includes a nucleotide sequence having 85% or more sequence identity (e.g., 90% or more, 95% or more, 97% or more, 98% or more, 99% or more, or 100% sequence identity) with any one of the sequences depicted in FIG. 2 (e.g., any one of FIGS. 2A-2Z, FIGS. 2AA-2ZZ, and FIGS. 2AAA-2FFF) (or in some cases the reverse complement of same). In some cases, the guide RNA comprises the nucleotide sequence (N)nX or the reverse complement of same, where N is any nucleotide, n is an integer from 15 to 30 (e.g., from 15 to 20, from 17 to 25, from 17 to 22, from 18 to 22, from 18 to 20, from 20 to 25, or from 25 to 30), and X is a nucleotide sequence having 85% or more sequence identity (e.g., 90% or more, 95% or more, 97% or more, 98% or more, 99% or more, or 100% sequence identity) with any one of the sequences depicted in FIG. 2 (e.g., any one of FIGS. 2A-2Z, FIGS. 2AA-2ZZ, and FIGS. 2AAA-2FFF).

In some cases, a guide RNA that binds a Cas12L polypeptide includes a nucleotide sequence depicted in FIG. 2 (e.g., any one of FIGS. 2A-2Z, FIGS. 2AA-2ZZ, and FIGS. 2AAA-2FFF) (or in some cases the reverse complement of same). In some cases, the guide RNA comprises the nucleotide sequence X(N)n, where N is any nucleotide, n is an integer from 15 to 30 (e.g., from 15 to 20, from 17 to 25, from 17 to 22, from 18 to 22, from 18 to 20, from 20 to 25, or from 25 to 30), and X is any one of the nucleotide sequences depicted in FIG. 2 (e.g., any one of FIGS. 2A-2Z, FIGS. 2AA-2ZZ, and FIGS. 2AAA-2FFF) (or in some cases the reverse complement of same).

In some cases, a guide RNA that binds a Cas12L polypeptide includes a nucleotide sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the sequences depicted in FIG. 2 (e.g., any one of FIGS. 2A-2Z, FIGS. 2AA-2ZZ, and FIGS. 2AAA-2FFF) (or in some cases the reverse complement of same). In some cases, the guide RNA comprises the nucleotide sequence X(N)n, where N is any nucleotide, n is an integer from 15 to 30 (e.g., from 15 to 20, from 17 to 25, from 17 to 22, from 18 to 22, from 18 to 20, from 20 to 25, or from 25 to 30), and X is a nucleotide sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the sequences depicted in FIG. 2 (e.g., any one of FIGS. 2A-2Z, FIGS. 2AA-2ZZ, and FIGS. 2AAA-2FFF).

In some cases, a guide RNA that binds a Cas12L polypeptide includes a nucleotide sequence having 85% or more sequence identity (e.g., 90% or more, 95% or more, 97% or more, 98% or more, 99% or more, or 100% sequence identity) with any one of the sequences depicted in FIG. 2 (e.g., any one of FIGS. 2A-2Z, FIGS. 2AA-2ZZ, and FIGS. 2AAA-2FFF) (or in some cases the reverse complement of same). In some cases, the guide RNA comprises the nucleotide sequence X(N)n, where N is any nucleotide, n is an integer from 15 to 30 (e.g., from 15 to 20, from 17 to 25, from 17 to 22, from 18 to 22, from 18 to 20, from 20 to 25, or from 25 to 30), and X is a nucleotide sequence having 85% or more sequence identity (e.g., 90% or more, 95% or more, 97% or more, 98% or more, 99% or more, or 100% sequence identity) with any one of the sequences depicted in FIG. 2 (e.g., any one of FIGS. 2A-2Z, FIGS. 2AA-2ZZ, and FIGS. 2AAA-2FFF).

FIG. 2A

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2A and designated "Cas12L_1_257905508." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2A. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2A. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2A. In some cases, a Cas12L protein includes an amino acid sequence having the Cas12L amino acid sequence depicted in FIG. 2A. In some cases, a Cas12L protein includes an amino acid sequence having the Cas12L protein sequence depicted in FIG. 2A, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2A) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2B

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2B and designated "Cas12L_2_196848753." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2B. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2B. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2B. In some cases, a Cas12L protein includes an amino acid sequence having the Cas12L amino acid sequence depicted in FIG. 2B. In some cases, a Cas12L protein includes an amino acid sequence having the Cas12L protein sequence depicted in FIG. 2B, with the exception that the sequence includes an amino acid substitution (e.g., 1, 2, or 3 amino acid substitutions) that reduces the naturally occurring catalytic activity of the protein. In some cases, the Cas12L polypeptide has a length of from 675 amino acids (aa) to 800 aa, e.g., from 675 aa to 700 aa, from 700 aa to 725 aa, from 725 aa to 735 aa, from 735 aa to 775 aa, or from 775 aa to 800 aa). In some cases, the Cas12L polypeptide has a length of 735 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2B) includes the following nucleotide sequence: ATTGTTGTAGACCTCTTTT-TATAAGGATTGAACAAC (SEQ ID NO:3) or the reverse complement of same. In some cases, the guide RNA comprises the nucleotide sequence (N)nATTGTTGTA-GACCTCTTTTTATAAGGATTGAACAAC (SEQ ID NO:4) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2C

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2C and designated "Cas12L_3_66741167." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2C. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2C. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2C. In some cases, a Cas12L protein includes an amino acid sequence having the Cas12L amino acid sequence depicted in FIG. 2C. In some cases, a Cas12L protein includes an amino acid sequence having the Cas12L protein sequence depicted in FIG. 2C, with the exception that the sequence includes an amino acid substitution (e.g., 1, 2, or 3 amino acid substitutions) that reduces the naturally occurring catalytic activity of the protein. In some cases, the Cas12L polypeptide has a length of from 725 amino acids (aa) to 875 aa, e.g., from 725 aa to 750 aa, from 750 aa to 778 aa, from 778 aa to 800 aa, from 800 aa to 825 aa, from 825 aa to 850 aa, or from 850 aa to 875 aa). In some cases, the Cas12L polypeptide has a length of 778 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2C) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2D

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2D and designated "Cas12L_4_67031163." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2D. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2D. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2D. In some cases, a Cas12L protein includes an amino acid sequence having the Cas12L amino acid sequence depicted in FIG. 2D. In some cases, a Cas12L protein includes an amino acid sequence having the Cas12L protein sequence depicted in FIG. 2D, with the exception that the sequence includes an amino acid substitution (e.g., 1, 2, or 3 amino acid substitutions) that reduces the naturally occurring catalytic activity of the protein. In some cases, the Cas12L polypeptide has a length of from 725 amino acids (aa) to 875 aa, e.g., from 725 aa to 750 aa, from 750 aa to 778 aa, from 778 aa to 800 aa, from 800 aa to 825 aa, from 825 aa to 850 aa, or from 850 aa to 875 aa). In some cases, the Cas12L polypeptide has a length of 778 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2D) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2E

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2E and designated "Cas12L_5_67793351." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2E. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2E. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2E. In some cases, a Cas12L protein includes an amino acid sequence having the Cas12L amino acid sequence depicted in FIG. 2E. In some cases, a Cas12L protein includes an amino acid sequence having the Cas12L protein sequence depicted in FIG. 2E, with the exception that the sequence includes an amino acid substitution (e.g., 1, 2, or 3 amino acid substitutions) that reduces the naturally occurring catalytic activity of the protein. In some cases, the Cas12L polypeptide has a length of from 725 amino acids (aa) to 875 aa, e.g., from 725 aa to 750 aa, from 750 aa to 778 aa, from 778 aa to 800 aa, from 800 aa to 825 aa, from 825 aa to 850 aa, or from 850 aa to 875 aa). In some cases, the Cas12L polypeptide has a length of 778 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2E) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2F

In some cases, a Cas12L protein (of the subject compositions and/or methods) includes a contiguous stretch of about 350 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2F and designated "Cas12L_6_67912869_partial." For example, in some cases, a Cas12L protein includes a contiguous stretch of about 350 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2F. In some cases, a Cas12L protein includes a contiguous stretch of about 350 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2F. In some cases, a Cas12L protein includes a contiguous stretch of about 350 amino acids having 90% or more sequence identity (e.g., 95% or more, 97% or more, 98% or more, 99% or more, or 100% sequence identity) with the Cas12L amino acid sequence depicted in FIG. 2F. In some cases, a Cas12L protein includes a contiguous stretch of about 350 amino acids comprising the Cas12L amino acid sequence depicted in FIG. 2F. In some cases, a Cas12L protein includes a contiguous stretch of about 350 amino acids having the Cas12L protein sequence depicted in FIG. 2F, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, or from 750 aa to 800 aa). In some cases, the Cas12L polypeptide has a length of from about 725 amino acids to about 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2F) includes the following nucleotide sequence: ATTGTTGTA-GATACCTTTTTGTAAGGATTGAACAAC (SEQ ID NO:5) or the reverse complement of same. In some cases, the guide RNA comprises the nucleotide sequence (N)nAT-TGTTGTAGATACCTTTTTGTAAGGATTGAACAAC (SEQ ID NO:6) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2G

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 98% or more, 99% or more, or 100% sequence identity) with the Cas12L amino acid sequence depicted in FIG. 2G and designated "Cas12L_7_68090316_partial." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2G. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2G. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2G. In some cases, a Cas12L protein includes an amino acid sequence having the Cas12L amino acid sequence depicted in FIG. 2G. In some cases, a Cas12L protein includes an amino acid sequence having the Cas12L protein sequence depicted in FIG. 2G, with the exception that the sequence includes an amino acid substitution (e.g., 1, 2, or 3 amino acid substitutions) that reduces the naturally occurring catalytic activity of the protein. In some cases, the Cas12L polypeptide has a length of from 650 amino acids (aa) to 800 aa, e.g., from 650 aa to 700 aa, from 700 aa to 717 aa, from 717 aa to 725 aa, from 725 aa to 750 aa, or from 750 aa to 800 aa). In some cases, the Cas12L polypeptide has a length of from about 717 amino acids to about 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2G) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2H

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2H and designated "Cas12L_8_68328292_partial." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2H. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2H. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2H. In some cases, a Cas12L protein includes an amino acid sequence having the Cas12L amino acid sequence depicted in FIG. 2H. In some cases, a Cas12L protein includes an amino acid sequence having the Cas12L protein sequence depicted in FIG. 2H, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 742 aa, from 742 aa to 750 aa, from 750 aa to 775 aa, or from 775 aa to 800 aa). In some cases, the Cas12L polypeptide has a length of from about 742 amino acids to about 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2H) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2I

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2I and designated "Cas12L_9_68454124." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2I. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2I. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2I. In some cases, a Cas12L protein includes an amino acid sequence having the Cas12L amino acid sequence depicted in FIG. 2I. In some cases, a Cas12L protein includes an amino acid sequence having the Cas12L protein sequence depicted in FIG. 2I, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 750 aa, from 750 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2I) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2J

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2J and designated "Cas12L_10_68605313." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2J. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2J. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2J. In some cases, a Cas12L protein includes an amino acid sequence having the Cas12L amino acid sequence depicted in FIG. 2J. In some cases, a Cas12L protein includes an amino acid sequence having the Cas12L protein sequence depicted in FIG. 2J, with the exception that the sequence includes an amino acid substitution (e.g., 1, 2, or 3 amino acid substitutions) that reduces the naturally occurring catalytic activity of the protein. In some cases, the Cas12L polypeptide has a length of from 725 amino acids (aa) to 825 aa, e.g., from 725 aa to 750 aa, from 750 aa to 775 aa, from 775 aa to 782 aa, from 782 aa to 800 aa, or from 800 aa to 825 aa). In some cases, the Cas12L polypeptide has a length of 782 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2J) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2K

In some cases, a Cas12L protein (of the subject compositions and/or methods) includes a contiguous stretch of about 92 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2K and designated "Cas12L_11_69266821_partial." For example, in some cases, a Cas12L protein includes a contiguous stretch of about 92 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2K. In some cases, a Cas12L protein includes a contiguous stretch of about 92 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2K. In some cases, a Cas12L protein includes a contiguous stretch of about 92 amino acids having 90% or more sequence identity (e.g., 95% or more, 97% or more, 98% or more, 99% or more, or 100% sequence identity) with the Cas12L amino acid sequence depicted in FIG. 2K. In some cases, a Cas12L protein includes a contiguous stretch of about 92 amino acids having the Cas12L amino acid sequence depicted in FIG. 2K. In some cases, a Cas12L protein includes a contiguous stretch of about 92 amino acids having the Cas12L protein sequence depicted in FIG. 2K, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2K) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2L

In some cases, a Cas12L protein (of the subject compositions and/or methods) includes a contiguous stretch of about 92 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2L and designated "Cas12L_12_69417229_partial." For example, in some cases, a Cas12L protein includes a contiguous stretch of about 92 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2L. In some cases, a Cas12L protein includes a contiguous stretch of about 92 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2L. In some cases, a Cas12L protein includes a contiguous stretch of about 92 amino acids having 90% or more sequence identity (e.g., 95% or more, 97% or more, 98% or more, 99% or more, or 100% sequence identity) with the Cas12L amino acid sequence depicted in FIG. 2L. In some cases, a Cas12L protein includes a contiguous stretch of about 92 amino acids having the Cas12L amino acid sequence depicted in FIG. 2L. In some cases, a Cas12L protein includes a contiguous stretch of about 92 amino acids having the Cas12L protein sequence depicted in FIG. 2L, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2L) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2M

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2M and designated "Cas12L_13_69733214." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2M. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2M. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2M. In some cases, a Cas12L protein includes an amino acid sequence having the Cas12L amino acid sequence depicted in FIG. 2M. In some cases, a Cas12L protein includes an amino acid sequence having the Cas12L protein sequence depicted in FIG. 2M, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2M) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2N

In some cases, a Cas12L protein (of the subject compositions and/or methods) includes a contiguous stretch of about 427 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2N and designated "Cas12L_14_70235246_partial." For example, in some cases, a Cas12L protein includes a contiguous stretch of about 427 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2N. In some cases, a Cas12L protein includes a contiguous stretch of about 427 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2N. In some cases, a Cas12L protein includes a contiguous stretch of about 427 amino acids having 90% or more sequence identity (e.g., 95% or more, 97% or more, 98% or more, 99% or more, or 100% sequence identity) with the Cas12L amino acid sequence depicted in FIG. 2N. In some cases, a Cas12L protein includes a contiguous stretch of about 427 amino acids having the Cas12L amino acid sequence depicted in FIG. 2N. In some cases, a Cas12L protein includes a contiguous stretch of about 427 amino acids having the Cas12L protein sequence depicted in FIG. 2N, with the exception that the sequence includes an amino acid substitution (e.g., 1, 2, or 3 amino acid substitutions) that reduces the naturally occurring catalytic activity of the protein. In some cases, the Cas12L polypeptide has a length of from 425 amino acids (aa) to 800 aa, e.g., from 425 aa to 500 aa, from 500 aa to 600 aa, from 600 aa to 700 aa, from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2N) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2O

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2O and designated "Cas12L_15_70724743." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2O. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2O. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2O. In some cases, a Cas12L protein includes an amino acid sequence having the Cas12L amino acid sequence depicted in FIG. 2O. In some cases, a Cas12L protein includes an amino acid sequence having the Cas12L protein sequence depicted in FIG. 2O, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2O) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2P

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2P and designated "Cas12L_16_70731038." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2P. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2P. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2P. In some cases, a Cas12L protein includes an amino acid sequence having the Cas12L amino acid sequence depicted in FIG. 2P. In some cases, a Cas12L protein includes an amino acid sequence having the Cas12L protein sequence depicted in FIG. 2P, with the exception that the sequence includes an amino acid substitution (e.g., 1, 2, or 3 amino acid substitutions) that reduces the naturally occurring catalytic activity of the protein. In some cases, the Cas12L polypeptide has a length of from 675 amino acids (aa) to 800 aa, e.g., from 675 aa to 700 aa, from 700 aa to 725 aa, from 725 aa to 735 aa, from 735 aa to 750 aa, from 750 aa to 775 aa, or from 775 aa to 800 aa). In some cases, the Cas12L polypeptide has a length of 735 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2P) includes the following nucleotide sequence: TAT-TGTTGTAGATACCTTTTTGTAAGGATTAAACAAC (SEQ ID NO:7) or the reverse complement of same. In some cases, the guide RNA comprises the nucleotide sequence (N)nTATTGTTGTAGATACCTTTTTGTAAGGAT-TAAACAAC (SEQ ID NO:8) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2Q

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2Q and designated "Cas12L_17_70959391." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2Q. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2Q. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2Q. In some cases, a Cas12L protein includes an amino acid sequence having the Cas12L amino acid sequence depicted in FIG. 2Q. In some cases, a Cas12L protein includes an amino acid sequence having the Cas12L protein sequence depicted in FIG. 2Q, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids.

FIG. 2R

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2R and designated "Cas12L_18_71078086." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2R. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2R. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2R. In some cases, a Cas12L protein includes an amino acid sequence having the Cas12L amino acid sequence depicted in FIG. 2R. In some cases, a Cas12L protein includes an amino acid sequence having the Cas12L protein sequence depicted in FIG. 2R, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2R) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2S

In some cases, a Cas12L protein (of the subject compositions and/or methods) includes a contiguous stretch of about 680 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2S and designated "Cas12L_19_71193509_partial." For example, in some cases, a Cas12L protein includes a contiguous stretch of about 680 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2S. In some cases, a Cas12L protein includes a contiguous stretch of about 680 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2S. In some cases, a Cas12L protein includes a contiguous stretch of about 680 amino acids having 90% or more sequence identity (e.g., 95% or more, 97% or more, 98% or more, 99% or more, or 100% sequence identity) with the Cas12L amino acid sequence depicted in FIG. 2S. In some cases, a Cas12L protein includes a contiguous stretch of about 680 amino acids having the Cas12L amino acid sequence depicted in FIG. 2S. In some cases, a Cas12L protein includes a contiguous stretch of about 680 amino acids having the Cas12L protein sequence depicted in FIG. 2S, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, or from 750 aa to 800 aa). In some cases, the Cas12L polypeptide has a length of from about 725 amino acids to about 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2S) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2T

In some cases, a Cas12L protein (of the subject compositions and/or methods) includes a contiguous stretch of about 516 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2T and designated "Cas12L_20_71210958_partial." For example, in some cases, a Cas12L protein includes a contiguous stretch of about 516 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2T. In some cases, a Cas12L protein includes a contiguous stretch of about 516 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2T. In some cases, a Cas12L protein includes a contiguous stretch of about 516 amino acids having 90% or more sequence identity (e.g., 95% or more, 97% or more, 98% or more, 99% or more, or 100% sequence identity) with the Cas12L amino acid sequence depicted in FIG. 2T. In some cases, a Cas12L protein includes a contiguous stretch of about 516 amino acids having the Cas12L amino acid sequence depicted in FIG. 2T. In some cases, a Cas12L protein includes a contiguous stretch of about 516 amino acids having the Cas12L protein sequence depicted in FIG. 2T, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, or from 750 aa to 800 aa). In some cases, the Cas12L polypeptide has a length of from about 725 amino acids to about 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2T) includes the following nucleotide sequence: AATGTTGTA-GATGCCTTTTTATAAGGATTAAACAACTTG (SEQ ID NO:9) or the reverse complement of same. In some cases, the guide RNA comprises the nucleotide sequence (N)nAATGTTGTAGATGCCTTTTTATAAGGAT-TAAACAACTTG (SEQ ID NO:10) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2U

In some cases, a Cas12L protein (of the subject compositions and/or methods) includes a contiguous stretch of about 585 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2U and designated "Cas12L_21_71317321_partial." For example, in some cases, a Cas12L protein includes a contiguous stretch of about 585 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2U. In some cases, a Cas12L protein includes a contiguous stretch of about 585 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2U. In some cases, a Cas12L protein includes a contiguous stretch of about 585 amino acids having 90% or more sequence identity (e.g., 95% or more, 97% or more, 98% or more, 99% or more, or 100% sequence identity) with the Cas12L amino acid sequence depicted in FIG. 2U. In some cases, a Cas12L protein includes a contiguous stretch of about 585 amino acids having the Cas12L amino acid sequence depicted in FIG. 2U. In some cases, a Cas12L protein includes a contiguous stretch of about 585 amino acids having the Cas12L protein sequence depicted in FIG. 2U, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, or from 750 aa to 800 aa). In some cases, the Cas12L polypeptide has a length of from about 725 amino acids to about 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2U) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2V

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2V and designated "Cas12L_22_71456687." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2V. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2V. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2V. In some cases, a Cas12L protein includes an amino acid sequence having the Cas12L amino acid sequence depicted in FIG. 2V. In some cases, a Cas12L protein includes an amino acid sequence having the Cas12L protein sequence depicted in FIG. 2V, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2V) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2W

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2W and designated "Cas12L_23_71708971." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2W. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2W. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2W. In some cases, a Cas12L protein includes an amino acid sequence having the Cas12L amino acid sequence depicted in FIG. 2W. In some cases, a Cas12L protein includes an amino acid sequence having the Cas12L protein sequence depicted in FIG. 2W, with the exception that the sequence includes an amino acid substitution (e.g., 1, 2, or 3 amino acid substitutions) that reduces the naturally occurring catalytic activity of the protein. In some cases, the Cas12L polypeptide has a length of from 500 amino acids (aa) to 800 aa, e.g., from 500 aa to 550 aa, from 550 aa to 585 aa, from 585 aa to 600 aa, from 600 aa to 650 aa, from 650 aa to 700 aa, from 700 aa to 725 aa, from 725 aa to 750 aa, from 750 aa to 775 aa, or from 775 aa to 800 aa). In some cases, the Cas12L polypeptide has a length of 585 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2W) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2X

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2X and designated "Cas12L_24_46035167_partial." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2X. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2X. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2X. In some cases, a Cas12L protein includes an amino acid sequence having the Cas12L amino acid sequence depicted in FIG. 2X. In some cases, a Cas12L protein includes an amino acid sequence having the Cas12L protein sequence depicted in FIG. 2X, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 758 aa, from 758 aa to 775 aa, or from 775 aa to 800 aa). In some cases, the Cas12L polypeptide has a length of 758 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2X) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2Y

In some cases, a Cas12L protein (of the subject compositions and/or methods) includes a contiguous stretch of about 596 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2Y and designated "Cas12L_25_46784254_partial." For example, in some cases, a Cas12L protein includes a contiguous stretch of about 596 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2Y. In some cases, a Cas12L protein includes a contiguous stretch of about 596 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2Y. In some cases, a Cas12L protein includes a contiguous stretch of about 596 amino acids having 90% or more sequence identity (e.g., 95% or more, 97% or more, 98% or more, 99% or more, or 100% sequence identity) with the Cas12L amino acid sequence depicted in FIG. 2Y. In some cases, a Cas12L protein includes a contiguous stretch of about 596 amino acids having the Cas12L amino acid sequence depicted in FIG. 2Y. In some cases, a Cas12L protein includes a contiguous stretch of about 596 amino acids having the Cas12L protein sequence depicted in FIG. 2Y, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, or from 750 aa to 800 aa). In some cases, the Cas12L polypeptide has a length of from about 725 amino acids to about 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2Y) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2Z

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2Z and designated "Cas12L_26_46464451." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2Z. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2Z. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2Z. In some cases, a Cas12L protein includes an amino acid sequence having the Cas12L amino acid sequence depicted in FIG. 2Z. In some cases, a Cas12L protein includes an amino acid sequence having the Cas12L protein sequence depicted in FIG. 2Z, with the exception that the sequence includes an amino acid substitution (e.g., 1, 2, or 3 amino acid substitutions) that reduces the naturally occurring catalytic activity of the protein. In some cases, the Cas12L polypeptide has a length of from 625 amino acids (aa) to 800 aa, e.g., from 625 aa to 640 aa, from 640 aa to 650 aa, from 650 aa to 700 aa, from 700 aa to 725 aa, from 725 aa to 750 aa, from 750 aa to 775 aa, or from 775 aa to 800 aa). In some cases, the Cas12L polypeptide has a length of 640 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2Z) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2AA

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2AA and designated "Cas12L_27_254489164." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2AA. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2AA. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2AA. In some cases, a Cas12L protein includes an amino acid sequence having the Cas12L amino acid sequence depicted in FIG. 2AA. In some cases, a Cas12L protein includes an amino acid sequence having the Cas12L protein sequence depicted in FIG. 2AA, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2AA) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2BB

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2BB and designated "Cas12L_28_255238293." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2BB. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2BB. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2BB. In some cases, a Cas12L protein includes an amino acid sequence having the Cas12L amino acid sequence depicted in FIG. 2BB. In some cases, a Cas12L protein includes an amino acid sequence having the Cas12L protein sequence depicted in FIG. 2BB, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 759 aa, from 759 aa to 775 aa, or from 775 aa to 800 aa). In some cases, the Cas12L polypeptide has a length of 759 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2BB) includes the following nucleotide sequence: ATTGTTGAAATAGTACTTTTATAGTC-TATATACAAC (SEQ ID NO:11) or the reverse complement of same. In some cases, the guide RNA comprises the nucleotide sequence (N)nATTGTTGAAATAGTACTTT-TATAGTCTATATACAAC (SEQ ID NO:12) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2CC

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2CC and designated "Cas12L_29_72167294." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2CC. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2CC. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2CC. In some cases, a Cas12L protein includes an amino acid sequence having the Cas12L amino acid sequence depicted in FIG. 2CC. In some cases, a Cas12L protein includes an amino acid sequence having the Cas12L protein sequence depicted in FIG. 2CC, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2CC) includes the following nucleotide sequence: TATTGTTGTAACTCTTATTTTGTATG-GAGTAAACAAC (SEQ ID NO:13) or the reverse complement of same. In some cases, the guide RNA comprises the nucleotide sequence (N)nTATTGTTGTAACTCTTAT-TTTGTATGGAGTAAACAAC (SEQ ID NO:14) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2DD

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2DD and designated "Cas12L_30_72369269." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2DD. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2DD. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2DD. In some cases, a Cas12L protein includes an amino acid sequence having the Cas12L amino acid sequence depicted in FIG. 2DD. In some cases, a Cas12L protein includes an amino acid sequence having the Cas12L protein sequence depicted in FIG. 2DD, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2DD) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2EE

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2EE and designated "Cas12L_31_72503976." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2EE. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2EE. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2EE. In some cases, a Cas12L protein includes an amino acid sequence having the Cas12L amino acid sequence depicted in FIG. 2EE. In some cases, a Cas12L protein includes an amino acid sequence having the Cas12L protein sequence depicted in FIG. 2EE, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2EE) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2FF

In some cases, a Cas12L protein (of the subject compositions and/or methods) includes a contiguous stretch of about 47 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2FF and designated "Cas12L_32_72547654_partial." For example, in some cases, a Cas12L protein includes a contiguous stretch of about 47 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2FF. In some cases, a Cas12L protein includes a contiguous stretch of about 47 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2FF. In some cases, a Cas12L protein includes a contiguous stretch of about 47 amino acids having 90% or more sequence identity (e.g., 95% or more, 97% or more, 98% or more, 99% or more, or 100% sequence identity) with the Cas12L amino acid sequence depicted in FIG. 2FF. In some cases, a Cas12L protein includes a contiguous stretch of about 47 amino acids having the Cas12L amino acid sequence depicted in FIG. 2FF. In some cases, a Cas12L protein includes a contiguous stretch of about 47 amino acids having the Cas12L protein sequence depicted in FIG. 2FF, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2FF) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2GG

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2GG and designated "Cas12L_33_72907394." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2GG. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2GG. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2GG. In some cases, a Cas12L protein includes an amino acid sequence having the Cas12L amino acid sequence depicted in FIG. 2GG. In some cases, a Cas12L protein includes an amino acid sequence having the Cas12L protein sequence depicted in FIG. 2GG, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2GG) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2HH

In some cases, a Cas12L protein (of the subject compositions and/or methods) includes a contiguous stretch of about 245 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2HH and designated "Cas12L_34_73124743_partial." For example, in some cases, a Cas12L protein includes a contiguous stretch of about 245 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2HH. In some cases, a Cas12L protein includes a contiguous stretch of about 245 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2HH. In some cases, a Cas12L protein includes a contiguous stretch of about 245 amino acids having 90% or more sequence identity (e.g., 95% or more, 97% or more, 98% or more, 99% or more, or 100% sequence identity) with the Cas12L amino acid sequence depicted in FIG. 2HH. In some cases, a Cas12L protein includes a contiguous stretch of about 245 amino acids having the Cas12L amino acid sequence depicted in FIG. 2HH. In some cases, a Cas12L protein includes a contiguous stretch of about 245 amino acids having the Cas12L protein sequence depicted in FIG. 2HH, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2HH) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2II

In some cases, a Cas12L protein (of the subject compositions and/or methods) includes a contiguous stretch of about 178 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2II and designated "Cas12L_35_73503649_partial." For example, in some cases, a Cas12L protein includes a contiguous stretch of about 178 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2II. In some cases, a Cas12L protein includes a contiguous stretch of about 178 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2II. In some cases, a Cas12L protein includes a contiguous stretch of about 178 amino acids having 90% or more sequence identity (e.g., 95% or more, 97% or more, 98% or more, 99% or more, or 100% sequence identity) with the Cas12L amino acid sequence depicted in FIG. 2II. In some cases, a Cas12L protein includes a contiguous stretch of about 178 amino acids having the Cas12L amino acid sequence depicted in FIG. 2II. In some cases, a Cas12L protein includes a contiguous stretch of about 178 amino acids having the Cas12L protein sequence depicted in FIG. 2II, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2II) includes the following nucleotide sequence:

ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2JJ

In some cases, a Cas12L protein (of the subject compositions and/or methods) includes a contiguous stretch of about 85 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2JJ and designated "Cas12L_36_73503649_partial." For example, in some cases, a Cas12L protein includes a contiguous stretch of about 85 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2JJ. In some cases, a Cas12L protein includes a contiguous stretch of about 85 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2JJ. In some cases, a Cas12L protein includes a contiguous stretch of about 85 amino acids having 90% or more sequence identity (e.g., 95% or more, 97% or more, 98% or more, 99% or more, or 100% sequence identity) with the Cas12L amino acid sequence depicted in FIG. 2JJ. In some cases, a Cas12L protein includes a contiguous stretch of about 85 amino acids having the Cas12L amino acid sequence depicted in FIG. 2JJ. In some cases, a Cas12L protein includes a contiguous stretch of about 85 amino acids having the Cas12L protein sequence depicted in FIG. 2JJ, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids.

FIG. 2KK

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2KK and designated "Cas12L_37_73472625." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2KK. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2KK. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2KK. In some cases, a Cas12L protein includes an amino acid sequence having the Cas12L amino acid sequence depicted in FIG. 2KK. In some cases, a Cas12L protein includes an amino acid sequence having the Cas12L protein sequence depicted in FIG. 2KK, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 767 aa, from 767 aa to 775 aa, or from 775 aa to 800 aa). In some cases, the Cas12L polypeptide has a length of 767 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2KK) includes the following nucleotide sequence: ATTGTTGTAACATCTAT-TTTGTAAGGTGTAAACAAC (SEQ ID NO:15) or the reverse complement of same. In some cases, the guide RNA comprises the nucleotide sequence (N)nATTGTTGTAA-CATCTATTTTGTAAGGTGTAAACAAC (SEQ ID NO:16) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2LL

In some cases, a Cas12L protein (of the subject compositions and/or methods) includes a contiguous stretch of about 652 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2LL and designated "Cas12L_38_73764039_partial." For example, in some cases, a Cas12L protein includes a contiguous stretch of about 652 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2LL. In some cases, a Cas12L protein includes a contiguous stretch of about 652 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2LL. In some cases, a Cas12L protein includes a contiguous stretch of about 652 amino acids having 90% or more sequence identity (e.g., 95% or more, 97% or more, 98% or more, 99% or more, or 100% sequence identity) with the Cas12L amino acid sequence depicted in FIG. 2LL. In some cases, a Cas12L protein includes a contiguous stretch of about 652 amino acids having the Cas12L amino acid sequence depicted in FIG. 2LL. In some cases, a Cas12L protein includes a contiguous stretch of about 652 amino acids having the Cas12L protein sequence depicted in FIG. 2LL, with the exception that the sequence includes an amino acid substitution (e.g., 1, 2, or 3 amino acid substitutions)

that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2LL) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2MM

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2MM and designated "Cas12L_40_74037305." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2MM. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2MM. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2MM. In some cases, a Cas12L protein includes an amino acid sequence having the Cas12L amino acid sequence depicted in FIG. 2MM. In some cases, a Cas12L protein includes an amino acid sequence having the Cas12L protein sequence depicted in FIG. 2MM, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 782 aa, or from 782 aa to 800 aa). In some cases, the Cas12L polypeptide has a length of 782 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2MM) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2NN

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2NN and designated "Cas12L_41_74408273_partial." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2NN. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2NN. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2NN. In some cases, a Cas12L protein includes an amino acid sequence having the Cas12L amino acid sequence depicted in FIG. 2NN. In some cases, a Cas12L protein includes an amino acid sequence having the Cas12L protein sequence depicted in FIG. 2NN, with the exception that the sequence includes an amino acid substitution (e.g., 1, 2, or 3 amino acid substitutions) that reduces the naturally occurring catalytic activity of the protein. In some cases, the Cas12L polypeptide has a length of from 850 amino acids (aa) to 950 aa, e.g., from 850 aa to 875 aa, from 875 aa to 889 aa, from 889 aa to 900 aa, or from 900 aa to 950 aa). In some cases, the Cas12L polypeptide has a length of 889 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2NN) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2OO

In some cases, a Cas12L protein (of the subject compositions and/or methods) includes a contiguous stretch of about 223 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2OO and designated "Cas12L_42_75186079_partial." For example, in some cases, a Cas12L protein includes a contiguous stretch of about 223 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2OO. In some cases, a Cas12L protein includes a contiguous stretch of about 223 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2OO. In some cases, a Cas12L protein includes a contiguous stretch of about 223 amino acids having 90% or more sequence identity (e.g., 95% or more, 97% or more, 98% or more, 99% or more, or 100% sequence identity) with the Cas12L amino acid sequence depicted in FIG. 2OO. In some cases, a Cas12L protein includes a contiguous stretch of about 223 amino acids having the Cas12L amino acid sequence depicted in FIG. 2OO. In some cases, a Cas12L protein includes a contiguous stretch of about 223 amino acids having the Cas12L protein sequence depicted in FIG. 2OO, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2OO) includes the following nucleotide sequence: AATTGTTGTAACTCTTATTTTGTATG-GAGTAAACAAC (SEQ ID NO:17) or the reverse complement of same. In some cases, the guide RNA comprises the nucleotide sequence (N)nAATTGTTGTAACTCTTAT-TTTGTATGGAGTAAACAAC (SEQ ID NO:18) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2PP

In some cases, a Cas12L protein (of the subject compositions and/or methods) includes a contiguous stretch of about 439 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2PP and designated "Cas12L_43_75257103_partial." For example, in some cases, a Cas12L protein includes a contiguous stretch of about 439 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2PP. In some cases, a Cas12L protein includes a contiguous stretch of about 439 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2PP. In some cases, a Cas12L protein includes a contiguous stretch of about 439 amino acids having 90% or more sequence identity (e.g., 95% or more, 97% or more, 98% or more, 99% or more, or 100% sequence identity) with the Cas12L amino acid sequence depicted in FIG. 2PP. In some cases, a Cas12L protein includes a contiguous stretch of about 439 amino acids having the Cas12L amino acid sequence depicted in FIG. 2PP. In some cases, a Cas12L protein includes a contiguous stretch of about 439 amino acids having the Cas12L protein sequence depicted in FIG. 2PP, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2PP) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2QQ

In some cases, a Cas12L protein (of the subject compositions and/or methods) includes a contiguous stretch of about 196 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2QQ and designated "Cas12L_44_75257103_partial." For example, in some cases, a Cas12L protein includes a contiguous stretch of about 196 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2QQ. In some cases, a Cas12L protein includes a contiguous stretch of about 196 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2QQ. In some cases, a Cas12L protein includes a contiguous stretch of about 196 amino acids having 90% or more sequence identity (e.g., 95% or more, 97% or more, 98% or more, 99% or more, or 100% sequence identity) with the Cas12L amino acid sequence depicted in FIG. 2QQ. In some cases, a Cas12L protein includes a contiguous stretch of about 196 amino acids having the Cas12L amino acid sequence depicted in FIG. 2QQ. In some cases, a Cas12L protein includes a contiguous stretch of about 196 amino acids having the Cas12L protein sequence depicted in FIG. 2QQ, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2QQ) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2RR

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2RR and designated "Cas12L_45_75616607_partial." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2RR. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2RR. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2RR. In some cases, a Cas12L protein includes an amino acid sequence having the Cas12L amino acid sequence depicted in FIG. 2RR. In some cases, a Cas12L protein includes an amino acid sequence having the Cas12L protein sequence depicted in FIG. 2RR, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 748 aa, from 748 aa to 775 aa, or from 775 aa to 800 aa). In some cases, the Cas12L polypeptide has a length of 748 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2RR) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2SS

In some cases, a Cas12L protein (of the subject compositions and/or methods) includes a contiguous stretch of about 481 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2SS and designated "Cas12L_46_75784289_partial." For example, in some cases, a Cas12L) includes a contiguous stretch of about 481 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2SS. In some cases, a Cas12L protein) includes a contiguous stretch of about 481 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2SS. In some cases, a Cas12L protein) includes a contiguous stretch of about 481 amino acids having 90% or more sequence identity (e.g., 95% or more, 97% or more, 98% or more, 99% or more, or 100% sequence identity) with the Cas12L amino acid sequence depicted in FIG. 2SS. In some cases, a Cas12L protein) includes a contiguous stretch of about 481 amino acids having the Cas12L amino acid sequence depicted in FIG. 2SS. In some cases, a Cas12L protein) includes a contiguous stretch of about 481 amino acids having the Cas12L protein sequence depicted in FIG. 2SS, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2SS) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2TT

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2TT and designated "Cas12L_47_76512228." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2TT. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2TT. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2TT. In some cases, a Cas12L protein includes an amino acid sequence having the Cas12L amino acid sequence depicted in FIG. 2TT. In some cases, a Cas12L protein includes an amino acid sequence having the Cas12L protein sequence depicted in FIG. 2TT, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2TT) includes the following nucleotide sequence: ATTGTTGTAACTTTTATTTTGTATG-GAGTAAACAAC (SEQ ID NO:19) or the reverse complement of same. In some cases, the guide RNA comprises the nucleotide sequence (N)nATTGTTGTAACTTTTAT-TTTGTATGGAGTAAACAAC (SEQ ID NO:20) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2UU

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2UU and designated "Cas12L_48_76600450." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2UU. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2UU. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2UU. In some cases, a Cas12L protein includes an amino acid sequence having the Cas12L amino acid sequence depicted in FIG. 2UU. In some cases, a Cas12L protein includes an amino acid sequence having the Cas12L protein sequence depicted in FIG. 2UU, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2UU) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2VV

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2VV and designated "Cas12L_49_44880081." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2VV. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2VV. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2VV. In some cases, a Cas12L protein includes an amino acid sequence having the Cas12L amino acid sequence depicted in FIG. 2VV. In some cases, a Cas12L protein includes an amino acid sequence having the Cas12L protein sequence depicted in FIG. 2VV, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2VV) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2WW

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2WW and designated "Cas12L_50_83012613." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2WW. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2WW. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2WW. In some cases, a Cas12L protein includes an amino acid sequence having the Cas12L amino acid sequence depicted in FIG. 2WW. In some cases, a Cas12L protein includes an amino acid sequence having the Cas12L protein sequence depicted in FIG. 2WW, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 735 aa, from 735 aa to 750 aa, from 750 aa to 775 aa, or from 775 aa to 800 aa). In some cases, the Cas12L polypeptide has a length of 735 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2WW) includes the following nucleotide sequence: AATGTTGTAGATACCTTTTTGTAAGGATT-GAACAAC (SEQ ID NO:21) or the reverse complement of same. In some cases, the guide RNA comprises the nucleotide sequence (N)nAATGTTGTAGA-TACCTTTTTGTAAGGATTGAACAAC (SEQ ID NO:22) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2XX

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2XX and designated "Cas12L_51_82983331." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2XX. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2XX. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2XX. In some cases, a Cas12L protein includes an amino acid sequence having the Cas12L amino acid sequence depicted in FIG. 2XX. In some cases, a Cas12L protein includes an amino acid sequence having the Cas12L protein sequence depicted in FIG. 2XX, with the exception that the sequence includes an amino acid substitution (e.g., 1, 2, or 3 amino acid substitutions) that reduces the naturally occurring catalytic activity of the protein. In some cases, the Cas12L polypeptide has a length of from 750 amino acids (aa) to 850 aa, e.g., from 750 aa to 779 aa, from 779 aa to 800 aa, or from 800 aa to 850 aa). In some cases, the Cas12L polypeptide has a length of 779 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2XX) includes the following nucleotide sequence: ATTGTTGTAATACTATTTTTGTAAAGTATAAACAAC (SEQ ID NO:23) or the reverse complement of same. In some cases, the guide RNA comprises the nucleotide sequence (N)nATTGTTGTAATACTAT-TTTTGTAAAGTATAAACAAC (SEQ ID NO:24) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2YY

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2YY and designated "Cas12L_52_76767885." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2YY. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2YY. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2YY. In some cases, a Cas12L protein includes an amino acid sequence having the Cas12L amino acid sequence depicted in FIG. 2YY. In some cases, a Cas12L protein includes an amino acid sequence having the Cas12L protein sequence depicted in FIG. 2YY, with the exception that the sequence includes an amino acid substitution (e.g., 1, 2, or 3 amino acid substitutions) that reduces the naturally occurring catalytic activity of the protein. In some cases, the Cas12L polypeptide has a length of from 550 amino acids (aa) to 700 aa, e.g., from 550 aa to 592 aa, from 592 aa to 625 aa, from 625 aa to 650 aa, or from 650 aa to 700 aa). In some cases, the Cas12L polypeptide has a length of 592 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2YY) includes the following nucleotide sequence: AATGTTGTAGATGCCTTTTTATAAGGAT-TAAACAAC (SEQ ID NO:25) or the reverse complement of same. In some cases, the guide RNA comprises the nucleotide sequence (N)nAATGTTGTAGATGCCTTTT-TATAAGGATTAAACAAC (SEQ ID NO:26) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2ZZ

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2ZZ and designated "Cas12L_53_77216451." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2ZZ. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2ZZ. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2ZZ. In some cases, a Cas12L protein includes an amino acid sequence having the Cas12L amino acid sequence depicted in FIG. 2ZZ. In some cases, a Cas12L protein includes an amino acid sequence having the Cas12L protein sequence depicted in FIG. 2ZZ, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2ZZ) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2AAA

In some cases, a Cas12L protein (of the subject compositions and/or methods) includes a contiguous stretch of about 29 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2AAA and designated "Cas12L_54_77468912_partial." For example, in some cases, a Cas12L protein includes a contiguous stretch of about 29 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2AAA. In some cases, a Cas12L protein includes a contiguous stretch of about 29 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2AAA. In some cases, a Cas12L protein includes a contiguous stretch of about 29 amino acids having 90% or more sequence identity (e.g., 95% or more, 97% or more, 98% or more, 99% or more, or 100% sequence identity) with the Cas12L amino acid sequence depicted in FIG. 2AAA. In some cases, a Cas12L protein includes a contiguous stretch of about 29 amino acids having the Cas12L amino acid sequence depicted in FIG. 2AAA. In some cases, a Cas12L protein includes a contiguous stretch of about 29 amino acids having the Cas12L protein sequence depicted in FIG. 2AAA, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2AAA) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2BBB

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2BBB and designated "Cas12L_55_77738117." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2BBB. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2BBB. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2BBB. In some cases, a Cas12L protein includes an amino acid sequence having the Cas12L amino acid sequence depicted in FIG. 2BBB. In some cases, a Cas12L protein includes an amino acid sequence having the Cas12L protein sequence depicted in FIG. 2BBB, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2BBB) includes the following nucleotide sequence: ATTGTTGTAATA-CACTTTTTATAAGGTATGAACAAC (SEQ ID NO:27) or the reverse complement of same. In some cases, the guide RNA comprises the nucleotide sequence (N)nAT-TGTTGTAATACACTTTTTATAAGGTATGAACAAC (SEQ ID NO:28) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2CCC

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2CCC and designated "Cas12L_56_65286425." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2CCC. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2CCC. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2CCC. In some cases, a Cas12L protein includes an amino acid sequence having the Cas12L amino acid sequence depicted in FIG. 2CCC. In some cases, a Cas12L protein includes an amino acid sequence having the Cas12L protein sequence depicted in FIG. 2CCC, with the exception that the sequence includes an amino acid substitution (e.g., 1, 2, or 3 amino acid substitutions) that reduces the naturally occurring catalytic activity of the protein. In some cases, the Cas12L polypeptide has a length of from 650 amino acids (aa) to 750 aa, e.g., from 650 aa to 692 aa, from 692 aa to 725 aa, or from 725 aa to 750 aa). In some cases, the Cas12L polypeptide has a length of 692 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2CCC) includes the following nucleotide sequence: ATTGTTGTAACTCTTATTTTGTATGGAGTAAACAAC (SEQ ID NO:1) or the reverse complement of same. In some cases, the guide RNA comprises the nucleotide sequence (N)nATTGTTGTAACTCTTATTTTGTATG-GAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2DDD

In some cases, a Cas12L protein (of the subject compositions and/or methods) includes a contiguous stretch of about 441 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2DDD and designated "Cas12L_57_65567118_partial." For example, in some cases, a Cas12L protein) includes a contiguous stretch of about 441 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2DDD. In some cases, a Cas12L protein) includes a contiguous stretch of about 441 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2DDD. In some cases, a Cas12L protein) includes a contiguous stretch of about 441 amino acids having 90% or more sequence identity (e.g., 95% or more, 97% or more, 98% or more, 99% or more, or 100% sequence identity) with the Cas12L amino acid sequence depicted in FIG. 2DDD. In some cases, a Cas12L protein) includes a contiguous stretch of about 441 amino acids having the Cas12L amino acid sequence depicted in FIG. 2DDD. In some cases, a Cas12L protein) includes a contiguous stretch of about 441 amino acids having the Cas12L protein sequence depicted in FIG. 2DDD, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2DDD) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2EEE

In some cases, a Cas12L protein (of the subject compositions and/or methods) includes a contiguous stretch of about 397 amino acids having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2EEE and designated "Cas12L_58_66287853_partial." For example, in some cases, a Cas12L protein includes a contiguous stretch of about 397 amino acids having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2EEE. In some cases, a Cas12L protein includes a contiguous stretch of about 397 amino acids having 80% or more sequence identity (e.g., 85% or more, 90% or more, 95% or more, 97% or more, 98% or more, 99% or more, or 100% sequence identity) with the Cas12L amino acid sequence depicted in FIG. 2EEE. In some cases, a Cas12L protein includes a contiguous stretch of about 397 amino acids having 90% or more sequence identity (e.g., 95% or more, 97% or more, 98% or more, 99% or more, or 100% sequence identity) with the Cas12L amino acid sequence depicted in FIG. 2EEE. In some cases, a Cas12L protein includes a contiguous stretch of about 397 amino acids having the Cas12L amino acid sequence depicted in FIG. 2EEE. In some cases, a Cas12L protein includes a contiguous stretch of about 397 amino acids having the Cas12L protein sequence depicted in FIG. 2EEE, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 750 aa, from 750 aa to 775 aa, or from 775 aa to 800 aa). In some cases, the Cas12L polypeptide has a length of from 725 amino acids to 775 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2EEE) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

FIG. 2FFF

In some cases, a Cas12L protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12L amino acid sequence depicted in FIG. 2FFF and designated "Cas12L_39_73877227." For example, in some cases, a Cas12L protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12L amino acid sequence depicted in FIG. 2FFF. In some cases, a Cas12L protein includes an amino acid sequence having 80% or more sequence identity (e.g., 85% or more, 90% or more, 95% or more, 97% or more, 98% or more, 99% or more, or 100% sequence identity) with the Cas12L amino acid sequence depicted in FIG. 2FFF. In some cases, a Cas12L protein includes an amino acid sequence having 90% or more sequence identity (e.g., 95% or more, 97% or more, 98% or more, 99% or more, or 100% sequence identity) with the Cas12L amino acid sequence depicted in FIG. 2FFF. In some cases, a Cas12L protein includes an amino acid sequence having the Cas12L amino acid sequence depicted in FIG. 2FFF. In some cases, a Cas12L protein includes an amino acid sequence having the Cas12L protein sequence depicted in FIG. 2FFF, with the exception that the sequence includes an amino acid substitution (e.g., 1, 2, or 3 amino acid substitutions) that reduces the naturally occurring catalytic activity of the protein. In some cases, the Cas12L polypeptide has a length of from 700 amino acids (aa) to 800 aa, e.g., from 700 aa to 725 aa, from 725 aa to 746 aa, from 746 aa to 775 aa, or from 775 aa to 800 aa). In some cases, the Cas12L polypeptide has a length of 746 amino acids. In some cases, a guide RNA that binds a Cas12L polypeptide (e.g., a Cas12L polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12L amino acid sequence depicted in FIG. 2FFF) includes the following nucleotide sequence: ATTGTTGTAACTCTTATTTTGTATG-GAGTAAACAAC (SEQ ID NO:1) or the reverse complement of same. In some cases, the guide RNA comprises the nucleotide sequence (N)nATTGTTGTAACTCTTAT-TTTGTATGGAGTAAACAAC (SEQ ID NO:2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30).

Cas12L Variants

A variant Cas12L protein has an amino acid sequence that is different by at least one amino acid (e.g., has a deletion, insertion, substitution, fusion) when compared to the amino acid sequence of the corresponding wild type Cas12L protein, e.g., when compared to the Cas12L amino acid sequence depicted in any one of FIGS. 2A-2Z, FIGS. 2AA-2ZZ, and FIGS. 2AAA-2FFF. In some cases, a Cas12L variant comprises from 1 amino acid substitution to 10 amino acid substitutions compared to the Cas12L amino acid sequence depicted in any one of FIGS. 2A-2Z, FIGS. 2AA-2ZZ, and FIGS. 2AAA-2FFF. In some cases, a Cas12L variant comprises from 1 amino acid substitution to 10 amino acid substitutions in the RuvC domain, compared to the Cas12L amino acid sequence depicted in any one of FIGS. 2A-2Z, FIGS. 2AA-2ZZ, and FIG. 2AAA-2FFF.

Variants—Catalytic Activity

In some cases, the Cas12L protein is a variant Cas12L protein, e.g., mutated relative to the naturally occurring catalytically active sequence, and exhibits reduced cleavage activity (e.g., exhibits 90%, or less, 80% or less, 70% or less, 60% or less, 50% or less, 40% or less, or 30% or less cleavage activity) when compared to the corresponding naturally occurring sequence. In some cases, such a variant Cas12L protein is a catalytically 'dead' protein (has substantially no cleavage activity) and can be referred to as a 'dCas12L.' In some cases, the variant Cas12L protein is a nickase (cleaves only one strand of a double stranded target nucleic acid, e.g., a double stranded target DNA). As described in more detail herein, in some cases, a Cas12L protein (in some case a Cas12L protein with wild type cleavage activity and in some cases a variant Cas12L with reduced cleavage activity, e.g., a dCas12L or a nickase Cas12L) is fused (conjugated) to a heterologous polypeptide that has an activity of interest (e.g., a catalytic activity of interest) to form a fusion protein (a fusion Cas12L protein).

In some cases, a variant Cas12L polypeptide comprises a substitution of one, two, or three amino acids of the active site residues indicated in FIG. 3A-3B, where the variant Cas12L polypeptide exhibits reduced catalytic activity compared to a control Cas12L polypeptide that does not include the one, two, or three substitutions.

Variants—Fusion Cas12L Polypeptides

As noted above, in some cases, a Cas12L protein (in some cases a Cas12L protein with wild type cleavage activity and in some cases a variant Cas12L with reduced cleavage activity, e.g., a dCas12L or a nickase Cas12L) is fused (conjugated) to a heterologous polypeptide that has an activity of interest (e.g., a catalytic activity of interest) to form a fusion protein. A heterologous polypeptide to which a Cas12L protein can be fused is referred to herein as a 'fusion partner.'

In some cases, the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, the fusion partner (heterologous polypeptide) is a reverse transcriptase. In some cases, the fusion partner is a base editor. In some cases, the fusion partner (heterologous polypeptide) is a deaminase.

In some cases, a fusion Cas12L protein includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a fusion Cas12L protein includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Kruppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases, the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/

SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragement of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

Additional examples of a suitable fusion partners are dihydrofolate reductase (DHFR) destabilization domain (e.g., to generate a chemically controllable fusion Cas12L protein), and a chloroplast transit peptide. Suitable chloroplast transit peptides include, but are not limited to:

```
                                        (SEQ ID NO: 29)
MASMISSSAVTTVSRASRGQSAAMAPFGGLKSMTGFPVRKVNTDITSITS
NGGRVKCMQVWPPIGKKKFETLSYLPPLTRDSRA;

(SEQ ID NO: 30)
MASMISSSAVTTVSRASRGQSAAMAPFGGLKSMTGFPVRKVNTDITSITS
NGGRVKS;

(SEQ ID NO: 31)
MASSMLSSATMVASPAQATMVAPFNGLKSSAAFPATRKANNDITSITSNG
GRVNCMQVWPPIEKKKFETLSYLPDLTDSGGRVNC;

(SEQ ID NO: 32)
MAQVSRICNGVQNPSLISNLSKSSQRKSPLSVSLKTQQHPRAYPISSSWG
LKKSGMTLIGSELRPLKVMSSVSTAC;

(SEQ ID NO: 33)
MAQVSRICNGVWNPSLISNLSKSSQRKSPLSVSLKTQQHPRAYPISSSWG
LKKSGMTLIGSELRPLKVMSSVSTAC;

(SEQ ID NO: 34)
MAQINNMAQGIQTLNPNSNFHKPQVPKSSSFLVFGSKKLKNSANSMLVLK
KDSIFMQLFCSFRISASVATAC;

(SEQ ID NO: 35)
MAALVTSQLATSGTVLSVTDRFRRPGFQGLRPRNPADAALGMRTVGASAA
PKQSRKPHRFDRRCLSMVV;

(SEQ ID NO: 36)
MAALTTSQLATSATGFGIADRSAPSSLLRHGFQGLKPRSPAGGDATSLSV
TTSARATPKQQRSVQRGSRRFPSVVVC;

(SEQ ID NO: 37)
MASSVLSSAAVATRSNVAQANMVAPFTGLKSAASFPVSRKQNLDITSIAS
NGGRVQC;

(SEQ ID NO: 38)
MESLAATSVFAPSRVAVPAARALVRAGTVVPTRRTSSTSGTSGVKCSAAV
TPQASPVISRSAAAA;
and (SEQ ID NO: 39)
MGAAATSMQSLKFSNRLVPPSRRLSPVPNNVTCNNLPKSAAPVRTVKCCA
SSWNSTINGAAAATTNGASAASS.
```

In some case, a Cas12L fusion polypeptide of the present disclosure comprises: a) a Cas12L polypeptide of the present disclosure; and b) a chloroplast transit peptide. Thus, for example, a Cas12L polypeptide/guide RNA complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the amino terminus (NH$_2$ terminus) of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a Cas12L fusion polypeptide of the present disclosure can comprise: a) a Cas12L polypeptide of the present disclosure; and b) an endosomal escape peptide. In some cases, an endosomal escape polypeptide comprises the amino acid sequence GLFXALLXLLXSLWXLLLXA (SEQ ID NO:72), wherein each X is independently selected from lysine, histidine, and arginine. In some cases, an endosomal escape polypeptide comprises the amino acid sequence GLFHALLHLLHSLWHLLLHA (SEQ ID NO:73).

For examples of some of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al, J Am Chem Soc. 2007 Jul. 18;129(28):8676-7; Rivenbark et al., Epigenetics. 2012 April; 7(4):350-60; Nucleic Acids Res. 2016 Jul. 8;44(12):5615-28; Gilbert et al., Cell. 2013 Jul. 18;154(2):442-51; Kearns et al., Nat Methods. 2015 May; 12(5):401-3; Mendenhall et al., Nat Biotechnol. 2013 December; 31(12):1133-6; Hilton et al., Nat Biotechnol. 2015 May; 33(5):510-7; Gordley et al., Proc Natl Acad Sci USA. 2009 Mar. 31;106(13):5053-8; Akopian et al., Proc Natl Acad Sci USA. 2003 Jul. 22;100(15):8688-91; Tan et., al., J Virol. 2006 Feb;80(4):1939-48; Tan et al., Proc Natl Acad Sci USA. 2003 Oct. 14;100(21):11997-2002; Papworth et al., Proc Natl Acad Sci USA. 2003 Feb. 18;100(4): 1621-6; Sanjana et al., Nat Protoc. 2012 Jan. 5;7(1):171-92; Beerli et al., Proc Natl Acad Sci USA. 1998 Dec 8;95(25): 14628-33; Snowden et al., Curr Biol. 2002 Dec. 23;12(24): 2159-66; Xu et.al., Xu et al., Cell Discov. 2016 May 3; 2:16009; Komor et al., Nature. 2016 Apr. 20;533(7603):420-4; Chaikind et al., Nucleic Acids Res. 2016 Aug. 11; Choudhury at. al., Oncotarget. 2016 Jun. 23; Du et al., Cold Spring Harb Protoc. 2016 Jan. 4; Pham et al., Methods Mol Biol. 2016; 1358:43-57; Balboa et al., Stem Cell Reports. 2015 Sep. 8;5(3):448-59; Hara et al., Sci Rep. 2015 Jun. 9; 5:11221; Piatek et al., Plant Biotechnol J. 2015 May; 13(4): 578-89; Hu et al., Nucleic Acids Res. 2014 April; 42(7): 4375-90; Cheng et al., Cell Res. 2013 October;23(10):1163-71; and Maeder et al., Nat Methods. 2013 October;10(10): 977-9.

Additional suitable heterologous polypeptides include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a fusion Cas12L polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject fusion Cas12L polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP Si, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a fusion Cas12L polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5′ splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cω-elements that are located in either the core exon region or the exon extension region (i.e., between the two alternative 5′ splice sites). For more examples, see WO2010075303, which is hereby incorporated by reference in its entirety.

Further suitable fusion partners include, but are not limited to, proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pill/Abyl, etc.).

Nucleases

In some cases, a subject fusion Cas12L polypeptide comprises: i) a Cas12L polypeptide of the present disclosure; and ii) a heterologous polypeptide (a "fusion partner"), where the heterologous polypeptide is a nuclease. Suitable nucleases include, but are not limited to, a homing nuclease polypeptide; a FokI polypeptide; a transcription activator-like effector nuclease (TALEN) polypeptide; a MegaTAL polypeptide; a meganuclease polypeptide; a zinc finger nuclease (ZFN); an ARCUS nuclease; and the like. The meganuclease can be engineered from an LADLIDADG homing endonuclease (LHE). A megaTAL polypeptide can comprise a TALE DNA binding domain and an engineered meganuclease. See, e.g., WO 2004/067736 (homing endonuclease); Urnov et al. (2005) Nature 435:646 (ZFN); Mussolino et al. (2011) Nucle. Acids Res. 39:9283 (TALE nuclease); Boissel et al. (2013) Nucl. Acids Res. 42:2591 (MegaTAL).

Reverse Transcriptases

In some cases, a subject fusion Cas12L polypeptide comprises: i) a Cas12L polypeptide of the present disclosure; and ii) a heterologous polypeptide (a "fusion partner"), where the heterologous polypeptide is a reverse transcriptase polypeptide. In some cases, the Cas12L polypeptide is catalytically inactive. Suitable reverse transcriptases include, e.g., a murine leukemia virus reverse transcriptase; a Rous sarcoma virus reverse transcriptase; a human immunodeficiency virus type I reverse transcriptase; a Moloney murine leukemia virus reverse transcriptase; and the like.

Base Editors

In some cases, a Cas12L fusion polypeptide of the present disclosure comprises: i) a Cas12L polypeptide of the present disclosure; and ii) a heterologous polypeptide (a "fusion partner"), where the heterologous polypeptide is a base editor. Suitable base editors include, e.g., an adenosine deaminase; a cytidine deaminase (e.g., an activation-induced cytidine deaminase (AID)); APOBEC3G; and the like); and the like.

A suitable adenosine deaminase is any enzyme that is capable of deaminating adenosine in DNA. In some cases, the deaminase is a TadA deaminase.

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

(SEQ ID NO: 74)

MSEVEFSHEYWMRHALTLAKRAWDEREVPVGAVLVHNNRVIGEGWNRPI

GRHDPTAHAEIMALRQGGLVMQNYRLIDATLYVTLEPCVMCAGAMIHSR

IGRVVFGARDAKTGAAGSLMDVLHHPGMNHRVEITEGILADECAALLSD

FFRMRRQEIKAQKKAQSSTD

In some cases, a suitable adenosine deaminase comprises an amino acid sequence having at least 80%, at least 85%, at least 90%, at least 95%, at least 98%, at least 99%, or 100%, amino

```
                                    (SEQ ID NO: 75)
MRRAFITGVFFLSEVEFSHEYWMRHALTLAKRAWDEREVPVGAVLVHNN

RVIGEGWNRPIGRHDPTAHAEIMALRQGGLVMQNYRLIDATLYVTLEPC

VMCAGAMIHSRIGRVVFGARDAKTGAAGSLMDVLHHPGMNHRVEITEGI

LADECAALLSDFFRMRRQEIKAQKKAQSSTD.
```

In some cases, a suitable adenosine deaminase comprises an amino acid sequence having at least 80%, at least 85%, at least 90%, at least 95%, at least 98%, at least 99%, or 100%, amino acid sequence identity to the following *Staphylococcus aureus* TadA amino acid sequence:

```
                                    (SEQ ID NO: 76)
MGSHMTNDIYFMTLAIEEAKKAAQLGEVPIGAIITKDDEVIARAHNLRE

TLQQPTAHAEHIAIERAAKVLGSWRLEGCTLYVTLEPCVMCAGTIVMSR

IPRVVYGADDPKGGCSGSLMNLLQQSNFNHRAIVDKGVLKEACSTLLTT

FFKNLRANKKSTN:
```

In some cases, a suitable adenosine deaminase comprises an amino acid sequence having at least 80%, at least 85%, at least 90%, at least 95%, at least 98%, at least 99%, or 100%, amino acid sequence identity to the following *Bacillus subtilis* TadA amino acid sequence:

```
                                    (SEQ ID NO: 77)
MTQDELYMKEAIKEAKKAEEKGEVPIGAVLVINGEIIARAHNLRETEQRS

IAHAEMLVIDEACKALGTWRLEGATLYVTLEPCPMCAGAVVLSRVEKVVF

GAFDPKGGCSGTLMNLLQEERFNHQAEVVSGVLEEECGGMLSAFFRELRK

KKKAARKNLSE
```

In some cases, a suitable adenosine deaminase comprises an amino acid sequence having at least 80%, at least 85%, at least 90%, at least 95%, at least 98%, at least 99%, or 100%, amino acid sequence identity to the following *Salmonella typhimurium* TadA:

```
                                    (SEQ ID NO: 78)
MPPAFITGVTSLSDVELDHEYWMRHALTLAKRAWDEREVPVGAVLVHNHR

VIGEGWNRPIGRHDPTAHAEIMALRQGGLVLQNYRLLDTTLYVTLEPCVM

CAGAMVHSRIGRVVFGARDAKTGAAGSLIDVLHHPGMNHRVEIIEGVLRD

ECATLLSDFFRMRRQEIKALKKADRAEGAGPAV
```

In some cases, a suitable adenosine deaminase comprises an amino acid sequence having at least 80%, at least 85%, at least 90%, at least 95%, at least 98%, at least 99%, or 100%, amino acid sequence identity to the following *Shewanella putrefaciens* TadA amino acid sequence:

```
                                    (SEQ ID NO: 79)
MDEYWMQVAMQMAEKAEAAGEVPVGAVLVKDGQQIATGYNLSISQHDPTA

HAEILCLRSAGKKLENYRLLDATLYITLEPCAMCAGAMVHSRIARVVYGA
```

```
-continued
RDEKTGAAGTVVNLLQHPAFNHQVEVTSGVLAEACSAQLSRFFKRRRDEK

KALKLAQRAQQGIE
```

In some cases, a suitable adenosine deaminase comprises an amino acid sequence having at least 80%, at least 85%, at least 90%, at least 95%, at least 98%, at least 99%, or 100%, amino acid sequence identity to the following *Haemophilus influenzae* F3031 TadA amino acid sequence:

```
                                    (SEQ ID NO: 80)
MDAAKVRSEFDEKMMRYALELADKAEALGEIPVGAVLVDDARNIIGEGWN

LSIVQSDPTAHAEIIALRNGAKNIQNYRLLNSTLYVTLEPCTMCAGAILH

SRIKRLVFGASDYKTGAIGSRFHFFDDYKMNHTLEITSGVLAEECSQKLS

TFFQKRREEKKIEKALLKSLSDK
```

In some cases, a suitable adenosine deaminase comprises an amino acid sequence having at least 80%, at least 85%, at least 90%, at least 95%, at least 98%, at least 99%, or 100%, amino acid sequence identity to the following *Caulobacter crescentus* TadA amino acid sequence:

```
                                    (SEQ ID NO: 81)
MRTDESEDQDHRMMRLALDAARAAAEAGETPVGAVILDPSTGEVIATAG

NGPIAAHDPTAHAEIAAMRAAAAKLGNYRLTDLTLVVTLEPCAMCAGAI

SHARIGRVVFGADDPKGGAVVHGPKFFAQPTCHWRPEVTGGVLADESAD

LLRGFFRARRKAKI
```

In some cases, a suitable adenosine deaminase comprises an amino acid sequence having at least 80%, at least 85%, at least 90%, at least 95%, at least 98%, at least 99%, or 100%, amino acid sequence identity to the following Geobacter sulfurreducens TadA amino acid sequence:

```
                                    (SEQ ID NO: 82)
MSSLKKTPIRDDAYWMGKAIREAAKAAARDEVPIGAVIVRDGAVIGRGH

NLREGSNDPSAHAEMIAIRQAARRSANWRLTGATLYVTLEPCLMCMGAI

ILARLERVVFGCYDPKGGAAGSLYDLSADPRLNHQVRLSPGVCQEECGT

MLSDFFRDLRRRKKAKATPALFIDERKVPPEP
```

Cytidine deaminases suitable for inclusion in a CRISPR/Cas effector polypeptide fusion polypeptide include any enzyme that is capable of deaminating cytidine in DNA.

In some cases, the cytidine deaminase is a deaminase from the apolipoprotein B mRNA-editing complex (APOBEC) family of deaminases. In some cases, the APOBEC family deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In some cases, the cytidine deaminase is an activation induced deaminase (AID).

In some cases, a suitable cytidine deaminase comprises an amino acid sequence having at least 80%, at least 85%, at least 90%, at least 95%, at least 98%, at least 99%, or 100%, amino acid sequence identity to the following amino acid sequence:

(SEQ ID NO: 83)
MDSLLMNRRKFLYQFKNVRWAKGRRETYLCYVVKRRDSATSFSLDFGY

LRNKNGCHVELLFLRYISDWDLDPGRCYRVTWFTSWSPCYDCARHVAD

FLRGNPNLSLRIFTARLYFCEDRKAEPEGLRRLHRAGVQIAIMTFKDY

FYCWNTFVENHERTFKAWEGLHENSVRLSRQLRRILLPLYEVDDLRDA

FRTLGL

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence: MDSLLMNRRK FLY-QFKNVRW AKGRRETYLC YVVKRRDSAT SFSLDFGYLR NKNGCHVELL FLRYISDWDL DPGRCYRVTW FTSWSPCYDC ARHVADFLRG NPNLSLRIFT ARLYFCEDRK AEPEGLRRLH RAG-VQIAIMT FKENHERTFK AWEGLHENSV RLSRQLR-RIL LPLYEVDDLR DAFRTLGL (SEQ ID NO:84).

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence: MDSLLMNRRK FLY-QFKNVRW AKGRRETYLC YVVKRRDSAT SFSLDFGYLR NKNGCHVELL FLRYISDWDL DPGRCYRVTW FTSWSPCYDC ARHVADFLRG NPNLSLRIFT ARLYFCEDRK AEPEGLRRLH RAG-VQIAIMT FKDYFYCWNT FVENHERTFK AWEGL-HENSV RLSRQLRRIL LPLYEVDDLR DAFRTLGL (SEQ ID NO:85).

Transcription Factors

In some cases, a Cas12L fusion polypeptide of the present disclosure comprises: i) a Cas12L polypeptide of the present disclosure; and ii) a heterologous polypeptide (a "fusion partner"), where the heterologous polypeptide is a transcription factor. A transcription factor can include: i) a DNA binding domain; and ii) a transcription activator. A transcription factor can include: i) a DNA binding domain; and ii) a transcription repressor. Suitable transcription factors include polypeptides that include a transcription activator or a transcription repressor domain (e.g., the Kruppel associated box (KRAB or SKD); the Mad mSIN3 interaction domain (SID); the ERF repressor domain (ERD), etc.); zinc-finger-based artificial transcription factors (see, e.g., Sera (2009) *Adv. Drug Deliv.* 61:513); TALE-based artificial transcription factors (see, e.g., Liu et al. (2013) Nat. *Rev. Genetics* 14:781); and the like. In some cases, the transcription factor comprises a VP64 polypeptide (transcriptional activation). In some cases, the transcription factor comprises a Kruppel-associated box (KRAB) polypeptide (transcriptional repression). In some cases, the transcription factor comprises a Mad mSIN3 interaction domain (SID) polypeptide (transcriptional repression). In some cases, the transcription factor comprises an ERF repressor domain (ERD) polypeptide (transcriptional repression). For example, in some cases, the transcription factor is a transcriptional activator, where the transcriptional activator is GAL4-VP16.

Recombinases

In some cases, a Cas12L fusion polypeptide of the present disclosure comprises: i) a Cas12L polypeptide of the present disclosure; and ii) a heterologous polypeptide (a "fusion partner"), where the heterologous polypeptide is a recombinase. Suitable recombinases include, e.g., a Cre recombinase; a Hin recombinase; a Tre recombinase; a FLP recombinase; and the like.

Examples of various additional suitable heterologous polypeptide (or fragments thereof) for a subject fusion Cas12L polypeptide include, but are not limited to, those described in the following applications (which publications are related to other CRISPR endonucleases such as Cas9, but the described fusion partners can also be used with Cas12L instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a Cas12L fusion polypeptide does not include an NLS so that the protein is not targeted to the nucleus (which can be advantageous, e.g., when the target nucleic acid is an RNA that is present in the cytosol). In some embodiments, the heterologous polypeptide can provide a tag (i.e., the heterologous polypeptide is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6XHis tag; a hemagglutinin (HA) tag; a FLAG tag; a Myc tag; and the like).

In some cases, a Cas12L protein (e.g., a wild type Cas12L protein, a variant Cas12L protein, a fusion Cas12L protein, a dCas12L protein, and the like) includes (is fused to) a nuclear localization signal (NLS) (e.g., in some cases 2 or more, 3 or more, 4 or more, or 5 or more NLSs). Thus, in some cases, a Cas12L polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases, a Cas12L protein (e.g., a wild type Cas12L protein, a variant Cas12L protein, a fusion Cas12L protein, a dCas12L protein, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases, a Cas12L protein (e.g., a wild type Cas12L protein, a variant Cas12L protein, a fusion Cas12L protein, a dCas12L protein, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO: 86); the NLS from nucleoplasmin (e.g., the nucleoplasmin bipartite NLS with the sequence KRPAATKKAGQAKKKK (SEQ ID NO:87)); the c-myc NLS having the amino acid sequence PAAKRVKLD (SEQ ID NO:88) or RQRR-NELKRSP (SEQ ID NO:89); the hRNPA1 M9 NLS having the sequence NQSSNFGPMKGGNFG-GRSSGPYGGGGQYFAKPRNQGGY (SEQ ID NO:90); the sequence RMRIZFKNKGKDTAELRRRRVEVS-VELRKAKKDEQILKRRNV (SEQ ID NO:91) of the IBB domain from importin-alpha; the sequences VSRKRPRP (SEQ ID NO: 92) and PPKKARED (SEQ ID NO:93) of the myoma T protein; the sequence PQPKKKPL (SEQ ID NO:94) of human p53; the sequence SALIKKKKMAP (SEQ ID NO:95) of mouse c-abl IV; the sequences DRLRR (SEQ ID NO: 96) and PKQKKRK (SEQ ID NO:97) of the influenza virus NS1; the sequence RKLKKKIKKL (SEQ ID NO:98) of the Hepatitis virus delta antigen; the sequence REKKKFLKRR (SEQ ID NO:99) of the mouse Mxl protein; the sequence KRKGDEVDGVDEVAKKKSKK (SEQ ID NO:100) of the human poly(ADP-ribose) polymerase; and the sequence RKCLQAGMNLEARKTKK (SEQ ID NO:101) of the steroid hormone receptors (human) gluco-corticoid. In general, NLS (or multiple NLSs) are of sufficient strength to drive accumulation of the Cas12L protein in a detectable amount in the nucleus of a eukaryotic cell. Detection of accumulation in the nucleus may be performed by any suitable technique. For example, a detectable marker may be fused to the Cas12L protein such that location within a cell may be visualized. Cell nuclei may also be isolated from cells, the contents of which may then be analyzed by any suitable process for detecting protein, such as immuno-histochemistry, Western blot, or enzyme activity assay. Accumulation in the nucleus may also be determined indirectly.

In some cases, a Cas12L fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type Cas12L polypeptide to generate a fusion protein, or linked to a variant Cas12L protein such as a dCas12L, nickase Cas12L, or fusion Cas12L protein, to generate a fusion protein). In some embodiments, a PTD is covalently linked to the carboxyl terminus of a polypeptide (e.g., linked to a wild type Cas12L to generate a fusion protein, or linked to a variant Cas12L protein such as a dCas12L, nickase Cas12L, or fusion Cas12L protein to generate a fusion protein). In some cases, the PTD is inserted internally in the Cas12L fusion polypeptide (i.e., is not at the N- or C-terminus of the Cas12L fusion polypeptide) at a suitable insertion site. In some cases, a subject Cas12L fusion polypeptide includes (is conjugated to, is fused to) one or more PTDs (e.g., two or more, three or more, four or more PTDs). In some cases, a PTD includes a nuclear localization signal (NLS) (e.g., in some cases 2 or more, 3 or more, 4 or more, or 5 or more NLSs). Thus, in some cases, a Cas12L fusion polypeptide includes one or more NLSs (e.g., 2 or more, 3 or more, 4 or more, or 5 or more NLSs). In some embodiments, a PTD is covalently linked to a nucleic acid (e.g., a Cas12L guide nucleic acid, a polynucleotide encoding a Cas12L guide nucleic acid, a polynucleotide encoding a Cas12L fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO:40); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human cal-citonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:41); Transportan GWTLNSAGYLLGKINL-KALAALAKKIL (SEQ ID NO:42); KALAWEAKLAKA-LAKALAKHLAKALAKALKCEA (SEQ ID NO:43); and RQIKIWFQNRRMKWKK (SEQ ID NO:44). Exemplary PTDs include but are not limited to, YGRKKRRQRRR (SEQ ID NO:40), RKKRRQRRR (SEQ ID NO:45); an arginine homopolymer of from 3 arginine residues to 50 arginine residues; Exemplary PTD domain amino acid sequences include, but are not limited to, any of the following: YGRKKRRQRRR (SEQ ID NO:40); RKKRRQRRR (SEQ ID NO:46); YARAAARQARA (SEQ ID NO:47); THRLPRRRRRR (SEQ ID NO:48); and GGRRARRRRRR (SEQ ID NO:49). In some embodiments, the PTD is an activatable CPP (ACPP) (Aguilera et al. (2009) *Integr Biol (Camb) June;* 1(5-6): 371-381). ACPPs comprise a polyca-tionic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyargi-nine and its inherent adhesiveness, thus "activating" the ACPP to traverse the membrane.

Linkers (e.g., for Fusion Partners)

In some embodiments, a subject Cas12L protein can fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers (G)$_n$, glycine-serine polymers (including, for example, (GS)$_n$, GSGGS$_n$ (SEQ ID NO: 50), GGSGGS$_n$ (SEQ ID NO:51), and GGGS$_n$ (SEQ ID NO: 52), where n is an integer of at least one), glycine-alanine polymers, alanine-serine polymers. Exemplary linkers can comprise amino acid sequences including, but not limited to, GGSG (SEQ ID NO:53), GGSGG (SEQ ID NO:54), GSGSG (SEQ ID NO:55), GSGGG (SEQ ID NO:56), GGGSG (SEQ ID NO:57), GSSSG (SEQ ID NO: 58), and the like. The ordinarily skilled artisan will recognize that design of a peptide conjugated to any desired element can include linkers that are all or partially flexible, such that the linker can include a flexible linker as well as one or more portions that confer less flexible structure.

Detectable Labels

In some cases, a Cas12L polypeptide of the present disclosure comprises a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilized EGFP (dEGFP), destabilized ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Protospacer Adjacent Motif (PAM)

A Cas12L protein binds to target DNA at a target sequence defined by the region of complementarity between the DNA-targeting RNA and the target DNA. As is the case for many CRISPR endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In some cases, the PAM for a Cas12L protein is immediately 5' of the target sequence of the non-complementary strand of the target DNA (the complementary strand: (i) hybridizes to the guide sequence of the guide RNA, while the non-complementary strand does not directly hybridize with the guide RNA; and (ii) is the reverse complement of the non-complementary strand).

In some cases, different Cas12L proteins (i.e., Cas12L proteins from various species) may be advantageous to use in the various provided methods in order to capitalize on various enzymatic characteristics of the different Cas12L proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). Cas12L proteins from different species may require different PAM sequences in the target DNA. Various methods (including in silico and/or wet lab methods) for identification of the appropriate PAM sequence are known in the art and are routine, and any convenient method can be used.

As shown in Example 1, a Cal12L polypeptide of the present disclosure can be reprogrammed (by complexing with a guide RNA) to cleave any sequence of a target nucleic acid (e.g., a target DNA) that is complementary to the targeting segment of the guide RNA, where the PAM is present on the 5' end of the target (e.g., a T-rich PAM for Cas),); additional RNA components are not required for the formation of functional effectors in vivo. In some cases, a PAM sequence is a T-rich sequence (e.g., TTR, where R is a purine). In some cases, a PAM sequence is TTA. In some cases, a PAM sequence is TTG.

Cas12L Guide RNA

A nucleic acid that binds to a Cas12L protein, forming a ribonucleoprotein complex (RNP), and targets the complex to a specific location within a target nucleic acid (e.g., a target DNA) is referred to herein as a "Cas12L guide RNA" or simply as a "guide RNA." It is to be understood that in some cases, a hybrid DNA/RNA can be made such that a Cas12L guide RNA includes DNA bases in addition to RNA bases, but the term "Cas12L guide RNA" is still used to encompass such a molecule herein.

A Cas12L guide RNA can be said to include two segments, a targeting segment and a protein-binding segment. The protein-binding segment is also referred to herein as the "constant region" of the guide RNA. The targeting segment of a Cas12L guide RNA includes a nucleotide sequence (a guide sequence) that is complementary to (and therefore hybridizes with) a specific sequence (a target site) within a target nucleic acid (e.g., a target dsDNA, a target ssRNA, a target ssDNA, the complementary strand of a double stranded target DNA, etc.). The protein-binding segment (or "protein-binding sequence") interacts with (binds to) a Cas12L polypeptide. The protein-binding segment of a subject Cas12L guide RNA can include two complementary stretches of nucleotides that hybridize to one another to form a double stranded RNA duplex (dsRNA duplex). Site-specific binding and/or cleavage of a target nucleic acid (e.g., genomic DNA, ds DNA, RNA, etc.) can occur at locations (e.g., target sequence of a target locus) determined by base-pairing complementarity between the Cas12L guide RNA (the guide sequence of the Cas12L guide RNA) and the target nucleic acid.

A Cas12L guide RNA and a Cas12L protein (e.g., a wild-type Cas12L protein; a variant Cas12L protein; a fusion Cas12L polypeptide; etc.) form a complex (e.g., bind via non-covalent interactions). The Cas12L guide RNA provides target specificity to the complex by including a targeting segment, which includes a guide sequence (a nucleotide sequence that is complementary to a sequence of a target nucleic acid). The Cas12L protein of the complex provides the site-specific activity (e.g., cleavage activity provided by the Cas12L protein and/or an activity provided by the fusion partner in the case of a fusion Cas12L protein). In other words, the Cas12L protein is guided to a target nucleic acid sequence (e.g. a target sequence) by virtue of its association with the Cas12L guide RNA.

The "guide sequence" also referred to as the "targeting sequence" of a Cas12L guide RNA can be modified so that the Cas12L guide RNA can target a Cas12L protein (e.g., a naturally occurring Cas12L protein, a fusion Cas12L polypeptide, and the like) to any desired sequence of any desired target nucleic acid, with the exception (e.g., as described herein) that the PAM sequence can be taken into account. Thus, for example, a Cas12L guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

Guide Sequence of a Cas12L Guide RNA

A subject Cas12L guide RNA includes a guide sequence (i.e., a targeting sequence), which is a nucleotide sequence that is complementary to a sequence (a target site) in a target nucleic acid. In other words, the guide sequence of a Cas12L guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a Cas12L guide RNA can be modified (e.g., by genetic engineering)/ designed to hybridize to any desired target sequence (e.g., while taking the PAM into account, e.g., when targeting a dsDNA target) within a target nucleic acid (e.g., a eukaryotic target nucleic acid such as genomic DNA).

In some cases, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 100% over 17 or more (e.g., 18 or more, 19 or more, 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 90% or more (e.g., 95% or more, 97% or more, 98% or more, 99% or more, or 100%) over 17-25 contiguous nucleotides. In some cases, the percent complementarity between the guide sequence and the target site of the target nucleic acid is 100% over 17-25 contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 17-30 nucleotides (nt) (e.g., from 17-25, 17-22, 17-20, 19-30, 19-25, 19-22, 19-20, 20-30, 20-25, or 20-22 nt). In some cases, the guide sequence has a length in a range of from 17-25 nucleotides (nt) (e.g., from 17-22, 17-20, 19-25, 19-22, 19-20, 20-25, or 20-22 nt). In some cases, the guide sequence has a length of 17 or more nt (e.g., 18 or more, 19 or more, 20 or more, 21 or more, or 22 or more nt; 19 nt, 20 nt, 21 nt, 22 nt, 23 nt, 24 nt, 25 nt, etc.). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases, the guide sequence has a length of 17 nt. In some cases, the guide sequence has a length of 18 nt. In some cases, the guide sequence has a length of 19 nt. In some cases the guide sequence has a length of 20 nt. In some cases the guide sequence has a length of 21 nt. In some cases the guide sequence has a length of 22 nt. In some cases the guide sequence has a length of 23 nt.

In some cases, the guide sequence (also referred to as a "spacer sequence") has a length of from 15 to 50 nucleotides (e.g., from 15 nucleotides (nt) to 20 nt, from 20 nt to 25 nt, from 25 nt to 30 nt, from 30 nt to 35 nt, from 35 nt to 40 nt, from 40 nt to 45 nt, or from 45 nt to 50 nt).

Protein-Binding Segment of a Cas12L Guide RNA

The protein-binding segment (the "constant region") of a subject Cas12L guide RNA interacts with a Cas12L protein. The Cas12L guide RNA guides the bound Cas12L protein to a specific nucleotide sequence within target nucleic acid via the above-mentioned guide sequence. The protein-binding segment of a Cas12L guide RNA can include two stretches of nucleotides that are complementary to one another and hybridize to form a double stranded RNA duplex (dsRNA duplex). Thus, in some cases, the protein-binding segment includes a dsRNA duplex.

In some cases, the dsRNA duplex region includes a range of from 5-25 base pairs (bp) (e.g., from 5-22, 5-20, 5-18, 5-15, 5-12, 5-10, 5-8, 8-25, 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 5 bp, 6 bp, 7 bp, 8 bp, 9 bp, 10 bp, etc.). In some cases, the dsRNA duplex region includes a range of from 6-15 base pairs (bp) (e.g., from 6-12, 6-10, or 6-8 bp, e.g., 6 bp, 7 bp, 8 bp, 9 bp, 10 bp, etc.). In some cases, the duplex region includes 5 or more bp (e.g., 6 or more, 7 or more, or 8 or more bp). In some cases, the duplex region includes 6 or more bp (e.g., 7 or more, or 8 or more bp). In some cases, not all nucleotides of the duplex region are paired, and therefore the duplex forming region can include a bulge. The term "bulge" herein is used to mean a stretch of nucleotides (which can be one nucleotide) that do not contribute to a double stranded duplex, but which are surround 5' and 3' by nucleotides that do contribute, and as such a bulge is considered part of the duplex region. In some cases, the dsRNA includes 1 or more bulges (e.g., 2 or more, 3 or more, 4 or more bulges). In some cases, the dsRNA duplex includes 2 or more bulges (e.g., 3 or more, 4 or more bulges). In some cases, the dsRNA duplex includes 1-5 bulges (e.g., 1-4, 1-3, 2-5, 2-4, or 2-3 bulges).

Thus, in some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 85%-100% complementarity (e.g., 90%-100%, 95%-100% complementarity) with one another. In some cases, the stretches of nucleotides that hybridize to one another to form the dsRNA duplex have 70%-95% complementarity (e.g., 75%-95%, 80%-95%, 85%-95%, 90%-95% complementarity) with one another.

In other words, in some embodiments, the dsRNA duplex includes two stretches of nucleotides that have 70%-100% complementarity (e.g., 75%-100%, 80%-10%, 85%-100%, 90%-100%, 95%-100% complementarity) with one another. In some cases, the dsRNA duplex includes two stretches of nucleotides that have 85%-100% complementarity (e.g., 90%-100%, 95%-100% complementarity) with one another. In some cases, the dsRNA duplex includes two stretches of nucleotides that have 70%-95% complementarity (e.g., 75%-95%, 80%-95%, 85%-95%, 90%-95% complementarity) with one another.

The duplex region of a subject Cas12L guide RNA can include one or more (1, 2, 3, 4, 5, etc) mutations relative to a naturally occurring duplex region. For example, in some cases a base pair can be maintained while the nucleotides contributing to the base pair from each segment can be different. In some cases, the duplex region of a subject Cas12L guide RNA includes more paired bases, less paired bases, a smaller bulge, a larger bulge, fewer bulges, more bulges, or any convenient combination thereof, as compared to a naturally occurring duplex region (of a naturally occurring Cas12L guide RNA).

Examples of various Cas9 guide RNAs can be found in the art, and in some cases variations similar to those introduced into Cas9 guide RNAs can also be introduced into Cas12L guide RNAs of the present disclosure (e.g., mutations to the dsRNA duplex region, extension of the 5' or 3' end for added stability for to provide for interaction with another protein, and the like). For example, see Jinek et al., Science. 2012 Aug. 17;337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24;110(39):15644-9; Jinek et al., Elife. 2013;2: e00471; Pattanayak et al., Nat Biotechnol. 2013 September; 31(9):839-43; Qi et al, Cell. 2013 Feb 28;152(5):1173-83; Wang et al., Cell. 2013 May 9;153(4):910-8; Auer et al., Genome Res. 2013 Oct. 31; Chen et al., Nucleic Acids Res. 2013 Nov. 1;41(20):e19; Cheng et al., Cell Res. 2013 Oct;23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October;10(10):1028-34; Ebina et al., Sci Rep. 2013; 3:2510; Fujii et. al, Nucleic Acids Res. 2013 Nov. 1;41(20): e187; Hu et al., Cell Res. 2013 November; 23(11):1322-5; Jiang et al., Nucleic Acids Res. 2013 Nov. 1;41(20):e188; Larson et al., Nat Protoc. 2013 November; 8(11):2180-96; Mali et. at., Nat Methods. 2013 Oct;10(10):957-63; Nakayama et al., Genesis. 2013 December; 51(12):835-43; Ran et al., Nat Protoc. 2013 November; 8(11):2281-308; Ran et al., Cell. 2013 Sep. 12;154(6):1380-9; Upadhyay et al., G3 (Bethesda). 2013 Dec. 9;3(12):2233-8; Walsh et al., Proc Natl Acad Sci USA. 2013 Sep. 24;110(39):15514-5; Xie et al., Mol Plant. 2013 Oct. 9; Yang et al., Cell. 2013 Sep. 12;154(6):1370-9; Briner et al., Mol Cell. 2014 Oct. 23;56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896;

20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956;20140356958;20140356959; 20140357523;20140357530;20140364333;and 20140377868; all of which are hereby incorporated by reference in their entirety.

Examples of constant regions suitable for inclusion in a Cas12L guide RNA are provided in FIGS. 2A-2Z, FIGS. 2AA-2ZZ, and FIGS. 2AAA-2FFF (e.g., where T is substituted with U). A Cas12L guide RNA can include a constant region having from 1 to 5 nucleotide substitutions compared to any one of the nucleotide sequences depicted in FIGS. 2A-2Z, FIGS. 2AA-2ZZ, and FIGS. 2AAA-2FFF.

The nucleotide sequences (with T substituted with U) can be combined with a spacer sequence (where the spacer sequence comprises a target nucleic acid-binding sequence ("guide sequence")) of choice that is from 15 to 50 nucleotides (e.g., from 15 nucleotides (nt) to 20 nt, from 20 nt to 25 nt, from 25 nt to 30 nt, from 30 nt to 35 nt, from 35 nt to 40 nt, from 40 nt to 45 nt, or from 45 nt to 50 nt in length). In some cases, the spacer sequence is 35-38 nucleotides in length. For example, any one of the nucleotide sequences (with T substituted with U) depicted in FIGS. 2A-2Z, FIGS. 2AA-2ZZ, and FIGS. 2AAA-2FFF can be included in a guide RNA comprising (N)n-constant region, where N is any nucleotide and n is an integer from 15 to 50 (e.g., from 15 to 20, from 20 to 25, from 25 to 30, from 30 to 35, from 35 to 38, from 35 to 40, from 40 to 45, or from 45 to 50).

As one example, the constant region of a Cas12L guide RNA can comprise the nucleotide sequence: AUUGUU-GUAACUCUUAUUUGUAUGGAGUAAACAAC (SEQ ID NO:59). As another example, the constant region of a Cas12L guide RNA can comprise the nucleotide sequence: AUUGUUGUAGACCUC-UUUUUAUAAGGAUUGAACAAC (SEQ ID NO:60; see FIG. 2B). As another example, the constant region of a Cas12L guide RNA can comprise the nucleotide sequence: UAUUGUUGUAGAUACCUUUUU-GUAAGGAUUAAACAAC (SEQ ID NO:61; see FIG. 2P). As another example, the constant region of a Cas12L guide RNA can comprise the nucleotide sequence: AAUGUU-GUAGAUGCCUUUUUAUAAGGAUUAAACAACUUG (SEQ ID NO:62; see FIG. 2T). As another example, the constant region of a Cas12L guide RNA can comprise the nucleotide sequence: AUUGUUGAAAUAGUAC-UUUUAUAGUCUAUAUACAAC (SEQ ID NO:63; see FIG. 2BB). As another example, the constant region of a Cas12L guide RNA can comprise the nucleotide sequence: UAUUGUUGUAACUCUUAUUUUGUAUGG-AGUAAACAAC (SEQ ID NO:64; see FIG. 2CC). As another example, the constant region of a Cas12L guide RNA can comprise the nucleotide sequence: AUUGUU-GUAACUUUUAUUUGUAUGGAGUAAACAAC (SEQ ID NO:65; see FIG. 2TT). As another example, the constant region of a Cas12L guide RNA can comprise the nucleotide sequence: AAUGUUGUAGAUACCUUUUU-GUAAGGAUUGAACAAC (SEQ ID NO:66; see FIG. 2WW). As another example, the constant region of a Cas12L guide RNA can comprise the nucleotide sequence: AUU-GUUGUAAUACUAUUUUUGUAAAGUAUAAACAAC (SEQ ID NO:67; see FIG. 2XX). As another example, the constant region of a Cas12L guide RNA can comprise the nucleotide sequence: AAUGUUGUAGAUGCC-UUUUUAUAAGGAUUAAACAAC (SEQ ID NO:68; see FIG. 2YY). As another example, the constant region of a Cas12L guide RNA can comprise the nucleotide sequence: AUUGUUGUAAUACACUUUUUAUAAG-GUAUGAACAAC (SEQ ID NO:69; see FIG. 2BBB). As another example, the constant region of a Cas12L guide RNA can comprise the nucleotide sequence: AUUGUU-GUAACAUCUAUUUUGUAAGGUGUAAACAAC (SEQ ID NO:70; see FIG. 2KK).

The reverse complement of any one of the nucleotide sequences depicted in FIGS. 2A-2Z, FIGS. 2AA-2ZZ, and FIGS. 2AAA-2FFF (but with T substituted with U) can be included in a guide RNA comprising constant region-(N)n, where N is any nucleotide and n is an integer from 15 to 50 (e.g., from 15 to 20, from 20 to 25, from 25 to 30, from 30 to 35, from 35 to 38, from 35 to 40, from 40 to 45, or from 45 to 50). As one example, a guide RNA can have the following nucleotide sequence: NNNNNNNNNNNNNNNNNNNNNNNNNNNNNNNNNN-NAUUGUUGUAACUCUUAUUU UGUAUGG-AGUAAACAAC (SEQ ID NO:71) or in some cases the reverse complement, where N is any nucleotide, e.g., where the stretch of Ns includes a target nucleic acid-binding sequence.

Cas12L Guide Polynucleotides

In some cases, a nucleic acid that binds to a Cas12L protein, forming a nucleic acid/Cas12L polypeptide complex, and that targets the complex to a specific location within a target nucleic acid (e.g., a target DNA) comprises ribonucleotides only, deoxyribonucleotides only, or a mixture of ribonucleotides and deoxyribonucleotides. In some cases, a guide polynucleotide comprises ribonucleotides only, and is referred to herein as a "guide RNA." In some cases, a guide polynucleotide comprises deoxyribonucleotides only, and is referred to herein as a "guide DNA." In some cases, a guide polynucleotide comprises both ribonucleotides and deoxyribonucleotides. A guide polynucleotide can comprise combinations of ribonucleotide bases, deoxyribonucleotide bases, nucleotide analogs, modified nucleotides, and the like; and may further include naturally-occurring backbone residues and/or linkages and/or non-naturally-occurring backbone residues and/or linkages.

Cas12L Systems

The present disclosure provides a Cas12L system. A Cas12L system of the present disclosure can comprise: a) a Cas12L polypeptide of the present disclosure and a Cas12L guide RNA; b) a Cas12L polypeptide of the present disclosure, a Cas12L guide RNA, and a donor template nucleic acid; c) a Cas12L fusion polypeptide of the present disclosure and a Cas12L guide RNA; d) a Cas12L fusion polypeptide of the present disclosure, a Cas12L guide RNA, and a donor template nucleic acid; e) an mRNA encoding a Cas12L polypeptide of the present disclosure; and a Cas12L guide RNA; f) an mRNA encoding a Cas12L polypeptide of the present disclosure, a Cas12L guide RNA, and a donor template nucleic acid; g) an mRNA encoding a Cas12L fusion polypeptide of the present disclosure; and a Cas12L guide RNA; h) an mRNA encoding a Cas12L fusion polypeptide of the present disclosure, a Cas12L guide RNA, and a donor template nucleic acid; i) a recombinant expression vector comprising a nucleotide sequence encoding a Cas12L polypeptide of the present disclosure and a nucleotide sequence encoding a Cas12L guide RNA; j) a recombinant expression vector comprising a nucleotide sequence encoding a Cas12L polypeptide of the present disclosure, a nucleotide sequence encoding a Cas12L guide RNA, and a nucleotide sequence encoding a donor template nucleic acid; k) a recombinant expression vector comprising a nucleotide sequence encoding a Cas12L fusion polypeptide of the present disclosure and a nucleotide sequence encoding a Cas12L guide RNA; 1) a recombinant expression vector comprising a nucleotide sequence encoding a Cas12L fusion polypeptide of the present disclosure, a nucleotide sequence encoding a Cas12L guide RNA, and a nucleotide sequence encoding a donor template nucleic acid; m) a first recombinant expression vector comprising a nucleotide sequence encoding a Cas12L polypeptide of the present disclosure, and a second recombinant expression vector comprising a nucleotide sequence encoding a Cas12L guide RNA; n) a first recombinant expression vector comprising a nucleotide sequence encoding a Cas12L polypeptide of the present disclosure, and a second recombinant expression vector comprising a nucleotide sequence encoding a Cas12L guide RNA; and a donor template nucleic acid; o) a first recombinant expression vector comprising a nucleotide sequence encoding a Cas12L fusion polypeptide of the present disclosure, and a second recombinant expression vector comprising a nucleotide sequence encoding a Cas12L guide RNA; p) a first recombinant expression vector comprising a nucleotide sequence encoding a Cas12L fusion polypeptide of the present disclosure, and a second recombinant expression vector comprising a nucleotide sequence encoding a Cas12L guide RNA; and a donor template nucleic acid; q) a recombinant expression vector comprising a nucleotide sequence encoding a Cas12L polypeptide of the present disclosure, a nucleotide sequence encoding a first Cas12L guide RNA, and a nucleotide sequence encoding a second Cas12L guide RNA; or r) a recombinant expression vector comprising a nucleotide sequence encoding a Cas12L fusion polypeptide of the present disclosure, a nucleotide sequence encoding a first Cas12L guide RNA, and a nucleotide sequence encoding a second Cas12L guide RNA; or some variation of one of (a) through (r).

Nucleic Acids

The present disclosure provides one or more nucleic acids comprising one or more of: a donor polynucleotide sequence, a nucleotide sequence encoding a Cas12L polypeptide (e.g., a wild type Cas12L protein, a nickase Cas12L protein, a dCas12L protein, fusion Cas12L protein, and the like), a Cas12L guide RNA, and a nucleotide sequence encoding a Cas12L guide RNA. The present disclosure provides a nucleic acid comprising a nucleotide sequence encoding a Cas12L fusion polypeptide. The present disclosure provides a recombinant expression vector that comprises a nucleotide sequence encoding a Cas12L polypeptide. The present disclosure provides a recombinant expression vector that comprises a nucleotide sequence encoding a Cas12L fusion polypeptide. The present disclosure provides a recombinant expression vector that comprises: a) a nucleotide sequence encoding a Cas12L polypeptide; and b) a nucleotide sequence encoding a Cas12L guide RNA(s). The present disclosure provides a recombinant expression vector that comprises: a) a nucleotide sequence encoding a Cas12L fusion polypeptide; and b) a nucleotide sequence encoding a Cas12L guide RNA(s). In some cases, the nucleotide sequence encoding the Cas12L protein and/or the nucleotide sequence encoding the Cas12L guide RNA is operably linked to a promoter that is operable in a cell type of choice (e.g., a prokaryotic cell, a eukaryotic cell, a plant cell, an animal cell, a mammalian cell, a primate cell, a rodent cell, a human cell, etc.).

In some cases, a nucleotide sequence encoding a Cas12L polypeptide of the present disclosure is codon optimized. This type of optimization can entail a mutation of a Cas12L-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized Cas12L-encoding nucleotide sequence could be used. As another non-limiting example, if the intended host cell were a mouse cell, then a mouse codon-optimized Cas12L-encoding nucleotide sequence could be generated. As another non-limiting example, if the intended host cell were a plant cell, then a plant codon-optimized Cas12L-encoding nucleotide sequence could be generated. As another non-limiting example, if the intended host cell were an insect cell, then an insect codon-optimized Cas12L-encoding nucleotide sequence could be generated.

Codon usage tables are readily available, for example, at the "Codon Usage Database" available at www[dot]kazusa[dot]or[dot]jp[forwardslash]codon. In some cases, a nucleic acid of the present disclosure comprises a Cas12L polypeptide-encoding nucleotide sequence that is codon optimized for expression in a eukaryotic cell. In some cases, a nucleic acid of the present disclosure comprises a Cas12L polypeptide-encoding nucleotide sequence that is codon optimized for expression in an animal cell. In some cases, a nucleic acid of the present disclosure comprises a Cas12L polypeptide-encoding nucleotide sequence that is codon optimized for expression in a fungus cell. In some cases, a nucleic acid of the present disclosure comprises a Cas12L polypeptide-encoding nucleotide sequence that is codon optimized for expression in a plant cell. In some cases, a nucleic acid of the present disclosure comprises a Cas12L polypeptide-encoding nucleotide sequence that is codon optimized for expression in a monocotyledonous plant species. In some cases, a nucleic acid of the present disclosure comprises a Cas12L polypeptide-encoding nucleotide sequence that is codon optimized for expression in a dicotyledonous plant species. In some cases, a nucleic acid of the present disclosure comprises a Cas12L polypeptide-encoding nucleotide sequence that is codon optimized for expression in a gymnosperm plant species. In some cases, a nucleic acid of the present disclosure comprises a Cas12L polypeptide-encoding nucleotide sequence that is codon optimized for expression in an angiosperm plant species. In some cases, a nucleic acid of the present disclosure comprises a Cas12L polypeptide-encoding nucleotide sequence that is codon optimized for expression in a corn cell. In some cases, a nucleic acid of the present disclosure comprises a Cas12L polypeptide-encoding nucleotide sequence that is codon optimized for expression in a soybean cell. In some cases, a nucleic acid of the present disclosure comprises a Cas12L polypeptide-encoding nucleotide sequence that is codon optimized for expression in a rice cell. In some cases, a nucleic acid of the present disclosure comprises a Cas12L polypeptide-encoding nucleotide sequence that is codon optimized for expression in a wheat cell. In some cases, a nucleic acid of the present disclosure comprises a Cas12L polypeptide-encoding nucleotide sequence that is codon optimized for expression in a cotton cell. In some cases, a nucleic acid of the present disclosure comprises a Cas12L polypeptide-encoding nucleotide sequence that is codon optimized for expression in a sorghum cell. In some cases, a nucleic acid of the present disclosure comprises a Cas12L polypeptide-encoding nucleotide sequence that is codon optimized for expression in an alfalfa cell. In some cases, a nucleic acid of the present disclosure comprises a Cas12L polypeptide-encoding nucleotide sequence that is codon optimized for expression in a sugar cane cell. In some cases, a nucleic acid of the present disclosure comprises a Cas12L polypeptide-encoding nucleotide sequence that is codon optimized for expression in an *Arabidopsis* cell. In some cases, a nucleic acid of the present disclosure comprises a Cas12L polypeptide-encoding nucleotide sequence that is codon optimized for expression in a tomato cell. In some cases, a nucleic acid of the present disclosure comprises a Cas12L polypeptide-encoding nucleotide sequence that is codon optimized for expression in a cucumber cell. In some cases, a nucleic acid of the present disclosure comprises a Cas12L polypeptide-encoding nucleotide sequence that is codon optimized for expression in a potato cell. In some cases, a nucleic acid of the present disclosure comprises a Cas12L polypeptide-encoding nucleotide sequence that is codon optimized for expression in an algae cell.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a Cas12L guide RNA that hybridizes to a target sequence of the target locus of the targeted genome (e.g., operably linked to a promoter that is operable in a target cell such as a eukaryotic cell); and (iii) a nucleotide sequence encoding a Cas12L protein (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a Cas12L guide RNA that hybridizes to a target sequence of the target locus of the targeted genome (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a Cas12L guide RNA that hybridizes to a target sequence of the target locus of the targeted genome (e.g., operably linked to a promoter that is operable in a target cell such as a eukaryotic cell); and (ii) a nucleotide sequence encoding a Cas12L protein (e.g., operably linked to a promoter that is operable in a target cell such as a eukaryotic cell).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

For plant applications, viral vectors based on Tobamoviruses, Potexviruses, Potyviruses, Tobraviruses, Tombusviruses, Geminiviruses, Bromoviruses, Carmoviruses, Alfamoviruses, or Cucumoviruses can be used. See, e.g., Peyret and Lomonossoff (2015) *Plant Biotechnol. J.* 13:1121. Suitable Tobamovirus vectors include, for example, a tomato mosaic virus (ToMV) vector, a tobacco mosaic virus (TMV) vector, a tobacco mild green mosaic virus (TMGMV) vector, a pepper mild mottle virus (PMMoV) vector, a paprika mild mottle virus (PaMMV) vector, a cucumber green mottle mosaic virus (CGMMV) vector, a kyuri green mottle mosaic virus (KGMMV) vector, a hibiscus latent fort pierce virus (HLFPV) vector, an odontoglossum ringspot virus (ORSV) vector, a rehmannia mosaic virus (ReMV) vector, a Sammon's opuntia virus (SOV) vector, a wasabi mottle virus (WMoV) vector, a youcai mosaic virus (YoMV) vector, a sunn-hemp mosaic virus (SHMV) vector, and the like. Suitable Potexvirus vectors include, for example, a potato virus X (PVX) vector, a potato aucubamosaicvirus (PAMV) vector, an Alstroemeria virus X (AlsVX) vector, a cactus virus X (CVX) vector, a Cymbidium mosaic virus (CymMV) vector, a hosta virus X (HVX) vector, a lily virus X (LVX) vector, a *Narcissus* mosaic virus (NMV) vector, a Nerine virus X (NVX) vector, a *Plantago asiatica* mosaic virus (PlAMV) vector, a strawberry mild yellow edge virus (SMYEV) vector, a tulip virus X (TVX) vector, a white clover mosaic virus (WClMV) vector, a bamboo mosaic virus (BaMV) vector, and the like. Suitable Potyvirus vectors include, for example, a potato virus Y (PVY) vector, a bean common mosaic virus (BCMV) vector, a clover yellow vein virus (ClYVV) vector, an East Asian *Passiflora* virus (EAPV) vector, a Freesia mosaic virus (FreMV) vector, a Japanese yam mosaic virus (JYMV) vector, a lettuce mosaic virus (LMV) vector, a Maize dwarf mosaic virus (MDMV) vector, an onion yellow dwarf virus (OYDV) vector, a *papaya* ringspot virus (PRSV) vector, a pepper mottle virus (PepMoV) vector, a *Perilla* mottle virus (PerMoV) vector, a plum pox virus (PPV) vector, a potato virus A (PVA) vector, a sorghum mosaic virus (SrMV) vector, a soybean mosaic virus (SMV) vector, a sugarcane mosaic virus (SCMV) vector, a tulip mosaic virus (TulMV) vector, a turnip mosaic virus (TuMV) vector, a watermelon mosaic virus (WMV) vector, a zucchini yellow mosaic virus (ZYMV) vector, a tobacco etch virus (TEV) vector, and the like. Suitable Tobravirus vectors include, for example, a tobacco rattle virus (TRV) vector and the like. Suitable Tombusvirus vectors include, for example, a tomato bushy stunt virus (TBSV) vector, an eggplant mottled crinkle virus (EMCV) vector, a grapevine Algerian latent virus (GALV) vector, and the like. Suitable Cucumovirus vectors include, for example, a cucumber mosaic virus (CMV) vector, a peanut stunt virus (PSV) vector, a tomato aspermy virus (TAV) vector, and the like. Suitable Bromovirus vectors include, for example, a brome mosaic virus (BMV) vector, a cowpea chlorotic mottle virus (CCMV) vector, and the like. Suitable Carmovirus vectors include, for example, a carnation mottle virus (CarMV) vector, a melon necrotic spot virus (MNSV) vector, a pea stem necrotic virus (PSNV) vector, a turnip crinkle virus (TCV) vector, and the like. Suitable Alfamovirus vectors include, for example, an alfalfa mosaic virus (AMV) vector, and the like.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a Cas12L guide RNA is operably linked to a control element, e.g., a transcriptional control element, such as a promoter. In some embodiments, a nucleotide sequence encoding a Cas12L protein or a Cas12L fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the Cas12L protein, thus resulting in a fusion Cas12L polypeptide.

In some embodiments, a nucleotide sequence encoding a Cas12L guide RNA and/or a Cas12L fusion polypeptide is operably linked to an inducible promoter. In some embodiments, a nucleotide sequence encoding a Cas12L guide RNA and/or a Cas12L fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1;31(17)), a human H1 promoter (H1), and the like.

In some cases, a nucleotide sequence encoding a Cas12L guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA in a eukaryotic cell it may sometimes be necessary to modify the sequence encoding the guide RNA to eliminate runs of Ts. In some cases, a nucleotide sequence encoding a Cas12L protein (e.g., a wild type Cas12L protein, a nickase Cas12L protein, a dCas12L protein, a fusion Cas12L protein and the like) is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

RNA polymerase III (Pol III) promoters can be used to drive the expression of non-protein coding RNA molecules (e.g., guide RNAs). In some cases, a suitable promoter is a Pol III promoter. In some cases, a Pol III promoter is operably linked to a nucleotide sequence encoding a guide RNA (gRNA). In some cases, a Pol III promoter is operably linked to a nucleotide sequence encoding a single-guide RNA (sgRNA). In some cases, a Pol III promoter is operably linked to a nucleotide sequence encoding a CRISPR RNA (crRNA). In some cases, a Pol III promoter is operably linked to a nucleotide sequence encoding a encoding a tracrRNA.

Non-limiting examples of Pol III promoters include a U6 promoter, an H1 promoter, a 5S promoter, an Adenovirus 2 (Ad2) VAI promoter, a tRNA promoter, and a 7SK promoter. See, for example, Schramm and Hernandez (2002) Genes & Development 16:2593-2620. In some cases, a Pol III promoter is selected from the group consisting of a U6 promoter, an H1 promoter, a 5S promoter, an Adenovirus 2 (Ad2) VAI promoter, a tRNA promoter, and a 7SK promoter. In some cases, a guide RNA-encoding nucleotide sequence is operably linked to a promoter selected from the group consisting of a U6 promoter, an H1 promoter, a 5S promoter, an Adenovirus 2 (Ad2) VAI promoter, a tRNA promoter, and a 7SK promoter. In some cases, a single-guide RNA-encoding nucleotide sequence is operably linked to a promoter selected from the group consisting of a U6 promoter, an H1 promoter, a 5S promoter, an Adenovirus 2 (Ad2) VAI promoter, a tRNA promoter, and a 7SK promoter.

Examples describing a promoter that can be used herein in connection with expression in plants, plant tissues, and plant cells include, but are not limited to, promoters described in: U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that can find use include a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al. Plant Molecular Biology (1987) 9: 315-324), the CaMV 35S promoter (Odell et al., Nature (1985) 313: 810-812), the figwort mosaic virus 35S-promoter (U.S. Pat. Nos. 6,051,753; 5,378,619), the sucrose synthase promoter (Yang and Russell, Proceedings of the National Academy of Sciences, USA (1990) 87: 4144-4148), the R gene complex promoter (Chandler et al., Plant Cell (1989) 1: 1175-1183), and the chlorophyll a/b binding protein gene promoter, PC1SV (U.S. Pat. No. 5,850,019), and AGRtu.nos (GenBank Accession V00087; Depicker et al., Journal of Molecular and Applied Genetics (1982) 1: 561-573; Bevan et al., 1983) promoters.

Methods of introducing a nucleic acid (e.g., a nucleic acid comprising a donor polynucleotide sequence, one or more nucleic acids encoding a Cas12L protein and/or a Cas12L guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a Cas12L protein can be provided as RNA. The RNA can be provided by direct chemical synthesis or may be transcribed in vitro from a DNA (e.g., encoding the Cas12L protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): el1756, and the commercially available TransMessenger® reagents from Qiagen, Stem-fectT™ RNA Transfection Kit from Stemgent, and Tran-sIT®-mRNA Transfection Kit from Mirus Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the Cas12L guide RNA; recombinant expression vectors encoding the Cas12L protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding Cas12L guide RNA and/or a Cas12L polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-3-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a Cas12L guide RNA and/or a Cas12L protein to a cell may include nucleic acid sequences that encode for selectable markers in the target cells, so as to identify cells that have taken up the Cas12L guide RNA and/or Cas12L protein.

A nucleic acid comprising a nucleotide sequence encoding a Cas12L polypeptide, or a Cas12L fusion polypeptide, is in some cases an RNA. Thus, a Cas12L fusion protein can be introduced into cells as RNA. Methods of introducing RNA into cells are known in the art and may include, for example, direct injection, transfection, or any other method used for the introduction of DNA. A Cas12L protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a Cas12L polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO:44). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

As noted above, in some cases, the target cell is a plant cell. Numerous methods for transforming chromosomes or plastids in a plant cell with a recombinant nucleic acid are known in the art, which can be used according to methods of the present application to produce a transgenic plant cell and/or a transgenic plant. Any suitable method or technique for transformation of a plant cell known in the art can be used. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants. Other methods for plant transformation, such as microinjection, electroporation, vacuum infiltration, pressure, sonication, silicon carbide fiber agitation, PEG-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and Agrobacterium-mediated transformation is described in U.S. Pat. Nos. 5,159,135; 5,824,877; 5,591,616; 6,384,301; 5,750,871; 5,463,174; and 5,188,958. Additional methods for transforming plants can be found in, for example, Compendium of Transgenic Crop Plants (2009) Blackwell Publishing. Any appropriate method known to those skilled in the art can be used to transform a plant cell with any of the nucleic acids provided herein.

A Cas12L polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a Cas12L guide RNA, encoding a Cas12L fusion protein, etc.) and proteins (e.g., a Cas12L fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A Cas12L polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A Cas12L polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a Cas12L polypeptide, or a Cas12L fusion polypeptide, of the present disclosure is at least 80% pure, at least 85% pure, at least 90% pure, at least 95% pure, at least 98% pure, or at least 99% pure (e.g., free of contaminants, non-Cas12L proteins or other macromolecules, etc.).

To induce cleavage or any desired modification to a target nucleic acid (e.g., genomic DNA), or any desired modification to a polypeptide associated with target nucleic acid, the Cas12L guide RNA and/or the Cas12L polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different Cas12L guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a Cas12L guide RNA that does not change when the guide sequence is changed to hybridized to a desired target sequence (e.g., sequences that contribute to the Cas12L binding aspect of the guide RNA, e.g., the sequences that contribute to the dsRNA duplex(es) of the Cas12L guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a Cas12L guide RNA, except that the portion encoding the guide sequence portion of the guide RNA is an insertion sequence (an insertion site). An insertion site is any nucleotide sequence used for the insertion of the desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some embodiments, a subject nucleic acid (e.g., a Cas12L guide RNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid has one or more nucleotides that are 2'-O-Methyl modified nucleotides. In some embodiments, a subject nucleic acid (e.g., a dsRNA, a siNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a dsRNA, a siNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids (e.g., a Cas12L guide RNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —CH$_2$—NH—O— CH$_2$—, —CH$_2$—N(CH$_3$)—O—CH$_2$-(known as a methylene (methylimino) or MMI backbone), —CH$_2$—O—N (CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P (=O)(OH)—O—CH$_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, *Biochemistry*, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.,* 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($-CH_2-$), group bridging the 2' oxygen atom and the 4' carbon atom wherein n is 1 or 2 (Singh et al., *Chem. Commun.,* 1998, 4, 455-456, the disclosure of which is incorporated herein by reference in its entirety). LNA and LNA analogs display very high duplex thermal stabilities with complementary DNA and RNA (Tm=+3 to +100° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.,* 2000, 97, 5633-5638, the disclosure of which is incorporated herein by reference in its entirety).

The synthesis and preparation of the LNA monomers adenine, cytosine, guanine, 5-methyl-cytosine, thymine and uracil, along with their oligomerization, and nucleic acid recognition properties have been described (e.g., Koshkin et al., *Tetrahedron,* 1998, 54, 3607-3630, the disclosure of which is incorporated herein by reference in its entirety). LNAs and preparation thereof are also described in WO 98/39352 and WO 99/14226, as well as U.S. applications 20120165514,20100216983,20090041809,20060117410, 20040014959,20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_n$ $ON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504, the disclosure of which is incorporated herein by reference in its entirety) i.e., an alkoxyalkoxy group. A further suitable modification includes 2'-dimethylaminooxyethoxy, i.e., a O($CH_2)_2ON$ $(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O-$CH_2$—O—$CH_2$—N($CH_3)_2$.

Other suitable sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C=C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, *Antisense Research and Applications,* pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methyl-cytosine substitutions have been shown to increase nucleic acid duplex stability by 0.6-1.2° C. (Sanghvi et al., eds., *Antisense Research and Applications*, CRC Press, Boca Raton, 1993, pp. 276-278; the disclosure of which is incorporated herein by reference in its entirety) and are suitable base substitutions, e.g., when combined with 2'-O-methoxy-ethyl sugar modifications.

Conjugates

Another possible modification of a subject nucleic acid involves chemically linking to the polynucleotide one or more moieties or conjugates which enhance the activity, cellular distribution or cellular uptake of the oligonucle-otide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexy-lamino-carbonyl-oxycholesterol moiety (Crooke et al., *J. Pharmacol. Exp. Ther.*, 1996, 277, 923-937).

A conjugate may include a "Protein Transduction Domain" or PTD (also known as a CPP-cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucle-otide. Exemplary PTDs include but are not limited to a minimal undecapeptide protein transduction domain (corresponding to residues 47-57 of HIV-1 TAT comprising YGRKKRRQRRR; SEQ ID NO:40); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natd. Acad. Sci. USA* 97:13003-13008); RRQRRTSKLMKR (SEQ ID NO:41); Transportan GWTLNSAGYLLGKINLKALAALAKKIL (SEQ ID NO:42); KALAWEAKLAKALAKA-LAKHLAKALAKALKCEA (SEQ ID NO:43); and RQIKIWFQNRRMKWKK (SEQ ID NO:44). Exemplary PTDs include but are not limited to, YGRKKRRQRRR (SEQ ID NO:40), RKKRRQRRR (SEQ ID NO:45); an arginine homopolymer of from 3 arginine residues to 50 arginine residues; Exemplary PTD domain amino acid sequences include, but are not limited to, any of the following: YGRKKRRQRRR SEQ ID NO:40); RKKRRQRR (SEQ ID NO:46); YARAAARQARA SEQ ID NO:47); THRLPRRRRRR (SEQ ID NO:48); and GGRRARRRRRR (SEQ ID NO:49). In some embodiments, the PTD is an activatable CPP (ACPP) (Aguilera et al. (2009) *Integr Biol (Camb)* June; 1(5-6): 371-381). ACPPs comprise a polyca-tionic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components into a Target Cell

A Cas12L guide RNA (or a nucleic acid comprising a nucleotide sequence encoding same) and/or a Cas12L polypeptide of the present disclosure (or a nucleic acid comprising a nucleotide sequence encoding same) and/or a Cas12L fusion polypeptide of the present disclosure (or a nucleic acid that includes a nucleotide sequence encoding a Cas12L fusion polypeptide of the present disclosure) and/or a donor polynucleotide (donor template) can be introduced into a host cell by any of a variety of well-known methods.

Any of a variety of compounds and methods can be used to deliver to a target cell a Cas12L system of the present disclosure (e.g., where a Cas12L system comprises: a) a Cas12L polypeptide of the present disclosure and a Cas12L guide RNA; b) a Cas12L polypeptide of the present disclosure, a Cas12L guide RNA, and a donor template nucleic acid; c) a Cas12L fusion polypeptide of the present disclosure and a Cas12L guide RNA; d) a Cas12L fusion polypeptide of the present disclosure, a Cas12L guide RNA, and a donor template nucleic acid; e) an mRNA encoding a Cas12L polypeptide of the present disclosure; and a Cas12L guide RNA; f) an mRNA encoding a Cas12L polypeptide of the present disclosure, a Cas12L guide RNA, and a donor template nucleic acid; g) an mRNA encoding a Cas12L fusion polypeptide of the present disclosure; and a Cas12L guide RNA; h) an mRNA encoding a Cas12L fusion polypeptide of the present disclosure, a Cas12L guide RNA, and a donor template nucleic acid; i) a recombinant expression vector comprising a nucleotide sequence encoding a Cas12L polypeptide of the present disclosure and a nucleotide sequence encoding a Cas12L guide RNA; j) a recombinant expression vector comprising a nucleotide sequence encoding a Cas12L polypeptide of the present disclosure, a nucleotide sequence encoding a Cas12L guide RNA, and a nucleotide sequence encoding a donor template nucleic acid; k) a recombinant expression vector comprising a nucleotide sequence encoding a Cas12L fusion polypeptide of the present disclosure and a nucleotide sequence encoding a Cas12L guide RNA; 1) a recombinant expression vector comprising a nucleotide sequence encoding a Cas12L fusion polypeptide of the present disclosure, a nucleotide sequence encoding a Cas12L guide RNA, and a nucleotide sequence encoding a donor template nucleic acid; m) a first recombinant expression vector comprising a nucleotide sequence encoding a Cas12L polypeptide of the present disclosure, and a second recombinant expression vector comprising a nucleotide sequence encoding a Cas12L guide RNA; n) a first recombinant expression vector comprising a nucleotide sequence encoding a Cas12L polypeptide of the present disclosure, and a second recombinant expression vector comprising a nucleotide sequence encoding a Cas12L guide RNA; and a donor template nucleic acid; o) a first recombinant expression vector comprising a nucleotide sequence encoding a Cas12L fusion polypeptide of the present disclosure, and a second recombinant expression vector comprising a nucleotide sequence encoding a Cas12L guide RNA; p) a first recombinant expression vector comprising a nucleotide sequence encoding a Cas12L fusion polypeptide of the present disclosure, and a second recombinant expression vector comprising a nucleotide sequence encoding a Cas12L guide RNA; and a donor template nucleic acid; q) a recombinant expression vector comprising a nucleotide sequence encoding a Cas12L polypeptide of the present disclosure, a nucleotide sequence encoding a first Cas12L guide RNA, and a nucleotide sequence encoding a second Cas12L guide RNA; or r) a recombinant expression vector comprising a nucleotide sequence encoding a Cas12L fusion polypeptide of the present disclosure, a nucleotide sequence encoding a first Cas12L guide RNA, and a nucleotide sequence encoding a second Cas12L guide RNA; or some variation of one of (a) through (r). As a non-limiting example, a Cas12L system of the present disclosure can be combined with a lipid. As another non-limiting example, a Cas12L system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

In some cases, a Cas12L polypeptide of the present disclosure is provided as a nucleic acid (e.g., an mRNA, a DNA, a plasmid, an expression vector, a viral vector, etc.) that encodes the Cas12L polypeptide. In some cases, the Cas12L polypeptide of the present disclosure is provided directly as a protein (e.g., without an associated guide RNA or with an associate guide RNA, i.e., as a ribonucleoprotein complex). A Cas12L polypeptide of the present disclosure can be introduced into a cell (provided to the cell) by any convenient method; such methods are known to those of ordinary skill in the art. As an illustrative example, a Cas12L polypeptide of the present disclosure can be injected directly into a cell (e.g., with or without a Cas12L guide RNA or nucleic acid encoding a Cas12L guide RNA, and with or without a donor polynucleotide). As another example, a preformed complex of a Cas12L polypeptide of the present disclosure and a Cas12L guide RNA (an RNP) can be introduced into a cell (e.g, eukaryotic cell) (e.g., via injection, via nucleofection; via a protein transduction domain (PTD) conjugated to one or more components, e.g., conjugated to the Cas12L protein, conjugated to a guide RNA, conjugated to a Cas12L polypeptide of the present disclosure and a guide RNA; etc.).

In some cases, a Cas12L fusion polypeptide (e.g., dCas12L fused to a fusion partner, nickase Cas12L fused to a fusion partner, etc.) of the present disclosure is provided as a nucleic acid (e.g., an mRNA, a DNA, a plasmid, an expression vector, a viral vector, etc.) that encodes the Cas12L fusion polypeptide. In some cases, the Cas12L fusion polypeptide of the present disclosure is provided directly as a protein (e.g., without an associated guide RNA or with an associate guide RNA, i.e., as a ribonucleoprotein complex). A Cas12L fusion polypeptide of the present disclosure can be introduced into a cell (provided to the cell) by any convenient method; such methods are known to those of ordinary skill in the art. As an illustrative example, a Cas12L fusion polypeptide of the present disclosure can be injected directly into a cell (e.g., with or without nucleic acid encoding a Cas12L guide RNA and with or without a donor polynucleotide). As another example, a preformed complex of a Cas12L fusion polypeptide of the present disclosure and a Cas12L guide RNA (an RNP) can be introduced into a cell (e.g., via injection, via nucleofection; via a protein transduction domain (PTD) conjugated to one or more components, e.g., conjugated to the Cas12L fusion protein, conjugated to a guide RNA, conjugated to a Cas12L fusion polypeptide of the present disclosure and a guide RNA; etc.).

In some cases, a nucleic acid (e.g., a Cas12L guide RNA; a nucleic acid comprising a nucleotide sequence encoding a Cas12L polypeptide of the present disclosure; etc.) is delivered to a cell (e.g., a target host cell) and/or a polypeptide (e.g., a Cas12L polypeptide; a Cas12L fusion polypeptide) in a particle, or associated with a particle. In some cases, a Cas12L system of the present disclosure is delivered to a cell in a particle, or associated with a particle. The terms "particle" and nanoparticle" can be used interchangeable, as appropriate. A recombinant expression vector comprising a nucleotide sequence encoding a Cas12L polypeptide of the present disclosure and/or a Cas12L guide RNA, an mRNA comprising a nucleotide sequence encoding a Cas12L polypeptide of the present disclosure, and guide RNA may be delivered simultaneously using particles or lipid envelopes; for instance, a Cas12L polypeptide and a Cas12L guide RNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a Cas12L polypeptide and a Cas12L guideRNA are mixed together, e.g., at a 1:1 molar ratio, e.g., at room temperature, e.g., for 30 minutes, e.g., in sterile, nuclease free 1×phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A Cas12L polypeptide of the present disclosure (or an mRNA comprising a nucleotide sequence encoding a Cas12L polypeptide of the present disclosure; or a recombinant expression vector comprising a nucleotide sequence encoding a Cas12L polypeptide of the present disclosure) and/or Cas12L guide RNA (or a nucleic acid such as one or more expression vectors encoding the Cas12L guide RNA) may be delivered simultaneously using particles or lipid envelopes. For example, a biodegradable core-shell structured nanoparticle with a poly(O-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a Cas12L polypeptide of the present disclosure, a Cas12L fusion polypeptide of the present disclosure, an RNP of the present disclosure, a nucleic acid of the present disclosure, or a Cas12L system of the present disclosure (e.g., where a Cas12L system comprises: a) a Cas12L polypeptide of the present disclosure and a Cas12L guide RNA; b) a Cas12L polypeptide of the present disclosure, a Cas12L guide RNA, and a donor template nucleic acid; c) a Cas12L fusion polypeptide of the present disclosure and a Cas12L guide RNA; d) a Cas12L fusion polypeptide of the present disclosure, a Cas12L guide RNA, and a donor template nucleic acid; e) an mRNA encoding a Cas12L polypeptide of the present disclosure; and a Cas12L guide RNA; f) an mRNA encoding a Cas12L polypeptide of the present disclosure, a Cas12L guide RNA, and a donor templat nucleic acid; g) an mRNA encoding a Cas12L fusion polypeptide of the present disclosure; and a Cas12L guide RNA; h) an mRNA encoding a Cas12L fusion polypeptide of the present disclosure, a Cas12L guide RNA, and a donor template nucleic acid; i) a recombinant expression vector comprising a nucleotide sequence encoding a Cas12L polypeptide of the present disclosure and a nucleotide sequence encoding a Cas12L guide RNA; j) a recombinant expression vector comprising a nucleotide sequence encoding a Cas12L polypeptide of the present disclosure, a nucleotide sequence encoding a Cas12L guide RNA, and a nucleotide sequence encoding a donor template nucleic acid; k) a recombinant expression vector comprising a nucleotide sequence encoding a Cas12L fusion polypeptide of the present disclosure and a nucleotide sequence encoding a Cas12L guide RNA; 1) a recombinant expression vector comprising a nucleotide sequence encoding a Cas12L fusion polypeptide of the present disclosure, a nucleotide sequence encoding a Cas12L guide RNA, and a nucleotide sequence encoding a donor template nucleic acid; m) a first recombinant expression vector comprising a nucleotide sequence encoding a Cas12L polypeptide of the present disclosure, and a second recombinant expression vector comprising a nucleotide sequence encoding a Cas12L guide RNA; n) a first recombinant expression vector comprising a nucleotide sequence encoding a Cas12L polypeptide of the present disclosure, and a second recombinant expression vector comprising a nucleotide sequence encoding a Cas12L guide RNA; and a donor template nucleic acid; o) a first recombinant expression vector comprising a nucleotide sequence encoding a Cas12L fusion polypeptide of the present disclosure, and a second recombinant expression vector comprising a nucleotide sequence encoding a Cas12L guide RNA; p) a first recombinant expression vector comprising a nucleotide sequence encoding a Cas12L fusion polypeptide of the present disclosure, and a second recombinant expression vector comprising a nucleotide sequence encoding a Cas12L guide RNA; and a donor template nucleic acid; q) a recombinant expression vector comprising a nucleotide sequence encoding a Cas12L polypeptide of the present disclosure, a nucleotide sequence encoding a first Cas12L guide RNA, and a nucleotide sequence encoding a second Cas12L guide RNA; or r) a recombinant expression vector comprising a nucleotide sequence encoding a Cas12L fusion polypeptide of the present disclosure, a nucleotide sequence encoding a first Cas12L guide RNA, and a nucleotide sequence encoding a second Cas12L guide RNA; or some variation of one of (a) through (r). In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a Cas12L polypeptide of the present disclosure, a Cas12L fusion polypeptide of the present disclosure, an RNP of the present disclosure, a nucleic acid of the present disclosure, or a Cas12L system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a Cas12L polypeptide of the present disclosure, a Cas12L fusion polypeptide of the present disclosure, an RNP of the present disclosure, a nucleic acid of the present disclosure, or a Cas12L system of the present disclosure, to a target cell.

In some cases, lipid nanoparticles (LNPs) are used to deliver a Cas12L polypeptide of the present disclosure, a Cas12L fusion polypeptide of the present disclosure, an RNP of the present disclosure, a nucleic acid of the present disclosure, or a Cas12L system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) may be used. A nucleic acid (e.g., a Cas12L guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). In some cases, 0.2% SP-DiOC18 is incorporated.

Spherical Nucleic Acid (SNAT™) constructs and other nanoparticles (particularly gold nanoparticles) can be used to deliver a Cas12L polypeptide of the present disclosure, a Cas12L fusion polypeptide of the present disclosure, an RNP of the present disclosure, a nucleic acid of the present disclosure, or a Cas12L system of the present disclosure, to a target cell.. See, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a Cas12L polypeptide of the present disclosure, a Cas12L fusion polypeptide of the present disclosure, an RNP of the present disclosure, a nucleic acid of the present disclosure, or a Cas12L system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a Cas12L polypeptide of the present disclosure, a Cas12L fusion polypeptide of the present disclosure, an RNP of the present disclosure, a nucleic acid of the present disclosure, or a Cas12L system of the present disclosure, to a target cell have a diameter of from 25 nm to 200 nm. In some cases, nanoparticles suitable for use in delivering a Cas12L polypeptide of the present disclosure, a Cas12L fusion polypeptide of the present disclosure, an RNP of the present disclosure, a nucleic acid of the present disclosure, or a Cas12L system of the present disclosure, to a target cell have a diameter of 100 nm or less In some cases, nanoparticles suitable for use in delivering a Cas12L polypeptide of the present disclosure, a Cas12L fusion polypeptide of the present disclosure, an RNP of the present disclosure, a nucleic acid of the present disclosure, or a Cas12L system of the present disclosure, to a target cell have a diameter of from 35 nm to 60 nm.

Nanoparticles suitable for use in delivering a Cas12L polypeptide of the present disclosure, a Cas12L fusion polypeptide of the present disclosure, an RNP of the present disclosure, a nucleic acid of the present disclosure, or a Cas12L system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a Cas12L polypeptide of the present disclosure, a Cas12L fusion polypeptide of the present disclosure, an RNP of the present disclosure, a nucleic acid of the present disclosure, or a Cas12L system of the present disclosure, to a target cell. A prototype nanoparticle of semi-solid nature is the liposome.

In some cases, an exosome is used to deliver a Cas12L polypeptide of the present disclosure, a Cas12L fusion polypeptide of the present disclosure, an RNP of the present disclosure, a nucleic acid of the present disclosure, or a Cas12L system of the present disclosure, to a target cell. Exosomes are endogenous nano-vesicles that transport RNAs and proteins, and which can deliver RNA to the brain and other target organs.

In some cases, a liposome is used to deliver a Cas12L polypeptide of the present disclosure, a Cas12L fusion polypeptide of the present disclosure, an RNP of the present disclosure, a nucleic acid of the present disclosure, or a Cas12L system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a Cas12L polypeptide of the present disclosure, a Cas12L fusion polypeptide of the present disclosure, an RNP of the present disclosure, a nucleic acid of the present disclosure, or a Cas12L system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N; N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a Cas12L polypeptide of the present disclosure, a Cas12L fusion polypeptide of the present disclosure, an RNP of the present disclosure, a nucleic acid of the present disclosure, or a Cas12L system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−0.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a Cas12L system of the present disclosure or component(s) thereof or nucleic acids encoding the same to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a Cas12L system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A Cas12L system of the present disclosure, or a component thereof, may be delivered encapsulated in PLGA microspheres such as that further described in US published applications 20130252281 and 20130245107 and 20130244279.

Supercharged proteins can be used to deliver a Cas12L polypeptide of the present disclosure, a Cas12L fusion polypeptide of the present disclosure, an RNP of the present disclosure, a nucleic acid of the present disclosure, or a Cas12L system of the present disclosure, to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo.

Cell Penetrating Peptides (CPPs) can be used to deliver a Cas12L polypeptide of the present disclosure, a Cas12L fusion polypeptide of the present disclosure, an RNP of the present disclosure, a nucleic acid of the present disclosure, or a Cas12L system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a Cas12L polypeptide of the present disclosure, a Cas12L fusion polypeptide of the present disclosure, an RNP of the present disclosure, a nucleic acid of the present disclosure (e.g., a Cas12L guide RNA, a nucleic acid encoding a Cas12L guide RNA, a nucleic acid encoding Cas12L polypeptide, a donor template, and the like), or a Cas12L system of the present disclosure, to a target cell (e.g., a target cell in vivo, where the target cell is a target cell in circulation, a target cell in a tissue, a target cell in an organ, etc.). An implantable device suitable for use in delivering a Cas12L polypeptide of the present disclosure, a Cas12L fusion polypeptide of the present disclosure, an RNP of the present disclosure, a nucleic acid of the present disclosure, or a Cas12L system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the Cas12L polypeptide, the Cas12L fusion polypeptide, the RNP, or the Cas12L system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear—auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intra-ocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Modified Host Cells

The present disclosure provides a modified cell comprising a Cas12L polypeptide of the present disclosure and/or a nucleic acid comprising a nucleotide sequence encoding a Cas12L polypeptide of the present disclosure. The present disclosure provides a modified cell comprising a Cas12L polypeptide of the present disclosure, where the modified cell is a cell that does not normally comprise a Cas12L polypeptide of the present disclosure. The present disclosure provides a modified cell (e.g., a genetically modified cell) comprising nucleic acid comprising a nucleotide sequence encoding a Cas12L polypeptide of the present disclosure. The present disclosure provides a genetically modified cell that is genetically modified with an mRNA comprising a nucleotide sequence encoding a Cas12L polypeptide of the present disclosure. The present disclosure provides a genetically modified cell that is genetically modified with a recombinant expression vector comprising a nucleotide sequence encoding a Cas12L polypeptide of the present disclosure. The present disclosure provides a genetically modified cell that is genetically modified with a recombinant expression vector comprising: a) a nucleotide sequence encoding a Cas12L polypeptide of the present disclosure; and b) a nucleotide sequence encoding a Cas12L guide RNA of the present disclosure. The present disclosure provides a genetically modified cell that is genetically modified with a recombinant expression vector comprising: a) a nucleotide sequence encoding a Cas12L polypeptide of the present disclosure; b) a nucleotide sequence encoding a Cas12L guide RNA of the present disclosure; and c) a nucleotide sequence encoding a donor template.

A cell that serves as a recipient for a Cas12L polypeptide of the present disclosure and/or a nucleic acid comprising a nucleotide sequence encoding a Cas12L polypeptide of the present disclosure and/or a Cas12L guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for a Cas12L polypeptide of the present disclosure and/or a nucleic acid comprising a nucleotide sequence encoding a Cas12L polypeptide of the present disclosure and/or a Cas12L guide RNA of the present disclosure is referred to as a "host cell" or a "target cell." A host cell or a target cell can be a recipient of a Cas12L system of the present disclosure. A host cell or a target cell can be a recipient of a Cas12L RNP of the present disclosure. A host cell or a target cell can be a recipient of a single component of a Cas12L system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, *cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34+ and CD3⁻. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (*rappini*), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, *chrysanthemum* leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

In some cases, the plant cell is a cell of a plant component such as a leaf, a stem, a root, a seed, a flower, pollen, an anther, an ovule, a pedicel, a fruit, a meristem, a cotyledon, a hypocotyl, a pod, an embryo, endosperm, an explant, a callus, or a shoot.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a Cas12L system of the present disclosure, or a component of a Cas12L system of the present disclosure.

A kit of the present disclosure can comprise: a) a Cas12L polypeptide of the present disclosure and a Cas12L guide RNA; b) a Cas12L polypeptide of the present disclosure, a Cas12L guide RNA, and a donor template nucleic acid; c) a Cas12L fusion polypeptide of the present disclosure and a Cas12L guide RNA; d) a Cas12L fusion polypeptide of the present disclosure, a Cas12L guide RNA, and a donor template nucleic acid; e) an mRNA encoding a Cas12L polypeptide of the present disclosure; and a Cas12L guide RNA; f) an mRNA encoding a Cas12L polypeptide of the present disclosure, a Cas12L guide RNA, and a donor template nucleic acid; g) an mRNA encoding a Cas12L fusion polypeptide of the present disclosure; and a Cas12L guide RNA; h) an mRNA encoding a Cas12L fusion polypeptide of the present disclosure, a Cas12L guide RNA, and a donor template nucleic acid; i) a recombinant expression vector comprising a nucleotide sequence encoding a Cas12L polypeptide of the present disclosure and a nucleotide sequence encoding a Cas12L guide RNA; j) a recombinant expression vector comprising a nucleotide sequence encoding a Cas12L polypeptide of the present disclosure, a nucleotide sequence encoding a Cas12L guide RNA, and a nucleotide sequence encoding a donor template nucleic acid; k) a recombinant expression vector comprising a nucleotide sequence encoding a Cas12L fusion polypeptide of the present disclosure and a nucleotide sequence encoding a Cas12L guide RNA; l) a recombinant expression vector comprising a nucleotide sequence encoding a Cas12L fusion polypeptide of the present disclosure, a nucleotide sequence encoding a Cas12L guide RNA, and a nucleotide sequence encoding a donor template nucleic acid; m) a first recombinant expression vector comprising a nucleotide sequence encoding a Cas12L polypeptide of the present disclosure, and a second recombinant expression vector comprising a nucleotide sequence encoding a Cas12L guide RNA; n) a first recombinant expression vector comprising a nucleotide sequence encoding a Cas12L polypeptide of the present disclosure, and a second recombinant expression vector comprising a nucleotide sequence encoding a Cas12L guide RNA; and a donor template nucleic acid; o) a first recombinant expression vector comprising a nucleotide sequence encoding a Cas12L fusion polypeptide of the present disclosure, and a second recombinant expression vector comprising a nucleotide sequence encoding a Cas12L guide RNA; p) a first recombinant expression vector comprising a nucleotide sequence encoding a Cas12L fusion polypeptide of the present disclosure, and a second recombinant expression vector comprising a nucleotide sequence encoding a Cas12L guide RNA; and a donor template nucleic acid; q) a recombinant expression vector comprising a nucleotide sequence encoding a Cas12L polypeptide of the present disclosure, a nucleotide sequence encoding a first Cas12L guide RNA, and a nucleotide sequence encoding a second Cas12L guide RNA; or r) a recombinant expression vector comprising a nucleotide sequence encoding a Cas12L fusion polypeptide of the present disclosure, a nucleotide sequence encoding a first Cas12L guide RNA, and a nucleotide sequence encoding a second Cas12L guide RNA; or some variation of one of (a) through (r).

A kit of the present disclosure can comprise: a) a component, as described above, of a Cas12L system of the present disclosure, or can comprise a Cas12L system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control Cas12L guide RNA; and the like. A kit of the present disclosure can comprise: a) a component, as described above, of a Cas12L system of the present disclosure, or can comprise a Cas12L system of the present disclosure; and b) a therapeutic agent.

A kit of the present disclosure can comprise a recombinant expression vector comprising: a) an insertion site for inserting a nucleic acid comprising a nucleotide sequence encoding a portion of a Cas12L guide RNA that hybridizes to a target nucleotide sequence in a target nucleic acid; and b) a nucleotide sequence encoding the Cas12L-binding portion of a Cas12L guide RNA. A kit of the present disclosure can comprise a recombinant expression vector comprising: a) an insertion site for inserting a nucleic acid comprising a nucleotide sequence encoding a portion of a Cas12L guide RNA that hybridizes to a target nucleotide sequence in a target nucleic acid; b) a nucleotide sequence encoding the Cas12L-binding portion of a Cas12L guide RNA; and c) a nucleotide sequence encoding a Cas12L polypeptide of the present disclosure.

Utility

A Cas12L polypeptide of the present disclosure, or a Cas12L fusion polypeptide of the present disclosure, finds use in a variety of methods (e.g., in combination with a Cas12L guide RNA and in some cases further in combination with a donor template). For example, a Cas12L polypeptide of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a Cas12L polypeptide of the present disclosure; and b) one or more (e.g., two) Cas12L guide RNAs. In some cases, a method of the present disclosure for modifying a target nucleic acid comprises contacting the target nucleic acid with: a) a Cas12L polypeptide of the present disclosure; b) a Cas12L guide RNA; and c) a donor nucleic acid (e.g, a donor template). In some cases, the contacting step is carried out in a cell in vitro. In some cases, the contacting step is carried out in a cell in vivo. In some cases, the contacting step is carried out in a cell ex vivo.

Because a method that uses a Cas12L polypeptide includes binding of the Cas12L polypeptide to a particular region in a target nucleic acid (by virtue of being targeted there by an associated Cas12L guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods, see, for example, Jinek et al., Science. 2012 Aug. 17;337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24;110(39):15644-9; Jinek et al., Elife. 2013;2:e00471; Pattanayak et al., Nat Biotechnol. 2013 September;31(9):839-43; Qi et al, Cell. 2013 Feb. 28;152(5):1173-83; Wang et al., Cell. 2013 May 9;153(4):910-8; Auer et al., Genome Res. 2013 Oct. 31; Chen et al., Nucleic Acids Res. 2013 Nov. 1;41(20):e19; Cheng et al., Cell Res. 2013 October;23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 Oct;10(10):1028-34; Ebina et al., Sci Rep. 2013; 3:2510; Fujii et al, Nucleic Acids Res. 2013 Nov. 1;41(20):e187; Hu et al., Cell Res. 2013 November; 23(11):1322-5; Jiang et al., Nucleic Acids Res. 2013 Nov. 1;41(20):e188; Larson et al., Nat Protoc. 2013 November; 8(11):2180-96; Mali et. at., Nat Methods. 2013 October;10(10):957-63; Nakayama et al., Genesis. 2013 December; 51(12):835-43; Ran et al., Nat Protoc. 2013 November; 8(11):2281-308; Ran et al., Cell. 2013 Sep. 12;154(6):1380-9; Upadhyay et al., G3 (Bethesda). 2013 Dec. 9;3(12):2233-8; Walsh et al., Proc Natl Acad Sci U.S. A. 2013 Sep. 24;110 (39):15514-5; Xie et al., Mol Plant. 2013 Oct. 9; Yang et al., Cell. 2013 Sep. 12;154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a Cas12L polypeptide or with a Cas12L fusion polypeptide, etc., encompass all methods for contacting the target nucleic acid. For example, a Cas12L polypeptide can be provided to a cell as protein, RNA (encoding the Cas12L polypeptide), or DNA (encoding the Cas12L polypeptide); while a Cas12L guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for Cas12L polypeptide; in the form of a protein for a Cas12L fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a Cas12L polypeptide or a Cas12L fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises introducing into a target cell a Cas12L locus, e.g., a nucleic acid comprising a nucleotide sequence encoding a Cas12L polypeptide as well as nucleotide sequences of about 1 kilobase (kb) to 5 kb in length surrounding the Cas12L-encoding nucleotide sequence from a cell (e.g., in some cases a cell that in its natural state (the state in which it occurs in nature) comprises a Cas12L locus) comprising a Cas12L locus, where the target cell does not normally (in its natural state) comprise a Cas12L locus. However, one or more spacer sequences, encoding guide sequences for the encoded crRNA(s), can be modified such that one or more target sequences of interest are targeted. Thus, for example, in some cases, a method of the present disclosure for modifying a target nucleic acid comprises introducing into a target cell a Cas12L locus, e.g., a nucleic acid obtained from a source cell (e.g., in some cases a cell that in its natural state (the state in which it occurs in nature) comprises a Cas12L locus), where the nucleic acid has a length of from 100 nucleotides (nt) to 5 kb in length (e.g., from 100 nt to 500 nt, from 500 nt to 1 kb, from 1 kb to 1.5 kb, from 1.5 kb to 2 kb, from 2 kb to 2.5 kb, from 2.5 kb to 3 kb, from 3 kb to 3.5 kb, from 3.5 kb to 4 kb, or from 4 kb to 5 kb in length) and comprises a nucleotide sequence encoding a Cas12L polypeptide. As noted above, in some such cases, one or more spacer sequences, encoding guide sequences for the encoded crRNA(s), can be modified such that one or more target sequences of interest are targeted. In some cases, the method comprises introducing into a target cell: i) a Cas12L locus; and ii) a donor DNA template. In some cases, the target nucleic acid is in a cell-free composition in vitro. In some cases, the target nucleic acid is present in a target cell. In some cases, the target nucleic acid is present in a target cell, where the target cell is a prokaryotic cell. In some cases, the target nucleic acid is present in a target cell, where the target cell is a eukaryotic cell. In some cases, the target nucleic acid is present in a target cell, where the target cell is a mammalian cell. In some cases, the target nucleic acid is present in a target cell, where the target cell is a plant cell.

In some cases, a method of the present disclosure for modifying a target nucleic acid comprises contacting a target nucleic acid with a Cas12L polypeptide of the present disclosure, or with a Cas12L fusion polypeptide of the present disclosure. In some cases, a method of the present disclosure for modifying a target nucleic acid comprises contacting a target nucleic acid with a Cas12L polypeptide and a Cas12L guide RNA. In some cases, a method of the present disclosure for modifying a target nucleic acid comprises contacting a target nucleic acid with a Cas12L polypeptide, a first Cas12L guide RNA, and a second Cas12L guide RNA In some cases, a method of the present disclosure for modifying a target nucleic acid comprises contacting a target nucleic acid with a Cas12L polypeptide of the present disclosure and a Cas12L guide RNA and a donor DNA template.

Target Nucleic Acids and Target Cells of Interest

A Cas12L polypeptide of the present disclosure, or a Cas12L fusion polypeptide of the present disclosure, when bound to a Cas12L guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the Cas12L guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuna, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to geneically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject Cas12L protein (and/or nucleic acid encoding the protein such as DNA and/or RNA), and/or Cas12L guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatos, cotton, *cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (*rappini*), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, *chrysanthemum* leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams, yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera*.

A cell is in some cases an insect cell. For example, in some cases, the cell is a cell of a mosquito, a grasshopper, a true bug, a fly, a flea, a bee, a wasp, an ant, a louse, a moth, or a beetle.

Introducing Components into a Target Cell

A Cas12L guide RNA (or a nucleic acid comprising a nucleotide sequence encoding same), and/or a Cas12L fusion polypeptide (or a nucleic acid comprising a nucleotide sequence encoding same) and/or a donor polynucleotide can be introduced into a host cell by any of a variety of well-known methods.

Methods of introducing a nucleic acid into a cell are known in the art, and any convenient method can be used to introduce a nucleic acid (e.g., an expression construct) into a taret cell (e.g., eukaryotic cell, human cell, stem cell, progenitor cell, and the like). Suitable methods are described in more detail elsewhere herein and include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like. Any or all of the components can be introduced into a cell as a composition (e.g., including any convenient combination of: a a Cas12L polypeptide, a Cas12L guide RNA, a donor polynucleotide, etc.) using known methods, e.g., such as nucleofection.

Donor Polynucleotide (Donor Template)

Guided by a Cas12L guide RNA, a Cas12L protein in some cases generates site-specific double strand breaks (DSBs) or single strand breaks (SSBs) (e.g., when the Cas12L protein is a nickase variant) within double-stranded DNA (dsDNA) target nucleic acids, which are repaired either by non-homologous end joining (NHEJ) or homology-directed recombination (HDR).

In some cases, contacting a target DNA (with a Cas12L protein and a Cas12L guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, Cas12L guide RNA (or DNA encoding same) and a Cas12L protein (or a nucleic acid encoding same, such as an RNA or a DNA, e.g, one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a Cas12L guide RNA and Cas12L protein is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into he genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the Cas12L protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair ot a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a Cas12L guide RNA and/or a Cas12L fusion polypeptide and/or donor polynucleotide.

Detection Methods

A Cas12L polypeptide of the present disclosure can promiscuously cleave non-targeted nucleic acid (e.g., single stranded DNA (ssDNA) or RNA) once activated by detection of a target DNA (double or single stranded). In some cases, once a Cas12L polypeptide of the present disclosure is activated by a guide RNA, which occurs when the guide RNA hybridizes to a target sequence of a target DNA (i.e., the sample includes the targeted DNA), the Cas12L polypeptide becomes a nuclease that promiscuously cleaves ssDNAs (i.e., the nuclease cleaves non-target ssDNAs, i.e., ssDNAs to which the guide sequence of the guide RNA does not hybridize). In some cases, once a Cas12L polypeptide of the present disclosure is activated by a guide RNA, which occurs when the guide RNA hybridizes to a target sequence of a target DNA (i.e., the sample includes the targeted DNA), the Cas12L polypeptide becomes a nuclease that promiscuously cleaves RNAs (i.e., the nuclease cleaves non-target RNAs, i.e., RNAs to which the guide sequence of the guide RNA does not hybridize). Thus, when the target DNA is present in the sample (e.g., in some cases above a threshold amount), the result is cleavage of ssDNAs or RNA in the sample, which can be detected using any convenient detection method (e.g., using a labeled single stranded detector DNA or a detector RNA).

Compositions and Methods for Detecting Target DNA

Provided are compositions and methods for detecting a target DNA (double stranded or single stranded) in a sample. In some cases, a detector DNA is used that is single stranded (ssDNA) and does not hybridize with the guide sequence of the guide RNA (i.e., the detector ssDNA is a non-target ssDNA). Such methods can include (a) contacting the sample with: (i) a Cas12L polypeptide of the present disclosure; (ii) a guide RNA comprising: a region that binds to the Cas12L polypeptide, and a guide sequence that hybridizes with the target DNA; and (iii) a detector DNA that is single stranded and does not hybridize with the guide sequence of the guide RNA; and (b) measuring a detectable signal produced by cleavage of the single stranded detector DNA by the Cas12L polypeptide, thereby detecting the target DNA. As noted above, once a Cas12L polypeptide of the present disclosure is activated by a guide RNA, which occurs when the sample includes a target DNA to which the guide RNA hybridizes (i.e., the sample includes the targeted target DNA), the Cas12L polypeptide is activated and functions as an endoribonuclease that non-specifically cleaves ssDNAs (including non-target ssDNAs) present in the sample. Thus, when the targeted target DNA is present in the sample (e.g., in some cases above a threshold amount), the result is cleavage of ssDNA (including non-target ssDNA) in the sample, which can be detected using any convenient detection method (e.g., using a labeled detector ssDNA).

Also provided are compositions and methods for cleaving single stranded DNAs (ssDNAs) (e.g., non-target ssDNAs). Such methods can include contacting a population of nucleic acids, wherein said population comprises a target DNA and a plurality of non-target ssDNAs, with: (i) a Cas12L polypeptide of the present disclosure; and (ii) a guide RNA comprising: a region that binds to the Cas12L polypeptide and a guide sequence that hybridizes with the target DNA, wherein the Cas12L polypeptide cleaves non-target ssDNAs of said plurality. Such a method can be used, e.g., to cleave foreign ssDNAs (e.g., viral DNAs) in a cell.

The contacting step of a subject method can be carried out in a composition comprising divalent metal ions. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

The guide RNA can be provided as RNA or as a nucleic acid encoding the guide RNA (e.g., a DNA such as a recombinant expression vector). The Cas12L polypeptide can be provided as a protein or as a nucleic acid encoding the protein (e.g., an mRNA, a DNA such as a recombinant expression vector). In some cases, two or more (e.g., 3 or more, 4 or more, 5 or more, or 6 or more) guide RNAs can be provided by (e.g., using a precursor guide RNA array, which can be cleaved by the Cas12L effector protein into individual ("mature") guide RNAs).

In some cases (e.g., when contacting with a guide RNA and a Cas12L polypeptide of the present disclosure, the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the measuring step. For example, in some cases the sample is contacted for 40 minutes or less prior to the measuring step. In some cases, the sample is contacted for 20 minutes or less prior to the measuring step. In some cases, the sample is contacted for 10 minutes or less prior to the measuring step. In some cases, the sample is contacted for 5 minutes or less prior to the measuring step. In some cases, the sample is contacted for 1 minute or less prior to the measuring step. In some cases, the sample is contacted for from 50 seconds to 60 seconds prior to the measuring step. In some cases, the sample is contacted for from 40 seconds to 50 seconds prior to the measuring step. In some cases, the sample is contacted for from 30 seconds to 40 seconds prior to the measuring step. In some cases, the sample is contacted for from 20 seconds to 30 seconds prior to the measuring step. In some cases, the sample is contacted for from 10 seconds to 20 seconds prior to the measuring step.

A method of the present disclosure for detecting a target DNA (single-stranded or double-stranded) in a sample can detect a target DNA with a high degree of sensitivity. In some cases, a method of the present disclosure can be used to detect a target DNA present in a sample comprising a plurality of DNAs (including the target DNA and a plurality of non-target DNAs), where the target DNA is present at one or more copies per $10^7$ non-target DNAs (e.g., one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs). In some cases, a method of the present disclosure can be used to detect a target DNA present in a sample comprising a plurality of DNAs (including the target DNA and a plurality of non-target DNAs), where the target DNA is present at one or more copies per $10^{18}$ non-target DNAs (e.g., one or more copies per $10^{15}$ non-target DNAs, one or more copies per $10^{12}$ non-target DNAs, one or more copies per $10^9$ non-target DNAs, one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs).

In some cases, a method of the present disclosure can detect a target DNA present in a sample, where the target DNA is present at from one copy per $10^7$ non-target DNAs to one copy per 10 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^{18}$ non-target DNAs to one copy per 10 non-target DNAs (e.g., from 1 copy per $10^{18}$ non-target DNAs to 1 copy per $10^2$ non-target DNAs, from 1 copy per $10^{15}$ non-target DNAs to 1 copy per $10^2$ non-target DNAs, from 1 copy per $10^{12}$ non-target DNAs to 1 copy per $10^2$ non-target DNAs, from 1 copy per $10^3$ non-target DNAs to 1 copy per $10^2$ non-target DNAs, from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^7$ non-target DNAs to one copy per 100 non-target DNAs (e.g., from 1 copy per $10^7$ non-target DNAs to 1 copy per $10^2$ non-target DNAs, from 1 copy per $10^7$ non-target DNAs to 1 copy per 10 non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 100 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 100 non-target DNAs, from 1 copy per $10^5$ non-target DNAs to 1 copy per $10^2$ non-target DNAs, from 1 copy per 105 non-target DNAs to 1 copy per $10^3$ non-target DNAs, or from 1 copy per $10^5$ non-target DNAs to 1 copy per $10^4$ non-target DNAs).

In some cases, the threshold of detection, for a subject method of detecting a target DNA in a sample, is 10 nM or less. The term "threshold of detection" is used herein to describe the minimal amount of target DNA that must be present in a sample in order for detection to occur. Thus, as an illustrative example, when a threshold of detection is 10 nM, then a signal can be detected when a target DNA is present in the sample at a concentration of 10 nM or more. In some cases, a method of the present disclosure has a threshold of detection of 5 nM or less. In some cases, a method of the present disclosure has a threshold of detection of 1 nM or less. In some cases, a method of the present disclosure has a threshold of detection of 0.5 nM or less. In some cases, a method of the present disclosure has a threshold of detection of 0.1 nM or less. In some cases, a method of the present disclosure has a threshold of detection of 0.05 nM or less. In some cases, a method of the present disclosure has a threshold of detection of 0.01 nM or less. In some cases, a method of the present disclosure has a threshold of detection of 0.005 nM or less. In some cases, a method of the present disclosure has a threshold of detection of 0.001 nM or less. In some cases, a method of the present disclosure has a threshold of detection of 0.0005 nM or less.

In some cases, a method of the present disclosure has a threshold of detection of 0.0001 nM or less. In some cases, a method of the present disclosure has a threshold of detection of 0.00005 nM or less. In some cases, a method of the present disclosure has a threshold of detection of 0.00001 nM or less. In some cases, a method of the present disclosure has a threshold of detection of 10 pM or less. In some cases, a method of the present disclosure has a threshold of detection of 1 pM or less. In some cases, a method of the present disclosure has a threshold of detection of 500 fM or less. In some cases, a method of the present disclosure has a threshold of detection of 250 fM or less. In some cases, a method of the present disclosure has a threshold of detection of 100 fM or less. In some cases, a method of the present disclosure has a threshold of detection of 50 fM or less. In some cases, a method of the present disclosure has a threshold of detection of 500 aM (attomolar) or less. In some cases, a method of the present disclosure has a threshold of detection of 250 aM or less. In some cases, a method of the present disclosure has a threshold of detection of 100 aM or less. In some cases, a method of the present disclosure has a threshold of detection of 50 aM or less. In some cases, a method of the present disclosure has a threshold of detection of 10 aM or less. In some cases, a method of the present disclosure has a threshold of detection of 1 aM or less.

In some cases, the threshold of detection (for detecting the target DNA in a subject method), is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 800 fM to 100 pM. In some cases, a method of the present disclosure has a threshold of detection in a range of from 1 pM to 10 pM. In some cases, a method of the present disclosure has a threshold of detection in a range of from 10 fM to 500 fM, e.g., from 10 fM to 50 fM, from 50 fM to 100 fM, from 100 fM to 250 fM, or from 250 fM to 500 fM.

In some cases, the minimum concentration at which a target DNA can be detected in a sample is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 800 fM to 100 pM. In some cases, the minimum concentration at which a target DNA can be detected in a sample is in a range of from 1 pM to 10 pM.

In some cases, the threshold of detection (for detecting the target DNA in a subject method), is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 1 aM to 800 aM. In some cases, a method of the present disclosure has a threshold of detection in a range of from 50 aM to 1 pM. In some cases, a method of the present disclosure has a threshold of detection in a range of from 50 aM to 500 fM.

In some cases, the minimum concentration at which a target DNA can be detected in a sample is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 1 aM to 500 pM. In some cases, the minimum concentration at which a target DNA can be detected in a sample is in a range of from 100 aM to 500 pM.

In some cases, a subject composition or method exhibits an attomolar (aM) sensitivity of detection. In some cases, a subject composition or method exhibits a femtomolar (fM) sensitivity of detection. In some cases, a subject composition or method exhibits a picomolar (pM) sensitivity of detection. In some cases, a subject composition or method exhibits a nanomolar (nM) sensitivity of detection.

Target DNA

A target DNA can be single stranded (ssDNA) or double stranded (dsDNA). When the target DNA is single stranded, there is no preference or requirement for a PAM sequence in the target DNA. However, when the target DNA is dsDNA, a PAM is usually present adjacent to the target sequence of the target DNA (e.g., see discussion of the PAM elsewhere herein). The source of the target DNA can be the same as the source of the sample, e.g., as described below.

The source of the target DNA can be any source. In some cases, the target DNA is a viral DNA (e.g., a genomic DNA of a DNA virus). As such, subject method can be for detecting the presence of a viral DNA amongst a population of nucleic acids (e.g., in a sample). A subject method can also be used for the cleavage of non-target ssDNAs in the present of a target DNA. For example, if a method takes place in a cell, a subject method can be used to promiscuously cleave non-target ssDNAs in the cell (ssDNAs that do not hybridize with the guide sequence of the guide RNA) when a particular target DNA is present in the cell (e.g., when the cell is infected with a virus and viral target DNA is detected).

Examples of possible target DNAs include, but are not limited to, viral DNAs such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), Epstein-barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. In some cases, the target DNA is parasite DNA. In some cases, the target DNA is bacterial DNA, e.g., DNA of a pathogenic bacterium.

Samples

A subject sample includes nucleic acid (e.g., a plurality of nucleic acids). The term "plurality" is used herein to mean two or more. Thus, in some cases, a sample includes two or more (e.g., 3 or more, 5 or more, 10 or more, 20 or more, 50 or more, 100 or more, 500 or more, 1,000 or more, or 5,000 or more) nucleic acids (e.g., DNAs). A subject method can be used as a very sensitive way to detect a target DNA present in a sample (e.g., in a complex mixture of nucleic acids such as DNAs). In some cases, the sample includes 5 or more DNAs (e.g., 10 or more, 20 or more, 50 or more, 100 or more, 500 or more, 1,000 or more, or 5,000 or more DNAs) that differ from one another in sequence. In some cases, the sample includes 10 or more, 20 or more, 50 or more, 100 or more, 500 or more, $10^3$ or more, $5 \times 10^3$ or more, $10^4$ or more, $5 \times 10^4$ or more, $10^5$ or more, $5 \times 10^5$ or more, $10^6$ or more $5 \times 10^6$ or more, or $10^7$ or more, DNAs. In some cases, the sample comprises from 10 to 20, from 20 to 50, from 50 to 100, from 100 to 500, from 500 to 10', from $10^3$ to $5 \times 10'$, from $5 \times 10^3$ to $10^4$, from $10^4$ to $5 \times 10^4$, from $5 \times 10^4$ to $10^5$, from $10^5$ to $5 \times 10^5$, from $5 \times 10^5$ to $10^6$, from $10^6$ to $5 \times 10^6$, or from $5 \times 10^6$ to $10^7$, or more than $10^7$, DNAs. In some cases, the sample comprises from 5 to $10^7$ DNAs (e.g., that differ from one another in sequence)(e.g., from 5 to $10^6$, from 5 to $10^5$, from 5 to 50,000, from 5 to 30,000, from 10 to $10^6$, from 10 to $10^5$, from 10 to 50,000, from 10 to 30,000, from 20 to $10^6$, from 20 to $10^5$, from 20 to 50,000, or from 20 to 30,000 DNAs). In some cases, the sample includes 20 or more DNAs that differ from one another in sequence. In some cases, the sample includes DNAs from a cell lysate (e.g., a eukaryotic cell lysate, a mammalian cell lysate, a human cell lysate, a prokaryotic cell lysate, a plant cell lysate, and the like). For example, in some cases the sample includes DNA from a cell such as a eukaryotic cell, e.g., a mammalian cell such as a human cell.

The term "sample" is used herein to mean any sample that includes DNA (e.g., in order to determine whether a target DNA is present among a population of DNAs). The sample can be derived from any source, e.g., the sample can be a synthetic combination of purified DNAs; the sample can be a cell lysate, an DNA-enriched cell lysate, or DNAs isolated and/or purified from a cell lysate. The sample can be from a patient (e.g., for the purpose of diagnosis). The sample can be from permeabilized cells. The sample can be from crosslinked cells. The sample can be in tissue sections. The sample can be from tissues prepared by crosslinking followed by delipidation and adjustment to make a uniform refractive index. Examples of tissue preparation by crosslinking followed by delipidation and adjustment to make a uniform refractive index have been described in, for example, Shah et al., Development (2016) 143, 2862-2867 doi:10.1242/dev.138560.

A "sample" can include a target DNA and a plurality of non-target DNAs. In some cases, the target DNA is present in the sample at one copy per 10 non-target DNAs, one copy per 20 non-target DNAs, one copy per 25 non-target DNAs, one copy per 50 non-target DNAs, one copy per 100 non-target DNAs, one copy per 500 non-target DNAs, one copy per $10^3$ non-target DNAs, one copy per $5 \times 10^3$ non-target DNAs, one copy per $10^4$ non-target DNAs, one copy per $5 \times 10^3$ non-target DNAs, one copy per $10^5$ non-target DNAs, one copy per $5 \times 10^5$ non-target DNAs, one copy per $10^6$ non-target DNAs, or less than one copy per $10^6$ non-target DNAs. In some cases, the target DNA is present in the sample at from one copy per 10 non-target DNAs to 1 copy per 20 non-target DNAs, from 1 copy per 20 non-target DNAs to 1 copy per 50 non-target DNAs, from 1 copy per 50 non-target DNAs to 1 copy per 100 non-target DNAs, from 1 copy per 100 non-target DNAs to 1 copy per 500 non-target DNAs, from 1 copy per 500 non-target DNAs to 1 copy per $10^3$ non-target DNAs, from 1 copy per $10^3$ non-target DNAs to 1 copy per $5 \times 10^3$ non-target DNAs, from 1 copy per $5 \times 10^3$ non-target DNAs to 1 copy per $10^4$ non-target DNAs, from 1 copy per $10^4$ non-target DNAs to 1 copy per $10^5$ non-target DNAs, from 1 copy per $10^5$ non-target DNAs to 1 copy per $10^6$ non-target DNAs, or from 1 copy per $10^6$ non-target DNAs to 1 copy per $10^7$ non-target DNAs.

Suitable samples include but are not limited to saliva, blood, serum, plasma, urine, aspirate, and biopsy samples. Thus, the term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., DNAs. The term "sample" encompasses biological samples such as a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising DNAs that is obtained from such cells (e.g., a cell lysate or other cell extract comprising DNAs).

A sample can comprise, or can be obtained from, any of a variety of cells, tissues, organs, or acellular fluids. Suitable sample sources include eukaryotic cells, bacterial cells, and archaeal cells. Suitable sample sources include single-celled organisms and multi-cellular organisms. Suitable sample sources include single-cell eukaryotic organisms; a plant or a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell, tissue, or organ; a cell, tissue, or organ from an invertebrate animal (e.g. fruit fly, cnidarian, echinoderm, nematode, an insect, an arachnid, etc.); a cell, tissue, fluid, or organ from a vertebrate animal (e.g., fish, amphibian, reptile, bird, mammal); a cell, tissue, fluid, or organ from a mammal (e.g., a human; a non-human primate; an ungulate; a feline; a bovine; an ovine; a caprine; etc.). Suitable sample sources include nematodes, protozoans, and the like. Suitable sample sources include parasites such as helminths, malarial parasites, etc.

Suitable sample sources include a cell, tissue, or organism of any of the six kingdoms, e.g., Bacteria (e.g., Eubacteria); Archaebacteria; Protista; Fungi; Plantae; and Animalia. Suitable sample sources include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g.,*flagellates* (e.g., *Euglena*), amoeboids (e.g., amoeba), sporozoans (e.g, Apicomplexa, Myxozoa, Microsporidia), and ciliates (e.g., Paramecium). Suitable sample sources include include members of the kingdom Fungi, including, but not limited to, members of any of the phyla: Basidiomycota (club fungi; e.g., members of *Agaricus, Amanita, Boletus*, Cantherellus, etc.); Ascomycota (sac fungi, including, e.g., *Saccharomyces*); Mycophycophyta (lichens); Zygomycota (conjugation fungi); and Deuteromycota. Suitable sample sources include include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sample sources include include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Suitable sources of a sample include cells, fluid, tissue, or organ taken from an organism; from a particular cell or group of cells isolated from an organism; etc. For example, where the organism is a plant, suitable sources include xylem, the phloem, the cambium layer, leaves, roots, etc. Where the organism is an animal, suitable sources include particular tissues (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some cases, the source of the sample is a (or is suspected of being a diseased cell, fluid, tissue, or organ. In some cases, the source of the sample is a normal (non-diseased) cell, fluid, tissue, or organ. In some cases, the source of the sample is a (or is suspected of being a pathogen-infected cell, tissue, or organ. For example, the source of a sample can be an individual who may or may not be infected—and the sample could be any biological sample (e.g., blood, saliva, biopsy, plasma, serum, bronchoalveolar lavage, sputum, a fecal sample, cerebrospinal fluid, a fine needle aspirate, a swab sample (e.g., a buccal swab, a cervical swab, a nasal swab), interstitial fluid, synovial fluid, nasal discharge, tears, buffy coat, a mucous membrane sample, an epithelial cell sample (e.g., epithelial cell scraping), etc.) collected from the individual. In some cases, the sample is a cell-free liquid sample. In some cases, the sample is a liquid sample that can comprise cells. Pathogens include viruses, fungi, helminths, protozoa, malarial parasites, *Plasmodium* parasites, *Toxoplasma* parasites, *Schistosoma* parasites, and the like. "Helminths" include roundworms, heartworms, and phytophagous nematodes (Nematoda), flukes (Tematoda), Acanthocephala, and tapeworms (Cestoda). Protozoan infections include infections from Giardia spp., *Trichomonas* spp., African trypanosomiasis, amoebic dysentery, babesiosis, balantidial dysentery, Chaga's disease, coccidiosis, malaria and toxoplasmosis. Examples of pathogens such as parasitic/protozoan pathogens include, but are not limited to: *Plasmodium falciparum, Plasmodium vivax, Trypanosoma cruzi* and *Toxoplasma gondii*. Fungal pathogens include, but are not limited to: *Cryptococcus neoformans, Histoplasma capsulatum, Coccidioides immitis, Blastomyces dermatitidis, Chlamydia trachomatis,* and *Candida albicans*. Pathogenic viruses include, e.g., immunodeficiency virus (e.g., HIV); influenza virus; dengue; West Nile virus; herpes virus; yellow fever virus; Hepatitis Virus C; Hepatitis Virus A; Hepatitis Virus B; papillomavirus; and the like. Pathogenic viruses can include DNA viruses such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. Pathogens can include, e.g., DNAviruses [e.g.: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like], *Mycobacterium tuberculosis, Streptococcus agalactiae,* methicillin-resistant *Staphylococcus aureus, Legionella pneumophila, Streptococcus pyogenes, Escherichia coli, Neisseria gonorrhoeae, Neisseria meningitidis,* Pneumococcus, *Cryptococcus neoformans, Histoplasma capsulatum, Hemophilus influenzae* B, *Treponema pallidum,* Lyme disease spirochetes, *Pseudomonas aeruginosa, Mycobacterium leprae, Brucella abortus,* rabies virus, influenza virus, cytomegalovirus, herpes simplex virus I, herpes simplex virus II, human serum parvolike virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Mycobacterium tuberculosis, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae*.

Measuring a Detectable Signal

In some cases, a subject method includes a step of measuring (e.g., measuring a detectable signal produced by Cas12L-mediated ssDNA cleavage). Because a Cas12L polypeptide of the present disclosure cleaves non-targeted ssDNA once activated, which occurs when a guide RNA hybridizes with a target DNA in the presence of a Cas12L effector protein, a detectable signal can be any signal that is produced when ssDNA is cleaved. For example, in some cases the step of measuring can include one or more of: gold nanoparticle based detection (e.g., see Xu et al., Angew Chem Int Ed Engl. 2007; 46(19):3468-70; and Xia et al., Proc Natl Acad Sci USA. 2010 Jun. 15;107(24):10837-41), fluorescence polarization, colloid phase transition/dispersion (e.g., Baksh et al., Nature. 2004 Jan. 8;427(6970):139-41), electrochemical detection, semiconductor-based sensing (e.g., Rothberg et al., Nature. 2011 Jul. 20;475(7356): 348-52; e.g., one could use a phosphatase to generate a pH change after ssDNA cleavage reactions, by opening 2'-3' cyclic phosphates, and by releasing inorganic phosphate into solution), and detection of a labeled detector ssDNA (see elsewhere herein for more details). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

The measuring can in some cases be quantitative, e.g., in the sense that the amount of signal detected can be used to determine the amount of target DNA present in the sample. The measuring can in some cases be qualitative, e.g., in the sense that the presence or absence of detectable signal can indicate the presence or absence of targeted DNA (e.g., virus, SNP, etc.). In some cases, a detectable signal will not be present (e.g., above a given threshold level) unless the targeted DNA(s) (e.g., virus, SNP, etc.) is present above a particular threshold concentration. In some cases, the threshold of detection can be titrated by modifying the amount of Cas12L effector, guide RNA, sample volume, and/or detector ssDNA (if one is used). As such, for example, as would be understood by one of ordinary skill in the art, a number of controls can be used if desired in order to set up one or more reactions, each set up to detect a different threshold level of target DNA, and thus such a series of reactions could be used to determine the amount of target DNA present in a sample (e.g., one could use such a series of reactions to determine that a target DNA is present in the sample 'at a concentration of at least X').

Examples of uses of a detection method of the present disclosure include, e.g., single nucleotide polymorphism (SNP) detection, cancer screening, detection of bacterial infection, detection of antibiotic resistance, detection of viral infection, and the like. The compositions and methods of this disclosure can be used to detect any DNA target. For example, any virus that integrates nucleic acid material into the genome can be detected because a subject sample can include cellular genomic DNA—and the guide RNA can be designed to detect integrated nucleotide sequence.

In some cases, a method of the present disclosure can be used to determine the amount of a target DNA in a sample (e.g., a sample comprising the target DNA and a plurality of non-target DNAs). Determining the amount of a target DNA in a sample can comprise comparing the amount of detectable signal generated from a test sample to the amount of detectable signal generated from a reference sample. Determining the amount of a target DNA in a sample can comprise: measuring the detectable signal to generate a test measurement; measuring a detectable signal produced by a reference sample to generate a reference measurement; and comparing the test measurement to the reference measurement to determine an amount of target DNA present in the sample.

For example, in some cases, a method of the present disclosure for determining the amount of a target DNA in a sample comprises: a) contacting the sample (e.g., a sample comprising the target DNA and a plurality of non-target DNAs) with: (i) a guide RNA that hybridizes with the target DNA, (ii) a Cas12L polypeptide of the present disclosure that cleaves RNAs present in the sample, and (iii) a detector ssDNA; b) measuring a detectable signal produced by Cas12L-mediated ssDNA cleavage (e.g., cleavage of the detector ssDNA), generating a test measurement; c) measuring a detectable signal produced by a reference sample to generate a reference measurement; and d) comparing the test measurement to the reference measurement to determine an amount of target DNA present in the sample.

As another example, in some cases, a method of the present disclosure for determining the amount of a target DNA in a sample comprises: a) contacting the sample (e.g., a sample comprising the target DNA and a plurality of non-target DNAs) with: i) a precursor guide RNA array comprising two or more guide RNAs each of which has a different guide sequence; (ii) a Cas12L polypeptide of the present disclosure that cleaves the precursor guide RNA array into individual guide RNAs, and also cleaves RNAs of the sample; and (iii) a detector ssDNA; b) measuring a detectable signal produced by Cas12L-mediated ssDNA cleavage (e.g., cleavage of the detector ssDNA), generating a test measurement; c) measuring a detectable signal produced by each of two or more reference samples to generate two or more reference measurements; and d) comparing the test measurement to the reference measurements to determine an amount of target DNA present in the sample.

Amplification of Nucleic Acids in the Sample

In some embodiments, sensitivity of a subject composition and/or method (e.g., for detecting the presence of a target DNA, such as viral DNA or a SNP, in cellular genomic DNA) can be increased by coupling detection with nucleic acid amplification. In some cases, the nucleic acids in a sample are amplified prior to contact with a Cas12L polypeptide of the present disclosure that cleaved ssDNA (e.g., amplification of nucleic acids in the sample can begin prior to contact with a Cas12L polypeptide of the present disclosure). In some cases, the nucleic acids in a sample are amplified simultaneously with contact with a Cas12L polypeptide of the present disclosure. For example, in some cases, a subject method includes amplifying nucleic acids of a sample (e.g., by contacting the sample with amplification components) prior to contacting the amplified sample with a Cas12L polypeptide of the present disclosure. In some cases, a subject method includes contacting a sample with amplification components at the same time (simultaneous with) that the sample is contacted with a Cas12L polypeptide of the present disclosure. If all components are added simultaneously (amplification components and detection components such as a Cas12L polypeptide of the present disclosure, a guide RNA, and a detector DNA), it is possible that the trans-cleavage activity of the Cas12L will begin to degrade the nucleic acids of the sample at the same time the nucleic acids are undergoing amplification. However, even if this is the case, amplifying and detecting simultaneously can still increase sensitivity compared to performing the method without amplification.

In some cases, specific sequences (e.g., sequences of a virus, sequences that include a SNP of interest) are amplified from the sample, e.g., using primers. As such, a sequence to which the guide RNA will hybridize can be amplified in order to increase sensitivity of a subject detection method—this could achieve biased amplification of a desired sequence in order to increase the number of copies of the sequence of interest present in the sample relative to other sequences present in the sample. As one illustrative example, if a subject method is being used to determine whether a given sample includes a particular virus (or a particular SNP), a desired region of viral sequence (or non-viral genomic sequence) can be amplified, and the region amplified will include the sequence that would hybridize to the guide RNA if the viral sequence (or SNP) were in fact present in the sample.

As noted above, in some cases the nucleic acids are amplified (e.g., by contact with amplification components)

prior to contacting the amplified nucleic acids with a Cas12L polypeptide of the present disclosure. In some cases, amplification occurs for 10 seconds or more, (e.g., 30 seconds or more, 45 seconds or more, 1 minute or more, 2 minutes or more, 3 minutes or more, 4 minutes or more, 5 minutes or more, 7.5 minutes or more, 10 minutes or more, etc.) prior to contact with a Cas12L polypeptide of the present disclosure. In some cases, amplification occurs for 2 minutes or more (e.g., 3 minutes or more, 4 minutes or more, 5 minutes or more, 7.5 minutes or more, 10 minutes or more, etc.) prior to contact with a Cas12L polypeptide of the present disclosure. In some cases, amplification occurs for a period of time in a range of from 10 seconds to 60 minutes (e.g., 10 seconds to 40 minutes, 10 seconds to 30 minutes, 10 seconds to 20 minutes, 10 seconds to 15 minutes, 10 seconds to 10 minutes, 10 seconds to 5 minutes, 30 seconds to 40 minutes, 30 seconds to 30 minutes, 30 seconds to 20 minutes, 30 seconds to 15 minutes, 30 seconds to 10 minutes, 30 seconds to 5 minutes, 1 minute to 40 minutes, 1 minute to 30 minutes, 1 minute to 20 minutes, 1 minute to 15 minutes, 1 minute to 10 minutes, 1 minute to 5 minutes, 2 minutes to 40 minutes, 2 minutes to 30 minutes, 2 minutes to 20 minutes, 2 minutes to 15 minutes, 2 minutes to 10 minutes, 2 minutes to 5 minutes, 5 minutes to 40 minutes, 5 minutes to 30 minutes, 5 minutes to 20 minutes, 5 minutes to 15 minutes, or 5 minutes to 10 minutes). In some cases, amplification occurs for a period of time in a range of from 5 minutes to 15 minutes. In some cases, amplification occurs for a period of time in a range of from 7 minutes to 12 minutes.

In some cases, a sample is contacted with amplification components at the same time as contact with a Cas12L polypeptide of the present disclosure. In some such cases, the Cas12L protein is inactive at the time of contact and is activated once nucleic acids in the sample have been amplified.

Various amplification methods and components will be known to one of ordinary skill in the art and any convenient method can be used (see, e.g., Zanoli and Spoto, Biosensors (Basel). 2013 Mar; 3(1): 18-43; Gill and Ghaemi, Nucleosides, Nucleotides, and Nucleic Acids, 2008, 27: 224-243; Craw and Balachandrana, Lab Chip, 2012, 12, 2469-2486; which are herein incorporated by reference in their entirety). Nucleic acid amplification can comprise polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP),co-amplification at lower denaturation temperature-PCR (COLD-PCR), allele-specific PCR, intersequence-specific PCR (ISS-PCR), whole genome amplification (WGA), inverse PCR, and thermal asymmetric interlaced PCR (TAIL-PCR).

In some cases, the amplification is isothermal amplification. The term "isothermal amplification" indicates a method of nucleic acid (e.g., DNA) amplification (e.g., using enzymatic chain reaction) that can use a single temperature incubation thereby obviating the need for a thermal cycler. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. By combining with a reverse transcription step, these amplification methods can be used to isothermally amplify RNA.

Examples of isothermal amplification methods include but are not limited to: loop-mediated isothermal Amplification (LAMP), helicase-dependent Amplification (HDA), recombinase polymerase amplification (RPA), strand displacement amplification (SDA), nucleic acid sequence-based amplification (NASBA), transcription mediated amplification (TMA), nicking enzyme amplification reaction (NEAR), rolling circle amplification (RCA), multiple displacement amplification (MDA), Ramification (RAM), circular helicase-dependent amplification (cHDA), single primer isothermal amplification (SPIA), signal mediated amplification of RNA technology (SMART), self-sustained sequence replication (3SR), genome exponential amplification reaction (GEAR) and isothermal multiple displacement amplification (IMDA).

In some cases, the amplification is recombinase polymerase amplification (RPA) (see, e.g., U.S. Pat. Nos. 8,030, 000; 8,426,134; 8,945,845; 9,309,502; and 9,663,820, which are hereby incorporated by reference in their entirety). Recombinase polymerase amplification (RPA) uses two opposing primers (much like PCR) and employs three enzymes—a recombinase, a single-stranded DNA-binding protein (SSB) and a strand-displacing polymerase. The recombinase pairs oligonucleotide primers with homologous sequence in duplex DNA, SSB binds to displaced strands of DNA to prevent the primers from being displaced, and the strand displacing polymerase begins DNA synthesis where the primer has bound to the target DNA. Adding a reverse transcriptase enzyme to an RPA reaction can facilitate detection RNA as well as DNA, without the need for a separate step to produce cDNA. One example of components for an RPA reaction is as follows (see, e.g., U.S. Pat. Nos. 8,030, 000; 8,426,134; 8,945,845; 9,309,502; 9,663,820): 50 mM Tris pH 8.4, 80 mM Potassium actetate, 10 mM Magnesium acetate, 2 mM DTT, 5% PEG compound (Carbowax-20M), 3 mM ATP, 30 mM Phosphocreatine, 100 ng/µl creatine kinase, 420 ng/µl gp32, 140 ng/µl UvsX, 35 ng/µl UvsY, 2000M dNTPs, 300 nM each oligonucleotide, 35 ng/µl Bsu polymerase, and a nucleic acid-containing sample).

In a transcription mediated amplification (TMA), an RNA polymerase is used to make RNA from a promoter engineered in the primer region, and then a reverse transcriptase synthesizes cDNA from the primer. A third enzyme, e.g., Rnase H can then be used to degrade the RNA target from cDNA without the heat-denatured step. This amplification technique is similar to Self-Sustained Sequence Replication (3SR) and Nucleic Acid Sequence Based Amplification (NASBA), but varies in the enzymes employed. For another example, helicase-dependent amplification (HDA) utilizes a thermostable helicase (Tte-UvrD) rather than heat to unwind dsDNA to create single-strands that are then available for hybridization and extension of primers by polymerase. For yet another example, a loop mediated amplification (LAMP) employs a thermostable polymerase with strand displacement capabilities and a set of four or more specific designed primers. Each primer is designed to have hairpin ends that, once displaced, snap into a hairpin to facilitate self-priming and further polymerase extension. In a LAMP reaction, though the reaction proceeds under isothermal conditions, an initial heat denaturation step is required for double-stranded targets. In addition, amplification yields a ladder pattern of various length products. For yet another example, a strand displacement amplification (SDA) combines the ability of a restriction endonuclease to nick the unmodified strand of its target DNA and an exonuclease-deficient DNA polymerase to extend the 3' end at the nick and displace the downstream DNA strand.

Detector DNA

In some cases, a subject method includes contacting a sample (e.g., a sample comprising a target DNA and a plurality of non-target ssDNAs) with: i) a Cas12L polypeptide of the present disclosure; ii) a guide RNA (or precursor guide RNA array); and iii) a detector DNA that is single stranded and does not hybridize with the guide sequence of the guide RNA. For example, in some cases, a subject method includes contacting a sample with a labeled single stranded detector DNA (detector ssDNA) that includes a fluorescence-emitting dye pair; the Cas12L polypeptide cleaves the labeled detector ssDNA after it is activated (by binding to the guide RNA in the context of the guide RNA hybridizing to a target DNA); and the detectable signal that is measured is produced by the fluorescence-emitting dye pair. For example, in some cases, a subject method includes contacting a sample with a labeled detector ssDNA comprising a fluorescence resonance energy transfer (FRET) pair or a quencher/fluor pair, or both. In some cases, a subject method includes contacting a sample with a labeled detector ssDNA comprising a FRET pair. In some cases, a subject method includes contacting a sample with a labeled detector ssDNA comprising a fluor/quencher pair.

Fluorescence-emitting dye pairs comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair," both of which terms are discussed in more detail below. The term "fluorescence-emitting dye pair" is used interchangeably with the phrase "a FRET pair and/or a quencher/fluor pair."

In some cases (e.g., when the detector ssDNA includes a FRET pair) the labeled detector ssDNA produces an amount of detectable signal prior to being cleaved, and the amount of detectable signal that is measured is reduced when the labeled detector ssDNA is cleaved. In some cases, the labeled detector ssDNA produces a first detectable signal prior to being cleaved (e.g., from a FRET pair) and a second detectable signal when the labeled detector ssDNA is cleaved (e.g., from a quencher/fluor pair). As such, in some cases, the labeled detector ssDNA comprises a FRET pair and a quencher/fluor pair.

In some cases, the labeled detector ssDNA comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. Thus, as used herein, the term "FRET" ("fluorescence resonance energy transfer"; also known as "Förster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

The donor-acceptor pair (a FRET donor moiety and a FRET acceptor moiety) is referred to herein as a "FRET pair" or a "signal FRET pair." Thus, in some cases, a subject labeled detector ssDNA includes two signal partners (a signal pair), when one signal partner is a FRET donor moiety and the other signal partner is a FRET acceptor moiety. A subject labeled detector ssDNA that includes such a FRET pair (a FRET donor moiety and a FRET acceptor moiety) will thus exhibit a detectable signal (a FRET signal) when the signal partners are in close proximity (e.g., while on the same RNA molecule), but the signal will be reduced (or absent) when the partners are separated (e.g., after cleavage of the RNA molecule by a Cas12L polypeptide of the present disclosure).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to those presented in Table 1. See also: Bajar et al. Sensors (Basel). 2016 Sep. 14;16(9); and Abraham et al. PLoS One. 2015 Aug. 3;10(8):e0134436.

TABLE 1

| Examples of FRET pairs (donor and acceptor FRET moieties) | |
| --- | --- |
| Donor | Acceptor |
| Tryptophan | Dansyl |
| IAEDANS (1) | DDPM (2) |
| BFP | DsRFP |
| Dansyl | Fluorescein isothiocyanate (FITC) |
| Dansyl | Octadecylrhodamine |
| Cyan fluorescent protein (CFP) | Green fluorescent protein (GFP) |
| CF (3) | Texas Red |
| Fluorescein | Tetramethylrhodamine |
| Cy3 | Cy5 |
| GFP | Yellow fluorescent protein (YFP) |
| BODIPY FL (4) | BODIPY FL (4) |
| Rhodamine 110 | Cy3 |
| Rhodamine 6G | Malachite Green |
| FITC | Eosin Thiosemicarbazide |
| B-Phycoerythrin | Cy5 |
| Cy5 | Cy5.5 |

(1) 5-(2-iodoacetylaminoethyl)aminonaphthalene-1-sulfonic acid
(2) N-(4-dimethylamino-3,5-dinitrophenyl)maleimide
(3) carboxyfluorescein succinimidyl ester
(4) 4,4-difluoro-4-bora-3a,4a-diaza-s-indacene In some cases, a detectable signal is produced when the labeled detector ssDNA is cleaved (e.g., in some cases, the labeled detector ssDNA comprises a quencher/fluor pair). One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the labeled detector ssDNA is cleaved. For example, in some cases, the signal exhibited by one signal partner (a signal moiety) is quenched by the other signal partner (a quencher signal moiety), e.g., when both are present on the same ssDNA molecule prior to cleavage by a Cas12L polypeptide of the present disclosure). Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector ssDNA by a Cas12L polypeptide of the present disclosure), but the signal will be quenched when the partners are in close proximity (e.g., prior to cleavage of the detector ssDNA by a Cas12L polypeptide of the present disclosure).

A quencher moiety can quench a signal from the signal moiety (e.g., prior to cleave of the detector ssDNA by a Cas12L polypeptide of the present disclosure) to various degrees. In some cases, a quencher moiety quenches the signal from the signal moiety where the signal detected in the presence of the quencher moiety (when the signal partners are in proximity to one another) is 95% or less of the signal detected in the absence of the quencher moiety (when the signal partners are separated). For example, in some cases, the signal detected in the presence of the quencher moiety can be 90% or less, 80% or less, 70% or less, 60% or less, 50% or less, 40% or less, 30% or less, 20% or less, 15% or less, 10% or less, or 5% or less of the signal detected in the absence of the quencher moiety. In some cases, no signal (e.g., above background) is detected in the presence of the quencher moiety.

In some cases, the signal detected in the absence of the quencher moiety (when the signal partners are separated) is at least 1.2 fold greater (e.g., at least 1.3fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (when the signal partners are in proximity to one another).

In some cases, the signal moiety is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases, the quencher moiety absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties include, but are not limited to: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., Annu Rev Biomed Eng. 2009; 11:25-47; as well as U.S. Pat. Nos. 8,822,673 and 8,586,718; U.S. patent publications 20140378330, 20140349295, 20140194611,20130323851, 20130224871,20110223677,20110190486,20110172420, 20060179585 and 20030003486; and international patent applications: WO200142505 and WO200186001, all of which are hereby incorporated by reference in their entirety.

In some cases, cleavage of a labeled detector ssDNA can be detected by measuring a colorimetric read-out. For example, the liberation of a fluorophore (e.g., liberation from a FRET pair, liberation from a quencher/fluor pair, and the like) can result in a wavelength shift (and thus color shift) of a detectable signal. Thus, in some cases, cleavage of a subject labeled detector ssDNA can be detected by a color-shift. Such a shift can be expressed as a loss of an amount of signal of one color (wavelength), a gain in the amount of another color, a change in the ration of one color to another, and the like.

In some cases, a CasL polypeptide of the present disclosure can cleave RNA in trans. Thus, in some instances, a labeled detector nucleic acid is a labeled RNA. Thus, the disclosure above relating to labeled detector DNA applies equally to a labeled detector RNA. In some cases, a labeled detector RNA includes one or more of a modified sugar, a modified base, and a modified backbone. For example, a labeled detector RNA can include one or more of a non-natural internucleoside linkage, a nucleic acid mimetic, a modified sugar moiety, a modified nucleobase, a locked nucleic acid (LNA), a peptide nucleic acid (PNA), a morpholino nucleic acid, and a cyclohexenyl nucleic acid (CeNA). In some cases, two or more labeled detector RNAs are used.

Transgenic, Non-Human Organisms

As described above, in some cases, a nucleic acid (e.g., a recombinant expression vector) of the present disclosure (e.g., a nucleic acid comprising a nucleotide sequence encoding a Cas12L polypeptide of the present disclosure; a nucleic acid comprising a nucleotide sequence encoding a Cas12L fusion polypeptide of the present disclosure; etc.), is used as a transgene to generate a transgenic non-human organism that produces a Cas12L polypeptide, or a Cas12L fusion polypeptide, of the present disclosure. The present disclosure provides a transgenic-non-human organism comprising a nucleotide sequence encoding a Cas12L polypeptide, or a Cas12L fusion polypeptide, of the present disclosure.

Transgenic, Non-Human Animals

The present disclosure provides a transgenic non-human animal, which animal comprises a transgene comprising a nucleic acid comprising a nucleotide sequence encoding a Cas12L polypeptide or a Cas12L fusion polypeptide. In some embodiments, the genome of the transgenic non-human animal comprises a nucleotide sequence encoding a Cas12L polypeptide,e or a Cas12L fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a Cas12L polypeptide, or a Cas12L fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some cases, a nucleic acid (e.g., a recombinant expression vector) of the present disclosure (e.g., a nucleic acid comprising a nucleotide sequence encoding a Cas12L polypeptide of the present disclosure; a nucleic acid comprising a nucleotide sequence encoding a Cas12L fusion polypeptide of the present disclosure; etc.), is used as a transgene to generate a transgenic plant that produces a Cas12L polypeptide, or a Cas12L fusion polypeptide, of the present disclosure. The present disclosure provides a transgenic plant comprising a nucleotide sequence encoding a Cas12L polypeptide, or a Cas12L fusion polypeptide, of the present disclosure. In some cases, the genome of the transgenic plant comprises a subject nucleic acid. In some cases, the transgenic plant is homozygous for the genetic modification. In some cases, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (i.e. in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid of the present disclosure (e.g., a nucleic acid (e.g., a recombinant expression vector) comprising a nucleotide sequence encoding a Cas12L polypeptide, or a Cas12L fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/ Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576, 198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a Cas12L polypeptide, or a Cas12L fusion polypeptide, of the present disclosure. Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a Cas12L polypeptide, or a Cas12L fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A composition comprising: a) a Cas12L polypeptide, or a nucleic acid molecule encoding the Cas12L polypeptide; and b) a Cas12L guide RNA, or one or more DNA molecules encoding the Cas12L guide RNA.

Aspect 2. The composition of aspect 1, wherein the Cas12L polypeptide comprises an amino acid sequence having 50% or more amino acid sequence identity to the amino acid sequence depicted in any one of FIGS. 2A-2Z, FIGS. 2AA-2ZZ, and FIGS. 2AAA-2FFF.

Aspect 3. The composition of aspect 1 or aspect 2, wherein the Cas12L guide RNA comprises a nucleotide sequence having 80%, 90%, 95%, 98%, 99%, or 100%, nucleotide sequence identity with any one of the crRNA sequences depicted in FIG. 7, FIGS. 2A-2Z, FIGS. 2AA-2ZZ, and FIGS. 2AAA-2FFF.

Aspect 4. The composition of aspect 1 or aspect 2, wherein the Cas12L polypeptide is fused to one or more nuclear localization signals (NLSs).

Aspect 5. The composition of any one of aspects 1-4, wherein the composition comprises a lipid.

Aspect 6. The composition of any one of aspects 1-4, wherein a) and b) are within a liposome.

Aspect 7. The composition of any one of aspects 1-4, wherein a) and b) are within a particle.

Aspect 8. The composition of any one of aspects 1-7, comprising one or more of: a buffer, a nuclease inhibitor, and a protease inhibitor.

Aspect 9. The composition of any one of aspects 1-8, wherein the Cas12L polypeptide comprises an amino acid sequence having 85% or more identity to the amino acid sequence depicted in any one of FIGS. 2A-2Z, FIGS. 2AA-2ZZ, and FIGS. 2AAA-2FFF.

Aspect 10. The composition of any one of aspects 1-9, wherein the Cas12L polypeptide is a nickase that can cleave only one strand of a double-stranded target nucleic acid molecule.

Aspect 11. The composition of any one of aspects 1-9, wherein the Cas12L polypeptide is a catalytically inactive Cas12L polypeptide (dCas12L).

Aspect 12. The composition of any one of aspects 1-11, wherein the Cas12L polypeptide has a length of from 700 amino acids to 800 amino acids.

Aspect 13. The composition of any one of aspects 1-12, further comprising a DNA donor template.

Aspect 14. A Cas12L fusion polypeptide comprising: a Cas12L polypeptide fused to a heterologous polypeptide.

Aspect 15. The Cas12L fusion polypeptide of Aspect 14, wherein the Cas12L polypeptide comprises an amino acid sequence having 50% or more identity to the amino acid sequence depicted in any one of FIGS. 2A-2Z, FIGS. 2AA-2ZZ, and FIGS. 2AAA-2FFF.

Aspect 16. The Cas12L fusion polypeptide of Aspect 14, wherein the Cas12L polypeptide comprises an amino acid sequence having 85% or more identity to the amino acid sequence depicted in any one of FIGS. 2A-2Z, FIGS. 2AA-2ZZ, and FIGS. 2AAA-2FFF.

Aspect 17. The Cas12L fusion polypeptide of any one of aspects 14-16, wherein the Cas12L polypeptide is a nickase that can cleave only one strand of a double-stranded target nucleic acid molecule.

Aspect 18. The Cas12L fusion polypeptide of any one of aspects 14-17, wherein the Cas12L polypeptide is a catalytically inactive Cas12L polypeptide (dCas12L).

Aspect 19. The Cas12L fusion polypeptide of any one of aspects 14-18, wherein the Cas12L polypeptide has a length of from 700 amino acids to 800 amino acids.

Aspect 20. The Cas12L fusion polypeptide of any one of aspects 14-19, wherein the heterologous polypeptide is fused to the N-terminus and/or the C-terminus of the Cas12L polypeptide.

Aspect 21. The Cas12L fusion polypeptide of any one of aspects 14-20, comprising a nuclear localization signal (NLS).

Aspect 22. The Cas12L fusion polypeptide of any one of aspects 14-21, wherein the heterologous polypeptide is a targeting polypeptide that provides for binding to a cell surface moiety on a target cell or target cell type.

Aspect 23. The Cas12L fusion polypeptide of any one of aspects 14-21, wherein the heterologous polypeptide exhibits enzymatic activity.

Aspect 24. The Cas12L fusion polypeptide of aspect 23, wherein the heterologous polypeptide exhibits one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 25. The Cas12L fusion polypeptide of aspect 23, wherein the heterologous polypeptide exhibits one or more enzymatic activities selected from: reverse transcriptase activity, nuclease activity, methyltransferase activity, demethylase activity, deamination activity, depurination activity, integrase activity, transposase activity, and recombinase activity.

Aspect 26. The Cas12L fusion polypeptide of any one of aspects 14-21, wherein the heterologous polypeptide exhibits an enzymatic activity that modifies a target polypeptide associated with a target nucleic acid.

Aspect 27. The Cas12L fusion polypeptide of aspect 26, wherein the heterologous polypeptide exhibits histone modification activity.

Aspect 28. The Cas12L fusion polypeptide of aspect 26 or aspect 27, wherein the heterologous polypeptide exhibits one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

Aspect 29. The Cas12L fusion polypeptide of aspect 28, wherein the heterologous polypeptide exhibits one or more enzymatic activities selected from: methyltransferase activity, demethylase activity, acetyltransferase activity, and deacetylase activity.

Aspect 30. The Cas12L fusion polypeptide of any one of aspects 14-21, wherein the heterologous polypeptide is an endosomal escape polypeptide.

Aspect 31. The Cas12L fusion polypeptide of aspect 30, wherein the endosomal escape polypeptide comprises an amino acid sequence selected from: GLFX-ALLXLLXSLWXLLLXA (SEQ ID NO:72), and GLF-HALLHLLHSLWHLLLHA (SEQ ID NO:73), wherein each X is independently selected from lysine, histidine, and arginine.

Aspect 32. The Cas12L fusion polypeptide of any one of aspects 14-21, wherein the heterologous polypeptide is a chloroplast transit peptide.

Aspect 33. The Cas12L fusion polypeptide of any one of aspects 14-21, wherein the heterologous polypeptide comprises a protein transduction domain.

Aspect 34. The Cas12L fusion polypeptide of any one of aspects 14-21, wherein the heterologous polypeptide is a protein that increases or decreases transcription.

Aspect 35. The Cas12L fusion polypeptide of aspect 34, wherein the heterologous polypeptide is a transcriptional repressor domain.

Aspect 36. The Cas12L fusion polypeptide of aspect 34, wherein the heterologous polypeptide is a transcriptional activation domain.

Aspect 37. The Cas12L fusion polypeptide of any one of aspects 14-21, wherein the heterologous polypeptide is a protein binding domain.

Aspect 38. A nucleic acid comprising a nucleotide sequence encoding the Cas12L fusion polypeptide of any one of aspects 14-37.

Aspect 39. The nucleic acid of Aspect 38, wherein the nucleotide sequence encoding the Cas12L fusion polypeptide is operably linked to a promoter.

Aspect 40. The nucleic acid of Aspect 39, wherein the promoter is functional in a eukaryotic cell.

Aspect 41. The nucleic acid of Aspect 40, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

Aspect 42. The nucleic acid of any one of Aspects 39-41, wherein the promoter is one or more of: a constitutive promoter, an inducible promoter, a cell type-specific promoter, and a tissue-specific promoter.

Aspect 43. The nucleic acid of any one of Aspects 38-42, wherein the nucleic acid is a recombinant expression vector.

Aspect 44. The nucleic acid of Aspect 43, wherein the recombinant expression vector is a recombinant adenoassociated viral vector, a recombinant retroviral vector, or a recombinant lentiviral vector.

Aspect 45. The nucleic acid of Aspect 39, wherein the promoter is functional in a prokaryotic cell.

Aspect 46. The nucleic acid of Aspect 38, wherein the nucleic acid molecule is an mRNA.

Aspect 47. One or more nucleic acids comprising: (a) a nucleotide sequence encoding a Cas12L guide RNA; and (b) a nucleotide sequence encoding a Cas12L polypeptide.

Aspect 48. The one or more nucleic acids of aspect 47, wherein the Cas12L polypeptide comprises an amino acid sequence having 50% or more identity to the amino acid sequence depicted in any one of FIGS. 2A-2Z, FIGS. 2AA-2ZZ, and FIGS. 2AAA-2FFF.

Aspect 49. The one or more nucleic acids of aspect 47, wherein the Cas12L polypeptide comprises an amino acid sequence having 85% or more identity to the amino acid depicted in any one of FIGS. 2A-2Z, FIGS. 2AA-2ZZ, and FIGS. 2AAA-2FFF.

Aspect 50. The one or more nucleic acids of any one of aspects 47-49, wherein the Cas12L guide RNA comprises a nucleotide sequence having 80% or more nucleotide sequence identity with any one of the crRNA sequences set forth in FIG. 7, FIGS. 2A-2Z, FIGS. 2AA-2ZZ, and FIGS. 2AAA-2FFF.

Aspect 51. The one or more nucleic acids of any one of aspects 47-50, wherein the Cas12L polypeptide is fused to one or more nuclear localization signals (NLSs).

Aspect 52. The one or more nucleic acids of any one of aspects 47-51, wherein the nucleotide sequence encoding the Cas12L guide RNA is operably linked to a promoter.

Aspect 53. The one or more nucleic acids of any one of aspects 47-52, wherein the nucleotide sequence encoding the Cas12L polypeptide is operably linked to a promoter.

Aspect 54. The one or more nucleic acids of Aspect 52 or Aspect 53, wherein the promoter operably linked to the nucleotide sequence encoding the Cas12L guide RNA, and/or the promoter operably linked to the nucleotide sequence encoding the Cas12L polypeptide, is functional in a eukaryotic cell.

Aspect 55. The one or more nucleic acids of Aspect 54, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

Aspect 56. The one or more nucleic acids of any one of Aspects 53-55, wherein the promoter is one or more of: a constitutive promoter, an inducible promoter, a cell type-specific promoter, and a tissue-specific promoter.

Aspect 57. The one or more nucleic acids of any one of Aspects 47-56, wherein the one or more nucleic acids is one or more recombinant expression vectors.

Aspect 58. The one or more nucleic acids of Aspect 57, wherein the one or more recombinant expression vectors are selected from: one or more adenoassociated viral vectors, one or more recombinant retroviral vectors, or one or more recombinant lentiviral vectors.

Aspect 59. The one or more nucleic acids of Aspect 53, wherein the promoter is functional in a prokaryotic cell.

Aspect 60. A eukaryotic cell comprising one or more of:
a) a Cas12L polypeptide, or a nucleic acid comprising a nucleotide sequence encoding the Cas12L polypeptide,
b) a Cas12L fusion polypeptide, or a nucleic acid comprising a nucleotide sequence encoding the Cas12L fusion polypeptide, and
c) a Cas12L guide RNA, or a nucleic acid comprising a nucleotide sequence encoding the Cas12L guide RNA.

Aspect 61. The eukaryotic cell of aspect 60, comprising the nucleic acid encoding the Cas12L polypeptide, wherein said nucleic acid is integrated into the genomic DNA of the cell.

Aspect 62. The eukaryotic cell of aspect 60 or aspect 61, wherein the eukaryotic cell is a plant cell, a mammalian cell, an insect cell, an arachnid cell, a fungal cell, a bird cell, a reptile cell, an amphibian cell, an invertebrate cell, a mouse cell, a rat cell, a primate cell, a non-human primate cell, or a human cell.

Aspect 63. A cell comprising a comprising a Cas12L fusion polypeptide, or a nucleic acid comprising a nucleotide sequence encoding the Cas12L fusion polypeptide.

Aspect 64. The cell of aspect 63, wherein the cell is a prokaryotic cell or a eukaryotic cell.

Aspect 65. The cell of aspect 63 or aspect 64, comprising the nucleic acid comprising a nucleotide sequence encoding the Cas12L fusion polypeptide, wherein said nucleic acid molecule is integrated into the genomic DNA of the cell.

Aspect 66. A method of modifying a target nucleic acid, the method comprising contacting the target nucleic acid with: a) a Cas12L polypeptide; and b) a Cas12L guide RNA comprising a guide sequence that hybridizes to a target sequence of the target nucleic acid, wherein said contacting results in modification of the target nucleic acid by the Cas12L polypeptide.

Aspect 67. The method of aspect 66, wherein said modification is cleavage of the target nucleic acid.

Aspect 68. The method of aspect 66 or aspect 67, wherein the target nucleic acid is selected from: double stranded DNA, single stranded DNA, RNA, genomic DNA, and extrachromosomal DNA.

Aspect 69. The method of any of aspects 66-68, wherein said contacting takes place in vitro outside of a cell.

Aspect 70. The method of any of aspects 66-68, wherein said contacting takes place inside of a cell in culture.

Aspect 71. The method of any of aspects 66-68, wherein said contacting takes place inside of a cell in vivo.

Aspect 72. The method of aspect 70 or aspect 71, wherein the cell is a eukaryotic cell.

Aspect 73. The method of aspect 72, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 74. The method of aspect 70 or aspect 71, wherein the cell is a prokaryotic cell.

Aspect 75. The method of any one of aspects 66-74, wherein said contacting results in genome editing.

Aspect 76. The method of any one of aspects 66-75, wherein said contacting comprises: introducing into a cell: (a) the Cas12L polypeptide, or a nucleic acid comprising a nucleotide sequence encoding the Cas12L polypeptide, and (b) the Cas12L guide RNA, or a nucleic acid comprising a nucleotide sequence encoding the Cas12L guide RNA.

Aspect 77. The method of aspect 76, wherein said contacting further comprises: introducing a DNA donor template into the cell.

Aspect 78. The method of any one of aspects 66-77, wherein the Cas12L guide RNA comprises a nucleotide sequence having 80% or more nucleotide sequence identity with any one of the crRNA sequences set forth in FIG. 7, FIGS. 2A-2Z, FIGS. 2AA-2ZZ, and FIGS. 2AAA-2FFF.

Aspect 79. The method of any one of aspects 66-78, wherein the Cas12L polypeptide is fused to a nuclear localization signal.

Aspect 80. A method of modulating transcription from a target DNA, modifying a target nucleic acid, or modifying a protein associated with a target nucleic acid, the method comprising contacting the target nucleic acid with: a) a Cas12L fusion polypeptide comprising a Cas12L polypeptide fused to a heterologous polypeptide; and b) a Cas12L guide RNA comprising a guide sequence that hybridizes to a target sequence of the target nucleic acid.

Aspect 81. The method of aspect 80, wherein the Cas12L guide RNA comprises a nucleotide sequence having 80% or more nucleotide sequence identity with any one of the crRNA sequences set forth in FIG. 7, FIGS. 2A-2Z, FIGS. 2AA-2ZZ, and FIGS. 2AAA-2FFF.

Aspect 82. The method of aspect 80 or aspect 81, wherein the Cas12L fusion polypeptide comprises nuclear localization signal.

Aspect 83. The method of any of aspects 80-82, wherein said modification is not cleavage of the target nucleic acid.

Aspect 84. The method of any of aspects 80-83, wherein the target nucleic acid is selected from: double stranded DNA, single stranded DNA, RNA, genomic DNA, and extrachromosomal DNA.

Aspect 85. The method of any of aspects 80-84, wherein said contacting takes place in vitro outside of a cell.

Aspect 86. The method of any of aspects 80-84, wherein said contacting takes place inside of a cell in culture.

Aspect 87. The method of any of aspects 80-84, wherein said contacting takes place inside of a cell in vivo.

Aspect 88. The method of aspect 86 or aspect 87, wherein the cell is a eukaryotic cell.

Aspect 89. The method of aspect 88, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 90. The method of aspect 86 or aspect 87, wherein the cell is a prokaryotic cell.

Aspect 91. The method of any one of aspects 80-90, wherein said contacting comprises: introducing into a cell: (a) the Cas12L fusion polypeptide, or a nucleic acid comprising a nucleotide sequence encoding the Cas12L fusion polypeptide, and (b) the Cas12L guide RNA, or a nucleic acid comprising a nucleotide sequence encoding the Cas12L guide RNA.

Aspect 92. The method of any one of aspects 80-91, wherein the Cas12L polypeptide is a catalytically inactive Cas12L polypeptide (dCas12L).

Aspect 93. The method of any one of aspects 80-92, wherein the Cas12L polypeptide has a length of from 700 amino acids to 800 amino acids.

Aspect 94. The method of any one of aspects 80-93, wherein the heterologous polypeptide exhibits an enzymatic activity.

Aspect 95. The method of aspect 94, wherein the heterologous polypeptide exhibits one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 96. The method of aspect 94, wherein the heterologous polypeptide exhibits one or more enzymatic activities selected from: reverse transcriptase activity, nuclease activity, methyltransferase activity, demethylase activity, deamination activity, depurination activity, integrase activity, transposase activity, and recombinase activity.

Aspect 97. The method of any one of aspects 80-93, wherein the heterologous polypeptide exhibits an enzymatic activity that modifies a target polypeptide associated with a target nucleic acid.

Aspect 98. The method of aspect 97, wherein the heterologous polypeptide exhibits histone modification activity.

Aspect 99. The method of aspect 97 or aspect 98, wherein the heterologous polypeptide exhibits one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

Aspect 100. The method of aspect 99, wherein the heterologous polypeptide exhibits one or more enzymatic activities selected from: methyltransferase activity, demethylase activity, acetyltransferase activity, and deacetylase activity.

Aspect 101. The method of any one of aspects 80-93, wherein the heterologous polypeptide is protein that increases or decreases transcription.

Aspect 102. The method of aspect 101, wherein the heterologous polypeptide is a transcriptional repressor domain.

Aspect 103. The method of aspect 101, wherein the heterologous polypeptide is a transcriptional activation domain.

Aspect 104. The method of any one of aspects 80-93, wherein the heterologous polypeptide is a protein biding domain.

Aspect 105. A transgenic, multicellular, non-human organism whose genome comprises a transgene comprising a nucleotide sequence encoding one or more of:

a) a Cas12L polypeptide, b) a Cas12L fusion polypeptide, and c) a Cas12L guide RNA.

Aspect 106. The transgenic, multicellular, non-human organism of aspect 105, wherein the Cas12L polypeptide comprises an amino acid sequence having 50% or more amino acid sequence identity to the amino acid sequence set forth in any one of FIGS. 2A-2Z, FIGS. 2AA-2ZZ, and FIGS. 2AAA-2FFF.

Aspect 107. The transgenic, multicellular, non-human organism of aspect 105, wherein the Cas12L polypeptide comprises an amino acid sequence having 85% or more amino acid sequence identity to the amino acid sequence set forth in any one of FIGS. 2A-2Z, FIGS. 2AA-2ZZ, and FIGS. 2AAA-2FFF.

Aspect 108. The transgenic, multicellular, non-human organism of any one of aspects $10^5$-$10^7$, wherein the organism is a plant, a monocotyledon plant, a dicotyledon plant, an invertebrate animal, an insect, an arthropod, an arachnid, a parasite, a worm, a cnidarian, a vertebrate animal, a fish, a reptile, an amphibian, an ungulate, a bird, a pig, a horse, a sheep, a rodent, a mouse, a rat, or a non-human primate.

Aspect 109. A system comprising:

a) a Cas12L polypeptide and a Cas12L guide RNA;

b) a Cas12L polypeptide, a Cas12L guide RNA, and a DNA donor template;

c) a Cas12L fusion polypeptide and a Cas12L guide RNA;

d) a Cas12L fusion polypeptide, a Cas12L guide RNA, and a DNA donor template;

e) an mRNA encoding a Cas12L polypeptide, and a Cas12L guide RNA;

f) an mRNA encoding a Cas12L polypeptide; a Cas12L guide RNA, and a DNA donor template;

g) an mRNA encoding a Cas12L fusion polypeptide, and a Cas12L guide RNA;

h) an mRNA encoding a Cas12L fusion polypeptide, a Cas12L guide RNA, and a DNA donor template;

i) one or more recombinant expression vectors comprising: i) a nucleotide sequence encoding a Cas12L polypeptide; and ii) a nucleotide sequence encoding a Cas12L guide RNA;

j) one or more recombinant expression vectors comprising: i) a nucleotide sequence encoding a Cas12L polypeptide; ii) a nucleotide sequence encoding a Cas12L guide RNA; and iii) a DNA donor template;

k) one or more recombinant expression vectors comprising: i) a nucleotide sequence encoding a Cas12L fusion polypeptide; and ii) a nucleotide sequence encoding a Cas12L guide RNA; and l) one or more recombinant expression vectors comprising: i) a nucleotide sequence encoding a Cas12L fusion polypeptide; ii) a nucleotide sequence encoding a Cas12L guide RNA; and a DNA donor template.

Aspect 110. The Cas12L system of aspect 109, wherein the Cas12L polypeptide comprises an amino acid sequence having 50% or more amino acid sequence identity to the amino acid sequence depicted in any of FIGS. 2A-2Z, FIGS. 2AA-2ZZ, and FIGS. 2AAA-2FFF.

Aspect 111. The Cas12L system of aspect 109, wherein the Cas12L polypeptide comprises an amino acid sequence having 85% or more amino acid sequence identity to the amino acid sequence depicted in any one of FIGS. 2A-2Z, FIGS. 2AA-2ZZ, and FIGS. 2AAA-2FFF.

Aspect 112. The Cas12L system of any of aspects 109-111, wherein the donor template nucleic acid has a length of from 8 nucleotides to 1000 nucleotides.

Aspect 113. The Cas12L system of any of aspects 109-111, wherein the donor template nucleic acid has a length of from 25 nucleotides to 500 nucleotides.

Aspect 114. A kit comprising the Cas12L system of any one of aspects 109-113.

Aspect 115. The kit of aspect 114, wherein the components of the kit are in the same container.

Aspect 116. The kit of aspect 114, wherein the components of the kit are in separate containers.

Aspect 117. A sterile container comprising the Cas12L system of any one of aspects 109-116.

Aspect 118. The sterile container of aspect 117, wherein the container is a syringe.

Aspect 119. An implantable device comprising the Cas12L system of any one of aspects 109-116.

Aspect 120. The implantable device of aspect 119, wherein the Cas12L system is within a matrix.

Aspect 121. The implantable device of aspect 119, wherein the Cas12L system is in a reservoir.

Aspect 122. A method of detecting a target DNA in a sample, the method comprising: (a) contacting the sample with: (i) a Cas12L polypeptide; (ii) a guide RNA comprising: a region that binds to the Cas12L polypeptide, and a guide sequence that hybridizes with the target DNA; and (iii) a detector nucleic acid that is single stranded and does not hybridize with the guide sequence of the guide RNA; and (b) measuring a detectable signal produced by cleavage of the single stranded detector nucleic acid by the Cas12L polypeptide, thereby detecting the target DNA.

Aspect 123. The method of aspect 122, wherein the target DNA is bacterial DNA.

Aspect 124. The method of aspect 122, wherein the target DNA is viral DNA.

Aspect 125. The method of aspect 124, wherein the target DNA is papovavirus, human papillomavirus (HPV), hepadnavirus, Hepatitis B Virus (HBV), herpesvirus, varicella zoster virus (VZV), Epstein-Barr virus (EBV), Kaposi's sarcoma-associated herpesvirus, adenovirus, poxvirus, or parvovirus DNA.

Aspect 126. The method of aspect 122, wherein the target DNA is from a human cell.

Aspect 127. The method of aspect 122, wherein the target DNA is human fetal or cancer cell DNA.

Aspect 128. The method of aspect 122, wherein the sample comprises a cell lysate.

Aspect 129. The method of aspect 122, wherein the sample comprises cells.

Aspect 130. The method of aspect 122, wherein the sample is a blood, serum, plasma, urine, aspirate, or biopsy sample.

Aspect 131. The method of any one of aspects 122-130, further comprising determining an amount of the target DNA present in the sample.

Aspect 132. The method of aspect 131, wherein said measuring a detectable signal comprises one or more of: visual based detection, sensor-based detection, color detection, gold nanoparticle-based detection, fluorescence polarization, colloid phase transition/dispersion, electrochemical detection, and semiconductor-based sensing.

Aspect 133. The method of any one of aspects 122-132, wherein the labeled detector nucleic acid is DNA.

Aspect 134. The method of any one of aspects 122-132, wherein the labeled detector nucleic acid is RNA.

Aspect 135. The method of any one of aspects 122-134, wherein the labeled detector nucleic acid comprises a modified nucleobase, a modified sugar moiety, and/or a modified nucleic acid linkage.

Aspect 136. The method of any one of aspects 122-135, wherein the detectable signal is detectable in less than 45 minutes.

Aspect 137. The method of any one of aspects 122-135, wherein the detectable signal is detectable in less than 30 minutes.

Aspect 138. The method of any one of aspects 122-137, further comprising amplifying the target DNA in the sample by loop-mediated isothermal amplification (LAMP), helicase-dependent amplification (HDA), recombinase polymerase amplification (RPA), strand displacement amplification (SDA), nucleic acid sequence-based amplification (NASBA), transcription mediated amplification (TMA), nicking enzyme amplification reaction (NEAR), rolling circle amplification (RCA), multiple displacement amplification (MDA), Ramification (RAM), circular helicase-dependent amplification (cHDA), single primer isothermal amplification (SPIA), signal mediated amplification of RNA technology (SMART), self-sustained sequence replication (3SR), genome exponential amplification reaction (GEAR), or isothermal multiple displacement amplification (IMDA).

Aspect 139. The method of any one of aspects 122-138, wherein target DNA in the sample is present at a concentration of less than 10 aM.

Aspect 140. The method according to any one of aspect 122-139, wherein the label of the labeled detector nucleic acid comprises a fluorescence-emitting dye pair.

Aspect 141. The method according to aspect 140, wherein the fluorescence-emitting dye pair is a fluorescence resonance energy transfer (FRET) pair.

Aspect 142. The method according to aspect 140, wherein the fluorescence-emitting dye pair is a quencher/fluor pair.

Aspect 143. The method according to any one of aspects 142-147, wherein the labeled detector nucleic acid comprises two or more fluorescence-emitting dye pairs.

Aspect 144. The method according to aspect 143, wherein said two or more fluorescence-emitting dye pairs include a fluorescence resonance energy transfer (FRET) pair and a quencher/fluor pair.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s);

nt, nucleotide(s); i.m., intramuscular(ly); i.p., intraperitoneal (ly); s.c., subcutaneous(ly); and the like.

Example 1: Casλ1 Cleaves Double-Stranded DNA with a TTR PAM

Figure 9:
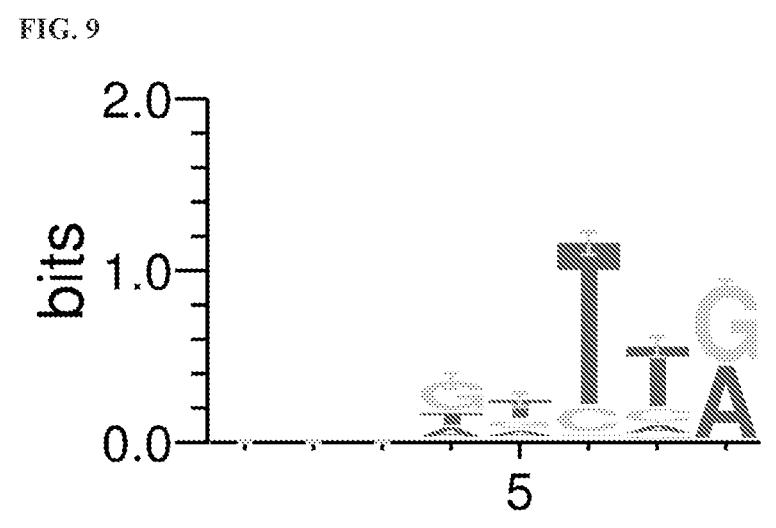
Figure 10:
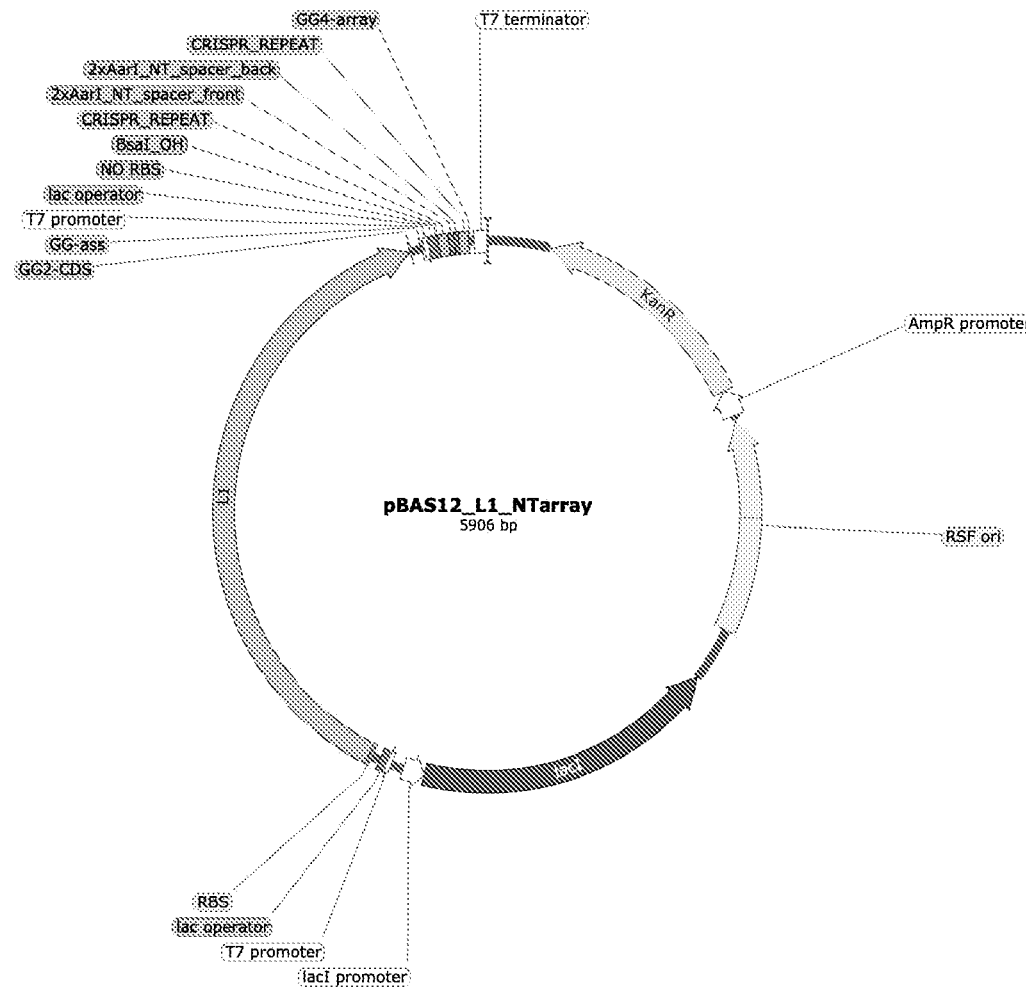
FIG. 10 provides a schematic depiction of plasmid pBAS12-L1-NTarray.
Figure 11:
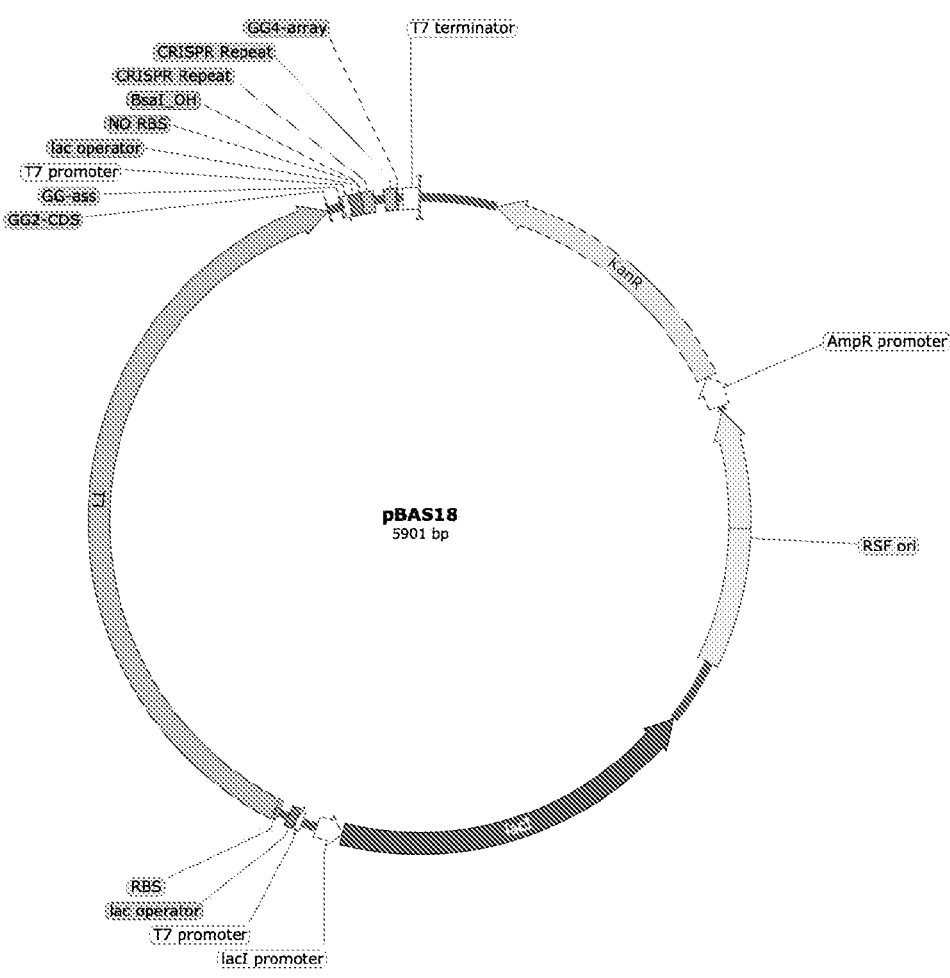
FIG. 11 provides a schematic depiction of plasmid pBAS18.

CRISPR-Cas effector complexes recognize a short protospacer adjacent motif (PAM) that is only present on the foreign DNA prior to DNA interference, so as to prevent self-targeting of the host DNA's CRISPR array. To experimentally test if Casλ is an RNA-guided DNA-targeting endonuclease and to test whether a PAM is required for DNA identification, PAM depletion assay was set up in *Escherichia coli* with the Cas11 protein homolog of the Cas, family. In the PAM depletion assay, Casλ targets a DNA sequence adjacent to a randomized sequence in a plasmid library, that is distinct from any sequence found in any native CasλCRISPR array. NGS sequencing revealed that Casλ and crRNA (as expressed from pBAS18; FIG. 11) are sufficient in bacteria to deplete plasmids with DNA sites complementary to the crRNA guide, when a PAM sequence as displayed is adjacent to the protospacer (FIG. 9), compared to Casλ paired with a non-targeting control guide RNA (as expressed from pBAS12; FIG. 10) that has no complementarity to the target plasmids. The results showed that Casλ can be reprogrammed to cleave any sequence of DNA that is complementary to the guide RNA where the PAM is present on the 5' end of the target (a T-rich PAM for Casλ1), and additional RNA components are not required for the formation of functional effectors in vivo.

Example 2: Programmable DNA Targeting

A flp recombination assay was performed in *E. coli* to eliminate the Kanamycin resistance cassette from *E. coli* strains that contain GFP and RFP expression cassettes integrated into the genome. Individual colonies of the *E. coli*ΔKan were picked to inoculate three 5 mL (LB) starter cultures to prepare electrocompetent cells the following day. 100 mL (LB) main cultures were inoculated from the starter cultures and grown vigorously shaking at 37° C. to an OD600 of 0.6-0.7 before preparation of electrocompetent cells by repeated ice-cold H2O and 10% glycerol washes. Cells were resuspended in 10% glycerol and 50 µL aliquots were flash frozen in liquid nitrogen and stored at −80° C.

Casλ vectors were generated containing codon optimized Cas11 gene and a guide comprised of its cognate repeat element and selections of spacers targeting the GFP DNA within the resulting *E. coli*ΔKan strain (pBAS41, pBAS42, pBAS43, pBAS44) were subcloned from pBAS12. Casλ vectors containing Cas11 and a guide composed of a non-cognate repeat unit from Casλ2 and a GFP-targeting spacer (TAGCATCACCTTCACCCTCTCCACGGACAG; SEQ ID NO:165) guide were also subcloned to form pBAS40. The Casλ vectors and Casλ vectors with a non-targeting guide control plasmid were transformed into 25 µL of electrocompetent cells with 100 ng of plasmid via electroporation in 0.1 mm electroporation cuvettes (Bio-Rad) on a Micropulser electroporator (Bio-Rad), cells were recovered in 1 mL recovery medium (Lucigen) shaking at 37° C. for one hour. 10-fold dilution series were then prepared and 3.5 µL of the respective dilutions were spot-plated on LB-Agar containing the appropriate antibiotics and IPTG inducer. Plates were incubated overnight at 37° C. and colonies were counted the following day to determine the transformation efficiency.

To assess the transformation efficiency, the mean and standard deviations were calculated from the cell forming units per ng transformed plasmids for the electroporation triplicates.

Figures 12A, 12B:
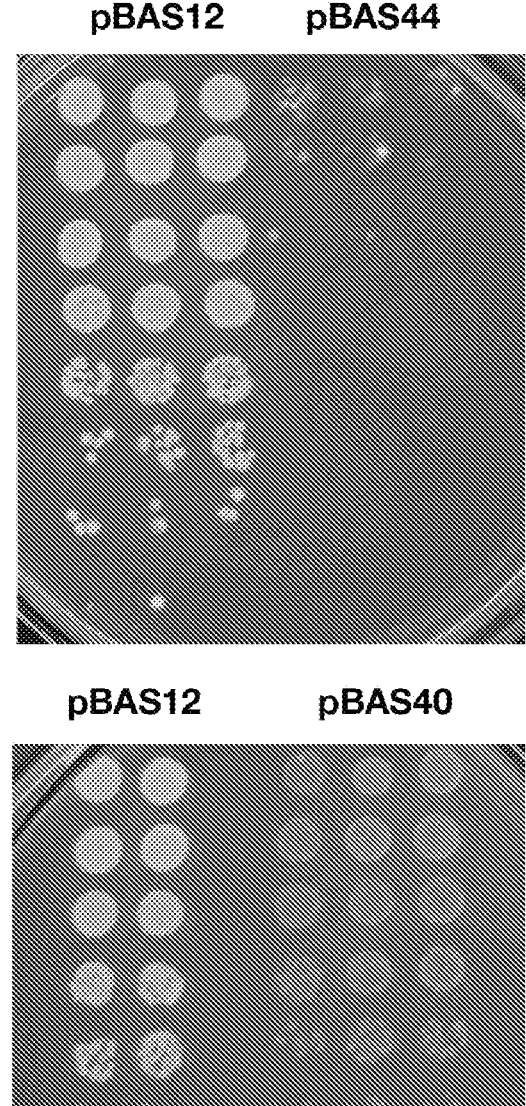
FIG. 12A-12C depict data showing that Cas, with GFP-targeting guides (pBAS44) showed a reduction in colony forming units (as a proxy for cell viability) of multiple orders of magnitude, in comparison to a negative control of Cas, with a non-targeting guide (pBAS12). Cas, with GFP-targeting guides using a repeat unit from another ortholog also showed inhibited growth and ablation of GFP.
Figure 12C:
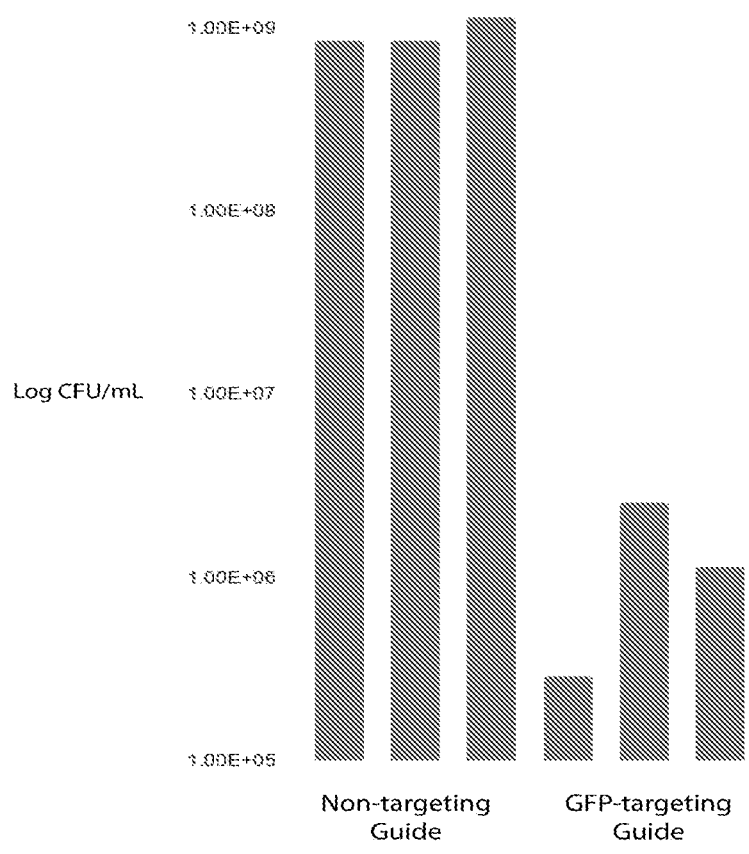

The data are shown in FIG. 12A-12C. The experiment showed marked reduction of GFP *E. coli* using Casλ vectors with their cognate guides (pBAS44) in comparison to the non-targeting control, indicating a double-stranded DNA break at the target region. The growth of primarily RFP-positive/GFP-negative colonies under blue light further supports the ability to confer targeted programmable genome editing to result in strains lacking GFP production. Growth inhibition using Casλ vectors with guides from a separate Casλ ortholog (pBAS40), with colonies observed expressing primarily RFP and no GFP, also indicate that Casλ orthologs may function using guides from related CRISPR-Cas systems to confer editing in cells, with a precise ablation of GFP production. This can be further expanded to HEK293T mammalian cells with integrated GFP, which indicate activity in mammalian cells. The sickly phenotype of *E. coli* colonies that have grown in both cases even in undiluted samples is also indicative of possible trans-cleavage of nucleic acids (RNA or DNA), which can be used for diagnostic purposes by providing a sample containing the target nucleic acid with the Casλ RNP and a single-stranded DNA fluorophore-quencher (ssDNA-FQ) reporter or RNA fluorophore-quencher (ssRNA-FQ) reporter molecule, generating a strong fluorescence signal in the presence of the target nucleic acid compared to a markedly lower fluorescence signal in its absence.

```
pBAS44 and pBAS40 spacer:
                              (SEQ ID NO: 165)
TAGCATCACCTTCACCCTCTCCACGGACAG.
```

FIG. 12A-12C. Casλ with GFP-targeting guides (pBAS44) showed a reduction in colony forming units (as a proxy for cell viability) of multiple orders of magnitude, in comparison to a negative control of Casλ with a non-targeting guide (pBAS12). Casλ with GFP-targeting guides using a repeat unit from another ortholog also showed inhibited growth and ablation of GFP.

Example 3: Casλ Purification

Purification of Casλ showed a protein size in line with computationally predicted values, of ~70-85 kDa. Casλ overexpression vectors containing a His Tag were transformed into chemically competent *E. coli* BL21(DE3)-Star (QB3-Macrolab, UC Berkeley) and incubated overnight at 37° C. on LB-Kan agar plates (50 μg/mL Kanamycin). Single colonies were picked to inoculate 50 mL (LB, Kanamycin 50 μg/mL) starter cultures which were incubated at 37° C. shaking vigorously overnight. The following day, 2 750 mL TB-Kan media (50 μg/mL Kanamycin) were inoculated with 40 mL starter culture and grown at 37° C. to an OD600 of 0.6, cooled down on ice and gene expression was subsequently induced with 0.5 mM IPTG followed by incubation overnight at 16° C.

The cells were harvested by centrifugation and resuspended in low salt buffer, and then subsequently lysed by sonication. The soluble fraction was loaded on a 5 mL Ni-NTA Superflow Cartridge (Qiagen) pre-equilibrated in wash buffer. Bound proteins were washed with 20 column volumes (CV) wash buffer and subsequently eluted in 5 CV elution buffer (50 mM HEPES-Na pH 7.5 RT, 500 mM NaCl, 500 mM imidazole, 5% glycerol and 0.5 mM TCEP). The eluted proteins were concentrated to 1 mL before injection into a HiLoad 16/600 Superdex 200 μg column (GE Healthcare) pre-equilibrated in size-exclusion chromatography buffer (20 mM HEPES-Na pH 7.5 RT, 500 mM NaCl, 5% glycerol and 0.5 mM TCEP). Peak fractions were concentrated to 1 mL and concentrations were determined using a NanoDrop 8000 Spectrophotometer (Thermo Scientific). Proteins were purified at a constant temperature of 4° C. and concentrated proteins were kept on ice to prevent aggregation, snap-frozen in liquid nitrogen, and stored at −80° C.

Sodium dodecyl sulfate-polyacrylamide gel electrophoresis (SDS-PAGE) of Casλ at various stages of protein purification showed a protein size in line with computationally predicted values of ~70 kDa.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising:
   a) a Cas12L polypeptide, or a nucleic acid molecule encoding the Cas12L polypeptide, wherein the Cas12L polypeptide comprises an amino acid sequence having 99% or more amino acid sequence identity with the amino acid sequence set forth in SEQ ID NO: 102; and
   b) a Cas12L guide RNA, or one or more DNA molecules encoding the Cas12L guide RNA, wherein the guide RNA is engineered such that the guide RNA's guide sequence is heterologous with the guide RNA's scaffold.

2. The composition of claim 1, wherein the Cas12L guide RNA comprises a nucleotide sequence having 80% or more nucleotide sequence identity with the crRNA sequence set forth as SEQ ID NO.

3. The composition of claim 1, wherein the Cas12L polypeptide is fused to a nuclear localization signal (NLS).

4. The composition of claim 1, wherein:
   i) the composition comprises a lipid;
   ii) a) and b) are within a liposome;
   iii) a) and b) are within a particle; or
   iv) the composition comprises one or more of: a buffer, a nuclease inhibitor, and a protease inhibitor.

5. The composition of claim 1, wherein the Cas12L polypeptide is a nickase that can cleave only one strand of a double-stranded target nucleic acid molecule.

6. The composition of claim 1, wherein the Cas12L polypeptide is a catalytically inactive Cas12L polypeptide (dCas12L).

7. The composition of claim 1, further comprising a DNA donor template.

8. The composition of claim 1, wherein the nucleic acid molecule encoding the Cas12L polypeptide is codon optimized such that the nucleotide sequence encoding the Cas12L polypeptide is non-naturally occurring.

9. The composition of claim 1, wherein the guide RNA comprises a guide sequence that is 100% complementary, over 17 or more continuous nucleotides, to a target sequence of a eukaryotic DNA.

10. The composition of claim 1, wherein the guide RNA comprises one or more base modifications, one or more backbone modifications, one or more modified sugar moieties, one or more non-natural internucleoside linkages, one or more polynucleotide mimetics, or any combination thereof.

11. The composition of claim 1, comprising the nucleic acid molecule encoding the Cas12L polypeptide, and/or the one or more DNA molecules encoding the Cas12L guide RNA.

12. The composition of claim 11, wherein the nucleic acid molecule encoding the Cas12L polypeptide comprises a codon optimized nucleotide sequence encoding the Cas12L polypeptide.

13. One or more nucleic acids comprising a nucleotide sequence encoding the Cas12L guide RNA and a nucleotide sequence encoding the Cas12L polypeptide of claim 1.

14. The one or more nucleic acids of claim 13, wherein the nucleotide sequence encoding the Cas12L polypeptide is non-naturally occurring because it is codon optimized.

15. The one or more nucleic acids of claim 13, wherein the nucleotide sequence encoding the Cas12L guide RNA is operably linked to a promoter that is functional in a eukaryotic cell, and/or the nucleotide sequence encoding the Cas12L polypeptide is operably linked to a promoter that is functional in a eukaryotic.

16. The one or more nucleic acids of claim 13, wherein the one or more nucleic acids is one or more recombinant expression vectors.

17. The one or more nucleic acids of claim 16, wherein the one or more recombinant expression vectors are one or more adenoassociated viral vectors, one or more recombinant retroviral vectors, or one or more recombinant lentiviral vectors.

18. A method of modifying a target nucleic acid, the method comprising contacting the target nucleic acid with:
   a) a Cas12L polypeptide that comprises an amino acid sequence having 99% or more amino acid sequence identity with the amino acid sequence set forth in SEQ ID NO: 102; and
   b) a Cas12L guide RNA comprising a guide sequence that hybridizes to a target sequence of the target nucleic acid, wherein the guide RNA is engineered such that the guide RNA's guide sequence is heterologous with the guide RNA's scaffold,
   wherein said contacting results in modification of the target nucleic acid by the Cas12L polypeptide.

19. The method of claim 18, wherein said contacting comprises introducing a nucleic acid molecule encoding the Cas12L polypeptide and/or a DNA molecule encoding the Cas12L guide RNA into a cell.

20. The method of claim 18, wherein said contacting comprises introducing the Cas12L polypeptide and the Cas12L guide RNA into the cell as a ribonucleoprotein (RNP) that comprises the Cas12L polypeptide and the Cas12L guide RNA.

* * * * *

SEQUENCE LISTING

```
<160> NUMBER OF SEQ ID NOS: 165

<210> SEQ ID NO 1
<211> LENGTH: 36
<212> TYPE: DNA
<213> ORGANISM: Artificial sequence
<220> FEATURE:
<223> OTHER INFORMATION: synthetic sequence

<400> SEQUENCE: 1
attgttgtaa ctcttatttt gtatggagta aacaac                              36

<210> SEQ ID NO 2
<211> LENGTH: 37
<212> TYPE: DNA
<213> ORGANISM: Artificial sequence
<220> FEATURE:
<223> OTHER INFORMATION: synthetic sequence
```

```
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 2
nattgttgta actcttattt tgtatggagt aaacaac                              37

<210> SEQ ID NO 3
<211> LENGTH: 36
<212> TYPE: DNA
<213> ORGANISM: Artificial sequence
<220> FEATURE:
<223> OTHER INFORMATION: synthetic sequence

<400> SEQUENCE: 3
attgttgtag acctcttttt ataaggattg aacaac                               36

<210> SEQ ID NO 4
<211> LENGTH: 37
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 4
nattgttgta gacctctttt tataaggatt gaacaac                              37

<210> SEQ ID NO 5
<211> LENGTH: 36
<212> TYPE: DNA
<213> ORGANISM: Artificial sequence
<220> FEATURE:
<223> OTHER INFORMATION: synthetic sequence

<400> SEQUENCE: 5
attgttgtag ataccttttt gtaaggattg aacaac                               36

<210> SEQ ID NO 6
<211> LENGTH: 37
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 6
nattgttgta gatacctttt tgtaaggatt gaacaac                              37

<210> SEQ ID NO 7
<211> LENGTH: 37
<212> TYPE: DNA
<213> ORGANISM: Artificial sequence
<220> FEATURE:
<223> OTHER INFORMATION: synthetic sequence

<400> SEQUENCE: 7
tattgttgta gatacctttt tgtaaggatt aaacaac                              37
```

-continued

```
<210> SEQ ID NO 8
<211> LENGTH: 38
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 8
ntattgttgt agataccttt ttgtaaggat taaacaac                            38

<210> SEQ ID NO 9
<211> LENGTH: 39
<212> TYPE: DNA
<213> ORGANISM: Artificial sequence
<220> FEATURE:
<223> OTHER INFORMATION: synthetic sequence

<400> SEQUENCE: 9
aatgttgtag atgccttttt ataaggatta aacaacttg                           39

<210> SEQ ID NO 10
<211> LENGTH: 40
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 10
naatgttgta gatgcctttt tataaggatt aaacaacttg                          40

<210> SEQ ID NO 11
<211> LENGTH: 36
<212> TYPE: DNA
<213> ORGANISM: Artificial sequence
<220> FEATURE:
<223> OTHER INFORMATION: synthetic sequence

<400> SEQUENCE: 11
attgttgaaa tagtactttt atagtctata tacaac                              36

<210> SEQ ID NO 12
<211> LENGTH: 37
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 12
nattgttgaa atagtacttt tatagtctat atacaac                             37

<210> SEQ ID NO 13
<211> LENGTH: 37
```

-continued

```
<212> TYPE: DNA
<213> ORGANISM: Artificial sequence
<220> FEATURE:
<223> OTHER INFORMATION: synthetic sequence

<400> SEQUENCE: 13
tattgttgta actcttattt tgtatggagt aaacaac                              37

<210> SEQ ID NO 14
<211> LENGTH: 38
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 14
ntattgttgt aactcttatt ttgtatggag taaacaac                             38

<210> SEQ ID NO 15
<211> LENGTH: 36
<212> TYPE: DNA
<213> ORGANISM: Artificial sequence
<220> FEATURE:
<223> OTHER INFORMATION: synthetic sequence

<400> SEQUENCE: 15
attgttgtaa catctatttt gtaaggtgta aacaac                               36

<210> SEQ ID NO 16
<211> LENGTH: 37
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 16
nattgttgta acatctattt tgtaaggtgt aaacaac                              37

<210> SEQ ID NO 17
<211> LENGTH: 37
<212> TYPE: DNA
<213> ORGANISM: Artificial sequence
<220> FEATURE:
<223> OTHER INFORMATION: synthetic sequence

<400> SEQUENCE: 17
aattgttgta actcttattt tgtatggagt aaacaac                              37

<210> SEQ ID NO 18
<211> LENGTH: 38
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide
```

-continued

<400> SEQUENCE: 18
naattgttgt aactcttatt ttgtatggag taaacaac                                38

<210> SEQ ID NO 19
<211> LENGTH: 36
<212> TYPE: DNA
<213> ORGANISM: Artificial sequence
<220> FEATURE:
<223> OTHER INFORMATION: synthetic sequence

<400> SEQUENCE: 19
attgttgtaa cttttatttt gtatggagta aacaac                                  36

<210> SEQ ID NO 20
<211> LENGTH: 37
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 20
nattgttgta actttatttt tgtatggagt aaacaac                                 37

<210> SEQ ID NO 21
<211> LENGTH: 36
<212> TYPE: DNA
<213> ORGANISM: Artificial sequence
<220> FEATURE:
<223> OTHER INFORMATION: synthetic sequence

<400> SEQUENCE: 21
aatgttgtag ataccttttt gtaaggattg aacaac                                  36

<210> SEQ ID NO 22
<211> LENGTH: 37
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 22
naatgttgta gataccctttt tgtaaggatt gaacaac                                37

<210> SEQ ID NO 23
<211> LENGTH: 36
<212> TYPE: DNA
<213> ORGANISM: Artificial sequence
<220> FEATURE:
<223> OTHER INFORMATION: synthetic sequence

<400> SEQUENCE: 23
attgttgtaa tactattttt gtaaagtata aacaac                                  36

<210> SEQ ID NO 24
<211> LENGTH: 37
<212> TYPE: DNA

-continued

```
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 24
nattgttgta atactatttt tgtaaagtat aaacaac                            37

<210> SEQ ID NO 25
<211> LENGTH: 36
<212> TYPE: DNA
<213> ORGANISM: Artificial sequence
<220> FEATURE:
<223> OTHER INFORMATION: synthetic sequence

<400> SEQUENCE: 25
aatgttgtag atgccttttt ataaggatta aacaac                             36

<210> SEQ ID NO 26
<211> LENGTH: 37
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 26
naatgttgta gatgcctttt tataaggatt aaacaac                            37

<210> SEQ ID NO 27
<211> LENGTH: 36
<212> TYPE: DNA
<213> ORGANISM: Artificial sequence
<220> FEATURE:
<223> OTHER INFORMATION: synthetic sequence

<400> SEQUENCE: 27
attgttgtaa tacacttttt ataaggtatg aacaac                             36

<210> SEQ ID NO 28
<211> LENGTH: 37
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: N is a sequence of 15 to 30 nucleotides where
      each nucleotide is comprised of any nucleotide

<400> SEQUENCE: 28
nattgttgta atacactttt tataaggtat gaacaac                            37

<210> SEQ ID NO 29
<211> LENGTH: 84
<212> TYPE: PRT
<213> ORGANISM: Artificial sequence
<220> FEATURE:
<223> OTHER INFORMATION: synthetic sequence
```

<400> SEQUENCE: 29

Met Ala Ser Met Ile Ser Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Ala

<210> SEQ ID NO 30
<211> LENGTH: 57
<212> TYPE: PRT
<213> ORGANISM: Artificial sequence
<220> FEATURE:
<223> OTHER INFORMATION: synthetic sequence

<400> SEQUENCE: 30

Met Ala Ser Met Ile Ser Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Ser
    50                  55

<210> SEQ ID NO 31
<211> LENGTH: 85
<212> TYPE: PRT
<213> ORGANISM: Artificial sequence
<220> FEATURE:
<223> OTHER INFORMATION: synthetic sequence

<400> SEQUENCE: 31

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
    50                  55                  60

Lys Lys Phe Glu Thr Leu Ser Tyr Leu Pro Asp Leu Thr Asp Ser Gly
65                  70                  75                  80

Gly Arg Val Asn Cys
                85

<210> SEQ ID NO 32
<211> LENGTH: 76
<212> TYPE: PRT
<213> ORGANISM: Artificial sequence
<220> FEATURE:
<223> OTHER INFORMATION: synthetic sequence

<400> SEQUENCE: 32

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
        50                  55                  60

Pro Leu Lys Val Met Ser Ser Val Ser Thr Ala Cys
65                  70                  75
```

<210> SEQ ID NO 33
<211> LENGTH: 76
<212> TYPE: PRT
<213> ORGANISM: Artificial sequence
<220> FEATURE:
<223> OTHER INFORMATION: synthetic sequence

<400> SEQUENCE: 33

```
Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
        50                  55                  60

Pro Leu Lys Val Met Ser Ser Val Ser Thr Ala Cys
65                  70                  75
```

<210> SEQ ID NO 34
<211> LENGTH: 72
<212> TYPE: PRT
<213> ORGANISM: Artificial sequence
<220> FEATURE:
<223> OTHER INFORMATION: synthetic sequence

<400> SEQUENCE: 34

```
Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
                20                  25                  30

Val Phe Gly Ser Lys Lys Leu Lys Asn Ser Ala Asn Ser Met Leu Val
            35                  40                  45

Leu Lys Lys Asp Ser Ile Phe Met Gln Leu Phe Cys Ser Phe Arg Ile
        50                  55                  60

Ser Ala Ser Val Ala Thr Ala Cys
65                  70
```

<210> SEQ ID NO 35
<211> LENGTH: 69
<212> TYPE: PRT
<213> ORGANISM: Artificial sequence
<220> FEATURE:
<223> OTHER INFORMATION: synthetic sequence

<400> SEQUENCE: 35

```
Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
```

-continued

```
                 20              25              30

Arg Asn Pro Ala Asp Ala Ala Leu Gly Met Arg Thr Val Gly Ala Ser
        35              40              45

Ala Ala Pro Lys Gln Ser Arg Lys Pro His Arg Phe Asp Arg Arg Cys
    50              55              60

Leu Ser Met Val Val
65

<210> SEQ ID NO 36
<211> LENGTH: 77
<212> TYPE: PRT
<213> ORGANISM: Artificial sequence
<220> FEATURE:
<223> OTHER INFORMATION: synthetic sequence

<400> SEQUENCE: 36

Met Ala Ala Leu Thr Thr Ser Gln Leu Ala Thr Ser Ala Thr Gly Phe
1               5              10              15

Gly Ile Ala Asp Arg Ser Ala Pro Ser Ser Leu Leu Arg His Gly Phe
        20              25              30

Gln Gly Leu Lys Pro Arg Ser Pro Ala Gly Gly Asp Ala Thr Ser Leu
        35              40              45

Ser Val Thr Thr Ser Ala Arg Ala Thr Pro Lys Gln Gln Arg Ser Val
    50              55              60

Gln Arg Gly Ser Arg Arg Phe Pro Ser Val Val Val Cys
65              70              75

<210> SEQ ID NO 37
<211> LENGTH: 57
<212> TYPE: PRT
<213> ORGANISM: Artificial sequence
<220> FEATURE:
<223> OTHER INFORMATION: synthetic sequence

<400> SEQUENCE: 37

Met Ala Ser Ser Val Leu Ser Ser Ala Ala Val Ala Thr Arg Ser Asn
1               5              10              15

Val Ala Gln Ala Asn Met Val Ala Pro Phe Thr Gly Leu Lys Ser Ala
        20              25              30

Ala Ser Phe Pro Val Ser Arg Lys Gln Asn Leu Asp Ile Thr Ser Ile
        35              40              45

Ala Ser Asn Gly Gly Arg Val Gln Cys
    50              55

<210> SEQ ID NO 38
<211> LENGTH: 65
<212> TYPE: PRT
<213> ORGANISM: Artificial sequence
<220> FEATURE:
<223> OTHER INFORMATION: synthetic sequence

<400> SEQUENCE: 38

Met Glu Ser Leu Ala Ala Thr Ser Val Phe Ala Pro Ser Arg Val Ala
1               5              10              15

Val Pro Ala Ala Arg Ala Leu Val Arg Ala Gly Thr Val Val Pro Thr
        20              25              30

Arg Arg Thr Ser Ser Thr Ser Gly Thr Ser Gly Val Lys Cys Ser Ala
        35              40              45

Ala Val Thr Pro Gln Ala Ser Pro Val Ile Ser Arg Ser Ala Ala Ala
    50              55              60
```

-continued

```
Ala
65

<210> SEQ ID NO 39
<211> LENGTH: 72
<212> TYPE: PRT
<213> ORGANISM: Artificial sequence
<220> FEATURE:
<223> OTHER INFORMATION: synthetic sequence

<400> SEQUENCE: 39

Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Ala Thr Thr
    50                  55                  60

Asn Gly Ala Ser Ala Ala Ser Ser
65                  70

<210> SEQ ID NO 40
<211> LENGTH: 11
<212> TYPE: PRT
<213> ORGANISM: Artificial sequence
<220> FEATURE:
<223> OTHER INFORMATION: synthetic sequence

<400> SEQUENCE: 40

Tyr Gly Arg Lys Lys Arg Arg Gln Arg Arg Arg
1               5                   10

<210> SEQ ID NO 41
<211> LENGTH: 12
<212> TYPE: PRT
<213> ORGANISM: Artificial sequence
<220> FEATURE:
<223> OTHER INFORMATION: synthetic sequence

<400> SEQUENCE: 41

Arg Arg Gln Arg Arg Thr Ser Lys Leu Met Lys Arg
1               5                   10

<210> SEQ ID NO 42
<211> LENGTH: 27
<212> TYPE: PRT
<213> ORGANISM: Artificial sequence
<220> FEATURE:
<223> OTHER INFORMATION: synthetic sequence

<400> SEQUENCE: 42

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 43
<211> LENGTH: 33
<212> TYPE: PRT
<213> ORGANISM: Artificial sequence
<220> FEATURE:
<223> OTHER INFORMATION: synthetic sequence
```

-continued

```
<400> SEQUENCE: 43

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 44
<211> LENGTH: 16
<212> TYPE: PRT
<213> ORGANISM: Drosophila melanogaster

<400> SEQUENCE: 44

Arg Gln Ile Lys Ile Trp Phe Gln Asn Arg Arg Met Lys Trp Lys Lys
1               5                   10                  15

<210> SEQ ID NO 45
<211> LENGTH: 9
<212> TYPE: PRT
<213> ORGANISM: Artificial sequence
<220> FEATURE:
<223> OTHER INFORMATION: synthetic sequence

<400> SEQUENCE: 45

Arg Lys Lys Arg Arg Gln Arg Arg Arg
1               5

<210> SEQ ID NO 46
<211> LENGTH: 8
<212> TYPE: PRT
<213> ORGANISM: Artificial sequence
<220> FEATURE:
<223> OTHER INFORMATION: synthetic sequence

<400> SEQUENCE: 46

Arg Lys Lys Arg Arg Gln Arg Arg
1               5

<210> SEQ ID NO 47
<211> LENGTH: 11
<212> TYPE: PRT
<213> ORGANISM: Artificial sequence
<220> FEATURE:
<223> OTHER INFORMATION: synthetic sequence

<400> SEQUENCE: 47

Tyr Ala Arg Ala Ala Ala Arg Gln Ala Arg Ala
1               5                   10

<210> SEQ ID NO 48
<211> LENGTH: 11
<212> TYPE: PRT
<213> ORGANISM: Artificial sequence
<220> FEATURE:
<223> OTHER INFORMATION: synthetic sequence

<400> SEQUENCE: 48

Thr His Arg Leu Pro Arg Arg Arg Arg Arg
1               5                   10

<210> SEQ ID NO 49
<211> LENGTH: 11
<212> TYPE: PRT
<213> ORGANISM: Artificial sequence
<220> FEATURE:
```

-continued

<223> OTHER INFORMATION: synthetic sequence

<400> SEQUENCE: 49

Gly Gly Arg Arg Ala Arg Arg Arg Arg Arg
1               5                   10

<210> SEQ ID NO 50
<211> LENGTH: 5
<212> TYPE: PRT
<213> ORGANISM: Artificial sequence
<220> FEATURE:
<223> OTHER INFORMATION: synthetic sequence

<400> SEQUENCE: 50

Gly Ser Gly Gly Ser
1               5

<210> SEQ ID NO 51
<211> LENGTH: 6
<212> TYPE: PRT
<213> ORGANISM: Artificial sequence
<220> FEATURE:
<223> OTHER INFORMATION: synthetic sequence

<400> SEQUENCE: 51

Gly Gly Ser Gly Gly Ser
1               5

<210> SEQ ID NO 52
<211> LENGTH: 4
<212> TYPE: PRT
<213> ORGANISM: Artificial sequence
<220> FEATURE:
<223> OTHER INFORMATION: synthetic sequence

<400> SEQUENCE: 52

Gly Gly Gly Ser
1

<210> SEQ ID NO 53
<211> LENGTH: 4
<212> TYPE: PRT
<213> ORGANISM: Artificial sequence
<220> FEATURE:
<223> OTHER INFORMATION: synthetic sequence

<400> SEQUENCE: 53

Gly Gly Ser Gly
1

<210> SEQ ID NO 54
<211> LENGTH: 5
<212> TYPE: PRT
<213> ORGANISM: Artificial sequence
<220> FEATURE:
<223> OTHER INFORMATION: synthetic sequence

<400> SEQUENCE: 54

Gly Gly Ser Gly Gly
1               5

<210> SEQ ID NO 55
<211> LENGTH: 5
<212> TYPE: PRT
<213> ORGANISM: Artificial sequence
<220> FEATURE:
<223> OTHER INFORMATION: synthetic sequence -continued

<400> SEQUENCE: 55

Gly Ser Gly Ser Gly
1               5

<210> SEQ ID NO 56
<211> LENGTH: 5
<212> TYPE: PRT
<213> ORGANISM: Artificial sequence
<220> FEATURE:
<223> OTHER INFORMATION: synthetic sequence

<400> SEQUENCE: 56

Gly Ser Gly Gly Gly
1               5

<210> SEQ ID NO 57
<211> LENGTH: 5
<212> TYPE: PRT
<213> ORGANISM: Artificial sequence
<220> FEATURE:
<223> OTHER INFORMATION: synthetic sequence

<400> SEQUENCE: 57

Gly Gly Gly Ser Gly
1               5

<210> SEQ ID NO 58
<211> LENGTH: 5
<212> TYPE: PRT
<213> ORGANISM: Artificial sequence
<220> FEATURE:
<223> OTHER INFORMATION: synthetic sequence

<400> SEQUENCE: 58

Gly Ser Ser Ser Gly
1               5

<210> SEQ ID NO 59
<211> LENGTH: 36
<212> TYPE: RNA
<213> ORGANISM: Artificial sequence
<220> FEATURE:
<223> OTHER INFORMATION: synthetic sequence

<400> SEQUENCE: 59
auuguuguaa cucuuauuuu guauggagua aacaac                                        36

<210> SEQ ID NO 60
<211> LENGTH: 36
<212> TYPE: RNA
<213> ORGANISM: Artificial sequence
<220> FEATURE:
<223> OTHER INFORMATION: synthetic sequence

<400> SEQUENCE: 60
auuguuguag accucuuuuu auaaggauug aacaac                                        36

<210> SEQ ID NO 61
<211> LENGTH: 37
<212> TYPE: RNA
<213> ORGANISM: Artificial sequence
<220> FEATURE:
<223> OTHER INFORMATION: synthetic sequence

<400> SEQUENCE: 61

-continued

```
uauuguugua gauaccuuuu uguaaggauu aaacaac                      37

<210> SEQ ID NO 62
<211> LENGTH: 39
<212> TYPE: RNA
<213> ORGANISM: Artificial sequence
<220> FEATURE:
<223> OTHER INFORMATION: synthetic sequence

<400> SEQUENCE: 62
aauguuguag augccuuuuu auaaggauua aacaacuug                    39

<210> SEQ ID NO 63
<211> LENGTH: 36
<212> TYPE: RNA
<213> ORGANISM: Artificial sequence
<220> FEATURE:
<223> OTHER INFORMATION: synthetic sequence

<400> SEQUENCE: 63
auuguugaaa uaguacuuuu auagucuaua uacaac                       36

<210> SEQ ID NO 64
<211> LENGTH: 37
<212> TYPE: RNA
<213> ORGANISM: Artificial sequence
<220> FEATURE:
<223> OTHER INFORMATION: synthetic sequence

<400> SEQUENCE: 64
uauuguugua acucuuauuu uguauggagu aaacaac                      37

<210> SEQ ID NO 65
<211> LENGTH: 36
<212> TYPE: RNA
<213> ORGANISM: Artificial sequence
<220> FEATURE:
<223> OTHER INFORMATION: synthetic sequence

<400> SEQUENCE: 65
auuguuguaa cuuuuauuuu guauggagua aacaac                       36

<210> SEQ ID NO 66
<211> LENGTH: 36
<212> TYPE: RNA
<213> ORGANISM: Artificial sequence
<220> FEATURE:
<223> OTHER INFORMATION: synthetic sequence

<400> SEQUENCE: 66
aauguuguag auaccuuuuu guaaggauug aacaac                       36

<210> SEQ ID NO 67
<211> LENGTH: 36
<212> TYPE: RNA
<213> ORGANISM: Artificial sequence
<220> FEATURE:
<223> OTHER INFORMATION: synthetic sequence

<400> SEQUENCE: 67
auuguuguaa uacuauuuuu guaaaguaua aacaac                       36

<210> SEQ ID NO 68
<211> LENGTH: 36
<212> TYPE: RNA
<213> ORGANISM: Artificial sequence
```

-continued

```
<220> FEATURE:
<223> OTHER INFORMATION: synthetic sequence

<400> SEQUENCE: 68
aauguuguag augccuuuuu auaaggauua aacaac                              36

<210> SEQ ID NO 69
<211> LENGTH: 36
<212> TYPE: RNA
<213> ORGANISM: Artificial sequence
<220> FEATURE:
<223> OTHER INFORMATION: synthetic sequence

<400> SEQUENCE: 69
auuguuguaa uacacuuuuu auaagguaug aacaac                              36

<210> SEQ ID NO 70
<211> LENGTH: 36
<212> TYPE: RNA
<213> ORGANISM: Artificial sequence
<220> FEATURE:
<223> OTHER INFORMATION: synthetic sequence

<400> SEQUENCE: 70
auuguuguaa caucuauuuu guaaggugua aacaac                              36

<210> SEQ ID NO 71
<211> LENGTH: 71
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(35)
<223> OTHER INFORMATION: n is any nucleotide

<400> SEQUENCE: 71
nnnnnnnnnn nnnnnnnnnn nnnnnnnnnn nnnnnauugu uguaacucuu auuuuguaug   60
gaguaaacaa c                                                         71

<210> SEQ ID NO 72
<211> LENGTH: 20
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (4)..(4)
<223> OTHER INFORMATION: X is selected from lysine, histidine, and
      arginine
<220> FEATURE:
<221> NAME/KEY: MISC_FEATURE
<222> LOCATION: (8)..(8)
<223> OTHER INFORMATION: X is selected from lysine, histidine, and
      arginine
<220> FEATURE:
<221> NAME/KEY: MISC_FEATURE
<222> LOCATION: (11)..(11)
<223> OTHER INFORMATION: X is selected from lysine, histidine, and
      arginine
<220> FEATURE:
<221> NAME/KEY: MISC_FEATURE
<222> LOCATION: (15)..(15)
<223> OTHER INFORMATION: X is selected from lysine, histidine, and
      arginine
<220> FEATURE:
<221> NAME/KEY: MISC_FEATURE
<222> LOCATION: (19)..(19)
```

<223> OTHER INFORMATION: X is selected from lysine, histidine, and
      arginine

<400> SEQUENCE: 72

```
Gly Leu Phe Xaa Ala Leu Leu Xaa Leu Leu Xaa Ser Leu Trp Xaa Leu
1               5                   10                  15

Leu Leu Xaa Ala
            20
```

<210> SEQ ID NO 73
<211> LENGTH: 20
<212> TYPE: PRT
<213> ORGANISM: Artificial sequence
<220> FEATURE:
<223> OTHER INFORMATION: synthetic sequence

<400> SEQUENCE: 73

```
Gly Leu Phe His Ala Leu Leu His Leu Leu His Ser Leu Trp His Leu
1               5                   10                  15

Leu Leu His Ala
            20
```

<210> SEQ ID NO 74
<211> LENGTH: 167
<212> TYPE: PRT
<213> ORGANISM: Artificial sequence
<220> FEATURE:
<223> OTHER INFORMATION: synthetic sequence

<400> SEQUENCE: 74

```
Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
                100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
        130                 135                 140

Leu Ser Asp Phe Phe Arg Met Arg Arg Gln Glu Ile Lys Ala Gln Lys
145                 150                 155                 160

Lys Ala Gln Ser Ser Thr Asp
                165
```

<210> SEQ ID NO 75
<211> LENGTH: 178
<212> TYPE: PRT
<213> ORGANISM: Artificial sequence
<220> FEATURE:
<223> OTHER INFORMATION: synthetic sequence

<400> SEQUENCE: 75

-continued

```
Met Arg Arg Ala Phe Ile Thr Gly Val Phe Phe Leu Ser Glu Val Glu
1               5                   10                  15

Phe Ser His Glu Tyr Trp Met Arg His Ala Leu Thr Leu Ala Lys Arg
            20                  25                  30

Ala Trp Asp Glu Arg Glu Val Pro Val Gly Ala Val Leu Val His Asn
            35                  40                  45

Asn Arg Val Ile Gly Glu Gly Trp Asn Arg Pro Ile Gly Arg His Asp
        50                  55                  60

Pro Thr Ala His Ala Glu Ile Met Ala Leu Arg Gln Gly Gly Leu Val
65                  70                  75                  80

Met Gln Asn Tyr Arg Leu Ile Asp Ala Thr Leu Tyr Val Thr Leu Glu
                85                  90                  95

Pro Cys Val Met Cys Ala Gly Ala Met Ile His Ser Arg Ile Gly Arg
            100                 105                 110

Val Val Phe Gly Ala Arg Asp Ala Lys Thr Gly Ala Ala Gly Ser Leu
            115                 120                 125

Met Asp Val Leu His His Pro Gly Met Asn His Arg Val Glu Ile Thr
        130                 135                 140

Glu Gly Ile Leu Ala Asp Glu Cys Ala Ala Leu Leu Ser Asp Phe Phe
145                 150                 155                 160

Arg Met Arg Arg Gln Glu Ile Lys Ala Gln Lys Lys Ala Gln Ser Ser
                165                 170                 175

Thr Asp
```

```
<210> SEQ ID NO 76
<211> LENGTH: 160
<212> TYPE: PRT
<213> ORGANISM: Staphylococcus aureus

<400> SEQUENCE: 76
```

```
Met Gly Ser His Met Thr Asn Asp Ile Tyr Phe Met Thr Leu Ala Ile
1               5                   10                  15

Glu Glu Ala Lys Lys Ala Ala Gln Leu Gly Glu Val Pro Ile Gly Ala
            20                  25                  30

Ile Ile Thr Lys Asp Asp Glu Val Ile Ala Arg Ala His Asn Leu Arg
            35                  40                  45

Glu Thr Leu Gln Gln Pro Thr Ala His Ala Glu His Ile Ala Ile Glu
        50                  55                  60

Arg Ala Ala Lys Val Leu Gly Ser Trp Arg Leu Glu Gly Cys Thr Leu
65                  70                  75                  80

Tyr Val Thr Leu Glu Pro Cys Val Met Cys Ala Gly Thr Ile Val Met
                85                  90                  95

Ser Arg Ile Pro Arg Val Val Tyr Gly Ala Asp Asp Pro Lys Gly Gly
            100                 105                 110

Cys Ser Gly Ser Leu Met Asn Leu Leu Gln Gln Ser Asn Phe Asn His
            115                 120                 125

Arg Ala Ile Val Asp Lys Gly Val Leu Lys Glu Ala Cys Ser Thr Leu
        130                 135                 140

Leu Thr Thr Phe Phe Lys Asn Leu Arg Ala Asn Lys Lys Ser Thr Asn
145                 150                 155                 160
```

```
<210> SEQ ID NO 77
<211> LENGTH: 161
<212> TYPE: PRT
<213> ORGANISM: Bacillus subtilis
```

<400> SEQUENCE: 77

```
Met Thr Gln Asp Glu Leu Tyr Met Lys Glu Ala Ile Lys Glu Ala Lys
1               5                   10                  15

Lys Ala Glu Glu Lys Gly Glu Val Pro Ile Gly Ala Val Leu Val Ile
            20                  25                  30

Asn Gly Glu Ile Ile Ala Arg Ala His Asn Leu Arg Glu Thr Glu Gln
        35                  40                  45

Arg Ser Ile Ala His Ala Glu Met Leu Val Ile Asp Glu Ala Cys Lys
    50                  55                  60

Ala Leu Gly Thr Trp Arg Leu Glu Gly Ala Thr Leu Tyr Val Thr Leu
65                  70                  75                  80

Glu Pro Cys Pro Met Cys Ala Gly Ala Val Val Leu Ser Arg Val Glu
                85                  90                  95

Lys Val Val Phe Gly Ala Phe Asp Pro Lys Gly Gly Cys Ser Gly Thr
                100                 105                 110

Leu Met Asn Leu Leu Gln Glu Glu Arg Phe Asn His Gln Ala Glu Val
            115                 120                 125

Val Ser Gly Val Leu Glu Glu Glu Cys Gly Gly Met Leu Ser Ala Phe
    130                 135                 140

Phe Arg Glu Leu Arg Lys Lys Lys Ala Ala Arg Lys Asn Leu Ser
145                 150                 155                 160

Glu
```

<210> SEQ ID NO 78
<211> LENGTH: 183
<212> TYPE: PRT
<213> ORGANISM: Salmonella typhimurium

<400> SEQUENCE: 78

```
Met Pro Pro Ala Phe Ile Thr Gly Val Thr Ser Leu Ser Asp Val Glu
1               5                   10                  15

Leu Asp His Glu Tyr Trp Met Arg His Ala Leu Thr Leu Ala Lys Arg
            20                  25                  30

Ala Trp Asp Glu Arg Glu Val Pro Val Gly Ala Val Leu Val His Asn
        35                  40                  45

His Arg Val Ile Gly Glu Gly Trp Asn Arg Pro Ile Gly Arg His Asp
    50                  55                  60

Pro Thr Ala His Ala Glu Ile Met Ala Leu Arg Gln Gly Gly Leu Val
65                  70                  75                  80

Leu Gln Asn Tyr Arg Leu Leu Asp Thr Thr Leu Tyr Val Thr Leu Glu
                85                  90                  95

Pro Cys Val Met Cys Ala Gly Ala Met Val His Ser Arg Ile Gly Arg
                100                 105                 110

Val Val Phe Gly Ala Arg Asp Ala Lys Thr Gly Ala Ala Gly Ser Leu
            115                 120                 125

Ile Asp Val Leu His His Pro Gly Met Asn His Arg Val Glu Ile Ile
    130                 135                 140

Glu Gly Val Leu Arg Asp Glu Cys Ala Thr Leu Leu Ser Asp Phe Phe
145                 150                 155                 160

Arg Met Arg Arg Gln Glu Ile Lys Ala Leu Lys Lys Ala Asp Arg Ala
                165                 170                 175

Glu Gly Ala Gly Pro Ala Val
                180
```

<210> SEQ ID NO 79
<211> LENGTH: 164
<212> TYPE: PRT
<213> ORGANISM: Shewanella putrefaciens

<400> SEQUENCE: 79

```
Met Asp Glu Tyr Trp Met Gln Val Ala Met Gln Met Ala Glu Lys Ala
1               5                   10                  15

Glu Ala Ala Gly Glu Val Pro Val Gly Ala Val Leu Val Lys Asp Gly
                20                  25                  30

Gln Gln Ile Ala Thr Gly Tyr Asn Leu Ser Ile Ser Gln His Asp Pro
            35                  40                  45

Thr Ala His Ala Glu Ile Leu Cys Leu Arg Ser Ala Gly Lys Lys Leu
        50                  55                  60

Glu Asn Tyr Arg Leu Leu Asp Ala Thr Leu Tyr Ile Thr Leu Glu Pro
65                  70                  75                  80

Cys Ala Met Cys Ala Gly Ala Met Val His Ser Arg Ile Ala Arg Val
                85                  90                  95

Val Tyr Gly Ala Arg Asp Glu Lys Thr Gly Ala Ala Gly Thr Val Val
                100                 105                 110

Asn Leu Leu Gln His Pro Ala Phe Asn His Gln Val Glu Val Thr Ser
            115                 120                 125

Gly Val Leu Ala Glu Ala Cys Ser Ala Gln Leu Ser Arg Phe Phe Lys
        130                 135                 140

Arg Arg Arg Asp Glu Lys Lys Ala Leu Lys Leu Ala Gln Arg Ala Gln
145                 150                 155                 160

Gln Gly Ile Glu
```

<210> SEQ ID NO 80
<211> LENGTH: 173
<212> TYPE: PRT
<213> ORGANISM: Haemophilus influenzae

<400> SEQUENCE: 80

```
Met Asp Ala Ala Lys Val Arg Ser Glu Phe Asp Glu Lys Met Met Arg
1               5                   10                  15

Tyr Ala Leu Glu Leu Ala Asp Lys Ala Glu Ala Leu Gly Glu Ile Pro
                20                  25                  30

Val Gly Ala Val Leu Val Asp Asp Ala Arg Asn Ile Ile Gly Glu Gly
            35                  40                  45

Trp Asn Leu Ser Ile Val Gln Ser Asp Pro Thr Ala His Ala Glu Ile
        50                  55                  60

Ile Ala Leu Arg Asn Gly Ala Lys Asn Ile Gln Asn Tyr Arg Leu Leu
65                  70                  75                  80

Asn Ser Thr Leu Tyr Val Thr Leu Glu Pro Cys Thr Met Cys Ala Gly
                85                  90                  95

Ala Ile Leu His Ser Arg Ile Lys Arg Leu Val Phe Gly Ala Ser Asp
                100                 105                 110

Tyr Lys Thr Gly Ala Ile Gly Ser Arg Phe His Phe Phe Asp Asp Tyr
            115                 120                 125

Lys Met Asn His Thr Leu Glu Ile Thr Ser Gly Val Leu Ala Glu Glu
        130                 135                 140

Cys Ser Gln Lys Leu Ser Thr Phe Phe Gln Lys Arg Arg Glu Glu Lys
145                 150                 155                 160

Lys Ile Glu Lys Ala Leu Leu Lys Ser Leu Ser Asp Lys
```

-continued

```
                 165                 170

<210> SEQ ID NO 81
<211> LENGTH: 161
<212> TYPE: PRT
<213> ORGANISM: Caulobacter crescentus

<400> SEQUENCE: 81

Met Arg Thr Asp Glu Ser Glu Asp Gln Asp His Arg Met Met Arg Leu
1               5                   10                  15

Ala Leu Asp Ala Ala Arg Ala Ala Ala Glu Ala Gly Glu Thr Pro Val
            20                  25                  30

Gly Ala Val Ile Leu Asp Pro Ser Thr Gly Glu Val Ile Ala Thr Ala
            35                  40                  45

Gly Asn Gly Pro Ile Ala Ala His Asp Pro Thr Ala His Ala Glu Ile
        50                  55                  60

Ala Ala Met Arg Ala Ala Ala Lys Leu Gly Asn Tyr Arg Leu Thr
65                  70                  75                  80

Asp Leu Thr Leu Val Val Thr Leu Glu Pro Cys Ala Met Cys Ala Gly
                85                  90                  95

Ala Ile Ser His Ala Arg Ile Gly Arg Val Val Phe Gly Ala Asp Asp
            100                 105                 110

Pro Lys Gly Gly Ala Val Val His Gly Pro Lys Phe Phe Ala Gln Pro
        115                 120                 125

Thr Cys His Trp Arg Pro Glu Val Thr Gly Gly Val Leu Ala Asp Glu
    130                 135                 140

Ser Ala Asp Leu Leu Arg Gly Phe Phe Arg Ala Arg Arg Lys Ala Lys
145                 150                 155                 160

Ile

<210> SEQ ID NO 82
<211> LENGTH: 179
<212> TYPE: PRT
<213> ORGANISM: Geobacter sulfurreducens

<400> SEQUENCE: 82

Met Ser Ser Leu Lys Lys Thr Pro Ile Arg Asp Asp Ala Tyr Trp Met
1               5                   10                  15

Gly Lys Ala Ile Arg Glu Ala Ala Lys Ala Ala Ala Arg Asp Glu Val
            20                  25                  30

Pro Ile Gly Ala Val Ile Val Arg Asp Gly Ala Val Ile Gly Arg Gly
            35                  40                  45

His Asn Leu Arg Glu Gly Ser Asn Asp Pro Ser Ala His Ala Glu Met
        50                  55                  60

Ile Ala Ile Arg Gln Ala Ala Arg Arg Ser Ala Asn Trp Arg Leu Thr
65                  70                  75                  80

Gly Ala Thr Leu Tyr Val Thr Leu Glu Pro Cys Leu Met Cys Met Gly
                85                  90                  95

Ala Ile Ile Leu Ala Arg Leu Glu Arg Val Val Phe Gly Cys Tyr Asp
            100                 105                 110

Pro Lys Gly Gly Ala Ala Gly Ser Leu Tyr Asp Leu Ser Ala Asp Pro
        115                 120                 125

Arg Leu Asn His Gln Val Arg Leu Ser Pro Gly Val Cys Gln Glu Glu
    130                 135                 140

Cys Gly Thr Met Leu Ser Asp Phe Phe Arg Asp Leu Arg Arg Arg Lys
145                 150                 155                 160
```

```
Lys Ala Lys Ala Thr Pro Ala Leu Phe Ile Asp Glu Arg Lys Val Pro
                165                 170                 175

Pro Glu Pro

<210> SEQ ID NO 83
<211> LENGTH: 198
<212> TYPE: PRT
<213> ORGANISM: Artificial sequence
<220> FEATURE:
<223> OTHER INFORMATION: synthetic sequence

<400> SEQUENCE: 83

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
                180                 185                 190

Phe Arg Thr Leu Gly Leu
            195

<210> SEQ ID NO 84
<211> LENGTH: 178
<212> TYPE: PRT
<213> ORGANISM: Artificial sequence
<220> FEATURE:
<223> OTHER INFORMATION: synthetic sequence

<400> SEQUENCE: 84

Phe Leu Tyr Gln Phe Lys Asn Val Arg Trp Ala Lys Gly Arg Arg Glu
1               5                   10                  15

Thr Tyr Leu Cys Tyr Val Val Lys Arg Arg Asp Ser Ala Thr Ser Phe
                20                  25                  30

Ser Leu Asp Phe Gly Tyr Leu Arg Asn Lys Asn Gly Cys His Val Glu
            35                  40                  45

Leu Leu Phe Leu Arg Tyr Ile Ser Asp Trp Asp Leu Asp Pro Gly Arg
        50                  55                  60

Cys Tyr Arg Val Thr Trp Phe Thr Ser Trp Ser Pro Cys Tyr Asp Cys
65                  70                  75                  80
```

```
Ala Arg His Val Ala Asp Phe Leu Arg Gly Asn Pro Asn Leu Ser Leu
                85                  90                  95

Arg Ile Phe Thr Ala Arg Leu Tyr Phe Cys Glu Asp Arg Lys Ala Glu
               100                 105                 110

Pro Glu Gly Leu Arg Arg Leu His Arg Ala Gly Val Gln Ile Ala Ile
           115                 120                 125

Met Thr Phe Lys Glu Asn His Glu Arg Thr Phe Lys Ala Trp Glu Gly
       130                 135                 140

Leu His Glu Asn Ser Val Arg Leu Ser Arg Gln Leu Arg Arg Ile Leu
145                 150                 155                 160

Leu Pro Leu Tyr Glu Val Asp Asp Leu Arg Asp Ala Phe Arg Thr Leu
               165                 170                 175

Gly Leu

<210> SEQ ID NO 85
<211> LENGTH: 188
<212> TYPE: PRT
<213> ORGANISM: Artificial sequence
<220> FEATURE:
<223> OTHER INFORMATION: synthetic sequence

<400> SEQUENCE: 85

Phe Leu Tyr Gln Phe Lys Asn Val Arg Trp Ala Lys Gly Arg Arg Glu
1               5                   10                  15

Thr Tyr Leu Cys Tyr Val Val Lys Arg Arg Asp Ser Ala Thr Ser Phe
                20                  25                  30

Ser Leu Asp Phe Gly Tyr Leu Arg Asn Lys Asn Gly Cys His Val Glu
            35                  40                  45

Leu Leu Phe Leu Arg Tyr Ile Ser Asp Trp Asp Leu Asp Pro Gly Arg
        50                  55                  60

Cys Tyr Arg Val Thr Trp Phe Thr Ser Trp Ser Pro Cys Tyr Asp Cys
65                  70                  75                  80

Ala Arg His Val Ala Asp Phe Leu Arg Gly Asn Pro Asn Leu Ser Leu
                85                  90                  95

Arg Ile Phe Thr Ala Arg Leu Tyr Phe Cys Glu Asp Arg Lys Ala Glu
               100                 105                 110

Pro Glu Gly Leu Arg Arg Leu His Arg Ala Gly Val Gln Ile Ala Ile
           115                 120                 125

Met Thr Phe Lys Asp Tyr Phe Tyr Cys Trp Asn Thr Phe Val Glu Asn
       130                 135                 140

His Glu Arg Thr Phe Lys Ala Trp Glu Gly Leu His Glu Asn Ser Val
145                 150                 155                 160

Arg Leu Ser Arg Gln Leu Arg Arg Ile Leu Leu Pro Leu Tyr Glu Val
                165                 170                 175

Asp Asp Leu Arg Asp Ala Phe Arg Thr Leu Gly Leu
            180                 185

<210> SEQ ID NO 86
<211> LENGTH: 7
<212> TYPE: PRT
<213> ORGANISM: SV40 virus

<400> SEQUENCE: 86

Pro Lys Lys Lys Arg Lys Val
1               5
```

```
<210> SEQ ID NO 87
<211> LENGTH: 16
<212> TYPE: PRT
<213> ORGANISM: Unknown
<220> FEATURE:
<223> OTHER INFORMATION: nucleoplasmin bipartite NLS

<400> SEQUENCE: 87

Lys Arg Pro Ala Ala Thr Lys Lys Ala Gly Gln Ala Lys Lys Lys Lys
1               5                   10                  15

<210> SEQ ID NO 88
<211> LENGTH: 9
<212> TYPE: PRT
<213> ORGANISM: Unknown
<220> FEATURE:
<223> OTHER INFORMATION: c-myc NLS

<400> SEQUENCE: 88

Pro Ala Ala Lys Arg Val Lys Leu Asp
1               5

<210> SEQ ID NO 89
<211> LENGTH: 11
<212> TYPE: PRT
<213> ORGANISM: Unknown
<220> FEATURE:
<223> OTHER INFORMATION: c-myc NLS

<400> SEQUENCE: 89

Arg Gln Arg Arg Asn Glu Leu Lys Arg Ser Pro
1               5                   10

<210> SEQ ID NO 90
<211> LENGTH: 38
<212> TYPE: PRT
<213> ORGANISM: Unknown
<220> FEATURE:
<223> OTHER INFORMATION: hRNPA1 M9 NLS

<400> SEQUENCE: 90

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 91
<211> LENGTH: 42
<212> TYPE: PRT
<213> ORGANISM: Unknown
<220> FEATURE:
<223> OTHER INFORMATION: IBB domain from importin-alpha

<400> SEQUENCE: 91

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 92
<211> LENGTH: 8
```

-continued

```
<212> TYPE: PRT
<213> ORGANISM: Unknown
<220> FEATURE:
<223> OTHER INFORMATION: myoma T protein

<400> SEQUENCE: 92

Val Ser Arg Lys Arg Pro Arg Pro
1               5

<210> SEQ ID NO 93
<211> LENGTH: 8
<212> TYPE: PRT
<213> ORGANISM: Unknown
<220> FEATURE:
<223> OTHER INFORMATION: myoma T protein

<400> SEQUENCE: 93

Pro Pro Lys Lys Ala Arg Glu Asp
1               5

<210> SEQ ID NO 94
<211> LENGTH: 8
<212> TYPE: PRT
<213> ORGANISM: Homo sapiens

<400> SEQUENCE: 94

Pro Gln Pro Lys Lys Lys Pro Leu
1               5

<210> SEQ ID NO 95
<211> LENGTH: 12
<212> TYPE: PRT
<213> ORGANISM: Mus musculus

<400> SEQUENCE: 95

Ser Ala Leu Ile Lys Lys Lys Lys Lys Met Ala Pro
1               5                   10

<210> SEQ ID NO 96
<211> LENGTH: 5
<212> TYPE: PRT
<213> ORGANISM: Influenza virus

<400> SEQUENCE: 96

Asp Arg Leu Arg Arg
1               5

<210> SEQ ID NO 97
<211> LENGTH: 7
<212> TYPE: PRT
<213> ORGANISM: Influenza virus

<400> SEQUENCE: 97

Pro Lys Gln Lys Lys Arg Lys
1               5

<210> SEQ ID NO 98
<211> LENGTH: 10
<212> TYPE: PRT
<213> ORGANISM: Hepatitus virus

<400> SEQUENCE: 98

Arg Lys Leu Lys Lys Lys Ile Lys Lys Leu
1               5                   10
```

```
<210> SEQ ID NO 99
<211> LENGTH: 10
<212> TYPE: PRT
<213> ORGANISM: Mus musculus

<400> SEQUENCE: 99

Arg Glu Lys Lys Lys Phe Leu Lys Arg Arg
1               5                   10

<210> SEQ ID NO 100
<211> LENGTH: 20
<212> TYPE: PRT
<213> ORGANISM: Homo sapiens

<400> SEQUENCE: 100

Lys Arg Lys Gly Asp Glu Val Asp Gly Val Asp Glu Val Ala Lys Lys
1               5                   10                  15

Lys Ser Lys Lys
            20

<210> SEQ ID NO 101
<211> LENGTH: 17
<212> TYPE: PRT
<213> ORGANISM: Homo sapiens

<400> SEQUENCE: 101

Arg Lys Cys Leu Gln Ala Gly Met Asn Leu Glu Ala Arg Lys Thr Lys
1               5                   10                  15

Lys

<210> SEQ ID NO 102
<211> LENGTH: 746
<212> TYPE: PRT
<213> ORGANISM: Artificial sequence
<220> FEATURE:
<223> OTHER INFORMATION: synthetic sequence

<400> SEQUENCE: 102

Met Ala Ser His Lys Lys Thr Glu Ser Asn Gln Ile Ile Lys Thr Phe
1               5                   10                  15

Ser Phe Lys Ile Lys Asn Ala Asn Gly Leu Ser Leu Asp Val Leu Asn
            20                  25                  30

Asp Ala Ile Thr Glu Tyr Gln Asn Tyr Tyr Asn Ile Cys Ser Asp Trp
        35                  40                  45

Ile Lys Asp His Leu Thr Met Lys Ile Ser Glu Leu Tyr Lys Tyr Ile
    50                  55                  60

Pro Asn Glu Lys Lys Asn Ser Gly Tyr Ala Leu Thr Leu Ile Ser Asp
65                  70                  75                  80

Glu Trp Lys Asp Lys Pro Met Tyr Met Met Phe Lys Lys Gly Tyr Pro
                85                  90                  95

Ala Asn Asn Arg Asp Asn Ala Ile Tyr Glu Thr Leu Asn Thr Cys Asn
                100                 105                 110

Thr Glu His Tyr Thr Gly Asn Ile Leu Asn Phe Ser Asp Thr Tyr Tyr
            115                 120                 125

Arg Arg Phe Gly Tyr Val Ala Ser Ala Ile Ser Asn Tyr Val Thr Lys
        130                 135                 140

Ile Ser Lys Met Ser Thr Gly Ser Arg Ser Lys Asn Ile Ser Asn Asp
145                 150                 155                 160

Ser Asp Val Asp Thr Ile Met Glu Gln Val Ile Tyr Glu Met Glu His
                165                 170                 175
```

```
Asn Gly Trp Thr Ser Val Lys Asp Trp Glu Asn Gln Met Glu Tyr Leu
            180                 185                 190

Glu Ser Lys Thr Asp Ser Asn Pro Asn Phe Val Tyr Arg Met Thr Thr
            195                 200                 205

Leu Tyr Glu Phe Tyr Lys Ser His Ile Asp Glu Val Asn Ser Lys Met
            210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
                245                 250                 255

Phe Asp Ile Thr Gln Ile Gly Gly Asn Ser Leu Asn Ile Lys Phe Ser
            260                 265                 270

Lys Asn Leu Asn Val Asp Val Phe Gly Arg Tyr Asp Val Ile Lys Asp
            275                 280                 285

Asn Thr Leu Leu Val Asp Ile Ile Asn Gly His Gly Ala Ser Phe Val
            290                 295                 300

Leu Lys Ile Ile Asn Asp Glu Ile Tyr Ile Asp Ile Asn Val Ser Val
305                 310                 315                 320

Pro Phe Asp Lys Lys Ile Ala Thr Thr Asn Lys Val Val Gly Ile Asp
                325                 330                 335

Val Asn Ile Lys His Met Leu Leu Ala Thr Asn Ile Leu Asp Asp Gly
            340                 345                 350

Asn Val Lys Gly Tyr Val Asn Ile Tyr Lys Glu Val Ile Asn Asp Ser
            355                 360                 365

Asp Phe Lys Lys Val Cys Asn Ser Thr Val Met Gln Tyr Phe Thr Asp
            370                 375                 380

Phe Ser Lys Phe Val Thr Phe Cys Pro Leu Glu Phe Asp Phe Leu Phe
385                 390                 395                 400

Ser Arg Val Cys Asn Gln Lys Gly Ile Tyr Asn Asp Asn Ser Ala Met
                405                 410                 415

Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
            435                 440                 445

Leu Arg Ser Gln Met Lys Ala Tyr Ala Ile Val Lys Asn Ala Tyr Tyr
450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu Asn Lys
                485                 490                 495

Leu Asp Asn Ile Ser Lys Lys Ile Leu Gly Cys Arg Asn Asn Ile Ile
            500                 505                 510

Gln Tyr Ser Tyr Asn Leu Phe Glu Ile Asn Gly Tyr Asp Met Val Ser
            515                 520                 525

Leu Glu Lys Leu Thr Ser Ser Gln Phe Lys Lys Pro Phe Pro Thr
            530                 535                 540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
                565                 570                 575

Asp Ile Ile Phe Asp Asn Asp Val Val Thr Asp Ala Lys Leu Ser Ala
            580                 585                 590
```

-continued

```
Lys Gly Glu Leu Ser Lys Phe Lys Asp Asp Phe Phe Asn Leu Met Ile
        595                 600                 605

Lys Ser Ile His Phe Ala Asp Ile Lys Asp Tyr Phe Ile Thr Leu Ser
        610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
                645                 650                 655

Ser Gly Lys Leu Lys Leu Ala Asn Lys His Lys Val Arg Ser Ser Gln
        660                 665                 670

Glu Lys His Ile Asn Gly Leu Asn Ala Asp Tyr Asn Ala Ala Arg Asn
        675                 680                 685

Ile Ala Tyr Ile Met Glu Asn Thr Asp Cys Arg Asn Met Phe Met Lys
        690                 695                 700

Gln Ser Arg Thr Asp Lys Ser Leu Tyr Asn Lys Pro Ser Tyr Glu Thr
705                 710                 715                 720

Phe Ile Lys Thr Gln Gly Ser Ala Val Ala Lys Leu Lys Lys Glu Gly
                725                 730                 735

Phe Val Lys Ile Leu Asp Glu Ala Ser Val
                740                 745
```

```
<210> SEQ ID NO 103
<211> LENGTH: 735
<212> TYPE: PRT
<213> ORGANISM: Artificial sequence
<220> FEATURE:
<223> OTHER INFORMATION: synthetic sequence

<400> SEQUENCE: 103
```

```
Met Ala His Lys Lys Asn Val Gly Ala Glu Ile Val Lys Thr Tyr Ser
1                 5                   10                  15

Phe Lys Val Lys Asn Thr Asn Gly Ile Thr Met Glu Lys Leu Met Asn
                20                  25                  30

Ala Ile Asp Glu Phe Gln Ser Tyr Tyr Asn Leu Cys Ser Asp Trp Ile
        35                  40                  45

Cys Lys Asn Leu Thr Thr Met Thr Ile Gly Asp Leu Asp Gln Tyr Ile
        50                  55                  60

Pro Glu Lys Ala Lys Gly Asn Thr Tyr Ala Thr Val Leu Leu Asp Glu
65                  70                  75                  80

Ala Trp Lys Asn Gln Pro Leu Tyr Lys Ile Phe Gly Lys Lys Tyr Ser
                85                  90                  95

Ser Asn Asn Arg Asn Asn Ala Leu Tyr Cys Ala Leu Ser Ser Val Ile
                100                 105                 110

Asp Met Thr Lys Glu Asn Val Leu Gly Phe Ser Lys Thr His Tyr Ile
        115                 120                 125

Arg Asn Asp Tyr Ile Leu Asn Val Ile Ser Asn Tyr Ala Ser Lys Leu
        130                 135                 140

Ser Lys Leu Asn Thr Gly Val Lys Ser Arg Ala Ile Lys Glu Thr Ser
145                 150                 155                 160

Asp Glu Ala Thr Ile Ile Glu Gln Val Ile Tyr Glu Met Glu His Asn
                165                 170                 175

Lys Trp Glu Ser Ile Glu Asp Trp Lys Asn Gln Ile Glu Tyr Leu Asn
                180                 185                 190

Ser Lys Thr Asp Tyr Asn Pro Thr Tyr Met Glu Arg Met Lys Thr Leu
        195                 200                 205
```

-continued

```
Ser Ala Tyr Tyr Ser Thr His Lys Ser Glu Val Asp Ala Lys Met Gln
    210             215             220

Glu Met Ala Val Glu Asn Leu Val Lys Phe Gly Gly Cys Arg Arg Asn
225             230             235             240

Asn Ser Lys Lys Ser Met Phe Ile Met Gly Ser Asn Thr Thr Asn Tyr
            245             250             255

Thr Ile Ser Tyr Ile Gly Gly Asn Ser Phe Asn Ile Asn Phe Ala Asn
            260             265             270

Ile Leu Asn Phe Asp Val Tyr Gly Arg Arg Asp Val Val Lys Asn Gly
            275             280             285

Glu Val Leu Val Asp Ile Met Ala Asn His Gly Asp Ser Ile Val Leu
    290             295             300

Lys Ile Val Asn Gly Glu Leu Tyr Ala Asp Val Pro Cys Ser Val Thr
305             310             315             320

Leu Asn Lys Val Glu Ser Asn Phe Asp Lys Val Val Gly Ile Asp Val
            325             330             335

Asn Met Lys His Met Leu Leu Ser Thr Ser Ile Thr Asp Asn Gly Ser
            340             345             350

Ser Asp Phe Leu Asn Ile Tyr Lys Glu Met Ser Asn Asn Ala Glu Phe
            355             360             365

Met Ala Leu Cys Pro Glu Glu Asp Arg Lys Tyr Tyr Lys Asp Ile Ser
    370             375             380

Lys Tyr Val Thr Phe Ala Pro Leu Glu Leu Asp Leu Leu Phe Ser Arg
385             390             395             400

Ile Ser Lys Gln Gly Lys Val Lys Met Glu Lys Val Tyr Ser Glu Ile
            405             410             415

Leu Glu Ala Leu Lys Trp Lys Phe Phe Ala Asn Gly Asp Asn Lys Asn
            420             425             430

Arg Ile Tyr Val Glu Ser Ile Gln Lys Ile Arg Gln Gln Ile Lys Ala
            435             440             445

Leu Cys Val Ile Lys Asn Ala Tyr Tyr Glu Gln Gln Ser Ala Tyr Asp
    450             455             460

Ile Asp Lys Thr Gln Glu Tyr Ile Glu Thr His Pro Phe Ser Leu Thr
465             470             475             480

Glu Lys Gly Met Ser Ile Lys Ser Lys Met Asp Lys Ile Cys Gln Thr
            485             490             495

Ile Ile Gly Cys Arg Asn Asn Ile Ile Asp Tyr Ala Tyr Ser Phe Phe
            500             505             510

Glu Arg Asn Gly Tyr Ser Ile Ile Gly Leu Glu Lys Leu Thr Ser Ser
            515             520             525

Gln Phe Glu Lys Thr Lys Ser Met Pro Thr Cys Lys Ser Leu Leu Asn
    530             535             540

Phe His Lys Val Leu Gly His Thr Leu Ser Glu Leu Glu Thr Leu Pro
545             550             555             560

Ile Asn Asp Val Val Lys Lys Gly Tyr Tyr Thr Phe Thr Thr Asp Asn
            565             570             575

Glu Gly Lys Ile Thr Asp Ala Ser Leu Ser Glu Lys Gly Lys Val Arg
            580             585             590

Lys Met Lys Asp Asp Phe Phe Asn Gln Ala Ile Lys Ala Ile His Phe
            595             600             605

Ala Asp Val Lys Asp Tyr Phe Ala Thr Leu Ser Asn Asn Gly Gln Thr
    610             615             620

Gly Ile Phe Phe Val Pro Ser Gln Phe Thr Ser Gln Met Asp Ser Asn
```

-continued

```
625                 630                 635                 640
Thr His Asn Leu Tyr Phe Glu Asn Ala Lys Asn Gly Gly Leu Lys Leu
                645                 650                 655

Ala Pro Lys Tyr Lys Val Arg Gln Thr Gln Glu Tyr His Leu Asn Gly
                660                 665                 670

Leu Pro Ala Asp Tyr Asn Ala Ala Arg Asn Ile Ala Tyr Ile Gly Leu
                675                 680                 685

Asp Glu Thr Met Arg Asn Thr Phe Leu Lys Lys Ala Asn Ser Asn Lys
                690                 695                 700

Ser Leu Tyr Asn Gln Pro Ile Tyr Asp Thr Gly Ile Lys Lys Thr Ala
705                 710                 715                 720

Gly Val Phe Ser Arg Met Lys Lys Leu Lys Arg Tyr Glu Ile Ile
                725                 730                 735
```

<210> SEQ ID NO 104
<211> LENGTH: 778
<212> TYPE: PRT
<213> ORGANISM: Artificial sequence
<220> FEATURE:
<223> OTHER INFORMATION: synthetic sequence

<400> SEQUENCE: 104

```
Met Arg Ile Ser Pro His Leu Phe Tyr Ile Phe Phe Lys Lys Ile Trp
1               5                   10                  15

Lys Cys His Phe Phe Val Leu Ser Leu Tyr Gln Leu Asn Gln Tyr Ile
                20                  25                  30

Met Ala Ser His Glu Lys Thr Glu Ser Asn Gln Ile Ile Lys Thr Phe
            35                  40                  45

Ser Phe Lys Ile Lys Asn Ala Asn Gly Leu Ser Leu Asp Val Leu Asn
        50                  55                  60

Asp Ala Ile Thr Glu Tyr Gln Asn Tyr Tyr Asn Ile Cys Ser Asp Trp
65                  70                  75                  80

Ile Lys Asp His Leu Thr Met Lys Ile Gly Glu Leu Tyr Lys Tyr Ile
                85                  90                  95

Pro Asp Glu Lys Lys Asn Ser Gly Tyr Ala Leu Thr Leu Ile Ser Asp
            100                 105                 110

Glu Trp Lys Asp Lys Pro Met Tyr Met Met Phe Lys Lys Gly Tyr Pro
        115                 120                 125

Ala Asn Asn Arg Asp Asn Ala Ile Tyr Glu Thr Leu Asn Thr Cys Asn
        130                 135                 140

Thr Glu His Tyr Thr Gly Asn Ile Leu Asn Phe Ser Asp Thr Tyr Tyr
145                 150                 155                 160

Arg Arg Phe Gly Tyr Val Ala Ser Ala Ile Ser Asn Tyr Val Thr Lys
                165                 170                 175

Ile Ser Lys Met Ser Thr Gly Ser Arg Ser Lys Asn Ile Ser Asn Asp
            180                 185                 190

Ser Asp Val Asp Thr Ile Met Glu Gln Val Ile Tyr Glu Met Glu His
        195                 200                 205

Asn Gly Trp Thr Ser Val Lys Asp Trp Glu Asn Gln Met Glu Tyr Leu
        210                 215                 220

Glu Ser Lys Thr Asp Ser Asn Pro Asn Phe Val Tyr Arg Met Thr Thr
225                 230                 235                 240

Leu Tyr Glu Phe Tyr Lys Ser His Ile Asp Glu Val Asn Ser Lys Met
                245                 250                 255

Glu Thr Met Ser Ile Asp Ser Leu Ile Lys Phe Gly Gly Cys Arg Arg
```

-continued

```
                260                 265                 270
Lys Asp Ser Lys Lys Ser Met Tyr Ile Met Gly Gly Ser Asn Thr Pro
            275                 280                 285

Phe Asp Ile Thr Gln Ile Gly Gly Asn Ser Leu Asn Ile Lys Phe Ser
            290                 295                 300

Lys Asn Leu Asn Val Asp Val Phe Gly Arg Tyr Asp Val Ile Lys Asp
305                 310                 315                 320

Asn Thr Leu Leu Val Asp Ile Ile Asn Gly His Gly Ala Ser Phe Val
                325                 330                 335

Leu Lys Ile Ile Asn Gly Glu Ile Tyr Ile Asp Ile Asn Val Ser Val
                340                 345                 350

Pro Phe Asp Lys Lys Ile Ala Thr Thr Asn Lys Val Val Gly Ile Asp
                355                 360                 365

Val Asn Ile Lys His Met Leu Leu Ala Thr Asn Ile Leu Asp Asp Gly
            370                 375                 380

Asn Val Asn Gly Tyr Val Asn Ile Tyr Lys Glu Val Ile Asn Asp Ser
385                 390                 395                 400

Asp Phe Lys Lys Val Cys Asn Ser Thr Val Met Lys Tyr Phe Thr Asp
                405                 410                 415

Phe Ser Lys Phe Val Thr Phe Cys Pro Leu Glu Phe Asp Phe Leu Phe
                420                 425                 430

Ser Arg Val Cys Asn Gln Lys Gly Ile Tyr Asn Asp Asn Ser Ala Met
            435                 440                 445

Glu Lys Ser Phe Ser Asp Val Leu Asn Lys Leu Lys Trp Asn Phe Ile
            450                 455                 460

Glu Thr Gly Asp Asn Thr Lys Arg Ile Tyr Ile Glu Asn Val Met Lys
465                 470                 475                 480

Leu Arg Ser Gln Met Lys Ala Tyr Ala Ile Val Lys Asn Ala Tyr Tyr
                485                 490                 495

Lys Gln Gln Ser Glu Tyr Asp Phe Gly Lys Ser Glu Glu Phe Ile Gln
                500                 505                 510

Glu His Pro Phe Ser Asn Thr Asp Lys Gly Ile Glu Ile Leu Asn Lys
            515                 520                 525

Leu Asp Asn Ile Ser Lys Lys Ile Leu Gly Cys Arg Asn Asn Ile Ile
            530                 535                 540

Gln Tyr Ser Tyr Asn Leu Phe Glu Ile Asn Gly Tyr Asp Met Ile Ser
545                 550                 555                 560

Leu Glu Lys Leu Thr Ser Ser Gln Phe Lys Lys Pro Phe Pro Thr
                565                 570                 575

Val Asn Ser Leu Leu Lys Tyr His Lys Ile Leu Gly Cys Thr Gln Glu
            580                 585                 590

Glu Met Glu Lys Lys Asp Ile Tyr Ser Val Ile Lys Lys Gly Tyr Tyr
                595                 600                 605

Asp Ile Ile Phe Asp Asn Asp Val Val Thr Asp Ala Lys Leu Ser Thr
            610                 615                 620

Lys Gly Glu Leu Ser Lys Phe Lys Asp Asp Phe Phe Asn Leu Met Ile
625                 630                 635                 640

Lys Ser Ile His Phe Ala Asp Ile Lys Asp Tyr Phe Ile Thr Leu Ser
                645                 650                 655

Asn Asn Gly Thr Ala Gly Val Ser Leu Val Pro Ser Tyr Phe Thr Ser
                660                 665                 670

Gln Met Asp Ser Ile Asp His Lys Ile Tyr Phe Val Gln Asp Asn Lys
                675                 680                 685
```

-continued

```
Ser Gly Lys Leu Lys Leu Ala Asn Lys His Lys Val Arg Ser Ser Gln
    690             695             700

Glu Lys His Ile Asn Gly Leu Asn Ala Asp Tyr Asn Ala Ala Arg Asn
705             710             715             720

Ile Ala Tyr Ile Met Glu Asn Thr Glu Cys Arg Asn Met Phe Met Lys
            725             730             735

Gln Ser Arg Thr Asp Lys Ser Leu Tyr Asn Lys Pro Ser Tyr Glu Thr
            740             745             750

Phe Ile Lys Thr Gln Gly Ser Ala Val Ala Lys Leu Lys Lys Glu Gly
        755             760             765

Phe Val Lys Ile Leu Asp Glu Ala Ser Val
    770             775

<210> SEQ ID NO 105
<211> LENGTH: 778
<212> TYPE: PRT
<213> ORGANISM: Artificial sequence
<220> FEATURE:
<223> OTHER INFORMATION: synthetic sequence

<400> SEQUENCE: 105

Met Arg Ile Ser Pro His Leu Phe Tyr Ile Phe Phe Lys Lys Ile Trp
1               5               10              15

Lys Ser His Phe Phe Val Leu Ser Leu Tyr Gln Leu Asn Gln Tyr Ile
            20              25              30

Met Ala Ser His Lys Lys Thr Glu Ser Asn Gln Ile Ile Lys Thr Phe
            35              40              45

Ser Phe Lys Ile Lys Asn Ala Asn Gly Leu Ser Leu Asp Val Leu Asn
    50              55              60

Asp Ala Ile Thr Glu Tyr Gln Asn Tyr Tyr Asn Ile Cys Ser Asp Trp
65              70              75              80

Ile Lys Asp His Leu Thr Met Lys Ile Gly Glu Leu Tyr Lys Tyr Ile
            85              90              95

Pro Asp Glu Lys Lys Asn Ser Gly Tyr Ala Leu Thr Leu Ile Ser Asp
            100             105             110

Glu Trp Lys Asp Lys Pro Met Tyr Met Met Phe Lys Lys Gly Tyr Pro
        115             120             125

Ala Asn Asn Arg Asp Asn Ala Ile Tyr Glu Thr Leu Asn Thr Cys Asn
    130             135             140

Thr Glu His Tyr Thr Gly Asn Ile Leu Asn Phe Pro Asp Thr Tyr Tyr
145             150             155             160

Arg Arg Phe Gly Tyr Val Ala Ser Thr Ile Ser Asn Tyr Val Thr Lys
            165             170             175

Ile Ser Lys Met Ser Thr Gly Ser Arg Ser Lys Asn Ile Ser Asn Asp
            180             185             190

Ser Asp Val Asp Thr Ile Met Glu Gln Val Ile Tyr Glu Met Glu His
            195             200             205

Asn Gly Trp Thr Ser Val Lys Asp Trp Glu Asn Gln Met Glu Tyr Leu
    210             215             220

Glu Ser Lys Thr Asp Ser Asn Pro Asn Phe Val Tyr Arg Met Thr Thr
225             230             235             240

Leu Tyr Glu Phe Tyr Lys Ser His Ile Asp Glu Val Asn Ser Lys Met
            245             250             255

Glu Thr Met Ser Ile Asp Ser Leu Ile Lys Phe Gly Gly Cys Arg Arg
            260             265             270
```

-continued

```
Lys Asp Ser Lys Lys Ser Met Tyr Ile Met Gly Gly Ser Asn Thr Pro
        275                 280                 285

Phe Asp Ile Thr Gln Ile Gly Gly Asn Ser Leu Asn Ile Lys Phe Ser
        290                 295                 300

Lys Asn Leu Asn Val Asp Val Phe Gly Arg Tyr Asp Val Ile Lys Asp
305                 310                 315                 320

Asn Thr Leu Leu Val Asp Ile Ile Asn Gly His Gly Ala Ser Phe Val
                325                 330                 335

Leu Lys Ile Ile Asn Gly Glu Ile Tyr Ile Asp Ile Asn Val Ser Val
                340                 345                 350

Pro Phe Asp Lys Lys Ile Ala Thr Thr Asn Lys Val Val Gly Ile Asp
        355                 360                 365

Val Asn Ile Lys His Met Leu Leu Ala Thr Asn Ile Leu Asp Asp Gly
        370                 375                 380

Asn Val Asn Gly Tyr Val Asn Ile Tyr Lys Glu Val Ile Asn Asp Ser
385                 390                 395                 400

Asp Phe Lys Lys Val Cys Asn Ser Thr Val Met Lys Tyr Phe Thr Asp
                405                 410                 415

Phe Ser Lys Phe Val Thr Phe Cys Pro Leu Glu Phe Asp Phe Leu Phe
                420                 425                 430

Ser Arg Val Cys Asn Gln Lys Gly Ile Tyr Asn Asp Asn Ser Ala Met
                435                 440                 445

Glu Lys Ser Phe Ser Asp Val Leu Asn Lys Leu Lys Trp Asn Phe Ile
        450                 455                 460

Glu Thr Gly Asp Asn Thr Lys Arg Ile Tyr Ile Glu Asn Val Met Lys
465                 470                 475                 480

Leu Arg Ser Gln Met Lys Ala Tyr Ala Ile Val Lys Asn Ala Tyr Tyr
                485                 490                 495

Lys Gln Gln Ser Glu Tyr Asp Phe Gly Lys Ser Glu Glu Phe Ile Gln
                500                 505                 510

Glu His Pro Phe Ser Asn Thr Asp Lys Gly Ile Glu Ile Leu Asn Lys
        515                 520                 525

Leu Asp Asn Ile Ser Lys Lys Ile Leu Gly Cys Arg Asn Asn Ile Ile
        530                 535                 540

Gln Tyr Ser Tyr Asn Leu Phe Glu Ile Asn Gly Tyr Asp Met Ile Ser
545                 550                 555                 560

Leu Glu Lys Leu Thr Ser Ser Gln Phe Lys Lys Asn Pro Phe Pro Thr
                565                 570                 575

Val Asn Ser Leu Leu Lys Tyr His Lys Ile Leu Gly Cys Thr Gln Glu
                580                 585                 590

Glu Met Glu Lys Lys Asp Ile Tyr Ser Val Ile Lys Lys Gly Tyr Tyr
                595                 600                 605

Asp Ile Ile Phe Asp Asn Asp Val Val Thr Asp Ala Lys Leu Ser Thr
        610                 615                 620

Lys Gly Glu Leu Ser Lys Phe Lys Asp Asp Phe Phe Asn Leu Met Ile
625                 630                 635                 640

Lys Ser Ile His Phe Ala Asp Ile Lys Asp Tyr Phe Ile Thr Leu Ser
                645                 650                 655

Asn Asn Gly Thr Ala Gly Val Ser Leu Val Pro Ser Tyr Phe Thr Ser
                660                 665                 670

Gln Met Asp Ser Ile Asp His Lys Ile Tyr Phe Val Gln Asp Asn Lys
        675                 680                 685
```

```
Ser Gly Lys Leu Lys Leu Ala Asn Lys His Lys Val Arg Ser Ser Gln
    690             695             700

Glu Lys His Ile Asn Gly Leu Asn Ala Asp Tyr Asn Ala Ala Arg Asn
705             710             715             720

Ile Ala Tyr Ile Met Glu Asn Thr Glu Cys Arg Asn Met Phe Met Lys
            725             730             735

Gln Ser Arg Thr Asp Lys Ser Leu Tyr Asn Lys Pro Ser Tyr Glu Thr
            740             745             750

Phe Ile Lys Thr Gln Gly Ser Ala Val Ala Lys Leu Lys Lys Glu Gly
        755             760             765

Phe Val Lys Ile Leu Asp Glu Ala Ser Val
    770             775
```

<210> SEQ ID NO 106
<211> LENGTH: 778
<212> TYPE: PRT
<213> ORGANISM: Artificial sequence
<220> FEATURE:
<223> OTHER INFORMATION: synthetic sequence

<400> SEQUENCE: 106

```
Met Arg Ile Ser Pro His Leu Phe Tyr Ile Phe Phe Lys Lys Ile Trp
1               5               10              15

Lys Cys His Ile Phe Val Leu Ser Leu Tyr Gln Leu Asn Gln Tyr Ile
            20              25              30

Met Ala Ser His Lys Lys Thr Glu Ser Asn Gln Ile Ile Lys Thr Phe
        35              40              45

Ser Phe Lys Ile Lys Asn Ala Asn Gly Leu Ser Leu Asp Val Leu Asn
    50              55              60

Asp Ala Ile Thr Glu Tyr Gln Asn Tyr Tyr Asn Ile Cys Ser Asp Trp
65              70              75              80

Ile Lys Asp His Leu Thr Met Lys Ile Gly Glu Leu Tyr Lys Tyr Ile
            85              90              95

Pro Asp Glu Lys Lys Asn Ser Gly Tyr Ala Leu Thr Leu Ile Ser Asp
            100             105             110

Glu Trp Lys Asp Lys Pro Met Tyr Met Met Phe Lys Lys Gly Tyr Pro
        115             120             125

Ala Asn Asn Arg Asp Asn Ala Ile Tyr Glu Thr Leu Asn Thr Cys Asn
    130             135             140

Thr Glu His Tyr Thr Gly Asn Ile Leu Asn Phe Ser Asp Thr Tyr Tyr
145             150             155             160

Arg Arg Phe Gly Tyr Val Ala Ser Thr Ile Ser Asn Tyr Val Thr Lys
            165             170             175

Ile Ser Lys Met Ser Thr Gly Ser Arg Ser Lys Asn Ile Ser Asn Asp
        180             185             190

Ser Asp Val Asp Thr Ile Met Glu Gln Val Ile Tyr Glu Met Glu His
    195             200             205

Asn Gly Trp Thr Ser Val Lys Asp Trp Glu Asn Gln Met Glu Tyr Leu
    210             215             220

Glu Ser Lys Thr Asp Ser Asn Pro Asn Phe Val Tyr Arg Met Thr Thr
225             230             235             240

Leu Tyr Glu Phe Tyr Lys Ser His Ile Asp Glu Val Asn Ser Lys Met
            245             250             255

Glu Thr Met Ser Ile Asp Ser Leu Ile Lys Phe Gly Gly Cys Arg Arg
        260             265             270
```

-continued

```
Lys Asp Ser Lys Lys Ser Met Tyr Ile Met Gly Gly Ser Asn Thr Pro
        275             280             285

Phe Asp Ile Thr Gln Ile Gly Gly Asn Ser Leu Asn Ile Lys Phe Ser
        290             295             300

Lys Asn Leu Asn Val Asp Val Phe Gly Arg Tyr Asp Val Ile Lys Asp
305             310             315             320

Asn Thr Leu Leu Val Asp Ile Ile Asn Gly His Gly Ala Ser Phe Val
            325             330             335

Leu Lys Ile Ile Asn Gly Glu Ile Tyr Ile Asp Ile Asn Val Ser Val
            340             345             350

Pro Phe Asp Lys Lys Ile Ala Thr Thr Asn Lys Val Val Gly Val Asp
        355             360             365

Val Asn Ile Lys His Met Leu Leu Ala Thr Asn Ile Leu Asp Asp Gly
    370             375             380

Asn Val Asn Gly Tyr Val Asn Ile Tyr Lys Glu Val Ile Asn Asp Ser
385             390             395             400

Asp Phe Lys Lys Val Cys Asn Ser Thr Val Met Lys Tyr Phe Thr Asp
            405             410             415

Phe Ser Lys Phe Val Thr Phe Cys Pro Leu Glu Phe Asp Phe Leu Phe
            420             425             430

Ser Arg Val Cys Asn Gln Lys Gly Ile Tyr Asn Asp Asn Ser Ala Met
            435             440             445

Glu Lys Ser Phe Ser Asp Val Leu Asn Lys Leu Lys Trp Asn Phe Ile
        450             455             460

Glu Thr Gly Asp Asn Thr Lys Arg Ile Tyr Ile Glu Asn Val Met Lys
465             470             475             480

Leu Arg Ser Gln Met Lys Ala Tyr Ala Ile Val Lys Asn Ala Tyr Tyr
            485             490             495

Lys Gln Gln Ser Glu Tyr Asp Phe Gly Lys Ser Glu Glu Phe Ile Gln
            500             505             510

Glu His Pro Phe Ser Asn Thr Asp Lys Gly Ile Glu Ile Leu Asn Lys
        515             520             525

Leu Asp Asn Ile Ser Lys Lys Ile Leu Gly Cys Arg Asn Asn Ile Ile
        530             535             540

Gln Tyr Ser Tyr Asn Leu Phe Glu Ile Asn Gly Tyr Asp Met Ile Ser
545             550             555             560

Leu Glu Lys Leu Thr Ser Ser Gln Phe Lys Lys Pro Phe Pro Thr
            565             570             575

Val Asn Ser Leu Leu Lys Tyr His Lys Ile Leu Gly Cys Thr Gln Glu
        580             585             590

Glu Met Glu Lys Lys Asp Ile Tyr Ser Val Ile Lys Lys Gly Tyr Tyr
        595             600             605

Asp Ile Ile Phe Asp Asn Asp Val Val Thr Asp Ala Lys Leu Ser Thr
        610             615             620

Lys Gly Glu Leu Ser Lys Phe Lys Asp Asp Phe Phe Asn Leu Met Ile
625             630             635             640

Lys Ser Ile His Phe Ala Asp Ile Lys Asp Tyr Phe Ile Thr Leu Ser
            645             650             655

Asn Asn Gly Thr Ala Gly Val Ser Leu Val Pro Ser Tyr Phe Thr Ser
            660             665             670

Gln Met Asp Ser Ile Asp His Lys Ile Tyr Phe Val Gln Asp Asn Lys
        675             680             685

Ser Gly Lys Leu Lys Leu Ala Asn Lys His Lys Val Arg Ser Ser Gln
```

-continued

```
            690               695               700
Glu Lys His Ile Asn Gly Leu Asn Ala Asp Tyr Asn Ala Ala Arg Asn
705                 710               715                 720

Ile Ala Tyr Ile Met Glu Asn Thr Asp Cys Arg Asn Met Phe Met Lys
                725               730               735

Gln Ser Arg Thr Asp Lys Ser Leu Tyr Asn Lys Pro Ser Tyr Glu Thr
                740               745               750

Phe Ile Lys Thr Gln Gly Ser Ala Val Ala Lys Leu Lys Lys Glu Gly
            755               760               765

Phe Val Lys Ile Leu Asp Glu Ala Ser Val
            770               775

<210> SEQ ID NO 107
<211> LENGTH: 351
<212> TYPE: PRT
<213> ORGANISM: Artificial sequence
<220> FEATURE:
<223> OTHER INFORMATION: synthetic sequence

<400> SEQUENCE: 107

Gln Tyr Val Thr Phe Ala Pro Leu Glu Leu Asp Leu Leu Phe Ser Arg
1               5                   10                  15

Ile Ser Lys Gln Gly Lys Val Lys Met Glu Lys Ala Tyr Ser Glu Ile
                20                  25                  30

Leu Glu Ala Leu Lys Trp Lys Phe Phe Ala Asn Gly Asp Asn Lys Asn
            35                  40                  45

Arg Ile Tyr Val Glu Ser Ile Gln Lys Ile Arg Gln Gln Ile Lys Ala
    50                  55                  60

Leu Cys Val Ile Lys Asn Ala Tyr Tyr Glu Gln Gln Ser Ala Tyr Asp
65                  70                  75                  80

Ile Asp Lys Thr Gln Glu Tyr Ile Glu Thr His Pro Phe Ser Leu Thr
                85                  90                  95

Glu Lys Gly Met Ser Ile Lys Ser Lys Met Asp Lys Ile Cys Gln Thr
                100                 105                 110

Ile Ile Gly Cys Arg Asn Asn Ile Ile Asp Tyr Ala Tyr Ser Phe Phe
            115                 120                 125

Glu Arg Asn Gly Tyr Thr Ile Ile Gly Leu Glu Lys Leu Thr Ser Ser
    130                 135                 140

Gln Phe Glu Lys Thr Lys Ser Met Pro Thr Cys Lys Ser Leu Leu Asn
145                 150                 155                 160

Phe His Lys Val Leu Gly His Thr Leu Ser Glu Leu Glu Thr Leu Pro
                165                 170                 175

Ile Asn Asp Val Val Lys Lys Gly Tyr Tyr Ala Phe Thr Thr Asp Asn
                180                 185                 190

Glu Gly Arg Ile Thr Asp Ala Ser Leu Ser Glu Lys Gly Lys Val Arg
            195                 200                 205

Lys Met Lys Asp Asp Phe Phe Asn Gln Ala Ile Lys Ala Ile His Phe
    210                 215                 220

Ala Asp Val Lys Asp Tyr Phe Ala Thr Leu Ser Asn Asn Gly Gln Thr
225                 230                 235                 240

Gly Ile Phe Phe Val Pro Ser Gln Phe Thr Ser Gln Met Asp Ser Asn
                245                 250                 255

Thr His Asn Leu Tyr Phe Glu Asn Ala Lys Asn Gly Gly Leu Lys Leu
                260                 265                 270

Ala Ser Lys Ser Lys Val Arg Lys Ser Gln Glu Tyr His Leu Asn Gly
```

-continued

```
             275                 280                 285

Leu Pro Ala Asp Tyr Asn Ala Ala Arg Asn Ile Ala Tyr Ile Gly Leu
    290                 295                 300

Asp Glu Ile Met Arg Asn Thr Phe Leu Lys Lys Ala Asn Ser Asn Lys
305                 310                 315                 320

Ser Leu Tyr Asn Gln Pro Ile Tyr Asp Thr Gly Ile Lys Lys Thr Ala
                325                 330                 335

Gly Val Phe Ser Arg Met Lys Lys Leu Lys Lys Tyr Lys Val Ile
                340                 345                 350

<210> SEQ ID NO 108
<211> LENGTH: 717
<212> TYPE: PRT
<213> ORGANISM: Artificial sequence
<220> FEATURE:
<223> OTHER INFORMATION: synthetic sequence

<400> SEQUENCE: 108

Val Leu Asn Asp Ala Ile Thr Glu Tyr Gln Asn Tyr Tyr Asn Ile Cys
1               5                   10                  15

Ser Asp Trp Ile Lys Asp His Leu Thr Met Lys Ile Gly Glu Leu Tyr
            20                  25                  30

Lys Tyr Ile Pro Asp Glu Lys Lys Asn Ser Gly Tyr Ala Leu Thr Leu
        35                  40                  45

Ile Ser Asp Glu Trp Lys Asp Lys Pro Met Tyr Met Met Phe Lys Lys
        50                  55                  60

Gly Tyr Pro Ala Asn Ser Arg Asp Asn Ala Ile Tyr Glu Ala Leu Asn
65                  70                  75                  80

Thr Cys Asn Thr Glu His Tyr Thr Gly Asn Ile Leu Asn Phe Ser Asp
                85                  90                  95

Thr Tyr Tyr Arg Arg Phe Gly Tyr Val Ala Ser Ala Ile Ser Asn Tyr
            100                 105                 110

Val Thr Lys Ile Ser Lys Met Ser Thr Gly Ser Arg Ser Lys Asn Ile
        115                 120                 125

Ser Asn Asp Ser Asp Val Asp Thr Ile Met Glu Gln Val Ile Tyr Glu
    130                 135                 140

Met Glu His Asn Gly Trp Thr Ser Val Lys Asp Trp Glu Asn Gln Met
145                 150                 155                 160

Glu Tyr Leu Glu Ser Lys Thr Asp Ser Asn Pro Asn Phe Val Tyr Arg
            165                 170                 175

Met Thr Thr Leu Tyr Glu Phe Tyr Lys Ser His Ile Asp Glu Val Asn
            180                 185                 190

Ser Lys Met Glu Thr Met Ser Ile Asp Ser Leu Ile Lys Phe Gly Gly
        195                 200                 205

Cys Arg Arg Lys Asp Ser Lys Lys Ser Met Tyr Ile Met Gly Gly Ser
    210                 215                 220

Asn Thr Pro Phe Asp Ile Thr Gln Ile Gly Gly Asn Ser Leu Asn Ile
225                 230                 235                 240

Lys Phe Ser Lys Asn Leu Asn Val Asp Val Phe Gly Arg Tyr Asp Val
            245                 250                 255

Ile Lys Asp Asn Thr Leu Leu Val Asp Ile Ile Asn Gly His Gly Ala
            260                 265                 270

Ser Phe Val Leu Lys Ile Ile Asn Asp Glu Ile Tyr Ile Asp Ile Asn
        275                 280                 285

Val Ser Val Pro Phe Asp Lys Lys Ile Ala Thr Thr Asn Lys Val Val
```

-continued

```
     290                 295                 300

Gly Ile Asp Val Asn Ile Lys His Met Leu Leu Ala Thr Asn Ile Leu
305                 310                 315                 320

Asp Asp Gly Asn Val Asn Gly Tyr Val Asn Ile Tyr Lys Glu Val Ile
                325                 330                 335

Asn Asp Ser Asp Phe Lys Lys Val Cys Asn Ser Thr Val Met Lys Tyr
                340                 345                 350

Phe Thr Asp Phe Ser Lys Phe Val Thr Phe Cys Pro Leu Glu Phe Asp
                355                 360                 365

Phe Leu Phe Ser Arg Val Cys Asn Gln Lys Gly Ile Tyr Asn Asp Asn
        370                 375                 380

Ser Ala Met Glu Lys Ser Phe Ser Asn Val Leu Asn Lys Leu Lys Trp
385                 390                 395                 400

Asn Phe Ile Glu Thr Gly Asp Asn Thr Lys Arg Ile Tyr Ile Glu Asn
                405                 410                 415

Val Met Lys Leu Arg Ser Gln Met Lys Ala Tyr Ala Ile Val Lys Asn
                420                 425                 430

Ala Tyr Tyr Lys Gln Gln Ser Glu Tyr Asp Phe Gly Lys Ser Glu Glu
                435                 440                 445

Phe Ile Gln Glu His Pro Phe Ser Asn Thr Asp Lys Gly Ile Glu Ile
        450                 455                 460

Leu His Lys Leu Asp Asn Ile Ser Lys Lys Ile Leu Gly Cys Arg Asn
465                 470                 475                 480

Asn Ile Ile Gln Tyr Ser Tyr Asn Leu Phe Glu Ile Asn Gly Tyr Asp
                485                 490                 495

Met Ile Ser Leu Glu Lys Leu Thr Ser Ser Gln Phe Lys Lys Lys Pro
                500                 505                 510

Phe Pro Thr Val Asn Ser Leu Leu Lys Tyr His Lys Ile Leu Gly Cys
                515                 520                 525

Thr Gln Glu Glu Met Glu Lys Lys Asp Ile Tyr Ser Val Ile Lys Lys
        530                 535                 540

Gly Tyr Tyr Asp Ile Ile Phe Asp Asn Asp Val Val Thr Asp Ala Lys
545                 550                 555                 560

Leu Ser Thr Lys Gly Glu Leu Ser Lys Phe Lys Asp Asp Phe Phe Asn
                565                 570                 575

Leu Met Ile Lys Ser Ile His Phe Ala Asp Ile Lys Asp Tyr Phe Ile
                580                 585                 590

Thr Leu Ser Asn Asn Gly Thr Ala Gly Val Ser Leu Val Pro Ser Tyr
                595                 600                 605

Phe Thr Ser Gln Met Asp Ser Ile Asp His Lys Ile Tyr Phe Val Gln
        610                 615                 620

Asp Asn Lys Ser Gly Lys Leu Lys Leu Ala Asn Lys His Lys Val Arg
625                 630                 635                 640

Ser Ser Gln Glu Lys His Ile Asn Gly Leu Asn Ala Asp Tyr Asn Ala
                645                 650                 655

Ala Arg Asn Ile Ala Tyr Ile Met Glu Asn Thr Asp Cys Arg Asn Met
                660                 665                 670

Phe Met Lys Gln Ser Arg Thr Asp Lys Ser Leu Tyr Asn Lys Pro Ser
                675                 680                 685

Tyr Glu Thr Phe Ile Lys Thr Gln Gly Ser Ala Val Ala Lys Leu Lys
        690                 695                 700

Lys Glu Gly Phe Met Lys Ile Leu Asp Glu Ala Ser Val
705                 710                 715
```

```
<210> SEQ ID NO 109
<211> LENGTH: 742
<212> TYPE: PRT
<213> ORGANISM: Artificial sequence
<220> FEATURE:
<223> OTHER INFORMATION: synthetic sequence

<400> SEQUENCE: 109

Ile Phe Phe Lys Lys Ile Trp Lys Cys His Ile Phe Val Leu Ser Leu
1               5                   10                  15

Tyr Gln Leu Asn Gln Tyr Ile Met Ala Ser His Lys Lys Thr Glu Ser
            20                  25                  30

Asn Gln Ile Ile Lys Thr Phe Ser Phe Lys Ile Lys Asn Ala Asn Gly
        35                  40                  45

Leu Ser Leu Asp Val Leu Asn Asp Ala Ile Thr Glu Tyr Gln Asn Tyr
    50                  55                  60

Tyr Asn Ile Cys Ser Asp Trp Ile Lys Asp His Leu Thr Met Lys Ile
65                  70                  75                  80

Gly Glu Leu Tyr Lys Tyr Ile Pro Asp Glu Lys Lys Asn Ser Gly Tyr
                85                  90                  95

Ala Leu Thr Leu Ile Ser Asp Glu Trp Lys Asp Lys Pro Met Tyr Met
            100                 105                 110

Met Phe Lys Lys Gly Tyr Pro Ala Asn Ser Arg Asp Asn Ala Ile Tyr
            115                 120                 125

Glu Ala Leu Asn Thr Cys Asn Thr Glu His Tyr Thr Gly Asn Ile Leu
    130                 135                 140

Asn Phe Ser Asp Thr Tyr Tyr Arg Arg Phe Gly Tyr Val Ala Ser Ala
145                 150                 155                 160

Ile Ser Asn Tyr Val Thr Lys Ile Ser Lys Met Ser Thr Gly Ser Arg
                165                 170                 175

Ser Lys Asn Ile Ser Asn Asp Ser Asp Val Asp Thr Ile Met Glu Gln
            180                 185                 190

Val Ile Tyr Glu Met Glu His Asn Gly Trp Thr Ser Val Lys Asp Trp
            195                 200                 205

Glu Asn Gln Met Glu Tyr Leu Glu Ser Lys Thr Asp Ser Asn Pro Asn
    210                 215                 220

Phe Val Tyr Arg Met Thr Thr Leu Tyr Glu Phe Tyr Lys Ser His Ile
225                 230                 235                 240

Asp Glu Val Asn Ser Lys Met Glu Thr Met Ser Ile Asp Ser Leu Ile
                245                 250                 255

Lys Phe Gly Gly Cys Arg Arg Lys Asp Ser Lys Lys Ser Met Tyr Ile
            260                 265                 270

Met Gly Gly Ser Asn Thr Pro Phe Asp Ile Thr Gln Ile Asp Gly Asn
            275                 280                 285

Ser Leu Asn Ile Lys Phe Ser Lys Asn Leu Asn Val Asp Val Phe Gly
    290                 295                 300

Arg Tyr Asp Val Ile Lys Asp Asn Thr Leu Leu Val Asp Ile Ile Asn
305                 310                 315                 320

Gly His Gly Ala Ser Phe Val Leu Lys Ile Ile Asn Asp Glu Ile Tyr
                325                 330                 335

Ile Asp Ile Asn Val Ser Val Pro Phe Asp Lys Lys Ile Ala Thr Thr
            340                 345                 350

Asn Lys Val Val Gly Val Asp Val Asn Ile Lys His Met Leu Leu Ala
            355                 360                 365
```

```
Thr Asn Ile Leu Asp Asp Gly Asn Val Asn Gly Tyr Val Asn Ile Tyr
    370             375             380

Lys Glu Val Ile Asn Asp Ser Asp Phe Lys Lys Val Cys Asn Ser Thr
385             390             395             400

Val Met Lys Tyr Phe Thr Asp Phe Ser Lys Phe Val Thr Phe Cys Pro
            405             410             415

Leu Glu Phe Asp Phe Leu Phe Ser Arg Val Cys Asn Gln Lys Gly Ile
            420             425             430

Tyr Asn Asp Asn Ser Ala Met Glu Lys Ser Phe Ser Asp Val Leu Asn
        435             440             445

Lys Leu Lys Trp Asn Phe Ile Glu Thr Gly Asp Asn Thr Lys Arg Ile
    450             455             460

Tyr Ile Glu Asn Val Met Lys Leu Arg Ser Gln Met Lys Ala Tyr Ala
465             470             475             480

Ile Val Lys Asn Ala Tyr Tyr Lys Gln Gln Ser Glu Tyr Asp Phe Gly
            485             490             495

Lys Ser Glu Glu Phe Ile Gln Glu His Pro Phe Ser Asn Thr Asp Lys
            500             505             510

Gly Ile Glu Ile Leu His Lys Leu Asp Asn Ile Ser Lys Lys Ile Leu
            515             520             525

Gly Cys Arg Asn Asn Ile Ile Gln Tyr Ser Tyr Asn Leu Phe Glu Ile
        530             535             540

Asn Gly Tyr Asp Met Ile Ser Leu Glu Lys Leu Thr Ser Ser Gln Phe
545             550             555             560

Lys Lys Lys Pro Phe Pro Thr Val Asn Ser Leu Leu Lys Tyr His Lys
            565             570             575

Ile Leu Gly Cys Thr Gln Glu Glu Met Glu Lys Lys Asp Ile Tyr Ser
            580             585             590

Val Ile Lys Lys Gly Tyr Tyr Asp Ile Ile Phe Asp Asn Asp Val Val
            595             600             605

Thr Asp Ala Lys Leu Ser Thr Lys Gly Glu Leu Ser Lys Phe Lys Asp
    610             615             620

Asp Phe Phe Asn Leu Met Ile Lys Ser Ile His Phe Ala Asp Ile Lys
625             630             635             640

Asp Tyr Phe Ile Thr Leu Ser Asn Asn Gly Thr Ala Gly Val Ser Leu
            645             650             655

Val Pro Ser Tyr Phe Thr Ser Gln Met Asp Ser Ile Asp His Lys Ile
            660             665             670

Tyr Phe Val Gln Asp Asn Lys Ser Gly Lys Leu Lys Leu Ala Asn Lys
            675             680             685

His Lys Val Arg Ser Ser Gln Glu Lys His Ile Asn Gly Leu Asn Ala
    690             695             700

Asp Tyr Asn Ala Ala Arg Asn Ile Ala Tyr Ile Met Glu Asn Thr Glu
705             710             715             720

Gln Gly Ser Ala Val Ala Lys Leu Lys Lys Glu Gly Phe Val Lys Ile
            725             730             735

Leu Asp Glu Ala Ser Val
            740
```

<210> SEQ ID NO 110
<211> LENGTH: 746
<212> TYPE: PRT
<213> ORGANISM: Artificial sequence
<220> FEATURE:

<223> OTHER INFORMATION: synthetic sequence

<400> SEQUENCE: 110

Met Ala Ser His Lys Lys Thr Glu Ser Asn Gln Ile Ile Lys Thr Phe
1               5                   10                  15

Ser Phe Lys Ile Lys Asn Ala Asn Gly Leu Ser Leu Asp Val Leu Asn
                20                  25                  30

Asp Ala Ile Thr Glu Tyr Gln Asn Tyr Tyr Asn Ile Cys Ser Asp Trp
            35                  40                  45

Ile Lys Asp His Leu Thr Met Lys Ile Gly Glu Leu Tyr Lys Tyr Ile
    50                  55                  60

Pro Asp Glu Lys Lys Asn Ser Gly Tyr Ala Leu Thr Leu Ile Ser Asp
65                  70                  75                  80

Glu Trp Lys Asp Lys Pro Met Tyr Met Met Phe Lys Lys Gly Tyr Pro
                85                  90                  95

Ala Asn Asn Arg Asp Asn Ala Ile Tyr Glu Thr Leu Asn Thr Cys Asn
                100                 105                 110

Thr Glu His Tyr Thr Gly Asn Ile Leu Asn Phe Ser Asp Thr Tyr Tyr
            115                 120                 125

Arg Arg Phe Gly Tyr Val Ala Ser Ala Ile Ser Asn Tyr Val Thr Lys
    130                 135                 140

Ile Ser Lys Met Ser Thr Gly Ser Arg Ser Lys Asn Ile Ser Asn Asp
145                 150                 155                 160

Ser Asp Val Asp Thr Ile Met Glu Gln Val Ile Tyr Glu Met Glu His
            165                 170                 175

Asn Gly Trp Thr Ser Val Lys Asp Trp Glu Asn Gln Met Glu Tyr Leu
            180                 185                 190

Glu Ser Lys Thr Asp Ser Asn Pro Asn Phe Val Tyr Arg Met Thr Thr
            195                 200                 205

Leu Tyr Glu Phe Tyr Lys Ser His Ile Asp Glu Val Asn Ser Lys Met
    210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
                245                 250                 255

Phe Asp Ile Thr Gln Ile Gly Gly Asn Ser Leu Asn Ile Lys Phe Ser
            260                 265                 270

Lys Asn Leu Asn Val Asp Val Phe Gly Arg Tyr Asp Val Ile Lys Asp
            275                 280                 285

Asn Thr Leu Leu Val Asp Ile Ile Asn Gly His Gly Ala Ser Phe Val
    290                 295                 300

Leu Lys Ile Ile Asn Gly Glu Ile Tyr Ile Asp Ile Asn Val Ser Val
305                 310                 315                 320

Pro Phe Asp Lys Lys Ile Ala Thr Thr Asn Lys Val Val Gly Val Asp
                325                 330                 335

Val Asn Ile Lys His Met Leu Leu Ala Thr Asn Ile Leu Asp Asp Gly
                340                 345                 350

Asn Val Asn Gly Tyr Val Asn Ile Tyr Lys Glu Val Ile Asn Asp Ser
            355                 360                 365

Asp Phe Lys Lys Val Cys Asn Ser Thr Val Met Lys Tyr Phe Thr Asp
    370                 375                 380

Phe Ser Lys Phe Val Thr Phe Cys Pro Leu Glu Phe Asp Phe Leu Phe
385                 390                 395                 400

-continued

```
Ser Arg Val Cys Asn Gln Lys Gly Ile Tyr Asn Asp Asn Ser Ala Met
            405                 410                 415

Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
            435                 440                 445

Leu Arg Ser Gln Met Lys Ala Tyr Ala Ile Val Lys Asn Ala Tyr Tyr
    450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu Asn Lys
                485                 490                 495

Leu Asp Asn Ile Ser Lys Lys Ile Leu Gly Cys Arg Asn Asn Ile Ile
            500                 505                 510

Gln Tyr Ser Tyr Asn Leu Phe Glu Ile Asn Gly Tyr Asp Met Ile Ser
            515                 520                 525

Leu Glu Lys Leu Thr Ser Ser Gln Phe Lys Lys Lys Pro Phe Pro Thr
    530                 535                 540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
                565                 570                 575

Asp Ile Ile Phe Asp Asn Asp Val Val Thr Asp Ala Lys Leu Ser Ala
            580                 585                 590

Lys Gly Glu Leu Ser Lys Phe Lys Asp Asp Phe Phe Asn Leu Met Ile
            595                 600                 605

Lys Ser Ile His Phe Ala Asp Ile Lys Asp Tyr Phe Ile Thr Leu Ser
    610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
                645                 650                 655

Ser Gly Lys Leu Lys Leu Ala Asn Lys His Lys Val Arg Ser Ser Gln
            660                 665                 670

Glu Lys His Ile Asn Gly Leu Asn Ala Asp Tyr Asn Ala Ala Arg Asn
            675                 680                 685

Ile Ala Tyr Ile Met Glu Asn Thr Glu Cys Arg Asn Met Phe Met Lys
    690                 695                 700

Gln Ser Arg Thr Asp Lys Ser Leu Tyr Asn Lys Pro Ser Tyr Glu Thr
705                 710                 715                 720

Phe Ile Lys Thr Gln Gly Ser Ala Val Ser Lys Leu Lys Lys Asp Gly
                725                 730                 735

Phe Val Lys Ile Leu Asp Glu Ala Ser Val
                740                 745
```

```
<210> SEQ ID NO 111
<211> LENGTH: 782
<212> TYPE: PRT
<213> ORGANISM: Artificial sequence
<220> FEATURE:
<223> OTHER INFORMATION: synthetic sequence

<400> SEQUENCE: 111

Met Met Lys Lys Met Arg Thr Asn Pro His Leu Phe Tyr Ile Cys Phe
1               5                   10                  15
```

-continued

```
Lys Lys Ile Trp Lys Cys His Phe Phe Ala Leu Ser Leu Tyr Gln Leu
            20                  25                  30

Asn Gln Tyr Ile Met Ala Ser His Lys Lys Thr Glu Ser Asn Gln Ile
            35                  40                  45

Ile Lys Thr Phe Ser Phe Lys Ile Lys Asn Ala Asn Gly Leu Ser Leu
            50                  55                  60

Asp Val Leu Asn Asp Ala Ile Thr Glu Tyr Gln Asn Tyr Tyr Asn Ile
65                  70                  75                  80

Cys Ser Asp Trp Ile Lys Asp His Leu Thr Met Lys Ile Gly Glu Leu
                85                  90                  95

Tyr Lys Tyr Ile Pro Asp Glu Lys Lys Asn Ser Gly Tyr Ala Leu Thr
            100                 105                 110

Leu Ile Ser Asp Glu Trp Lys Asp Lys Pro Met Tyr Met Met Phe Lys
            115                 120                 125

Lys Gly Tyr Pro Ala Asn Ser Arg Asp Asn Ala Ile Tyr Glu Ala Leu
            130                 135                 140

Asn Thr Cys Asn Thr Glu His Tyr Thr Gly Asn Ile Leu Asn Phe Ser
145                 150                 155                 160

Asp Thr Tyr Tyr Arg Arg Phe Gly Tyr Val Ala Ser Thr Ile Ser Asn
                165                 170                 175

Tyr Val Thr Lys Ile Ser Lys Met Ser Thr Gly Ser Arg Ser Lys Asn
            180                 185                 190

Ile Ser Asn Asp Ser Asp Val Asp Thr Ile Met Glu Gln Val Ile Tyr
            195                 200                 205

Glu Met Glu His Asn Gly Trp Thr Ser Val Lys Asp Trp Glu Asn Gln
            210                 215                 220

Met Glu Tyr Leu Glu Ser Lys Thr Asp Ser Asn Pro Asn Phe Val Tyr
225                 230                 235                 240

Arg Met Thr Thr Leu Tyr Glu Phe Tyr Lys Ser His Ile Asp Glu Val
                245                 250                 255

Asn Ser Lys Met Glu Thr Met Ser Ile Asp Ser Leu Ile Lys Phe Gly
            260                 265                 270

Gly Cys Arg Arg Lys Asp Ser Lys Lys Ser Met Tyr Ile Met Gly Gly
            275                 280                 285

Ser Asn Thr Pro Phe Asp Ile Thr Gln Ile Gly Gly Asn Ser Leu Asn
            290                 295                 300

Ile Lys Phe Ser Lys Asn Leu Asn Val Asp Val Phe Gly Arg Tyr Asp
305                 310                 315                 320

Val Ile Lys Asp Asn Thr Leu Leu Val Asp Ile Ile Asn Glu His Gly
                325                 330                 335

Ala Ser Phe Val Leu Lys Ile Ile Asn Asp Glu Ile Tyr Ile Asp Ile
            340                 345                 350

Asn Val Ser Val Pro Phe Asp Lys Lys Ile Ala Thr Thr Asn Lys Val
            355                 360                 365

Val Gly Val Asp Val Asn Ile Lys His Met Leu Leu Ala Thr Asn Ile
            370                 375                 380

Leu Asp Asp Gly Asn Val Asn Gly Tyr Val Asn Ile Tyr Lys Glu Val
385                 390                 395                 400

Ile Asn Asp Ser Asp Phe Lys Lys Val Cys Asn Ser Thr Val Met Lys
                405                 410                 415

Tyr Phe Thr Asp Phe Ser Lys Phe Val Thr Phe Cys Pro Leu Glu Phe
                420                 425                 430

Asp Phe Leu Phe Ser Arg Val Cys Asn Gln Lys Gly Ile Tyr Asn Asp
```

-continued

```
            435               440               445

Asn Ser Ala Met Glu Lys Ser Phe Ser Asp Val Leu Asn Lys Leu Lys
    450               455               460

Trp Asn Phe Ile Glu Thr Gly Asp Asn Thr Lys Arg Ile Tyr Ile Glu
465               470               475               480

Asn Val Met Lys Leu Arg Ser Gln Met Lys Ala Tyr Ala Ile Val Lys
                485               490               495

Asn Ala Tyr Tyr Lys Gln Gln Ser Glu Tyr Asp Phe Gly Lys Ser Glu
                500               505               510

Glu Phe Ile Gln Glu His Pro Phe Ser Asn Thr Asp Lys Gly Ile Glu
                515               520               525

Ile Leu Asn Lys Leu Asp Asn Ile Ser Lys Lys Ile Leu Gly Cys Arg
    530               535               540

Asn Asn Ile Ile Gln Tyr Ser Tyr Asn Leu Phe Glu Ile Asn Gly Tyr
545               550               555               560

Asp Met Ile Ser Leu Glu Lys Leu Thr Ser Ser Gln Phe Lys Lys Lys
                565               570               575

Pro Phe Pro Thr Val Asn Ser Leu Leu Lys Tyr His Lys Ile Leu Gly
                580               585               590

Cys Thr Gln Glu Glu Met Glu Lys Lys Asp Ile Tyr Ser Val Ile Lys
                595               600               605

Lys Gly Tyr Tyr Asp Ile Ile Phe Asp Asn Asp Val Val Thr Asp Ala
    610               615               620

Lys Leu Ser Thr Lys Gly Glu Leu Ser Lys Phe Lys Asp Asp Phe Phe
625               630               635               640

Asn Leu Met Ile Lys Ser Ile His Phe Ala Asp Ile Lys Asp Tyr Phe
                645               650               655

Ile Thr Leu Ser Asn Asn Gly Thr Ala Gly Val Ser Leu Val Pro Ser
                660               665               670

Tyr Phe Thr Ser Gln Met Asp Ser Ile Asp His Lys Ile Tyr Phe Val
                675               680               685

Gln Asp Asn Lys Ser Gly Lys Leu Lys Leu Ala Asn Lys His Lys Val
    690               695               700

Arg Ser Ser Gln Glu Lys His Ile Asn Gly Leu Asn Ala Asp Tyr Asn
705               710               715               720

Ala Ala Arg Asn Ile Ala Tyr Ile Met Glu Asn Thr Glu Cys Arg Asn
                725               730               735

Met Phe Met Lys Gln Ser Arg Thr Asp Lys Ser Leu Tyr Asn Lys Pro
                740               745               750

Ser Tyr Glu Thr Phe Ile Lys Thr Gln Gly Ser Ala Val Ala Lys Leu
                755               760               765

Lys Lys Glu Gly Phe Val Lys Ile Leu Asp Glu Ala Ser Ala
    770               775               780
```

```
<210> SEQ ID NO 112
<211> LENGTH: 92
<212> TYPE: PRT
<213> ORGANISM: Artificial sequence
<220> FEATURE:
<223> OTHER INFORMATION: synthetic sequence

<400> SEQUENCE: 112

Asn Lys Ser Gly Lys Leu Lys Leu Ala Asn Lys His Lys Val Arg Ser
1               5               10               15

Ser Gln Glu Lys His Ile Asn Gly Leu Asn Ala Asp Tyr Asn Ala Ala
```

-continued

```
                    20              25              30

Arg Asn Ile Ala Tyr Ile Met Glu Asn Thr Glu Cys Arg Asn Met Phe
        35              40              45

Met Lys Gln Ser Arg Thr Asp Lys Ser Leu Tyr Asn Lys Pro Ser Tyr
    50              55              60

Glu Thr Phe Ile Lys Thr Gln Gly Ser Ala Val Ala Lys Leu Lys Lys
65              70              75              80

Glu Gly Phe Val Lys Ile Leu Asp Glu Ala Ser Val
                85              90

<210> SEQ ID NO 113
<211> LENGTH: 746
<212> TYPE: PRT
<213> ORGANISM: Artificial sequence
<220> FEATURE:
<223> OTHER INFORMATION: synthetic sequence

<400> SEQUENCE: 113

Met Ala Ser His Lys Lys Thr Glu Ser Asn Gln Ile Ile Lys Thr Phe
1               5               10              15

Ser Phe Lys Ile Lys Asn Ala Asn Gly Leu Ser Leu Asp Val Leu Asn
                20              25              30

Asp Ala Ile Thr Glu Tyr Gln Asn Tyr Tyr Asn Ile Cys Ser Asp Trp
        35              40              45

Ile Lys Asp His Leu Thr Met Lys Ile Gly Glu Leu Tyr Lys Tyr Ile
    50              55              60

Pro Asp Glu Lys Lys Asn Ser Gly Tyr Ala Leu Thr Leu Ile Ser Asp
65              70              75              80

Glu Trp Lys Asp Lys Pro Met Tyr Met Met Phe Lys Lys Gly Tyr Pro
                85              90              95

Ala Asn Ser Arg Asp Asn Ala Ile Tyr Glu Ala Leu Asn Thr Cys Asn
                100             105             110

Thr Glu His Tyr Thr Gly Asn Ile Leu Asn Phe Ser Asp Thr Tyr Tyr
        115             120             125

Arg Arg Phe Gly Tyr Val Ala Ser Thr Ile Ser Asn Tyr Val Thr Lys
    130             135             140

Ile Ser Lys Met Ser Thr Gly Ser Arg Ser Lys Asn Ile Ser Asn Asp
145             150             155             160

Ser Asp Val Asp Thr Ile Met Glu Gln Val Ile Tyr Glu Met Glu His
            165             170             175

Asn Gly Trp Thr Ser Val Lys Asp Trp Glu Asn Gln Met Glu Tyr Leu
            180             185             190

Glu Ser Lys Thr Asp Ser Asn Pro Asn Phe Val Tyr Arg Met Thr Thr
        195             200             205

Leu Tyr Glu Phe Tyr Lys Ser His Ile Asp Glu Val Asn Ser Lys Met
    210             215             220

Glu Thr Met Ser Ile Asp Ser Leu Ile Lys Phe Gly Gly Cys Arg Arg
225             230             235             240

Lys Asp Ser Lys Lys Ser Met Tyr Ile Met Gly Gly Ser Asn Thr Pro
            245             250             255

Phe Asp Ile Thr Gln Ile Gly Gly Asn Ser Leu Asn Ile Lys Phe Ser
        260             265             270

Lys Asn Leu Asn Val Asp Val Phe Gly Arg Tyr Asp Val Ile Lys Asp
    275             280             285

Asn Thr Leu Leu Val Asp Ile Ile Asn Gly His Gly Ala Ser Phe Val
```

```
      290                  295                  300

Leu Lys Ile Ile Asn Gly Glu Ile Tyr Ile Asp Ile Asn Val Ser Val
305                  310                  315                  320

Pro Phe Asp Lys Lys Ile Ala Thr Thr Asn Lys Val Val Gly Val Asp
                  325                  330                  335

Val Asn Ile Lys His Met Leu Leu Ala Thr Asn Ile Leu Asp Asp Gly
                  340                  345                  350

Asn Val Asn Gly Tyr Val Asn Ile Tyr Lys Glu Val Ile Asn Asp Ser
                  355                  360                  365

Asp Phe Lys Lys Val Cys Asn Ser Thr Val Met Lys Tyr Phe Thr Asp
         370                  375                  380

Phe Ser Lys Phe Val Thr Phe Cys Pro Leu Glu Phe Asp Phe Leu Phe
385                  390                  395                  400

Ser Arg Val Cys Asn Gln Lys Gly Ile Tyr Asn Asp Asn Ser Ala Met
                  405                  410                  415

Glu Lys Ser Phe Ser Asp Val Leu Asn Lys Leu Lys Trp Asn Phe Ile
                  420                  425                  430

Glu Thr Gly Asp Asn Thr Lys Arg Ile Tyr Ile Glu Asn Val Met Lys
                  435                  440                  445

Leu Arg Ser Gln Met Lys Ala Tyr Ala Ile Val Lys Asn Ala Tyr Tyr
         450                  455                  460

Lys Gln Gln Ser Glu Tyr Asp Phe Gly Lys Ser Glu Glu Phe Ile Gln
465                  470                  475                  480

Glu His Pro Phe Ser Asn Thr Asp Lys Gly Ile Glu Ile Leu Asn Lys
                  485                  490                  495

Leu Asp Asn Ile Ser Lys Lys Ile Leu Gly Cys Arg Asn Asn Ile Ile
                  500                  505                  510

Gln Tyr Ser Tyr Asn Leu Phe Glu Ile Asn Gly Tyr Asp Met Ile Ser
         515                  520                  525

Leu Glu Lys Leu Thr Ser Ser Gln Phe Glu Lys Lys Pro Phe Pro Thr
         530                  535                  540

Val Asn Ser Leu Leu Lys Tyr His Lys Ile Leu Gly Cys Thr Gln Glu
545                  550                  555                  560

Glu Met Glu Lys Lys Asp Ile Tyr Ser Val Ile Lys Lys Gly Tyr Tyr
                  565                  570                  575

Asp Ile Ile Phe Asp Asn Asp Val Val Thr Asp Ala Lys Leu Ser Thr
                  580                  585                  590

Lys Gly Glu Leu Ser Lys Phe Lys Asp Asp Phe Phe Asn Leu Met Ile
         595                  600                  605

Lys Ser Ile His Phe Ala Asp Ile Lys Asp Tyr Phe Ile Thr Leu Ser
         610                  615                  620

Asn Asn Gly Thr Ala Gly Val Ser Leu Val Pro Ser Tyr Phe Thr Ser
625                  630                  635                  640

Gln Met Asp Ser Ile Asp His Lys Ile Tyr Phe Val Gln Asp Asn Lys
                  645                  650                  655

Ser Gly Lys Leu Lys Leu Ala Asn Lys His Lys Val Arg Ser Ser Gln
                  660                  665                  670

Glu Lys His Ile Asn Gly Leu Asn Ala Asp Tyr Asn Ala Ala Arg Asn
         675                  680                  685

Ile Ala Tyr Ile Met Glu Asn Thr Asp Cys Arg Asn Met Phe Met Lys
         690                  695                  700

Gln Ser Arg Thr Asp Lys Ser Leu Tyr Asn Lys Pro Ser Tyr Glu Thr
705                  710                  715                  720
```

-continued

```
Phe Ile Lys Thr Gln Gly Ser Ala Val Ala Lys Leu Lys Lys Glu Gly
                725             730             735

Phe Val Lys Ile Leu Asp Glu Ala Ser Val
            740             745

<210> SEQ ID NO 114
<211> LENGTH: 427
<212> TYPE: PRT
<213> ORGANISM: Artificial sequence
<220> FEATURE:
<223> OTHER INFORMATION: synthetic sequence

<400> SEQUENCE: 114

Val Pro Phe Asp Lys Lys Ile Ala Thr Thr Asn Lys Val Val Gly Val
1               5               10              15

Asp Val Asn Ile Lys His Met Leu Leu Ala Thr Asn Ile Leu Asp Asp
            20              25              30

Gly Asn Val Asn Gly Tyr Val Asn Ile Tyr Lys Glu Val Ile Asn Asp
            35              40              45

Ser Asp Phe Lys Lys Val Cys Asn Ser Thr Val Met Lys Tyr Phe Thr
    50              55              60

Asp Phe Ser Lys Phe Val Thr Phe Cys Pro Leu Glu Phe Asp Phe Leu
65              70              75              80

Phe Ser Arg Val Cys Asn Gln Lys Gly Ile Tyr Asn Asp Asn Ser Ala
            85              90              95

Met Glu Lys Ser Phe Ser Asp Val Leu Asn Lys Leu Lys Trp Asn Phe
            100             105             110

Ile Glu Thr Gly Asp Asn Thr Lys Arg Ile Tyr Ile Glu Asn Val Met
            115             120             125

Lys Leu Arg Ser Gln Met Lys Ala Tyr Ala Ile Val Lys Asn Ala Tyr
    130             135             140

Tyr Lys Gln Gln Ser Glu Tyr Asp Phe Gly Lys Ser Glu Glu Phe Ile
145             150             155             160

Gln Glu His Pro Phe Ser Asn Thr Asp Lys Gly Ile Glu Ile Leu Asn
            165             170             175

Lys Leu Asp Asn Ile Ser Lys Lys Ile Leu Gly Cys Arg Asn Asn Ile
            180             185             190

Ile Gln Tyr Ser Tyr Asn Leu Phe Glu Ile Asn Gly Tyr Asp Met Ile
            195             200             205

Ser Leu Glu Lys Leu Thr Ser Ser Gln Phe Lys Lys Lys Ser Phe Pro
    210             215             220

Thr Val Asp Ser Leu Leu Lys Tyr His Lys Ile Leu Gly Cys Thr Gln
225             230             235             240

Glu Glu Met Glu Lys Lys Asp Ile Tyr Ser Val Ile Lys Lys Gly Tyr
            245             250             255

Tyr Asp Ile Ile Phe Asp Asn Asp Val Val Thr Asp Ala Lys Leu Ser
            260             265             270

Thr Lys Gly Glu Leu Ser Lys Phe Lys Asp Asp Phe Phe Asn Leu Met
            275             280             285

Ile Lys Ser Ile His Phe Ala Asp Ile Lys Asp Tyr Phe Ile Thr Leu
    290             295             300

Ser Asn Asn Gly Thr Ala Gly Val Ser Leu Val Pro Ser Tyr Phe Thr
305             310             315             320

Ser Gln Met Asp Ser Ile Asp His Lys Ile Tyr Phe Val Gln Asp Asn
            325             330             335
```

-continued

```
Lys Ser Gly Lys Leu Lys Leu Ala Asn Lys His Lys Val Arg Ser Ser
            340                 345                 350

Gln Glu Lys His Ile Asn Gly Leu Asn Ala Asp Tyr Asn Ala Ala Arg
            355                 360                 365

Asn Ile Ala Tyr Ile Met Glu Asn Thr Asp Cys Arg Asn Met Phe Met
            370                 375                 380

Lys Gln Ser Arg Thr Asp Lys Ser Leu Tyr Asn Lys Pro Ser Tyr Glu
385                 390                 395                 400

Thr Phe Ile Lys Thr Gln Gly Ser Ala Val Ala Lys Leu Lys Lys Glu
            405                 410                 415

Gly Phe Val Lys Ile Leu Asp Glu Ala Ser Val
            420                 425

<210> SEQ ID NO 115
<211> LENGTH: 746
<212> TYPE: PRT
<213> ORGANISM: Artificial sequence
<220> FEATURE:
<223> OTHER INFORMATION: synthetic sequence

<400> SEQUENCE: 115

Met Ala Ser His Lys Lys Thr Glu Ser Asn Gln Ile Ile Lys Thr Phe
1               5                   10                  15

Ser Phe Lys Ile Lys Asn Ala Asn Gly Leu Ser Leu Asp Val Leu Asn
            20                  25                  30

Asp Ala Ile Thr Glu Tyr Gln Asn Tyr Tyr Asn Ile Cys Ser Asp Trp
            35                  40                  45

Ile Lys Asp His Leu Thr Met Lys Ile Gly Glu Leu Tyr Lys Tyr Ile
    50                  55                  60

Pro Asp Glu Lys Lys Asn Ser Gly Tyr Ala Leu Thr Leu Ile Ser Asp
65                  70                  75                  80

Glu Trp Lys Asp Lys Pro Met Tyr Met Met Phe Lys Lys Gly Tyr Pro
            85                  90                  95

Ala Asn Asn Arg Asp Asn Ala Ile Tyr Glu Thr Leu Asn Thr Cys Asn
            100                 105                 110

Thr Glu His Tyr Thr Gly Asn Ile Leu Asn Phe Ser Asp Thr Tyr Tyr
            115                 120                 125

Arg Arg Phe Gly Tyr Val Ala Ser Ala Ile Ser Asn Tyr Val Thr Lys
            130                 135                 140

Ile Ser Lys Met Ser Thr Gly Ser Arg Ser Lys Asn Ile Ser Asn Asp
145                 150                 155                 160

Ser Asp Val Asp Thr Ile Met Glu Gln Val Ile Tyr Glu Met Glu His
            165                 170                 175

Asn Gly Trp Thr Ser Val Lys Asp Trp Glu Asn Gln Met Glu Tyr Leu
            180                 185                 190

Glu Ser Lys Thr Asp Ser Asn Pro Asn Phe Val Tyr Arg Met Thr Thr
            195                 200                 205

Leu Tyr Glu Phe Tyr Lys Ser His Ile Asp Glu Val Asn Ser Lys Met
    210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
            245                 250                 255

Phe Asp Ile Thr Gln Ile Gly Gly Asn Ser Leu Asn Ile Lys Phe Ser
            260                 265                 270
```

```
Lys Asn Leu Asn Val Asp Val Phe Gly Arg Tyr Asp Val Ile Lys Asp
        275                 280                 285

Asn Thr Leu Leu Val Asp Ile Ile Asn Gly His Gly Ala Ser Phe Val
    290                 295                 300

Leu Lys Ile Ile Asn Gly Glu Ile Tyr Ile Asp Ile Asn Val Ser Val
305                 310                 315                 320

Pro Phe Asp Lys Lys Ile Ala Thr Thr Asn Lys Val Val Gly Val Asp
                325                 330                 335

Val Asn Ile Lys His Met Leu Leu Ala Thr Asn Ile Leu Asp Asp Gly
                340                 345                 350

Asn Val Asn Gly Tyr Val Asn Ile Tyr Lys Glu Val Ile Asn Asp Ser
        355                 360                 365

Asp Phe Lys Lys Val Cys Asn Ser Thr Val Met Lys Tyr Phe Thr Asp
        370                 375                 380

Phe Ser Lys Phe Val Thr Phe Cys Pro Leu Glu Phe Asp Phe Leu Phe
385                 390                 395                 400

Ser Arg Val Cys Asn Gln Lys Gly Ile Tyr Asn Asp Asn Ser Ala Met
            405                 410                 415

Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
        435                 440                 445

Leu Arg Ser Gln Met Lys Ala Tyr Ala Ile Val Lys Asn Ala Tyr Tyr
    450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu Asn Lys
            485                 490                 495

Leu Asp Asn Ile Ser Lys Lys Ile Leu Gly Cys Arg Asn Asn Ile Ile
            500                 505                 510

Gln Tyr Ser Tyr Asn Leu Phe Glu Ile Asn Gly Tyr Asp Met Ile Ser
        515                 520                 525

Leu Glu Lys Leu Thr Ser Ser Gln Phe Lys Lys Lys Pro Phe Pro Thr
    530                 535                 540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
            565                 570                 575

Asp Ile Ile Phe Asp Asn Asp Val Val Thr Asp Ala Lys Leu Ser Thr
            580                 585                 590

Lys Gly Glu Leu Ser Lys Phe Lys Asp Asp Phe Phe Asn Leu Met Ile
        595                 600                 605

Lys Ser Ile His Phe Ala Asp Ile Lys Asp Tyr Phe Ile Thr Leu Ser
    610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
            645                 650                 655

Ser Gly Lys Leu Lys Leu Ala Asn Lys His Lys Val Arg Ser Ser Gln
        660                 665                 670

Glu Lys His Ile Asn Gly Leu Asn Ala Asp Tyr Asn Ala Ala Arg Asn
        675                 680                 685
```

-continued

```
Ile Ala Tyr Ile Met Glu Asn Thr Glu Cys Arg Asn Met Phe Met Lys
    690             695             700

Gln Ser Arg Thr Asp Lys Ser Leu Tyr Asn Lys Pro Ser Tyr Glu Thr
705             710             715             720

Phe Ile Lys Thr Gln Gly Ser Ala Val Ala Lys Leu Lys Lys Glu Gly
            725             730             735

Phe Val Lys Ile Leu Asp Glu Ala Ser Val
            740             745

<210> SEQ ID NO 116
<211> LENGTH: 735
<212> TYPE: PRT
<213> ORGANISM: Artificial sequence
<220> FEATURE:
<223> OTHER INFORMATION: synthetic sequence

<400> SEQUENCE: 116

Met Ala His Lys Lys Asn Ile Gly Ala Glu Ile Val Lys Thr Tyr Ser
1               5               10              15

Phe Lys Val Lys Asn Thr Asn Gly Ile Thr Met Glu Lys Leu Met Asn
            20              25              30

Ala Ile Asp Glu Tyr Gln Ser Tyr Tyr Asn Leu Cys Ser Asp Trp Ile
        35              40              45

Cys Lys Asn Leu Thr Thr Met Thr Ile Gly Asp Leu Asp Arg Tyr Ile
    50              55              60

Pro Glu Lys Ala Lys Asp Asn Ile Tyr Ala Thr Val Leu Leu Asp Glu
65              70              75              80

Val Trp Lys Asn Gln Pro Leu Tyr Lys Ile Phe Gly Lys Lys Tyr Ser
            85              90              95

Ser Asn Asn Arg Ile Asn Ala Leu Tyr Cys Thr Leu Ser Ser Val Ile
            100             105             110

Asp Ile Asn Lys Lys Asn Ile Leu Gly Leu Ser Gln Thr Tyr Tyr Ala
        115             120             125

Arg Asn Gly Tyr Ile Leu Asn Val Ile Ser Asn Tyr Ala Ser Lys Leu
    130             135             140

Ser Lys Leu Asn Thr Gly Val Lys Arg His Thr Ile Lys Glu Thr Ser
145             150             155             160

Asp Glu Ala Thr Ile Val Glu Gln Val Ile Tyr Glu Met Glu His Asn
            165             170             175

Lys Trp Glu Ser Ile Glu Asp Trp Lys Asn Gln Ile Glu Tyr Leu Asn
            180             185             190

Ser Lys Thr Asp Tyr Asn Pro Thr Tyr Met Glu Arg Met Lys Thr Leu
        195             200             205

Ser Ala Tyr Tyr Ser Glu His Lys Ser Glu Val Asp Ala Lys Met Gln
    210             215             220

Glu Met Ala Val Glu Asn Leu Val Lys Phe Gly Gly Cys Arg Arg Asn
225             230             235             240

Asn Ser Lys Lys Ser Met Phe Ile Met Gly Ser Ser Lys Thr Thr Tyr
            245             250             255

Thr Ile Ser Tyr Ile Gly Asp Asn Cys Phe Asn Ile Asn Phe Ala Asn
            260             265             270

Ile Leu Asn Phe Asp Val Tyr Gly Arg Arg Asp Val Val Lys Asn Gly
        275             280             285

Glu Val Leu Val Asp Ile Met Ala Asn His Gly Asp Ser Ile Val Leu
    290             295             300
```

-continued

```
Lys Ile Val Asn Gly Glu Leu Tyr Ala Asp Val Pro Cys Ser Thr Thr
305             310                 315                 320

Leu Asn Lys Val Glu Ser Thr Phe Asp Lys Val Ala Gly Ile Asp Val
                325                 330                 335

Asn Met Lys His Met Leu Leu Ser Thr Ser Val Thr Asp Asn Gly Asn
            340                 345                 350

Ser Asp Phe Val Asn Ile Tyr Lys Glu Met Ser Asn Asn Ala Glu Phe
            355                 360                 365

Met Ala Leu Cys Pro Glu Glu Asp Arg Lys Tyr Tyr Lys Asp Ile Ser
        370                 375                 380

Gln Tyr Val Thr Phe Ala Pro Leu Glu Leu Asp Leu Leu Phe Ser Arg
385                 390                 395                 400

Ile Ser Lys Gln Gly Lys Val Lys Met Glu Lys Ala Tyr Ser Glu Ile
                405                 410                 415

Leu Glu Ala Leu Lys Trp Lys Phe Phe Ala Asn Gly Asp Asn Lys Asn
                420                 425                 430

Arg Ile Tyr Val Glu Asn Ile Gln Lys Ile Arg Gln Gln Ile Lys Ala
            435                 440                 445

Leu Cys Val Ile Lys Asn Ala Tyr Tyr Glu Gln Gln Ser Ala Tyr Asp
        450                 455                 460

Ile Asp Lys Thr Gln Glu Tyr Ile Glu Ala His Pro Phe Ser Leu Thr
465                 470                 475                 480

Glu Lys Gly Met Ser Ile Lys Ser Lys Met Asp Asn Ile Cys Arg Thr
                485                 490                 495

Ile Ile Gly Cys Arg Asn Asn Ile Ile Asp Tyr Ala Tyr Ser Phe Phe
                500                 505                 510

Glu Arg Asn Asp Tyr Ser Ile Ile Gly Leu Glu Lys Leu Thr Ser Ser
            515                 520                 525

Gln Phe Glu Lys Thr Lys Ser Leu Pro Thr Cys Lys Ser Leu Leu Asn
        530                 535                 540

Phe His Lys Val Leu Gly His Thr Leu Ser Glu Leu Glu Thr Leu Pro
545                 550                 555                 560

Ile Asn Asp Val Val Lys Lys Gly Tyr Tyr Thr Phe Thr Thr Asp Asn
                565                 570                 575

Glu Gly Arg Ile Thr Asp Ala Ser Leu Ser Glu Lys Gly Lys Val Arg
            580                 585                 590

Lys Met Lys Asp Asp Phe Phe Asn Gln Ala Ile Lys Ala Ile His Phe
            595                 600                 605

Ala Asp Val Lys Asp Tyr Phe Ala Thr Leu Ser Asn Asn Gly Gln Thr
        610                 615                 620

Gly Ile Phe Phe Val Pro Ser Gln Phe Thr Ser Gln Met Asp Ser Asn
625                 630                 635                 640

Thr His Thr Leu Tyr Phe Glu Asn Ala Lys Asn Gly Gly Leu Lys Leu
                645                 650                 655

Ala Ser Lys Tyr Lys Val Arg Lys Ser Gln Glu Tyr His Leu Asn Gly
            660                 665                 670

Leu Pro Ala Asp Tyr Asn Ala Ala Arg Asn Ile Ala Tyr Ile Gly Leu
        675                 680                 685

Asp Glu Ile Met Arg Asn Thr Phe Leu Lys Lys Ala Asn Ser Asn Lys
        690                 695                 700

Ser Leu Tyr Asn Gln Pro Ile Tyr Asp Thr Gly Ile Lys Lys Thr Ala
705                 710                 715                 720

Gly Val Phe Ser Arg Met Lys Lys Leu Lys Lys Tyr Lys Val Ile
```

-continued

```
                725                 730                 735

<210> SEQ ID NO 117
<211> LENGTH: 746
<212> TYPE: PRT
<213> ORGANISM: Artificial sequence
<220> FEATURE:
<223> OTHER INFORMATION: synthetic sequence

<400> SEQUENCE: 117

Met Ala Ser His Lys Lys Thr Glu Ser Asn Gln Ile Ile Lys Thr Phe
1               5                   10                  15

Ser Phe Lys Ile Lys Asn Ala Asn Gly Leu Ser Leu Asp Val Leu Asn
                20                  25                  30

Asp Ala Ile Thr Glu Tyr Gln Asn Tyr Tyr Asn Ile Cys Ser Asp Trp
            35                  40                  45

Ile Lys Asp His Leu Thr Met Lys Ile Gly Glu Leu Tyr Lys Tyr Ile
        50                  55                  60

Pro Asp Glu Lys Lys Asn Ser Gly Tyr Ala Leu Thr Leu Ile Ser Asp
65                  70                  75                  80

Glu Trp Lys Asp Lys Pro Met Tyr Met Met Phe Lys Lys Gly Tyr Pro
                85                  90                  95

Ala Asn Ser Arg Asp Asn Ala Ile Tyr Glu Ala Leu Asn Thr Cys Asn
                100                 105                 110

Thr Glu His Tyr Thr Gly Asn Ile Leu Asn Phe Ser Asp Thr Tyr Tyr
            115                 120                 125

Arg Arg Phe Gly Tyr Val Ala Ser Thr Ile Ser Asn Tyr Val Thr Lys
        130                 135                 140

Ile Ser Lys Met Ser Thr Gly Ser Arg Ser Lys Asn Ile Ser Asn Asp
145                 150                 155                 160

Ser Asp Val Asp Thr Ile Met Glu Gln Val Ile Tyr Glu Met Glu His
                165                 170                 175

Asn Gly Trp Thr Ser Val Lys Asp Trp Glu Asn Gln Met Glu Tyr Leu
                180                 185                 190

Glu Ser Lys Thr Asp Ser Asn Pro Asn Phe Val Tyr Arg Met Thr Thr
            195                 200                 205

Leu Tyr Glu Phe Tyr Lys Ser His Ile Asp Glu Val Asn Ser Lys Met
        210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
                245                 250                 255

Phe Asp Ile Thr Gln Ile Gly Gly Asn Ser Leu Asn Ile Lys Phe Ser
            260                 265                 270

Lys Asn Leu Asn Val Asp Val Phe Gly Arg Tyr Asp Val Ile Lys Asp
            275                 280                 285

Asn Thr Leu Leu Val Asp Ile Ile Asn Gly His Gly Ala Ser Phe Val
        290                 295                 300

Leu Lys Ile Ile Asn Gly Glu Ile Tyr Ile Asp Ile Asn Val Ser Val
305                 310                 315                 320

Pro Phe Asp Lys Lys Ile Ala Thr Thr Asn Lys Val Val Gly Val Asp
                325                 330                 335

Val Asn Ile Lys His Met Leu Leu Ala Thr Asn Ile Leu Asp Asp Gly
            340                 345                 350

Asn Val Asn Gly Tyr Val Asn Ile Tyr Lys Glu Val Ile Asn Asp Ser
```

-continued

```
                355                  360                  365

Asp Phe Lys Lys Val Cys Asn Ser Thr Val Met Gln Tyr Phe Thr Asp
    370                  375                  380

Phe Ser Lys Phe Val Thr Phe Cys Pro Leu Glu Phe Asp Phe Leu Phe
385                  390                  395                  400

Ser Arg Val Cys Asn Gln Lys Gly Ile Tyr Asn Asp Asn Ser Ala Met
                405                  410                  415

Glu Lys Ser Phe Ser Asp Val Leu Asn Lys Leu Lys Trp Asn Phe Ile
                420                  425                  430

Glu Thr Gly Asp Asn Thr Lys Arg Ile Tyr Ile Glu Asn Val Met Lys
                435                  440                  445

Leu Arg Ser Gln Met Lys Ala Tyr Ala Ile Val Lys Asn Ala Tyr Tyr
    450                  455                  460

Lys Gln Gln Ser Glu Tyr Asp Phe Gly Lys Ser Glu Glu Phe Ile Gln
465                  470                  475                  480

Glu His Pro Phe Ser Asn Thr Asp Lys Gly Ile Glu Ile Leu Asn Lys
                485                  490                  495

Leu Asp Asn Ile Ser Lys Lys Ile Leu Gly Cys Arg Asn Asn Ile Ile
                500                  505                  510

Gln Tyr Ser Tyr Asn Leu Phe Glu Ile Asn Gly Tyr Asp Met Ile Ser
                515                  520                  525

Leu Glu Lys Leu Thr Ser Ser Gln Phe Lys Lys Lys Pro Phe Pro Thr
    530                  535                  540

Val Asn Ser Leu Leu Lys Tyr His Lys Ile Leu Gly Cys Thr Gln Glu
545                  550                  555                  560

Glu Met Glu Lys Lys Asp Ile Tyr Ser Val Ile Lys Lys Gly Tyr Tyr
                565                  570                  575

Asp Ile Ile Phe Asp Asn Asp Val Val Thr Asp Ala Lys Leu Ser Thr
                580                  585                  590

Lys Gly Glu Leu Ser Lys Phe Lys Asp Asp Phe Phe Asn Leu Met Ile
                595                  600                  605

Lys Ser Ile His Phe Ala Asp Ile Lys Asp Tyr Phe Ile Thr Leu Ser
    610                  615                  620

Asn Asn Gly Thr Ala Gly Val Ser Leu Val Pro Ser Tyr Phe Thr Ser
625                  630                  635                  640

Gln Met Asp Ser Ile Asp His Lys Ile Tyr Phe Val Gln Asp Asn Lys
                645                  650                  655

Ser Gly Lys Leu Lys Leu Ala Asn Lys His Lys Val Arg Ser Ser Gln
                660                  665                  670

Glu Lys His Ile Asn Gly Leu Asn Ala Asp Tyr Asn Ala Ala Arg Asn
                675                  680                  685

Ile Ala Tyr Ile Met Glu Asn Thr Glu Cys Arg Asn Met Phe Met Lys
    690                  695                  700

Gln Ser Arg Thr Asp Lys Ser Leu Tyr Asn Lys Pro Ser Tyr Glu Thr
705                  710                  715                  720

Phe Ile Lys Thr Gln Gly Ser Ala Val Ala Lys Leu Lys Lys Glu Gly
                725                  730                  735

Phe Val Lys Ile Ile Asp Glu Ala Ser Val
                740                  745
```

```
<210> SEQ ID NO 118
<211> LENGTH: 746
<212> TYPE: PRT
<213> ORGANISM: Artificial sequence
```

-continued

<220> FEATURE:
<223> OTHER INFORMATION: synthetic sequence

<400> SEQUENCE: 118

```
Met Ala Ser His Lys Lys Thr Glu Ser Asn Gln Ile Ile Lys Thr Phe
1               5                   10                  15

Ser Phe Lys Ile Lys Asn Ala Asn Gly Leu Ser Leu Asp Val Leu Asn
                20                  25                  30

Asp Ala Ile Thr Glu Tyr Gln Asn Tyr Tyr Asn Ile Cys Ser Asp Trp
            35                  40                  45

Ile Lys Asp His Leu Thr Met Lys Ile Gly Glu Leu Tyr Lys Tyr Ile
        50                  55                  60

Pro Asp Glu Lys Lys Asn Ser Gly Tyr Ala Leu Thr Leu Ile Ser Asp
65                  70                  75                  80

Glu Trp Lys Asp Lys Pro Met Tyr Met Met Phe Lys Lys Gly Tyr Pro
                85                  90                  95

Ala Asn Asn Arg Asp Asn Ala Ile Tyr Glu Ala Leu Asn Thr Cys Asn
                100                 105                 110

Thr Glu His Tyr Thr Gly Asn Ile Leu Asn Phe Ser Asp Thr Tyr Tyr
            115                 120                 125

Arg Arg Phe Gly Tyr Val Ala Ser Thr Ile Ser Asn Tyr Val Thr Lys
        130                 135                 140

Ile Ser Lys Met Ser Thr Gly Ser Arg Ser Lys Asn Ile Ser Asn Asp
145                 150                 155                 160

Ser Asp Val Asp Thr Ile Met Glu Gln Val Ile Tyr Glu Met Glu His
                165                 170                 175

Asn Gly Trp Thr Ser Val Lys Asp Trp Glu Asn Gln Met Glu Tyr Leu
                180                 185                 190

Glu Ser Lys Thr Asp Ser Asn Pro Asn Phe Val Tyr Arg Met Thr Thr
            195                 200                 205

Leu Tyr Glu Phe Tyr Lys Ser His Ile Asp Glu Val Asn Ser Lys Met
        210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
                245                 250                 255

Phe Asp Ile Thr Gln Ile Gly Gly Asn Ser Leu Asn Ile Lys Phe Ser
            260                 265                 270

Lys Asn Leu Asn Val Asp Val Phe Gly Arg Tyr Asp Val Ile Lys Asp
        275                 280                 285

Asn Thr Leu Leu Val Asp Ile Ile Asn Gly His Gly Ala Ser Phe Val
        290                 295                 300

Leu Lys Ile Ile Asn Gly Glu Ile Tyr Ile Asp Ile Asn Val Ser Val
305                 310                 315                 320

Pro Phe Asp Lys Lys Ile Ala Thr Thr Asn Lys Val Val Gly Val Asp
                325                 330                 335

Val Asn Ile Lys His Met Leu Leu Ala Thr Asn Ile Leu Asp Asp Gly
                340                 345                 350

Asn Val Asn Gly Tyr Val Asn Ile Tyr Lys Glu Val Ile Asn Asp Ser
            355                 360                 365

Asp Phe Lys Lys Val Cys Asn Ser Thr Val Met Lys Tyr Phe Thr Asp
        370                 375                 380

Phe Ser Lys Phe Val Thr Phe Cys Pro Leu Glu Phe Asp Phe Leu Phe
385                 390                 395                 400
```

-continued

```
Ser Arg Val Cys Asn Gln Lys Gly Ile Tyr Asn Asp Asn Ser Ala Met
                405                 410                 415

Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
            435                 440                 445

Leu Arg Ser Gln Met Lys Ala Tyr Ala Ile Val Lys Asn Ala Tyr Tyr
    450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu Asn Lys
                485                 490                 495

Leu Asp Asn Ile Ser Lys Lys Ile Leu Gly Cys Arg Asn Asn Ile Ile
            500                 505                 510

Gln Tyr Ser Tyr Asn Leu Phe Glu Ile Asn Gly Tyr Asp Met Ile Ser
            515                 520                 525

Leu Glu Lys Leu Thr Ser Ser Gln Phe Lys Lys Lys Pro Phe Pro Thr
    530                 535                 540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
            565                 570                 575

Asp Ile Ile Phe Asp Asn Gly Val Val Thr Asp Ala Lys Leu Ser Thr
            580                 585                 590

Lys Gly Glu Leu Ser Lys Phe Lys Asp Asp Phe Phe Asn Leu Met Ile
            595                 600                 605

Lys Ser Ile His Phe Ala Asp Ile Lys Asp Tyr Phe Ile Thr Leu Ser
    610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
                645                 650                 655

Ser Gly Lys Leu Lys Leu Ala Asn Lys His Lys Val Arg Ser Ser Gln
            660                 665                 670

Glu Lys His Ile Asn Gly Leu Asn Ala Asp Tyr Asn Ala Ala Arg Asn
            675                 680                 685

Ile Ala Tyr Ile Met Glu Asn Thr Glu Cys Arg Asn Met Phe Met Lys
    690                 695                 700

Gln Ser Arg Thr Asp Lys Ser Leu Tyr Asn Lys Pro Ser Tyr Glu Thr
705                 710                 715                 720

Phe Ile Lys Thr Gln Gly Ser Ala Val Ala Lys Leu Lys Lys Glu Gly
            725                 730                 735

Phe Val Lys Ile Leu Asp Glu Ala Ser Val
            740                 745
```

```
<210> SEQ ID NO 119
<211> LENGTH: 680
<212> TYPE: PRT
<213> ORGANISM: Artificial sequence
<220> FEATURE:
<223> OTHER INFORMATION: synthetic sequence

<400> SEQUENCE: 119

Glu Lys Lys Asn Ser Gly Tyr Ala Leu Thr Leu Ile Ser Asp Glu Trp
1               5                   10                  15
```

-continued

```
Lys Asp Lys Pro Met Tyr Met Met Phe Lys Lys Gly Tyr Pro Ala Asn
        20                  25                  30

Asn Arg Asp Asn Ala Ile Tyr Glu Thr Leu Asn Thr Cys Asn Thr Glu
        35                  40                  45

His Tyr Thr Gly Asn Ile Leu Asn Phe Ser Asp Thr Tyr Tyr Arg Arg
    50                  55                  60

Phe Gly Tyr Val Ala Ser Ala Ile Ser Asn Tyr Val Thr Lys Ile Ser
65                  70                  75                  80

Lys Met Ser Thr Gly Ser Arg Ser Lys Asn Ile Ser Asn Asp Ser Asp
                85                  90                  95

Val Asp Thr Ile Met Glu Gln Val Ile Tyr Glu Met Glu His Asn Gly
            100                 105                 110

Trp Thr Ser Val Lys Asp Trp Glu Asn Gln Met Glu Tyr Leu Glu Ser
        115                 120                 125

Lys Thr Asp Ser Asn Pro Asn Phe Val Tyr Arg Met Thr Thr Leu Tyr
    130                 135                 140

Glu Phe Tyr Lys Ser His Ile Asp Glu Val Asn Ser Lys Met Glu Thr
145                 150                 155                 160

Met Ser Ile Asp Ser Leu Ile Lys Phe Gly Gly Cys Arg Arg Lys Asp
            165                 170                 175

Ser Lys Lys Ser Met Tyr Ile Met Gly Gly Ser Asn Thr Pro Phe Asp
                180                 185                 190

Ile Thr Gln Ile Gly Gly Asn Ser Leu Asn Ile Lys Phe Ser Lys Asn
            195                 200                 205

Leu Asn Val Asp Val Phe Gly Arg Tyr Asp Val Ile Lys Asp Asn Thr
    210                 215                 220

Leu Leu Val Asp Ile Ile Asn Glu His Gly Ala Ser Phe Val Leu Lys
225                 230                 235                 240

Ile Ile Asn Asp Glu Ile Tyr Ile Asp Ile Asn Val Ser Val Pro Phe
            245                 250                 255

Asp Lys Lys Ile Ala Thr Thr Asn Lys Val Val Gly Val Asp Val Asn
            260                 265                 270

Ile Lys His Met Leu Leu Ala Thr Asn Ile Leu Asp Asp Gly Asn Val
        275                 280                 285

Asn Gly Tyr Val Asn Ile Tyr Lys Glu Val Ile Asn Asp Ser Asp Phe
    290                 295                 300

Lys Lys Val Cys Asn Ser Thr Val Met Lys Tyr Phe Thr Asp Phe Ser
305                 310                 315                 320

Lys Phe Val Thr Phe Cys Pro Leu Glu Phe Asp Phe Leu Phe Ser Arg
            325                 330                 335

Val Cys Asn Gln Lys Gly Ile Tyr Asn Asp Asn Ser Ala Met Glu Lys
            340                 345                 350

Ser Phe Ser Asp Val Leu Asn Lys Leu Lys Trp Asn Phe Ile Glu Thr
        355                 360                 365

Gly Asp Asn Thr Lys Arg Ile Tyr Ile Glu Asn Val Met Lys Leu Arg
    370                 375                 380

Ser Gln Met Lys Ala Tyr Ala Ile Val Lys Asn Ala Tyr Tyr Lys Gln
385                 390                 395                 400

Gln Ser Glu Tyr Asp Phe Gly Lys Ser Glu Glu Phe Ile Gln Glu His
                405                 410                 415

Pro Phe Ser Asn Thr Asp Lys Gly Ile Glu Ile Leu Asn Lys Leu Asp
            420                 425                 430
```

```
Asn Ile Ser Lys Lys Ile Leu Gly Cys Arg Asn Asn Ile Ile Gln Tyr
        435             440             445

Ser Tyr Asn Leu Phe Glu Ile Asn Gly Tyr Asp Met Ile Ser Leu Glu
        450             455             460

Lys Leu Thr Ser Ser Gln Phe Lys Lys Lys Pro Phe Pro Thr Val Asn
465             470             475             480

Ser Leu Leu Lys Tyr His Lys Ile Leu Gly Cys Thr Gln Glu Glu Met
                485             490             495

Glu Lys Lys Asp Ile Tyr Ser Val Ile Lys Lys Gly Tyr Tyr Asp Ile
                500             505             510

Ile Phe Asp Asn Asp Val Val Thr Asp Ala Lys Leu Ser Thr Lys Gly
            515             520             525

Glu Leu Ser Lys Phe Lys Asp Asp Phe Phe Asn Leu Met Ile Lys Ser
        530             535             540

Ile His Phe Ala Asp Ile Lys Asp Tyr Phe Ile Thr Leu Ser Asn Asn
545             550             555             560

Gly Thr Val Gly Val Ser Leu Val Pro Ser Tyr Phe Thr Ser Gln Met
                565             570             575

Asp Ser Ile Asp His Lys Ile Tyr Phe Val Gln Asp Asn Lys Ser Gly
            580             585             590

Lys Leu Lys Leu Ala Asn Lys His Lys Val Arg Ser Ser Gln Glu Lys
        595             600             605

His Ile Asn Gly Leu Asn Ala Asp Tyr Asn Ala Ala Arg Asn Ile Ala
        610             615             620

Tyr Ile Met Glu Asn Asn Glu Cys Arg Asn Met Phe Met Lys Gln Ser
625             630             635             640

Arg Thr Asp Lys Ser Leu Tyr Asn Lys Pro Ser Tyr Glu Thr Phe Ile
                645             650             655

Lys Thr Gln Gly Ser Ala Val Ala Lys Leu Lys Lys Glu Gly Phe Val
            660             665             670

Lys Ile Leu Asp Glu Ala Ser Val
        675             680

<210> SEQ ID NO 120
<211> LENGTH: 516
<212> TYPE: PRT
<213> ORGANISM: Artificial sequence
<220> FEATURE:
<223> OTHER INFORMATION: synthetic sequence

<400> SEQUENCE: 120

Asp Ala Lys Met Gln Glu Met Ala Val Glu Asn Leu Val Lys Phe Gly
1               5               10              15

Gly Cys Arg Arg Asn Asn Ser Lys Ser Met Phe Ile Met Gly Ser
            20              25              30

Ser Lys Thr Thr Tyr Thr Ile Ser Tyr Ile Gly Asp Asn Cys Phe Asn
        35              40              45

Ile Asn Phe Ala Asn Ile Leu Asn Phe Asp Val Tyr Gly Arg Arg Asp
        50              55              60

Val Val Lys Asn Gly Glu Val Leu Val Asp Ile Met Ala Asn His Gly
65              70              75              80

Asp Ser Ile Val Leu Lys Ile Val Asn Gly Glu Leu Tyr Ala Asp Val
                85              90              95

Pro Cys Ser Thr Thr Leu Asn Lys Val Glu Ser Thr Phe Asp Lys Val
            100             105             110
```

```
Ala Gly Ile Asp Val Asn Met Lys His Met Leu Leu Ser Thr Ser Val
        115                 120                 125

Thr Asp Asn Gly Asn Ser Asp Phe Val Asn Ile Tyr Lys Glu Ile Ser
    130                 135                 140

Asn Asn Ala Glu Phe Met Ala Leu Cys Pro Glu Glu Asp Arg Lys Tyr
145                 150                 155                 160

Tyr Lys Asp Ile Ser Gln Tyr Val Thr Phe Ala Pro Leu Glu Leu Asp
                165                 170                 175

Leu Leu Phe Ser Arg Ile Ser Lys Gln Gly Lys Val Lys Met Glu Lys
            180                 185                 190

Ala Tyr Ser Glu Ile Leu Glu Thr Leu Lys Trp Lys Phe Phe Ala Asn
        195                 200                 205

Gly Asp Asn Lys Asn Arg Ile Tyr Val Glu Ser Ile Gln Lys Ile Arg
    210                 215                 220

Gln Gln Ile Lys Ala Leu Cys Val Ile Lys Asn Ala Tyr Tyr Glu Gln
225                 230                 235                 240

Gln Ser Ala Tyr Asp Ile Asp Lys Thr Gln Glu Tyr Ile Glu Ala His
                245                 250                 255

Pro Phe Ser Leu Thr Glu Lys Gly Met Ser Ile Lys Ser Lys Met Asp
            260                 265                 270

Asn Ile Cys Arg Thr Ile Ile Gly Cys Arg Asn Asn Ile Ile Asp Tyr
        275                 280                 285

Ala Tyr Ser Phe Phe Glu Arg Asn Asp Tyr Ser Ile Ile Gly Leu Glu
        290                 295                 300

Lys Leu Thr Ser Ser Gln Phe Glu Lys Thr Lys Ser Leu Pro Thr Cys
305                 310                 315                 320

Lys Ser Leu Leu Asn Phe His Lys Val Leu Gly His Thr Leu Ser Glu
            325                 330                 335

Leu Glu Thr Leu Pro Ile Asn Asp Val Val Lys Lys Gly Tyr Tyr Thr
            340                 345                 350

Phe Thr Thr Asp Asn Glu Gly Arg Ile Thr Asp Ala Ser Leu Ser Glu
            355                 360                 365

Lys Gly Lys Val Arg Lys Met Lys Asp Asp Phe Phe Asn Gln Ala Ile
    370                 375                 380

Lys Ala Ile His Phe Ala Asp Val Lys Asp Tyr Phe Ala Thr Leu Ser
385                 390                 395                 400

Asn Asn Gly Gln Thr Gly Ile Phe Phe Val Pro Ser Gln Phe Thr Ser
                405                 410                 415

Gln Met Asp Ser Asn Thr His Thr Leu Tyr Phe Glu Asn Ala Lys Asn
            420                 425                 430

Gly Gly Leu Lys Leu Ala Ser Lys Tyr Gln Val Arg Gln Thr Gln Glu
        435                 440                 445

Tyr His Leu Asn Gly Leu Pro Ala Asp Tyr Asn Ala Ala Arg Asn Ile
    450                 455                 460

Ala Tyr Ile Gly Leu Asp Glu Thr Met Arg Asn Thr Phe Leu Lys Lys
465                 470                 475                 480

Ala Asn Ser Asn Lys Ser Leu Tyr Asn Gln Pro Ile Tyr Asp Thr Gly
                485                 490                 495

Ile Lys Lys Thr Ala Gly Val Phe Ser Arg Met Lys Lys Leu Lys Arg
            500                 505                 510

Tyr Glu Ile Ile
            515
```

-continued

```
<210> SEQ ID NO 121
<211> LENGTH: 585
<212> TYPE: PRT
<213> ORGANISM: Artificial sequence
<220> FEATURE:
<223> OTHER INFORMATION: synthetic sequence

<400> SEQUENCE: 121

Asp Val Asp Thr Ile Met Glu Gln Val Ile Tyr Glu Met Glu His Asn
1               5                   10                  15

Gly Trp Thr Ser Val Lys Asp Trp Glu Asn Gln Met Glu Tyr Leu Glu
            20                  25                  30

Ser Lys Thr Asp Ser Asn Pro Asn Phe Val Tyr Arg Met Thr Thr Leu
        35                  40                  45

Tyr Glu Phe Tyr Lys Ser His Ile Asp Glu Val Asn Ser Lys Met Glu
    50                  55                  60

Thr Met Ser Ile Asp Ser Leu Ile Lys Phe Gly Gly Cys Arg Arg Lys
65                  70                  75                  80

Asp Ser Lys Lys Ser Met Tyr Ile Met Gly Gly Ser Asn Thr Pro Phe
                85                  90                  95

Asp Ile Thr Gln Ile Gly Gly Asn Ser Leu Asn Ile Lys Phe Ser Lys
            100                 105                 110

Asn Leu Asn Val Asp Val Phe Gly Arg Tyr Asp Val Ile Lys Asp Asn
        115                 120                 125

Thr Leu Leu Val Asp Ile Ile Asn Gly His Gly Ala Ser Phe Val Leu
    130                 135                 140

Lys Ile Ile Asn Gly Glu Ile Tyr Ile Asp Ile Asn Val Ser Val Pro
145                 150                 155                 160

Phe Asp Lys Lys Ile Ala Thr Thr Asn Lys Val Val Gly Val Asp Val
                165                 170                 175

Asn Ile Lys His Met Leu Leu Ala Thr Asn Ile Leu Asp Asp Gly Asn
            180                 185                 190

Val Asn Gly Tyr Val Asn Ile Tyr Lys Glu Val Ile Asn Asp Ser Asp
        195                 200                 205

Phe Lys Lys Val Cys Asn Ser Thr Val Met Lys Tyr Phe Thr Asp Phe
    210                 215                 220

Ser Lys Phe Val Thr Phe Cys Pro Leu Glu Phe Asp Phe Leu Phe Ser
225                 230                 235                 240

Arg Val Cys Asn Gln Lys Gly Ile Tyr Asn Asp Asn Ser Ala Met Glu
                245                 250                 255

Lys Ser Phe Ser Asp Val Leu Asn Lys Leu Lys Trp Asn Phe Ile Glu
            260                 265                 270

Thr Gly Asp Asn Thr Lys Arg Ile Tyr Ile Glu Asn Val Met Lys Leu
        275                 280                 285

Arg Ser Gln Met Lys Ala Tyr Ala Ile Val Lys Asn Ala Tyr Tyr Lys
    290                 295                 300

Gln Gln Ser Glu Tyr Asp Phe Gly Lys Ser Glu Glu Phe Ile Gln Glu
305                 310                 315                 320

His Pro Phe Ser Asn Thr Asp Lys Gly Ile Glu Ile Leu Asn Lys Leu
                325                 330                 335

Asp Asn Ile Ser Lys Lys Ile Leu Gly Cys Arg Asn Asn Ile Ile Gln
            340                 345                 350

Tyr Ser Tyr Asn Leu Phe Glu Ile Asn Gly Tyr Asp Met Ile Ser Leu
        355                 360                 365

Glu Lys Leu Thr Ser Ser Gln Phe Lys Lys Lys Pro Phe Pro Thr Val
```

-continued

```
            370             375             380
Asn Ser Leu Leu Lys Tyr His Lys Ile Leu Gly Cys Thr Gln Glu Glu
385             390             395             400

Met Glu Lys Lys Asp Ile Tyr Ser Val Ile Lys Lys Gly Tyr Tyr Asp
                405             410             415

Ile Ile Phe Asp Asn Asp Val Val Thr Asp Ala Lys Leu Ser Thr Lys
                420             425             430

Gly Glu Leu Ser Lys Phe Lys Asp Asp Phe Phe Asn Leu Met Ile Lys
            435             440             445

Ser Ile His Phe Ala Asp Ile Lys Asp Tyr Phe Ile Thr Leu Ser Asn
            450             455             460

Asn Gly Thr Ala Gly Val Ser Leu Val Pro Ser Tyr Phe Thr Ser Gln
465             470             475             480

Met Asp Ser Ile Asp His Lys Ile Tyr Phe Val Gln Asp Asn Lys Ser
                485             490             495

Gly Lys Leu Lys Leu Ala Asn Lys His Lys Val Arg Ser Ser Gln Glu
            500             505             510

Lys His Ile Asn Gly Leu Asn Ala Asp Tyr Asn Ala Ala Arg Asn Ile
            515             520             525

Ala Tyr Ile Met Glu Asn Thr Glu Cys Arg Asn Met Phe Met Lys Gln
            530             535             540

Ser Arg Thr Asp Lys Ser Leu Tyr Asn Lys Pro Ser Tyr Glu Thr Phe
545             550             555             560

Ile Lys Thr Gln Gly Ser Ala Val Ala Lys Leu Lys Lys Glu Gly Phe
                565             570             575

Val Lys Ile Ile Asp Glu Ala Ser Val
                580             585

<210> SEQ ID NO 122
<211> LENGTH: 746
<212> TYPE: PRT
<213> ORGANISM: Artificial sequence
<220> FEATURE:
<223> OTHER INFORMATION: synthetic sequence

<400> SEQUENCE: 122

Met Ala Ser His Lys Lys Thr Glu Ser Asn Gln Ile Ile Lys Thr Phe
1               5               10              15

Ser Phe Lys Ile Lys Asn Ala Asn Gly Leu Ser Leu Asp Val Leu Asn
                20              25              30

Asp Ala Ile Thr Glu Tyr Gln Asn Tyr Asn Ile Cys Ser Asp Trp
            35              40              45

Ile Lys Asp His Leu Thr Met Lys Ile Gly Glu Leu Tyr Lys Tyr Ile
            50              55              60

Pro Asp Glu Lys Lys Asn Ser Gly Tyr Ala Leu Thr Leu Ile Ser Asp
65              70              75              80

Glu Trp Lys Asp Lys Pro Met Tyr Met Met Phe Lys Lys Gly Tyr Pro
                85              90              95

Ala Asn Ser Arg Asp Asn Ala Ile Tyr Glu Ala Leu Asn Thr Cys Asn
            100             105             110

Thr Glu His Tyr Thr Gly Asn Ile Leu Asn Phe Ser Asp Thr Tyr Tyr
            115             120             125

Arg Arg Phe Gly Tyr Val Ala Ser Ala Ile Ser Asn Tyr Val Thr Lys
            130             135             140

Ile Ser Lys Met Ser Thr Gly Ser Arg Ser Lys Asn Ile Ser Asn Asp
```

-continued

```
145              150              155              160

Ser Asp Val Asp Thr Ile Met Glu Gln Val Ile Tyr Glu Met Glu His
                165              170              175

Asn Gly Trp Thr Ser Val Lys Asp Trp Glu Asn Gln Met Glu Tyr Leu
            180              185              190

Glu Ser Lys Thr Asp Ser Asn Pro Asn Phe Val Tyr Arg Met Thr Thr
        195              200              205

Leu Tyr Glu Phe Tyr Lys Ser His Ile Asp Glu Val Asn Ser Lys Met
    210              215              220

Glu Thr Met Ser Ile Asp Ser Leu Ile Lys Phe Gly Gly Cys Arg Arg
225              230              235              240

Lys Asp Ser Lys Lys Ser Met Tyr Ile Met Gly Gly Ser Asn Thr Pro
            245              250              255

Phe Asp Ile Thr Gln Ile Gly Gly Asn Ser Leu Asn Ile Lys Phe Ser
            260              265              270

Lys Asn Leu Asn Val Asp Val Phe Gly Arg Tyr Asp Val Ile Lys Asp
            275              280              285

Asn Thr Leu Leu Val Asp Ile Ile Asn Glu His Gly Ala Ser Phe Val
        290              295              300

Leu Lys Ile Ile Asn Asp Glu Ile Tyr Ile Asp Ile Asn Val Ser Val
305              310              315              320

Pro Phe Asp Lys Lys Ile Ala Thr Thr Asn Lys Val Val Gly Val Asp
            325              330              335

Val Asn Ile Lys His Met Leu Leu Ala Thr Asn Ile Leu Asp Asp Gly
            340              345              350

Asn Val Asn Gly Tyr Val Asn Ile Tyr Lys Glu Val Ile Asn Asp Ser
            355              360              365

Asp Phe Lys Lys Val Cys Asn Ser Thr Val Met Lys Tyr Phe Thr Asp
        370              375              380

Phe Ser Lys Phe Val Thr Phe Cys Pro Leu Glu Phe Asp Phe Leu Phe
385              390              395              400

Ser Arg Val Cys Asn Gln Lys Gly Ile Tyr Asn Asp Asn Ser Ala Met
            405              410              415

Glu Lys Ser Phe Ser Asp Val Leu Asn Lys Leu Lys Trp Asn Phe Ile
            420              425              430

Glu Thr Gly Asp Asn Thr Lys Arg Ile Tyr Ile Glu Asn Val Met Lys
            435              440              445

Leu Arg Ser Gln Met Lys Ala Tyr Ala Ile Val Lys Asn Ala Tyr Tyr
    450              455              460

Lys Gln Gln Ser Glu Tyr Asp Phe Gly Lys Ser Glu Glu Phe Ile Gln
465              470              475              480

Glu His Pro Phe Ser Asn Thr Asp Lys Gly Ile Glu Ile Leu Asn Lys
            485              490              495

Leu Asp Asn Ile Ser Lys Lys Ile Leu Gly Cys Arg Asn Asn Ile Ile
            500              505              510

Gln Tyr Ser Tyr Asn Leu Phe Glu Ile Asn Gly Tyr Asp Met Ile Ser
            515              520              525

Leu Glu Lys Leu Thr Ser Ser Gln Phe Glu Lys Lys Pro Phe Pro Thr
    530              535              540

Val Asn Ser Leu Leu Lys Tyr His Lys Ile Leu Gly Cys Thr Gln Glu
545              550              555              560

Glu Met Glu Lys Lys Asp Ile Tyr Ser Val Ile Lys Lys Gly Tyr Tyr
            565              570              575
```

```
Asp Ile Ile Phe Asp Asn Asp Val Val Thr Asp Ala Lys Leu Ser Thr
            580                 585                 590

Lys Gly Glu Leu Ser Lys Phe Lys Asp Asp Phe Phe Asn Leu Met Ile
            595                 600                 605

Lys Ser Ile His Phe Ala Asp Ile Lys Asp Tyr Phe Ile Thr Leu Ser
            610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
                    645                 650                 655

Ser Gly Lys Leu Lys Leu Ala Asn Lys His Lys Val Arg Ser Ser Gln
            660                 665                 670

Glu Lys His Ile Asn Gly Leu Asn Ala Asp Tyr Asn Ala Ala Arg Asn
            675                 680                 685

Ile Ala Tyr Ile Met Glu Asn Thr Glu Cys Arg Asn Met Phe Met Lys
            690                 695                 700

Gln Ser Arg Thr Asp Lys Ser Leu Tyr Asn Lys Pro Ser Tyr Glu Thr
705                 710                 715                 720

Phe Ile Lys Thr Gln Gly Ser Ala Val Ala Lys Leu Lys Lys Glu Gly
                    725                 730                 735

Phe Val Lys Ile Leu Asp Glu Ala Ser Val
                    740                 745
```

```
<210> SEQ ID NO 123
<211> LENGTH: 585
<212> TYPE: PRT
<213> ORGANISM: Artificial sequence
<220> FEATURE:
<223> OTHER INFORMATION: synthetic sequence

<400> SEQUENCE: 123
```

```
Asp Val Asp Thr Ile Met Glu Gln Val Ile Tyr Glu Met Glu His Asn
1               5                   10                  15

Gly Trp Thr Ser Val Lys Asp Trp Glu Asn Gln Met Glu Tyr Leu Glu
            20                  25                  30

Ser Lys Thr Asp Ser Asn Pro Asn Phe Val Tyr Arg Met Thr Thr Leu
            35                  40                  45

Tyr Glu Phe Tyr Lys Ser His Ile Asp Glu Val Asn Ser Lys Met Glu
            50                  55                  60

Thr Met Ser Ile Asp Ser Leu Ile Lys Phe Gly Gly Cys Arg Arg Lys
65                  70                  75                  80

Asp Ser Lys Lys Ser Met Tyr Ile Met Gly Gly Ser Asn Thr Pro Phe
                    85                  90                  95

Asp Ile Thr Gln Ile Gly Gly Asn Ser Leu Asn Ile Lys Phe Ser Lys
            100                 105                 110

Asn Leu Asn Val Asp Val Phe Gly Arg Tyr Asp Val Ile Lys Asp Asn
            115                 120                 125

Thr Leu Leu Val Asp Ile Ile Asn Glu His Gly Ala Ser Phe Val Leu
            130                 135                 140

Lys Ile Ile Asn Asp Glu Ile Tyr Ile Asp Ile Asn Val Ser Val Pro
145                 150                 155                 160

Phe Asp Lys Lys Ile Ala Thr Thr Asn Lys Val Val Gly Val Asp Val
                    165                 170                 175

Asn Ile Lys His Met Leu Leu Ala Thr Asn Ile Leu Asp Asp Gly Asn
            180                 185                 190
```

```
Val Asn Gly Tyr Val Asn Ile Tyr Lys Glu Val Ile Asn Asp Ser Asp
        195                 200                 205

Phe Lys Lys Val Cys Asn Ser Thr Val Met Lys Tyr Phe Thr Asp Phe
    210                 215                 220

Ser Lys Phe Val Thr Phe Cys Pro Leu Glu Phe Asp Phe Leu Phe Ser
225                 230                 235                 240

Arg Val Cys Asn Gln Lys Gly Ile Tyr Asn Asp Asn Ser Ala Met Glu
                245                 250                 255

Lys Ser Phe Ser Asp Val Leu Asn Lys Leu Lys Trp Asn Phe Ile Glu
                260                 265                 270

Thr Gly Asp Asn Thr Lys Arg Ile Tyr Ile Glu Asn Val Met Lys Leu
                275                 280                 285

Arg Ser Gln Met Lys Ala Tyr Ala Ile Val Lys Asn Ala Tyr Tyr Lys
        290                 295                 300

Gln Gln Ser Glu Tyr Asp Phe Gly Lys Ser Glu Glu Phe Ile Gln Glu
305                 310                 315                 320

His Pro Phe Ser Asn Thr Asp Lys Gly Ile Glu Ile Leu Asn Lys Leu
                325                 330                 335

Asp Asn Ile Ser Lys Lys Ile Leu Gly Cys Arg Asn Asn Ile Ile Gln
                340                 345                 350

Tyr Ser Tyr Asn Leu Phe Glu Ile Asn Gly Tyr Asp Met Ile Ser Leu
        355                 360                 365

Glu Lys Leu Thr Ser Ser Gln Phe Lys Lys Lys Pro Phe Pro Thr Val
        370                 375                 380

Asp Ser Leu Leu Lys Tyr His Lys Ile Leu Gly Cys Thr Gln Glu Glu
385                 390                 395                 400

Met Glu Lys Lys Asp Ile Tyr Ser Val Ile Lys Lys Gly Tyr Tyr Asp
                405                 410                 415

Ile Ile Phe Asp Asn Asp Val Val Thr Asp Ala Lys Leu Ser Thr Lys
                420                 425                 430

Gly Glu Leu Ser Lys Phe Lys Asp Asp Phe Phe Asn Leu Met Ile Lys
        435                 440                 445

Ser Ile His Phe Ala Asp Ile Lys Asp Tyr Phe Ile Thr Leu Ser Asn
        450                 455                 460

Asn Gly Thr Ala Gly Val Ser Leu Val Pro Ser Tyr Phe Thr Ser Gln
465                 470                 475                 480

Met Asp Ser Ile Asp His Lys Ile Tyr Phe Val Gln Asp Asn Lys Ser
                485                 490                 495

Gly Lys Leu Lys Leu Ala Asn Lys His Lys Val Arg Ser Ser Gln Glu
                500                 505                 510

Lys His Ile Asn Gly Leu Asn Ala Asp Tyr Asn Ala Ala Arg Asn Ile
        515                 520                 525

Ala Tyr Ile Met Glu Asn Thr Asp Cys Arg Asn Met Phe Met Lys Gln
        530                 535                 540

Ser Arg Thr Asp Lys Ser Leu Tyr Asn Lys Pro Ser Tyr Glu Thr Phe
545                 550                 555                 560

Ile Lys Thr Gln Gly Ser Ala Val Ala Lys Leu Lys Lys Glu Gly Phe
                565                 570                 575

Val Lys Ile Leu Asp Glu Ala Ser Val
                580                 585
```

<210> SEQ ID NO 124
<211> LENGTH: 758

-continued

```
<212> TYPE: PRT
<213> ORGANISM: Artificial sequence
<220> FEATURE:
<223> OTHER INFORMATION: synthetic sequence

<400> SEQUENCE: 124

Phe Val Leu Ser Leu Tyr Gln Leu Asn Gln Tyr Ile Met Ala Ser His
1               5                   10                  15

Lys Lys Thr Glu Ser Asn Gln Ile Ile Lys Thr Phe Ser Phe Lys Ile
            20                  25                  30

Lys Asn Ala Asn Gly Leu Ser Leu Asp Val Leu Asn Asp Ala Ile Thr
        35                  40                  45

Glu Tyr Gln Asn Tyr Tyr Asn Ile Cys Ser Asp Trp Ile Lys Asp His
    50                  55                  60

Leu Thr Met Lys Ile Gly Glu Leu Tyr Lys Tyr Ile Pro Asp Glu Lys
65                  70                  75                  80

Lys Asn Ser Gly Tyr Ala Leu Thr Leu Ile Ser Asp Glu Trp Lys Asp
            85                  90                  95

Lys Pro Met Tyr Met Met Phe Lys Lys Gly Tyr Pro Ala Asn Asn Arg
            100                 105                 110

Asp Asn Ala Ile Tyr Glu Thr Leu Asn Thr Cys Asn Thr Glu His Tyr
        115                 120                 125

Thr Gly Asn Ile Leu Asn Phe Ser Asp Thr Tyr Tyr Arg Arg Phe Gly
    130                 135                 140

Tyr Val Ala Ser Thr Ile Ser Asn Tyr Val Thr Lys Ile Ser Lys Met
145                 150                 155                 160

Ser Thr Gly Ser Arg Ser Lys Asn Ile Ser Asn Asp Ser Asp Val Asp
            165                 170                 175

Thr Ile Met Glu Gln Val Ile Tyr Glu Met Glu His Asn Gly Trp Thr
            180                 185                 190

Ser Val Lys Asp Trp Glu Asn Gln Met Glu Tyr Leu Glu Ser Lys Thr
            195                 200                 205

Asp Ser Asn Pro Asn Phe Val Tyr Arg Met Thr Thr Leu Tyr Glu Phe
    210                 215                 220

Tyr Lys Ser His Ile Asp Glu Val Asn Ser Lys Met Glu Thr Met Ser
225                 230                 235                 240

Ile Asp Ser Leu Ile Lys Phe Gly Gly Cys Arg Arg Lys Asp Ser Lys
            245                 250                 255

Lys Ser Met Tyr Ile Met Gly Gly Ser Asn Thr Pro Phe Asp Ile Thr
            260                 265                 270

Gln Ile Gly Gly Asn Ser Leu Asn Ile Lys Phe Ser Lys Asn Leu Asn
            275                 280                 285

Val Asp Val Phe Gly Arg Tyr Asp Val Ile Lys Asp Asn Thr Leu Leu
    290                 295                 300

Val Asp Ile Ile Asn Gly His Gly Ala Ser Phe Val Leu Lys Ile Ile
305                 310                 315                 320

Asn Gly Glu Ile Tyr Ile Asp Ile Asn Val Ser Val Pro Phe Asp Lys
            325                 330                 335

Lys Ile Ala Thr Thr Asn Lys Val Val Gly Val Asp Val Asn Ile Lys
            340                 345                 350

His Met Leu Leu Ala Thr Asn Ile Leu Asp Asp Gly Asn Val Asn Gly
        355                 360                 365

Tyr Val Asn Ile Tyr Lys Glu Val Ile Asn Asp Ser Asp Phe Lys Lys
    370                 375                 380
```

```
Val Cys Asn Ser Thr Val Met Lys Tyr Phe Thr Asp Phe Ser Lys Phe
385             390             395             400

Val Thr Phe Cys Pro Leu Glu Phe Asp Phe Leu Phe Ser Arg Val Cys
            405             410             415

Asn Gln Lys Gly Ile Tyr Asn Asp Asn Ser Ala Met Glu Lys Ser Phe
            420             425             430

Ser Asp Val Leu Asn Lys Leu Lys Trp Asn Phe Ile Glu Thr Gly Asp
            435             440             445

Asn Thr Lys Arg Ile Tyr Ile Glu Asn Val Met Lys Leu Arg Ser Gln
    450             455             460

Met Lys Ala Tyr Ala Ile Val Lys Asn Ala Tyr Tyr Lys Gln Gln Ser
465             470             475             480

Glu Tyr Asp Phe Gly Lys Ser Glu Glu Phe Ile Gln Glu His Pro Phe
            485             490             495

Ser Asn Thr Asp Lys Gly Ile Glu Ile Leu Asn Lys Leu Asp Asn Ile
            500             505             510

Ser Lys Lys Ile Leu Gly Cys Arg Asn Asn Ile Ile Gln Tyr Ser Tyr
            515             520             525

Asn Leu Phe Glu Ile Asn Gly Tyr Asp Met Ile Ser Leu Glu Lys Leu
    530             535             540

Thr Ser Ser Gln Phe Lys Lys Lys Ser Phe Pro Thr Val Asp Ser Leu
545             550             555             560

Leu Lys Tyr His Lys Ile Leu Gly Cys Thr Gln Glu Glu Met Glu Lys
            565             570             575

Lys Asp Ile Tyr Ser Val Ile Lys Lys Gly Tyr Tyr Asp Ile Ile Phe
            580             585             590

Asp Asn Asp Val Val Thr Asp Ala Lys Leu Ser Thr Lys Gly Glu Leu
    595             600             605

Ser Lys Phe Lys Asp Asp Phe Phe Asn Leu Met Ile Lys Ser Ile His
    610             615             620

Phe Ala Asp Ile Lys Asp Tyr Phe Ile Thr Leu Ser Asn Asn Gly Thr
625             630             635             640

Ala Gly Val Ser Leu Val Pro Ser Tyr Phe Thr Ser Gln Met Asp Ser
            645             650             655

Ile Asp His Lys Ile Tyr Phe Val Gln Asp Asn Lys Ser Gly Lys Leu
            660             665             670

Lys Leu Ala Asn Lys His Lys Val Arg Ser Ser Gln Glu Lys His Ile
            675             680             685

Asn Gly Leu Asn Ala Asp Tyr Asn Ala Ala Arg Asn Ile Ala Tyr Ile
    690             695             700

Met Glu Asn Asn Glu Cys Arg Asn Met Phe Met Lys Gln Ser Arg Thr
705             710             715             720

Asp Lys Ser Leu Tyr Asn Lys Pro Ser Tyr Glu Thr Phe Ile Lys Thr
            725             730             735

Gln Gly Ser Ala Val Ala Lys Leu Lys Lys Glu Gly Phe Val Lys Ile
            740             745             750

Leu Asp Glu Ala Ser Val
            755
```

<210> SEQ ID NO 125
<211> LENGTH: 596
<212> TYPE: PRT
<213> ORGANISM: Artificial sequence
<220> FEATURE:
<223> OTHER INFORMATION: synthetic sequence -continued

```
<400> SEQUENCE: 125

Gly Ser Arg Ser Lys Asn Ile Ser Asn Asp Ser Asp Val Asp Thr Ile
1               5                   10                  15

Met Glu Gln Val Ile Tyr Glu Met Glu His Asn Gly Trp Thr Ser Val
                20                  25                  30

Lys Asp Trp Glu Asn Gln Met Glu Tyr Leu Glu Ser Lys Thr Asp Ser
            35                  40                  45

Asn Pro Asn Phe Val Tyr Arg Met Thr Thr Leu Tyr Glu Phe Tyr Lys
        50                  55                  60

Ser His Ile Asp Glu Val Asn Ser Lys Met Glu Thr Met Ser Ile Asp
65                  70                  75                  80

Ser Leu Ile Lys Phe Gly Gly Cys Arg Arg Lys Asp Ser Lys Lys Ser
                85                  90                  95

Met Tyr Ile Met Gly Gly Ser Asn Thr Pro Phe Asp Ile Thr Gln Ile
                100                 105                 110

Gly Gly Asn Ser Leu Asn Ile Lys Phe Ser Lys Asn Leu Asn Val Asp
            115                 120                 125

Val Phe Gly Arg Tyr Asp Val Ile Lys Asp Asn Thr Leu Leu Val Asp
        130                 135                 140

Ile Ile Asn Gly His Gly Ala Ser Phe Val Leu Lys Ile Ile Asn Gly
145                 150                 155                 160

Glu Ile Tyr Ile Asp Ile Asn Val Ser Val Pro Phe Asp Lys Lys Ile
                165                 170                 175

Ala Thr Thr Asn Lys Val Val Gly Val Asp Val Asn Ile Lys His Met
            180                 185                 190

Leu Leu Ala Thr Asn Ile Leu Asp Asp Gly Asn Val Asn Gly Tyr Val
        195                 200                 205

Asn Ile Tyr Lys Glu Val Ile Asn Asp Ser Asp Phe Lys Lys Val Cys
    210                 215                 220

Asn Ser Thr Val Met Lys Tyr Phe Thr Asp Phe Ser Lys Phe Val Thr
225                 230                 235                 240

Phe Cys Pro Leu Glu Phe Asp Phe Leu Phe Ser Arg Val Cys Asn Gln
            245                 250                 255

Lys Gly Ile Tyr Asn Asp Asn Ser Ala Met Glu Lys Ser Phe Ser Asp
            260                 265                 270

Val Leu Asn Lys Leu Lys Trp Asn Phe Ile Glu Thr Gly Asp Asn Thr
        275                 280                 285

Lys Arg Ile Tyr Ile Glu Asn Val Met Lys Leu Arg Ser Gln Met Lys
    290                 295                 300

Ala Tyr Ala Ile Val Lys Asn Ala Tyr Tyr Lys Gln Gln Ser Glu Tyr
305                 310                 315                 320

Asp Phe Gly Lys Ser Glu Glu Phe Ile Gln Glu His Pro Phe Ser Asn
            325                 330                 335

Thr Asp Lys Gly Ile Glu Ile Leu Asn Lys Leu Asp Asn Ile Ser Lys
        340                 345                 350

Lys Ile Leu Gly Cys Arg Asn Asn Ile Ile Gln Tyr Ser Tyr Asn Leu
        355                 360                 365

Phe Glu Ile Asn Gly Tyr Asp Met Ile Ser Leu Glu Lys Leu Thr Ser
    370                 375                 380

Ser Gln Phe Lys Lys Lys Ser Phe Pro Thr Val Asp Ser Leu Leu Lys
385                 390                 395                 400

Tyr His Lys Ile Leu Gly Cys Thr Gln Glu Glu Met Glu Lys Lys Asp
```

-continued

```
                405               410               415

Ile Tyr Ser Val Ile Lys Lys Gly Tyr Tyr Asp Ile Ile Phe Asp Asn
        420               425               430

Asp Val Val Thr Asp Ala Lys Leu Ser Thr Lys Gly Glu Leu Ser Lys
        435               440               445

Phe Lys Asp Asp Phe Phe Asn Leu Met Ile Lys Ser Ile His Phe Ala
    450               455               460

Asp Ile Lys Asp Tyr Phe Ile Thr Leu Ser Asn Asn Gly Thr Ala Gly
465               470               475               480

Val Ser Leu Val Pro Ser Tyr Phe Thr Ser Gln Met Asp Ser Ile Asp
                485               490               495

His Lys Ile Tyr Phe Val Gln Asp Asn Lys Ser Gly Lys Leu Lys Leu
            500               505               510

Ala Asn Lys His Lys Val Arg Ser Ser Gln Glu Lys His Ile Asn Gly
            515               520               525

Leu Asn Ala Asp Tyr Asn Ala Ala Arg Asn Ile Ala Tyr Ile Met Glu
        530               535               540

Asn Asn Glu Cys Arg Asn Met Phe Met Lys Gln Ser Arg Thr Asp Lys
545               550               555               560

Ser Leu Tyr Asn Lys Pro Ser Tyr Glu Thr Phe Ile Lys Thr Gln Gly
                565               570               575

Ser Ala Val Ala Lys Leu Lys Lys Glu Gly Phe Val Lys Ile Leu Asp
                580               585               590

Glu Ala Ser Val
                595

<210> SEQ ID NO 126
<211> LENGTH: 640
<212> TYPE: PRT
<213> ORGANISM: Artificial sequence
<220> FEATURE:
<223> OTHER INFORMATION: synthetic sequence

<400> SEQUENCE: 126

Met Ala Ser His Lys Lys Thr Glu Ser Asn Gln Ile Ile Lys Thr Phe
1               5                10                15

Ser Phe Lys Ile Lys Asn Ala Asn Gly Leu Ser Leu Asp Val Leu Asn
            20                25                30

Asp Ala Ile Thr Glu Tyr Gln Asn Tyr Tyr Asn Ile Cys Ser Asp Trp
        35                40                45

Ile Lys Asp His Leu Thr Met Lys Ile Gly Glu Leu Tyr Lys Tyr Ile
    50                55                60

Pro Asp Glu Lys Lys Asn Ser Gly Tyr Ala Leu Thr Leu Ile Ser Asp
65                70                75                80

Glu Trp Lys Asp Lys Pro Met Tyr Met Met Phe Lys Lys Gly Tyr Pro
                85                90                95

Ala Asn Asn Arg Asp Asn Ala Ile Tyr Glu Thr Leu Asn Thr Cys Asn
            100               105               110

Thr Glu His Tyr Thr Gly Asn Ile Leu Asn Phe Ser Asp Thr Tyr Tyr
        115               120               125

Arg Arg Phe Gly Tyr Val Ala Ser Thr Ile Ser Asn Tyr Val Thr Lys
        130               135               140

Ile Ser Lys Met Ser Thr Gly Ser Arg Ser Lys Asn Ile Ser Asn Asp
145               150               155               160

Ser Asp Val Asp Thr Ile Met Glu Gln Val Ile Tyr Glu Met Glu His
```

-continued

```
                165                    170                   175
Asn Gly Trp Thr Ser Val Lys Asp Trp Glu Asn Gln Met Glu Tyr Leu
            180                   185                   190
Glu Ser Lys Thr Asp Ser Asn Pro Asn Phe Val Tyr Arg Met Thr Thr
            195                   200                   205
Leu Tyr Glu Phe Tyr Lys Ser His Ile Asp Glu Val Asn Ser Lys Met
            210                   215                   220
Glu Thr Met Ser Ile Asp Ser Leu Ile Lys Phe Gly Gly Cys Arg Arg
225                   230                   235                   240
Lys Asp Ser Lys Lys Ser Met Tyr Ile Met Gly Gly Ser Asn Thr Pro
            245                   250                   255
Phe Asp Ile Thr Gln Ile Asp Gly Asn Ser Leu Asn Ile Lys Phe Ser
            260                   265                   270
Lys Asn Leu Asn Val Asp Val Phe Gly Arg Tyr Asp Val Ile Lys Asp
            275                   280                   285
Asn Thr Leu Leu Val Asp Ile Ile Asn Gly His Gly Ala Ser Phe Val
            290                   295                   300
Leu Lys Ile Ile Asn Gly Glu Ile Tyr Ile Asp Ile Asn Val Ser Val
305                   310                   315                   320
Pro Phe Asp Lys Lys Ile Ala Thr Thr Asn Lys Val Val Gly Val Asp
            325                   330                   335
Val Asn Ile Lys His Met Leu Leu Ala Thr Asn Ile Leu Asp Asp Gly
            340                   345                   350
Asn Val Asn Gly Tyr Val Asn Ile Tyr Lys Glu Val Ile Asn Asp Ser
            355                   360                   365
Asp Phe Lys Lys Val Cys Asn Ser Thr Val Met Lys Tyr Phe Thr Asp
            370                   375                   380
Phe Ser Lys Phe Val Thr Phe Cys Pro Leu Glu Phe Asp Phe Leu Phe
385                   390                   395                   400
Ser Arg Val Cys Asn Gln Lys Gly Ile Tyr Asn Asp Asn Ser Ala Met
            405                   410                   415
Glu Lys Ser Phe Ser Asp Val Leu Asn Lys Leu Lys Trp Asn Phe Ile
            420                   425                   430
Glu Thr Gly Asp Asn Thr Lys Arg Ile Tyr Ile Glu Asn Val Met Lys
            435                   440                   445
Leu Arg Ser Gln Met Lys Ala Tyr Ala Ile Val Lys Asn Ala Tyr Tyr
            450                   455                   460
Lys Gln Gln Ser Glu Tyr Asp Phe Gly Lys Ser Glu Glu Phe Ile Gln
465                   470                   475                   480
Glu His Pro Phe Ser Asn Thr Asp Lys Gly Ile Glu Ile Leu Asn Lys
            485                   490                   495
Leu Asp Asn Ile Ser Lys Lys Ile Leu Gly Cys Arg Asn Asn Ile Ile
            500                   505                   510
Gln Tyr Ser Tyr Asn Leu Phe Glu Ile Asn Gly Tyr Asp Met Ile Ser
            515                   520                   525
Leu Glu Lys Leu Thr Ser Ser Gln Phe Lys Lys Lys Pro Phe Pro Thr
            530                   535                   540
Val Asn Ser Leu Leu Lys Tyr His Lys Ile Leu Gly Cys Thr Gln Glu
545                   550                   555                   560
Glu Met Glu Lys Lys Asp Ile Tyr Ser Val Ile Lys Lys Gly Tyr Tyr
            565                   570                   575
Asp Ile Ile Phe Asp Asn Gly Val Val Ile Asp Ala Lys Leu Ser Ala
            580                   585                   590
```

-continued

```
Lys Gly Glu Leu Ser Lys Phe Lys Asp Asp Phe Phe Asn Leu Met Ile
        595               600               605

Lys Ser Ile His Phe Ala Asp Ile Lys Asp Tyr Phe Ile Thr Leu Ser
        610               615               620

Asn Asn Gly Thr Ala Gly Val Ser Leu Val Asp Leu Phe Cys Pro Arg
625               630               635               640

<210> SEQ ID NO 127
<211> LENGTH: 759
<212> TYPE: PRT
<213> ORGANISM: Artificial sequence
<220> FEATURE:
<223> OTHER INFORMATION: synthetic sequence

<400> SEQUENCE: 127

Met Ala His Lys Lys Asn Leu Glu Gly Glu Asn Leu Gln Val Lys Thr
1               5               10               15

Ile Cys Leu Lys Ala Asn Leu Ser Lys Glu Glu Val Lys Glu Lys Trp
        20               25               30

Leu Pro Val Ile Asn Glu Tyr Asn Val Tyr Tyr Asn Arg Met Ser Asp
        35               40               45

Tyr Ile Cys Ser Leu Leu Gly Thr Asn Ile Thr Ile Gly Glu Phe Ala
        50               55               60

Glu Gln Leu Ser Ile Glu Lys Arg Lys Asn Gly Tyr Phe Thr Ile Cys
65               70               75               80

Gln Asp Asp Lys Phe Lys Asn Glu Ser Leu Tyr Lys Ile Phe His Lys
                85               90               95

Ser Phe Pro Ile Asn His Gly Thr Asn Ile Ile Asn Asn Ile Ile Ser
        100               105               110

Glu Lys Asn Ile Asp Gln Tyr Asp Gly Asn Thr Leu Gly Phe Arg Pro
        115               120               125

Thr Met Tyr Arg Leu Arg Gly Tyr Val Asp Ser Val Ile Gly Asn Tyr
        130               135               140

Arg Thr Thr Ile Arg Thr Ile Lys Pro Ser Val Lys Arg His Lys Ile
145               150               155               160

Ser Val Asp Ser Ser Phe Asp Glu Lys Met Glu Gln Cys Ile Tyr Glu
        165               170               175

Ile Gln Lys Gly Asn Leu Lys Thr Val Ser Glu Trp Asn Asn Lys Ile
        180               185               190

Asp Tyr Leu Leu Ser Lys Ser Asp Met Asn Pro Leu Thr Ile Asp Arg
        195               200               205

Phe Asn Leu Leu Arg Asp Phe Tyr Val Asp Asn Glu Thr Glu Val Asn
        210               215               220

Glu Lys Ser Asn Asn Ser Ser Ile Glu Gln Leu Val Lys Phe Gly Gly
225               230               235               240

Cys His Arg Lys Gly Asp Asn Met Thr Leu Ser Leu Thr Glu Ala Asn
                245               250               255

Phe Ser Ile Glu Glu Ile Asp Asp Ser Tyr Gly Tyr Leu Leu Thr Leu
        260               265               270

His Thr Asp Ser Gly Asp Tyr Lys Ile Pro Leu Met Gly Ser Lys Met
        275               280               285

Leu Lys Lys Gly Asp Lys Cys Leu Ile Asp Phe Val Asn Cys Lys Lys
        290               295               300

Gly Lys Ser Leu Thr Ala Lys Ile Asp Asn Asp Tyr Asn Leu Tyr Phe
305               310               315               320
```

-continued

```
His Phe Val Val Tyr Ser Asn Phe Glu Lys Ile Glu Asp Asp Asn Ile
            325                 330                 335

Asn Asn Val Val Gly Val Asp Val Asn Ser Lys His Met Leu Leu Met
            340                 345                 350

Thr Asn Val Ile Asp Asp Asn Ile Asp Gly Tyr Val Asn Ile Tyr Lys
            355                 360                 365

Ala Leu Val Asn Asp Asp Glu Phe Lys Ser Leu Val Thr Lys Ser Glu
            370                 375                 380

Tyr Asp Asp Tyr Val Thr Met Ser Lys Tyr Val Thr Phe Cys Pro Ile
385                 390                 395                 400

Glu Leu Lys Tyr Leu Tyr Ala Arg Tyr Cys Val Gln Lys Asp Tyr Pro
            405                 410                 415

Ile Ser Asn Lys Asp Val Ala Ile Glu Gln Cys Ile Ser Arg Val Ile
            420                 425                 430

Asp Lys Leu Cys Lys Glu Thr Leu Asp Ser Arg Ala Asn Asn Tyr Leu
            435                 440                 445

Cys Met Val Arg Arg Ile Arg His Tyr Tyr Lys Ser Tyr Tyr Val Leu
            450                 455                 460

Lys Met Thr Tyr Tyr Asp Lys Met Ser Glu Tyr Asp Thr Asn Met Glu
465                 470                 475                 480

Tyr Asn Asp Ile Ser Thr Thr Ser Lys Glu Thr Met Asp Gln Arg Arg
            485                 490                 495

Phe Glu Asn Ser Phe Arg Glu Thr Asp Cys Ala Lys Glu Ile Leu Ser
            500                 505                 510

Lys Leu Asp Lys Ile Gly Asn Asp Ile Leu Gly Cys Arg Asn Asn Ile
            515                 520                 525

Leu Thr Tyr Ala Tyr Lys Leu Phe Glu Glu Leu Gly Tyr Asp Thr Ile
            530                 535                 540

Ala Leu Glu Asn Leu Glu Ser Ser Gln Phe Asp Lys Met Lys Ser Leu
545                 550                 555                 560

Pro Ser Cys Gln Ser Met Leu Lys Tyr His Lys Leu Glu Gly Lys Thr
            565                 570                 575

Met Glu Glu Val Met Ser Asn Thr Ser Val Lys Ser Leu Ile Glu Asn
            580                 585                 590

Glu Tyr Tyr Asp Phe Ser Leu Asn Asp Asn Lys Thr Val Glu Asn Ile
            595                 600                 605

Thr Tyr Thr Lys Asn Gly Leu Met Lys Lys Gly Phe Asp Glu Phe Phe
            610                 615                 620

Asn Leu Phe Met Lys Ile Ile His Phe Ala Asp Ile Lys Asp Lys Phe
625                 630                 635                 640

Leu Gln Leu Tyr Asn Asn Gly Ser Val Lys Val Ile Leu Val Pro Ser
            645                 650                 655

Tyr Phe Thr Ser Gln Met Asp Ser Ser Asn His Ser Ile Tyr Met Glu
            660                 665                 670

Lys Ser Lys Asn Asp Lys Leu Val Phe Ala Ser Lys His Lys Val Arg
            675                 680                 685

Lys Thr Gln Glu Thr His Leu Asn Gly Leu Asn Ala Asp Tyr Asn Ala
            690                 695                 700

Ala Cys Asn Ile Ala Tyr Ile Ala Lys Asp Ile Lys Trp Arg Glu Lys
705                 710                 715                 720

Phe Cys Lys Lys Thr Ser Asn Asn Gly Tyr Ser Thr Pro Phe Tyr Asp
            725                 730                 735
```

-continued

```
Cys Ala Thr Lys Asn Gln Ile Glu Met Val Lys Arg Ile Lys Gln Leu
            740                 745                 750

Asn Ala Ile Lys Met Leu Ala
        755

<210> SEQ ID NO 128
<211> LENGTH: 746
<212> TYPE: PRT
<213> ORGANISM: Artificial sequence
<220> FEATURE:
<223> OTHER INFORMATION: synthetic sequence

<400> SEQUENCE: 128

Met Ala Ser His Lys Lys Thr Glu Ser Asn Gln Ile Ile Lys Thr Phe
1               5                   10                  15

Ser Phe Lys Ile Lys Asn Ala Asn Gly Leu Ser Leu Asp Val Leu Asn
            20                  25                  30

Asp Ala Ile Thr Glu Tyr Gln Asn Tyr Tyr Asn Ile Cys Ser Asp Trp
        35                  40                  45

Ile Lys Asp His Leu Thr Met Lys Ile Gly Glu Leu Tyr Lys Tyr Ile
    50                  55                  60

Pro Asp Glu Lys Lys Asn Ser Gly Tyr Ala Leu Thr Leu Ile Ser Asp
65                  70                  75                  80

Glu Trp Lys Asp Lys Pro Met Tyr Met Met Phe Lys Lys Gly Tyr Pro
                85                  90                  95

Ala Asn Ser Arg Asp Asn Ala Ile Tyr Glu Ala Leu Asn Thr Cys Asn
            100                 105                 110

Thr Glu His Tyr Thr Gly Asn Ile Leu Asn Phe Ser Asp Thr Tyr Tyr
            115                 120                 125

Arg Arg Phe Gly Tyr Val Ala Ser Thr Ile Ser Asn Tyr Val Thr Lys
        130                 135                 140

Ile Ser Lys Met Ser Thr Gly Ser Arg Ser Lys Asn Ile Ser Asn Asp
145                 150                 155                 160

Ser Asp Val Asp Thr Ile Met Glu Gln Val Ile Tyr Glu Met Glu His
                165                 170                 175

Asn Gly Trp Thr Ser Val Lys Asp Trp Glu Asn Gln Met Glu Tyr Leu
            180                 185                 190

Glu Ser Lys Thr Asp Ser Asn Pro Asn Phe Val Tyr Arg Met Thr Thr
            195                 200                 205

Leu Tyr Glu Phe Tyr Lys Ser His Ile Asp Glu Val Asn Ser Lys Met
        210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
            245                 250                 255

Phe Asp Ile Thr Gln Ile Gly Gly Asn Ser Leu Asn Ile Lys Phe Ser
            260                 265                 270

Lys Asn Leu Asn Val Asp Val Phe Gly Arg Tyr Asp Val Ile Lys Asp
        275                 280                 285

Asn Thr Leu Leu Val Asp Ile Ile Asn Gly His Gly Ala Ser Phe Val
    290                 295                 300

Leu Lys Ile Ile Asn Asp Glu Ile Tyr Ile Asp Ile Asn Val Ser Val
305                 310                 315                 320

Pro Phe Asp Lys Lys Ile Ala Thr Thr Asn Lys Val Val Gly Val Asp
            325                 330                 335
```

-continued

```
Val Asn Ile Lys His Met Leu Leu Ala Thr Asn Ile Leu Asp Asp Gly
        340                 345                 350

Asn Val Asn Gly Tyr Val Asn Ile Tyr Lys Glu Val Ile Asn Asp Ser
        355                 360                 365

Asp Phe Lys Lys Val Cys Asn Ser Thr Val Met Lys Tyr Phe Thr Asp
    370                 375                 380

Phe Ser Lys Phe Val Thr Phe Cys Pro Leu Glu Phe Asp Phe Leu Phe
385                 390                 395                 400

Ser Arg Val Cys Asn Gln Lys Gly Ile Tyr Asn Asp Asn Ser Ala Met
            405                 410                 415

Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
        435                 440                 445

Leu Arg Ser Gln Met Lys Ala Tyr Ala Ile Val Lys Asn Ala Tyr Tyr
    450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu Asn Lys
                485                 490                 495

Leu Asp Asn Ile Ser Lys Lys Ile Leu Gly Cys Arg Asn Asn Ile Ile
            500                 505                 510

Gln Tyr Ser Tyr Asn Leu Phe Glu Ile Asn Gly Tyr Asp Met Ile Ser
            515                 520                 525

Leu Glu Lys Leu Thr Ser Ser Gln Phe Lys Lys Lys Ser Phe Pro Thr
    530                 535                 540

Val Asp Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
                565                 570                 575

Asp Ile Ile Phe Asp Asn Asp Val Val Thr Asp Ala Lys Leu Ser Thr
            580                 585                 590

Lys Gly Glu Leu Ser Lys Phe Lys Asp Asp Phe Phe Asn Leu Met Ile
        595                 600                 605

Lys Ser Ile His Phe Ala Asp Ile Lys Asp Tyr Phe Ile Thr Leu Ser
    610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
                645                 650                 655

Ser Gly Lys Leu Lys Leu Ala Asn Lys His Lys Val Arg Ser Ser Gln
            660                 665                 670

Glu Lys His Ile Asn Gly Leu Asn Ala Asp Tyr Asn Ala Ala Arg Asn
        675                 680                 685

Ile Ala Tyr Ile Met Glu Asn Thr Glu Cys Arg Asn Met Phe Met Lys
    690                 695                 700

Gln Ser Arg Thr Asp Lys Ser Leu Tyr Asn Lys Pro Ser Tyr Glu Thr
705                 710                 715                 720

Phe Ile Lys Thr Gln Gly Ser Ala Val Ala Lys Leu Lys Lys Glu Gly
                725                 730                 735

Phe Val Lys Ile Leu Asp Glu Ala Ser Val
                740                 745
```

```
<210> SEQ ID NO 129
<211> LENGTH: 746
<212> TYPE: PRT
<213> ORGANISM: Artificial sequence
<220> FEATURE:
<223> OTHER INFORMATION: synthetic sequence

<400> SEQUENCE: 129

Met Ala Ser His Lys Lys Thr Glu Ser Asn Gln Ile Ile Lys Thr Phe
1               5                   10                  15

Ser Phe Lys Ile Lys Asn Ala Asn Gly Leu Ser Leu Asp Val Leu Asn
            20                  25                  30

Asp Ala Ile Thr Glu Tyr Gln Asn Tyr Tyr Asn Ile Cys Ser Asp Trp
        35                  40                  45

Ile Lys Asp His Leu Thr Met Lys Ile Gly Glu Leu Tyr Lys Tyr Ile
    50                  55                  60

Pro Asp Glu Lys Lys Asn Ser Gly Tyr Ala Leu Thr Leu Ile Ser Asp
65                  70                  75                  80

Glu Trp Lys Asp Lys Pro Met Tyr Met Met Phe Lys Lys Gly Tyr Pro
                85                  90                  95

Ala Asn Ser Arg Asp Asn Ala Ile Tyr Glu Ala Leu Asn Thr Cys Asn
            100                 105                 110

Thr Glu His Tyr Thr Gly Asn Ile Leu Asn Phe Ser Asp Thr Tyr Tyr
            115                 120                 125

Arg Arg Phe Gly Tyr Val Ala Ser Ala Ile Ser Asn Tyr Val Thr Lys
    130                 135                 140

Ile Ser Lys Met Ser Thr Gly Ser Arg Ser Lys Asn Ile Ser Asn Asp
145                 150                 155                 160

Ser Asp Val Asp Thr Ile Met Glu Gln Val Ile Tyr Glu Met Glu His
            165                 170                 175

Asn Gly Trp Thr Ser Val Lys Asp Trp Glu Asn Gln Met Glu Tyr Leu
            180                 185                 190

Glu Ser Lys Thr Asp Ser Asn Pro Asn Phe Val Tyr Arg Met Thr Thr
            195                 200                 205

Leu Tyr Glu Phe Tyr Lys Ser His Ile Asp Glu Val Asn Ser Lys Met
    210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
            245                 250                 255

Phe Asp Ile Thr Gln Ile Asp Gly Asn Ser Leu Asn Ile Lys Phe Ser
            260                 265                 270

Lys Asn Leu Asn Val Asp Val Phe Gly Arg Tyr Asp Val Ile Lys Asp
            275                 280                 285

Asn Thr Leu Leu Val Asp Ile Ile Asn Gly His Gly Ala Ser Phe Val
    290                 295                 300

Leu Lys Ile Ile Asn Asp Glu Ile Tyr Ile Asp Ile Asn Val Ser Val
305                 310                 315                 320

Pro Phe Asp Lys Lys Ile Ala Thr Thr Asn Lys Val Val Gly Ile Asp
            325                 330                 335

Val Asn Ile Lys His Met Leu Leu Ala Thr Asn Ile Leu Asp Asp Gly
            340                 345                 350

Asn Val Asn Gly Tyr Val Asn Ile Tyr Lys Glu Val Ile Asn Asp Ser
            355                 360                 365

Asp Phe Lys Lys Val Cys Asn Ser Thr Val Met Lys Tyr Phe Thr Asp
```

-continued

```
      370                 375                 380

Phe Ser Lys Phe Val Thr Phe Cys Pro Leu Glu Phe Asp Phe Leu Phe
385                 390                 395                 400

Ser Arg Val Cys Asn Gln Lys Gly Ile Tyr Asn Asp Asn Ser Ala Met
                405                 410                 415

Glu Lys Ser Phe Ser Asn Val Leu Asn Lys Leu Lys Trp Asn Phe Ile
            420                 425                 430

Glu Thr Gly Asp Asn Thr Lys Arg Ile Tyr Ile Glu Asn Val Met Lys
            435                 440                 445

Leu Arg Ser Gln Met Lys Ala Tyr Ala Ile Val Lys Asn Ala Tyr Tyr
    450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu Asn Lys
                485                 490                 495

Leu Asp Asn Ile Ser Lys Lys Ile Leu Gly Cys Arg Asn Asn Ile Ile
                500                 505                 510

Gln Tyr Ser Tyr Asn Leu Phe Glu Ile Asn Gly Tyr Asp Met Ile Ser
            515                 520                 525

Leu Glu Lys Leu Thr Ser Ser Gln Phe Lys Lys Lys Pro Phe Pro Thr
    530                 535                 540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
            565                 570                 575

Asp Ile Ile Phe Asp Asn Asp Val Val Thr Asp Ala Lys Leu Ser Ala
            580                 585                 590

Lys Gly Glu Leu Ser Lys Phe Lys Asp Asp Phe Phe Asn Leu Met Ile
            595                 600                 605

Lys Ser Ile His Phe Ala Asp Ile Lys Asp Tyr Phe Ile Thr Leu Ser
    610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
                645                 650                 655

Ser Gly Lys Leu Lys Leu Ala Asn Lys His Lys Val Arg Ser Ser Gln
                660                 665                 670

Glu Lys His Ile Asn Gly Leu Asn Ala Asp Tyr Asn Ala Ala Arg Asn
            675                 680                 685

Ile Ala Tyr Ile Met Glu Asn Thr Asp Cys Arg Asn Met Phe Met Lys
    690                 695                 700

Gln Ser Arg Thr Asp Lys Ser Leu Tyr Asn Lys Pro Ser Tyr Glu Thr
705                 710                 715                 720

Phe Ile Lys Thr Gln Gly Ser Ala Val Ala Lys Leu Lys Lys Glu Gly
                725                 730                 735

Phe Val Lys Ile Leu Asp Glu Ala Ser Val
                740                 745
```

<210> SEQ ID NO 130
<211> LENGTH: 746
<212> TYPE: PRT
<213> ORGANISM: Artificial sequence
<220> FEATURE:
<223> OTHER INFORMATION: synthetic sequence -continued

<400> SEQUENCE: 130

```
Met Ala Ser His Lys Lys Thr Glu Ser Asn Gln Ile Ile Lys Thr Phe
1               5                   10                  15

Ser Phe Lys Ile Lys Asn Ala Asn Gly Leu Ser Leu Asp Val Leu Asn
                20                  25                  30

Asp Ala Ile Thr Glu Tyr Gln Asn Tyr Tyr Asn Ile Cys Ser Asp Trp
            35                  40                  45

Ile Lys Asp His Leu Thr Met Lys Ile Gly Glu Leu Tyr Lys Tyr Ile
    50                  55                  60

Pro Asp Glu Lys Lys Asn Ser Gly Tyr Ala Leu Thr Leu Ile Ser Asp
65                  70                  75                  80

Glu Trp Lys Asp Lys Pro Met Tyr Met Met Phe Lys Lys Gly Tyr Pro
                85                  90                  95

Ala Asn Asn Arg Asp Asn Ala Ile Tyr Glu Thr Leu Asn Thr Cys Asn
                100                 105                 110

Thr Glu His Tyr Thr Gly Asn Ile Leu Asn Phe Ser Asp Thr Tyr Tyr
            115                 120                 125

Arg Arg Phe Gly Tyr Val Ala Ser Thr Ile Ser Asn Tyr Val Thr Lys
    130                 135                 140

Ile Ser Lys Met Ser Thr Arg Ser Arg Ser Lys Asn Ile Ser Asn Asp
145                 150                 155                 160

Ser Asp Val Asp Thr Ile Met Glu Gln Val Ile Tyr Glu Met Glu His
                165                 170                 175

Asn Gly Trp Thr Ser Val Lys Asp Trp Glu Asn Gln Met Glu Tyr Leu
            180                 185                 190

Glu Ser Lys Thr Asp Ser Asn Pro Asn Phe Val Tyr Arg Met Thr Thr
            195                 200                 205

Leu Tyr Glu Phe Tyr Lys Ser His Ile Asp Glu Val Asn Ser Lys Met
    210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
                245                 250                 255

Phe Asp Ile Thr Gln Ile Gly Gly Asn Ser Leu Asn Ile Lys Phe Ser
            260                 265                 270

Lys Asn Leu Asn Val Asp Val Phe Gly Arg Tyr Asp Val Ile Lys Asp
            275                 280                 285

Asn Thr Leu Leu Val Asp Ile Ile Asn Gly His Gly Ala Ser Phe Val
    290                 295                 300

Leu Lys Ile Ile Asn Gly Glu Ile Tyr Ile Asp Ile Asn Val Ser Val
305                 310                 315                 320

Pro Phe Asp Lys Lys Ile Ala Thr Thr Asn Lys Val Val Gly Ile Asp
                325                 330                 335

Val Asn Ile Lys His Met Leu Leu Ala Thr Asn Ile Leu Asp Asp Gly
            340                 345                 350

Asn Val Asn Gly Tyr Val Asn Ile Tyr Lys Glu Val Ile Asn Asp Ser
            355                 360                 365

Asp Phe Lys Lys Val Cys Asn Ser Thr Val Met Lys Tyr Phe Thr Asp
    370                 375                 380

Phe Ser Lys Phe Val Thr Phe Cys Pro Leu Glu Phe Asp Phe Leu Phe
385                 390                 395                 400

Ser Arg Val Cys Asn Gln Lys Gly Ile Tyr Asn Asp Asn Ser Ala Met
                405                 410                 415
```

-continued

```
Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
            435                 440                 445

Leu Arg Ser Gln Met Lys Ala Tyr Ala Ile Val Lys Asn Ala Tyr Tyr
            450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu Asn Lys
                485                 490                 495

Leu Asp Asn Ile Ser Lys Lys Ile Leu Gly Cys Arg Asn Asn Ile Ile
                500                 505                 510

Gln Tyr Ser Tyr Asn Leu Phe Glu Ile Asn Gly Tyr Asp Met Ile Ser
            515                 520                 525

Leu Glu Lys Leu Thr Ser Ser Gln Phe Lys Lys Lys Pro Phe Pro Thr
            530                 535                 540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
                565                 570                 575

Asp Ile Ile Phe Asp Asn Asp Val Val Thr Asp Ala Lys Leu Ser Thr
                580                 585                 590

Lys Gly Glu Leu Ser Lys Phe Lys Asp Asp Phe Phe Asn Leu Met Ile
            595                 600                 605

Lys Ser Ile His Phe Ala Asp Ile Lys Asp Tyr Phe Ile Thr Leu Ser
            610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
                645                 650                 655

Ser Gly Lys Leu Lys Leu Ala Asn Lys His Lys Val Arg Ser Ser Gln
                660                 665                 670

Glu Lys His Ile Asn Gly Leu Asn Ala Asp Tyr Asn Ala Ala Arg Asn
            675                 680                 685

Ile Ala Tyr Ile Met Glu Asn Thr Asp Cys Arg Asn Met Phe Met Lys
            690                 695                 700

Gln Ser Arg Thr Asp Lys Ser Leu Tyr Asn Lys Pro Ser Tyr Glu Thr
705                 710                 715                 720

Phe Ile Lys Thr Gln Gly Ser Ala Val Ala Lys Leu Lys Lys Glu Gly
                725                 730                 735

Phe Val Lys Ile Leu Asp Glu Ala Ser Val
            740                 745
```

```
<210> SEQ ID NO 131
<211> LENGTH: 47
<212> TYPE: PRT
<213> ORGANISM: Artificial sequence
<220> FEATURE:
<223> OTHER INFORMATION: synthetic sequence

<400> SEQUENCE: 131
```

```
Asn Met Phe Met Lys Gln Ser Arg Thr Asp Lys Ser Leu Tyr Asn Lys
1               5                   10                  15

Pro Ser Tyr Glu Thr Phe Ile Lys Thr Gln Gly Ser Ala Val Ala Lys
            20                  25                  30
```

-continued

```
Leu Lys Lys Glu Gly Phe Val Lys Ile Leu Asp Glu Ala Ser Val
        35              40              45

<210> SEQ ID NO 132
<211> LENGTH: 746
<212> TYPE: PRT
<213> ORGANISM: Artificial sequence
<220> FEATURE:
<223> OTHER INFORMATION: synthetic sequence

<400> SEQUENCE: 132

Met Ala Ser His Lys Lys Thr Glu Ser Asn Gln Ile Ile Lys Thr Phe
1               5               10              15

Ser Phe Lys Ile Lys Asn Ala Asn Gly Leu Ser Leu Asp Val Leu Asn
                20              25              30

Asp Ala Ile Thr Glu Tyr Gln Asn Tyr Tyr Asn Ile Cys Ser Asp Trp
            35              40              45

Ile Lys Asp His Leu Thr Met Lys Ile Gly Glu Leu Tyr Lys Tyr Ile
        50              55              60

Pro Asp Glu Lys Lys Asn Ser Gly Tyr Ala Leu Thr Leu Ile Ser Asp
65              70              75              80

Glu Trp Lys Asp Lys Pro Met Tyr Met Met Phe Lys Lys Gly Tyr Pro
                85              90              95

Ala Asn Asn Arg Asp Asn Ala Ile Tyr Glu Thr Leu Asn Thr Cys Asn
                100             105             110

Thr Glu His Tyr Thr Gly Asn Ile Leu Asn Phe Ser Asp Thr Tyr Tyr
            115             120             125

Arg Arg Phe Gly Tyr Val Ala Ser Thr Ile Ser Asn Tyr Val Thr Lys
        130             135             140

Ile Ser Lys Met Ser Thr Gly Ser Arg Ser Lys Asn Ile Ser Asn Asp
145             150             155             160

Ser Asp Val Asp Thr Ile Met Glu Gln Val Ile Tyr Glu Met Glu His
                165             170             175

Asn Gly Trp Thr Ser Val Lys Asp Trp Glu Asn Gln Met Glu Tyr Leu
            180             185             190

Glu Ser Lys Thr Asp Ser Asn Pro Asn Phe Val Tyr Arg Met Thr Thr
        195             200             205

Leu Tyr Glu Phe Tyr Lys Ser His Ile Asp Glu Val Asn Ser Lys Met
        210             215             220

Glu Thr Met Ser Ile Asp Ser Leu Ile Lys Phe Gly Gly Cys Arg Arg
225             230             235             240

Lys Asp Ser Lys Lys Ser Met Tyr Ile Met Gly Gly Ser Asn Thr Pro
                245             250             255

Phe Asp Ile Thr Gln Ile Gly Gly Asn Phe Leu Asn Ile Lys Phe Ser
            260             265             270

Lys Asn Leu Asn Val Asp Val Phe Gly Arg Tyr Asp Val Ile Lys Asp
        275             280             285

Asn Thr Leu Leu Val Asp Ile Ile Asn Glu His Gly Ala Ser Phe Val
        290             295             300

Leu Lys Ile Ile Asn Asp Glu Ile Tyr Ile Asp Ile Asn Val Ser Val
305             310             315             320

Pro Phe Asp Lys Lys Ile Ala Thr Thr Asn Lys Val Val Gly Val Asp
                325             330             335

Val Asn Ile Lys His Met Leu Leu Ala Thr Asn Ile Leu Asp Asp Gly
        340             345             350
```

-continued

```
Asn Val Asn Gly Tyr Val Asn Ile Tyr Lys Glu Val Ile Asn Asp Ser
        355                 360                 365

Asp Phe Lys Lys Val Cys Asn Ser Thr Val Met Lys Tyr Phe Thr Asp
    370                 375                 380

Phe Ser Lys Phe Val Thr Phe Cys Pro Leu Glu Phe Asp Phe Leu Phe
385                 390                 395                 400

Ser Arg Val Cys Asn Gln Lys Gly Ile Tyr Asn Asp Asn Ser Ala Met
            405                 410                 415

Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
        435                 440                 445

Leu Arg Ser Gln Met Lys Ala Tyr Ala Ile Val Lys Asn Ala Tyr Tyr
    450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu His Lys
            485                 490                 495

Leu Asp Asn Ile Ser Lys Lys Ile Leu Gly Cys Arg Asn Asn Ile Ile
            500                 505                 510

Gln Tyr Ser Tyr Asn Leu Phe Glu Ile Asn Gly Tyr Asp Met Ile Ser
        515                 520                 525

Leu Glu Lys Leu Thr Ser Ser Gln Phe Lys Lys Lys Pro Phe Pro Thr
    530                 535                 540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
            565                 570                 575

Asp Ile Ile Phe Asp Asn Asp Val Val Thr Asp Ala Lys Leu Ser Thr
            580                 585                 590

Lys Gly Glu Leu Ser Lys Phe Lys Asp Asp Phe Phe Asn Leu Met Ile
        595                 600                 605

Lys Ser Ile His Phe Ala Asp Ile Lys Asp Tyr Phe Ile Thr Leu Ser
    610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
            645                 650                 655

Ser Gly Lys Leu Lys Leu Ala Asn Lys His Lys Val Arg Ser Ser Gln
            660                 665                 670

Glu Lys His Ile Asn Gly Leu Asn Ala Asp Tyr Asn Ala Ala Arg Asn
        675                 680                 685

Ile Ala Tyr Ile Met Glu Asn Thr Glu Cys Arg Asn Met Phe Met Lys
    690                 695                 700

Gln Ser Arg Thr Asp Lys Ser Leu Tyr Asn Lys Pro Ser Tyr Glu Thr
705                 710                 715                 720

Phe Ile Lys Thr Gln Gly Ser Ala Val Ala Lys Leu Lys Lys Glu Gly
            725                 730                 735

Phe Val Lys Ile Leu Asp Glu Ala Ser Val
        740                 745
```

<210> SEQ ID NO 133
<211> LENGTH: 245

<212> TYPE: PRT
<213> ORGANISM: Artificial sequence
<220> FEATURE:
<223> OTHER INFORMATION: synthetic sequence

<400> SEQUENCE: 133

```
Lys Lys Ile Leu Gly Cys Arg Asn Asn Ile Ile Gln Tyr Ser Tyr Asn
1               5                   10                  15

Leu Phe Glu Ile Asn Gly Tyr Asp Met Ile Ser Leu Glu Lys Leu Thr
                20                  25                  30

Ser Ser Gln Phe Lys Lys Lys Pro Phe Pro Thr Val Asn Ser Leu Leu
            35                  40                  45

Lys Tyr His Lys Ile Leu Gly Cys Thr Gln Glu Glu Met Glu Lys Lys
    50                  55                  60

Asp Ile Tyr Ser Val Ile Lys Lys Gly Tyr Tyr Asp Ile Ile Phe Asp
65                  70                  75                  80

Asn Asp Val Val Thr Asp Ala Lys Leu Ser Thr Lys Gly Glu Leu Ser
                85                  90                  95

Lys Phe Lys Asp Asp Phe Phe Asn Leu Met Ile Lys Ser Ile His Phe
            100                 105                 110

Ala Asp Ile Lys Asp Tyr Phe Ile Thr Leu Ser Asn Asn Gly Thr Ala
            115                 120                 125

Gly Val Ser Leu Val Pro Ser Tyr Phe Thr Ser Gln Met Asp Ser Ile
    130                 135                 140

Asp His Lys Ile Tyr Phe Val Gln Asp Asn Lys Ser Gly Lys Leu Lys
145                 150                 155                 160

Leu Ala Asn Lys His Lys Val Arg Ser Ser Gln Glu Lys His Ile Asn
                165                 170                 175

Gly Leu Asn Ala Asp Tyr Asn Ala Ala Arg Asn Ile Ala Tyr Ile Met
            180                 185                 190

Glu Asn Thr Glu Cys Arg Asn Met Phe Met Lys Gln Ser Arg Thr Asp
            195                 200                 205

Lys Ser Leu Tyr Asn Lys Pro Ser Tyr Glu Thr Phe Ile Lys Thr Gln
    210                 215                 220

Gly Ser Ala Val Ala Lys Leu Lys Lys Glu Gly Phe Val Lys Ile Leu
225                 230                 235                 240

Asp Glu Ala Ser Val
            245
```

<210> SEQ ID NO 134
<211> LENGTH: 178
<212> TYPE: PRT
<213> ORGANISM: Artificial sequence
<220> FEATURE:
<223> OTHER INFORMATION: synthetic sequence

<400> SEQUENCE: 134

```
Asn Ala Tyr Tyr Lys Gln Gln Ser Glu Tyr Asp Phe Gly Lys Ser Glu
1               5                   10                  15

Glu Phe Ile Gln Glu His Pro Phe Ser Asn Thr Asp Lys Gly Ile Glu
                20                  25                  30

Ile Leu His Lys Leu Asp Asn Ile Ser Lys Lys Ile Leu Gly Cys Arg
            35                  40                  45

Asn Asn Ile Ile Gln Tyr Ser Tyr Asn Leu Phe Glu Ile Asn Gly Tyr
    50                  55                  60

Asp Met Ile Ser Leu Glu Lys Leu Thr Ser Ser Gln Phe Glu Lys Lys
65                  70                  75                  80
```

-continued

```
Pro Phe Pro Thr Val Asn Ser Leu Leu Lys Tyr His Lys Ile Leu Gly
                85                  90                  95

Cys Thr Gln Glu Glu Met Glu Lys Lys Asp Ile Tyr Ser Val Ile Lys
                100                 105                 110

Lys Gly Tyr Tyr Asp Ile Ile Phe Asp Asn Asp Val Val Thr Asp Ala
                115                 120                 125

Lys Leu Ser Thr Lys Gly Glu Leu Ser Lys Phe Lys Asp Asp Phe Phe
    130                 135                 140

Asn Leu Met Ile Lys Ser Ile His Phe Ala Asp Ile Lys Asp Tyr Phe
145                 150                 155                 160

Ile Thr Leu Ser Asn Asn Gly Thr Val Gly Val Ser Leu Val Pro Ser
                165                 170                 175

Thr Val

<210> SEQ ID NO 135
<211> LENGTH: 85
<212> TYPE: PRT
<213> ORGANISM: Artificial sequence
<220> FEATURE:
<223> OTHER INFORMATION: synthetic sequence

<400> SEQUENCE: 135

Met Ala Asn Lys His Lys Val Arg Ser Ser Gln Glu Lys His Ile Asn
1               5                   10                  15

Gly Leu Asn Ala Asp Tyr Asn Ala Ala Arg Asn Ile Ala Tyr Ile Ile
                20                  25                  30

Glu Asn Thr Glu Cys Arg Asn Met Phe Met Lys Gln Ser Arg Thr Asp
                35                  40                  45

Lys Ser Leu Tyr Asn Lys Pro Ser Tyr Glu Thr Phe Ile Lys Thr Gln
    50                  55                  60

Gly Ser Thr Val Ala Lys Leu Lys Lys Glu Gly Phe Val Lys Ile Leu
65                  70                  75                  80

Asp Glu Ala Ser Val
                85

<210> SEQ ID NO 136
<211> LENGTH: 767
<212> TYPE: PRT
<213> ORGANISM: Artificial sequence
<220> FEATURE:
<223> OTHER INFORMATION: synthetic sequence

<400> SEQUENCE: 136

Met Ala His Lys Lys Gln Lys Glu Glu Asn Glu Ile Ile Lys Thr Ile
1               5                   10                  15

Ser Leu Lys Val Lys Asp Tyr Ala Gly Tyr Pro Ile Val Glu Ala Met
                20                  25                  30

Arg Glu Tyr Thr Lys Tyr Tyr Asn Lys Ile Ser Gln Trp Ile Asn Ser
                35                  40                  45

Asn Leu Leu Thr Ile Lys Ile Gly Glu Leu Ser Ala Phe Met Pro Asp
    50                  55                  60

Glu Cys Lys Thr His Asn Tyr Tyr Thr Tyr Met Met Ser Pro Asp Trp
65                  70                  75                  80

Val Asn Glu Pro Leu Tyr Lys Met Phe Met Lys Gly Phe His Ala Gln
                85                  90                  95

His Cys Asp Asn Ile Leu Phe Asn Val Val Lys Thr Leu Asn Ile Asp
                100                 105                 110
```

-continued

```
Glu Tyr Ala Gly Asn Ser Leu Gly Leu Ser Ala Ser Cys Phe Arg Arg
        115                 120                 125

Ser Gly Tyr Phe Gln Asn Val Val Ser Asn Tyr Lys Ser Lys Phe Ala
        130                 135                 140

Asn Pro His Ile Ser Ile Arg Arg Lys Asn Leu Ser Asp Leu Pro Thr
145                 150                 155                 160

Glu Asp Glu Leu Val Glu Gln Cys Ile Tyr Glu Ile Gln Asn Gly Leu
                165                 170                 175

Ser Ser Lys Thr Lys Trp Glu Glu Gln Ile Glu Tyr Leu Lys Glu Arg
                180                 185                 190

Asp Asp Ser Lys Gln Ile Tyr Leu Thr Arg Leu Asn Thr Leu Phe Met
                195                 200                 205

Tyr Tyr Lys Ala Asn Lys Asp Phe Val Asp Glu Gln Ile Gln Ile Lys
        210                 215                 220

Ser Val Glu Ser Leu Ala Asn Phe Gly Gly Cys Val Arg Lys Asp Asp
225                 230                 235                 240

Lys Leu Ser Met Asn Leu Val Phe Ser Ser Asn Ser Pro Tyr Lys Val
                245                 250                 255

Val Leu Asn Glu Lys Arg Asn Gly Tyr Ile Leu Ser Tyr Ser Asn Asn
                260                 265                 270

Phe Ser Ile Glu Leu Tyr Gly Asn Arg Met Gly Leu Leu Asn Gly Val
                275                 280                 285

Glu Val Phe Asn Val Gly Asp Lys His Ser Asn Asn Ile Thr Phe Lys
        290                 295                 300

Met Asp Asn Asp Glu Leu Phe Val Asn Ile Pro Val Ser Val Asn Phe
305                 310                 315                 320

Val Lys Lys Ala Asn Glu Thr Asn Lys Val Val Gly Val Asp Val Asn
                325                 330                 335

Leu Lys His Ser Ile Phe Ala Thr Asn Ile Ile Asp Asp Gly Lys Leu
                340                 345                 350

Asp Gly Phe Val Asn Ile Tyr Arg Glu Leu Leu Asn Asp Val Asp Phe
        355                 360                 365

Val Lys Ser Cys Pro Asn Glu Leu Leu Asn Phe Ile Leu Asp Val Glu
        370                 375                 380

Lys Tyr Ala Phe Phe Met Pro Leu Glu Leu Gly Leu Leu Ser Ser Arg
385                 390                 395                 400

Val Met Asn Gln Cys Gly Tyr Ser Thr Ile Gly Lys Tyr Glu Lys Leu
                405                 410                 415

Phe Thr Thr Glu Glu His Phe Phe Arg Val Leu Arg Gln Leu Glu Lys
                420                 425                 430

Arg Phe Gln Glu Ser Gly Glu Asn Gln Lys Arg Ile Tyr Ile Glu Asn
        435                 440                 445

Val Ile Lys Met Arg Ala Gln Val Lys Ala Tyr Phe Thr Leu Lys Tyr
        450                 455                 460

Ala Tyr Asn Lys Ala Asn Lys Asp Tyr Asp Leu Lys Met Gly Phe Val
465                 470                 475                 480

Asp Glu Ser Thr Ala Asn Lys Glu Thr Met Asp Gln Arg Arg Phe Glu
                485                 490                 495

Asn Gln Phe Val Asn Thr Tyr Thr Ala Lys Glu Ile Leu Gly Lys Met
        500                 505                 510

Arg Arg Ile Ala Asn Val Ile Thr Ser Cys Arg Asn Asn Ile Ile Cys
        515                 520                 525
```

-continued

```
Tyr Met Tyr Lys Ile Phe Glu Asn Asn Gly Tyr Gly Val Val Ala Leu
    530                 535                 540

Glu Lys Leu Gln Ser Ser Gln Met Lys Lys Glu Lys Arg Ile Pro Ser
545                 550                 555                 560

Leu Leu Ser Leu Leu Lys Lys Gln Lys Val Glu Gly Tyr Thr Ile Asn
                565                 570                 575

Glu Leu Lys Asp Lys Ser Val Phe Lys Phe Ile Glu Arg Gly Tyr Tyr
                580                 585                 590

Thr Phe Asp Phe Asp Asp Asp Asn Lys Ile Thr Gly Val Gln Phe Ser
                595                 600                 605

Asp Ala Gly Glu Val Val Asn Met Glu Thr Glu Leu His Asn Leu Ala
    610                 615                 620

Leu Lys Thr Ile His Phe Ala Asp Ala Lys Asp Tyr Phe Val Thr Leu
625                 630                 635                 640

Ser Asn Asn Gly Ser Val Ser Val Ala Leu Val Pro Ser Gln Phe Thr
                645                 650                 655

Ser Gln Met Asp Ser Thr Lys His Val Leu Tyr Ala Lys Lys Asn Asn
                660                 665                 670

Lys Gly Lys Leu Gly Ile Val Ser Glu His Glu Val Arg Pro Lys Gln
                675                 680                 685

Glu Cys His Ile Asn Gly Leu Asn Gly Asp Tyr Asn Ala Ala Cys Asn
    690                 695                 700

Ile Ala Tyr Ile Phe Glu Asn Asp Glu Trp Arg Asn Ala Phe Met Lys
705                 710                 715                 720

Met Asn Pro Asn Glu Tyr Gly Lys Ala Leu Phe Glu Thr Asn Met Glu
                725                 730                 735

Ser Thr Ser Thr Ile Ile Asn Thr Leu Lys Lys Ile Asn Pro Asp Asn
                740                 745                 750

Ile Ile Ser Phe Asp Glu Tyr Glu Lys Thr Lys Lys Val Ala Ala
        755                 760                 765
```

```
<210> SEQ ID NO 137
<211> LENGTH: 652
<212> TYPE: PRT
<213> ORGANISM: Artificial sequence
<220> FEATURE:
<223> OTHER INFORMATION: synthetic sequence

<400> SEQUENCE: 137

Tyr Pro Ala Asn Ser Arg Asp Asn Ala Ile Tyr Glu Ala Leu Asn Thr
1               5                   10                  15

Cys Asn Thr Glu His Tyr Thr Gly Asn Ile Leu Asn Phe Ser Asp Thr
                20                  25                  30

Tyr Tyr Arg Arg Phe Gly Tyr Val Ala Ser Ala Ile Ser Asn Tyr Val
            35                  40                  45

Thr Lys Ile Ser Lys Met Ser Thr Gly Ser Arg Ser Lys Asn Ile Ser
        50                  55                  60

Asn Asp Ser Asp Val Asp Thr Ile Met Glu Gln Val Ile Tyr Glu Met
65                  70                  75                  80

Glu His Asn Gly Trp Thr Ser Val Lys Asp Trp Glu Asn Gln Met Glu
                85                  90                  95

Tyr Leu Glu Ser Lys Thr Asp Ser Asn Pro Asn Phe Val Tyr Arg Met
                100                 105                 110

Thr Thr Leu Tyr Glu Phe Tyr Lys Ser His Ile Asp Glu Val Asn Ser
        115                 120                 125
```

-continued

```
Lys Met Glu Thr Met Ser Ile Asp Ser Leu Ile Lys Phe Gly Gly Cys
    130                 135                 140

Arg Arg Lys Asp Ser Lys Lys Ser Met Tyr Ile Met Gly Gly Ser Asn
145                 150                 155                 160

Thr Pro Phe Asp Ile Thr Gln Ile Gly Gly Asn Ser Leu Asn Ile Lys
                165                 170                 175

Phe Ser Lys Asn Leu Asn Val Asp Val Phe Gly Arg Tyr Asp Val Ile
                180                 185                 190

Lys Asp Asn Thr Leu Leu Val Asp Ile Ile Asn Gly His Gly Ala Ser
            195                 200                 205

Phe Val Leu Lys Ile Ile Asn Gly Glu Ile Tyr Ile Asp Ile Asn Val
    210                 215                 220

Ser Val Pro Phe Asp Lys Lys Ile Ala Thr Thr Asn Lys Val Val Gly
225                 230                 235                 240

Val Asp Val Asn Ile Lys His Met Leu Leu Ala Thr Asn Ile Leu Asp
                245                 250                 255

Asp Gly Asn Val Lys Gly Tyr Val Asn Ile Tyr Lys Glu Val Ile Asn
                260                 265                 270

Asp Ser Asp Phe Lys Lys Val Cys Asn Ser Thr Val Met Lys Tyr Phe
            275                 280                 285

Thr Asp Phe Ser Lys Phe Val Thr Phe Cys Pro Leu Glu Phe Asp Phe
    290                 295                 300

Leu Phe Ser Arg Val Cys Asn Gln Lys Gly Ile Tyr Asn Asp Asn Ser
305                 310                 315                 320

Ala Met Glu Lys Ser Phe Ser Asp Val Leu Asn Lys Leu Lys Trp Asn
                325                 330                 335

Phe Ile Glu Thr Gly Asp Asn Thr Lys Arg Ile Tyr Ile Glu Asn Val
                340                 345                 350

Met Lys Leu Arg Ser Gln Met Lys Ala Tyr Ala Ile Val Lys Asn Ala
            355                 360                 365

Tyr Tyr Lys Gln Gln Ser Glu Tyr Asp Phe Gly Lys Ser Glu Glu Phe
    370                 375                 380

Ile Gln Glu His Pro Phe Ser Asn Thr Asp Lys Gly Ile Glu Ile Leu
385                 390                 395                 400

Asn Lys Leu Asp Asn Ile Ser Lys Lys Ile Leu Gly Cys Arg Asn Asn
                405                 410                 415

Ile Ile Gln Tyr Ser Tyr Asn Leu Phe Glu Ile Asn Gly Tyr Asp Met
                420                 425                 430

Ile Ser Leu Glu Lys Leu Thr Ser Ser Gln Phe Lys Lys Lys Ser Phe
            435                 440                 445

Pro Thr Val Asn Ser Leu Leu Lys Tyr His Lys Ile Leu Gly Cys Thr
    450                 455                 460

Gln Glu Glu Met Glu Lys Lys Asp Ile Tyr Ser Val Ile Lys Lys Gly
465                 470                 475                 480

Tyr Tyr Asp Ile Ile Phe Asp Asn Asp Val Val Thr Asp Ala Lys Leu
                485                 490                 495

Ser Thr Lys Gly Glu Leu Ser Lys Phe Lys Asp Asp Phe Phe Asn Leu
            500                 505                 510

Met Ile Lys Ser Ile His Phe Ala Asp Ile Lys Asp Tyr Phe Ile Thr
            515                 520                 525

Leu Ser Asn Asn Gly Thr Ala Gly Val Ser Leu Val Pro Ser Tyr Phe
    530                 535                 540

Thr Ser Gln Met Asp Ser Ile Asp His Lys Ile Tyr Phe Val Gln Asp
```

-continued

```
545             550             555             560

Asn Lys Ser Gly Lys Leu Lys Leu Ala Asn Lys His Lys Val Arg Ser
            565             570             575

Ser Gln Glu Lys His Ile Asn Gly Leu Asn Ala Asp Tyr Asn Ala Ala
            580             585             590

Arg Asn Ile Ala Tyr Ile Met Glu Asn Thr Glu Cys Arg Asn Met Phe
        595             600             605

Met Lys Gln Ser Arg Thr Asp Lys Ser Leu Tyr Asn Lys Pro Ser Tyr
    610             615             620

Glu Thr Phe Ile Lys Thr Gln Gly Ser Ala Val Ala Lys Leu Lys Lys
625             630             635             640

Glu Gly Phe Val Lys Ile Leu Asp Glu Ala Ser Val
            645             650
```

```
<210> SEQ ID NO 138
<211> LENGTH: 782
<212> TYPE: PRT
<213> ORGANISM: Artificial sequence
<220> FEATURE:
<223> OTHER INFORMATION: synthetic sequence

<400> SEQUENCE: 138

Met Met Lys Lys Met Arg Ile Ser Pro His Leu Phe Tyr Ile Phe Phe
1               5               10              15

Lys Lys Ile Trp Lys Cys His Phe Phe Val Leu Ser Leu Tyr Gln Leu
            20              25              30

Asn Gln Tyr Ile Met Ala Ser His Lys Lys Thr Glu Ser Asn Gln Ile
        35              40              45

Ile Lys Thr Phe Ser Phe Lys Ile Lys Asn Ala Asn Gly Leu Ser Leu
    50              55              60

Asp Val Leu Asn Asp Ala Ile Thr Glu Tyr Gln Asn Tyr Tyr Asn Ile
65              70              75              80

Cys Ser Asp Trp Ile Lys Asp His Leu Thr Met Lys Ile Gly Glu Leu
            85              90              95

Tyr Lys Tyr Ile Pro Asp Glu Lys Lys Asn Ser Gly Tyr Ala Leu Thr
            100             105             110

Leu Ile Ser Asp Glu Trp Lys Asp Lys Pro Met Tyr Met Met Phe Lys
        115             120             125

Lys Gly Tyr Pro Ala Asn Asn Arg Asp Asn Ala Ile Tyr Glu Thr Leu
    130             135             140

Asn Thr Cys Asn Thr Glu His Tyr Thr Gly Asn Ile Leu Asn Phe Ser
145             150             155             160

Asp Thr Tyr Tyr Arg Arg Phe Gly Tyr Val Ala Ser Ala Ile Ser Asn
            165             170             175

Tyr Val Thr Lys Ile Ser Lys Met Ser Thr Gly Ser Arg Ser Lys Asn
            180             185             190

Ile Ser Asn Asp Ser Asp Val Asp Thr Ile Met Glu Gln Val Ile Tyr
        195             200             205

Glu Met Glu His Asn Gly Trp Thr Ser Val Lys Asp Trp Glu Asn Gln
    210             215             220

Met Glu Tyr Leu Glu Ser Lys Thr Asp Ser Asn Pro Asn Phe Val Tyr
225             230             235             240

Arg Met Thr Thr Leu Tyr Glu Phe Tyr Lys Ser His Ile Asp Glu Val
            245             250             255

Asn Ser Lys Met Glu Thr Met Ser Ile Asp Ser Leu Ile Lys Phe Gly
```

```
                 260              265               270

Gly Cys Arg Arg Lys Asp Ser Lys Lys Ser Met Tyr Ile Met Gly Gly
            275             280              285

Ser Asn Thr Pro Phe Asp Ile Thr Gln Ile Gly Gly Asn Ser Leu Asn
        290             295         300

Ile Lys Phe Ser Lys Asn Leu Asn Val Asp Val Phe Gly Arg Tyr Asp
305             310              315              320

Val Ile Lys Asp Asn Thr Leu Leu Val Asp Ile Ile Asn Glu His Gly
            325             330              335

Ala Ser Phe Val Leu Lys Ile Ile Asn Asp Glu Ile Tyr Ile Asp Ile
            340             345         350

Asn Val Ser Val Pro Phe Asp Lys Lys Ile Ala Thr Thr Asn Lys Val
        355             360         365

Val Gly Val Asp Val Asn Ile Lys His Met Leu Leu Ala Thr Asn Ile
    370             375              380

Leu Asp Asp Gly Asn Val Asn Gly Tyr Val Asn Ile Tyr Lys Glu Val
385             390             395              400

Ile Asn Asp Ser Asp Phe Lys Lys Val Cys Asn Ser Thr Val Met Lys
            405             410              415

Tyr Phe Thr Asp Phe Ser Lys Phe Val Thr Phe Cys Pro Leu Glu Phe
            420             425              430

Asp Phe Leu Phe Ser Arg Val Cys Asn Gln Lys Gly Ile Tyr Asn Asp
            435             440         445

Asn Ser Ala Met Glu Lys Ser Phe Ser Asn Val Leu Asn Lys Leu Lys
        450             455         460

Trp Asn Phe Ile Glu Thr Gly Asp Asn Thr Lys Arg Ile Tyr Ile Glu
465             470         475              480

Asn Val Met Lys Leu Arg Ser Gln Met Lys Ala Tyr Ala Ile Val Lys
            485             490              495

Asn Ala Tyr Tyr Lys Gln Gln Ser Glu Tyr Asp Phe Gly Lys Ser Glu
            500             505         510

Glu Phe Ile Gln Glu His Pro Phe Ser Asn Thr Asp Lys Gly Ile Glu
        515             520         525

Ile Leu Asn Lys Leu Asp Asn Ile Ser Lys Lys Ile Leu Gly Cys Arg
    530             535         540

Asn Asn Ile Ile Gln Tyr Ser Tyr Asn Leu Phe Glu Ile Asn Gly Tyr
545             550             555              560

Asp Met Ile Ser Leu Glu Lys Leu Thr Ser Ser Gln Phe Lys Lys Lys
            565             570              575

Pro Phe Pro Thr Val Asn Ser Leu Leu Lys Tyr His Lys Ile Leu Gly
            580             585         590

Cys Thr Gln Glu Glu Met Glu Lys Lys Asp Ile Tyr Ser Val Ile Lys
        595             600         605

Lys Gly Tyr Tyr Asp Ile Ile Phe Asp Asn Asp Val Val Thr Asp Ala
    610             615         620

Lys Leu Ser Thr Lys Gly Glu Leu Ser Lys Phe Lys Asp Asp Phe Phe
625             630             635              640

Asn Leu Met Ile Lys Ser Ile His Phe Ala Asp Ile Lys Asp Tyr Phe
            645             650              655

Ile Thr Leu Ser Asn Asn Gly Thr Ala Gly Val Ser Leu Val Pro Ser
            660             665         670

Tyr Phe Thr Ser Gln Met Asp Ser Ile Asp His Lys Ile Tyr Phe Val
            675             680         685
```

-continued

```
Gln Asp Asn Lys Ser Gly Lys Leu Lys Leu Ala Asn Lys His Lys Val
    690             695             700

Arg Ser Ser Gln Glu Lys His Ile Asn Gly Leu Asn Ala Asp Tyr Asn
705             710             715             720

Ala Ala Arg Asn Ile Ala Tyr Ile Met Glu Asn Thr Asp Cys Arg Asn
            725             730             735

Met Phe Met Lys Gln Ser Arg Thr Asp Lys Ser Leu Tyr Asn Lys Pro
            740             745             750

Ser Tyr Glu Thr Phe Ile Lys Thr Gln Gly Ser Ala Val Ala Lys Leu
            755             760             765

Lys Lys Glu Gly Phe Val Lys Ile Leu Asp Glu Ala Ser Val
    770             775             780

<210> SEQ ID NO 139
<211> LENGTH: 889
<212> TYPE: PRT
<213> ORGANISM: Artificial sequence
<220> FEATURE:
<223> OTHER INFORMATION: synthetic sequence

<400> SEQUENCE: 139

Trp Thr Asp Glu Asp Tyr Cys Lys Phe Phe Ala Lys Tyr Gly Met Ser
1               5               10              15

Glu Glu Cys Gln Lys Trp Met Cys Arg Asp Val Tyr Asp Tyr Arg Ile
            20              25              30

Lys Asp Phe Val Asp Tyr Glu Lys Phe Asp Asp Ser Lys Ile Glu Glu
            35              40              45

Glu Gln Glu Glu Tyr Ser Glu Ile Pro Val Glu Ser Glu Asp Ser Ser
    50              55              60

Pro Ser Thr Ser Glu Thr Leu Pro Lys Ser Ile Tyr Asp Leu Asp Leu
65              70              75              80

Arg Arg Leu Asp Pro Asn Pro Glu Ile Pro Glu Asp Glu Lys Tyr Asn
            85              90              95

Glu Glu Asp Leu Lys Asn Ala Tyr Pro Asp Lys Tyr Glu Arg Phe Glu
            100             105             110

Lys Asp Gly Glu Asp Tyr Ser Tyr Ile Phe Phe Lys Lys Ile Trp Lys
            115             120             125

Cys His Phe Phe Val Leu Ser Leu Tyr Gln Leu Asn Gln Tyr Ile Met
    130             135             140

Ala Ser His Lys Lys Thr Glu Ser Asn Gln Ile Ile Lys Thr Phe Ser
145             150             155             160

Phe Lys Ile Lys Asn Ala Asn Gly Leu Ser Leu Asp Val Leu Asn Asp
            165             170             175

Ala Ile Thr Glu Tyr Gln Asn Tyr Tyr Asn Ile Cys Ser Asp Trp Ile
            180             185             190

Lys Asp His Leu Thr Met Lys Ile Gly Glu Leu Tyr Lys Tyr Ile Pro
            195             200             205

Asp Glu Lys Lys Asn Ser Gly Tyr Ala Leu Thr Leu Ile Ser Asp Glu
    210             215             220

Trp Lys Asp Lys Pro Met Tyr Met Met Phe Lys Lys Gly Tyr Pro Ala
225             230             235             240

Asn Asn Arg Asp Asn Ala Ile Tyr Glu Ala Leu Asn Thr Cys Asn Thr
            245             250             255

Glu His Tyr Thr Gly Asn Ile Leu Asn Phe Ser Asp Thr Tyr Tyr Arg
            260             265             270
```

-continued

```
Arg Phe Gly Tyr Val Ala Ser Thr Ile Ser Asn Tyr Val Thr Lys Ile
        275                 280                 285

Ser Lys Met Ser Thr Gly Ser Arg Ser Lys Asn Ile Ser Asn Asp Ser
        290                 295                 300

Asp Val Asp Thr Ile Met Glu Gln Val Ile Tyr Glu Met Glu His Asn
305                 310                 315                 320

Gly Trp Thr Ser Val Lys Asp Trp Glu Asn Gln Met Glu Tyr Leu Glu
                325                 330                 335

Ser Lys Thr Asp Ser Asn Pro Asn Phe Val Tyr Arg Met Thr Thr Leu
                340                 345                 350

Tyr Glu Phe Tyr Lys Ser His Ile Asp Glu Val Asn Ser Lys Met Glu
        355                 360                 365

Thr Met Ser Ile Asp Ser Leu Ile Lys Phe Gly Gly Cys Arg Arg Lys
        370                 375                 380

Asp Ser Lys Lys Ser Met Tyr Ile Met Gly Gly Ser Asn Thr Pro Phe
385                 390                 395                 400

Asp Ile Thr Gln Ile Asp Gly Asn Ser Leu Asn Ile Lys Phe Ser Lys
                405                 410                 415

Asn Leu Asn Val Asp Val Phe Gly Arg Tyr Asp Val Ile Lys Asp Asn
                420                 425                 430

Thr Leu Leu Val Asp Ile Ile Asn Gly His Gly Ala Ser Phe Val Leu
                435                 440                 445

Lys Ile Ile Asn Asp Glu Ile Tyr Ile Asp Ile Asn Val Ser Val Pro
        450                 455                 460

Phe Asp Lys Lys Ile Ala Thr Thr Asn Lys Val Val Gly Val Asp Val
465                 470                 475                 480

Asn Ile Lys His Met Leu Leu Ala Thr Asn Ile Leu Asp Asp Gly Asn
                485                 490                 495

Val Asn Gly Tyr Val Asn Ile Tyr Lys Glu Val Ile Asn Asp Ser Asp
                500                 505                 510

Phe Lys Lys Val Cys Asn Ser Thr Val Met Lys Tyr Phe Thr Asp Phe
        515                 520                 525

Ser Lys Phe Val Thr Phe Cys Pro Leu Glu Phe Asp Phe Leu Phe Ser
        530                 535                 540

Arg Val Cys Asn Gln Lys Gly Ile Tyr Asn Asp Asn Ser Ala Met Glu
545                 550                 555                 560

Lys Ser Phe Ser Asp Val Leu Asn Lys Leu Lys Trp Asn Phe Ile Glu
                565                 570                 575

Thr Gly Asp Asn Thr Lys Arg Ile Tyr Ile Glu Asn Val Met Lys Leu
                580                 585                 590

Arg Ser Gln Met Lys Ala Tyr Ala Ile Val Lys Asn Ala Tyr Tyr Lys
                595                 600                 605

Gln Gln Ser Glu Tyr Asp Phe Gly Lys Ser Glu Glu Phe Ile Gln Glu
        610                 615                 620

His Pro Phe Ser Asn Thr Asp Lys Gly Ile Glu Ile Leu Asn Lys Leu
625                 630                 635                 640

Asp Asn Ile Ser Lys Lys Ile Leu Gly Cys Arg Asn Asn Ile Ile Gln
                645                 650                 655

Tyr Ser Tyr Asn Leu Phe Glu Ile Asn Gly Tyr Asp Met Ile Ser Leu
                660                 665                 670

Glu Lys Leu Thr Ser Ser Gln Phe Glu Lys Lys Pro Phe Pro Thr Val
        675                 680                 685
```

```
Asn Ser Leu Leu Lys Tyr His Lys Ile Leu Gly Cys Thr Gln Glu Glu
    690             695             700

Met Glu Lys Lys Asp Ile Tyr Ser Val Ile Lys Lys Gly Tyr Tyr Asp
705             710             715             720

Ile Ile Phe Asp Asn Gly Val Val Thr Asp Ala Lys Leu Ser Thr Lys
            725             730             735

Gly Glu Leu Ser Lys Phe Lys Asp Asp Phe Phe Asn Leu Met Ile Lys
            740             745             750

Ser Ile His Phe Ala Asp Ile Lys Asp Tyr Phe Ile Thr Leu Ser Asn
            755             760             765

Asn Gly Thr Ala Gly Val Ser Leu Val Pro Ser Tyr Phe Thr Ser Gln
    770             775             780

Met Asp Ser Ile Asp His Lys Ile Tyr Phe Val Gln Asp Asn Lys Ser
785             790             795             800

Gly Lys Leu Lys Leu Ala Asn Lys His Lys Val Arg Ser Ser Gln Glu
            805             810             815

Lys His Ile Asn Gly Leu Asn Ala Asp Tyr Asn Ala Ala Arg Asn Ile
            820             825             830

Ala Tyr Ile Met Glu Asn Thr Glu Cys Arg Asn Met Phe Met Lys Gln
            835             840             845

Ser Arg Thr Asp Lys Ser Leu Tyr Asn Lys Pro Ser Tyr Glu Thr Phe
    850             855             860

Ile Lys Thr Gln Gly Ser Ala Val Ala Lys Leu Lys Lys Glu Gly Phe
865             870             875             880

Val Lys Ile Leu Asp Glu Ala Ser Val
            885

<210> SEQ ID NO 140
<211> LENGTH: 223
<212> TYPE: PRT
<213> ORGANISM: Artificial sequence
<220> FEATURE:
<223> OTHER INFORMATION: synthetic sequence

<400> SEQUENCE: 140

Tyr Asp Met Ile Ser Leu Glu Lys Leu Thr Ser Ser Gln Phe Lys Lys
1               5               10              15

Lys Pro Phe Pro Thr Val Asn Ser Leu Leu Lys Tyr His Lys Ile Leu
            20              25              30

Gly Cys Thr Glu Glu Glu Met Glu Lys Lys Asp Ile Tyr Ser Val Ile
            35              40              45

Lys Lys Gly Tyr Tyr Asp Ile Ile Phe Asp Asn Asp Val Val Thr Asp
    50              55              60

Ala Lys Leu Ser Thr Lys Gly Glu Leu Ser Lys Phe Lys Asp Asp Phe
65              70              75              80

Phe Asn Leu Met Ile Lys Ser Ile His Phe Ala Asp Ile Lys Asp Tyr
            85              90              95

Phe Ile Thr Leu Ser Asn Asn Gly Thr Ala Gly Val Ser Leu Val Pro
            100             105             110

Ser Tyr Phe Thr Ser Gln Met Asp Ser Ile Asp His Lys Ile Tyr Phe
            115             120             125

Val Gln Asp Asn Lys Ser Gly Lys Leu Lys Leu Ala Asn Lys His Lys
    130             135             140

Val Arg Ser Ser Gln Glu Lys His Ile Asn Gly Leu Asn Ala Asp Tyr
145             150             155             160
```

-continued

```
Asn Ala Ala Arg Asn Ile Ala Tyr Ile Met Glu Asn Thr Glu Cys Arg
                165                 170                 175

Asn Met Phe Met Lys Gln Ser Arg Thr Asp Lys Ser Leu Tyr Asn Lys
            180                 185                 190

Pro Ser Tyr Glu Thr Phe Ile Lys Thr Gln Gly Ser Ala Val Ala Lys
        195                 200                 205

Leu Lys Lys Glu Gly Phe Val Lys Ile Leu Asp Glu Ala Ser Ala
    210                 215                 220

<210> SEQ ID NO 141
<211> LENGTH: 439
<212> TYPE: PRT
<213> ORGANISM: Artificial sequence
<220> FEATURE:
<223> OTHER INFORMATION: synthetic sequence

<400> SEQUENCE: 141

Met Lys Ile Gly Glu Leu Tyr Lys Tyr Ile Pro Asp Glu Lys Lys Asn
1               5                   10                  15

Ser Gly Tyr Ala Leu Thr Leu Ile Ser Asp Glu Trp Lys Asp Lys Pro
            20                  25                  30

Met Tyr Met Met Phe Lys Lys Gly Tyr Pro Ala Asn Asn Arg Asp Asn
        35                  40                  45

Ala Ile Tyr Glu Thr Leu Asn Thr Cys Asn Thr Glu His Tyr Thr Gly
    50                  55                  60

Asn Ile Leu Asn Phe Ser Asp Thr Tyr Tyr Arg Arg Phe Gly Tyr Val
65                  70                  75                  80

Ala Ser Ala Ile Ser Asn Tyr Val Thr Lys Ile Ser Lys Met Ser Thr
                85                  90                  95

Gly Ser Arg Ser Lys Asn Ile Ser Asn Asp Ser Asp Val Asp Thr Ile
            100                 105                 110

Met Glu Gln Val Ile Tyr Glu Met Glu His Asn Gly Trp Thr Ser Val
            115                 120                 125

Lys Asp Trp Glu Asn Gln Met Glu Tyr Leu Glu Ser Lys Thr Asp Ser
    130                 135                 140

Asn Pro Asn Phe Val Tyr Arg Met Thr Thr Leu Tyr Glu Phe Tyr Lys
145                 150                 155                 160

Ser His Ile Asp Glu Val Asn Ser Lys Met Glu Thr Met Ser Ile Asp
            165                 170                 175

Ser Leu Ile Lys Phe Gly Gly Cys Arg Arg Lys Asp Ser Lys Lys Ser
            180                 185                 190

Met Tyr Ile Met Gly Gly Ser Asn Thr Pro Phe Asp Ile Thr Gln Ile
        195                 200                 205

Asp Gly Asn Ser Leu Asn Ile Lys Phe Ser Lys Asn Leu Asn Val Asp
    210                 215                 220

Val Phe Gly Arg Tyr Asp Val Ile Lys Asp Asn Thr Leu Leu Val Asp
225                 230                 235                 240

Ile Ile Asn Gly His Gly Ala Ser Phe Val Leu Lys Ile Ile Asn Gly
                245                 250                 255

Glu Ile Tyr Ile Asp Ile Asn Val Ser Val Pro Phe Asp Lys Lys Ile
            260                 265                 270

Ala Thr Thr Asn Lys Val Val Gly Val Asp Val Asn Ile Lys His Met
        275                 280                 285

Leu Leu Ala Thr Asn Ile Leu Asp Asp Gly Asn Val Asn Gly Tyr Val
    290                 295                 300
```

-continued

```
Asn Ile Tyr Lys Glu Val Ile Asn Asp Ser Asp Phe Lys Lys Val Cys
305                 310                 315                 320

Asn Ser Thr Val Met Lys Tyr Phe Thr Asp Phe Ser Lys Phe Val Thr
                325                 330                 335

Phe Cys Pro Leu Glu Phe Asp Phe Leu Phe Ser Arg Val Cys Asn Gln
            340                 345                 350

Lys Gly Ile Tyr Asn Asp Asn Ser Ala Met Glu Lys Ser Phe Ser Asp
            355                 360                 365

Val Leu Asn Lys Leu Lys Trp Asn Phe Ile Glu Thr Gly Asp Asn Thr
        370                 375                 380

Lys Arg Ile Tyr Ile Glu Asn Val Met Lys Leu Arg Ser Gln Met Lys
385                 390                 395                 400

Ala Tyr Ala Ile Val Lys Asn Ala Tyr Tyr Lys Gln Gln Ser Glu Tyr
                405                 410                 415

Asp Phe Gly Lys Ser Glu Glu Phe Ile Gln Glu Tyr Asp Phe Phe Gly
                420                 425                 430

Glu Thr Tyr Gln Phe Ser Ile
            435

<210> SEQ ID NO 142
<211> LENGTH: 196
<212> TYPE: PRT
<213> ORGANISM: Artificial sequence
<220> FEATURE:
<223> OTHER INFORMATION: synthetic sequence

<400> SEQUENCE: 142

Met Ile Ser Leu Glu Lys Leu Thr Ser Ser Gln Phe Lys Lys Lys Pro
1               5                   10                  15

Phe Pro Thr Val Asn Ser Leu Leu Lys Tyr His Lys Ile Leu Gly Cys
                20                  25                  30

Thr Gln Glu Glu Met Glu Lys Lys Lys Gly Tyr Tyr Asp Ile Ile Phe
            35                  40                  45

Asp Asn Asp Val Val Thr Asp Ala Lys Leu Ser Thr Lys Gly Glu Leu
        50                  55                  60

Ser Lys Phe Lys Asp Asp Phe Phe Asn Leu Met Ile Lys Ser Ile His
65                  70                  75                  80

Phe Ala Asp Ile Lys Asp Tyr Phe Ile Thr Leu Ser Asn Asn Gly Thr
                85                  90                  95

Ala Gly Val Ser Leu Val Pro Ser Tyr Phe Thr Ser Gln Met Asp Arg
            100                 105                 110

Ala Asn Lys His Lys Val Arg Ser Ser Gln Glu Lys His Ile Asn Gly
        115                 120                 125

Leu Asn Ala Asp Tyr Asn Ala Ala Arg Asn Ile Ala Tyr Ile Met Glu
        130                 135                 140

Asn Thr Glu Cys Arg Asn Met Phe Met Lys Gln Ser Arg Thr Asp Lys
145                 150                 155                 160

Ser Leu Tyr Asn Lys Pro Ser Tyr Glu Thr Phe Ile Lys Thr Gln Gly
                165                 170                 175

Ser Ala Val Ala Lys Leu Lys Lys Glu Gly Phe Val Lys Ile Leu Asp
            180                 185                 190

Glu Ala Ser Val
            195

<210> SEQ ID NO 143
<211> LENGTH: 748
```

-continued

```
<212> TYPE: PRT
<213> ORGANISM: Artificial sequence
<220> FEATURE:
<223> OTHER INFORMATION: synthetic sequence

<400> SEQUENCE: 143

Tyr Ile Met Ala Ser His Lys Lys Thr Glu Ser Asn Gln Ile Ile Lys
1               5                   10                  15

Thr Phe Ser Phe Lys Ile Lys Asn Ala Asn Gly Leu Ser Leu Asp Val
                20                  25                  30

Leu Asn Asp Ala Ile Thr Glu Tyr Gln Asn Tyr Tyr Asn Ile Cys Ser
        35                  40                  45

Asp Trp Ile Lys Asp His Leu Thr Met Lys Ile Gly Glu Leu Tyr Lys
    50                  55                  60

Tyr Ile Pro Asp Glu Lys Lys Asn Ser Gly Tyr Ala Leu Thr Leu Ile
65                  70                  75                  80

Ser Asp Glu Trp Lys Asp Lys Pro Met Tyr Met Met Phe Lys Lys Gly
                85                  90                  95

Tyr Pro Ala Asn Ser Arg Asp Asn Ala Ile Tyr Glu Thr Leu Asn Thr
            100                 105                 110

Cys Asn Thr Glu His Tyr Thr Gly Asn Ile Leu Asn Phe Ser Asp Thr
            115                 120                 125

Tyr Tyr Arg Arg Phe Gly Tyr Val Ala Ser Thr Ile Ser Asn Tyr Val
        130                 135                 140

Thr Lys Ile Ser Lys Met Ser Thr Gly Ser Arg Ser Lys Asn Ile Ser
145                 150                 155                 160

Asn Asp Ser Asp Val Asp Thr Ile Met Glu Gln Val Ile Tyr Glu Met
            165                 170                 175

Glu His Asn Gly Trp Thr Ser Val Lys Asp Trp Glu Asn Gln Met Glu
            180                 185                 190

Tyr Leu Glu Ser Lys Thr Asp Ser Asn Pro Asn Phe Val Tyr Arg Met
        195                 200                 205

Thr Thr Leu Tyr Glu Phe Tyr Lys Ser His Ile Asp Glu Val Asn Ser
    210                 215                 220

Lys Met Glu Thr Met Ser Ile Asp Ser Leu Ile Lys Phe Gly Gly Cys
225                 230                 235                 240

Arg Arg Lys Asp Ser Lys Lys Ser Met Tyr Ile Met Gly Gly Ser Asn
            245                 250                 255

Thr Pro Phe Asp Ile Thr Gln Ile Gly Gly Asn Ser Leu Asn Ile Lys
            260                 265                 270

Phe Ser Lys Asn Leu Asn Val Asp Val Phe Gly Arg Tyr Asp Val Ile
        275                 280                 285

Lys Asp Asn Thr Leu Leu Val Asp Ile Ile Asn Gly His Gly Ala Ser
    290                 295                 300

Phe Val Leu Lys Ile Ile Asn Gly Glu Ile Tyr Ile Asp Ile Asn Val
305                 310                 315                 320

Ser Val Pro Phe Asp Lys Lys Ile Ala Thr Thr Asn Lys Val Val Gly
            325                 330                 335

Val Asp Val Asn Ile Lys His Met Leu Leu Ala Thr Asn Ile Leu Asp
            340                 345                 350

Asp Gly Asn Val Asn Gly Tyr Val Asn Ile Tyr Lys Glu Val Ile Asn
        355                 360                 365

Asp Ser Asp Phe Lys Lys Val Cys Asn Ser Thr Val Met Lys Tyr Phe
    370                 375                 380
```

-continued

```
Thr Asp Phe Ser Lys Phe Val Thr Phe Cys Pro Leu Glu Phe Asp Phe
385                 390                 395                 400

Leu Phe Ser Arg Val Cys Asn Gln Lys Gly Ile Tyr Asn Asp Asn Ser
                405                 410                 415

Ala Met Glu Lys Ser Phe Ser Asn Val Leu Asn Lys Leu Lys Trp Asn
                420                 425                 430

Phe Ile Glu Thr Gly Asp Asn Thr Lys Arg Ile Tyr Ile Glu Asn Val
            435                 440                 445

Met Lys Leu Arg Ser Gln Met Lys Ala Tyr Ala Ile Val Lys Asn Ala
        450                 455                 460

Tyr Tyr Lys Gln Gln Ser Glu Tyr Asp Phe Gly Lys Ser Glu Glu Phe
465                 470                 475                 480

Ile Gln Glu His Pro Phe Ser Asn Thr Asp Lys Gly Ile Glu Ile Leu
                485                 490                 495

Asn Lys Leu Asp Asn Ile Ser Lys Lys Ile Leu Gly Cys Arg Asn Asn
                500                 505                 510

Ile Ile Gln Tyr Ser Tyr Asn Leu Phe Glu Ile Asn Gly Tyr Asp Met
            515                 520                 525

Ile Ser Leu Glu Lys Leu Thr Ser Ser Gln Phe Glu Lys Lys Pro Phe
        530                 535                 540

Pro Thr Val Asn Ser Leu Leu Lys Tyr His Lys Ile Leu Gly Cys Thr
545                 550                 555                 560

Gln Glu Glu Met Glu Lys Lys Asp Ile Tyr Ser Val Ile Lys Lys Gly
                565                 570                 575

Tyr Tyr Asp Ile Ile Phe Asp Asn Gly Val Val Thr Asp Ala Lys Leu
            580                 585                 590

Ser Thr Lys Gly Glu Leu Ser Lys Phe Lys Asp Asp Phe Phe Asn Leu
        595                 600                 605

Met Ile Lys Ser Ile His Phe Ala Asp Ile Lys Asp Tyr Phe Ile Thr
    610                 615                 620

Leu Ser Asn Asn Gly Thr Ala Gly Val Ser Leu Val Pro Ser Tyr Phe
625                 630                 635                 640

Thr Ser Gln Met Asp Ser Ile Asp His Lys Ile Tyr Phe Val Gln Asp
                645                 650                 655

Asn Lys Ser Gly Lys Leu Lys Leu Ala Asn Lys His Lys Val Arg Ser
            660                 665                 670

Ser Gln Glu Lys His Ile Asn Gly Leu Asn Ala Asp Tyr Asn Ala Ala
        675                 680                 685

Arg Asn Ile Ala Tyr Ile Met Glu Asn Thr Glu Cys Arg Asn Met Phe
    690                 695                 700

Met Lys Gln Ser Arg Thr Asp Lys Ser Leu Tyr Asn Lys Pro Ser Tyr
705                 710                 715                 720

Glu Thr Phe Ile Lys Thr Gln Gly Ser Ala Val Ala Lys Leu Lys Lys
                725                 730                 735

Glu Gly Phe Val Lys Ile Leu Asp Glu Ala Ser Val
                740                 745
```

<210> SEQ ID NO 144
<211> LENGTH: 481
<212> TYPE: PRT
<213> ORGANISM: Artificial sequence
<220> FEATURE:
<223> OTHER INFORMATION: synthetic sequence

<400> SEQUENCE: 144

-continued

Ser Leu Asn Ile Lys Phe Ser Lys Asn Leu Asn Val Asp Val Phe Gly
1               5                   10                  15

Arg Tyr Asp Val Ile Lys Asp Asn Thr Leu Leu Val Asp Ile Ile Asn
                20                  25                  30

Gly His Gly Ala Ser Phe Val Leu Lys Ile Ile Asn Gly Glu Ile Tyr
            35                  40                  45

Ile Asp Ile Asn Val Ser Val Pro Phe Asp Lys Lys Ile Ala Thr Thr
    50                  55                  60

Asn Lys Val Val Gly Val Asp Val Asn Ile Lys His Met Leu Leu Ala
65                  70                  75                  80

Thr Asn Ile Leu Asp Asp Gly Asn Val Asn Gly Tyr Val Asn Ile Tyr
                85                  90                  95

Lys Glu Val Ile Asn Asp Ser Asp Phe Lys Lys Val Cys Asn Ser Thr
            100                 105                 110

Val Met Lys Tyr Phe Thr Asp Phe Ser Lys Phe Val Thr Phe Cys Pro
        115                 120                 125

Leu Glu Phe Asp Phe Leu Phe Ser Arg Val Cys Asn Gln Lys Gly Ile
    130                 135                 140

Tyr Asn Asp Asn Ser Ala Met Glu Lys Ser Phe Ser Asp Val Leu Asn
145                 150                 155                 160

Lys Leu Lys Trp Asn Phe Ile Glu Thr Gly Asp Asn Thr Lys Arg Ile
                165                 170                 175

Tyr Ile Glu Asn Val Met Lys Leu Arg Ser Gln Met Lys Ala Tyr Ala
            180                 185                 190

Ile Val Lys Asn Ala Tyr Tyr Lys Gln Gln Ser Glu Tyr Asp Phe Gly
        195                 200                 205

Lys Ser Glu Glu Phe Ile Gln Glu His Pro Phe Ser Asn Thr Asp Lys
    210                 215                 220

Gly Ile Glu Ile Leu Asn Lys Leu Asp Asn Ile Ser Lys Lys Ile Leu
225                 230                 235                 240

Gly Cys Arg Asn Asn Ile Ile Gln Tyr Ser Tyr Asn Leu Phe Glu Ile
                245                 250                 255

Asn Gly Tyr Asp Met Ile Ser Leu Glu Lys Leu Thr Ser Ser Gln Phe
            260                 265                 270

Lys Lys Lys Pro Phe Pro Thr Val Asn Ser Leu Leu Lys Tyr His Lys
        275                 280                 285

Ile Leu Gly Cys Thr Gln Glu Glu Met Glu Lys Lys Asp Ile Tyr Ser
    290                 295                 300

Val Ile Lys Lys Gly Tyr Tyr Asp Ile Ile Phe Asp Asn Gly Val Val
305                 310                 315                 320

Ile Asp Ala Lys Leu Ser Ala Lys Gly Glu Leu Ser Lys Phe Lys Asp
                325                 330                 335

Asp Phe Phe Asn Leu Met Ile Lys Ser Ile His Phe Ala Asp Ile Lys
            340                 345                 350

Asp Tyr Phe Ile Thr Leu Ser Asn Asn Gly Thr Ala Gly Val Ser Leu
        355                 360                 365

Val Pro Ser Tyr Phe Thr Ser Gln Met Asp Ser Ile Asp His Lys Ile
    370                 375                 380

Tyr Phe Val Gln Asp Asn Lys Ser Gly Lys Leu Lys Leu Ala Asn Lys
385                 390                 395                 400

His Lys Val Arg Ser Ser Gln Glu Lys His Ile Asn Gly Leu Asn Ala
                405                 410                 415

Asp Tyr Asn Ala Ala Arg Asn Ile Ala Tyr Ile Met Glu Asn Thr Glu

-continued

```
                 420             425             430

Cys Arg Asn Met Phe Met Lys Gln Ser Arg Thr Asp Lys Ser Leu Tyr
        435             440             445

Asn Lys Pro Ser Tyr Glu Thr Phe Ile Lys Thr Gln Gly Ser Ala Val
        450             455             460

Ala Lys Leu Lys Lys Glu Gly Phe Val Lys Ile Leu Asp Glu Ala Ser
465             470             475             480

Val

<210> SEQ ID NO 145
<211> LENGTH: 746
<212> TYPE: PRT
<213> ORGANISM: Artificial sequence
<220> FEATURE:
<223> OTHER INFORMATION: synthetic sequence

<400> SEQUENCE: 145

Met Ala Ser His Lys Lys Thr Glu Ser Asn Gln Ile Ile Lys Thr Phe
1               5               10              15

Ser Phe Lys Ile Lys Asn Ala Asn Gly Leu Ser Leu Asp Val Leu Asn
                20              25              30

Asp Ala Ile Thr Glu Tyr Gln Asn Tyr Tyr Asn Ile Cys Ser Asp Trp
        35              40              45

Ile Lys Asp His Leu Thr Met Lys Ile Gly Glu Leu Tyr Lys Tyr Ile
        50              55              60

Pro Asp Glu Lys Lys Asn Ser Gly Tyr Ala Leu Thr Leu Ile Ser Asp
65              70              75              80

Glu Trp Lys Asp Lys Pro Met Tyr Met Met Phe Lys Lys Gly Tyr Pro
                85              90              95

Ala Asn Asn Arg Asp Asn Ala Ile Tyr Glu Thr Leu Asn Thr Cys Asn
            100             105             110

Thr Glu His Tyr Thr Gly Asn Ile Leu Asn Phe Ser Asp Thr Tyr Tyr
            115             120             125

Arg Arg Phe Gly Tyr Val Ala Ser Ala Ile Ser Asn Tyr Val Thr Lys
        130             135             140

Ile Ser Lys Met Ser Thr Gly Ser Arg Ser Lys Asn Ile Ser Asn Asp
145             150             155             160

Ser Asp Val Asp Thr Ile Met Glu Gln Val Ile Tyr Glu Met Glu His
            165             170             175

Asn Gly Trp Thr Ser Val Lys Asp Trp Glu Asn Gln Met Glu Tyr Leu
            180             185             190

Glu Ser Lys Thr Asp Ser Asn Pro Asn Phe Val Tyr Arg Met Thr Thr
            195             200             205

Leu Tyr Glu Phe Tyr Lys Ser His Ile Asp Glu Val Asn Ser Lys Met
        210             215             220

Glu Thr Met Ser Ile Asp Ser Leu Ile Lys Phe Gly Gly Cys Arg Arg
225             230             235             240

Lys Asp Ser Lys Lys Ser Met Tyr Ile Met Gly Gly Ser Asn Thr Pro
                245             250             255

Phe Asp Ile Thr Gln Ile Gly Gly Asn Ser Leu Asn Ile Lys Phe Ser
            260             265             270

Lys Asn Leu Asn Val Asp Val Phe Gly Arg Tyr Asp Val Ile Lys Asp
        275             280             285

Asn Thr Leu Leu Val Asp Ile Ile Asn Glu His Gly Ala Ser Phe Val
        290             295             300
```

-continued

```
Leu Lys Ile Ile Asn Asp Glu Ile Tyr Ile Asp Ile Asn Val Ser Val
305             310             315             320

Pro Phe Asp Lys Lys Ile Ala Thr Thr Asn Lys Val Val Gly Ile Asp
            325             330             335

Val Asn Ile Lys His Met Leu Leu Ala Thr Asn Ile Leu Asp Asp Gly
            340             345             350

Asn Val Asn Gly Tyr Val Asn Ile Tyr Lys Glu Val Ile Asn Asp Ser
            355             360             365

Asp Phe Lys Lys Val Cys Asn Ser Thr Val Met Lys Tyr Phe Thr Asp
            370             375             380

Phe Ser Lys Phe Val Thr Phe Cys Pro Leu Glu Phe Asp Phe Leu Phe
385             390             395             400

Ser Arg Val Cys Asn Gln Lys Gly Ile Tyr Asn Asp Asn Ser Ala Met
            405             410             415

Glu Lys Ser Phe Ser Asp Val Leu Asn Lys Leu Lys Trp Asn Phe Ile
            420             425             430

Glu Thr Gly Asp Asn Thr Lys Arg Ile Tyr Ile Glu Asn Val Met Lys
            435             440             445

Leu Arg Ser Gln Met Lys Ala Tyr Ala Ile Val Lys Asn Ala Tyr Tyr
            450             455             460

Lys Gln Gln Ser Glu Tyr Asp Phe Gly Lys Ser Glu Glu Phe Ile Gln
465             470             475             480

Glu His Pro Phe Ser Asn Thr Asp Lys Gly Ile Glu Ile Leu Asn Lys
            485             490             495

Leu Asp Asn Ile Ser Lys Lys Ile Leu Gly Cys Arg Asn Asn Ile Ile
            500             505             510

Gln Tyr Ser Tyr Asn Leu Phe Glu Ile Asn Gly Tyr Asp Met Ile Ser
            515             520             525

Leu Glu Lys Leu Thr Ser Ser Gln Phe Lys Lys Lys Ser Phe Pro Thr
            530             535             540

Val Asp Ser Leu Leu Lys Tyr His Lys Ile Leu Gly Cys Thr Gln Glu
545             550             555             560

Glu Met Glu Lys Lys Asp Ile Tyr Ser Val Ile Lys Lys Gly Tyr Tyr
            565             570             575

Asp Ile Ile Phe Asp Asn Asp Val Val Thr Asp Ala Lys Leu Ser Thr
            580             585             590

Lys Gly Glu Leu Ser Lys Phe Lys Asp Asp Phe Phe Asn Leu Met Ile
            595             600             605

Lys Ser Ile His Phe Ala Asp Ile Lys Asp Tyr Phe Ile Thr Leu Ser
            610             615             620

Asn Asn Gly Thr Ala Gly Val Ser Leu Val Pro Ser Tyr Phe Thr Ser
625             630             635             640

Gln Met Asp Ser Ile Asp His Lys Ile Tyr Phe Val Gln Asp Asn Lys
            645             650             655

Ser Gly Lys Leu Lys Leu Ala Asn Lys His Lys Val Arg Ser Ser Gln
            660             665             670

Glu Lys His Ile Asn Gly Leu Asn Ala Asp Tyr Asn Ala Ala Arg Asn
            675             680             685

Ile Ala Tyr Ile Met Glu Asn Thr Glu Cys Arg Asn Met Phe Met Lys
            690             695             700

Gln Ser Arg Thr Asp Lys Ser Leu Tyr Asn Lys Pro Ser Tyr Glu Thr
705             710             715             720
```

-continued

```
Phe Ile Lys Thr Gln Gly Ser Ala Val Ala Lys Leu Lys Lys Glu Gly
            725                 730                 735

Phe Val Lys Ile Leu Asp Glu Ala Ser Val
            740                 745

<210> SEQ ID NO 146
<211> LENGTH: 746
<212> TYPE: PRT
<213> ORGANISM: Artificial sequence
<220> FEATURE:
<223> OTHER INFORMATION: synthetic sequence

<400> SEQUENCE: 146

Met Ala Ser His Lys Lys Thr Glu Ser Asn Gln Ile Ile Lys Thr Phe
1               5                   10                  15

Ser Phe Lys Ile Lys Asn Ala Asn Gly Leu Ser Leu Asp Val Leu Asn
            20                  25                  30

Asp Ala Ile Thr Glu Tyr Gln Asn Tyr Tyr Asn Ile Cys Ser Asp Trp
            35                  40                  45

Ile Lys Asp His Leu Thr Met Lys Ile Gly Glu Leu Tyr Lys Tyr Ile
    50                  55                  60

Pro Asp Glu Lys Lys Asn Ser Gly Tyr Ala Leu Thr Leu Ile Ser Asp
65                  70                  75                  80

Glu Trp Lys Asp Lys Pro Met Tyr Met Met Phe Lys Lys Gly Tyr Pro
            85                  90                  95

Ala Asn Asn Arg Asp Asn Ala Ile Tyr Glu Thr Leu Asn Thr Cys Asn
            100                 105                 110

Thr Glu His Tyr Thr Gly Asn Ile Leu Asn Phe Ser Asp Thr Tyr Tyr
            115                 120                 125

Arg Arg Phe Gly Tyr Val Ala Ser Ala Ile Ser Asn Tyr Val Thr Lys
    130                 135                 140

Ile Ser Lys Met Ser Thr Gly Ser Arg Ser Lys Asn Ile Ser Asn Asp
145                 150                 155                 160

Ser Asp Val Asp Thr Ile Met Glu Gln Val Ile Tyr Glu Met Glu His
            165                 170                 175

Asn Gly Trp Thr Ser Val Lys Asp Trp Glu Asn Gln Met Glu Tyr Leu
            180                 185                 190

Glu Ser Lys Thr Asp Ser Asn Pro Asn Phe Val Tyr Arg Met Thr Thr
            195                 200                 205

Leu Tyr Glu Phe Tyr Lys Ser His Ile Asp Glu Val Asn Ser Lys Met
    210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
            245                 250                 255

Phe Asp Ile Thr Gln Ile Asp Gly Asn Ser Leu Asn Ile Lys Phe Ser
            260                 265                 270

Lys Asn Leu Asn Val Asp Val Phe Gly Arg Tyr Asp Val Ile Lys Asp
            275                 280                 285

Asn Thr Leu Leu Val Asp Ile Ile Asn Gly His Gly Ala Ser Phe Val
    290                 295                 300

Leu Lys Ile Ile Asn Asp Glu Ile Tyr Ile Asp Ile Asn Val Ser Val
305                 310                 315                 320

Pro Phe Asp Lys Lys Ile Ala Thr Thr Asn Lys Val Val Gly Val Asp
            325                 330                 335
```

-continued

```
Val Asn Ile Lys His Met Leu Leu Ala Thr Asn Ile Leu Asp Asp Gly
            340                 345                 350

Asn Val Asn Gly Tyr Val Asn Ile Tyr Lys Glu Val Ile Asn Asp Ser
            355                 360                 365

Asp Phe Lys Lys Val Cys Asn Ser Thr Val Met Lys Tyr Phe Thr Asp
    370                 375                 380

Phe Ser Lys Phe Val Thr Phe Cys Pro Leu Glu Phe Asp Phe Leu Phe
385                 390                 395                 400

Ser Arg Val Cys Asn Gln Lys Gly Ile Tyr Asn Asp Asn Ser Ala Met
            405                 410                 415

Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
            435                 440                 445

Leu Arg Ser Gln Met Lys Ala Tyr Ala Ile Val Lys Asn Ala Tyr Tyr
    450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu Asn Lys
            485                 490                 495

Leu Asp Asn Ile Ser Lys Lys Ile Leu Gly Cys Arg Asn Asn Ile Ile
            500                 505                 510

Gln Tyr Ser Tyr Asn Leu Phe Glu Ile Asn Gly Tyr Asp Met Ile Ser
            515                 520                 525

Leu Glu Lys Leu Thr Ser Ser Gln Phe Lys Lys Pro Phe Pro Thr
    530                 535                 540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
            565                 570                 575

Asp Ile Ile Phe Asp Asn Asp Val Val Thr Asp Ala Lys Leu Ser Thr
            580                 585                 590

Lys Gly Glu Leu Ser Lys Phe Lys Asp Asp Phe Phe Asn Leu Met Ile
            595                 600                 605

Lys Ser Ile His Phe Ala Asp Ile Lys Asp Tyr Phe Ile Thr Leu Ser
    610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
            645                 650                 655

Ser Gly Lys Leu Lys Leu Ala Asn Lys His Lys Val Arg Ser Ser Gln
            660                 665                 670

Glu Lys His Ile Asn Gly Leu Asn Ala Asp Tyr Asn Ala Ala Arg Asn
            675                 680                 685

Ile Ala Tyr Ile Met Glu Asn Thr Glu Cys Arg Asn Met Phe Met Lys
    690                 695                 700

Gln Ser Arg Thr Asp Lys Ser Leu Tyr Asn Lys Pro Ser Tyr Glu Thr
705                 710                 715                 720

Phe Ile Lys Thr Gln Gly Ser Ala Val Ala Lys Leu Lys Lys Glu Gly
            725                 730                 735

Phe Met Lys Ile Leu Asp Glu Ala Ser Val
            740                 745
```

```
<210> SEQ ID NO 147
<211> LENGTH: 746
<212> TYPE: PRT
<213> ORGANISM: Artificial sequence
<220> FEATURE:
<223> OTHER INFORMATION: synthetic sequence

<400> SEQUENCE: 147

Met Ala Ser His Lys Lys Thr Glu Ser Asn Gln Ile Ile Lys Thr Phe
1               5                   10                  15

Ser Phe Lys Leu Lys Asn Ala Asn Gly Leu Ser Leu Asp Val Leu Asn
                20                  25                  30

Asp Ala Ile Thr Glu Tyr Gln Asn Tyr Tyr Asn Ile Cys Ser Asp Trp
            35                  40                  45

Ile Lys Asp His Leu Thr Met Lys Ile Gly Glu Leu Tyr Lys Tyr Ile
    50                  55                  60

Pro Asp Glu Lys Lys Asn Ser Gly Tyr Ala Leu Thr Leu Ile Ser Asp
65                  70                  75                  80

Glu Trp Lys Asp Lys Pro Met Tyr Met Met Phe Lys Lys Gly Tyr Pro
                85                  90                  95

Ala Asn Asn Arg Asp Asn Ala Ile Tyr Glu Ala Leu Asn Thr Cys Asn
                100                 105                 110

Thr Glu His Tyr Thr Gly Asn Ile Leu Asn Phe Ser Asp Thr Tyr Tyr
            115                 120                 125

Arg Arg Phe Gly Tyr Val Ala Ser Thr Ile Ser Asn Tyr Val Thr Lys
        130                 135                 140

Ile Ser Lys Met Ser Thr Gly Ser Arg Ser Lys Asn Ile Ser Asn Asp
145                 150                 155                 160

Ser Asp Val Asp Thr Ile Met Glu Gln Val Ile Tyr Glu Met Glu His
                165                 170                 175

Asn Gly Trp Thr Ser Val Lys Asp Trp Glu Asn Gln Met Glu Tyr Leu
            180                 185                 190

Glu Ser Lys Thr Asp Ser Asn Pro Asn Phe Val Tyr Arg Met Thr Thr
            195                 200                 205

Leu Tyr Glu Phe Tyr Lys Ser His Ile Asp Glu Val Asn Ser Lys Met
    210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
                245                 250                 255

Phe Asp Ile Thr Gln Ile Gly Ser Asn Ser Leu Asn Ile Lys Phe Ser
            260                 265                 270

Lys Asn Leu Asn Val Asp Val Phe Gly Arg Tyr Asp Val Ile Lys Asp
        275                 280                 285

Asn Thr Leu Leu Val Asp Ile Ile Lys Gly His Gly Ala Ser Phe Ala
    290                 295                 300

Leu Lys Ile Ile Asn Asp Glu Ile Tyr Ile Asp Ile Asn Val Ser Val
305                 310                 315                 320

Pro Phe Asp Lys Lys Ile Ala Thr Thr Asn Lys Val Val Gly Ile Asp
                325                 330                 335

Val Asn Ile Lys His Met Leu Leu Ala Thr Asn Ile Leu Asp Asp Gly
            340                 345                 350

Asn Val Asn Gly Tyr Val Asn Ile Tyr Lys Glu Val Ile Asn Asp Ser
        355                 360                 365

Asp Phe Lys Lys Val Cys Asn Ser Thr Val Met Lys Tyr Phe Thr Asp
```

-continued

```
       370             375             380

Phe Ser Lys Phe Val Thr Phe Cys Pro Leu Glu Phe Asp Phe Leu Phe
385             390             395             400

Ser Arg Val Cys Asn Gln Lys Gly Ile Tyr Asn Asp Asn Ser Ala Met
            405             410             415

Glu Lys Ser Phe Ser Asp Val Leu Asn Lys Leu Lys Trp Asn Phe Ile
            420             425             430

Glu Thr Gly Asp Asn Thr Lys Arg Ile Tyr Ile Glu Asn Val Met Lys
            435             440             445

Leu Arg Ser Gln Met Lys Ala Tyr Ala Ile Val Lys Asn Ala Tyr Tyr
    450             455             460

Lys Gln Gln Ser Glu Tyr Asp Phe Gly Lys Ser Glu Glu Phe Ile Gln
465             470             475             480

Glu His Pro Phe Ser Asn Thr Asp Lys Gly Ile Glu Ile Leu His Lys
            485             490             495

Leu Asp Asn Ile Ser Lys Lys Ile Leu Gly Cys Arg Asn Asn Ile Ile
            500             505             510

Gln Tyr Ser Tyr Asn Leu Phe Glu Ile Asn Gly Tyr Asp Met Ile Ser
            515             520             525

Leu Glu Lys Leu Thr Ser Ser Gln Phe Lys Lys Lys Pro Phe Pro Thr
    530             535             540

Val Asn Ser Leu Leu Lys Tyr His Lys Ile Leu Gly Cys Thr Gln Glu
545             550             555             560

Glu Met Glu Lys Lys Asp Ile Tyr Ser Val Ile Lys Lys Gly Tyr Tyr
            565             570             575

Asp Ile Ile Phe Asp Asn Asp Val Val Thr Asp Ala Lys Leu Ser Thr
            580             585             590

Lys Gly Glu Leu Ser Lys Phe Lys Asp Asp Phe Phe Asn Leu Met Ile
            595             600             605

Lys Ser Ile His Phe Ala Asp Ile Lys Asp Tyr Phe Ile Thr Leu Ser
    610             615             620

Asn Asn Gly Thr Ala Gly Val Ser Leu Val Pro Ser Phe Phe Thr Ser
625             630             635             640

Gln Met Asp Ser Ile Asp His Lys Ile Tyr Phe Val Gln Asp Asn Lys
            645             650             655

Ser Gly Lys Leu Lys Leu Ala Asn Lys His Lys Val Arg Ser Ser Gln
            660             665             670

Glu Lys His Ile Asn Gly Leu Asn Ala Asp Tyr Asn Ala Ala Arg Asn
            675             680             685

Ile Ala Tyr Ile Met Glu Asn Thr Glu Cys Arg Asn Met Phe Met Lys
    690             695             700

Gln Ser Arg Thr Asp Lys Ser Leu Tyr Asn Lys Pro Ser Tyr Glu Thr
705             710             715             720

Phe Ile Lys Thr Gln Gly Ser Ala Val Ala Lys Leu Lys Lys Glu Gly
            725             730             735

Phe Val Lys Ile Leu Asp Glu Ala Ser Val
            740             745
```

<210> SEQ ID NO 148
<211> LENGTH: 735
<212> TYPE: PRT
<213> ORGANISM: Artificial sequence
<220> FEATURE:
<223> OTHER INFORMATION: synthetic sequence -continued

```
<400> SEQUENCE: 148

Met Ala His Lys Lys Asn Ile Gly Ala Glu Ile Val Lys Thr Tyr Ser
1               5                   10                  15

Phe Lys Val Lys Asn Thr Asn Gly Ile Thr Met Glu Lys Leu Met Asn
                20                  25                  30

Ala Ile Asp Glu Tyr Gln Ser Tyr Tyr Asn Leu Cys Ser Asp Trp Ile
            35                  40                  45

Cys Lys Asn Leu Thr Thr Met Thr Ile Gly Asp Leu Asp Gln Tyr Ile
        50                  55                  60

Pro Glu Lys Ala Lys Asp Asn Thr Tyr Ala Thr Val Leu Leu Asp Glu
65                  70                  75                  80

Ala Trp Lys Asn Gln Pro Leu Tyr Lys Ile Phe Gly Lys Lys Tyr Ser
                85                  90                  95

Ser Asn Asn Arg Asp Ala Val Leu Tyr His Ala Leu Ser Ser Ile Val
            100                 105                 110

Asn Ala Ser Glu Lys Asn Ile Leu Gly Ile Ser Lys Thr Tyr Tyr Ala
        115                 120                 125

Arg Lys Gly Tyr Val Leu Asn Val Ala Ser Asn Tyr Ala Ser Lys Leu
    130                 135                 140

Ser Lys Leu Asn Thr Gly Val Lys Ser Arg Ala Ile Lys Glu Thr Ser
145                 150                 155                 160

Asp Glu Glu Thr Ile Ile Glu Gln Val Ile Tyr Glu Met Glu His Asn
                165                 170                 175

Lys Trp Glu Ser Ile Glu Asp Trp Lys Asn Gln Ile Glu Tyr Leu Asn
            180                 185                 190

Ser Lys Thr Asp Tyr Asn Pro Thr Tyr Met Glu Arg Met Lys Thr Leu
        195                 200                 205

Ser Ala Tyr Tyr Ser Glu His Lys Ser Glu Val Asp Ala Lys Met Gln
    210                 215                 220

Glu Met Ala Val Glu Asn Leu Val Lys Phe Gly Gly Cys Arg Arg Asn
225                 230                 235                 240

Asn Ser Lys Lys Ser Met Phe Ile Met Gly Thr Thr Asn Thr Asn Tyr
                245                 250                 255

Thr Ile Ser Tyr Ile Gly Gly Asn Ser Phe Asn Ile Asn Phe Ala Asn
            260                 265                 270

Ile Leu Asn Phe Asp Val Tyr Gly Arg Arg Asp Val Val Lys Asn Gly
        275                 280                 285

Glu Val Leu Val Asp Ile Met Ala Asn His Gly Asp Ser Ile Val Leu
    290                 295                 300

Lys Ile Val Asn Gly Glu Leu Tyr Ala Asp Val Pro Cys Ser Val Thr
305                 310                 315                 320

Leu Asn Lys Val Glu Ser Asn Phe Asp Lys Val Val Gly Ile Asp Val
                325                 330                 335

Asn Met Lys His Met Leu Leu Ser Thr Ser Val Thr Asp Asn Gly Ser
            340                 345                 350

Leu Asp Phe Leu Asn Ile Tyr Lys Glu Met Ser Asn Asn Ala Glu Phe
        355                 360                 365

Met Ala Leu Cys Ser Glu Asp Asp Arg Lys Tyr Tyr Lys Asp Ile Ser
    370                 375                 380

Gln Tyr Val Thr Phe Ala Pro Leu Glu Leu Asp Leu Leu Phe Ser Arg
385                 390                 395                 400

Ile Ser Lys Gln Gly Lys Val Lys Met Glu Lys Ala Tyr Ser Glu Ile
                405                 410                 415
```

-continued

```
Leu Glu Ala Leu Lys Trp Lys Phe Phe Ala Asn Gly Asp Asn Lys Asn
            420             425             430

Arg Ile Tyr Val Glu Ser Ile Gln Lys Ile Arg Gln Gln Ile Lys Ala
            435             440             445

Leu Cys Ile Ile Lys Asn Ala Tyr Tyr Glu Gln Gln Ser Ala Tyr Asp
            450             455             460

Ile Asp Lys Thr Gln Glu Tyr Ile Glu Ala His Pro Phe Ser Leu Thr
465             470             475             480

Glu Lys Gly Met Ser Ile Lys Ser Lys Met Asp Asn Ile Cys Arg Thr
            485             490             495

Ile Ile Gly Cys Arg Asn Asn Ile Ile Asp Tyr Ala Tyr Ser Phe Phe
            500             505             510

Glu Arg Asn Asp Tyr Ser Ile Ile Gly Leu Glu Lys Leu Thr Ser Ala
            515             520             525

Gln Phe Glu Lys Thr Lys Ser Leu Pro Thr Cys Lys Ser Leu Leu Asn
            530             535             540

Phe His Lys Val Leu Gly His Thr Leu Ser Glu Leu Gly Thr Leu Pro
545             550             555             560

Ile Asn Asp Val Val Lys Lys Gly Tyr Tyr Thr Phe Thr Thr Asp Asn
            565             570             575

Glu Gly Arg Ile Thr Asp Ala Ser Leu Ser Glu Lys Gly Lys Val Arg
            580             585             590

Lys Met Lys Asp Asp Phe Phe Asn Gln Thr Ile Lys Ala Ile His Phe
            595             600             605

Ala Asp Val Lys Asp Tyr Phe Ala Thr Leu Ser Asn Asn Gly Gln Thr
            610             615             620

Gly Ile Phe Phe Val Pro Ser Gln Phe Thr Ser Gln Met Asp Ser Ser
625             630             635             640

Thr His Asn Leu Tyr Phe Glu Asn Ala Lys Asn Gly Gly Leu Lys Leu
            645             650             655

Ala Pro Lys Tyr Lys Val Arg Gln Met Gln Glu Tyr His Leu Asn Gly
            660             665             670

Leu Pro Ala Asp Tyr Asn Ala Ala Arg Asn Ile Ala Tyr Ile Gly Leu
            675             680             685

Asp Glu Thr Met Arg Asn Thr Phe Leu Lys Lys Ala Asn Ser Asn Lys
            690             695             700

Ser Leu Tyr Asn Gln Pro Ile Tyr Asp Thr Gly Ile Lys Lys Thr Ala
705             710             715             720

Gly Val Phe Tyr Arg Met Lys Lys Leu Lys Arg Tyr Glu Ile Ile
            725             730             735
```

```
<210> SEQ ID NO 149
<211> LENGTH: 779
<212> TYPE: PRT
<213> ORGANISM: Artificial sequence
<220> FEATURE:
<223> OTHER INFORMATION: synthetic sequence

<400> SEQUENCE: 149
```

```
Met Lys Arg Asn Gln Lys His Ile Lys Asn Ile Glu Glu Ser Glu Thr
1               5               10              15

Ile Lys Thr Ile Ser Phe Lys Val Lys Asp Tyr Ala Gly Ile Pro Ile
            20              25              30

Val Glu Ala Met His Glu Tyr Arg Asn Tyr Tyr Asn Arg Leu Ser Arg
            35              40              45
```

-continued

```
Phe Ile Asn Ser Lys Leu Leu Thr Met Thr Ile Gly Glu Leu Ala Ser
    50                  55                  60

Leu Leu Pro Glu Arg Cys Lys Ser Lys Gly Tyr Tyr Leu Tyr Met Thr
65                  70                  75                  80

Ser Asp Glu Trp Val Asn Glu Tyr Val Tyr Lys Met Phe Met Glu Ser
                85                  90                  95

Phe Asn Ser Gln Ser Cys Asp Asn Ile Trp Phe Asn Tyr Ile Lys Met
                100                 105                 110

Asn Asn Pro Glu Glu Tyr Asn Gly Asn Ile Leu Gly Ile Ser Asp Ser
            115                 120                 125

Tyr Tyr Arg Arg Asn Gly Tyr Phe Ile Asn Val Ile Ser Asn Tyr Lys
    130                 135                 140

Thr Lys Phe Lys Ser Pro Gln Ile Asn Val Lys Ser Lys Lys Leu Ser
145                 150                 155                 160

Glu Ser Pro Thr Glu Glu Glu Leu Lys Glu Gln Cys Val Tyr Glu Tyr
                165                 170                 175

Val Lys His Asn Leu His Ser Lys Lys Asp Trp Glu Glu Gln Ile Lys
            180                 185                 190

Tyr Leu Asp Glu Arg Gly Glu Ser Lys Ile Asn Ile Leu Glu Arg Ile
            195                 200                 205

Arg Thr Leu Tyr Gln Tyr Tyr Lys Glu Asn Ile Pro Thr Ile Lys Glu
    210                 215                 220

Tyr Ile Glu Leu Lys Ser Ile Glu Ser Ile Glu Lys Phe Gly Gly Cys
225                 230                 235                 240

Val Arg Lys Glu Asp Lys Leu Ser Met Ser Leu Gln Tyr Val Ser Thr
                245                 250                 255

His Asn Tyr Glu Ile Lys Leu Asn Asp Thr Arg Asn Gly Tyr Ile Ile
            260                 265                 270

Ser Gly Ile Ser Lys Asp Leu Ser Phe Glu Val Tyr Gly Asn Arg Met
            275                 280                 285

Gly Leu Leu Gly Gly Glu Glu Ile Leu Asn Ile Pro Glu Lys His Ser
    290                 295                 300

Thr Ser Ile Thr Phe Val Met Arg Asn Asn Ser Leu Tyr Val Asp Ile
305                 310                 315                 320

Pro Val Ala Val Pro Phe Ser Lys Val Ile Asn Asp Cys Asp Gly Lys
                325                 330                 335

Thr Val Gly Ile Asp Val Asn Leu Lys His Ala Leu Phe Ala Thr Ser
            340                 345                 350

Glu Val Asp Asn Gly Gln Phe Tyr Asp Tyr Val Asn Val Tyr Ala Glu
            355                 360                 365

Leu Leu Lys Asp Glu Asn Phe Val Lys Val Cys His Lys Glu Leu Leu
    370                 375                 380

Asp Tyr Ile Lys Asp Val Ser Lys Tyr Val Phe Phe Ala Pro Ile Glu
385                 390                 395                 400

Leu Asn Leu Leu Leu Ser Arg Val Met Lys Gln Lys Gly Tyr Glu Asn
                405                 410                 415

Ile Asp Asn Tyr Lys Lys Leu Tyr Lys Val Glu Glu Ala Tyr Leu Cys
            420                 425                 430

Val Leu Asp Lys Leu Gln Lys Arg Phe Ile Asp Glu Gly Asn Asn Thr
            435                 440                 445

Lys Arg Ile Tyr Ile Glu Asn Leu Lys Lys Met Arg Ala Gln Met Lys
    450                 455                 460
```

-continued

```
Ala Tyr Tyr Ile Leu Lys Asp Thr Tyr Ser Lys Tyr Gln Lys Asp Tyr
465                 470                 475                 480

Asp Ile Glu Met Gly Phe Val Asp Glu Ser Thr Glu Ser Lys Glu Thr
                485                 490                 495

Met Asp Ala Arg Arg Ser Glu Asn Pro Phe Arg Ser Thr Asp Ile Ala
            500                 505                 510

Gln Asp Ile Leu Lys Lys Met Asn Asn Val Gly Lys Thr Val Glu Ala
            515                 520                 525

Cys Arg Asn Asn Ile Ile Ala Tyr Ile Tyr Lys Val Phe Glu Asn Ser
            530                 535                 540

Asp Phe Ala Thr Ile Val Leu Glu Lys Leu Gln Ser Ser Gln Met Lys
545                 550                 555                 560

Lys His Lys Arg Ile Pro Thr Val Asn Ser Leu Leu Lys Tyr His His
                565                 570                 575

Val Glu Gly His Thr Ile Glu Glu Thr Lys Glu Met Lys Ile Tyr Asp
                580                 585                 590

Val Val Glu Lys Gly Tyr Tyr Asn Phe Ile Val Asn Glu Lys Asn Glu
                595                 600                 605

Ile Ile Asp Ala Thr Leu Thr Asp Lys Gly Lys Val Ile Met Ile Glu
            610                 615                 620

Ala Glu Phe Tyr Asn Phe Ala Leu Lys Ser Ile His Phe Ala Asp Ala
625                 630                 635                 640

Lys Asp Tyr Phe Ile Thr Leu Ser Asn Asn Gly Ser Val Asn Ile Ala
                645                 650                 655

Leu Val Pro Ser Gln Phe Thr Ser Gln Met Asp Ser Ile Arg His Ala
                660                 665                 670

Ile Phe Val Thr Lys Gly Lys Lys Gly Lys Lys Val Ile Val Asp Lys
                675                 680                 685

Lys Tyr Val Arg Pro Lys Gln Glu Lys His Ile Asn Gly Leu Asn Gly
            690                 695                 700

Asp Tyr Asn Ala Ser Arg Asn Ile Ala Tyr Ile Phe Glu Asn Glu Glu
705                 710                 715                 720

Leu Arg Glu Glu Leu Leu Lys Lys Glu Glu Glu Tyr Asn Lys Tyr Gly
                725                 730                 735

Lys Val Leu Tyr Asp Thr Leu Ile Lys Phe Pro Ser Gly Val Ile Asn
                740                 745                 750

Lys Leu Lys Lys Phe Gly Asp Lys Tyr Met Thr Thr Ile Glu Asn Leu
                755                 760                 765

Asp Glu Ile Gln Val Glu Asp Val Ala Tyr Val
            770                 775
```

<210> SEQ ID NO 150
<211> LENGTH: 592
<212> TYPE: PRT
<213> ORGANISM: Artificial sequence
<220> FEATURE:
<223> OTHER INFORMATION: synthetic sequence

<400> SEQUENCE: 150

```
Met Ser Lys Leu Asn Thr Gly Val Lys Arg His Thr Ile Lys Glu Thr
1               5                   10                  15

Ser Asp Glu Ala Thr Ile Val Glu Gln Val Ile Tyr Glu Met Glu His
            20                  25                  30

Asn Lys Trp Glu Ser Ile Glu Asp Trp Lys Asn Gln Ile Glu Tyr Leu
        35                  40                  45
```

-continued

```
Asn Ser Lys Thr Asp Tyr Asn Pro Thr Tyr Met Glu Arg Met Lys Thr
    50                  55                  60

Leu Ser Ala Tyr Tyr Ser Glu His Lys Ser Glu Val Asp Ala Lys Met
65                  70                  75                  80

Gln Glu Met Ala Val Glu Asn Leu Val Lys Phe Gly Gly Cys Arg Arg
                85                  90                  95

Asn Asn Ser Lys Lys Ser Met Phe Ile Met Gly Ser Ser Lys Thr Thr
               100                 105                 110

Tyr Thr Ile Ser Tyr Ile Gly Asp Asn Cys Phe Asn Ile Asn Phe Ala
               115                 120                 125

Asn Ile Leu Asn Phe Asp Val Tyr Gly Arg Arg Asp Val Val Lys Asn
    130                 135                 140

Gly Glu Val Leu Val Asp Ile Met Ala Asn His Gly Asp Ser Ile Val
145                 150                 155                 160

Leu Lys Ile Val Asn Gly Glu Leu Tyr Ala Asp Val Pro Cys Ser Thr
               165                 170                 175

Thr Leu Asn Lys Val Glu Ser Thr Phe Asp Lys Val Ala Gly Ile Asp
               180                 185                 190

Val Asn Met Lys His Met Leu Leu Ser Thr Ser Val Thr Asp Asn Gly
               195                 200                 205

Asn Ser Asp Phe Val Asn Ile Tyr Lys Glu Met Ser Asn Asn Ala Glu
    210                 215                 220

Phe Met Ala Leu Cys Pro Glu Glu Asp Arg Lys Tyr Tyr Lys Asp Ile
225                 230                 235                 240

Ser Gln Tyr Val Thr Phe Ala Pro Leu Glu Leu Asp Leu Leu Phe Ser
               245                 250                 255

Arg Ile Ser Lys Gln Gly Lys Val Lys Met Glu Lys Ala Tyr Ser Glu
               260                 265                 270

Ile Leu Glu Thr Leu Lys Trp Lys Phe Phe Ala Asn Gly Asp Asn Lys
               275                 280                 285

Asn Arg Ile Tyr Val Glu Ser Ile Gln Lys Ile Arg Gln Gln Ile Lys
    290                 295                 300

Ala Leu Cys Val Ile Lys Asn Ala Tyr Tyr Glu Gln Gln Ser Ala Tyr
305                 310                 315                 320

Asp Ile Asp Lys Thr Gln Glu Tyr Ile Glu Ala His Pro Phe Ser Leu
               325                 330                 335

Thr Glu Lys Gly Met Ser Ile Lys Ser Lys Met Asp Asn Ile Cys Arg
               340                 345                 350

Thr Ile Ile Gly Cys Arg Asn Asn Ile Ile Asp Tyr Ala Tyr Ser Phe
               355                 360                 365

Phe Glu Arg Asn Asp Tyr Ser Ile Ile Gly Leu Glu Lys Leu Thr Ser
    370                 375                 380

Ser Gln Phe Glu Lys Thr Lys Ser Leu Pro Thr Cys Lys Ser Leu Leu
385                 390                 395                 400

Asn Phe His Lys Val Leu Gly His Thr Leu Ser Glu Leu Glu Thr Leu
               405                 410                 415

Pro Ile Asn Asp Val Val Lys Lys Gly Tyr Tyr Thr Phe Thr Thr Asp
               420                 425                 430

Asn Glu Gly Arg Ile Thr Asp Ala Ser Leu Ser Glu Lys Gly Lys Val
               435                 440                 445

Arg Lys Met Lys Asp Asp Phe Phe Asn Gln Ala Ile Lys Ala Ile His
    450                 455                 460

Phe Ala Asp Val Lys Asp Tyr Phe Ala Thr Leu Ser Asn Asn Gly Gln
```

-continued

```
465            470            475            480

Thr Gly Ile Phe Phe Val Pro Ser Gln Phe Thr Ser Gln Met Asp Ser
            485            490            495

Asn Thr His Thr Leu Tyr Phe Glu Asn Ala Lys Asn Gly Gly Leu Lys
            500            505            510

Leu Ala Ser Lys Tyr Lys Val Arg Gln Thr Gln Glu Tyr His Leu Asn
            515            520            525

Gly Leu Pro Ala Asp Tyr Asn Ala Ala Arg Asn Ile Ala Tyr Ile Gly
            530            535            540

Leu Asp Glu Thr Met Arg Asn Thr Phe Leu Lys Lys Ala Asn Ser Asn
545            550            555            560

Lys Ser Leu Tyr Asn Gln Pro Ile Tyr Asp Thr Gly Ile Lys Lys Thr
            565            570            575

Ala Gly Val Phe Ser Arg Met Lys Lys Leu Lys Arg Tyr Glu Ile Ile
            580            585            590

<210> SEQ ID NO 151
<211> LENGTH: 746
<212> TYPE: PRT
<213> ORGANISM: Artificial sequence
<220> FEATURE:
<223> OTHER INFORMATION: synthetic sequence

<400> SEQUENCE: 151

Met Ala Ser His Lys Lys Thr Glu Ser Asn Gln Ile Ile Lys Thr Phe
1            5            10            15

Ser Phe Lys Ile Lys Asn Ala Asn Gly Leu Ser Leu Asp Val Leu Asn
            20            25            30

Asp Ala Ile Thr Glu Tyr Gln Asn Tyr Tyr Asn Ile Cys Ser Asp Trp
            35            40            45

Ile Lys Asp His Leu Thr Met Lys Ile Gly Glu Leu Tyr Lys Tyr Ile
            50            55            60

Pro Asp Glu Lys Lys Asn Ser Gly Tyr Ala Leu Thr Leu Ile Ser Asp
65            70            75            80

Glu Trp Lys Asp Lys Pro Met Tyr Met Met Phe Lys Lys Gly Tyr Pro
            85            90            95

Ala Asn Asn Arg Asp Asn Ala Ile Tyr Glu Ala Leu Asn Thr Cys Asn
            100            105            110

Thr Glu His Tyr Thr Gly Asn Ile Leu Asn Phe Ser Asp Thr Tyr Tyr
            115            120            125

Arg Arg Phe Gly Tyr Val Ala Ser Ala Ile Ser Asn Tyr Val Thr Lys
            130            135            140

Ile Ser Lys Met Ser Thr Gly Ser Arg Ser Lys Asn Ile Ser Asn Asp
145            150            155            160

Ser Asp Val Asp Thr Ile Met Glu Gln Val Ile Tyr Glu Met Glu His
            165            170            175

Asn Gly Trp Thr Ser Val Lys Asp Trp Glu Asn Gln Met Glu Tyr Leu
            180            185            190

Glu Ser Lys Thr Asp Ser Asn Pro Asn Phe Val Tyr Arg Met Thr Thr
            195            200            205

Leu Tyr Glu Phe Tyr Lys Ser His Ile Asp Glu Val Asn Ser Lys Met
            210            215            220

Glu Thr Met Ser Ile Asp Ser Leu Ile Lys Phe Gly Gly Cys Arg Arg
225            230            235            240

Lys Asp Ser Lys Lys Ser Met Tyr Ile Met Gly Gly Ser Asn Thr Pro
```

```
                    245                 250                 255

Phe Asp Ile Thr Gln Ile Gly Gly Asn Ser Leu Asn Ile Lys Phe Ser
            260                 265                 270

Lys Asn Leu Asn Val Asp Val Phe Gly Arg Tyr Asp Val Ile Lys Asp
            275                 280                 285

Asn Thr Leu Leu Val Asp Ile Ile Asn Gly His Gly Ala Ser Phe Val
    290                 295                 300

Leu Lys Ile Ile Asn Asp Glu Ile Tyr Ile Asp Ile Asn Val Ser Val
305                 310                 315                 320

Pro Phe Asp Lys Lys Ile Ala Thr Thr Asn Lys Val Val Gly Ile Asp
                325                 330                 335

Val Asn Ile Lys His Met Leu Leu Ala Thr Asn Ile Leu Asp Asp Gly
            340                 345                 350

Asn Val Asn Gly Tyr Val Asn Ile Tyr Lys Glu Val Ile Asn Asp Ser
            355                 360                 365

Asp Phe Lys Lys Val Cys Asn Ser Thr Val Met Lys Tyr Phe Thr Asp
    370                 375                 380

Phe Ser Lys Phe Val Thr Phe Cys Pro Leu Glu Phe Asp Phe Leu Phe
385                 390                 395                 400

Ser Arg Val Cys Asn Gln Lys Gly Ile Tyr Asn Asp Asn Ser Ala Met
                405                 410                 415

Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
            435                 440                 445

Leu Arg Ser Gln Met Lys Ala Tyr Ala Ile Val Lys Asn Ala Tyr Tyr
    450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu Asn Lys
                485                 490                 495

Leu Asp Asn Ile Ser Lys Lys Ile Leu Gly Cys Arg Asn Asn Ile Ile
            500                 505                 510

Gln Tyr Ser Tyr Asn Leu Phe Glu Ile Asn Gly Tyr Asp Met Ile Ser
            515                 520                 525

Leu Glu Lys Leu Thr Ser Ser Gln Phe Lys Lys Pro Phe Pro Thr
    530                 535                 540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
                565                 570                 575

Asp Ile Ile Phe Asp Asn Asp Val Val Thr Asp Ala Lys Leu Ser Thr
            580                 585                 590

Lys Gly Glu Leu Ser Lys Phe Lys Asp Asp Phe Phe Asn Leu Met Ile
            595                 600                 605

Lys Ser Ile His Phe Ala Asp Ile Lys Asp Tyr Phe Ile Thr Leu Ser
    610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
                645                 650                 655

Ser Gly Lys Leu Lys Leu Ala Asn Lys His Lys Val Arg Ser Ser Gln
            660                 665                 670
```

-continued

```
Glu Lys His Ile Asn Gly Leu Asn Ala Asp Tyr Asn Ala Ala Arg Asn
        675             680             685

Ile Ala Tyr Ile Met Glu Asn Thr Asp Cys Arg Asn Met Phe Met Lys
        690             695             700

Gln Ser Arg Thr Asp Lys Ser Leu Tyr Asn Lys Pro Ser Tyr Glu Thr
705             710             715             720

Phe Ile Lys Thr Gln Gly Ser Ala Val Ala Lys Leu Lys Lys Glu Gly
            725             730             735

Phe Val Lys Ile Leu Asp Glu Ala Ser Val
            740             745

<210> SEQ ID NO 152
<211> LENGTH: 29
<212> TYPE: PRT
<213> ORGANISM: Artificial sequence
<220> FEATURE:
<223> OTHER INFORMATION: synthetic sequence

<400> SEQUENCE: 152

Tyr Glu Thr Phe Ile Lys Thr Gln Gly Ser Ala Val Ala Lys Leu Lys
1               5               10              15

Lys Glu Gly Phe Val Lys Ile Leu Asp Glu Ala Ser Val
            20              25

<210> SEQ ID NO 153
<211> LENGTH: 738
<212> TYPE: PRT
<213> ORGANISM: Artificial sequence
<220> FEATURE:
<223> OTHER INFORMATION: synthetic sequence

<400> SEQUENCE: 153

Met Ala Ser His Ser Ser Leu Ser Asn Asn Gln Ile Phe Lys Thr Phe
1               5               10              15

Ser Phe Lys Val Lys Ser Ser Asn Leu Ser Lys Asp Phe Phe Asp Val
            20              25              30

Ile Lys Glu Tyr Gln Glu Tyr Tyr Asn Lys Cys Ser Asp Val Ile Leu
        35              40              45

Glu Asn Leu Thr Cys Ile Lys Ile Gly Asp Ile Phe Asp Met Ile Pro
    50              55              60

Glu Lys Ser Lys Lys Ser Asp Tyr Ala Gln Tyr Ala Ile Ser Asp Glu
65              70              75              80

Trp Lys Asn Val Pro Leu Tyr Asn Ile Phe Ser Lys Ala Phe Ala Pro
                85              90              95

Met His Arg Asp Asn Leu Leu Tyr Ile Trp Leu Thr Lys Leu Val Pro
            100             105             110

Tyr Thr Gly Asn Leu Leu Lys Ile Ser Asp Thr Phe Tyr Lys Arg Asn
        115             120             125

Gly Phe Ile Lys Ser Val Ile Ser Asn Tyr Thr Thr Ser Phe Thr Asn
        130             135             140

Ile Lys Pro Lys Val Lys Phe Gln Lys Leu Thr Gly Asp Asp Ser His
145             150             155             160

Glu Met Leu Leu Thr Gln Thr Ile Cys Asp Met Val Lys Phe Asn Leu
            165             170             175

Tyr Asp Ile Lys Ser Trp Glu Glu Met Val Ser Tyr Phe Glu Met Lys
            180             185             190

Ser Glu Thr Ser Glu Asp Thr Leu Asn Arg Ile His Thr Leu Phe Asp
```

-continued

```
             195                 200                 205
Phe Tyr Lys Asn Asn Thr Pro Glu Val Glu Asp Lys Tyr Asn Glu Leu
    210                 215                 220

Val Thr Glu Ser Leu Ser Lys Phe Gly Gly Cys Arg Arg Asp Met Ser
225                 230                 235                 240

Lys Leu Thr Met Ser Ile Gln Leu Ser Lys Lys Val Ile Lys Val Thr
                245                 250                 255

His Gly Tyr Asn Thr Leu Asn Tyr Lys Tyr Gly Lys Leu Ile Asp Leu
                260                 265                 270

Glu Leu Trp Gly Arg Lys Asp Ile Ile Asn Asn Asp Glu Leu Leu Ile
                275                 280                 285

Asn Leu Glu Asn Val Cys Glu Met Ile Val Phe Lys Ile Lys Asn Gly
    290                 295                 300

Glu Ile Tyr Val Asp Ile Pro Phe Lys Val Asp Phe Ile Lys Lys Asp
305                 310                 315                 320

Gln Thr Ile Asp Lys Ile Ala Gly Val Asp Ala Asn Ile Lys His Met
                325                 330                 335

Leu Leu Ser Thr Ser Val Lys Asp Glu Asn Leu Ile Gly Tyr Thr Asn
                340                 345                 350

Ile Tyr Lys Glu Val Ile Asn Asp Ser Asp Phe Gln Lys Val Cys Asp
                355                 360                 365

Asn Lys Thr Met Lys Ile Leu Gln Glu Ile Ser Asn Tyr Val Thr Phe
    370                 375                 380

Ala Pro Ile Glu Phe Asp Met Leu Phe Ser Arg Ile Ser Lys Gln Arg
385                 390                 395                 400

Glu Met Lys Asp Lys Tyr Ile Asn Met Glu Ile Ala Phe Thr Asn Val
                405                 410                 415

Leu Asn Lys Leu Lys Gln Lys Phe Ile Val Asn Ser Asp Asn Lys Asn
                420                 425                 430

Arg Ile Tyr Ile Glu Ser Ile Leu Lys Ile Arg Ser Gln Leu Lys Ser
                435                 440                 445

Tyr Ala Ile Leu Glu Glu Val Lys Tyr Lys Lys Ala Ser Glu Tyr Asp
    450                 455                 460

Ser Ala Ile Val Glu Glu Phe Gly Val Glu Tyr Leu Glu Thr His Pro
465                 470                 475                 480

Phe Lys Asp Thr Glu Thr Tyr Lys Glu Ile Asn Lys Lys Ile Leu Asn
                485                 490                 495

Ile Ser Glu Asn Ile Ile Gly Cys Arg Asn Asn Ile Ile Gln Tyr Ala
                500                 505                 510

Tyr Lys Ile Phe Glu Ser Asn Gly Phe Asp Met Ile Ser Leu Glu Asn
                515                 520                 525

Leu Thr Asn Ser Asn Phe Lys Lys Glu Lys Asn Met Pro Thr Ile Lys
    530                 535                 540

Ser Leu Leu Ser Tyr His His Val Leu Gly Lys Thr Asn Glu Glu Ile
545                 550                 555                 560

Glu Lys Leu Asp Val Tyr Ser Val Ile Lys Lys Gly Tyr Tyr Thr Phe
                565                 570                 575

Glu Tyr Lys Asp Gly Lys Val Val Asn Ala Lys Leu Ser Glu Ile Gly
                580                 585                 590

Glu Met Ile Lys Ile Lys Thr Thr Met Phe Asn Met Met Ile Lys Ser
                595                 600                 605

Ile His Phe Ala Glu Ile Lys Asp Tyr Phe Ile Thr Leu Ala Asn Asn
    610                 615                 620
```

-continued

```
Gly Glu Val Gly Val Ser Leu Val Pro Ser Tyr Tyr Thr Ser Gln Met
625             630             635             640

Asp Ser Thr Asp His Lys Val Phe Gly Leu Leu Ser Lys Lys Gly Lys
                645             650             655

Trp Thr Leu Val Asp Lys Arg Lys Val Arg Lys Asn Gln Glu Thr His
            660             665             670

Ile Asn Gly Leu Asn Ala Asp Tyr Asn Ala Ala Lys Asn Ile Ala Phe
            675             680             685

Ile Leu Ser Asp Glu Val Trp Arg Asn Lys Phe Thr Lys Lys Thr Lys
            690             695             700

Thr Pro Lys Tyr Asn Thr Pro Ser Tyr Tyr Thr Ser Ile Asn Ser Gln
705             710             715             720

Gly Lys Met Leu Arg Ala Leu Lys Ser Leu Lys Ala Phe Lys Glu Phe
                725             730             735

Lys Ile
```

```
<210> SEQ ID NO 154
<211> LENGTH: 692
<212> TYPE: PRT
<213> ORGANISM: Artificial sequence
<220> FEATURE:
<223> OTHER INFORMATION: synthetic sequence

<400> SEQUENCE: 154

Met Lys Ile Gly Glu Leu Tyr Lys Tyr Ile Pro Asp Glu Lys Lys Asn
1               5               10              15

Ser Gly Tyr Ala Leu Thr Leu Ile Ser Asp Glu Trp Lys Asp Lys Pro
                20              25              30

Met Tyr Met Met Phe Lys Lys Gly Tyr Pro Ala Asn Asn Arg Asp Asn
            35              40              45

Ala Ile Tyr Glu Ala Leu Asn Thr Cys Asn Thr Glu His Tyr Thr Gly
            50              55              60

Asn Ile Leu Asn Phe Ser Asp Thr Tyr Tyr Arg Arg Phe Gly Tyr Val
65              70              75              80

Ala Ser Ala Ile Ser Asn Tyr Val Thr Lys Ile Ser Lys Met Ser Thr
                85              90              95

Gly Ser Arg Ser Lys Asn Ile Ser Asn Asp Ser Asp Val Asp Thr Ile
                100             105             110

Met Glu Gln Val Ile Tyr Glu Met Glu His Asn Gly Trp Thr Ser Val
            115             120             125

Lys Asp Trp Glu Asn Gln Met Glu Tyr Leu Glu Ser Lys Thr Asp Ser
            130             135             140

Asn Pro Asn Phe Val Tyr Arg Met Thr Thr Leu Tyr Glu Phe Tyr Lys
145             150             155             160

Ser His Ile Asp Glu Val Asn Ser Lys Met Glu Thr Met Ser Ile Asp
                165             170             175

Ser Leu Ile Lys Phe Gly Gly Cys Arg Arg Lys Asp Ser Lys Lys Ser
                180             185             190

Met Tyr Ile Met Gly Gly Ser Asn Thr Pro Phe Asp Ile Thr Gln Ile
            195             200             205

Gly Gly Asn Ser Leu Asn Ile Lys Phe Ser Lys Asn Leu Asn Val Asp
            210             215             220

Val Phe Gly Arg Tyr Asp Val Ile Lys Asp Asn Thr Leu Leu Val Asp
225             230             235             240
```

-continued

```
Ile Ile Asn Glu His Gly Ala Ser Phe Val Leu Lys Ile Ile Asn Asp
            245             250             255

Glu Ile Tyr Ile Asp Ile Asn Val Ser Val Pro Phe Asp Lys Lys Ile
            260             265             270

Ala Thr Thr Asn Lys Val Val Gly Ile Asp Val Asn Ile Lys His Met
            275             280             285

Leu Leu Ala Thr Asn Ile Leu Asp Asp Gly Asn Val Asn Gly Tyr Val
    290             295             300

Asn Ile Tyr Lys Glu Val Ile Asn Asp Ser Asp Phe Lys Lys Val Cys
305             310             315             320

Asn Ser Thr Val Met Gln Tyr Phe Thr Asp Phe Ser Lys Phe Val Thr
            325             330             335

Phe Cys Pro Leu Glu Phe Asp Phe Leu Phe Ser Arg Val Cys Asn Gln
            340             345             350

Lys Gly Ile Tyr Asn Asp Asn Ser Ala Met Glu Lys Ser Phe Ser Asp
            355             360             365

Val Leu Asn Lys Leu Lys Trp Asn Phe Ile Glu Thr Gly Asp Asn Thr
    370             375             380

Lys Arg Ile Tyr Ile Glu Asn Val Met Lys Leu Arg Ser Gln Met Lys
385             390             395             400

Ala Tyr Ala Ile Val Lys Asn Ala Tyr Tyr Lys Gln Gln Ser Glu Tyr
            405             410             415

Asp Phe Gly Lys Ser Glu Glu Phe Ile Gln Glu His Pro Phe Ser Asn
            420             425             430

Thr Asp Lys Gly Ile Glu Ile Leu Asn Lys Leu Asp Asn Ile Ser Lys
            435             440             445

Lys Ile Leu Gly Cys Arg Asn Asn Ile Ile Gln Tyr Ser Tyr Asn Leu
    450             455             460

Phe Glu Ile Asn Gly Tyr Asp Met Ile Ser Leu Glu Lys Leu Thr Ser
465             470             475             480

Ser Gln Phe Lys Lys Lys Pro Phe Pro Thr Val Asn Ser Leu Leu Lys
            485             490             495

Tyr His Lys Ile Leu Gly Cys Thr Gln Glu Glu Met Glu Lys Lys Asp
            500             505             510

Ile Tyr Ser Val Ile Lys Lys Gly Tyr Tyr Asp Ile Ile Phe Asp Asn
            515             520             525

Asp Val Val Thr Asp Ala Lys Leu Ser Thr Lys Gly Glu Leu Ser Lys
    530             535             540

Phe Lys Asp Asp Phe Phe Asn Leu Met Ile Lys Ser Ile His Phe Ala
545             550             555             560

Asp Ile Lys Asp Tyr Phe Ile Thr Leu Ser Asn Asn Gly Thr Ala Gly
            565             570             575

Val Ser Leu Val Pro Ser Tyr Phe Thr Ser Gln Met Asp Ser Ile Asp
            580             585             590

His Lys Ile Tyr Phe Val Gln Asp Asn Lys Ser Gly Lys Leu Lys Leu
            595             600             605

Ala Asn Lys His Lys Val Arg Ser Ser Gln Glu Lys His Ile Asn Gly
    610             615             620

Leu Asn Ala Asp Tyr Asn Ala Ala Arg Asn Ile Ala Tyr Ile Met Glu
625             630             635             640

Asn Thr Glu Cys Arg Asn Met Phe Met Lys Gln Ser Arg Thr Asp Lys
            645             650             655

Ser Leu Tyr Asn Lys Pro Ser Tyr Glu Thr Phe Ile Lys Thr Gln Gly
```

-continued

```
                    660             665             670

Ser Ala Val Ala Lys Leu Lys Lys Glu Gly Phe Val Lys Ile Leu Asp
            675             680             685

Glu Ala Ser Val
    690

<210> SEQ ID NO 155
<211> LENGTH: 441
<212> TYPE: PRT
<213> ORGANISM: Artificial sequence
<220> FEATURE:
<223> OTHER INFORMATION: synthetic sequence

<400> SEQUENCE: 155

Lys Ile Ile Asn Asp Glu Ile Tyr Ile Asp Ile Asn Val Ser Val Pro
1               5                  10                  15

Phe Asp Lys Lys Ile Ala Thr Thr Asn Lys Val Val Gly Ile Asp Val
            20                  25                  30

Asn Ile Lys His Met Leu Leu Ala Thr Asn Ile Leu Asp Asp Gly Asn
        35                  40                  45

Val Asn Gly Tyr Val Asn Ile Tyr Lys Glu Val Ile Asn Asp Ser Asp
    50                  55                  60

Phe Lys Lys Val Cys Asn Ser Thr Val Met Lys Tyr Phe Thr Asp Phe
65                  70                  75                  80

Ser Lys Phe Val Thr Phe Cys Pro Leu Glu Phe Asp Phe Leu Phe Ser
                85                  90                  95

Arg Val Cys Asn Gln Lys Gly Ile Tyr Asn Asp Asn Ser Ala Met Glu
            100                 105                 110

Lys Ser Phe Ser Asp Val Leu Asn Arg Leu Lys Trp Asn Phe Ile Glu
        115                 120                 125

Thr Gly Asp Asn Thr Lys Arg Ile Tyr Ile Glu Asn Val Met Lys Leu
    130                 135                 140

Arg Ser Gln Met Lys Ala Tyr Ala Ile Val Lys Asn Ala Tyr Tyr Lys
145                 150                 155                 160

Gln Gln Ser Glu Tyr Asp Phe Gly Lys Ser Glu Glu Phe Ile Gln Glu
                165                 170                 175

His Pro Phe Ser Asn Thr Asp Lys Gly Ile Glu Ile Leu Asn Lys Leu
            180                 185                 190

Asp Asn Ile Ser Lys Lys Ile Leu Gly Cys Arg Asn Asn Ile Ile Gln
        195                 200                 205

Tyr Ser Tyr Asn Leu Phe Glu Ile Asn Gly Tyr Asp Met Ile Ser Leu
    210                 215                 220

Glu Lys Leu Thr Ser Ser Gln Phe Lys Lys Pro Phe Pro Thr Val
225                 230                 235                 240

Asn Ser Leu Leu Lys Tyr His Lys Ile Arg Gly Gly Thr Gln Glu Glu
                245                 250                 255

Met Glu Lys Lys Asp Ile Tyr Ser Val Ile Lys Lys Gly Tyr Tyr Asp
            260                 265                 270

Ile Ile Phe Asp Asn Asp Val Val Thr Asp Ala Lys Leu Ser Thr Lys
        275                 280                 285

Gly Glu Leu Ser Lys Phe Lys Asp Asp Phe Phe Asn Leu Met Ile Lys
    290                 295                 300

Ser Ile His Phe Ala Asp Ile Lys Asp Tyr Phe Ile Thr Leu Ser Asn
305                 310                 315                 320

Asn Gly Thr Ala Gly Val Ser Leu Val Pro Ser Tyr Phe Thr Ser Gln
```

-continued

```
                325               330               335
Met Asp Ser Ile Asp His Lys Ile Tyr Phe Val Gln Asp Asn Lys Ser
            340               345               350

Gly Lys Leu Lys Leu Ala Asn Lys His Lys Val Arg Ser Ser Gln Glu
        355               360               365

Lys His Ile Asn Gly Leu Asn Ala Asp Tyr Asn Ala Ala Arg Asn Ile
    370               375               380

Ala Tyr Ile Met Glu Asn Asn Glu Cys Arg Asn Met Phe Met Lys Gln
385               390               395               400

Ser Arg Thr Asp Lys Ser Leu Tyr Asn Lys Pro Ser Tyr Glu Thr Phe
            405               410               415

Ile Lys Thr Gln Gly Ser Ala Val Ala Lys Leu Lys Lys Glu Gly Phe
        420               425               430

Val Lys Ile Leu Asp Glu Ala Ser Val
        435               440
```

```
<210> SEQ ID NO 156
<211> LENGTH: 397
<212> TYPE: PRT
<213> ORGANISM: Artificial sequence
<220> FEATURE:
<223> OTHER INFORMATION: synthetic sequence

<400> SEQUENCE: 156

Asp Asp Gly Asn Val Asn Gly Tyr Val Asn Ile Tyr Lys Glu Val Ile
1               5                 10                15

Asn Asp Ser Asp Phe Lys Lys Val Cys Asn Ser Thr Val Met Lys Tyr
            20                25                30

Phe Thr Asp Phe Ser Lys Phe Val Thr Phe Cys Pro Leu Glu Phe Asp
        35                40                45

Phe Leu Phe Ser Arg Val Cys Asn Gln Lys Gly Ile Tyr Asn Asp Asn
    50                55                60

Ser Ala Met Glu Lys Ser Phe Ser Asp Val Leu Asn Lys Leu Lys Trp
65                70                75                80

Asn Phe Ile Glu Thr Gly Asp Asn Thr Lys Arg Ile Tyr Ile Glu Asn
            85                90                95

Val Met Lys Leu Arg Ser Gln Met Lys Ala Tyr Ala Ile Val Lys Asn
            100               105               110

Ala Tyr Tyr Lys Gln Gln Ser Glu Tyr Asp Phe Gly Lys Ser Glu Glu
        115               120               125

Phe Ile Gln Glu His Pro Phe Ser Asn Thr Asp Lys Gly Ile Glu Ile
    130               135               140

Leu Asn Lys Leu Asp Asn Ile Ser Lys Lys Ile Leu Gly Cys Arg Asn
145               150               155               160

Asn Ile Ile Gln Tyr Ser Tyr Asn Leu Phe Glu Ile Asn Gly Tyr Asp
            165               170               175

Met Ile Ser Leu Glu Lys Leu Thr Ser Ser Gln Phe Lys Lys Lys Pro
        180               185               190

Phe Pro Thr Val Asn Ser Leu Leu Lys Tyr His Lys Ile Leu Gly Cys
        195               200               205

Thr Gln Glu Glu Met Glu Lys Lys Asp Ile Tyr Ser Val Ile Lys Lys
    210               215               220

Gly Tyr Tyr Asp Ile Ile Phe Asp Asn Asp Val Val Thr Asp Ala Lys
225               230               235               240

Leu Ser Thr Lys Gly Glu Leu Ser Lys Phe Lys Asp Asp Phe Phe Asn
```

-continued

```
                   245               250               255

Leu Met Ile Lys Ser Ile His Phe Ala Asp Ile Lys Asp Tyr Phe Ile
            260               265               270

Thr Leu Ser Asn Asn Gly Thr Ala Gly Val Ser Leu Val Pro Ser Tyr
            275               280               285

Phe Thr Ser Gln Met Asp Ser Ile Asp His Lys Ile Tyr Phe Val Gln
            290               295               300

Asp Asn Lys Ser Gly Lys Leu Lys Leu Ala Asn Lys His Lys Val Arg
305               310               315               320

Ser Ser Gln Glu Lys His Ile Asn Gly Leu Asn Ala Asp Tyr Asn Ala
            325               330               335

Ala Arg Asn Ile Ala Tyr Ile Met Glu Asn Thr Glu Cys Arg Asn Met
            340               345               350

Phe Met Lys Gln Ser Arg Thr Asp Lys Ser Leu Tyr Asn Lys Pro Ser
            355               360               365

Tyr Glu Thr Phe Ile Lys Thr Gln Gly Ser Ala Val Ala Lys Leu Lys
            370               375               380

Lys Asp Gly Phe Val Lys Ile Leu Asp Glu Ala Ser Ala
385               390               395

<210> SEQ ID NO 157
<211> LENGTH: 746
<212> TYPE: PRT
<213> ORGANISM: Artificial sequence
<220> FEATURE:
<223> OTHER INFORMATION: synthetic sequence

<400> SEQUENCE: 157

Met Ala Ser His Lys Lys Thr Glu Ser Asn Gln Ile Ile Lys Thr Phe
1               5                10               15

Ser Phe Lys Ile Lys Asn Ala Asn Gly Leu Ser Leu Asp Val Leu Asn
            20               25               30

Asp Ala Ile Thr Glu Tyr Gln Asn Tyr Tyr Asn Ile Cys Ser Asp Trp
            35               40               45

Ile Lys Asp His Leu Thr Met Lys Ile Gly Glu Leu Tyr Lys Tyr Ile
            50               55               60

Pro Asp Glu Lys Lys Asn Ser Gly Tyr Ala Leu Thr Leu Ile Ser Asp
65               70               75               80

Glu Trp Lys Asp Lys Pro Met Tyr Met Met Phe Lys Lys Gly Tyr Pro
            85               90               95

Ala Asn Ser Arg Asp Asn Ala Ile Tyr Glu Ala Leu Asn Thr Cys Asn
            100              105              110

Thr Glu His Tyr Thr Gly Asn Ile Leu Asn Phe Ser Asp Thr Tyr Tyr
            115              120              125

Arg Arg Phe Gly Tyr Val Ala Ser Ala Ile Ser Asn Tyr Val Thr Lys
            130              135              140

Ile Ser Lys Met Ser Thr Gly Ser Arg Ser Lys Asn Ile Ser Asn Asp
145              150              155              160

Ser Asp Val Asp Thr Ile Met Glu Gln Val Ile Tyr Glu Met Glu His
            165              170              175

Asn Gly Trp Thr Ser Val Lys Asp Trp Glu Asn Gln Met Glu Tyr Leu
            180              185              190

Glu Ser Lys Thr Asp Ser Asn Pro Asn Phe Val Tyr Arg Met Thr Thr
            195              200              205

Leu Tyr Glu Phe Tyr Lys Ser His Ile Asp Glu Val Asn Ser Lys Met
```

-continued

```
         210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
                245                 250                 255

Phe Asp Ile Thr Gln Ile Asp Gly Asn Ser Leu Asn Ile Lys Phe Ser
                260                 265                 270

Lys Asn Leu Asn Val Asp Val Phe Gly Arg Tyr Asp Val Ile Lys Asp
            275                 280                 285

Asn Thr Leu Leu Val Asp Ile Ile Asn Gly His Gly Ala Ser Phe Val
        290                 295                 300

Leu Lys Ile Ile Asn Gly Glu Ile Tyr Ile Asp Ile Asn Val Ser Val
305                 310                 315                 320

Pro Phe Asp Lys Lys Ile Ala Thr Thr Asn Lys Val Val Gly Ile Asp
                325                 330                 335

Val Asn Ile Lys His Met Leu Leu Ala Thr Asn Ile Leu Asp Asp Gly
            340                 345                 350

Asn Val Asn Gly Tyr Val Asn Ile Tyr Lys Glu Val Ile Asn Asp Ser
            355                 360                 365

Asp Phe Lys Lys Val Cys Asn Ser Thr Val Met Lys Tyr Phe Thr Asp
        370                 375                 380

Phe Ser Lys Phe Val Thr Phe Cys Pro Leu Glu Phe Asp Phe Leu Phe
385                 390                 395                 400

Ser Arg Val Cys Asn Gln Lys Gly Ile Tyr Asn Asp Asn Ser Ala Met
            405                 410                 415

Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
            435                 440                 445

Leu Arg Ser Gln Met Lys Ala Tyr Ala Ile Val Lys Asn Ala Tyr Tyr
        450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu Asn Lys
                485                 490                 495

Leu Asp Asn Ile Ser Lys Lys Ile Leu Gly Cys Arg Asn Asn Ile Ile
            500                 505                 510

Gln Tyr Ser Tyr Asn Leu Phe Glu Ile Asn Gly Tyr Asp Met Ile Ser
            515                 520                 525

Leu Glu Lys Leu Thr Ser Ser Gln Phe Lys Lys Lys Pro Phe Pro Thr
        530                 535                 540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
                565                 570                 575

Asp Ile Ile Phe Asp Asn Asp Val Val Thr Asp Ala Lys Leu Ser Thr
                580                 585                 590

Lys Gly Glu Leu Ser Lys Phe Lys Asp Asp Phe Phe Asn Leu Met Ile
            595                 600                 605

Lys Ser Ile His Phe Ala Asp Ile Lys Asp Tyr Phe Ile Thr Leu Ser
        610                 615                 620

Asn Asn Gly Thr Ala Gly Val Ser Leu Val Pro Ser Tyr Phe Thr Ser
625                 630                 635                 640
```

-continued

```
Gln Met Asp Ser Ile Asp His Lys Ile Tyr Phe Val Gln Asp Asn Lys
            645             650             655

Ser Gly Lys Leu Lys Leu Ala Asn Lys His Lys Val Arg Ser Ser Gln
            660             665             670

Glu Lys His Ile Asn Gly Leu Asn Ala Asp Tyr Asn Ala Ala Arg Asn
        675             680             685

Ile Ala Tyr Ile Met Glu Asn Thr Glu Cys Arg Asn Met Phe Met Lys
        690             695             700

Gln Ser Arg Thr Asp Lys Ser Leu Tyr Asn Lys Pro Ser Tyr Glu Thr
705             710             715             720

Phe Ile Lys Thr Gln Gly Ser Ala Val Ala Lys Leu Lys Lys Glu Gly
            725             730             735

Phe Val Lys Ile Leu Asp Glu Ala Ser Val
            740             745

<210> SEQ ID NO 158
<211> LENGTH: 736
<212> TYPE: PRT
<213> ORGANISM: Artificial sequence
<220> FEATURE:
<223> OTHER INFORMATION: synthetic sequence

<400> SEQUENCE: 158

Met Ala His Lys Lys Asn Val Gly Ala Glu Ile Val Lys Thr Tyr Ser
1               5               10              15

Phe Lys Val Lys Asn Thr Asn Gly Ile Thr Met Glu Lys Leu Met Asn
            20              25              30

Ala Ile Asp Glu Phe Gln Ser Tyr Tyr Asn Leu Cys Ser Asp Trp Ile
        35              40              45

Cys Lys Asn Leu Thr Thr Met Thr Ile Gly Asp Leu Asp Gln Tyr Ile
        50              55              60

Pro Glu Lys Ala Lys Gly Asn Thr Tyr Ala Thr Val Leu Leu Asp Glu
65              70              75              80

Ala Trp Lys Asn Gln Pro Leu Tyr Lys Ile Phe Gly Lys Lys Tyr Ser
            85              90              95

Ser Asn Asn Arg Asn Asn Ala Leu Tyr Cys Ala Leu Ser Ser Val Ile
            100             105             110

Asp Met Thr Lys Glu Asn Val Leu Gly Phe Ser Lys Thr His Tyr Ile
            115             120             125

Arg Asn Asp Tyr Ile Leu Asn Val Ile Ser Asn Tyr Ala Ser Lys Leu
        130             135             140

Ser Lys Leu Asn Thr Gly Val Lys Ser Arg Ala Ile Lys Glu Thr Ser
145             150             155             160

Asp Glu Ala Thr Ile Ile Glu Gln Val Ile Tyr Glu Met Glu His Asn
            165             170             175

Lys Trp Glu Ser Ile Glu Asp Trp Lys Asn Gln Ile Glu Tyr Leu Asn
            180             185             190

Ser Lys Thr Asp Tyr Asn Pro Thr Tyr Met Glu Arg Met Lys Thr Leu
            195             200             205

Ser Ala Tyr Tyr Ser Thr His Lys Ser Glu Val Asp Ala Lys Met Gln
        210             215             220

Glu Met Ala Val Glu Asn Leu Val Lys Phe Gly Gly Cys Arg Arg Asn
225             230             235             240

Asn Ser Lys Lys Ser Met Phe Ile Met Gly Ser Asn Thr Thr Asn Tyr
            245             250             255
```

-continued

```
Thr Ile Ser Tyr Ile Gly Gly Asn Ser Phe Asn Ile Asn Phe Ala Asn
        260                 265                 270

Ile Leu Asn Phe Asp Val Tyr Gly Arg Arg Asp Val Val Lys Asn Gly
        275                 280                 285

Glu Val Leu Val Asp Ile Met Ala Asn His Gly Asp Ser Ile Val Leu
        290                 295                 300

Lys Ile Val Asn Gly Glu Leu Tyr Ala Asp Val Pro Cys Ser Val Thr
305                 310                 315                 320

Leu Asn Lys Val Glu Ser Asn Phe Asp Lys Val Val Gly Ile Asp Val
                325                 330                 335

Asn Met Lys His Met Leu Leu Ser Thr Ser Ile Thr Asp Asn Gly Ser
            340                 345                 350

Ser Asp Phe Leu Asn Ile Tyr Lys Glu Met Ser Asn Asn Ala Glu Phe
            355                 360                 365

Met Ala Leu Cys Pro Glu Glu Asp Arg Lys Tyr Tyr Lys Asp Ile Ser
        370                 375                 380

Lys Tyr Val Thr Phe Ala Pro Leu Glu Leu Asp Leu Leu Phe Ser Arg
385                 390                 395                 400

Ile Ser Lys Gln Gly Lys Val Lys Met Glu Lys Val Tyr Ser Glu Ile
                405                 410                 415

Leu Glu Ala Leu Lys Trp Lys Phe Phe Ala Asn Gly Asp Asn Lys Asn
            420                 425                 430

Arg Ile Tyr Val Glu Ser Ile Gln Lys Ile Arg Gln Gln Ile Lys Ala
            435                 440                 445

Leu Cys Val Ile Lys Asn Ala Tyr Tyr Glu Gln Gln Ser Ala Tyr Asp
        450                 455                 460

Ile Asp Lys Thr Gln Glu Tyr Ile Glu Thr His Pro Phe Ser Leu Thr
465                 470                 475                 480

Glu Lys Gly Met Ser Ile Lys Ser Lys Met Asp Lys Ile Cys Gln Thr
                485                 490                 495

Ile Ile Gly Cys Arg Asn Asn Ile Ile Asp Tyr Ala Tyr Ser Phe Phe
                500                 505                 510

Glu Arg Asn Gly Tyr Ser Ile Ile Gly Leu Glu Lys Leu Thr Ser Ser
            515                 520                 525

Gln Phe Glu Lys Thr Lys Ser Met Pro Thr Cys Lys Ser Leu Leu Asn
        530                 535                 540

Phe His Lys Val Leu Gly His Thr Leu Ser Glu Leu Glu Thr Leu Pro
545                 550                 555                 560

Ile Asn Asp Val Val Lys Lys Gly Tyr Tyr Thr Phe Thr Thr Asp Asn
                565                 570                 575

Glu Gly Lys Ile Thr Asp Asp Ala Ser Leu Ser Glu Lys Gly Lys Val
            580                 585                 590

Arg Lys Met Lys Asp Asp Phe Phe Asn Gln Ala Ile Lys Ala Ile His
        595                 600                 605

Phe Ala Asp Val Lys Asp Tyr Phe Ala Thr Leu Ser Asn Asn Gly Gln
        610                 615                 620

Thr Gly Ile Phe Phe Val Pro Ser Gln Phe Thr Ser Gln Met Asp Ser
625                 630                 635                 640

Asn Thr His Asn Leu Tyr Phe Glu Asn Ala Lys Asn Gly Gly Leu Lys
                645                 650                 655

Leu Ala Pro Lys Tyr Lys Val Arg Gln Thr Gln Glu Tyr His Leu Asn
        660                 665                 670
```

-continued

```
Gly Leu Pro Ala Asp Tyr Asn Ala Ala Arg Asn Ile Ala Tyr Ile Gly
        675             680             685

Leu Asp Glu Thr Met Arg Asn Thr Phe Leu Lys Lys Ala Asn Ser Asn
        690             695             700

Lys Ser Leu Tyr Asn Gln Pro Ile Tyr Asp Thr Gly Ile Lys Lys Thr
705             710             715             720

Ala Gly Val Phe Ser Arg Met Lys Lys Leu Lys Arg Tyr Glu Ile Ile
                725             730             735

<210> SEQ ID NO 159
<211> LENGTH: 757
<212> TYPE: PRT
<213> ORGANISM: Artificial sequence
<220> FEATURE:
<223> OTHER INFORMATION: synthetic sequence

<400> SEQUENCE: 159

Met Ala His Lys Lys Asn Leu Glu Gly Glu Asn Leu Gln Val Lys Thr
1               5               10              15

Ile Cys Leu Lys Ala Asn Leu Ser Lys Glu Glu Val Lys Glu Lys Trp
                20              25              30

Leu Pro Val Ile Asn Glu Tyr Asn Val Tyr Tyr Asn Arg Met Ser Asp
            35              40              45

Tyr Ile Cys Ser Leu Leu Gly Thr Asn Ile Thr Ile Gly Glu Phe Ala
        50              55              60

Glu Gln Leu Ser Ile Glu Lys Arg Lys Asn Gly Tyr Phe Thr Ile Cys
65              70              75              80

Gln Asp Asp Lys Phe Lys Asn Glu Ser Leu Tyr Lys Ile Phe His Lys
                85              90              95

Ser Phe Pro Ile Asn His Gly Thr Asn Ile Ile Asn Asn Ile Ile Ser
            100             105             110

Glu Lys Asn Ile Asp Gln Tyr Asp Gly Asn Thr Leu Gly Phe Arg Pro
        115             120             125

Thr Met Tyr Arg Leu Arg Gly Tyr Val Asp Ser Val Ile Gly Asn Tyr
    130             135             140

Arg Thr Thr Ile Arg Thr Ile Lys Pro Ser Val Lys Arg His Lys Ile
145             150             155             160

Ser Val Asp Ser Ser Phe Asp Glu Lys Met Glu Gln Cys Ile Tyr Glu
            165             170             175

Ile Gln Lys Gly Asn Leu Lys Thr Val Ser Glu Trp Asn Asn Lys Ile
            180             185             190

Asp Tyr Leu Leu Ser Lys Ser Asp Met Asn Pro Leu Thr Ile Asp Arg
        195             200             205

Phe Asn Leu Leu Arg Asp Phe Tyr Val Asp Asn Glu Thr Glu Val Asn
    210             215             220

Glu Lys Ser Asn Asn Ser Ser Ile Glu Gln Leu Val Lys Phe Gly Gly
225             230             235             240

Cys His Arg Lys Gly Asp Asn Met Thr Leu Ser Leu Thr Glu Ala Asn
                245             250             255

Phe Ser Ile Glu Glu Ile Asp Asp Ser Tyr Gly Tyr Leu Leu Thr Leu
            260             265             270

His Thr Asp Ser Gly Asp Tyr Lys Ile Pro Leu Met Gly Ser Lys Met
        275             280             285

Leu Lys Lys Gly Asp Lys Cys Leu Ile Asp Phe Val Asn Asn Cys Lys
    290             295             300
```

-continued

```
Lys Gly Lys Ser Leu Thr Ala Lys Ile Asp Asn Asp Tyr Asn Leu Tyr
305             310             315             320

Phe His Phe Val Val Tyr Ser Asn Phe Glu Lys Ile Glu Asp Asp Asn
                325             330             335

Ile Asn Asn Val Val Gly Val Asp Val Asn Ser Lys His Met Leu Leu
            340             345             350

Met Thr Asn Val Ile Asp Asp Asn Ile Asp Gly Tyr Val Asn Ile Tyr
            355             360             365

Lys Ala Leu Val Asn Asp Asp Glu Phe Lys Ser Leu Val Thr Lys Ser
            370             375             380

Glu Tyr Asp Asp Tyr Val Thr Met Ser Lys Tyr Val Thr Phe Cys Pro
385             390             395             400

Ile Glu Leu Lys Tyr Leu Tyr Ala Arg Tyr Cys Val Gln Lys Asp Tyr
                405             410             415

Pro Ile Ser Asn Lys Asp Val Ala Ile Glu Gln Cys Ile Ser Arg Val
                420             425             430

Ile Asp Lys Leu Cys Lys Glu Thr Leu Asp Ser Arg Ala Asn Asn Tyr
            435             440             445

Leu Cys Met Val Arg Arg Ile Arg His Tyr Tyr Lys Ser Tyr Tyr Val
            450             455             460

Leu Lys Met Thr Tyr Tyr Asp Lys Met Ser Glu Tyr Asp Thr Asn Met
465             470             475             480

Glu Tyr Asn Asp Ile Ser Thr Thr Ser Lys Glu Thr Met Asp Gln Arg
                485             490             495

Arg Phe Glu Asn Ser Phe Arg Glu Thr Asp Cys Ala Lys Glu Ile Leu
            500             505             510

Ser Lys Leu Asp Lys Ile Gly Asn Asp Ile Leu Gly Cys Arg Asn Asn
            515             520             525

Ile Leu Thr Tyr Ala Tyr Lys Leu Phe Glu Glu Leu Gly Tyr Asp Thr
            530             535             540

Ile Ala Leu Glu Asn Leu Glu Ser Ser Gln Phe Asp Lys Met Lys Ser
545             550             555             560

Leu Pro Ser Cys Gln Ser Met Leu Lys Tyr His Lys Leu Glu Gly Lys
                565             570             575

Thr Met Glu Glu Val Met Ser Asn Thr Ser Val Lys Ser Leu Ile Glu
            580             585             590

Asn Glu Tyr Tyr Asp Phe Ser Leu Asn Asp Asn Lys Thr Val Glu Asn
            595             600             605

Ile Thr Tyr Thr Lys Asn Gly Leu Met Lys Lys Gly Phe Asp Glu Phe
            610             615             620

Phe Asn Leu Phe Met Lys Ile His Phe Ala Asp Ile Lys Asp Lys Phe
625             630             635             640

Leu Gln Leu Tyr Asn Asn Gly Ser Val Lys Val Ile Leu Val Pro Ser
                645             650             655

Tyr Phe Thr Ser Gln Met Asp Ser Asn His Ser Ile Tyr Met Glu Lys
                660             665             670

Ser Lys Asn Asp Lys Leu Val Phe Ala Ser Lys His Lys Val Arg Lys
            675             680             685

Thr Gln Glu Thr His Leu Asn Gly Leu Asn Ala Asp Tyr Asn Ala Cys
            690             695             700

Asn Ile Ala Tyr Ile Ala Lys Asp Ile Lys Trp Arg Glu Lys Phe Cys
705             710             715             720

Lys Lys Thr Ser Asn Asn Gly Tyr Ser Thr Pro Phe Tyr Asp Cys Ala
```

```
                   725                 730                 735

Thr Lys Asn Gln Ile Glu Met Val Lys Arg Ile Lys Gln Leu Asn Ala
            740                 745                 750

Ile Lys Met Leu Ala
        755

<210> SEQ ID NO 160
<211> LENGTH: 767
<212> TYPE: PRT
<213> ORGANISM: Artificial sequence
<220> FEATURE:
<223> OTHER INFORMATION: synthetic sequence

<400> SEQUENCE: 160

Met Ala His Lys Lys Gln Lys Glu Glu Asn Glu Ile Ile Lys Thr Ile
1               5                   10                  15

Ser Leu Lys Val Lys Asp Tyr Ala Gly Tyr Pro Ile Val Glu Ala Met
            20                  25                  30

Arg Glu Tyr Thr Lys Tyr Tyr Asn Lys Ile Ser Gln Trp Ile Asn Ser
        35                  40                  45

Asn Leu Leu Thr Ile Lys Ile Gly Glu Leu Ser Ala Phe Met Pro Asp
        50                  55                  60

Glu Cys Lys Thr His Asn Tyr Tyr Thr Tyr Met Met Ser Pro Asp Trp
65                  70                  75                  80

Val Asn Glu Pro Leu Tyr Lys Met Phe Met Lys Gly Phe His Ala Gln
            85                  90                  95

His Cys Asp Asn Ile Leu Phe Asn Val Val Lys Thr Leu Asn Ile Asp
            100                 105                 110

Glu Tyr Ala Gly Asn Ser Leu Gly Leu Ser Ala Ser Cys Phe Arg Arg
            115                 120                 125

Ser Gly Tyr Phe Gln Asn Val Val Ser Asn Tyr Lys Ser Lys Phe Ala
        130                 135                 140

Asn Pro His Ile Ser Ile Arg Arg Lys Asn Leu Ser Asp Leu Pro Thr
145                 150                 155                 160

Glu Asp Glu Leu Val Glu Gln Cys Ile Tyr Glu Ile Gln Asn Gly Leu
            165                 170                 175

Ser Ser Lys Thr Lys Trp Glu Glu Gln Ile Glu Tyr Leu Lys Glu Arg
            180                 185                 190

Asp Asp Ser Lys Gln Ile Tyr Leu Thr Arg Leu Asn Thr Leu Phe Met
        195                 200                 205

Tyr Tyr Lys Ala Asn Lys Asp Phe Val Asp Glu Gln Ile Gln Ile Lys
        210                 215                 220

Ser Val Glu Ser Leu Ala Asn Phe Gly Gly Cys Val Arg Lys Asp Asp
225                 230                 235                 240

Lys Leu Ser Met Asn Leu Val Phe Ser Ser Asn Ser Pro Tyr Lys Val
            245                 250                 255

Val Leu Asn Glu Lys Arg Asn Gly Tyr Ile Leu Ser Tyr Ser Asn Asn
            260                 265                 270

Phe Ser Ile Glu Leu Tyr Gly Asn Arg Met Gly Leu Leu Asn Gly Val
        275                 280                 285

Glu Val Phe Asn Val Gly Asp Lys His Ser Asn Asn Ile Thr Phe Lys
        290                 295                 300

Met Asp Asn Asp Glu Leu Phe Val Asn Ile Pro Val Ser Val Asn Phe
305                 310                 315                 320

Val Lys Lys Ala Asn Glu Thr Asn Lys Val Val Gly Val Asp Val Asn
```

```
                     325                   330                   335

Leu Lys His Ser Ile Phe Ala Thr Asn Ile Ile Asp Asp Gly Lys Leu
            340                   345                   350

Asp Gly Phe Val Asn Ile Tyr Arg Glu Leu Leu Asn Asp Val Asp Phe
                355                   360                   365

Val Lys Ser Cys Pro Asn Glu Leu Leu Asn Phe Ile Leu Asp Val Glu
            370                   375                   380

Lys Tyr Ala Phe Phe Met Pro Leu Glu Leu Gly Leu Leu Ser Ser Arg
385                   390                   395                   400

Val Met Asn Gln Cys Gly Tyr Ser Thr Ile Gly Lys Tyr Glu Lys Leu
                    405                   410                   415

Phe Thr Thr Glu Glu His Phe Phe Arg Val Leu Arg Gln Leu Glu Lys
                420                   425                   430

Arg Phe Gln Glu Ser Gly Glu Asn Gln Lys Arg Ile Tyr Ile Glu Asn
                435                   440                   445

Val Ile Lys Met Arg Ala Gln Val Lys Ala Tyr Phe Thr Leu Lys Tyr
    450                   455                   460

Ala Thr Asn Lys Ala Asn Lys Asp Tyr Asp Leu Lys Met Gly Phe Val
465                   470                   475                   480

Asp Glu Ser Thr Ala Asn Lys Glu Thr Met Asp Gln Arg Arg Phe Glu
                    485                   490                   495

Asn Gln Phe Val Asn Thr Tyr Thr Ala Lys Glu Ile Leu Gly Lys Met
                500                   505                   510

Arg Arg Ile Ala Asn Val Ile Thr Ser Cys Arg Asn Asn Ile Ile Cys
                515                   520                   525

Tyr Met Tyr Lys Ile Phe Glu Asn Asn Gly Tyr Gly Val Val Ala Leu
    530                   535                   540

Glu Lys Leu Gln Ser Ser Gln Met Lys Lys Glu Lys Arg Ile Pro Ser
545                   550                   555                   560

Leu Leu Ser Leu Leu Lys Lys Gln Lys Val Glu Gly Tyr Thr Ile Asn
                565                   570                   575

Glu Leu Lys Asp Lys Ser Val Phe Lys Phe Ile Glu Arg Gly Tyr Tyr
                580                   585                   590

Thr Phe Asp Phe Asp Asp Asn Lys Ile Thr Gly Val Gln Phe Ser
                595                   600                   605

Asp Ala Gly Glu Val Val Asn Met Glu Thr Glu Leu His Asn Leu Ala
    610                   615                   620

Leu Lys Thr Ile His Phe Ala Asp Ala Lys Asp Tyr Phe Val Thr Leu
625                   630                   635                   640

Ser Asn Asn Gly Ser Val Ser Val Ala Leu Val Pro Ser Gln Phe Thr
                645                   650                   655

Ser Gln Met Asp Ser Thr Lys His Val Leu Tyr Ala Lys Lys Asn Asn
                660                   665                   670

Lys Gly Lys Leu Gly Ile Val Ser Glu His Glu Val Arg Pro Lys Gln
                675                   680                   685

Glu Cys His Ile Asn Gly Leu Asn Gly Asp Tyr Asn Ala Ala Cys Asn
    690                   695                   700

Ile Ala Tyr Ile Phe Glu Asn Asp Glu Trp Arg Asn Ala Phe Met Lys
705                   710                   715                   720

Met Asn Pro Asn Glu Tyr Gly Lys Ala Leu Phe Glu Thr Asn Met Glu
                725                   730                   735

Ser Thr Ser Thr Ile Ile Asn Thr Leu Lys Lys Ile Asn Pro Asp Asn
                740                   745                   750
```

```
Ile Ile Ser Phe Asp Glu Tyr Glu Lys Thr Lys Lys Val Ala Ala
        755                 760                 765

<210> SEQ ID NO 161
<211> LENGTH: 889
<212> TYPE: PRT
<213> ORGANISM: Artificial sequence
<220> FEATURE:
<223> OTHER INFORMATION: synthetic sequence

<400> SEQUENCE: 161

Trp Thr Asp Glu Asp Tyr Cys Lys Phe Phe Ala Lys Tyr Gly Met Ser
1               5                   10                  15

Glu Glu Cys Gln Lys Trp Met Cys Arg Asp Val Tyr Asp Tyr Arg Ile
                20                  25                  30

Lys Asp Phe Val Asp Tyr Glu Lys Phe Asp Asp Ser Lys Ile Glu Glu
            35                  40                  45

Glu Gln Glu Glu Tyr Ser Glu Ile Pro Val Glu Ser Glu Asp Ser Ser
        50                  55                  60

Pro Ser Thr Ser Glu Thr Leu Pro Lys Ser Ile Tyr Asp Leu Asp Leu
65                  70                  75                  80

Arg Arg Leu Asp Pro Asn Pro Glu Ile Pro Glu Asp Glu Lys Tyr Asn
                85                  90                  95

Glu Glu Asp Leu Lys Asn Ala Tyr Pro Asp Lys Tyr Glu Arg Phe Glu
            100                 105                 110

Lys Asp Gly Glu Asp Tyr Ser Tyr Ile Phe Phe Lys Lys Ile Trp Lys
            115                 120                 125

Cys His Phe Phe Val Leu Ser Leu Tyr Gln Leu Asn Gln Tyr Ile Met
    130                 135                 140

Ala Ser His Lys Lys Thr Glu Ser Asn Gln Ile Ile Lys Thr Phe Ser
145                 150                 155                 160

Phe Lys Ile Lys Asn Ala Asn Gly Leu Ser Leu Asp Val Leu Asn Asp
                165                 170                 175

Ala Ile Thr Glu Tyr Gln Asn Tyr Tyr Asn Ile Cys Ser Asp Trp Ile
            180                 185                 190

Lys Asp His Leu Thr Met Lys Ile Gly Glu Leu Tyr Lys Tyr Ile Pro
            195                 200                 205

Asp Glu Lys Lys Asn Ser Gly Tyr Ala Leu Thr Leu Ile Ser Asp Glu
        210                 215                 220

Trp Lys Asp Lys Pro Met Tyr Met Met Phe Lys Lys Gly Tyr Pro Ala
225                 230                 235                 240

Asn Asn Arg Asp Asn Ala Ile Tyr Glu Ala Leu Asn Thr Cys Asn Thr
            245                 250                 255

Glu His Tyr Thr Gly Asn Ile Leu Asn Phe Ser Asp Thr Tyr Tyr Arg
            260                 265                 270

Arg Phe Gly Tyr Val Ala Ser Thr Ile Ser Asn Tyr Val Thr Lys Ile
            275                 280                 285

Ser Lys Met Ser Thr Gly Ser Arg Ser Lys Asn Ile Ser Asn Asp Ser
        290                 295                 300

Asp Val Asp Thr Ile Met Glu Gln Val Ile Tyr Glu Met Glu His Asn
305                 310                 315                 320

Gly Trp Thr Ser Val Lys Asp Trp Glu Asn Gln Met Glu Tyr Leu Glu
            325                 330                 335

Ser Lys Thr Asp Ser Asn Pro Asn Phe Val Tyr Arg Met Thr Thr Leu
            340                 345                 350
```

```
Tyr Glu Phe Tyr Lys Ser His Ile Asp Glu Val Asn Ser Lys Met Glu
    355                 360                 365

Thr Met Ser Ile Asp Ser Leu Ile Lys Phe Gly Gly Cys Arg Arg Lys
    370                 375                 380

Asp Ser Lys Lys Ser Met Tyr Ile Met Gly Gly Ser Asn Thr Pro Phe
385                 390                 395                 400

Asp Ile Thr Gln Ile Asp Gly Asn Ser Leu Asn Ile Lys Phe Ser Lys
                405                 410                 415

Asn Leu Asn Val Asp Val Phe Gly Arg Tyr Asp Val Ile Lys Asp Asn
                420                 425                 430

Thr Leu Leu Val Asp Ile Ile Asn Gly His Gly Ala Ser Phe Val Leu
                435                 440                 445

Lys Ile Ile Asn Asp Glu Ile Tyr Ile Asp Ile Asn Val Ser Val Pro
    450                 455                 460

Phe Asp Lys Lys Ile Ala Thr Thr Asn Lys Val Val Gly Val Asp Val
465                 470                 475                 480

Asn Ile Lys His Met Leu Leu Ala Thr Asn Ile Leu Asp Asp Gly Asn
                485                 490                 495

Val Asn Gly Tyr Val Asn Ile Tyr Lys Glu Val Ile Asn Asp Ser Asp
                500                 505                 510

Phe Lys Lys Val Cys Asn Ser Thr Val Met Lys Tyr Phe Thr Asp Phe
                515                 520                 525

Ser Lys Phe Val Thr Phe Cys Pro Leu Glu Phe Asp Phe Leu Phe Ser
    530                 535                 540

Arg Val Cys Asn Gln Lys Gly Ile Tyr Asn Asp Asn Ser Ala Met Glu
545                 550                 555                 560

Lys Ser Phe Ser Asp Val Leu Asn Lys Leu Lys Trp Asn Phe Ile Glu
                565                 570                 575

Thr Gly Asp Asn Thr Lys Arg Ile Tyr Ile Glu Asn Val Met Lys Leu
                580                 585                 590

Arg Ser Gln Met Lys Ala Tyr Ala Ile Val Lys Asn Ala Tyr Tyr Lys
                595                 600                 605

Gln Gln Ser Glu Tyr Asp Phe Gly Lys Ser Glu Glu Phe Ile Gln Glu
    610                 615                 620

His Pro Phe Ser Asn Thr Asp Lys Gly Ile Glu Ile Leu Asn Lys Leu
625                 630                 635                 640

Asp Asn Ile Ser Lys Lys Ile Leu Gly Cys Arg Asn Asn Ile Ile Gln
                645                 650                 655

Tyr Ser Tyr Asn Leu Phe Glu Ile Asn Gly Tyr Asp Met Ile Ser Leu
                660                 665                 670

Glu Lys Leu Thr Ser Ser Gln Phe Glu Lys Lys Pro Phe Pro Thr Val
                675                 680                 685

Asn Ser Leu Leu Lys Tyr His Lys Ile Leu Gly Cys Thr Gln Glu Glu
    690                 695                 700

Met Glu Lys Lys Asp Ile Tyr Ser Val Ile Lys Lys Gly Tyr Tyr Asp
705                 710                 715                 720

Ile Ile Phe Asp Asn Gly Val Val Thr Asp Ala Lys Leu Ser Thr Lys
                725                 730                 735

Gly Glu Leu Ser Lys Phe Lys Asp Asp Phe Phe Asn Leu Met Ile Lys
                740                 745                 750

Ser Ile His Phe Ala Asp Ile Lys Asp Tyr Phe Ile Thr Leu Ser Asn
    755                 760                 765
```

-continued

```
Asn Gly Thr Ala Gly Val Ser Leu Val Pro Ser Tyr Phe Thr Ser Gln
    770             775             780

Met Asp Ser Ile Asp His Lys Ile Tyr Phe Val Gln Asp Asn Lys Ser
785             790             795             800

Gly Lys Leu Lys Leu Ala Asn Lys His Lys Val Arg Ser Ser Gln Glu
            805             810             815

Lys His Ile Asn Gly Leu Asn Ala Asp Tyr Asn Ala Ala Arg Asn Ile
            820             825             830

Ala Tyr Ile Met Glu Asn Thr Glu Cys Arg Asn Met Phe Leu Lys Gln
        835             840             845

Ser Arg Thr Asp Lys Ser Leu Tyr Asn Lys Pro Ser Tyr Glu Thr Phe
    850             855             860

Ile Lys Thr Gln Gly Ser Ala Val Ala Lys Leu Lys Lys Glu Gly Phe
865             870             875             880

Val Lys Ile Leu Asp Glu Ala Ser Val
            885
```

```
<210> SEQ ID NO 162
<211> LENGTH: 37
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (14)..(14)
<223> OTHER INFORMATION: n is a, c, g, or u

<400> SEQUENCE: 162
wauuguugua rmwnyywuuu uruawggwku raacaac                               37

<210> SEQ ID NO 163
<211> LENGTH: 37
<212> TYPE: RNA
<213> ORGANISM: Artificial sequence
<220> FEATURE:
<223> OTHER INFORMATION: synthetic sequence

<400> SEQUENCE: 163
aauuguugua acucuuauuu uguauggagu aaacaac                               37

<210> SEQ ID NO 164
<211> LENGTH: 36
<212> TYPE: RNA
<213> ORGANISM: Artificial sequence
<220> FEATURE:
<223> OTHER INFORMATION: synthetic sequence

<400> SEQUENCE: 164
auuguuguag auaccuuuuu guaaggauug aacaac                                36

<210> SEQ ID NO 165
<211> LENGTH: 30
<212> TYPE: DNA
<213> ORGANISM: Artificial sequence
<220> FEATURE:
<223> OTHER INFORMATION: synthetic sequence

<400> SEQUENCE: 165
tagcatcacc ttcaccctct ccacggacag                                      30
```